US012448447B2

(12) United States Patent
Kley et al.

(10) Patent No.: US 12,448,447 B2
(45) **Date of Patent: *Oct. 21, 2025**

(54) CD8 BINDING AGENTS

(71) Applicants: Orionis Biosciences Inc., Waltham, MA (US); Orionis Biosciences BV, Ghent (BE)

(72) Inventors: Nikolai Kley, Newton, MA (US); Jan Tavernier, Balegem (BE); Lennart Zabeau, Ghent (BE); Erik Depla, Ghent (BE)

(73) Assignees: Orionis Biosciences, Inc., Waltham, MA (US); Orionis Biosciences BV, Ghent (BE)

( * ) Notice: Subject to any disclaimer, the term of this patent is extended or adjusted under 35 U.S.C. 154(b) by 43 days.

This patent is subject to a terminal disclaimer.

(21) Appl. No.: 18/060,694

(22) Filed: Dec. 1, 2022

(65) Prior Publication Data

US 2023/0142099 A1 May 11, 2023

Related U.S. Application Data

(63) Continuation of application No. 16/634,325, filed as application No. PCT/US2018/045741 on Aug. 8, 2018, now Pat. No. 11,566,072.

(60) Provisional application No. 62/542,920, filed on Aug. 9, 2017.

(51) Int. Cl.
*C07K 16/28* (2006.01)
*C07K 14/56* (2006.01)

(52) U.S. Cl.
CPC .......... *C07K 16/2815* (2013.01); *C07K 14/56* (2013.01); *C07K 2317/22* (2013.01); *C07K 2317/24* (2013.01); *C07K 2317/565* (2013.01); *C07K 2317/569* (2013.01); *C07K 2319/02* (2013.01)

(58) Field of Classification Search
None
See application file for complete search history.

(56) References Cited

U.S. PATENT DOCUMENTS

| | | | | |
|---|---|---|---|---|
| 5,914,254 | A | 6/1999 | Mascarenhas et al. | |
| 8,980,267 | B2 | 3/2015 | Grewal et al. | |
| 9,139,634 | B2 | 9/2015 | Morrison et al. | |
| 9,315,567 | B2 | 4/2016 | Chang et al. | |
| 9,492,562 | B2 | 11/2016 | Tavernier et al. | |
| 9,534,056 | B2 | 1/2017 | Grewal et al. | |
| 9,732,135 | B2 | 8/2017 | Tavernier et al. | |
| 9,878,014 | B2 | 1/2018 | Tavernier et al. | |
| 9,914,759 | B2 | 3/2018 | Tavernier et al. | |
| 9,932,409 | B2 | 4/2018 | Tavernier et al. | |
| 10,034,919 | B2 | 7/2018 | Tavernier et al. | |
| 10,035,835 | B2 | 7/2018 | Tavernier et al. | |
| 10,072,059 | B2 | 9/2018 | Tavernier et al. | |
| 10,407,480 | B2 | 9/2019 | Tavernier et al. | |
| 10,640,542 | B2 | 5/2020 | Tavernier et al. | |
| 11,566,072 | B2 * | 1/2023 | Kley .................... | A61K 38/191 |
| 2010/0172868 | A1 | 7/2010 | Morrison et al. | |
| 2010/0297076 | A1 | 11/2010 | Morrison et al. | |
| 2011/0020273 | A1 | 1/2011 | Chang et al. | |
| 2011/0081341 | A1 | 4/2011 | Honjo et al. | |
| 2011/0104112 | A1 | 5/2011 | Morrison et al. | |
| 2011/0224407 | A1 | 9/2011 | Langer et al. | |
| 2011/0274658 | A1 | 11/2011 | Silver et al. | |
| 2013/0137856 | A1 | 5/2013 | Steyaert et al. | |
| 2013/0183298 | A1 | 7/2013 | Le et al. | |
| 2013/0230517 | A1 | 9/2013 | Grewal et al. | |
| 2014/0271462 | A1 | 9/2014 | Ho et al. | |
| 2014/0348789 | A1 | 11/2014 | Tavernier et al. | |
| 2015/0139951 | A1 | 5/2015 | Grewal et al. | |
| 2015/0313965 | A1 | 11/2015 | Pogue et al. | |
| 2018/0186894 | A1 | 7/2018 | Tavernier et al. | |
| 2018/0333465 | A1 | 11/2018 | Tavernier et al. | |
| 2018/0334488 | A1 | 11/2018 | Tavernier et al. | |
| 2018/0334489 | A1 | 11/2018 | Tavernier et al. | |
| 2019/0010199 | A1 | 1/2019 | Tavernier et al. | |
| 2019/0071500 | A1 | 3/2019 | Kley et al. | |
| 2019/0144553 | A1 | 5/2019 | Kley et al. | |
| 2019/0194284 | A1 | 6/2019 | Kley et al. | |
| 2019/0202934 | A1 | 7/2019 | Tavernier et al. | |
| 2019/0351021 | A1 | 11/2019 | Tavernier et al. | |
| 2019/0352406 | A1 | 11/2019 | Tavernier et al. | |

(Continued)

FOREIGN PATENT DOCUMENTS

| | | | |
|---|---|---|---|
| RU | 2011127226 | A | 1/2013 |
| WO | WO 91/02754 | A1 | 3/1991 |

(Continued)

OTHER PUBLICATIONS

Rabia et al Understanding and overcoming trade-offs between antibody affinity, specificity, stability and solubility (Biochemical Engineering Journal 137 (2018) 365-374) (Year: 2018).*

(Continued)

*Primary Examiner* — Janet L Andres
*Assistant Examiner* — Brian Hartnett
(74) *Attorney, Agent, or Firm* — Morgan, Lewis & Bockius LLP

(57) ABSTRACT

The present invention relates, in part, to agents that bind CD8 and their use as therapeutic and diagnostic agents. The present invention further relates to pharmaceutical compositions comprising the CD8 binding agents and their use in the treatment of various diseases, including, for example, cancers.

14 Claims, 24 Drawing Sheets

Specification includes a Sequence Listing.

(56) References Cited

U.S. PATENT DOCUMENTS

| | | | |
|---|---|---|---|
| 2019/0367575 | A1 | 12/2019 | Tavernier et al. |
| 2019/0367604 | A1 | 12/2019 | Kley et al. |
| 2020/0071414 | A1 | 3/2020 | Kley et al. |
| 2020/0087411 | A1 | 3/2020 | Kley et al. |

FOREIGN PATENT DOCUMENTS

| | | | |
|---|---|---|---|
| WO | 2000/055305 | A1 | 9/2000 |
| WO | WO 03/033720 | A2 | 4/2003 |
| WO | WO 2006/053883 | A1 | 5/2006 |
| WO | WO 2006/115800 | A2 | 11/2006 |
| WO | 2007/110231 | A2 | 10/2007 |
| WO | WO 2008/014612 | A1 | 2/2008 |
| WO | WO 2008/124086 | A2 | 10/2008 |
| WO | WO 2009/003145 | A1 | 12/2008 |
| WO | WO 2009/013484 | A1 | 1/2009 |
| WO | WO 2009/039409 | A1 | 3/2009 |
| WO | WO 2010/036918 | A2 | 4/2010 |
| WO | WO 2010/066740 | A1 | 6/2010 |
| WO | WO 2011/020783 | A2 | 2/2011 |
| WO | WO 2011/029870 | A1 | 3/2011 |
| WO | WO 2012/170072 | A1 | 12/2012 |
| WO | WO 2013/053008 | A2 | 4/2013 |
| WO | WO 2013/059885 | A2 | 5/2013 |
| WO | WO 2013/107791 | A1 | 7/2013 |
| WO | WO 2013/134138 | A1 | 9/2013 |
| WO | WO 2014/122183 | A1 | 8/2014 |
| WO | WO 2014/164553 | A1 | 10/2014 |
| WO | WO 2015/007520 | A1 | 1/2015 |
| WO | WO 2015/007536 | A2 | 1/2015 |
| WO | WO 2015/007542 | A1 | 1/2015 |
| WO | WO 2015/007903 | A1 | 1/2015 |
| WO | WO 2015/018528 | A1 | 2/2015 |
| WO | WO 2017/077382 | A1 | 5/2017 |
| WO | WO 2017/134302 | A2 | 8/2017 |
| WO | WO 2017/194782 | A2 | 11/2017 |

OTHER PUBLICATIONS

Sabir et al. Construction of naive camelids VHH repertoire in phage display-based libraryC. R. Biologies 337 (2014) 244-249 (Year: 2014).*

Lloyd et al.Modelling the human immune response: performance of a 1011 human antibody repertoire against a broad panel of therapeutically relevant antigens. Protein Engineering, Design & Selection vol. 22 No. 3 pp. 159-168, 2009. (Year: 2009).*

Acres, et al., "Fusokine Interleukin-2/Interleukin-18, a Novel Potent Innate and Adaptive Immune Stimulator with Decreased Toxicity," Cancer Res., vol. 65, No. 20, pp. 9536-9546, 2005.

Baba, et al., "Identification of CCR6, the Specific Receptor for a Novel Lymphocyte-Directed CC Chemokine LARC," The Journal of Biological Chemistry, vol. 272, No. 23, pp. 14893-14898, 1997.

Barbara, et al., "Dissociation of TNF-α cytotoxic and proinflammatory activities by p55 receptor-and p75 receptor-selective TNF-α mutants," EMBO Journal, vol. 13, No. 4, pp. 843-850, 1994.

Bork, et al., "Go hunting in sequence databases but watch out for the traps." Trends in Genetics, vol. 12, pp. 125-427, 1996.

Bork, "Powers and Pitfalls in Sequence Analysis: The 70% Hurdle," Genome Research, vol. 10, pp. 398-400, 2000.

Boschert, et al., "Single chain TNF derivatives with individually mutated receptor binding sites reveal differential stoichiometry of ligand receptor complex formation for TNFR1 and TNFR2," Cellular Signalling 22 (7):1088-1096, 2010.

Bremer, et al., "Superior activity of fusion protein scFvRit:sFasL over cotreatment with rituximab and Fas agonists," Cancer Res. 68: 597-604, 2008.

Camacho, et al., "Structure of an Interleukin-1β Mutant With Reduced Bioactivity Shows Multiple Subtle Changes in Conformation That Affect Protein-Protein Recognition," Biochemistry, vol. 32, No. 34, pp. 8749-8757, 1993.

Coulstock, et al., "Liver-Targeting of Interferon-Alpha with Tissue Specific Domain Antibodies," PLOS ONE, vol. 8, No. 2, pp. 1-11, 2013.

De Bruyn, et al., "Antibody-Based Fusion Proteins to Target Death Receptors in Cancer," Cancer Letters, vol. 332, pp. 175-183, 2013.

Deffar, et al., "Nanobodies—The New Concept in Antibody Engineering," African Journal of Biotechnology, vol. 8, No. 12, pp. 2645-2652, 2009.

Dijkmans, et al., "Murine Interferon-γ Interleukin-1 Fusion Proteins Used as Antigens for the Generation of Hybridomas Producing Monoclonal Anti-Interleukin-1 Antibodies," Cytokine, vol. 3, No. 2, pp. 134-140, 1991.

Dimitrov, "Engineered CH2 Domains (Nanoantibodies)," mAbs, Landes Bioscience, vol. 1, No. 1, pp. 26-28, 2009.

Frey, et al., "Antibody-Based Targeting of Interferon-Alpha to the Tumor Neovasculature: A Critical Evaluation," ntegrative Biology, vol. 3, pp. 468-478, 2011.

Garcin, et al., "High Efficiency cell-specific targeting of cytokine activity," Nature Communications, vol. 5, No. 8, 9 pages, 2014.

Garlanda, et al., "The Interleukin-1 Family: Back to the Future," Immunity, 39 (6): pp. 1003-1018, Dec. 12, 2013.

Holler, et al., "Two Adjacent Trimeric Fas Ligands are Required for Fas Signaling and Formation of a Death-Inducing Signaling Complex," Molecular and Cellular Biology, vol. 23, No. 4, pp. 1428-1440, 2003.

Huang, et al., "A Trimeric Anti-HER2/neu ScFv and Tumor Necrosis Factor-[alpha] Fusion Protein Induces HER2/Neu Signaling and Facilitates Repair of Injured Epithelia," The Journal of Pharmacology and Experimental Therapeutics, vol. 316, No. 3, pp. 983-991, 2006.

Idoyaga, et al., "Comparable T helper 1 (Th1) and CD8 T-cell immunity by targeting HIV gag p24 to CD8 dendritic cells within antibodies to Langerin, DEC205, and Clec9A," PNAS, vol. 108, No. 6, pp. 2384-2389, Jan. 24, 2011.

International Search Report & Written Opinion, PCT Application No. PCT/EP17/52553, dated Jul. 12, 2017, 14 pages.

Kircheis, et al., "Biological activity of mutants of human tumour necrosis factor-alpha," Immunology, pp. 433-438, Jul. 1, 1992.

Krippner-Heidenreich, et al., "Single-Chain TNF, a TNF Derivative with Enhanced Stability and Antitumoral Activity," The Journal of Immunology, vol. 180, pp. 8176-8183, 2008.

Lahoud, et al., "Targeting Antigen to Mouse Dendritic Cells via Clec9A Induces Potent CD4 T Cell Responses Biased toward a Follicular Helper Phenotype," The Journal of Immunology, vol. 187, No. 2, pp. 842-850, Jul. 15, 2011.

Loetscher, et al., "Human Tumor Necrosis Factor α (TNFα) Mutants with Exclusive Specificity for 55-kDA or 75-kDa TNF Receptors," Journal of Biological Chemistry, American Society for Biochemistry and Molecular Biology, US, vol. 268, No. 35, pp. 26350-26357, 1993.

Masci, et al., "New and Modified Interferon alfas: Preclinical and Clinical Data," Current Oncology Reports, vol. 5, pp. 108-113, 2003.

Minn, "Interferons and the Immunogenic Effects of Cancer Therapy," Trends In Immunology, vol. 36, No. 11, pp. 725-737, Nov. 1, 2015.

Ngo, et al., "Computational Complexity, Protein Structure Prediction, and the Levinthal Paradox. The Protein Folding Problem and Tertiary Structure Prediction," Edited by: Mertz et al., (Birkhauser, Boston), pp. 491-495, 1994.

Pan, et al., "Mutation of the IFNAR-1 Receptor Binding Site of Human IFN-α2 Generates Type I IFN Competitive Antagonists," Biochemistry, vol. 47, pp. 12018-12027, 2008.

Patris, et al., "Nanoimmunoassay onto a screen printed electrode for HER2 breast cancer biomarker determination," Talanta, 2014, vol. 130, pp. 164-170, 2014.

Penafuerte, et al., "The Human Ortholog of Granulocyte Macrophage Colony-Stimulating Factor and Interleukin-2 fusion Protein Induces Potent Ex Vivo Natural Killer Cell Activation and Maturation," Cancer Res, vol. 69, No. 23, pp. 9020-9028, 2009.

Picco, et al., "Targeting DNGR-1 (CLEC9A) with antibody/MUC1 peptide conjugates as a vaccine for carcinomas," European Journal of Immunology, vol. 44, No. 7, pp. 1947-1955, Apr. 17, 2014.

(56) References Cited

OTHER PUBLICATIONS

Puskas, et al., "Development of an attenuated interleukin-2 fusion protein that can be activated by tumour-expressed proteases," Immunology, vol. 133, No. 2, pp. 206-220, Jun. 23, 2011.

Rafei, et al., "A MCP1 Fusokine with CCR2-Specific Tumoricidal Activity," Molecular Cancer, vol. 10, No. 121, pp. 1-11, 2011.

Rafei, et al., "An Engineered GM-CSF-CCL2 Fusokine Is a Potent Inhibitor of CCR2-Driven Inflammation as Demonstrated in a Murine Model of Inflammatory Arthritis," The Journal of Immunology, vol. 183, pp. 1759-1766, 2009.

Roisman, et al., "Structure of the Interferon-Receptor Complex Determined by Distant Constraints from Double Mutant Cycles and Flexible Docking," PNAS, vol. 98, No. 23, pp. 13231-13236, 2001.

Rovero, et al., "Insertion of the DNA for the 163-171 Peptide of IL 1 II Enables a DNA Vaccine Encoding $p185^{neu}$ to inhibit Mammary Carcinogenesis in Her-2/neu Transgenic BALB/c Mice," Gene Therapy, vol. 8, pp. 447-452, 2001.

Sancho, et al., "Identification of a dendritic cell receptor that couples sensing of necrosis to immunity," Nature, Nature Publishing Group, United Kingdom, vol. 453, No. 7240, pp. 899-903, Apr. 16, 2009.

Schutyser, et al., "The CC Chemokine CCL20 and its Receptor CCR6," Cytokine & Growth Factor Reviews, vol. 14, pp. 409-426, 2003.

Vaneycken, et al., "Preclinical Screening of Anti-HER2 Nanobodies for Molecular Imaging of Breast Cancer", The ASEB Journal, vol. 25, pp. 2433-2446, 2011.

Weber, et al., "Single Amino Acid Changes that Render Human IFN-$\alpha$2 Biologically Active on Mouse Cells," The EMBO Journal, vol. 6, No. 3, pp. 591-598, 1987.

Wells, "Additivity of Mutational Effects in Proteins," Biochemistry, vol. 29, No. 37, pp. 8509-8517, 1990.

Wesolowski, et al., "Single Domain Antibodies: Promising Experimental and Therapeutic Tools in Infection and Immunity," Med. Microbiol. Immunol., vol. 198, pp. 157-174, 2009.

Zitvogel, et al., "Type I interferons in anticancer immunity," The Journal of Immunology, vol. 15, No. 7, pp. 405-141, Jun. 1, 2015.

Chain B, The Catalytic Domain of Murine Urokinase-type Plasminogen Activator in Complex With the Active Site Binding Inhibitory Nanobody Nb22, PDB: 5LHR_B, downloaded from the internet, <http:www.ncbi.nlm.nih.gov/protein/5LHR_B?report=genbank&log$=protalign&blast_rank=1&RID=Y68GP6VC015>, Nov. 7, 2018, 2 pages.

International Search Report & Written Opinion, PCT. Appl. No. PCT/US18/45741, dated Dec. 14, 2018, 15 pages.

ToIC family protein [Hydrogenovibrio crunogenus], NCBI Reference Sequence: WP_011369874.1, downloaded from the internet, <https:www.ncbi.nlm.nih.gov/protein/WP_011369874.1?reporting=genbank&log$=protalign&blast_rank=1&RID=Y6Aj*PT7015>, Nov. 7, 2018, 1 page.

Rashidian, et al., "Predicting the response to CTLA-4 blockade by longitudinal non-invasive monitoring of CD8 T cells", Journal of Experimental Evidence, 214(8), pp. 2243-2255 (2017).

Rock, et al., "CDR3 Length in Antigen-specific Immune Receptors," J. Exp. Med., vol. 179, pp. 323-328, Jan. 1994.

* cited by examiner

FIGURE 1 (CONTINUED)

```
SEQ ID NO: 1080 2CDA1   : CAGGTGCAGCTGCAGGAGTCTGGGGGAGGATTGGTGCAGGCTGGGGGCTCCCTGAGACTCTCCTGTGCAGCCTCTGGAGGCACCT------------TCAGTAATTATGTCA : 100
SEQ ID NO: 1081 2CDA77  : CAGGTGCAGCTGCAGGAGTCTGGGGGAGGATTGGTGCAGGCTGGGGGCTCTCTGAGACTCTCCTGTGCAGCCTCTACACCCACCT------------TCAGTAGCTATAACA : 100
SEQ ID NO: 1082 2CDA75  : CAGGTGCAGCTGCAGGAGTCTGGGGGAGGATTGGTGCAGGCTGGGGGCTCTCTGAGACTCTCCTGTGCAGCCTCTGGACGCGCCT------------TCAGTAGCTATTTCA : 100
SEQ ID NO: 1083 1CDA75  : CAGGTGCAGCTGCAGGAGTCTGGGGGAGGATTGGTGCAGGCTGGGGGCTCTCTGAGACTCTCCTGTGCAGCCTCTGGACGCACCT------------TCAGTACCTATCCCG : 100
SEQ ID NO: 1084 2CDA68  : CAGGTGCAGCTGCAGGAGTCTGGGGGAGGATTGGTGCAGGCTGGGGGCTCTCTGAGACTCTCCTGTGCAGCCTCTGGACGCACCT------------TCAGTAGCTATGTCA : 100
SEQ ID NO: 1085 1CDA43  : CAGGTGCAGCTGCAGGAGTCTGGGGGAGGATTGGTGCAGGCTGGGGGCTCTCTGAGACTCTCCTGTGTAGCCTCTGGGCACACCT------------TCAGTAGCTATACCA : 100
SEQ ID NO: 1086 1CDA73  : CAGGTGCAGCTGCAGGAGTCTGGGGGAGGATTGGTGCAGGCTGGGGGCTCTCTGAGACTCTCCTGTGCAGCCTCTGGGCACACCT------------TCAGTAGCTATACAA : 100
SEQ ID NO: 1087 1CDA15  : CAGGTGCAGCTGCAGGAGTCTGGGGGAGGATTGGTGCAGGCTGGGGGCTCTCTGAGACTCTCCTGTGCAGCCTCTGGGCGCACCT------------TCAGTAGCTATACCA : 100
SEQ ID NO: 1088 1CDA7   : CAGGTGCAGCTGCAGGAGTCTGGGGGAGGATTGGTGCAGGCTGGGGGCTCTCTGAGACTCTCCTGCGCAGCCTCTGGACGCAGCT------------TTAGTAGCTATACCC : 100
SEQ ID NO: 1089 1CDA17  : CAGGTGCAGCTGCAGGAGTCTGGGGGAGGATTGGTGCAGGCTGGGGGCTCTCTGAGACTCTCCTGTGCAGCCTCTGGACGCACCTCTGGACGCACCTTTAGTAGCTATACTA : 112
SEQ ID NO: 1090 1CDA18  : CAGGTGCAGCTGCAGGAGTCTGGGGGAGGCTTGGTGCAGCCTGGGGGGTCTCTGAGACTCTCCTGTTTAGCCTCTGGACGCACCT------------TCAGTAGCTATGCCA : 100
SEQ ID NO: 1091 1CDA26  : CAGGTGCAGCTGCAGGAGTCTGGGGGAGGATTGGTGCAGGCTGGGGGCTCTCTGAGACTCTCCTGTGCAGCCTCTGGACGTACCT------------TCAGTAGCGACACCA : 100
SEQ ID NO: 1092 1CDA68  : CAGGTGCAGCTGCAGGAGTCTGGGGGAGGATTGGTGCAGGCTGGTGCCTCTCTGAGACTCTCCTGTGCAGCCTCTGGACGCACCT------------TCAGTAATTATAACG : 100
SEQ ID NO: 1093 3CDA31  : CAGGTGCAGCTGCAGGAGTCTGGGGGAGGATTGGTGCAGGCTGGGGACTCTCTGAGACTCTCCTGTGCAGGCTCTGAAGGCACCC------------TCAGTAGCTATGGCA : 100
SEQ ID NO: 1094 3CDA73  : CAGGTGCAGCTGCAGGAGTCTGGAGGAGGATTGGTGCAGGCTGGGGACTCTCTGAGACTCTCCTGTGCAGGCTCTGAAGGCACCT------------TCAGTAGCTATGGCA : 100
SEQ ID NO: 1095 2CDA5   : CAGGTGCAGCTGCAGGAGTCTGGGGGAGGATTGGTGCAGGCTGGGGACTCTCTGAGACTCACCTGTACAGCCTCTGGACGCACCT------------TCAGTAACTATGGCA : 100
SEQ ID NO: 1096 2CDA87  : CAGGTGCAGCTGCAGGAGTCTGGGGGAGGATTGGTGCAGGCTGGGGGCTCTCTGAGACTCTCCTGTAAAGCCTCTGGAGGCACCT------------TCAGTGGCTATATCA : 100
SEQ ID NO: 1097 1CDA45  : CAGGTGCAGCTGCAGGAGTCTGGGGGAGGATTGGTGCAAGCTGGGGGCTCTCTGAGACTCTCCTGTGCAGCCTCTGGACGCACCT------------TCAGTAGCTATGTGA : 100
SEQ ID NO: 1098 1CDA58  : CAGGTGCAGCTGCAGGAGTCTGGAGGAGGATTGGTGCAAGCTAGGGGCTCTCTGACGCTCTCCTGTGCAGCCTCTGGACGCACCT------------TCAGTAACTATGTAA : 100
SEQ ID NO: 1099 1CDA67  : CAGGTGCAGCTGCAGGAGTCTGGAGGAGGATTGGTGCAGGCTGGGGCCTCTCTGAGACTCTCCTGTTCAGCCTCTGGACGCACCT------------TCAGTGACTATCGCA : 100
SEQ ID NO: 1100 1CDA92  : CAGGTGCAGCTGCAGGAGTCTGGGGGAGGATTGGTGCAGGCTGGGGGCTCTCTGAGACTCTCCTGTGTAGGCGACGGACGCACCT------------TCAGTAGTTATATTA : 100
SEQ ID NO: 1101 2CDA73  : CAGGTGCAGCTGCAGGAGTCTGGGGGAGGGTTGGTGCAGGCTGGGGGCTCTCTGAGACTCTCCTGTGCAGCCTCTGGACGCACCT------------TAAGTAGCAATCCGA : 100
SEQ ID NO: 1102 1CDA12  : CAGGTGCAGCTGCAGGAGTCTGGAGGAGGATTGGTGCAGGATGGGGGCTCTCTGAGACTCTCCTGTGCATTCTCTGGACGCACCT------------TTAGTAGTTATACTA : 100
SEQ ID NO: 1103 1CDA19  : CAGGTGCAGCTGCAGGAGTCTGGGGGAGGATTGGTGCAGGCTGGGGACTCTCTGAGACTCTCCTGTGCAGCCTCTGGACTTACCT------------TCAGTAACTATATAA : 100
SEQ ID NO: 1104 1CDA28  : CAGGTGCAGCTGCAGGAGTCTGGGGGAGGATTGGTGCAGGCTGGGGACTCTCTGAGACTCTCCTGTGCAGCCTCTGGACTTACCT------------TCAGCAACTATATAA : 100
SEQ ID NO: 1105 1CDA65  : CAGGTGCAGCTGCAGGAGTCTGGAGGAGGCTTGGTGCAGCCTGGGGGGTCTCTGAGACTCTCCTGTGCAGCCTCTGGAAGTATCT------------TCAGTATCAATGTCA : 100
SEQ ID NO: 1106 1CDA48  : CAGGTGCAGCTGCAGGAGTCTGGGGGAGGCTTGGTGCAGCCTGGGGGGTCTCTGACACTCTCCTGTGCAGCCTCTGGATTCGCCT------------TCGGTTTCTTCGACA : 100
```

```
                             120         *         140         *         160         *         180         *         200         *         220
SEQ ID NO: 1038 3CDA11  : TAGGCTGGTTCCGCCAGGCCCCAGGG---AAGGAGCGTGAGGGAATCTCATGTATTA---GTAGTGATGGTAGCACAGGCTATGCAGACTCCGTGAAGGGCCGATTCACCAT : 206
SEQ ID NO: 1039 3CDA48  : TAGGCTGGTTCCGCCAGGTCCCAGGG---AAGGAGCGTGAGGGAATCTCATGTATTA---GTAGTGATGGTAGCACAGGCTATGCAGACTCCGTGAAGGGCCGATTCACCAT : 206
SEQ ID NO: 1040 3CDA89  : TAGCCTGGTTCCGCCAGGCCCCAGGGGGAAGGAGCGTGAGGGAATCTCATGTATTA---GTAGTGATGGTAGCACAGGCTATGCAGACTCCGTGAAGGGCCGATTCACCAT : 209
SEQ ID NO: 1041 2CDA91  : TAGGCTGGTTCCGCCAGGCCCCAGGG---AAGGAGCGTGAGGGAATCTCATGTATTA---GTAGTGATGGTAGCACAGGCTATGCAGACTCCGTGAAGGGCCGATTCACCAT : 206
SEQ ID NO: 1042 2CDA92  : TAGGCTGGTTCCGCCAGGCCCCAGGG---AAGGAGCGTGAGGGAATTGGATGTATTAAAAGTAGTGATGGTACCACAGGCTATGCAGACTCCGTGAAGGGCCGATTCACCAT : 209
SEQ ID NO: 1043 3CDA18  : TAGGCTGGTTCCGCCAGGCCCCAGGG---AAGGAGCGTGAGGGAATCTCATGTTATAGTAGTAGTGATGGTAGCACAGGCTATGCAGACTCCGTGAAGGGCCGATTCACCAT : 209
SEQ ID NO: 1044 3CDA24  : TAGGCTGGTTCCGCCAGGCCCCAGGG---AAGGAGCGTGAGGGAATCTCATGCTATAGTAGTAGTGATGGTAGCACAGGCTTTGCAGACTCCGTGAAGGGCCGATTCACCAT : 209
SEQ ID NO: 1045 3CDA70  : TAGGCTGGTTCCGCCAGGCCCCAGGG---AAGGAGCGTGAGGGAATCTCATGTTATAGTAGTAGTGATGGTAACACAGGCTATGCAGACTCCGTGAAGGGCCGATTCACCAT : 209
SEQ ID NO: 1046 2CDA69  : TAGGCTGGTTCCGCCAGGCCCCAGGG---AAGGAGCGTGAGGGAATCTCATGTTATAGTAGTAGTGATGGTAGCACAGGGTTTGCAGACTCCGTGAAGGGCCGATTCACCAT : 209
SEQ ID NO: 1047 3CDA90  : TAGCCTGGTTCCGCCAGGCCCCAGGG---AAGGAGCGTGAGGGAATCTCATGTATTA---GTAGTGATGGTAGCACAGGCTATGCAGATTCCGTGCGGGGCCGATTCACCAT : 206
SEQ ID NO: 1048 2CDA88  : TAGCCTGGTTCCGCCAGGCCCCAGGG---AAGGAGCGTGAGGGAATCTCATGTATTA---GTAGTGATGGTAGCACAGGCTATGCAGATTCCGTGCGGGGCCGATTCACCAT : 206
SEQ ID NO: 1049 3CDA37  : TAGGCTGGTTCCGCCAGGCCCCAGGG---AAGGAGCGTGAGGGATTCTCATGCTTTAGTACGCGTGATGGTAACGCTGGCTATGCAGACTCCGTGAAGGGCCGATTCACCAT : 209
SEQ ID NO: 1050 3CDA40  : TAGGCTGGTTCCGCCAGGCCCCAGGG---AAGAAGCGTGAGGGATTCTCATGTTTTAGTAGTCGTGATGGTAGCACTGGCTATGCAGACTCCGTGAAGGGCCGATTCACCAT : 209
SEQ ID NO: 1051 3CDA41  : TAGGCTGGTTCCGCCAGGCCCCAGGG---AAGGAGCGTGAGGGATTCTCATGTTTTAGTAGTCGTGATGGTAGCACAGGCTATGCAGACTCCGTGAAGGGCCGATTCACCAT : 209
```

FIGURE 1 (CONTINUED)

SEQ ID NO: 1052 3CDA3 : TAGCCTGGTTCCGCCGGGCCCCAGGG---AAGGAGCGTGAGGGAATCTCATGTATTAGTAGTAGTGATGGTAGCACAGGTTATGCAGACTCCGTGAAGGGCCGATTCACCAT : 209
SEQ ID NO: 1053 3CDA29 : TAGCCTGGTTCCGCCGGGCCCCAGGG---AAGGAGCGTGAGGGAATCTCATGTATTAGTAGTAGTGATGGTAGCACAGGTTATGCAGACTCCGTGAAGGGCCGATTCACCAT : 209
SEQ ID NO: 1054 3CDA32 : TAGCCTGGTTCCGCCGGGCCCCAGGG---AAGGAGCGTGAGGGCATCTCATGTTTTAGTAGTAGTGATGGTAGCGCAGGCTATGCAGACTCCGTGAAGGGCCGATTCACCGT : 209
SEQ ID NO: 1055 3CDA8 : TAGGCTGGTTCCGTCAGGCCCCAGGG---AAGGAGCGTGAGGGAATCTCATGTTATAGTAGCCGTGATGGTACCACAGGCTATGCAGACTCCGTGAAGGGCCGATTCACCAT : 209
SEQ ID NO: 1056 3CDA65 : TAGGCTGGTTCCGCCAGGCCCCAGGG---AAGGAGCGTGAGGGGGTCTCATGTATTAGTAGTCCGGATGGTAGCACATACTATGCAGACTCCGTGAAGGGCCGATTCACCAT : 209
SEQ ID NO: 1057 3CDA19 : TAGGCTGGTTCCGCCAGGCCCCAGGG---AAGGAGCGTGAGGGAATCTCGTGTTTCAGTAGTAGTGATGGTAGCACAGGCTTTGCAGACTCCGTGAAGGGCCGGTTCACCAT : 209
SEQ ID NO: 1058 3CDA83 : TAGGCTGGTTCCGCCAGGCCCCAGGG---AAGGAGCGTGAGGGAATCTCGTGTTTCAGTAGTAGTGATGGTAGCACAGGCTTTGCAGACTCCGTGAAGGGCCGGTTCACCAT : 209
SEQ ID NO: 1059 2CDA95 : TAGGCTGGTTCCGGCAGGCCCCAGGG---AAGGAGCGTGAGGGCGTCTCATGTATTAGTAGTAAGGAGGGTAGCACATACTATGCAGACTCCGTGAAGGGCCGATTCACCAT : 209
SEQ ID NO: 1060 1CDA88 : TGGCCTGGTTCCGCCAGGCTCCAGGG---AAGGAGCGTGAGGGGGTCTCATGTATTAGTAGTCCGGATGGTAGCACATACTATGCAGACTCCGTGAAGGGCCGATTCACCAT : 209
SEQ ID NO: 1061 2CDA81 : TAGCCTGGTTCCGCCAGGCCCCAGGGAAGGA---GCGTGAGGGGATCTCCTGTATTAGTAATACGGATAGTAGCACATACTATGCAGACTCCGTGAAGGGCCGATTCACCAT : 209
SEQ ID NO: 1062 3CDA21 : TAGCCTGGTTCCGCCAGGCCCCAGGGAAGGA---GCGTGAGGGGATCTCCTGTATTAGTAATACGGATAGTAGCACATTCTATGCAGACTCCGTGAAGGGCCGATTCACCAT : 209
SEQ ID NO: 1063 3CDA57 : TAGCCTGGTTCCGCCAGGCCCCAGGGAAGGA---GCGTGAGGGGATCTCCTGTATTAGTAATACGGATAGTAGCACATACTATGCAGACTCCGTCAAGGGCCGATTCACCAT : 209
SEQ ID NO: 1064 3CDA33 : TAGCCTGGTTCCGCCAGGCCCCGGGGAAGGA---GCGTGAGGGGGTCTCCTGTATTAGTAATACGGATAGTAGCACATACTATGCAGACTCCGTAAAGGGCCGATTCACCAT : 209
SEQ ID NO: 1065 2CDA62 : TAGCCTGGTTCCGCCAGGCCCCAGGGAAGGA---GCGTGAGGGGGTCTCCTGTATTAGTAATACGGATAGTAGCACATACTATGCAGACTCCGTGAAGGGCCGGTTCACCAT : 209
SEQ ID NO: 1066 2CDA93 : TAGCCTGGTTCCGCCAGGCCCCAGGGAAGGA---GCGTGAGGGGGTCTCCTGTATTAGTAATACGGATAGTAGCACATACTATGCAGACTCCGTGAAGGGCCGATTCACCAT : 209
SEQ ID NO: 1067 3CDA28 : TAGGCTGGTTTCGCCAGGCCCCAGGGAAGGACCAGCGTGAGGGTATCTCCTGTATTAGTAATACGGATAGTAGCACATACTATGCAGACTCCGTGAAGGGCCGATTCACCAT : 212
SEQ ID NO: 1068 1CDA37 : TAGGCTGGTTCCGCCAGGCCCCAGGG---AAGGAGCGCGAGGGGGTCTCATGTATTAGTAGTAGTGATCGTAACACATACTATGCAGACTCCGTGAAGGGCCGATTCACCAT : 209
SEQ ID NO: 1069 2CDA28 : TGGCCTGGTTCCGCCAGTCTCCAGGG---AAGGAGCGTGAGGGGATCTCCTGTATTAGTAATACGGATAGTAGCACATACTATGCAGACTCCGTGAAGGGCCGATTCACCAT : 209
SEQ ID NO: 1070 1CDA47 : TAGGTTGGTTCCGCCAGGCCCCAGGG---AAGGAGCGTGAGGGGGTCGCATGTATTAGTAGTAAAGATGGTAGCACATACTATGCAGACTCCGTGAAGGGCCGCTTCACCAT : 206
SEQ ID NO: 1071 3CDA86 : TCGGCTGGTTCCGCCAGGCCCCAGGA---AAGGAGCGTGAGGGGGTTTCATGTATTAGTAGTGGAGATGGTACCACATACTATACAGACTCCGTGAAGGGCCGATTCACCAT : 209
SEQ ID NO: 1072 2CDA22 : TAGCCTGGTTCCGCCAGGCCCCAGGG---AAGGAGCGTGAGGGGGTCTCATGTATTGAAAGAAGTGATGGTAGCACATACTATGCAGACTCCGTGAAGGGCCGATTCACCAT : 209
SEQ ID NO: 1073 2CDA74 : TAGGCTGGTTCCGCCAGGCCCCAGGG---AAGGAGCGTGAGGGGGTCTCATGTATTAGCAGGAGTGATGGTAGCACATACTATGCAGACTCCGTCAGGGGCCGATTCACCAT : 209
SEQ ID NO: 1074 1CDA56 : TGGGCTGGTTCCGCCAGGCTCCAGGG---AAGGAGCGTGAGTTTGTAGCAGCTATTGTCTGGAGTGGTGGTAGCACATACTATGCAGACTCCGTGAAGGGCCGATTCACCAT : 209
SEQ ID NO: 1075 2CDA84 : TGGCCTGGTTCCGCCAGGCTCCAGGG---AAGGAGCGTGAGTTTGTAGCAGCTATTGCCTGGAGTGCTGGTAGCACATACTATGCAGACTCCGTGAAGGGCCGATTCGCCAT : 209
SEQ ID NO: 1076 1CDA89 : TGGGCTGGTTCCGCCAGCCTCCAGGG---AAGGAGCGTGAGTTTGTAGCAGCTGTGTTGTGGTCTGGTGTTAGTACAGCCTATGCAGACTCCGTGAAGGGCCGATTCACCAT : 209
SEQ ID NO: 1077 1CDA24 : TGGGCTGGTTCCGCCAGGCTCCAGGG---AGGGAGCGTGAGTTTGTAGCAGCTATTACATGGAGTGGTGTTAGCACTGTCTATACAGACTCCGTGAAGGGCCGATTCACCGT : 209
SEQ ID NO: 1078 1CDA14 : TGGGCTGGTTCCGCCAGGCTCCAGGG---AAGGAGCGTGAGTTTGTAGCAGCTATTGGCTGGAGTGCTGATATCACAGTCTATGCAGACTCCGTGAAGGGCCGATTCACCAT : 209
SEQ ID NO: 1079 1CDA93 : TGGGCTGGTTCCGCCAGGCTCTAGGG---AAGGAGCGTGAGTTTGTAGCAGCTATCGGCTGGAATGGTGGTATCACATACTATGCAGACTCCGTGAAGGGCCGATTCGCCAT : 209
SEQ ID NO: 1080 2CDA1 : TGGGCTGGTTCCGCCAGGCTCCAGGG---AAGGAGCGTGAGTTTGTAGGTTTTATTACCTGGAGTGGTGCTAGTACATACTATGCAGATTCCGTGAAGGGCCGATTCACTAT : 209
SEQ ID NO: 1081 2CDA77 : TGGGCTGGTTCCGCCAGGCTCCAGGG---AAGGAGCGTGAGTTTGTAGCAGCTATTATCTGGAGTGGTAGTATGACATACTATGCAGACTCCATGAAGGGCCGATTCACCGT : 209
SEQ ID NO: 1082 2CDA75 : TGGGCTGGTTCCGCCAGACTCCAGGG---AAGGAGCGGGAGTTTGTAGCAAATATTGGCTGGACTGGTGATATGACATACTATGCAGACTCCGTGAAGGGCCGATTCACCAT : 209
SEQ ID NO: 1083 1CDA75 : TGGGCTGGTTCCGCCAGGCTCCAGGG---AAGGAGCGTGAGTTTGTCGCAGTTATTCTCTGGAGTGGTGTTAGCACATACTATGCAGACTCCGTGAAGGGCCGATTCACCAT : 209
SEQ ID NO: 1084 2CDA68 : TGGGCTGGTTCCGCCAGGCTCCAGGG---AAGGAGCGTGAATTTGTAGCGCAAATTAGCTGGAGTGCTGGTAGCATATACTATGCAGACTCCGTGAAGGGCCGATTCACCAT : 209
SEQ ID NO: 1085 1CDA43 : TGGGCTGGTTCCGCCAGGCTCCAGGG---AAGGAGCGTGAGTTTGTAGCATTTATTGACTGGAGTGGTGGTGGTACATATTATGCCAACTCCGTGAAGGGCCGATTCACCAT : 209
SEQ ID NO: 1086 1CDA73 : TGGGCTGGTTCCGCCAGGCTCCAGGG---AAGGAGCGTGAGTTTGTAGCATTTATTGACTGGAGTGGTGGTGGTACATATTATGCCGACTCCGTGAAGGGCCGATTCACCAT : 209
SEQ ID NO: 1087 1CDA15 : TGGGCTGGTTCCGCCAGGCTCCAGGG---AAGGAGCGTGAGTTTGTAGCATTTATTGACTGGAGTGGTGGTGGTACATATTATGACGACTCCGTGAAGGGCCGATTCACCAT : 209
SEQ ID NO: 1088 1CDA7 : TGGCCTGGTTCCGCCAGGCTCCAGGG---AAGGAGCGTGAGTTTGTAGCAAGTATTACCTGGGGTGGTGGTAACACATACTATCCAGACTCCGTGAAGGGCCGATTCACCAT : 209
SEQ ID NO: 1089 1CDA17 : TGGGCTGGTTCCGCCAGGCTCCAGGG---AAGGAGCGTGAGTTTGTAGCAACTATTACCTGGGGTGGTGGAAGTACATATTATGCTGACTCCGTGAAGGGCCGATTCACCAT : 221
SEQ ID NO: 1090 1CDA18 : TGGGCTGGTTCCGCCAGGCTCCAGGG---AAGGAGCGTGAGTTTGTAGCAGCTATTAGCTGGAGTGGTGGTCCCACTGTCTATGCAGACCACGTAAAGGGCCGATTCACCAT : 209
SEQ ID NO: 1091 1CDA26 : TGGGCTGGTTCCGCCAGGCTCCAGGG---AAGGAGCGTGAGTTTGTAGGAGCGATTATGTGGAGTGGTGCATTTACACACTATGCAGACTCCGTGAAGGGCCGATTCACCAT : 209
SEQ ID NO: 1092 1CDA58 : TGGGCTGGTTCCGCCAGGCTCCGGGT---AAGGAGCGTGAGTTTGTCTCATTTATTAGCTGGATAAGTGACATCACATACTATTCAGACTCCGTGAAGGGCCGATTCATCAT : 209
SEQ ID NO: 1093 3CDA31 : TTGGCTGGTTCCGCCAGGCTCCAGGG---AAGGAGCGTGAGTTTGTAGGAGGTATTAACTGGAGTGGCGATAGCACAGACTATGCAGACTCCGTGAAGGGCCGATTCACCAT : 209
SEQ ID NO: 1094 3CDA73 : TTGGCTGGTTCCGCCAGGCTCCAGGG---AAGGAGCGTGAGTTTGTAGGAGGTATTAACTGGAGTGGCGATAGCACAGACTATGCAGACTCCGTGAAGGGCCGATTCACCAT : 209
SEQ ID NO: 1095 2CDA5 : TAGGCTGGTTCCGCCAGGCTCCAGGG---AAGGAGCGTGAATTTGTAGCAGGTATTAACTGGAGTGGCGAAAGCGCCGACTATGCAGACTCCGTGAAGGGCCGATTCACCAT : 209

FIGURE 1 (CONTINUED)

```
SEQ ID NO: 1096 2CDA87 : TGGGCTGGTTCCGCCAGGCTCCAGGG---AAGGAGCGTGAGTTTGTAGCAGCTAATACTTGGAGTGGTGGTCCCACATACTATTCAGACTCCGTGAAGGGCCGATTCACCAT : 209
SEQ ID NO: 1097 1CDA45 : TAGGGTGGTTCCGCCAGGCTCCAGGG---AAGGAGCGTGAGTTTGTCGCAGTTATTACTTGGAGTGGTGATAGCACATACTCTTCAGACTCCCTGAAGGGCCGATTCACCAT : 209
SEQ ID NO: 1098 1CDA58 : TAGGCTGGTTCCGCCAGGCTCCAGGG---GAGGAGCGTGAGTTTGTCGCAGTTGTTACCTGGAGTGGTGATAGCACATACTCTTCAGACTCCCTGAAGGGCCGATTCACCAT : 209
SEQ ID NO: 1099 1CDA87 : TGGGCTGGTTCCGCCAGGCGCCAGGG---AAGGAGCGTGAGTGGGTAGCAGCTATTAGCTCGAGTGGTTATCACACATACTATGCAGACTCCGTGAAGGGCCGATTCACCAT : 209
SEQ ID NO: 1100 1CDA92 : TCGGCTGGTTCCGCCAGGCTCCAGGG---AACGAGCGTGAGTTTGTAGTCGCTATTACCTGGGATGGTAGCGCTACAACCTATGCAGACTCCGTGAAGGGCCGGTTCACCGT : 209
SEQ ID NO: 1101 2CDA73 : TGGCCTGGTTCCGCCAGGCTGCCGGG---AAGGAGCGTGAGTTTGTAGCAGGTATGTCGTGGAATCCTGGTCCCGCAGTCTATGCAGACTCCGTGAAGGGCCGATTCACCAT : 209
SEQ ID NO: 1102 1CDA12 : TGGGCTGGTTCCGCCAGGGTCCAGGG---AAGGAGCGTGAGTTTGTAGCAGCTACTGTCTGGACTGGTGCTGGTACAGTTTATGCTGACTCCGTGAAGGGCCGATTCACCAT : 209
SEQ ID NO: 1103 1CDA19 : TGGGCTGGTTCCGTCAGGCCCCAGGG---AAGGAGCGTGAGTTTGTAGCAGCTATTACCTGGGGTGGTGGTAGCACAGTCTATGCAGACTCCGTAGAGGGCCGATTCACCAT : 209
SEQ ID NO: 1104 1CDA28 : TGGGCTGGTTCCGTCAGGCCCCAGGG---AAGGAGCGTGAATTTGTAGCAGCTATTACCTGGGGTGGTGGTAGCACAGTCTATGCAGACTCCGTAGAGGGCCGATTCACCAT : 209
SEQ ID NO: 1105 1CDA65 : TGGGCTGGTACCGCCAGACTCCAGGG---AAGGAGCGCGAGTTGGTCGCAAAAATTACT---AATTTGGTATTACAAGCTATGCAGATTCCGCACAGGGCCGATTCACCAT : 206
SEQ ID NO: 1106 1CDA49 : TGACCTGGGTCCGCCAGGCTCCAGGA---AAGGGGCTCGAATGGGTCTCAGGTATTAATAGTATTGGTGGTAGCACAACCTATGCAGACTCCGTGAAGGGCCGATTCACCAT : 209

                            *       240         *       260         *       280         *       300         *       320         *
SEQ ID NO: 1038 3CDA11 : CTCCAGTGACAACGCCAAGAACACGGTATATCTGCAAATGAACAGCCTGAAACCTGAGGACACGGCCGTTTATTACTGTGCAGCAGA-----TTTCAACGTGTGGTCCCCCC : 313
SEQ ID NO: 1039 3CDA49 : TTCCAGTGACAACGCCAAGAACACGGTATATCTGCAAATCAACAGCCTGAAACCTGAGGACACGGCCGTTTATTACTGTGCAGCAGA-----TTTCAACGTGTGGTCCCCCC : 313
SEQ ID NO: 1040 3CDA59 : CTCCAGTGACAACGCCAAGAACATGGTATATCTGCAAATGAACAGCCTGAAACCTGAGGACACGGCCCTTTATTACTGTGCAGCAGA-----TTTCAACGTGTGGTCCCCCC : 316
SEQ ID NO: 1041 2CDA91 : CTCCAGTGACAACGCCAAGAACACGGTATATCTGCAAATGAACAGCCTGAAACCTGAGGACACGGCCGTTTATTACTGTGCAGCAGA-----TTTCAACGTGTGGTCCCCCC : 313
SEQ ID NO: 1042 2CDA92 : CTCCAGTGACAACGCCAAGAACACGGTATATCTGCAAATGAACAGCCTGAAACCTGAGGACACGGCCGTTTATTACTGTGCAGCAGA-----TTTCAACGTGTGGTCCCCCC : 316
SEQ ID NO: 1043 3CDA18 : CTCCAGTGACAACGCCAAGAACACGGTATATCTGCAAATGAACAGCCTGAAACCTGAGGACACGGCCGTTTATTACTGTGCAGCAGA-----TTTCAACGTGTGGTCCCCCC : 316
SEQ ID NO: 1044 3CDA24 : CTCCAGTGACAACGCCAAGAACACGGTATATCTGCAAATGAACAGCCTGAGACCTGAGGACACGGCCGTTTATTACTGTGCAGCAGA-----TTTCAACGTGTGGTCCCCCC : 316
SEQ ID NO: 1045 3CDA70 : CTCCAGTGACAACGCCAAGAACACGGTATATCTGCAAATGAACAGCCTGAGACCTGAGGACACGGCCGTTTATTACTGTGCAGCAGA-----TTTCAACGTGTGGTCCCCCC : 316
SEQ ID NO: 1046 2CDA69 : CTCCAGTGACAACGCCAAGAACACGGTATATCTGCAAATGAACAACCTGAGACCTGAGGACACGGCCGTTTATTACTGTGCAGCAGA-----TTCCAACGTGTGGTCCCCCC : 316
SEQ ID NO: 1047 3CDA90 : CTCCAGTGACAACGCCAAGAACACGGTATATCTGCAAATGAACAGCCTGAAACCTGAGGACACGGCCGTTTATTACTGTGCAGCAGA-----TTTCAACGTGTGGTCCCCCC : 313
SEQ ID NO: 1048 2CDA88 : CTCCAGTGACAACGCCAAGAACACGGTATATCTGCAAATGAACAGCCTGAAACCTGAGGACACGGCCGTTTATTACTGTGCAGCAGA-----TTTCAACGTGTGGTCCCCCC : 313
SEQ ID NO: 1049 3CDA37 : CTCCAGTGACAACGCCAAGAACACGGTATATCTGCAAATGAACAACCTGAAACCTGAGGACACGGCCGTTTATTATTGTGCAGCAGA-----TTTCAACGTGTGGTCCCCCC : 316
SEQ ID NO: 1050 3CDA40 : CTCCAGTGACAACGCCAAGAACACGGTATATCTGCAAATGAACAGCCTGAAACCTGAGGACACGGCCGTTTATTATTGTGCAGCAGA-----TTTCAACGTGTGGTCCCCCC : 316
SEQ ID NO: 1051 3CDA41 : CTCCAGTGACAACGCCAAGAACACGGTATATCTGCAAATGAACAGCCTGAAACCTGAGGACACGGCCGTTTATTATTGTGCAGCAGA-----TTTCAACGTGTGGTCCCCCC : 316
SEQ ID NO: 1052 3CDA3 : CACCAGTGACAGCGCCAAGAACACGGTTTATCTGCAAATGAACAGCCTGAAACCTGAGGACACGGCCGTTTATTACTGTGCAGCAGA-----TTCCAACGTGTGGTCCCCCC : 316
SEQ ID NO: 1053 3CDA29 : CTCCAGTGACAACGCCAAGAACACGGTATATCTGCAAATGACCAGTCTGAAACCTGAGGACACGGCCGTTTATTACTGTGCAGCAGA-----TTCCAACGTGTGGTCCCCCC : 316
SEQ ID NO: 1054 3CDA32 : CTCCAGTGACAACGCCAAGAACACGGTATATCTGCAAATGAACAGCCTGAAACCTGAGGACACGGCCGTTTATTACTGTGCAGCAGA-----TTCCAACGTGTGGTCCCCCC : 316
SEQ ID NO: 1055 3CDA8 : CTCCAGTGACAACGCCAAGAACACGGTATATCTGCAAATGAACAGCCTGAAACCTGAGGACACGGCCGTTTATTACTGTGCAGCAGA-----TTTCAATGTGTGGTCCCCCC : 316
SEQ ID NO: 1056 3CDA65 : CTCCAGTGACAACGCCAAGAACACGGTGTATCTGCAAATGAACAGCCTGAAACCTGAGGACACGGCCGTTTATTACTGTGCAGCAGA-----TTTCAACGTGTGGTCCCCCC : 316
SEQ ID NO: 1057 3CDA19 : CTCCAGTGACAACGCCACGAACACGGTATATCTGGAAATGAACAGCCTGAAACCTGAGGACACGGCCGTTTATTACTGTGCAGCAGA-----TTTCAACGTGTGGTCCCCCC : 316
SEQ ID NO: 1058 3CDA93 : CTCCAGTGACAACGCCACGAACACGGTATATCTGCAAATGAACAGCCTGAAACCTGAGGACACGGCCGTTTATTACTGTGCAGCAGA-----TTTCAACGTGTGGTCCCCCC : 316
SEQ ID NO: 1059 2CDA95 : CTCCAGTGACAACGCCAAGAACACGGTGTATCTGCAAATGAGCAGCCTGAAACCTGAGGACACGGCCGTCTATTACTGCGCAGCAGA-----TGGTAACGTGTGGTCCCCCC : 316
SEQ ID NO: 1060 1CDA98 : CTCCAGTGACAACGCCAAGAACACGGTGTATCTGCAAATGAACAGCCTGAAACCTGAGGACACGGCCGTTTATTACTGTGCAGCAGA-----TTTCAACGTGTGGTCCCCCC : 316
SEQ ID NO: 1061 2CDA81 : CTCCAGTGACAGCGCCAAGAACACGGTGCATCTGCAAATGAGCAGCCTGAAACCTGAGGACACGGCCGTCTATTACTGCGCAGCAGA-----TGGCAACGTGTGGTCCCCCC : 316
SEQ ID NO: 1062 3CDA21 : CTCCAGTGACAACGCCAAGAACACGGTGCATCTGCAGATGAGCAGCCTGAAACCTGAGGACACGGCCGTCTATTACTGCGCAGCAGA-----TGGCAACGTGTGGTCCCCCC : 316
SEQ ID NO: 1063 3CDA57 : CTCCAGTGACAACGCCAAGAACACGGTGCATCTGCAAATGAGCAGCCTGAAACCTGAGGACACGGCCGTCTATTACTGCGCAGCAGA-----TGGCAACGTGTGGTCCCCCC : 316
SEQ ID NO: 1064 3CDA33 : CTCCAGTGACAACGCCAAGAACACGGTGTATCTGCAAATGAGCAGCCTGAAACCTGAGGACACGGCCGTCTATTACTGCGCAGCAGA-----TGGTAACGTGTGGTCCCCCC : 316
SEQ ID NO: 1065 2CDA62 : CTCCAGTGACAACGCCAAGAACACGGTGCATCTGCAAATGAGCAGCCTGAAACCCGAGGACACGGCCGTCTATTACTGCGCAGCAGA-----TGGCAACGTGTGGTCCCCCC : 316
SEQ ID NO: 1066 2CDA93 : CTCCAGTGACAACGCCAAGAACACGGTGTATCTGCAAATGAGCAGCCTGAAACCTGAGGACACGGCCGTCTATTACTGCGCAGCAGA-----TGGTAACGTGTGGTCCCCCC : 316
SEQ ID NO: 1067 3CDA28 : CTCCAGTGACAACGCCAAGAACACGGTGCATCTGCAAATGAGCAGCCTGAAACCTGAGGACACGGCCGTCTATTACTGCGCAGCAGA-----TGGCAACGTGTGGTCCCCCC : 319
```

FIGURE 1 (CONTINUED)

```
SEQ ID NO: 1068 1CDA37 : CTCCGGTGACAATGCCAAGAACACGGTGTATCTGCAAATGAACAACCTGAAACCTGAGGACACGGCCGTTTATTACTGCGCAGCAGA-----TGGCAACGTGTGGTCCCCCC : 316
SEQ ID NO: 1069 2CDA28 : CTCCAGTGACAACGCCAAGAGCACGGTGCATCTGCAAATGAGCAGCCTGAAACCTGAGGACACGGCCGTCTATTACTGCGCCGCAGA-----TGGCAACGTGTGGTCCCCCC : 316
SEQ ID NO: 1070 1CDA47 : GTCCGTAGACAAGACCAAGAACACGGTGTATCTGCAGATGAGCAGCCTGAAACCTGAGGACACGGCCGTCTATTACTGCGCAGCAGA-----TGGCAACGTGTGGTCCCCCC : 313
SEQ ID NO: 1071 3CDA86 : CTCCACCGACAACGCCAAGAACACGGTGTATCTGCAAATGAACAGCCTGAAACCTGAGGACACGGCCGTCTATTACTGCGCAGCAGA-----TGGCAACGTGTGGTCCCCCC : 316
SEQ ID NO: 1072 2CDA22 : CTCCAGTGACAACGCCAAGAACACGGTATATCTACAAATGAACAGCCTGAAACCTGAGGACACGGCCGTTTATTACTGTGCAGTAGGG---TCCGCCAATTCAGGAGAGTTT : 318
SEQ ID NO: 1073 2CDA74 : CTCCAGTGACAACGCCAAGAACACGGTGTATCTACAAATGAACAGCCTCAAACCTGAGGACACGGCCGTTTATTACTGTGCAGCAGAGACGTCCGCCGATTCAGGAGAGTTT : 321
SEQ ID NO: 1074 1CDA86 : CTCCAGAGACAACGCCAAGAACACGGTGTATCTGCAAATGAACAGCCTGAAACCTGAGGACACGGCCGTTTATTACTGTGCAGCAGT----------ACTCATACGATAC-- : 309
SEQ ID NO: 1075 2CDA94 : CTCCAGAGACAACGCCGAGAACACGGTGTATCTGCAAATGAACAGCCTGAAACCTGAGGACACGGCCGTTTATTACTGTGCAGCA---------------CGTATAAT---- : 302
SEQ ID NO: 1076 1CDA89 : CTCCAGAGACAACGCCAAGAACACGGTGTATCTGCAGATGAACAACCTGAAACCTGATGACACGGCCGTTTATTACTGTGCAGCCCA----------CGAGAGTACATAC-- : 309
SEQ ID NO: 1077 1CDA24 : CTCCAGAGACAACGCCAAGAACACGGTGTATCTGCAAATGAACAGCCTGAAACCTGAGGACACGGCTGTTTATTACTGTGCAGCAGAT----AGTCCCCCCAGGACATAC-- : 315
SEQ ID NO: 1078 1CDA14 : CTCCAGAGACAACGCCGAGAATATGGTGTATCTGCAAATGAACAGTCTGAACCCTGAGGACACGGCCGTTTATTACTGTGCAGCA-------AATTCACGTGCATATTAT-- : 312
SEQ ID NO: 1079 1CDA93 : CTCCAGAGACAACGCCAAGAACACGGTGTATCTGCAAATGAACAGCCTGAAACCTGAGGACACGGCCGTTTATTACTGTGCAGCC-------GCTACCCTT-CAAGTTAC-- : 311
SEQ ID NO: 1080 2CDA1 : CTCCAGAGACAACGCCGAGAACACGGTGTATCTGCAAATGAACAGCCTGAAACCTGAGGACACGGCCGTTTATTACTGTGCAGC---------------CACTCTATTT-- : 303
SEQ ID NO: 1081 2CDA77 : CTCCATAGACAACGCCAAGAACACGGTGTATCTGCAAATGAACAGCCTGAAACCTGAGGACACGGCCGTTTATTACTGTGCAGCA--------------CAACGGATAT-- : 304
SEQ ID NO: 1082 2CDA75 : CTCGCGAGACAACGCCAAGAACACGGTGTATCTGCAAATGAACAGCCTGAAACCTGAGGACACGGCCGTTTATTATTGTGCAGCAGCG------------GGCAGCGCA-- : 306
SEQ ID NO: 1083 1CDA75 : CTCCAGAGACAACGCACAGAACACGGTGTATCTGCAAATGGACAGTCTGAAACCTGAGGACACGGCCGTTTATTACTGTGCAGTCCCC----AGGTCTCACTTTACTACT-- : 315
SEQ ID NO: 1084 2CDA68 : CTCCAATGACAACGCCAAGCGTACGGTGTATCTGCAAATGAACAGCCTGAAACCTGAGGACACGGCCGTTTATTACTGTGCCGAGCGG----GGCT---ATGCTTACTGC-- : 312
SEQ ID NO: 1085 1CDA43 : CTCCAGAGACAACGCCGAGAACACGGTGTATCTGCAAATGAACAACCTGAAACCTGAGGACACGGCCGTTTATTACTGTGCAGC---A----GCTCAGCGCCTTGG------ : 308
SEQ ID NO: 1086 1CDA73 : CTCCAGAGACAACGCCGAGAACACGGTGTATCTGCAAATGAACAACCTGAAACCTGAGGACACGGCCGTTTATTACTGTGCAGC---A----GCTCAGCGCCTTGG------ : 308
SEQ ID NO: 1087 1CDA15 : CTCCAGAGACAACGCCGAGAACACGGTGTATCTGCAAATGAACAACCTGGAACCTGAGGACACGGCCGTTTATTACTGTGCAGC---A----GCTCAGCGCCTTGG------ : 308
SEQ ID NO: 1088 1CDA7 : CTCCAGAGACGACGCCAAGAACACGGTGTATCTGCAAATGAACAGCCTGAAACCTGAGGACACGGCCGTTTATTACTGTGCAGCCAAA----GGCCTTCGTAATAGC----- : 312
SEQ ID NO: 1089 1CDA17 : CTCCAGAGACAACGCCAACAACACGGTGTATCTGCAAATGAACAGCCTGAAACCTGAGGACACGGCCGTTTATTACTGCGCAGCCTCA----G-TCAAGGTAGTAGCTGG-- : 326
SEQ ID NO: 1090 1CDA18 : CTCCAGGGACAACGCCAAGAACACGGTGTATCTGCAAGTGAACAGCCTGAAACCTGAGGACACGGCCGATTATTACTGTGCAGCTAAG----AGACTTGACTATAGC----- : 312
SEQ ID NO: 1091 1CDA26 : TTCCAGAGACAACGCAAAGAACACGGTGTATCTGCAAATGAACGCGCTGAAACCGGAGGACACGGCCGTTTATTACTGTGCAGTAAT------------TCCGGGCAGA-- : 306
SEQ ID NO: 1092 1CDA68 : CTCCAGAGACAACGCCAAGAATATGGTGTATCTGCAAATGAACAGCCTGAAACCTGAGGACACGGCCGTTTATTACTGTGCAGCG----------CATCCTCCAGACCCA-- : 309
SEQ ID NO: 1093 3CDA31 : CTCCAGAGACAGCGCCAAGAACACGGTGTATCTGCAAATGAACAGCCTGAAACCTGAGGACACGGCCGTTTATTACTGTGCAGC-------------------------- : 293
SEQ ID NO: 1094 3CDA73 : CTCCAGAGACAACGCCAAGAACACGGTGTATCTGCAAATGAACAGCCTGAAACCTGAGGACACGGCCGTTTATTACTGTGCAGC-------------------------- : 293
SEQ ID NO: 1095 2CDA5 : CTCCAGAGACAACGCCAAGAACACGGTGTATCTGCAAATGAACAGCCTGAAACCTGAGGACACGGCCGTTTATTACTGTGCAGC-------------------------- : 293
SEQ ID NO: 1096 2CDA87 : TTCCAGAGACAACGCCAAGAACACGGTGTATCTGCAAATGAACACCCTGAAACCTGAAGACACGGCCGTTTATCAATGTGCAGCACGA----GACTATCGTGGTAT------ : 311
SEQ ID NO: 1097 1CDA45 : CTCCAGAGACAACGCCAAGAACACAGTCTATCTACAAATGAACGCCCTGAACCCTGAGGACACGGCCGTTTATTACTGTGCAGCTATA----CCTCCCAGAGCCTACTCC-- : 315
SEQ ID NO: 1098 1CDA58 : CTCCAGAGACAACGCCAAGAACACAGTCTATCTACAAATGAACAACCTGAACCCTGAGGACACGGCCGTTTATTACTGTGCGGCTATG----CCCCCCAGGGCCTACACC-- : 315
SEQ ID NO: 1099 1CDA87 : CTCCAGAGACAACGCCAAGAACACAGGGTATCTGCAGATGAGCAGCCTGAAACCTGAGGACACGGCCGTTTATTATTGTGCAGT---------------CGTTAAATAC-- : 303
SEQ ID NO: 1100 1CDA92 : CTCCAGAGACAGCGCCAAGAACACGGCGTATCTGCAAATGAACAGTCTGAAACCTGAGGACACGGCCGTTTATTACTGTGCAGCAGTA----CCGGCCCGAGGCCT------ : 311
SEQ ID NO: 1101 2CDA73 : CTCCAGAGACAGCGCCGAGAACACGGTGTATCTGCAAATGAACAGCCTGAAACCAGAAGACACGGCCGTTTATTACTGTGCAGGAGCG------------GCTCGAGCA-- : 306
SEQ ID NO: 1102 1CDA12 : CTCCAGAGACAACGCCAAGAACACGGTGTATCTTCAAATGAACAGCCTGAGGCCTGAGGACACGGCCGTTTATTACTGTGCAGCGGAT----CAAGCAAGTGTACCCCCTCC : 317
SEQ ID NO: 1103 1CDA19 : CTCCAGAGACGGCACCAAGAACACGGTGTCTCTACAGATGAACAGCCTACTACCTGAGGACACGGCCGTTTACTACTGTGCAGCCGCC----GGGGGTTCGGGGCG------ : 311
SEQ ID NO: 1104 1CDA28 : CTCCAGAGACGGCACCAAGAACACGGTGTCTCTACAGATGAACAGCCTACAGCCTGAGGACACGGCCGTTTACTACTGTGCAGCCGCC----GGGGCTTCGGGGCG------ : 311
SEQ ID NO: 1105 1CDA65 : CTCCAGAGGCAACGCCAAGAACACGGTGTATCTGCAAATGAACAGCCTGAAACCTGAGGACACGGCCGTCTATTATTGTAATTTAGA---CACTACGGTTGGGGTCCGCCC : 315
SEQ ID NO: 1106 1CDA49 : CTCCAGAGACAACGCCAAGAACGAGCTGTATCTGCAAATGAACAGCCTGAAACCTGACGACACGGCCGTGTATTACTGTGCGA------------AATCTAGAAGCTCCTA : 308

                             340         *        360         *        380         *        400         *        420         *        440
SEQ ID NO: 1038 3CDA11 : CCATCTGCGGTAGTAATTGGTACGGGCCGCCACCGGGGGGCATGGACTACTGGGGCAAAGGGACCCAGGTCACCGTCTCCTCAGCGGCCGCATACCCGTACGACGTTCCGGA : 425
SEQ ID NO: 1039 3CDA48 : CCATCTGCGGTAGTATTTGGTACGGGCCGCCACCGGGGGGCATGGACTACTGGGGCAAAGGGACCCAGGTCACCGTCTCCTCAGCGGCCGCATACCCGTACGACGTTCCGGA : 425
```

FIGURE 1 (CONTINUED)

SEQ ID NO: 1040 3CDA88 : CCATCTGTAGTAGTAACTGGTACGGGCCGCCACCGCGGGGCATGGACTACTGGGGCAAAGGGACCCAGGTCACCGTCTCCTCAGCGGCCGCATACCCGTACGACGTTCCGGA : 428
SEQ ID NO: 1041 2CDA91 : CCATCTGCGGTAGTAATTGGTACGGGCCGCCACCGGGGGGCATGGACTACTGGGGCAAAGGGACCCAGGTCACCGTCTCCTCTGCGGCCGCATACCCGTACGACGTTCCGGA : 425
SEQ ID NO: 1042 2CDA92 : CCATCTGCGGTAGTATTTGGTACGGGCCGCCACCGGGGGGCATGGACTACTGGGGCAAAGGGACCCAGGTCACCGTCTCCTCAGCGGCCGCATACCCGTACGACGTTCCGGA : 428
SEQ ID NO: 1043 3CDA18 : CCATCTGCGGTAGTAGCTGGTACGGGCCGCCACCGGGGGGCATGGACTACTGGGGCAAAGGGACCCAGGTCACCGTCTCCTCAGCGGCCGCATACCCGTACGACGTTCCGGA : 428
SEQ ID NO: 1044 3CDA24 : CCATCTGCGGTAGTAGGTGGTACGGGCCGCCACCGGGGGGCATGGCCTACTGGGGCAAAGGAACCCAGGTCACCGTCTCCTCAGCGGCCGCATACCCGTACGACGTTCCGGA : 428
SEQ ID NO: 1045 3CDA70 : CCATCTGCGGTAGTAGCTGGTACGGGCCGCCACCGGGGGGCATGGCCTACTGGGGCAAAGGGACCCAGGTCACCGTCTCCTCAGCGGCCGCATACCCGTACGACGTTCCGGA : 428
SEQ ID NO: 1046 2CDA89 : CCATCTGCGGTAGTAGGTGGTACGGGCCGCCACCGGGGGGCATGGCCTACTGGGGCAAAGGGACCCAGGTCACCGTCTCCTCAGCGGCCGCATACCCGTACGACGTTCCGGA : 428
SEQ ID NO: 1047 3CDA90 : CCATTTGCGGTAGTATTTGGTACGGGCCGCCACCGCGGGGCATGGACTACTGGGGCAAAGGGACCCAGGTCACCGTCTCCTCAGCGGCCGCATACCCGTACGACGTTCCGGA : 425
SEQ ID NO: 1048 2CDA88 : CCATTTGCGGTAGTATTTGGTACGGGCCGCCACCGCGGGGCATGGACTACTGGGGCAAAGGGACCCAGGTCACCGTCTCCTCAGCGGCCGCATACCCGTACGACGTTCCGGA : 425
SEQ ID NO: 1049 3CDA37 : CCATCTGCGGTAGTCGCTGGTACGGGCCGCCACCGGGGGGCATGGACTACTGGGGCAAAGGGACCCAGGTCACCGTCTCCTCAGCGGCCGCATACCCGTACGACGTTCCGGA : 428
SEQ ID NO: 1050 3CDA40 : CCATCTGCGGTAGTCGCTGGTACGGGCCGCCACCGGGGGGCATGGACTACTGGGGCAAAGGGACCCAGGTCACCGTCTCCTCAGCGGCCGCATACCCGTACGACGTTCCGGA : 428
SEQ ID NO: 1051 3CDA41 : CCATCTGCGGTAGTCGCTGGTACGGGCCGCCACCGGGGGGCATGGACTACTGGGGCAAAGGGACCCAGGTCACCGTCTCCTCAGCGGCCGCATACCCGTACGACGTTCCGGA : 428
SEQ ID NO: 1052 3CDA3 : CCATCTGCGGTCGTACCTGGTACGGGCCGCCACCGGGGGGCATGGACTACTGGGGCAAAGGGACCCAGGTCACCGTCTCCTCAGCGGCCGCATACCCGTACGACGTTCCGGA : 428
SEQ ID NO: 1053 3CDA29 : CCATCTGCGGTAAAACCTGGTACGGGCCGCCACCAGGGGGCATGGACTACTGGGGCAAAGGGACCCAGGTCACCGTCTCCTCAGCGGCCGCATACCCGTACGACGTTCCGGA : 428
SEQ ID NO: 1054 3CDA32 : CCATCTGCGGTAGTACCTGGTACGGGCCGCCACCGGGGGGCATGGCCTACTGGGGCAAAGGGACCCAGGTCACCGTCTCCTCAGCGGCCGCATACCCGTACGACGTTCCGGA : 428
SEQ ID NO: 1055 3CDA8 : CCATCTGCGGTAGTATCTGGTACGGGCCGCCACCGGGGGGCATGGCCTACTGGGGCCAGGGGACCCAGGTCACCGTCTCCTCAGCGGCCGCATACCCGTACGACGTTCCGGA : 428
SEQ ID NO: 1056 3CDA65 : CCATCTGCGGTAGTGTA------GGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1057 3CDA19 : CCATTTGCGGTAGTAGGTGGTACGGGCCGCCACCGGGGGGCATGGAGTACTGGGGCAAAGGGACCCAGGTCACCGTCTCCTCAGCGGCCGCATACCCGTACGACGTTCCGGA : 428
SEQ ID NO: 1058 3CDA83 : CCATTTGCGGTAGTAGCTGGTACGGGCCGCCACCGGGGGGTATGGAATACTGGGGCAAAGGGACCCAGGTCACCGTCTCCTCAGCGGCCGCATACCCGTACGACGTTCCGGA : 428
SEQ ID NO: 1059 2CDA95 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1060 1CDA88 : CCATCTGCGGTAGTGTA------GGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1061 2CDA81 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1062 3CDA21 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1063 3CDA57 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1064 3CDA33 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1065 2CDA62 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1066 2CDA93 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1067 3CDA28 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 425
SEQ ID NO: 1068 1CDA37 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1069 2CDA28 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1070 1CDA47 : CCATCTGCAGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 419
SEQ ID NO: 1071 3CDA86 : CCATCTGCGGTAGTGC------CGGGCCGCCACCGGGGGGCATGGACTACTGGGGCAAAGGGACCCAGGTCACCGTCTCCTCAGCGGCCGCATACCCGTACGACGTTCCGGA : 422
SEQ ID NO: 1072 2CDA22 : CGATTCGGTTGGGTACTTAAACCTGACCTCTAT-----------AACTACTGGGGCCAGGGGACCCAGGTCACCGTCTCCTCAGCGGCCGCATACCCGTACGACGTTCCGGA : 419
SEQ ID NO: 1073 2CDA74 : CGATTCGGTTGGGTACTTAAACCTAGTCTCTAT-----------GACTACTGGGGCCAGGGGACCCAGGTCACCGTCTCCTCAGCGGCCGCATACCCGTACGACGTTCCGGA : 422
SEQ ID NO: 1074 1CDA86 : -TATAGTGGTGGTTACCAGGGGCTCTCGGACGCGAATGAGTAT-GACTACTGGGGCCAGGGGACCCAGGTCACCGTCTCCTCAGCGGCCGCATACCCGTACGACGTTCCGGA : 419
SEQ ID NO: 1075 2CDA94 : -TACTGTAGCGACTATGAGA----CTCGACAGCGATT----AT-GACTACTGGGGCCAGGGGACCCAGGTCACCGTCTCCTCAGCGGCCGCATACCCGTACGACGTTCCGGA : 404
SEQ ID NO: 1076 1CDA83 : -TATAGTGGTACTTACTAC---CTCACCGACCCTCGGAGATAT-GTCTACTGGGGCCAGGGGACCCAGGTCACCGTCTCCTCAGCGGCCGCATACCCGTACGACGTTCCGGA : 416
SEQ ID NO: 1077 1CDA24 : -TCGAGTGGTAGT---GTGAACCTGGAAGACGGGAGTGAGTAT-GACTACTGGGGCCAGGGGACCCAGGTCACCGTCTCCTCAGCGGCCGCATACCCGTACGACGTTCCGGA : 422
SEQ ID NO: 1078 1CDA14 : -AGCAGTAGTTACGACTTAGGGCGACTTGCCTCG------TAT-GACTACTGGGGCCAGGGCACCCAGGTCACCGTCTCCTCAGCGGCCGCATACCCGTACGACGTTCCGGA : 416
SEQ ID NO: 1079 1CDA93 : -TG--GTAGTTACTACTTAGACCTATCCACCGTGGACATATAT-GACAACTGGGGCCAGGGGACCCAGGTCACCGTCTCCTCAGCGGCCGCATACCCGTACGACGTTCCGGA : 419
SEQ ID NO: 1080 2CDA1 : -AGGTCCAACGGCCCGAAAGACCTATCTTCGGGCTATGAGTAT-GACTACTGGGGCCAGGGGACCCAGGTCACCGTCTCCTCAGCGGCCGCATACCCGTACGACGTTCCGGA : 413
SEQ ID NO: 1081 2CDA77 : -T-TGGAGCTCAGCCTATGGACCTTTCTG------GGGATTAT-GAGTACTGGGGCCAGGGGACCCAGGTCACCGTCTCCTCAGCGGCCGCATACCCGTACGACGTTCCGGA : 407
SEQ ID NO: 1082 2CDA75 : -TATAGCGGTAGTTACTGGAACATAACGATGGCGGCCAATTAT-GACTACTGGGGCCAGGGGACCCAGGTCACCGTCTCCTCAGCGGCCGCATACCCGTACGACGTTCCGGA : 416
SEQ ID NO: 1083 1CDA75 : -GCTCAAGACATGGGTCAAGACATGGGTGCCCCTTCGTGGTAT-GAGTACTGGGGCCAGGGGACCCAGGTCACCGTCTCCTCAGCGGCCGCATACCCGTACGACGTTCCGGA : 425

FIGURE 1 (CONTINUED)

```
SEQ ID NO: 1084 2CDA68 : -TCAGACGATGGCTGTCAGAGGACCCAAGAC---------TAT-GACTACTGGGGCCAGGGGACCCAGGTCACCGTCTCCTCAGCGGCCGCATACCCGTACGACGTTCCGGA : 413
SEQ ID NO: 1085 1CDA43 : ------------ATCTG------TCACGGACTATACTAAGTAT-GACTACTGGGGCCAGGGGACCCAGGTCACCGTCTCCTCAGCGGCCGCATACCCGTACGACGTTCCGGA : 401
SEQ ID NO: 1086 1CDA73 : ------------ATCTG------TCACGGACTATACTAAGTAT-GACTACTGGGGCCAGGGGACCCAGGTCACCGTCTCCTCAGCGGCCGCATACCCGTACGACGTTCCGGA : 401
SEQ ID NO: 1087 1CDA15 : ------------ATCCG------TCACGGACTATACTAAGTAT-GACTACTGGGGCCAGGGGACCCAGGTCACCGTCTCCTCAGCGGCCGCATACCCGTACGACGTTCCGGA : 401
SEQ ID NO: 1088 1CDA7 : -------GACTGGATC------TCCGGCGGGGTATGAATAT-GACTACTGGGGCCAGGGGACCCAGGTCACCGTCTCCTCAGCGGCCGCATACCCGTACGACGTTCCGGA : 410
SEQ ID NO: 1089 1CDA17 : -TTCAGGAATCGATATA------TCTGGATCCAGAA--ATTAT-GACTACTGGGGCCAGGGGACCCAGGTCACCGTCTCCTCAGCGGCCGCATACCCGTACGACGTTCCGGA : 428
SEQ ID NO: 1090 1CDA18 : -------GCCACTGACAAGGGCGTTGACTTGTCAGATGAGTAT-GACTACTGGGGCCAGGGGACCCAGGTCACCGTCTCCTCAGCGGCCGCATACCCGTACGACGTTCCGGA : 416
SEQ ID NO: 1091 1CDA26 : -GGTAGTGCCTTACCCATAGACGTGGGGAAGAGCGATGAGTAT-GAGTATTGGGGCCAGGGGACCCAGGTCACCGTCTCCTCAGCGGCCGCATACCCGTACGACGTTCCGGA : 416
SEQ ID NO: 1092 1CDA68 : -TCTCGTGGGGGAGAGTGGCGCTTGCAAACTCCGTCGGAATAT-GACTACTGGGGCCAGGGGACCCAGGTCACCGTCTCCTCAGCGGCCGCATACCCGTACGACGTTCCGGA : 419
SEQ ID NO: 1093 3CDA31 : ------------CGGTGAAAGTGGTGTTTGGGTAGGGGGCTTG-GACTACTGGGGCCAGGGGACCCAGGTCACCGTCTCCTCAGCGGCCGCATACCCGTACGACGTTCCGGA : 392
SEQ ID NO: 1094 3CDA73 : ------------CGGTGAAAGTGGTGTTTGGGTAGGGGGCTTG-GACTACTGGGGCCAGGGGACCCAGGTCACCGTCTCCTCAGCGGCCGCATACCCGTACGACGTTCCGGA : 392
SEQ ID NO: 1095 2CDA5 : ------------CGGTGAAAGTGGTGTTTGGGTAGGGGGCTTG-GACTACTGGGKCCAGGGGACCCAGGTCACCGTCTCCTCAGCGGCCGCATACCCGTACGACGTTCCGGA : 392
SEQ ID NO: 1096 2CDA87 : ---------------TAAAGACCTCGATCTAAAGGGGGATTAT-GACTACTGGGGCCAGGGGACCCAGGTCACCGTCTCCTCAGCGGCCGCATACCCGTACGACGTTCCGGA : 407
SEQ ID NO: 1097 1CDA45 : -GGTGGGAGTTACTCCT------TAAAGGACCAATCGAAGTAT-GAATACTGGGGCCAGGGGACCCAGGTCACCGTCTCCTCAGCGGCCGCATACCCGTACGACGTTCCGGA : 419
SEQ ID NO: 1098 1CDA58 : -GGTAGGAGTGTCTCCT------TAAAGGACCAATCGAAGTAT-GAATACTGGGGCCAGGGGACCCAGGTCACCGTCTCCTCAGCGGCCGCATACCCGTACGACGTTCCGGA : 419
SEQ ID NO: 1099 1CDA87 : -TTGAGTGGTAGTTACT---------CCTATGCCGGACAGTAT-AACTTCTGGGGCCAGGGGACCCAGGTCACCGTCTCCTCAGCGGCCGCATACCCGTACGACGTTCCGGA : 404
SEQ ID NO: 1100 1CDA32 : ------------GACAATGGATCTAGAAAATAGCGACATATAT-GACCACTGGGGCCGGGGGACCCAGGTCACCGTCTCCTCAGCGGCCGCATACCCGTACGACGTTCCGGA : 410
SEQ ID NO: 1101 2CDA73 : -TGGTGGAGTGGTAGTTACGACTACACCCGTATGAATAATTAT-GACTACTGGGGCCCGGGGACCCAGGTCACCGTCTCCTCAGCGGCCGCATACCCGTACGACGTTCCGGA : 416
SEQ ID NO: 1102 1CDA12 : GTACGGTAGTGAACGGTACGACATCGCGAGTCCTAGTGAATAT-GACTATTGGGGCCAGGGGACCCAGGTCACCGTCTCCTCAGCGGCCGCATACCCGTACGACGTTCCGGA : 428
SEQ ID NO: 1103 1CDA13 : ------------GCTTCGTGATCTAAAAGTGGGTCAGAACTAT-GACTACTGGGGCCAGGGGACCCAGGTCACCGTCTCCTCAGCGGCCGCATACCCGTACGACGTTCCGGA : 410
SEQ ID NO: 1104 1CDA28 : ------------GCTTCGTGATCTAAAAGTGGGTCAGAACTAT-GACTACTGGGGCCAGGGGACCCAGGTCACCGTCTCCTCAGCGGCCGCATACCCGTACGACGTTCCGGA : 410
SEQ ID NO: 1105 1CDA65 : CCGTATCAG-----------------------------------TACTGGGGCCAGGGGACCCAGGTCACCGTCTCCTCAGCGGCCGCATACCCGTACGACGTTCCGGA : 389
SEQ ID NO: 1106 1CDA48 : CAGTAATAACTGGCG-------------------------------CCCCCCGGGCCAGGGGACCCAGGTCACCGTCTCCTCAGCGGCCGCATACCCGTACGACGTTCCGGA : 389
```

```
                          *        460         *
SEQ ID NO: 1038 3CDA11 : CTACGGTTCCCACCACCATCACCATCACTAG : 456
SEQ ID NO: 1039 3CDA48 : CTACGGTTCCCACCACCATCACCATCACTAG : 456
SEQ ID NO: 1040 3CDA88 : CTACGGTTCCCACCACCATCACCATCACTAG : 459
SEQ ID NO: 1041 2CDA91 : CTACGGTTCCCACCACCATCACCATCACTAG : 456
SEQ ID NO: 1042 2CDA92 : CTACGGTTCCCACCACCATCACCATCACTAG : 459
SEQ ID NO: 1043 3CDA18 : CTACGGTTCCCACCACCATCACCATCACTAG : 459
SEQ ID NO: 1044 3CDA24 : CTACGGTTCCCACCACCATCACCATCACTAG : 459
SEQ ID NO: 1045 3CDA70 : CTACGGTTCCCACCACCATCACCATCACTAG : 459
SEQ ID NO: 1046 2CDA89 : CTACGGTTCCCACCACCATCACCATCACTAG : 459
SEQ ID NO: 1047 3CDA90 : CTACGGTTCCCACCACCATCACCATCACTAG : 456
SEQ ID NO: 1048 2CDA88 : CTACGGTTCCCACCACCATCACCATCACTAG : 456
SEQ ID NO: 1049 3CDA37 : CTACGGTTCCCACCACCATCACCATCACTAG : 459
SEQ ID NO: 1050 3CDA40 : CTACGGTTCCCACCACCATCACCATCACTAG : 459
SEQ ID NO: 1051 3CDA41 : CTACGGTTCCCACCACCATCACCATCACTAG : 459
SEQ ID NO: 1052 3CDA3 : CTACGGTTCCCACCACCATCACCATCACTAG : 459
SEQ ID NO: 1053 3CDA29 : CTACGGTTCCCACCACCATCACCATCACTAG : 459
SEQ ID NO: 1054 3CDA32 : CTACGGTTCCCACCACCATCACCATCACTAG : 459
SEQ ID NO: 1055 3CDA8 : CTACGGTTCCCACCACCATCACCATCACTAG : 459
```

FIGURE 1 (CONTINUED)

SEQ ID NO: 1056 3CDA65 : CTACGGTTCCCACCACCATCACCATCACTAG : 453
SEQ ID NO: 1057 3CDA19 : CTACGGTTCCCACCACCATCACCATCACTAG : 459
SEQ ID NO: 1058 3CDA83 : CTACGGTTCCCACCACCATCACCATCACTAG : 459
SEQ ID NO: 1059 2CDA95 : CTACGGTTCCCACCACCATCACCATCACTAG : 453
SEQ ID NO: 1060 1CDA38 : CTACGGTTCCCACCACCATCACCATCACTAG : 453
SEQ ID NO: 1061 2CDA81 : CTACGGTTCCCACCACCATCACCATCACTAG : 453
SEQ ID NO: 1062 3CDA21 : CTACGGTTCCCACCACCATCACCATCACTAG : 453
SEQ ID NO: 1063 3CDA57 : CTACGGTTCCCACCACCATCACCATCACTAG : 453
SEQ ID NO: 1064 3CDA33 : CTACGGTTCCCACCACCATCACCATCACTAG : 453
SEQ ID NO: 1065 2CDA62 : CTACGGTTCCCACCACCATCACCATCACTAG : 453
SEQ ID NO: 1066 2CDA93 : CTACGGTTCCCACCACCATCACCATCACTAG : 453
SEQ ID NO: 1067 3CDA28 : CTACGGTTCCCACCACCATCACCATCACTAG : 456
SEQ ID NO: 1068 1CDA37 : CTACGGTTCCCACCACCATCACCATCACTAG : 453
SEQ ID NO: 1069 2CDA28 : CTACGGTTCCCACCACCATCACCATCACTAG : 453
SEQ ID NO: 1070 1CDA47 : CTACGGTTCCCACCACCATCACCATCACTAG : 450
SEQ ID NO: 1071 3CDA36 : CTACGGTTCCCACCACCATCACCATCACTAG : 453
SEQ ID NO: 1072 2CDA22 : CTACGGTTCCCACCACCATCACCATCACTAG : 450
SEQ ID NO: 1073 2CDA74 : CTACGGTTCCCACCACCATCACCATCACTAG : 453
SEQ ID NO: 1074 1CDA86 : CTACGGTTCCCACCACCATCACCATCACTAG : 450
SEQ ID NO: 1075 2CDA94 : CTACGGTTCCCACCACCATCACCATCACTAG : 435
SEQ ID NO: 1076 1CDA89 : CTACGGTTCCCACCACCATCACCATCACTAG : 447
SEQ ID NO: 1077 1CDA24 : CTACGGTTCCCACCACCATCACCATCACTAG : 453
SEQ ID NO: 1078 1CDA14 : CTACGGTTCCCACCACCATCACCATCACTAG : 447
SEQ ID NO: 1079 1CDA93 : CTACGGTTCCCACCACCATCACCATCACTAG : 450
SEQ ID NO: 1080 2CDA1 : CTACGGTTCCCACCACCATCACCATCACTAG : 444
SEQ ID NO: 1081 2CDA77 : CTACGGTTCCCACCACCATCACCATCACTAG : 438
SEQ ID NO: 1082 2CDA75 : CTACGGTTCCCACCACCATCACCATCACTAG : 447
SEQ ID NO: 1083 1CDA75 : CTACGGTTCCCACCACCATCACCATCACTAG : 456
SEQ ID NO: 1084 2CDA68 : CTACGGTTCCCACCACCATCACCATCACTAG : 444
SEQ ID NO: 1085 1CDA43 : CTACGGTTCCCACCACCATCACCATCACTAG : 432
SEQ ID NO: 1086 1CDA73 : CTACGGTTCCCACCACCATCACCATCACTAG : 432
SEQ ID NO: 1087 1CDA15 : CTACGGTTCCCACCACCATCACCATCACTAG : 432
SEQ ID NO: 1088 1CDA7 : CTACGGTTCCCACCACCATCACCATCACTAG : 441
SEQ ID NO: 1089 1CDA17 : CTACGGTTCCCACCACCATCACCATCACTAG : 459
SEQ ID NO: 1090 1CDA18 : CTACGGTTCCCACCACCATCACCATCACTAG : 447
SEQ ID NO: 1091 1CDA26 : CTACGGTTCCCACCACCATCACCATCACTAG : 447
SEQ ID NO: 1092 1CDA68 : CTACGGTTCCCACCACCATCACCATCACTAG : 450
SEQ ID NO: 1093 3CDA31 : CTACGGTTCCCACCACCATCACCATCACTAG : 423
SEQ ID NO: 1094 3CDA73 : CTACGGTTCCCACCACCATCACCATCACTAG : 423
SEQ ID NO: 1095 2CDA5 : CTACGGTTCCCACCACCATCACCATCACTAG : 423
SEQ ID NO: 1096 2CDA87 : CTACGGTTCCCACCACCATCACCATCACTAG : 438
SEQ ID NO: 1097 1CDA45 : CTACGGTTCCCACCACCATCACCATCACTAG : 450
SEQ ID NO: 1098 1CDA58 : CTACGGTTCCCACCACCATCACCATCACTAG : 450
SEQ ID NO: 1099 1CDA87 : CTACGGTTCCCACCACCATCACCATCACTAG : 435

FIGURE 1 (CONTINUED)

SEQ ID NO: 1100 1CDA92 : CTACGGTTCCCACCACCATCACCATCACTAG : 441
SEQ ID NO: 1101 2CDA73 : CTACGGTTCCCACCACCATCACCATCACTAG : 447
SEQ ID NO: 1102 1CDA12 : CTACGGTTCCCACCACCATCACCATCACTAG : 459
SEQ ID NO: 1103 1CDA19 : CTACGGTTCCCACCACCATCACCATCACTAG : 441
SEQ ID NO: 1104 1CDA28 : CTACGGTTCCCACCACCATCACCATCACTAG : 441
SEQ ID NO: 1105 1CDA65 : CTACGGTTCCCACCACCATCACCATCACTAG : 420
SEQ ID NO: 1106 1CDA48 : CTACGGTTCCCACCACCATCACCATCACTAG : 420

FIGURE 2

```
                                    *        20         *        40         *        60         *        80         *       100         *
SEQ ID NO: 1107 3CDA11 : QVQLQESGGGLVQAGGSLRLSCAASGFT----FDDYTIGWFRQAPG-KEREGISCISS-DGSTGYADSVKGRFTISSDNAKNTVYLQMNSLKPEDTAVYYCAADFNVWSPPI : 106
SEQ ID NO: 1108 3CDA18 : QVQLQESGGGLVQAGGSLRLSCAASGFS----SDDYTIGWFRQAPG-KEREGISCYSSSDGSTGYADSVKGRFTISSDNAKNTVYLQMNSLKPEDTAVYYCAADFNVWSPPI : 107
SEQ ID NO: 1109 3CDA48 : QVQLQESGGGLVQAGGSLRLSCAASGFS----FDDYTIGWFRQVPG-KEREGISCISS-DGSTGYADSVKGRFTISSDNAKNTVYLQINSLKPEDTAVYYCAADFNVWSPPI : 106
SEQ ID NO: 1110 3CDA91 : QVQLQESGGGLAQVGGSLRLSCTASGFT----FDDYTIGWFRQAPG-KEREGISCISS-DGSTGYADSVKGRFTISSDNAKNTVYLQMNSLKPEDTAVYYCAADFNVWSPPI : 106
SEQ ID NO: 1111 3CDA90 : QVQLQESGGGLVQAGGSLRLSCAASGFT----FDDYTIAWFRQAPG-KEREGISCISS-DGSTGYADSVRGRFTISSDNAKNTVYLQMNSLKPEDTAVYYCAADFNVWSPPI : 106
SEQ ID NO: 1112 3CDA88 : QVQLQESGGGLVQAGGSLRLSCAASGFT----FDDYTIAWFRQAPGGKEREGISCISS-DGSTGYADSVKGRFTISSDNAKNMVYLQMNSLKPEDTALYYCAADFNVWSPPI : 107
SEQ ID NO: 1113 2CDA92 : QVQLQESGGGLVQAGGSLRLSCAASGFS----SDDYTIGWFRQAPG-KEREGIGCIKSSDGTTGYADSVKGRFTISSDNAKNTVYLQMNSLKPEDTAVYYCAADFNVWSPPI : 107
SEQ ID NO: 1114 3CDA19 : QVQLQESGGGLVQAGGSLRLSCAASGFS----SDDYTIGWFRQAPG-KEREGISCFSSSDGSTGFADSVKGRFTISSDNATNTVYLEMNSLKPEDTAVYYCAADFNVWSPPI : 107
SEQ ID NO: 1115 3CDA53 : QVQLQESGGGLVQAGGSLRLSCAASGFS----SDDYTIGWFRQAPG-KEREGISCFSSSDGSTGFADSVKGRFTISSDNATNTVYLQMNSLKPEDTAVYYCAADFNVWSPPI : 107
SEQ ID NO: 1116 3CDA40 : QVQLQESGGGLVQAGGSLRLSCEVSGLS----SDDYTIGWFRQAPG-KKREGFSCFSSRDGSTGYADSVKGRFTISSDNAKNTVYLQMNSLKPEDTAVYYCAADFNVWSPPI : 107
SEQ ID NO: 1117 3CDA41 : QVQLQESGGGLVQAGGSLRLSCAASGFS----SDDYTIGWFRQAPG-KEREGFSCFSSRDGSTGYADSVKGRFTISSDNAKNTVYLQMNSLKPEDTAVYYCAADFNVWSPPI : 107
SEQ ID NO: 1118 3CDA37 : QVQLQESGGGLVQAGGSLRLSCEVSGLS----SDDYTIGWFRQAPG-KEREGFSCFSTRDGNAGYADSVKGRFTISSDNAKNTVYLQMNNLKPEDTAVYYCAADFNVWSPPI : 107
SEQ ID NO: 1119 3CDA3  : QVQLQESGGGLVQAGGSLRLSCAASGFS----SDDYTIAWFRRAPG-KEREGISCISSSDGSTGYADSVKGRFTITSDSAKNTVYLQMNSLKPEDTAVYYCAADSNVWSPPI : 107
SEQ ID NO: 1120 3CDA29 : QVQLQESGGGLVQAGGSLRLSCAASGFS----SDDYTIAWFRRAPG-KEREGISCISSSDGSTGYADSVKGRFTISSDNAKNTVYLQMTSLKPEDTAVYYCAADSNVWSPPI : 107
SEQ ID NO: 1121 3CDA65 : QVQLQESGGGLVQAGGSLXLSCAASGFT----FDDYAIGWFRQAPG-KEREGVSCISSPDGSTYYADSVKGRFTISSDNAKNTVYLQMNSLKPEDTAVYYCAADFNVWSPPI : 107
SEQ ID NO: 1122 3CDA8  : QVQLQESGGGLVQPGGSLRLSCAASGFS----SDDYTIGWFRQAPG-KEREGISCYSSRDGTTGYADSVKGRFTISSDNAKNTVYLQMNSLKPEDTAVYYCAADFNVWSPPI : 107
SEQ ID NO: 1123 3CDA24 : QVQLQESGGGLVQAGGSLRLSCAASGFS----SDDYTIGWFRQAPG-KEREGISCYSSSDGSTGFADSVKGRFTISSDNAKNTVYLQMNSLRPEDTAVYYCAADFNVWSPPI : 107
SEQ ID NO: 1124 2CDA89 : QVQLQESGGGLVQAGGYLRLSCAASGFS----SDDYTIGWFRQAPG-KEREGISCYSSSDGSTGFADSVKGRFTISSDNAKNTVYLQMNNLRPEDTAVYYCAADSNVWSPPI : 107
SEQ ID NO: 1125 2CDA88 : QVQLQESGGGLVQAGDSLKLSCATSGRS----FSSYTIAWFRQAPG-KEREGISCISS-DGSTGYADSVRGRFTISSDNAKNTVYLQMNSLKPEDTAVYYCAADFNVWSPPI : 106
SEQ ID NO: 1126 3CDA70 : QVQLQESGGGLVQAGASLRLSCKASGFT----FGDYTIGWFRQAPG-KEREGISCYSSSDGNTGYADSVKGRFTISSDNAKNTVYLQMNSLRPEDTAVYYCAADFNVWSPPI : 107
SEQ ID NO: 1127 3CDA32 : QVQLQESGGGLVQAGGSLRLSCAASGFS----SDDYTIAWFRRAPG-KEREGISCFSSSDGSAGYADSVKGRFTVSSDNAKNTVYLQMNSLKPEDTAVYYCAADSNVWSPPI : 107
SEQ ID NO: 1128 2CDA95 : QVQLQESGGGLVQAGGSLRLSCAASGFA----FDGYAIGWFRQAPG-KEREGVSCISSKEGSTYYADSVKGRFTISSDNAKNTVYLQMSSLKPEDTAVYYCAADGNVWSPPI : 107
SEQ ID NO: 1129 1CDA88 : QVQLQESGGGLVQAGDSLKLSCAASGLT----FSNYIMAWFRQAPG-KEREGVSCISSPDGSTYYADSVKGRFTISSDNAKNTVYLQMNSLKPEDTAVYYCAADFNVWSPPI : 107
SEQ ID NO: 1130 2CDA81 : QVQLQESGGGLVQAGGSLRLSCATFGFT----FDDYAIAWFRQAPG-KEREGISCISNTDSSTYYADSVKGRFTISSDSAKNTVHLQMSSLKPEDTAVYYCAADGNVWSPPI : 107
SEQ ID NO: 1131 3CDA57 : QVQLQESGGGLVQAGGSLRLSCATFGFT----FDDYAIAWFRQAPG-KEREGISCISNTDSSTYYADSVKGRFTISSDNAKNTVHLQMSSLKPEDTAVYYCAADGNVWSPPI : 107
SEQ ID NO: 1132 3CDA21 : QVQLQESGGGLVQAGGSLRLSCATFGFS----FDDYAIAWFRQAPG-KEREGISCISKTDSSTFYADSVKGRFTISSDNAKNTVHLQMSSLKPEDTAVYYCAADGNVWSPPI : 107
SEQ ID NO: 1133 3CDA33 : QVQLQESGGGLVQAGGSLRLSCATSGFT----FDDYAIAWFRQAPG-KEREGVSCISNTDSSTYYADSVKGRFTISSDNAKNTVYLQMSSLKPEDTAVYYCAADGNVWSPPI : 107
SEQ ID NO: 1134 2CDA62 : QVQLQESGGGLVQPGGSLRLSCATFGFP----FDDYAIAWFRQAPG-KEREGVSCISNTDSSTYYADSVKGRFTISSDNAKNTVHLQMSSLKPEDTAVYYCAADGNVWSPPI : 107
SEQ ID NO: 1135 2CDA93 : QVQLQESGGGLAQAGGSLRLSCAASGFT----FDQYTIAWFRQAPG-KEREGVSCISNTDSSTYYADSVKGRFTISSDNAKNTVYLQMSSLKPEDTAVYYCAADGNVWSPPI : 107
SEQ ID NO: 1136 3CDA28 : QVQLQESGGGLVQVGGSLRLSCTISGFT----GNDLAIGWFRQAPGKDQREGISCISNTDSSTYYADSVKGRFTISSDNAKNTVHLQMSSLKPEDTAVYYCAADGNVWSPPI : 108
SEQ ID NO: 1137 2CDA28 : QVQLQESGGGLVQAGGSLRLSCTASGRT----FSSYTVAWFRQSPG-KEREGISCISNTDSSTYYADSVKGRFTISSDNAKSTVHLQMSSLKPEDTAVYYCAADGNVWSPPI : 107
SEQ ID NO: 1138 1CDA47 : QVQLQESGGGLVQAEGSLKLSC-ISGFA----FDGYAIGWFRQAPG-KEREGVACISSKDGSTYYADSVKGRFTMSVDKTKNTVYLQMSSLKPEDTAVYYCAADGNVWSPPI : 106
SEQ ID NO: 1139 3CDA86 : QVQLQESGGGLVQAGDSLRLSCTASGVS----IGDYNIGWFRQAPG-KEREGVSCISSGDGTTYYTDSVKGRFTISTDNAKNTVYLQMNSLKPEDTAVYYCAADGNVWSPPI : 107
SEQ ID NO: 1140 1CDA37 : QVQLQESGGGLVQAGGSLRLSCAGSGFT----LDYYGIGWFRQAPG-KEREGVSCISSSDRNTYYADSVKGRFTISGDNAKNTVYLQMNNLKPEDTAVYYCAADGNVWSPPI : 107
SEQ ID NO: 1141 2CDA22 : QVQLQESGGGLVQAGGSLRLSCAASGFT----FDDYAIAWFRQAPG-KEREGVSCIERSDGSTYYADSVKGRFTISSDNAKNTVYLQMNSLKPEDTAVYYCAVG-SANS--- : 103
SEQ ID NO: 1142 2CDA74 : QVQLQESGGGLVQAGGSLRLSCAVSGFT----FDNYAIGWFRQAPG-KEREGVSCISRSDGSTYYADSVRGRFTISSDNAKNTVYLQMNSLKPEDTAVYYCAAETSADS--- : 104
SEQ ID NO: 1143 1CDA56 : QVQLQESGGGLVQAGGSLRLSCAASGRT----FSNYAMGWFRQAPG-KEREFVAAIVWSGGSTYYADSVKGRFTISRDNAKNTVYLQMNSLKPEDTAVYYCAA-VL--IRYY : 104
SEQ ID NO: 1144 2CDA94 : QVQLQESGGGLVQAGGSLRLSCAASGRT----FSSYAMAWFRQAPG-KEREFVAAIAWSAGSTYYADSVKGRFAISRDNAENTVYLQMNSLKPEDTAVYYCAA-RI--ITVA : 104
SEQ ID NO: 1145 1CDA17 : QVQLQESGGGLVQAGGSLRLSCAASGRTSGRTFSSYTMGWFRQAPG-KEREFVATITWGGGSTYYADSVKGRFTISRDNANNTVYLQMNSLKPEDTAVYYCAA-S---VKVV : 107
SEQ ID NO: 1146 1CDA89 : QVQLQESGGGLVQAGGSLRLSCAASGRT----FSNSVMGWFRQPPG-KEREFVAAVLWSGVSTAYADSVKGRFTISRDNAKNTVYLQMNNLKPDDTAVYYCAA-HE--STYY : 104
SEQ ID NO: 1147 2CDA1  : QVQLQESGGGLVQAGGSLRLSCAASGGT----FSNYVMGWFRQAPG-KEREFVGFITWSGASTYYADSVKGRFTISRDNAENTVYLQMNSLKPEDTAVYYCAA-TL--FR-- : 102
SEQ ID NO: 1148 2CDA75 : QVQLQESGGGLVQAGGSLRLSCAASGRA----FSSYFMGWFRQTPG-KEREFVANIGWTGDMIYYADSVKGRFTISRDNAKNTVYLQMNSLKPEDTAVYYCAA-A---GSAY : 103
SEQ ID NO: 1149 1CDA43 : QVQLQESGGGLVQAGGSLRLSCVASGHT----FSSYTMGWFRQAPG-KEREFVAFIDWSGGGTYYANSVKGRFTISRDNAENTVYLQMNNLKPEDTAVYYCAA--------- :  98
```

FIGURE 2 (CONTINUED)

```
SEQ ID NO: 1150 1CDA73 : QVQLQESGGGLVQAGGSLRLSCAASGHT----FSSYIMGWFRQAPG-KEREFVAFIDWSGGGTYYADSVKGRFTISRDNAENTVYLQMNNLKPEDTAVYYCAA--------- :  98
SEQ ID NO: 1151 1CDA15 : QVQLQESGGGLVQAGGSLRLSCAASGRT----FSSYTMGWFRQAPG-KEREFVAFIDWSGGGTYYDDSVKGRFTISRDNAENTVYLQMNNLEPEDTAVYYCAA--------- :  98
SEQ ID NO: 1152 1CDA24 : QVQLQESGGGLVQAGGSLRLSCAASGRT----FSSYTMGWFRQAPG-REREFVAAITWSGVSTVYIDSVKGRFTVSRDNAKNTVYLQMNSLKPEDTAVYYCAADSP--PRIY : 105
SEQ ID NO: 1153 1CDA75 : QVQLQESGGGLVQAGGSLRLSCAASGRT----FSTYPVGWFRQAPG-KEREFVAVILWSGVSTYYADSVKGRFTISRDNAQNTVYLQMDSLKPEDTAVYYCAVPRS--HFTI : 105
SEQ ID NO: 1154 1CDA26 : QVQLQESGGGLVQAGGSLRLSCAASGRT----FSSDTMGWFRQAPG-KEREFVGAIMWSGAFTHYADSVKGRFTISRDNAKNTVYLQMNALKPEDTAVYYCAV-----IPGR : 102
SEQ ID NO: 1155 3CDA31 : QVQLQESGGGLVQAGDSLRLSCAGSEGT----LSSYGIGWFRQAPG-KEREFVGGINWSGDSTDYADSVKGRFTISRDSAKNTVYLQMNSLKPEDTAVYYCAAGES--GVWV : 105
SEQ ID NO: 1156 3CDA73 : QVQLQESGGGLVQAGDSLRLSCAGSEGT----FSSYGIGWFRQAPG-KEREFVGGINWSGDSTDYADSVKGRFTISRDNAKNTVYLQMNSLKPEDTAVYYCAAGES--GVWV : 105
SEQ ID NO: 1157 2CDA5  : QVQLQESGGGLVQAGDSLRLTCIASGRT----FSNYGIGWFRQAPG-KEREFVAGINWSGESADYADSVKGRFTISRDNAKNTVYLQMNSLKPEDTAVYYCAAGES--GVWV : 105
SEQ ID NO: 1158 2CDA57 : QVQLQESGGGLVQAGGSLRLSCKASGGT----FSGYIMGWFRQAPG-KEREFVAANTWSGGPTYYSDSVKGRFTISRDNAKNTVYLQMNTLKPEDTAVYQCAAR-------- :  99
SEQ ID NO: 1159 1CDA12 : QVQLQESGGGLVQDGGSLRLSCAFSGRT----FSSYTMGWFRQGPG-KEREFVAATVWTGAGTVYADSVKGRFTISRDNAKNTVYLQMNSLRPEDTAVYYCAADQA--SVPP : 105
SEQ ID NO: 1160 1CDA93 : QVQLQESGGGLVQAGGSLRLSCAASGRT----FSSYVMGWFRQALG-KEREFVAAIGWNGGITYYADSVKGRFAISRDNAKNTVYLQMNSLKPEDTAVYYCAAATL--QV-- : 103
SEQ ID NO: 1161 2CDA77 : QVQLQESGGGLVQAGGSLRLSCAASTPT----FSSYNMGWFRQAPG-KEREFVAAIIWSGSMTYYADSMKGRFTVSIDNAKNTVYLQMNSLKPEDTAVYYCAAQRI------ : 101
SEQ ID NO: 1162 1CDA7  : QVQLQESGGGLVQAGGSLRLSCAASGRS----FSSYTLAWFRQAPG-KEREFVASITWGGGNTYYPDSVKGRFTISRDDAKNTVYLQMNSLKPEDTAVYYCAAK-------- :  99
SEQ ID NO: 1163 1CDA14 : QVQLQESGGGLVQAGASLRLSCAASGRT----FSSYIMGWFRQAPG-KEREFVAAIGWSADITVYADSVKGRFTISRDNAENMVYLQMNSLNPEDTAVYYCAANSR------ : 101
SEQ ID NO: 1164 2CDA69 : QVQLQESGGGLVQAGGSLRLSCAASGRT----FSSYVMGWFRQAPG-KEREFVAQISWSAGSIYYADSVKGRFTISNDNAKRTVYLQMNSLKPEDTAVYYCAERGY--AYCS : 105
SEQ ID NO: 1165 1CDA18 : QVQLQESGGGLVQPGGSLRLSCLASGRT----FSSYAMGWFRQAPG-KEREFVAAISWSGGPTVYADHVKGRFTISRDNAKNTVYLQVNSLKPEDTADYYCAAKRL------ : 101
SEQ ID NO: 1166 1CDA45 : QVQLQESGGGLVQAGGSLRLSCAASGRT----FSSYVIGWFRQAPG-KEREFVAVITWSGDSTYSSDSLKGRFTISRDNAKNTVYLQMNALNPEDTAVYYCAA-----IPPR : 102
SEQ ID NO: 1167 1CDA58 : QVQLQESGGGLVQARGSLTLSCAASGRT----FSNYVIGWFRQAPG-EEREFVAVVTWSGDSTYSSDSLKGRFTISRDNAKNTVYLQMNNLNPEDTAVYYCAA-----MPPR : 102
SEQ ID NO: 1168 1CDA68 : QVQLQESGGGLVQAGASLRLSCAASGRT----FSNYNVGWFRQAPG-KEREFVSFISWISDIIYYSDSVKGRFIISRDNAKNMVYLQMNSLKPEDTAVYYCAAH-----PPD : 102
SEQ ID NO: 1169 1CDA87 : QVQLQESGGGLVQAGASLRLSCSASGRT----FSDYRMGWFRQAPG-KEREWVAAISSSGYHTYYADSVKGRFTISRDNAKNTGYLQMSSLKPEDTAVYYCAVVKYL----- : 102
SEQ ID NO: 1170 1CDA19 : QVQLQESGGGLVQAGDSLRLSCAASGLT----FSNYIMGWFRQAPG-KEREFVAAITWGGGSTVYADSVEGRFTISRDGTKNTVSLQMNSLLPEDTAVYYCAAAG------- : 100
SEQ ID NO: 1171 1CDA28 : QVQLQESGGGLVQAGDSLRLSCAASGLT----FSNYIMGWFRQAPG-KEREFVAAITWGGGSTVYADSVEGRFTISRDGTKNTVSLQMNSLQPEDTAVYYCAAAG------- : 100
SEQ ID NO: 1172 2CDA73 : QVQLQESGGGLVQAGGSLRLSCAASGRT----LSSNPMAWFRQAAG-KEREFVAGMSWNPGPAVYADSVKGRFTISRDSAENTVYLQMNSLKPEDTAVYYCAGAARAWW--- : 104
SEQ ID NO: 1173 1CDA92 : QVQLQESGGGLVQAGGSLRLSCVGDGRT----FSSYIIGWFRQAPG-NEREFVVAITWDGSATTYADSVKGRFTVSRDSAKNTAYLQMNSLKPEDTAVYYCAA--------V :  99
SEQ ID NO: 1174 1CDA65 : QVQLQESGGGLVQPGGSLRLSCAASG----SIFSINVMGWYRQTPG-KERELVAKIT-NFGITSYADSAQGRFTISRGNAKNTVYLQMNSLKPEDTAVYYCNLDITGWGPP- : 105
SEQ ID NO: 1175 1CDA48 : QVQLQESGGGLVQPGGSLTLSCAASGFA----FGFFDMTWVRQAPG-KGLEWVSGINSIGGSTTYADSVKGRFTISRDNAKNELYLQMNSLKPDDTAVYYCAKSRSSYS--- : 104

                                  120         *        140         *        160
SEQ ID NO: 1107 3CDA11 : CGSNWYG--PPPGGMDYW---GKGTQVTVSSAAAYPYDVPDYGSHHHHHHX : 152
SEQ ID NO: 1108 3CDA18 : CGSSWYG--PPPGGMDYW---GKGTQVTVSSAAAYPYDVPDYGSHHHHHHX : 153
SEQ ID NO: 1109 3CDA45 : CGSIWYG--PPPGGMDYW---GKGTQVTVSSAAAYPYDVPDYGSHHHHHHX : 152
SEQ ID NO: 1110 2CDA91 : CGSNWYG--PPPGGMDYW---GKGTQVTVSSAAAYPYDVPDYGSHHHHHHX : 152
SEQ ID NO: 1111 3CDA90 : CGSIWYG--PPPRGMDYW---GKGTQVTVSSAAAYPYDVPDYGSHHHHHHX : 152
SEQ ID NO: 1112 3CDA88 : CSSNWYG--PPPRGMDYW---GKGTQVTVSSAAAYPYDVPDYGSHHHHHHX : 153
SEQ ID NO: 1113 2CDA92 : CGSIWYG--PPPGGMDYW---GKGTQVTVSSAAAYPYDVPDYGSHHHHHHX : 153
SEQ ID NO: 1114 3CDA19 : CGSRWYG--PPPGGMEYW---GKGTQVTVSSAAAYPYDVPDYGSHHHHHHX : 153
SEQ ID NO: 1115 3CDA83 : CGSSWYG--PPPGGMEYW---GKGTQVTVSSAAAYPYDVPDYGSHHHHHHX : 153
SEQ ID NO: 1116 3CDA40 : CGSRWYG--PPPGGMDYW---GKGTQVTVSSAAAYPYDVPDYGSHHHHHHX : 153
SEQ ID NO: 1117 3CDA41 : CGSRWYG--PPPGGMDYW---GKGTQVTVSSAAAYPYDVPDYGSHHHHHHX : 153
SEQ ID NO: 1118 3CDA37 : CGSRWYG--PPPGGMDYW---GKGTQVTVSSAAAYPYDVPDYGSHHHHHHX : 153
SEQ ID NO: 1119 3CDA3  : CGRTWYG--PPPGGMDYW---GKGTQVTVSSAAAYPYDVPDYGSHHHHHHX : 153
SEQ ID NO: 1120 3CDA29 : CGKTWYG--PPPGGMDYW---GKGTQVTVSSAAAYPYDVPDYGSHHHHHHX : 153
SEQ ID NO: 1121 3CDA65 : CGS--VG--PPPGGMDYW---GKGTQVTVSSAAAYPYDVPDYGSHHHHHHX : 151
```

FIGURE 2 (CONTINUED)

SEQ ID NO: 1122 3CDA8 : CGSIWYG--PPPGGMAYW---GQGTQVTVSSAAAYPYDVPDYGSHHHHHHX : 153
SEQ ID NO: 1123 3CDA24 : CGSRWYG--PPPGGMAYW---GKGTQVTVSSAAAYPYDVPDYGSHHHHHHX : 153
SEQ ID NO: 1124 2CDA89 : CGSRWYG--PPPGGMAYW---GKGTQVTVSSAAAYPYDVPDYGSHHHHHHX : 153
SEQ ID NO: 1125 2CDA88 : CGSIWYG--PPPRGMDYW---GKGTQVTVSSAAAYPYDVPDYGSHHHHHHX : 152
SEQ ID NO: 1126 3CDA70 : CGSSWYG--PPPGGMAYW---GKGTQVTVSSAAAYPYDVPDYGSHHHHHHX : 153
SEQ ID NO: 1127 3CDA32 : CGSTWYG--PPPGGMAYW---GKGTQVTVSSAAAYPYDVPDYGSHHHHHHX : 153
SEQ ID NO: 1128 2CDA95 : CGSA--G--PPPGGMDYW---GKGTQVTVSSAAAYPYDVPDYGSHHHHHHX : 151
SEQ ID NO: 1129 1CDA88 : CGS--VG--PPPGGMDYW---GKGTQVTVSSAAAYPYDVPDYGSHHHHHHX : 151
SEQ ID NO: 1130 2CDA81 : CGSA--G--PPPGGMDYW---GKGTQVTVSSAAAYPYDVPDYGSHHHHHHX : 151
SEQ ID NO: 1131 3CDA57 : CGSA--G--PPPGGMDYW---GKGTQVTVSSAAAYPYDVPDYGSHHHHHHX : 151
SEQ ID NO: 1132 3CDA21 : CGSA--G--PPPGGMDYW---GKGTQVTVSSAAAYPYDVPDYGSHHHHHHX : 151
SEQ ID NO: 1133 3CDA33 : CGSA--G--PPPGGMDYW---GKGTQVTVSSAAAYPYDVPDYGSHHHHHHX : 151
SEQ ID NO: 1134 2CDA62 : CGSA--G--PPPGGMDYW---GKGTQVTVSSAAAYPYDVPDYGSHHHHHHX : 151
SEQ ID NO: 1135 2CDA93 : CGSA--G--PPPGGMDYW---GKGTQVTVSSAAAYPYDVPDYGSHHHHHHX : 151
SEQ ID NO: 1136 3CDA28 : CGSA--G--PPPGGMDYW---GKGTQVTVSSAAAYPYDVPDYGSHHHHHHX : 152
SEQ ID NO: 1137 2CDA28 : CGSA--G--PPPGGMDYW---GKGTQVTVSSAAAYPYDVPDYGSHHHHHHX : 151
SEQ ID NO: 1138 1CDA47 : CSSA--G--PPPGGMDYW---GKGTQVTVSSAAAYPYDVPDYGSHHHHHHX : 150
SEQ ID NO: 1139 3CDA86 : CGSA--G--PPPGGMDYW---GKGTQVTVSSAAAYPYDVPDYGSHHHHHHX : 151
SEQ ID NO: 1140 1CDA37 : CGSA--G--PPPGGMDYW---GKGTQVTVSSAAAYPYDVPDYGSHHHHHHX : 151
SEQ ID NO: 1141 2CDA22 : -GEFRFGWVLKPDLYNYW---GQGTQVTVSSAAAYPYDVPDYGSHHHHHHX : 150
SEQ ID NO: 1142 2CDA74 : -GEFRFGWVLKPSLYDYW---GQGTQVTVSSAAAYPYDVPDYGSHHHHHHX : 151
SEQ ID NO: 1143 1CDA86 : S-GGYQ-GLSDANEYDYW---GQGTQVTVSSAAAYPYDVPDYGSHHHHHHX : 150
SEQ ID NO: 1144 2CDA94 : T-------MRLDSDYDYW---GQGTQVTVSSAAAYPYDVPDYGSHHHHHHX : 145
SEQ ID NO: 1145 1CDA17 : A-GSGI-DISGSRNYDYW---GQGTQVTVSSAAAYPYDVPDYGSHHHHHHX : 153
SEQ ID NO: 1146 1CDA89 : S-GTYY--LTDPRRYVYW---GQGTQVTVSSAAAYPYDVPDYGSHHHHHHX : 149
SEQ ID NO: 1147 2CDA1 : S-NGPK-DLSSGYEYDYW---GQGTQVTVSSAAAYPYDVPDYGSHHHHHHX : 148
SEQ ID NO: 1148 2CDA75 : S-GSYW-NITMAANYDYW---GQGTQVTVSSAAAYPYDVPDYGSHHHHHHX : 149
SEQ ID NO: 1149 1CDA43 : A-QRLG-SVTDYTKYDYW---GQGTQVTVSSAAAYPYDVPDYGSHHHHHHX : 144
SEQ ID NO: 1150 1CDA73 : A-QRLG-SVTDYTKYDYW---GQGTQVTVSSAAAYPYDVPDYGSHHHHHHX : 144
SEQ ID NO: 1151 1CDA15 : A-QRLG-SVTDYTKYDYW---GQGTQVTVSSAAAYPYDVPDYGSHHHHHHX : 144
SEQ ID NO: 1152 1CDA24 : S-SGSV-NLEDGSEYDYW---GQGTQVTVSSAAAYPYDVPDYGSHHHHHHX : 151
SEQ ID NO: 1153 1CDA75 : A-QEMGQDMGAPSWYEYW---GQGTQVTVSSAAAYPYDVPDYGSHHHHHHX : 152
SEQ ID NO: 1154 1CDA26 : G-SALPIDVGKSDEYEYW---GQGTQVTVSSAAAYPYDVPDYGSHHHHHHX : 149
SEQ ID NO: 1155 3CDA31 : G-G-----------LDYW---GQGTQVTVSSAAAYPYDVPDYGSHHHHHHX : 141
SEQ ID NO: 1156 3CDA73 : G-G-----------LDYW---GQGTQVTVSSAAAYPYDVPDYGSHHHHHHX : 141
SEQ ID NO: 1157 2CDA5 : G-G-----------LDYW---XQGTQVTVSSAAAYPYDVPDYGSHHHHHHX : 141
SEQ ID NO: 1158 2CDA87 : D-YRGIKDLDLKGDYDYW---GQGTQVTVSSAAAYPYDVPDYGSHHHHHHX : 146
SEQ ID NO: 1159 1CDA12 : PYGSERYDIASPSEYDYW---GQGTQVTVSSAAAYPYDVPDYGSHHHHHHX : 153
SEQ ID NO: 1160 1CDA93 : -TGSYYLDLSTVDIYDNW---GQGTQVTVSSAAAYPYDVPDYGSHHHHHHX : 150
SEQ ID NO: 1161 2CDA77 : -FGAQPMDLS--GDYEYW---GQGTQVTVSSAAAYPYDVPDYGSHHHHHHX : 146
SEQ ID NO: 1162 1CDA7 : GLANSEWDLRRGYEYDYW---GQGTQVTVSSAAAYPYDVPDYGSHHHHHHX : 147
SEQ ID NO: 1163 1CDA14 : AYYSSSYDLGRLASYDYW---GQGTQVTVSSAAAYPYDVPDYGSHHHHHHX : 149
SEQ ID NO: 1164 2CDA68 : DDG-----CQRTQDYDYW---GQGTQVTVSSAAAYPYDVPDYGSHHHHHHX : 148
SEQ ID NO: 1165 1CDA18 : DYSATDKGVDLSDEYDYW---GQGTQVTVSSAAAYPYDVPDYGSHHHHHHX : 149

FIGURE 2 (CONTINUED)

```
SEQ ID NO: 1166 1CDA45 : AYSGGSYSLHDQSKYEYW---GQGTQVTVSSAAAYPYDVPDYGSHHHHHHX : 150
SEQ ID NO: 1167 1CDA56 : AYTGRSVSLHDQSKYEYW---GQGTQVTVSSAAAYPYDVPDYGSHHHHHHX : 150
SEQ ID NO: 1168 1CDA68 : PSRGGEWRLQTPSEYDYW---GQGTQVTVSSAAAYPYDVPDYGSHHHHHHX : 150
SEQ ID NO: 1169 1CDA67 : -----SGSYSYAGQYNFW---GQGTQVTVSSAAAYPYDVPDYGSHHHHHHX : 145
SEQ ID NO: 1170 1CDA19 : -GSGRLADLKVGQNYDYW---GQGTQVTVSSAAAYPYDVPDYGSHHHHHHX : 147
SEQ ID NO: 1171 1CDA26 : -ASGRLADLKVGQNYDYW---GQGTQVTVSSAAAYPYDVPDYGSHHHHHHX : 147
SEQ ID NO: 1172 2CDA73 : ---SGSYDYTRMMNYDYW---GPGTQVTVSSAAAYPYDVPDYGSHHHHHHX : 149
SEQ ID NO: 1173 1CDA92 : PARGLTMDLENSDIYDHW---GRGTQVTVSSAAAYPYDVPDYGSHHHHHHX : 147
SEQ ID NO: 1174 1CDA65 : -------------FYQYW---GQGTQVTVSSAAAYPYDVPDYGSHHHHHHX : 140
SEQ ID NO: 1175 1CDA48 : ---------------MNWRPPGQGTQVTVSSAAAYPYDVPDYGSHHHHHHX : 140
```

FIGURE 3

| Group | Member(s) |
|---|---|
| 1 | 3CDA11, 3CDA18, 3CDA48, 2CDA91, 3CDA90, 3CDA88, 2CDA92, 3CDA19, 3CDA83, 3CDA40, 3CDA41, 3CDA37, 3CDA3, 3CDA29, 3CDA8, 3CDA24, 2CDA89, 2CDA88, 3CDA70, 3CDA32 |
| 2 | 3CDA65, 2CDA95, 1CDA88, 2CDA81, 3CDA57, 3CDA21, 3CDA33, 2CDA62, 2CDA93, 3CDA28, 2CDA28, 1CDA47, 3CDA86, 1CDA37 |
| 3 | 2CDA22 |
| 4 | 2CDA74 |
| 5 | 1CDA86 |
| 6 | 2CDA94 |
| 7 | 1CDA17 |
| 8 | 1CDA89 |
| 9 | 2CDA1 |
| 10 | 2CDA75 |
| 11 | 1CDA43, 1CDA73, 1CDA15 |
| 12 | 1CDA24 |
| 13 | 1CDA75 |
| 14 | 1CDA26 |
| 15 | 3CDA31, 3CDA73, 2CDA5 |
| 16 | 2CDA87 |
| 17 | 1CDA12 |
| 18 | 1CDA93 |
| 19 | 2CDA77 |
| 20 | 1CDA7 |
| 21 | 1CDA14 |

FIGURE 3 (CONTINUED)

| | |
|---|---|
| 22 | 2CDA68 |
| 23 | 1CDA18 |
| 24 | 1CDA45, 1CDA58 |
| 25 | 1CDA68 |
| 26 | 1CDA87 |
| 27 | 1CDA19, 1CDA28 |
| 28 | 2CDA73 |
| 29 | 1CDA92 |
| 30 | 1CDA65 |
| 31 | 1CDA48 |

CD8 BINDING AGENTS

CROSS-REFERENCE TO RELATED APPLICATIONS

The present application is a continuation of U.S. patent application Ser. No. 16/634,325, filed Jan. 27, 2020 (now U.S. Pat. No. 11,566,072), which is a National Stage Entry of PCT/US2018/045741, filed Aug. 8, 2018, which claims the benefit of and priority to U.S. Provisional Patent Application No. 62/542,920, filed Aug. 9, 2017, the content of which is hereby incorporated by reference in its entirety.

FIELD

The present invention relates, in part, to binding agents (e.g., antibodies, such as, without limitation, VHHs) which bind CD8 and their use as therapeutic and diagnostic agents.

DESCRIPTION OF THE TEXT FILE SUBMITTED ELECTRONICALLY

Sequence Listing

The contents of the text file submitted electronically herewith are incorporated herein by reference in their entirety. A computer readable XML format copy of the Sequence Listing (filename: ORN-032C1_114384-5032.xml, date recorded: Dec. 23, 2022; file size: 1,653,916 bytes).

BACKGROUND

Activated $CD8^+$ T lymphocytes (also known as cytotoxic T cells or CTLs) represent the main line of defense against a wide gamut of microbial pathogens. Further still, CTLs also play an important role in antitumor immunity. Specifically, these effector cells can curb cancer development through mechanisms including production of interferon (IFN)-γ and cytotoxins, exocytosis of lytic proteins (e.g., perforin, granzymes), and receptor-ligand binding of FAS molecules.

Nevertheless, microbial pathogens and tumor cells have developed various mechanisms to escape immune destruction by CTLs. For example, tumors can evade immune surveillance by crippling CTL functionality via, for instance, production of immune suppressive cytokines and engagement of immune checkpoint inhibition, either by the cancer cells themselves or by non-cancerous cells present in the tumor microenvironment. Cancer cells have also been shown to delete CTLs through apoptosis.

Accordingly, there remains a need for improved immunotherapeutic agents, including, for example, those that can effectively derail tumor evasion and enhance anti-tumor immunity as mediated, for example, by CTLs.

SUMMARY

In various aspects, the present invention relates to CD8 binding agents having at least one targeting moiety that specifically binds to CD8. In various embodiments, these CD8 binding agents bind to, but do not functionally modulate (including, without limitation, partially or fully neutralizing) CD8. Therefore, in various embodiments, the present CD8 binding agents have use in, for instance, recruiting a CD8-expressing cell to a site of interest while still allowing the CD8-expressing cell to signal via CD8 (i.e. the binding of the CD8 binding agent does not reduce or eliminate CD8 signaling at the site of interest). In an embodiment, the targeting moiety is a single domain antibody (VHH). In various embodiments, the CD8 binding agent further comprises a signaling agent, e.g., without limitation, an interferon, an interleukin, and a tumor necrosis factor, that may be modified to attenuate activity. In various embodiments, the CD8 binding agent comprises additional targeting moieties that bind to other antigens of interest. In an embodiment, the other antigens of interest are present on tumor cells. In another embodiment, the other antigens of interest are present on immune cells. In these embodiments, the present CD8 binding agent may directly or indirectly recruit an immune cell, e.g. an immune cell that can kill and/or suppress a tumor cell (e.g., cytotoxic T cells), to a site of action (such as, by way of non-limiting example, the tumor microenvironment).

In various embodiments, the present CD8 binding agents find use in the treatment of various diseases or disorders such as cancer, infections, immune disorders, autoimmune diseases, and other diseases and disorders, and the present invention encompasses various methods of treatment.

BRIEF DESCRIPTION OF DRAWINGS

FIG. 2 shows the amino acid sequences of 69 different VHHs specific for human CD8. Complementarity determining regions (CDR1, CDR2 and CDR3) as indicated are defined according to Kabat. Gaps were introduced in order to align sequences. The above 69 different VHHs belong to 31 different CDR3 groups (see FIG. 3). VHHs belonging to the same group are very similar and their amino acid sequences suggest that they are from clonally-related B-cells resulting from somatic hypermutation or from the same B-cell but diversified due to RT and/or PCR error during library construction. VHHs belonging to the same group recognize the same epitope but their other characteristics (e.g. affinity, potency, stability, expression yield, etc.) can be different.

FIG. 3 provides a table depicting that the 69 different VHHs belonged to 31 different CDR3 groups.

DETAILED DESCRIPTION

Figure 1:
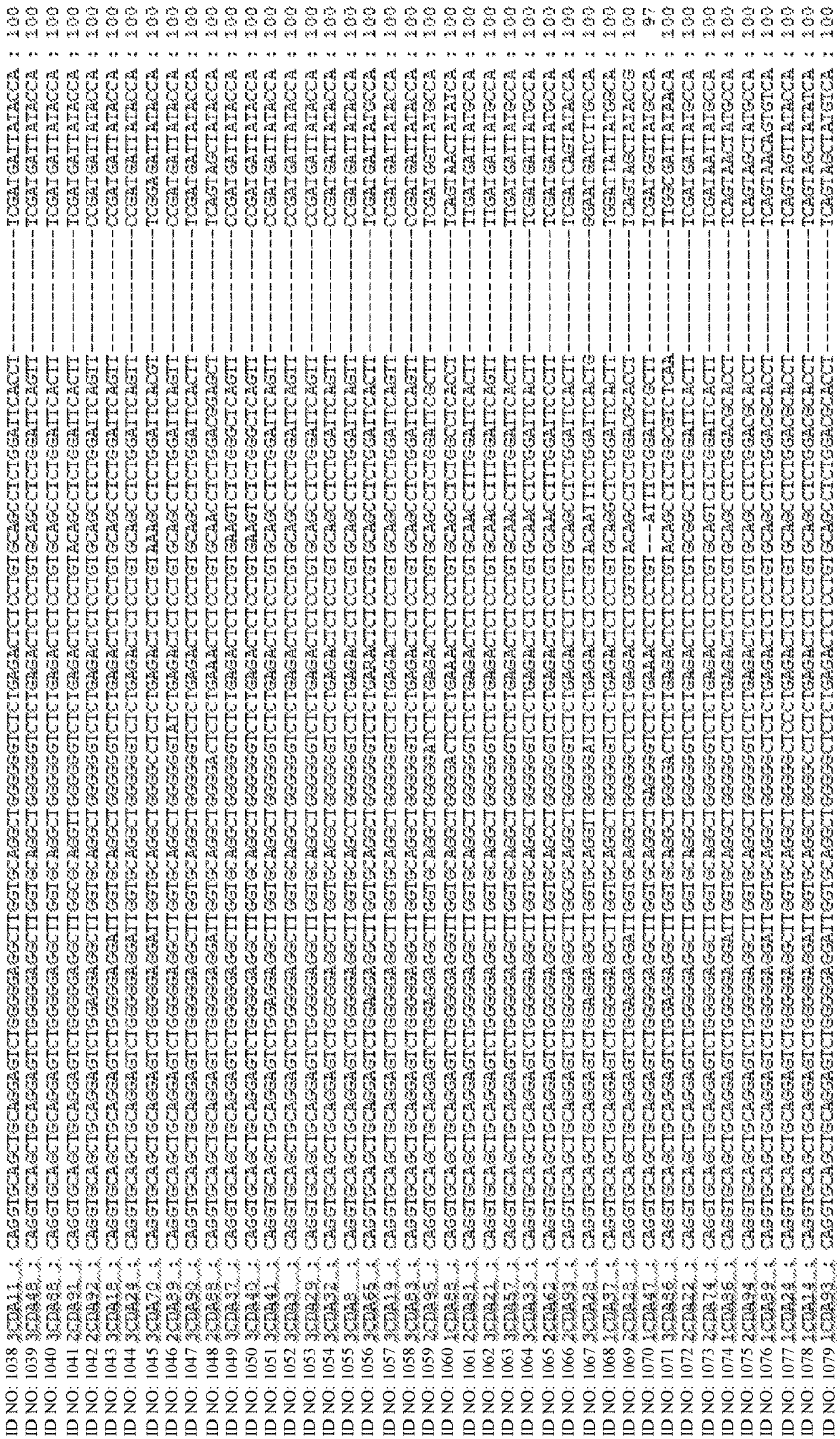
FIG. 1 depicts the nucleotide sequence of 69 different VHHs specific for human CD8. Gaps were introduced in order to align sequences.

The present invention is based, in part, on the discovery of agents (e.g. antibodies such as, by way of non-limiting example, VHHs) that recognize and bind to CD8. In various embodiments, these CD8 binding agents bind to, but do not functionally modulate CD8. In various embodiments, these CD8 binding agents may bind to and directly or indirectly recruit immune cells to sites in need of therapeutic action (e.g. a tumor). The present invention further provides pharmaceutical compositions comprising the CD8 binding agents and their use in the treatment of various diseases.

CD8 Binding Agents

In various embodiments, the present CD8 binding agent is a protein-based agent capable of specific binding to CD8. In various embodiments, the present CD8 binding agent is a protein-based agent capable of specific binding to CD8 without functionally modulating (e.g. partial or complete neutralization) CD8.

CD8 is a heterodimeric type I transmembrane glycoprotein, whose α and β chains are both comprised of an immunoglobulin (Ig)-like extracellular domain connected by an extended O-glycosylated stalk to a single-pass transmembrane domain and a short cytoplasmic tail (Li et al., 2013). The cytoplasmic region of the CD8 α-chain contains two cysteine motifs that serve as a docking site for src tyrosine kinase p56lck (Lck). In contrast, this Lck binding domain appears to be absent from the CD8 β chain, suggesting that the β chain is not involved in downstream signaling (Artyomov et al., 2010). CD8 functions as a co-receptor for the T-cell receptor with its principle role being the recruitment of Lck to the TCR-pMHC complex following co-receptor binding to MHC (Turner et al., 1990, Veillette et al., 1988). The increase in the local concentration of this kinase activates a signaling cascade that recruits and activates ζ-chain-associated protein kinase 70 (ZAP-70), subsequently leading to the amplification of T-cell activation signals (Purbhoo et al., 2001, Laugel et al., 2007a).

In various embodiments, the CD8 binding agent of the invention comprises a targeting moiety having an antigen recognition domain that recognizes an epitope present on the CD8 α and/or β chains. In an embodiment, the antigen-recognition domain recognizes one or more linear epitopes on the CD8 α and/or β chains. As used herein, a linear epitope refers to any continuous sequence of amino acids present on the CD8 α and/or β chains. In another embodiment, the antigen-recognition domain recognizes one or more conformational epitopes present on the CD8 α and/or β chains. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the CD8 binding agent of the present invention may bind to the full-length and/or mature forms and/or isoforms and/or splice variants and/or fragments and/or any other naturally occurring or synthetic analogs, variants, or mutants of human CD8 α and/or β chains. In various embodiments, the CD8 binding agent of the invention may bind to any forms of the human CD8 α and/or β chains, including monomeric, dimeric, heterodimeric, multimeric and associated forms. In an embodiment, the CD8 binding agent binds to the monomeric form of CD8 α chain or CD8 β chain. In another embodiment, the CD8 binding agent binds to a homodimeric form comprised of two CD8 α chains or two CD8 β chains. In a further embodiment, the CD8 binding agent binds to a heterodimeric form comprised of one CD8 α chain and one CD8 β chain.

In an embodiment, the present CD8 binding agent comprises a targeting moiety with an antigen recognition domain that recognizes one or more epitopes present on the human CD8 α chain. In an embodiment, the human CD8α chain comprises the amino acid sequence of Isoform 1 (SEQ ID NO:1).

In an embodiment, the human CD8 α chain comprises the amino acid sequence of Isoform 2 (SEQ ID NO:2).

In an embodiment, the human CD8 α chain comprises the amino acid sequence of Isoform 3 (SEQ ID NO:3).

In an embodiment, the present CD8 binding agent comprises a targeting moiety with an antigen recognition domain that recognizes one or more epitopes present on the human CD8 β chain. In an embodiment, the human CD8 β chain comprises the amino acid sequence of Isoform 1 (SEQ ID NO:4).

In an embodiment, the human CD8 β chain comprises the amino acid sequence of Isoform 2 (SEQ ID NO:5).

In an embodiment, the human CD8 β chain comprises the amino acid sequence of Isoform 3 (SEQ ID NO:6).

In an embodiment, the human CD8 β chain comprises the amino acid sequence of Isoform 4 (SEQ ID NO:7).

In an embodiment, the human CD8 β chain comprises the amino acid sequence of Isoform 5 (SEQ ID NO:8).

In an embodiment, the human CD8 β chain comprises the amino acid sequence of Isoform 6 (SEQ ID NO:9).

In an embodiment, the human CD8 β chain comprises the amino acid sequence of Isoform 7 (SEQ ID NO:10).

In an embodiment, the human CD8 β chain comprises the amino acid sequence of Isoform 8 (SEQ ID NO:11).

In various embodiments, the present CD8 binding agent comprises a targeting moiety capable of specific binding.

In various embodiments, the CD8 binding agent comprises a targeting moiety having an antigen recognition domain such as an antibody or derivatives thereof. In an embodiment, the CD8 binding agent comprises a targeting moiety which is an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the CD8 binding agent comprises a targeting moiety which is an antibody derivative or format. In some embodiments, the present CD8 binding agent comprises a targeting moiety which is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a $F(ab')_2$, a peptide mimetic molecule, or a synthetic molecule, as described in US Patent Nos. or Patent Publication Nos. U.S. Pat. No. 7,417,130, US 2004/132094, U.S. Pat. No. 5,831,012, US 2004/023334, U.S. Pat. Nos. 7,250, 297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the CD8 binding agent comprises a targeting moiety which is a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain ($V_HH$) and two constant domains (CH2 and CH3).

In an embodiment, the CD8 binding agent comprises a VHH. In some embodiments, the VHH is a humanized VHH or camelized VHH.

In some embodiments, the VHH comprises a fully human $V_H$ domain, e.g. a HUMABODY (Crescendo Biologics, Cambridge, UK). In some embodiments, fully human $V_H$ domain, e.g. a HUMABODY is monovalent, bivalent, or trivalent. In some embodiments, the fully human $V_H$ domain, e.g. a HUMABODY is mono- or multi-specific such as monospecific, bispecific, or trispecific. Illustrative fully human $V_H$ domains, e.g. a HUMABODIES are described in, for example, WO2016/113555 and WO2016/113557, the entire disclosure of which is incorporated by reference.

In some embodiments, the CD8 binding agent comprises a targeting moiety which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the CD8 binding agent comprises a VHH having a variable domain comprising at least one CDR1, CDR2, and/or CDR3 sequences.

In some embodiments, the CDR1 sequence is selected from:

GRSFSSYTLA; (SEQ ID NO: 12)

GRTFSSYTMG; (SEQ ID NO: 13)

GRTFSSYIMG; (SEQ ID NO: 14)

-continued

GRTFSSYTMG; (SEQ ID NO: 15)

GRTSGRTFSSYTMG; (SEQ ID NO: 16)

GRTFSSYAMG; (SEQ ID NO: 17)

GLTFSNYIMG; (SEQ ID NO: 18)

GRTFSSYTMG; (SEQ ID NO: 19)

GRTFSSDTMG; (SEQ ID NO: 20)

GLTFSNYIMG; (SEQ ID NO: 21)

GFTLDYYGIG; (SEQ ID NO: 22)

GHTFSSYTMG; (SEQ ID NO: 23)

GRTFSSYVIG; (SEQ ID NO: 24)

GFAFDGYAIG; (SEQ ID NO: 25)

GFAFGFFDMT; (SEQ ID NO: 26)

GRTFSNYVIG; (SEQ ID NO: 27)

GSIFSINVMG; (SEQ ID NO: 28)

GRTFSNYNVG; (SEQ ID NO: 29)

GHTFSSYTMG; (SEQ ID NO: 30)

GRTFSTYPVG; (SEQ ID NO: 31)

GRTFSNYAMG; (SEQ ID NO: 32)

GRTFSDYRMG; (SEQ ID NO: 33)

GLTFSNYIMA; (SEQ ID NO: 34)

GRTFSNSVMG; (SEQ ID NO: 35)

GRTFSSYIIG; (SEQ ID NO: 36)

GRTFSSYVMG; (SEQ ID NO: 37)

GGTFSNYVMG; (SEQ ID NO: 38)

GRTFSNYGIG; (SEQ ID NO: 39)

GFTFDDYAIA; (SEQ ID NO: 40)

GRTFSSYTVA; (SEQ ID NO: 41)

-continued (SEQ ID NO: 42)
GFPFDDYAIA;

(SEQ ID NO: 43)
GRTFSSYVMG;

(SEQ ID NO: 44)
GRTLSSNPMA;

(SEQ ID NO: 45)
GFTFDNYAIG;

(SEQ ID NO: 46)
GRAFSSYFMG;

(SEQ ID NO: 47)
TPTFSSYNMG;

(SEQ ID NO: 48)
GFTFDDYAIA;

(SEQ ID NO: 49)
GGTFSGYIMG;

(SEQ ID NO: 50)
GRSFSSYTIA;

(SEQ ID NO: 51)
GFSSDDYTIG;

(SEQ ID NO: 52)
GFTFDDYTIG;

(SEQ ID NO: 53)
GFSSDDYTIG;

(SEQ ID NO: 54)
GFTFDQYTIA;

(SEQ ID NO: 55)
GRTFSSYAMA;

(SEQ ID NO: 56)
GFAFDGYAIG;

(SEQ ID NO: 57)
GFSSDDYTIA;

(SEQ ID NO: 58)
GFSSDDYTIG;

(SEQ ID NO: 59)
GFTFDDYTIG;

(SEQ ID NO: 60)
GFSSDDYTIG;

(SEQ ID NO: 61)
GFSSDDYTIG;

(SEQ ID NO: 62)
GFSFDDYAIA;

(SEQ ID NO: 63)
GFSSDDYTIG;

(SEQ ID NO: 64)
GFTGNDLAIG;

(SEQ ID NO: 65)
GFSSDDYTIA;

(SEQ ID NO: 66)
EGTLSSYGIG;

(SEQ ID NO: 67)
GFSSDDYTIA;

(SEQ ID NO: 68)
GFTFDDYAIA;

-continued (SEQ ID NO: 69)
GLSSDDYTIG;

(SEQ ID NO: 70)
GLSSDDYTIG;

(SEQ ID NO: 71)
GFSSDDYTIG;

(SEQ ID NO: 73)
GFTFDDYAIA;

(SEQ ID NO: 72)
GFSFDDYTIG;

(SEQ ID NO: 74)
GFTFDDYAIG;

(SEQ ID NO: 75)
GFTFGDYTIG;

(SEQ ID NO: 76)
EGTFSSYGIG;

(SEQ ID NO: 77)
GFSSDDYTIG;

(SEQ ID NO: 78)
GVSIGDYNIG;

(SEQ ID NO: 79)
GFTFDDYTIA;

(SEQ ID NO: 80)
GFTFDDYTIA.

In some embodiments, the CDR2 sequence is selected from:

(SEQ ID NO: 81)
ASITWGGGNTY;

(SEQ ID NO: 82)
AATVWTGAGTV;

(SEQ ID NO: 83)
AAIGWSADITV;

(SEQ ID NO: 84)
AFIDWSGGGTY;

(SEQ ID NO: 85)
ATITWGGGSTY;

(SEQ ID NO: 86)
AAISWSGGPTV;

(SEQ ID NO: 87)
AAITWGGGSTV;

(SEQ ID NO: 88)
AAITWSGVSTV;

(SEQ ID NO: 89)
GAIMWSGAFTH;

(SEQ ID NO: 90)
AAITWGGGSTV;

(SEQ ID NO: 91)
SCISSSDRNTY;

(SEQ ID NO: 92)
AFIDWSGGGTY;

(SEQ ID NO: 93)
AVITWSGDSTY;

-continued (SEQ ID NO: 94)
ACISSKDGSTY;

(SEQ ID NO: 95)
SGINSIGGSTT;

(SEQ ID NO: 96)
AVVTWSGDSTY;

(SEQ ID NO: 97)
AKITNFGITS;

(SEQ ID NO: 98)
SFISWISDITY;

(SEQ ID NO: 99)
AFIDWSGGGTY;

(SEQ ID NQ: 100)
AVILWSGVSTY;

(SEQ ID NO: 101)
AAIVWSGGSTY;

(SEQ ID NO: 102)
AAISSSGYHTY;

(SEQ ID NO: 103)
SCISSPDGSTY;

(SEQ ID NO: 104)
AAVLWSGVSTA;

(SEQ ID NO: 105)
VAITWDGSATT;

(SEQ ID NO: 106)
AAIGWNGGITY;

(SEQ ID NO: 107)
GFITWSGASTY;

(SEQ ID NQ: 108)
AGINWSGESAD;

(SEQ ID NO: 109)
SCIERSDGSTY;

(SEQ ID NO: 110)
SCISNTDSSTY;

(SEQ ID NO: 111)
SCISNTDSSTY;

(SEQ ID NO: 112)
AQISWSAGSIY;

(SEQ ID NO: 113)
AGMSWNPGPAV;

(SEQ ID NO: 114)
SCISRSDGSTY;

(SEQ ID NO: 115)
ANIGWTGDMTY;

(SEQ ID NO: 116)
AAIIWSGSMTY;

(SEQ ID NO: 117)
SCISNTDSSTY;

(SEQ ID NO: 118)
AANTWSGGPTY;

(SEQ ID NO: 119)
SCISSDGSTG;

(SEQ ID NQ: 120)
SCYSSSDGSTG;

-continued (SEQ ID NO: 121)
SCISSDGSTG;

(SEQ ID NO: 122)
GCIKSSDGTTG;

(SEQ ID NO: 123)
SCISNTDSSTY;

(SEQ ID NO: 124)
AAIAWSAGSTY;

(SEQ ID NO: 125)
SCISSKEGSTY;

(SEQ ID NO: 126)
SCISSSDGSTG;

(SEQ ID NO: 127)
SCYSSRDGTTG;

(SEQ ID NO: 128)
SCISSDGSTG;

(SEQ ID NO: 129)
SCYSSSDGSTG;

(SEQ ID NO: 130)
SCFSSSDGSTG;

(SEQ ID NO: 131)
SCISNTDSSTF;

(SEQ ID NO: 132)
SCYSSSDGSTG;

(SEQ ID NO: 133)
SCISNTDSSTY;

(SEQ ID NO: 134)
SCISSSDGSTG;

(SEQ ID NO: 135)
GGINWSGDSTD;

(SEQ ID NO: 136)
SCFSSSDGSAG;

(SEQ ID NO: 137)
SCISNTDSSTY;

(SEQ ID NO: 138)
SCFSTRDGNAG;

(SEQ ID NO: 139)
SCFSSRDGSTG;

(SEQ ID NO: 140)
SCFSSRDGSTG;

(SEQ ID NO: 141)
SCISSDGSTG;

(SEQ ID NO: 142)
SCISNTDSSTY;

(SEQ ID NO: 143)
SCISSPDGSTY;

(SEQ ID NO: 144)
SCYSSSDGNTG;

(SEQ ID NO: 145)
GGINWSGDSTD;

(SEQ ID NO: 146)
SCFSSSDGSTG;

(SEQ ID NO: 147)
SCISSGDGTTY;

-continued (SEQ ID NO: 148)
SCISSDGSTG;

(SEQ ID NO: 149)
SCISSDGSTG;
and (SEQ ID NO: 1221)
SSISRSDGSTY.

In some embodiments, the CDR3 sequence is selected from:

(SEQ ID NO: 150)
AKGLRNSDWDLRRGYEYDY;

(SEQ ID NO: 151)
ADQASVPPPYGSERYDIASPSEYDY;

(SEQ ID NO: 152)
ANSRAYYSSSYDLGRLASYDY;

(SEQ ID NO: 153)
AAQRLGSVTDYTKYDY;

(SEQ ID NO: 154)
ASVKWAGSGIDISGSRNYDY;

(SEQ ID NO: 155)
AKRLDYSATDKGVDLSDEYDY;

(SEQ ID NO: 156)
AAGGSGRLRDLKVGQNYDY;

(SEQ ID NO: 157)
ADSPPRTYSSGSVNLEDGSEYDY;

(SEQ ID NO: 158)
VIPGRGSALPIDVGKSDEYEY;

(SEQ ID NO: 159)
AAGASGRLRDLKVGQNYDY;

(SEQ ID NQ: 160)
ADGNVWSPPICGSAGPPPGGMDY;

(SEQ ID NO: 161)
AAQRLGSVTDYTKYDY;

(SEQ ID NO: 162)
AIPPRAYSGGSYSLKDQSKYEY;

(SEQ ID NO: 163)
ADGNVWSPPICSSAGPPPGGMDY;

(SEQ ID NO: 164)
KSRSSYSNN;

(SEQ ID NO: 165)
AMPPRAYTGRSVSLKDQSKYEY;

(SEQ ID NO: 166)
LDTTGWGPPPYQY;

(SEQ ID NO: 167)
AHPPDPSRGGEWRLQTPSEYDY;

(SEQ ID NO: 168)
AAQRLGSVTDYTKYDY;

(SEQ ID NO: 169)
VPRSHFTTAQDMGQDMGAPSWYEY;

(SEQ ID NQ: 170)
AVLIRYYSGGYQGLSDANEYDY;

(SEQ ID NO: 171)
WKYLSGSYSYAGQYNF;

-continued (SEQ ID NO: 172)
ADFNVWSPPICGSVGPPPGGMDY;

(SEQ ID NO: 173)
AHESTYYSGTYYLTDPRRYVY;

(SEQ ID NO: 174)
AVPARGLTMDLENSDIYDH;

(SEQ ID NO: 175)
AATLQVTGSYYLDLSTVDIYDN;

(SEQ ID NO: 176)
ATLFRSNGPKDLSSGYEYDY;

(SEQ ID NO: 177)
AGESGVWVGGLDY;

(SEQ ID NO: 178)
VGSANSGEFRFGWVLKPDLYNY;

(SEQ ID NO: 179)
ADGNVWSPPICGSAGPPPGGMDY;

(SEQ ID NQ: 180)
ADGNVWSPPICGSAGPPPGGMDY;

(SEQ ID NO: 181)
ERGYAYCSDDGCQRTQDYDY;

(SEQ ID NO: 182)
GAARAWWSGSYDYTRMNNYDY;

(SEQ ID NO: 183)
AETSADSGEFRFGWVLKPSLYDY;

(SEQ ID NO: 184)
AAGSAYSGSYWNITMAANYDY;

(SEQ ID NO: 185)
AQRIFGAQPMDLSGDYEY;

(SEQ ID NO: 186)
ADGNVWSPPICGSAGPPPGGMDY;

(SEQ ID NO: 187)
ARDYRGIKDLDLKGDYDY;

(SEQ ID NO: 188)
ADFNVWSPPICGSIWYGPPPRGMDY;

(SEQ ID NO: 189)
ADSNVWSPPICGSRWYGPPPGGMAY;

(SEQ ID NQ: 190)
ADFNVWSPPICGSNWYGPPPGGMDY;

(SEQ ID NO: 191)
ADFNVWSPPICGSIWYGPPPGGMDY;

(SEQ ID NO: 192)
ADGNVWSPPICGSAGPPPGGMDY;

(SEQ ID NO: 193)
ARIITVATMRLDSDYDY;

(SEQ ID NO: 194)
ADGNVWSPPICGSAGPPPGGMDY;

(SEQ ID NO: 195)
ADSNVWSPPICGRTWYGPPPGGMDY;

(SEQ ID NO: 196)
ADFNVWSPPICGSIWYGPPPGGMAY;

(SEQ ID NO: 197)
ADFNVWSPPICGSNWYGPPPGGMDY;

(SEQ ID NO: 198)
ADFNVWSPPICGSSWYGPPPGGMDY;

-continued (SEQ ID NO: 199)
ADFNVWSPPICGSRWYGPPPGGMEY;

(SEQ ID NQ: 200)
ADGNVWSPPICGSAGPPPGGMDY;

(SEQ ID NQ: 201)
ADFNVWSPPICGSRWYGPPPGGMAY;

(SEQ ID NQ: 202)
ADGNVWSPPICGSAGPPPGGMDY;

(SEQ ID NQ: 203)
ADSNVWSPPICGKTWYGPPPGGMDY;

(SEQ ID NQ: 204)
AGESGVWVGGLDY;

(SEQ ID NO: 205)
ADSNVWSPPICGSTWYGPPPGGMAY;

(SEQ ID NQ: 206)
ADGNVWSPPICGSAGPPPGGMDY;

(SEQ ID NQ: 207)
ADFNVWSPPICGSRWYGPPPGGMDY;

(SEQ ID NQ: 208)
ADFNVWSPPICGSRWYGPPPGGMDY;

-continued (SEQ ID NO: 209)
ADFNVWSPPICGSRWYGPPPGGMDY;

(SEQ ID NO: 210)
ADFNVWSPPICGSIWYGPPPGGMDY;

(SEQ ID NO: 211)
ADGNVWSPPICGSAGPPPGGMDY;

(SEQ ID NO: 212)
ADFNVWSPPICGSVGPPPGGMDY;

(SEQ ID NO: 213)
ADFNVWSPPICGSSWYGPPPGGMAY;

(SEQ ID NO: 214)
AGESGVWGGLDY;

(SEQ ID NO: 215)
ADFNVWSPPICGSSWYGPPPGGMEY;

(SEQ ID NO: 216)
ADGNVWSPPICGSAGPPPGGMDY;

(SEQ ID NO: 217)
ADFNVWSPPICSSNWYGPPPRGMDY;

(SEQ ID NO: 218)
ADFNVWSPPICGSIWYGPPPRGMDY.

In various embodiments, the CD8 binding agent comprises an amino acid sequence selected from the following sequences:

1CDA 7
(SEQ ID NO: 219)
QVQLQESGGGLVQAGGSLRLSCAASGRSFSSYTLAWFRQAPGKEREFVASITWGGGNTYYPDSVKGRFTISRD
DAKNTVYLQMNSLKPEDTAVYYCAAKGLRNSDWDLRRGYEYDYWGQGTQVTVSSAAAYPYDVPDYGSHHHHH
H;

1CDA 12
(SEQ ID NO: 220)
QVQLQESGGGLVQDGGSLRLSCAFSGRTFSSYTMGWFRQGPGKEREFVAATVWTGAGTVYADSVKGRFTISR
DNAKNTVYLQMNSLRPEDTAVYYCAADQASVPPPYGSERYDIASPSEYDYWGQGTQVTVSSAAAYPYDVPDYG
SHHHHHH;

1CDA 14
(SEQ ID NO: 221)
QVQLQESGGGLVQAGASLRLSCAASGRTFSSYIMGWFRQAPGKEREFVAAIGWSADITVYADSVKGRFTISRDN
AENMVYLQMNSLNPEDTAVYYCAANSRAYYSSSYDLGRLASYDYWGQGTQVTVSSAAAYPYDVPDYGSHHHH
HH;

1CDA 15
(SEQ ID NO: 222)
QVQLQESGGGLVQAGGSLRLSCAASGRTFSSYTMGWFRQAPGKEREFVAFIDWSGGGTYYDDSVKGRFTISR
DNAENTVYLQMNNLEPEDTAVYYCAAAQRLGSVTDYTKYDYWGQGTQVTVSSAAAYPYDVPDYGSHHHHHH;

1CDA 17
(SEQ ID NO: 223)
QVQLQESGGGLVQAGGSLRLSCAASGRTSGRTFSSYTMGWFRQAPGKEREFVATITWGGGSTYYADSVKGRF
TISRDNANNTVYLQMNSLKPEDTAVYYCAASVKWAGSGIDISGSRNYDYWGQGTQVTVSSAAAYPYDVPDYGS
HHHHHH;

1CDA 18
(SEQ ID NO: 224)
QVQLQESGGGLVQPGGSLRLSCLASGRTFSSYAMGWFRQAPGKEREFVAAISWSGGPTVYADHVKGRFTISRD
NAKNTVYLQVNSLKPEDTADYYCAAKRLDYSATDKGVDLSDEYDYWGQGTQVTVSSAAAYPYDVPDYGSHHHH
HH;

-continued

1CDA 19

(SEQ ID NO: 225)
QVQLQESGGGLVQAGDSLRLSCAASGLTFSNYIMGWFRQAPGKEREFVAAITWGGGSTVYADSVEGRFTISRD

GTKNTVSLQMNSLLPEDTAVYYCAAAGGSGRLRDLKVGQNYDYWGQGTQVTVSSAAAYPYDVPDYGSHHHHH

H;

1CDA 24

(SEQ ID NO: 226)
QVQLQESGGGLVQAGGSLRLSCAASGRTFSSYTMGWFRQAPGREREFVAAITWSGVSTVYTDSVKGRFTVSR

DNAKNTVYLQMNSLKPEDTAVYYCAADSPPRTYSSGSVNLEDGSEYDYWGQGTQVTVSSAAAYPYDVPDYGS

HHHHHH;

1CDA 26

(SEQ ID NO: 227)
QVQLQESGGGLVQAGGSLRLSCAASGRTFSSDTMGWFRQAPGKEREFVGAIMWSGAFTHYADSVKGRFTISR

DNAKNTVYLQMNALKPEDTAVYYCAVIPGRGSALPIDVGKSDEYEYWGQGTQVTVSSAAAYPYDVPDYGSHHH

HHH;

1CDA 28

(SEQ ID NO: 228)
QVQLQESGGGLVQAGDSLRLSCAASGLTFSNYIMGWFRQAPGKEREFVAAITWGGGSTVYADSVEGRFTISRD

GTKNTVSLQMNSLQPEDTAVYYCAAAGASGRLRDLKVGQNYDYWGQGTQVTVSSAAAYPYDVPDYGSHHHHH

H;

1CDA 37

(SEQ ID NO: 229)
QVQLQESGGGLVQAGGSLRLSCAGSGFTLDYYGIGWFRQAPGKEREGVSCISSSDRNTYYADSVKGRFTISGD

NAKNTVYLQMNNLKPEDTAVYYCAADGNVWSPPICGSAGPPPGGMDYWGKGTQVTVSSAAAYPYDVPDYGSH

HHHHH;

1CDA 43

(SEQ ID NQ: 230)
QVQLQESGGGLVQAGGSLRLSCVASGHTFSSYTMGWFRQAPGKEREFVAFIDWSGGGTYYANSVKGRFTISR

DNAENTVYLQMNNLKPEDTAVYYCAAAQRLGSVTDYTKYDYWGQGTQVTVSSAAAYPYDVPDYGSHHHHHH;

1CDA 45

(SEQ ID NO: 231)
QVQLQESGGGLVQAGGSLRLSCAASGRTFSSYVIGWFRQAPGKEREFVAVITWSGDSTYSSDSLKGRFTISRDN

AKNTVYLQMNALNPEDTAVYYCAAIPPRAYSGGSYSLKDQSKYEYWGQGTQVTVSSAAAYPYDVPDYGSHHHH

HH;

1CDA 47

(SEQ ID NO: 232)
QVQLQESGGGLVQAEGSLKLSCISGFAFDGYAIGWFRQAPGKEREGVACISSKDGSTYYADSVKGRFTMSVDK

TKNTVYLQMSSLKPEDTAVYYCAADGNVWSPPICSSAGPPPGGMDYWGKGTQVTVSSAAAYPYDVPDYGSHH

HHHH;

1CDA 48

(SEQ ID NO: 233)
QVQLQESGGGLVQPGGSLTLSCAASGFAFGFFDMTWVRQAPGKGLEWVSGINSIGGSTTYADSVKGRFTISRD

NAKNELYLQMNSLKPDDTAVYYCAKSRSSYSNNWRPPGQGTQVTVSSAAAYPYDVPDYGSHHHHHH;

1CDA 58

(SEQ ID NO: 234)
QVQLQESGGGLVQARGSLTLSCAASGRTFSNYVIGWFRQAPGEEREFVAWTWSGDSTYSSDSLKGRFTISRD

NAKNTVYLQMNNLNPEDTAVYYCAAMPPRAYTGRSVSLKDQSKYEYWGQGTQVTVSSAAAYPYDVPDYGSHH

HHHH;

1CDA 65

(SEQ ID NO: 235)
QVQLQESGGGLVQPGGSLRLSCAASGSIFSINVMGWYRQTPGKERELVAKITNFGITSYADSAQGRFTISRGNAK

NTVYLQMNSLKPEDTAVYYCNLDTTGWGPPPYQYWGQGTQVTVSSAAAYPYDVPDYGSHHHHHH;

-continued

1CDA 68
(SEQ ID NO: 236)
QVQLQESGGGLVQAGASLRLSCAASGRTFSNYNVGWFRQAPGKEREFVSFISWISDITYYSDSVKGRFIISRDNA
KNMVYLQMNSLKPEDTAVYYCAAHPPDPSRGGEWRLQTPSEYDYWGQGTQVTVSSAAAYPYDVPDYGSHHH
HHH;

1CDA 73
(SEQ ID NO: 237)
QVQLQESGGGLVQAGGSLRLSCAASGHTFSSYTMGWFRQAPGKEREFVAFIDWSGGGTYYADSVKGRFTISR
DNAENTVYLQMNNLKPEDTAVYYCAAAQRLGSVTDYTKYDYWGQGTQVTVSSAAAYPYDVPDYGSHHHHHH;

1CDA 75
(SEQ ID NO: 238)
QVQLQESGGGLVQAGGSLRLSCAASGRTFSTYPVGWFRQAPGKEREFVAVILWSGVSTYYADSVKGRFTISRD
NAQNTVYLQMDSLKPEDTAVYYCAVPRSHFTTAQDMGQDMGAPSWYEYWGQGTQVTVSSAAAYPYDVPDYG
SHHHHHH;

1CDA 86
(SEQ ID NO: 239)
QVQLQESGGGLVQAGGSLRLSCAASGRTFSNYAMGWFRQAPGKEREFVAAIVWSGGSTYYADSVKGRFTISR
DNAKNTVYLQMNSLKPEDTAVYYCAAVLIRYYSGGYQGLSDANEYDYWGQGTQVTVSSAAAYPYDVPDYGSHH
HHHH;

1CDA 87
(SEQ ID NO: 240)
QVQLQESGGGLVQAGASLRLSCSASGRTFSDYRMGWFRQAPGKEREWVAAISSSGYHTYYADSVKGRFTISR
DNAKNTGYLQMSSLKPEDTAVYYCAWVKYLSGSYSYAGQYNFWGQGTQVTVSSAAAYPYDVPDYGSHHHHHH;

1CDA 88
(SEQ ID NO: 241)
QVQLQESGGGLVQAGDSLKLSCAASGLTFSNYIMAWFRQAPGKEREGVSCISSPDGSTYYADSVKGRFTISSDN
AKNTVYLQMNSLKPEDTAVYYCAADFNVWSPPICGSVGPPPGGMDYWGKGTQVTVSSAAAYPYDVPDYGSHH
HHHH;

1CDA 89
(SEQ ID NO: 242)
QVQLQESGGGLVQAGGSLRLSCAASGRTFSNSVMGWFRQPPGKEREFVAAVLWSGVSTAYADSVKGRFTISR
DNAKNTVYLQMNNLKPDDTAVYYCAAHESTYYSGTYYLTDPRRYVYWGQGTQVTVSSAAAYPYDVPDYGSHH
HHHH;

1CDA 92
(SEQ ID NO: 243)
QVQLQESGGGLVQAGGSLRLSCVGDGRTFSSYIIGWFRQAPGNEREFWAITWDGSATTYADSVKGRFTVSRD
SAKNTAYLQMNSLKPEDTAVYYCAAVPARGLTMDLENSDIYDHWGRGTQVTVSSAAAYPYDVPDYGSHHHHHH;

1CDA 93
(SEQ ID NO: 244)
QVQLQESGGGLVQAGGSLRLSCAASGRTFSSYVMGWFRQALGKEREFVAAIGWNGGITYYADSVKGRFAISRD
NAKNTVYLQMNSLKPEDTAVYYCAAATLQVTGSYYLDLSTVDIYDNWGQGTQVTVSSAAAYPYDVPDYGSHHH
HHH;

2CDA 1
(SEQ ID NO: 245)
QVQLQESGGGLVQAGGSLRLSCAASGGTFSNYVMGWFRQAPGKEREFVGFITWSGASTYYADSVKGRFTISR
DNAENTVYLQMNSLKPEDTAVYYCAATLFRSNGPKDLSSGYEYDYWGQGTQVTVSSAAAYPYDVPDYGSHHH
HHH;

2CDA 5
(SEQ ID NO: 246)
QVQLQESGGGLVQAGDSLRLTCTASGRTFSNYGIGWFRQAPGKEREFVAGINWSGESADYADSVKGRFTISRD
NAKNTVYLQMNSLKPEDTAVYYCAAGESGVWVGGLDYWXQGTQVTVSSAAAYPYDVPDYGSHHHHHH;

-continued

2CDA 22

(SEQ ID NO: 247)

QVQLQESGGGLVQAGGSLRLSCAASGFTFDDYAIAWFRQAPGKEREGVSCIERSDGSTYYADSVKGRFTISSDN

AKNTVYLQMNSLKPEDTAVYYCAVGSANSGEFRFGWVLKPDLYNYWGQGTQVTVSSAAAYPYDVPDYGSHHH

HHH;

2CDA 28

(SEQ ID NO: 248)

QVQLQESGGGLVQAGGSLRLSCTASGRTFSSYTVAWFRQSPGKEREGISCISNTDSSTYYADSVKGRFTISSDN

AKSTVHLQMSSLKPEDTAVYYCAADGNVWSPPICGSAGPPPGGMDYWGKGTQVTVSSAAAYPYDVPDYGSHH

HHHH;

2CDA 62

(SEQ ID NO: 249)

QVQLQESGGGLVQPGGSLRLSCATFGFPFDDYAIAWFRQAPGKEREGVSCISNTDSSTYYADSVKGRFTISSDN

AKNTVHLQMSSLKPEDTAVYYCAADGNVWSPPICGSAGPPPGGMDYWGKGTQVTVSSAAAYPYDVPDYGSHH

HHHH;

2CDA 68

(SEQ ID NO: 250)

QVQLQESGGGLVQAGGSLRLSCAASGRTFSSYVMGWFRQAPGKEREFVAQISWSAGSIYYADSVKGRFTISND

NAKRTVYLQMNSLKPEDTAVYYCAERGYAYCSDDGCQRTQDYDYWGQGTQVTVSSAAAYPYDVPDYGSHHH

HHH;

2CDA 73

(SEQ ID NO: 251)

QVQLQESGGGLVQAGGSLRLSCAASGRTLSSNPMAWFRQAAGKEREFVAGMSWNPGPAVYADSVKGRFTISR

DSAENTVYLQMNSLKPEDTAVYYCAGAARAWWSGSYDYTRMNNYDYWGPGTQVTVSSAAAYPYDVPDYGSH

HHHHH;

2CDA 74

(SEQ ID NO: 252)

QVQLQESGGGLVQAGGSLRLSCAVSGFTFDNYAIGWFRQAPGKEREGVSCISRSDGSTYYADSVRGRFTISSD

NAKNTVYLQMNSLKPEDTAVYYCAAETSADSGEFRFGWVLKPSLYDYWGQGTQVTVSSAAAYPYDVPDYGSH

HHHHH;

2CDA 74(C50S)

(SEQ ID NO: 216)

QVQLQESGGGLVQAGGSLRLSCAVSGFTFDNYAIGWFRQAPGKEREGVSSISRSDGSTYYADSVRGRFTISSD

NAKNTVYLQMNSLKPEDTAVYYCAAETSADSGEFRFGWVLKPSLYDYWGQGTQVTVSS;

2CDA 75

(SEQ ID NO: 253)

QVQLQESGGGLVQAGGSLRLSCAASGRAFSSYFMGWFRQTPGKEREFVANIGWTGDMTYYADSVKGRFTISR

DNAKNTVYLQMNSLKPEDTAVYYCAAAGSAYSGSYWNITMAANYDYWGQGTQVTVSSAAAYPYDVPDYGSHH

HHHH;

2CDA 77

(SEQ ID NO: 254)

QVQLQESGGGLVQAGGSLRLSCAASTPTFSSYNMGWFRQAPGKEREFVAAIIWSGSMTYYADSMKGRFTVSID

NAKNTVYLQMNSLKPEDTAVYYCAAQRIFGAQPMDLSGDYEYWGQGTQVTVSSAAAYPYDVPDYGSHHHHHH;

2CDA 81

(SEQ ID NO: 255)

QVQLQESGGGLVQAGGSLRLSCATFGFTFDDYAIAWFRQAPGKEREGISCISNTDSSTYYADSVKGRFTISSDSA

KNTVHLQMSSLKPEDTAVYYCAADGNVWSPPICGSAGPPPGGMDYWGKGTQVTVSSAAAYPYDVPDYGSHHH

HHH;

-continued

2CDA 87

(SEQ ID NO: 256)

QVQLQESGGGLVQAGGSLRLSCKASGGTFSGYIMGWFRQAPGKEREFVAANTWSGGPTYYSDSVKGRFTISR

DNAKNTVYLQMNTLKPEDTAVYQCAARDYRGIKDLDLKGDYDYWGQGTQVTVSSAAAYPYDVPDYGSHHHHH

H;

2CDA 88

(SEQ ID NO: 257)

QVQLQESGGGLVQAGDSLKLSCATSGRSFSSYTIAWFRQAPGKEREGISCISSDGSTGYADSVRGRFTISSDNA

KNTVYLQMNSLKPEDTAVYYCAADFNVWSPPICGSIWYGPPPRGMDYWGKGTQVTVSSAAAYPYDVPDYGSH

HHHHH;

2CDA 89

(SEQ ID NO: 258)

QVQLQESGGGLVQAGGYLRLSCAASGFSSDDYTIGWFRQAPGKEREGISCYSSSDGSTGFADSVKGRFTISSD

NAKNTVYLQMNNLRPEDTAVYYCAADSNVWSPPICGSRWYGPPPGGMAYWGKGTQVTVSSAAAYPYDVPDY

GSHHHHHH;

2CDA 91

(SEQ ID NO: 259)

QVQLQESGGGLAQVGGSLRLSCTASGFTFDDYTIGWFRQAPGKEREGISCISSDGSTGYADSVKGRFTISSDNA

KNTVYLQMNSLKPEDTAVYYCAADFNVWSPPICGSNWYGPPPGGMDYWGKGTQVTVSSAAAYPYDVPDYGSH

HHHHH;

2CDA 92

(SEQ ID NQ: 260)

QVQLQESGGGLVQAGGSLRLSCAASGFSSDDYTIGWFRQAPGKEREGIGCIKSSDGTTGYADSVKGRFTISSDN

AKNTVYLQMNSLKPEDTAVYYCAADFNVWSPPICGSIWYGPPPGGMDYWGKGTQVTVSSAAAYPYDVPDYGS

HHHHHH;

2CDA 93

(SEQ ID NO: 261)

QVQLQESGGGLAQAGGSLRLSCAASGFTFDQYTIAWFRQAPGKEREGVSCISNTDSSTYYADSVKGRFTISSDN

AKNTVYLQMSSLKPEDTAVYYCAADGNVWSPPICGSAGPPPGGMDYWGKGTQVTVSSAAAYPYDVPDYGSHH

HHHH;

2CDA 94

(SEQ ID NO: 262)

QVQLQESGGGLVQAGGSLRLSCAASGRTFSSYAMAWFRQAPGKEREFVAAIAWSAGSTYYADSVKGRFAISRD

NAENTVYLQMNSLKPEDTAVYYCAARIITVATMRLDSDYDYWGQGTQVTVSSAAAYPYDVPDYGSHHHHHH;

2CDA 95

(SEQ ID NO: 263)

QVQLQESGGGLVQAGGSLRLSCAASGFAFDGYAIGWFRQAPGKEREGVSCISSKEGSTYYADSVKGRFTISSD

NAKNTVYLQMSSLKPEDTAVYYCAADGNVWSPPICGSAGPPPGGMDYWGKGTQVTVSSAAAYPYDVPDYGSH

HHHHH;

3CDA 3

(SEQ ID NO: 264)

QVQLQESGGGLVQAGGSLRLSCAASGFSSDDYTIAWFRRAPGKEREGISCISSSDGSTGYADSVKGRFTITSDS

AKNTVYLQMNSLKPEDTAVYYCAADSNVWSPPICGRTWYGPPPGGMDYWGKGTQVTVSSAAAYPYDVPDYGS

HHHHHH;

3CDA 8

(SEQ ID NO: 265)

QVQLQESGGGLVQPGGSLRLSCAASGFSSDDYTIGWFRQAPGKEREGISCYSSRDGTTGYADSVKGRFTISSD

NAKNTVYLQMNSLKPEDTAVYYCAADFNVWSPPICGSIWYGPPPGGMAYWGQGTQVTVSSAAAYPYDVPDYG

SHHHHHH;

-continued

3CDA 11

(SEQ ID NO: 266)
QVQLQESGGGLVQAGGSLRLSCAASGFTFDDYTIGWFRQAPGKEREGISCISSDGSTGYADSVKGRFTISSDNA

KNTVYLQMNSLKPEDTAVYYCAADFNVWSPPICGSNWYGPPPGGMDYWGKGTQVTVSSAAAYPYDVPDYGSH

HHHHH;

3CDA 18

(SEQ ID NO: 267)
QVQLQESGGGLVQAGGSLRLSCAASGFSSDDYTIGWFRQAPGKEREGISCYSSSDGSTGYADSVKGRFTISSD

NAKNTVYLQMNSLKPEDTAVYYCAADFNVWSPPICGSSWYGPPPGGMDYWGKGTQVTVSSAAAYPYDVPDYG

SHHHHHH;

3CDA 19

(SEQ ID NO: 268)
QVQLQESGGGLVQAGGSLRLSCAASGFSSDDYTIGWFRQAPGKEREGISCFSSSDGSTGFADSVKGRFTISSD

NATNTVYLEMNSLKPEDTAVYYCAADFNVWSPPICGSRWYGPPPGGMEYWGKGTQVTVSSAAAYPYDVPDYG

SHHHHHH;

3CDA 21

(SEQ ID NO: 269)
QVQLQESGGGLVQAGGSLRLSCATFGFSFDDYAIAWFRQAPGKEREGISCISNTDSSTFYADSVKGRFTISSDNA

KNTVHLQMSSLKPEDTAVYYCAADGNVWSPPICGSAGPPPGGMDYWGKGTQVTVSSAAAYPYDVPDYGSHHH

HHH;

3CDA 24

(SEQ ID NQ: 270)
QVQLQESGGGLVQAGGSLRLSCAASGFSSDDYTIGWFRQAPGKEREGISCYSSSDGSTGFADSVKGRFTISSD

NAKNTVYLQMNSLRPEDTAVYYCAADFNVWSPPICGSRWYGPPPGGMAYWGKGTQVTVSSAAAYPYDVPDYG

SHHHHHH;

3CDA 28

(SEQ ID NO: 271)
QVQLQESGGGLVQVGGSLRLSCTISGFTGNDLAIGWFRQAPGKDQREGISCISNTDSSTYYADSVKGRFTISSDN

AKNTVHLQMSSLKPEDTAVYYCAADGNVWSPPICGSAGPPPGGMDYWGKGTQVTVSSAAAYPYDVPDYGSHH

HHHH;

3CDA 29

(SEQ ID NO: 272)
QVQLQESGGGLVQAGGSLRLSCAASGFSSDDYTIAWFRRAPGKEREGISCISSSDGSTGYADSVKGRFTISSDN

AKNTVYLQMTSLKPEDTAVYYCAADSNVWSPPICGKTWYGPPPGGMDYWGKGTQVTVSSAAAYPYDVPDYGS

HHHHHH;

3CDA 31

(SEQ ID NO: 273)
QVQLQESGGGLVQAGDSLRLSCAGSEGTLSSYGIGWFRQAPGKEREFVGGINWSGDSTDYADSVKGRFTISRD

SAKNTVYLQMNSLKPEDTAVYYCAAGESGVWVGGLDYWGQGTQVTVSSAAAYPYDVPDYGSHHHHHH;

3CDA 32

(SEQ ID NO: 274)
QVQLQESGGGLVQAGGSLRLSCAASGFSSDDYTIAWFRRAPGKEREGISCFSSSDGSAGYADSVKGRFTVSSD

NAKNTVYLQMNSLKPEDTAVYYCAADSNVWSPPICGSTWYGPPPGGMAYWGKGTQVTVSSAAAYPYDVPDYG

SHHHHHH;

3CDA 33

(SEQ ID NO: 275)
QVQLQESGGGLVQAGGSLRLSCATSGFTFDDYAIAWFRQAPGKEREGVSCISNTDSSTYYADSVKGRFTISSDN

AKNTVYLQMSSLKPEDTAVYYCAADGNVWSPPICGSAGPPPGGMDYWGKGTQVTVSSAAAYPYDVPDYGSHH

HHHH;

-continued

3CDA 37
(SEQ ID NO: 276)
QVQLQESGGGLVQAGGSLRLSCEVSGLSSDDYTIGWFRQAPGKEREGFSCFSTRDGNAGYADSVKGRFTISSD
NAKNTVYLQMNNLKPEDTAVYYCAADFNVWSPPICGSRWYGPPPGGMDYWGKGTQVTVSSAAAYPYDVPDYG
SHHHHHH;

3CDA 40
(SEQ ID NO: 277)
QVQLQESGGGLVQAGGSLRLSCEVSGLSSDDYTIGWFRQAPGKKREGFSCFSSRDGSTGYADSVKGRFTISSD
NAKNTVYLQMNSLKPEDTAVYYCAADFNVWSPPICGSRWYGPPPGGMDYWGKGTQVTVSSAAAYPYDVPDYG
SHHHHHH;

3CDA 41
(SEQ ID NO: 278)
QVQLQESGGGLVQAGGSLRLSCAASGFSSDDYTIGWFRQAPGKEREGFSCFSSRDGSTGYADSVKGRFTISSD
NAKNTVYLQMNSLKPEDTAVYYCAADFNVWSPPICGSRWYGPPPGGMDYWGKGTQVTVSSAAAYPYDVPDYG
SHHHHHH;

3CDA 48
(SEQ ID NO: 279)
QVQLQESGGGLVQAGGSLRLSCAASGFSFDDYTIGWFRQVPGKEREGISCISSDGSTGYADSVKGRFTISSDNA
KNTVYLQINSLKPEDTAVYYCAADFNVWSPPICGSIWYGPPPGGMDYWGKGTQVTVSSAAAYPYDVPDYGSHH
HHHH;

3CDA 57
(SEQ ID NQ: 280)
QVQLQESGGGLVQAGGSLRLSCATFGFTFDDYAIAWFRQAPGKEREGISCISNTDSSTYYADSVKGRFTISSDNA
KNTVHLQMSSLKPEDTAVYYCAADGNVWSPPICGSAGPPPGGMDYWGKGTQVTVSSAAAYPYDVPDYGSHHH
HHH;

3CDA 65
(SEQ ID NO: 281)
QVQLQESGGGLVQAGGSLXLSCAASGFTFDDYAIGWFRQAPGKEREGVSCISSPDGSTYYADSVKGRFTISSDN
AKNTVYLQMNSLKPEDTAVYYCAADFNVWSPPICGSVGPPPGGMDYWGKGTQVTVSSAAAYPYDVPDYGSHH
HHHH;

3CDA 70
(SEQ ID NO: 282)
QVQLQESGGGLVQAGASLRLSCKASGFTFGDYTIGWFRQAPGKEREGISCYSSSDGNTGYADSVKGRFTISSD
NAKNTVYLQMNSLRPEDTAVYYCAADFNVWSPPICGSSWYGPPPGGMAYWGKGTQVTVSSAAAYPYDVPDYG
SHHHHHH;

3CDA 73
(SEQ ID NO: 283)
QVQLQESGGGLVQAGDSLRLSCAGSEGTFSSYGIGWFRQAPGKEREFVGGINWSGDSTDYADSVKGRFTISRD
NAKNTVYLQMNSLKPEDTAVYYCAAGESGVWVGGLDYWGQGTQVTVSSAAAYPYDVPDYGSHHHHHH;

3CDA 83
(SEQ ID NO: 284)
QVQLQESGGGLVQAGGSLRLSCAASGFSSDDYTIGWFRQAPGKEREGISCFSSSDGSTGFADSVKGRFTISSD
NATNTVYLQMNSLKPEDTAVYYCAADFNVWSPPICGSSWYGPPPGGMEYWGKGTQVTVSSAAAYPYDVPDYG
SHHHHHH;

3CDA 86
(SEQ ID NO: 285)
QVQLQESGGGLVQAGDSLRLSCTASGVSIGDYNIGWFRQAPGKEREGVSCISSGDGTTYYTDSVKGRFTISTDN
AKNTVYLQMNSLKPEDTAVYYCAADGNVWSPPICGSAGPPPGGMDYWGKGTQVTVSSAAAYPYDVPDYGSHH
HHHH;

-continued

3CDA 88

(SEQ ID NO: 286)

QVQLQESGGGLVQAGGSLRLSCAASGFTFDDYTIAWFRQAPGGKEREGISCISSDGSTGYADSVKGRFTISSDN

AKNMVYLQMNSLKPEDTALYYCAADFNVWSPPICSSNWYGPPPRGMDYWGKGTQVTVSSAAAYPYDVPDYGS

HHHHHH;

or

3CDA 90

(SEQ ID NO: 287)

QVQLQESGGGLVQAGGSLRLSCAASGFTFDDYTIAWFRQAPGKEREGISCISSDGSTGYADSVRGRFTISSDNA

KNTVYLQMNSLKPEDTAVYYCAADFNVWSPPICGSIWYGPPPRGMDYWGKGTQVTVSSAAAYPYDVPDYGSH

HHHHH.

In various exemplary embodiments, the CD8 binding agent comprises an amino acid sequence selected from any one of the above sequences without the terminal histidine tag sequence (i.e., HHHHHH, SEQ ID NO: 1213).

In some embodiments, the CD8 binding agent comprises an amino acid sequence selected from any one of the above sequences without the HA tag (i.e., YPYDVPDYGS; SEQ ID NO: 1214).

In some embodiments, the CD8 binding agent comprises an amino acid sequence selected from any one of the above sequences without the AAA linker.

In some embodiments, the CD8 binding agent comprises an amino acid sequence selected from any one of the above sequences without the AAA linker, HA tag, and terminal histidine tag sequence (i.e.,

AAAYPYDVPDYGSHHHHHH; SEQ ID NO: 1215).

In various embodiments, the present invention contemplates the use of any natural or synthetic analogs, mutants, variants, alleles, homologs and orthologs (herein collectively referred to as "analogs") of the CD8 binding agent of the invention as described herein. In various embodiments, the amino acid sequence of the CD8 binding agent further includes an amino acid analog, an amino acid derivative, or other non-classical amino acids.

In various embodiments, the CD8 binding agent comprises a targeting moiety comprising a sequence that is at least 60% identical to any one of the sequences disclosed herein. For example, the CD8 binding agent may comprise a targeting moiety comprising a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any one of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the sequences disclosed herein.

In various embodiments, the CD8 binding agent comprises a targeting moiety comprising an amino acid sequence having one or more amino acid mutations with respect to any one of the sequences disclosed herein. In various embodiments, the CD8 binding agent comprises a targeting moiety comprising an amino acid sequence having one, or two, or three, or four, or five, or six, or seen, or eight, or nine, or ten, or fifteen, or twenty amino acid mutations with respect to any one of the sequences disclosed herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, lie; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In various embodiments, the amino acid mutation may be in the CDRs of the targeting moiety (e.g., the CDR1, CDR2 or CDR3 regions). In another embodiment, amino acid alteration may be in the framework regions (FRs) of the targeting moiety (e.g., the FR1, FR2, FR3, or FR4 regions).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In various embodiments, the mutations do not substantially reduce the present CD8 binding agent's capability to specifically bind to CD8. In various embodiments, the mutations do not substantially reduce the present CD8 binding agent's capability to specifically bind to CD8 without functionally modulating CD8.

In various embodiments, the binding affinity of the CD8 binding agent of the invention for the full-length and/or mature forms and/or isoforms and/or splice variants and/or fragments and/or any other naturally occurring or synthetic analogs, variants, or mutants (including monomeric, dimeric, heterodimeric, multimeric and/or associated forms) of human CD8 α and/or β chains may be described by the equilibrium dissociation constant ($K_D$). In various embodiments, the CD8 binding agent comprises a targeting moiety that binds to the full-length and/or mature forms and/or isoforms and/or splice variants and/or fragments and/or any other naturally occurring or synthetic analogs, variants, or mutants (including monomeric, dimeric, heterodimeric, multimeric and/or associated forms) of human CD8 α and/or β chains with a $K_D$ of less than about 1 uM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, or about 5 nM, or about 1 nM.

In various embodiments, the CD8 binding agent comprises a targeting moiety that binds but does not functionally modulate the antigen of interest, i.e., CD8. For instance, in various embodiments, the targeting moiety of the CD8 binding agent simply targets the antigen but does not substantially functionally modulate the antigen, e.g. it does not substantially inhibit, reduce or neutralize a biological effect that the antigen has. In various embodiments, the targeting moiety of the CD8 binding agent binds an epitope that is physically separate from an antigen site that is important for its biological activity (e.g. an antigen's active site).

Such non-functionally modulating (e.g. non-neutralizing) binding finds use in various embodiments of the present invention, including methods in which the present CD8 binding agent is used to directly or indirectly recruit active immune cells to a site of need via an effector antigen. For example, in various embodiments, the present CD8 binding agent may be used to directly or indirectly recruit cytotoxic T cells via CD8 to a tumor cell in a method of reducing or eliminating a tumor (e.g. the CD8 binding agent may comprise a targeting moiety having an anti-CD8 antigen recognition domain and a targeting moiety having a recognition domain (e.g. an antigen recognition domain) directed against a tumor antigen or receptor). In such embodiments, it is desirable to directly or indirectly recruit CD8-expressing cytotoxic T cells but not to neutralize the CD8 activity. In these embodiments, CD8 signaling is an important piece of the tumor reducing or eliminating effect.

Therapeutic Agents Comprising the Present CD8 Binding Agents

Chimeras and Fusions with Signaling Agents

In various embodiments, the CD8 binding agent of the invention is part of a chimera or fusion with one or more signaling agents. Accordingly, the present invention provides for chimeric or fusion proteins that include, for example, a targeting moiety against CD8 and one or more signaling agents.

In various embodiments, the signaling agent is modified to have reduced affinity or activity for one or more of its receptors, which allows for attenuation of activity (inclusive of agonism or antagonism) and/or prevents non-specific signaling or undesirable sequestration of the chimeric or fusion protein. In various embodiments, the signaling agent is antagonistic in its wild type form and bears one or more mutations that attenuate its antagonistic activity. In various embodiments, the signaling agent is antagonistic due to one or more mutations, e.g. an agonistic signaling agent is converted to an antagonistic signaling agent and, such a converted signaling agent, optionally, also bears one or more mutations that attenuate its antagonistic activity (e.g. as described in WO 2015/007520, the entire contents of which are hereby incorporated by reference).

Accordingly, in various embodiments, the signaling agent is a modified (e.g. mutant) form of the signaling agent having one or more modifications (e.g. mutations). In various embodiments, the mutations allow for the modified signaling agent to have one or more of attenuated activity such as one or more of reduced binding affinity, reduced endogenous activity, and reduced specific bioactivity relative to unmutated, i.e. the wild type form of the signaling agent (e.g. comparing the same signaling agent in a wild type form versus a modified (e.g. mutant) form). In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in various embodiments, the mutations allow for the signaling agent to have improved safety, e.g. reduced systemic toxicity, reduced side effects, and reduced off-target effects relative to unmutated, i.e. wild type, signaling agent (e.g. comparing the same signaling agent in a wild type form versus a modified (e.g. mutant) form).

As described herein, the agent may have improved safety due to one of more modifications, e.g. mutations. In various embodiments, improved safety means that the present chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window.

In various embodiments, the signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In various embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or mutations that reduce its binding affinity or activity for one or more of its receptors or that substantially reduce or ablate binding affinity or activity for one or more of its receptors.

In some embodiments, the reduced affinity or activity at the receptor is restorable by attachment with one or more of the targeting moieties as described herein (e.g., targeting moiety against CD8). In other embodiments, the reduced affinity or activity at the receptor is not substantially restorable by the activity of one or more of the targeting moieties.

In various embodiments, the chimeric proteins of the present invention reduce off-target effects because their signaling agents have mutations that weaken or ablate binding affinity or activity at a receptor. In various embodiments, this reduction in side effects is observed relative with, for example, the wild type signaling agents. In various embodiments, the signaling agent is active on target cells because the targeting moiety(ies) compensates for the missing/insufficient binding (e.g., without limitation and/or avidity) required for substantial activation. In various embodiments, the modified signaling agent is substantially inactive en route to the site of therapeutic activity and has its effect substantially on specifically targeted cell types which greatly reduces undesired side effects.

In some embodiments, the signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor. In some embodiments, the mutation(s) that reduce binding and/or activity at one receptor is the same as the mutation(s) that substantially reduce or ablate at another receptor. In some embodiments, the present chimeric proteins have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially restorable with a targeting moiety (e.g., a targeting moiety against CD8 or any other targeting moiety described herein). In some embodiments, the substantial reduction or ablation of binding or activity is restorable with a targeting moiety. In various embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins away from the site of therapeutic action. For instance, in some embodiments, this obviates the need of high doses of the present chimeric proteins that compensate for loss at the other receptor. Such ability to reduce dose further provides a lower likelihood of side effects.

In various embodiments, the modified signaling agent comprises one or more mutations that cause the signaling agent to have reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_I$ and/or $IC_{50}$), for one or more of its receptors. In various embodiments, the reduced affinity at the immumodulating agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent.

In embodiments wherein the modified signaling agent has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent.

In some embodiments, the modified signaling agent comprises one or more mutations that cause the signaling agent to have reduced affinity for its receptor that is lower than the binding affinity of the targeting moiety(ies) for its(their) receptor(s). In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

In various embodiments, the signaling agent is an immune-modulating agent, e.g. one or more of an interleukin, interferon, and tumor necrosis factor.

In some embodiments, the signaling agent is an interleukin or a modified interleukin, including for example IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; IL-36 or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. Interleukin activity can be determined using assays known in the art: Matthews et al., in *Lymphokines and Interferens: A Practical Approach*, Clemens et al., eds, IRL Press, Washington, D.C. 1987, pp. 221-225; and Orencole & Dinarello (1989) Cytokine 1, 14-20.

In some embodiments, the signaling agent is an interferon or a modified version of an interferon such as interferon types I, II, and III. Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon $\overline{\omega}$.

In some embodiments, the signaling agent is a tumor necrosis factor (TNF) or a modified version of a tumor necrosis factor (TNF) or a protein in the TNF family, including but not limited to, TNF-α, TNF-β, LT-β, CD40L, CD27L, CD30L, FASL, 4-1BBL, OX40L, and TRAIL.

The amino acid sequences of the wild type signaling agents described herein are well known in the art. Accordingly, in various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified signaling agent comprises an amino acid sequence having one or more amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions, as described elsewhere herein. In various embodiments, the substitutions may also include non-classical amino acids as described elsewhere herein.

As described herein, the modified signaling agents bear mutations that affect affinity and/or activity at one or more receptors. In various embodiments, there is reduced affinity and/or activity at a therapeutic receptor, e.g. a receptor through which a desired therapeutic effect is mediated (e.g. agonism or antagonism). In various embodiments, the modified signaling agents bear mutations that substantially reduce or ablate affinity and/or activity at a receptor, e.g. a receptor through which a desired therapeutic effect is not mediated (e.g. as the result of promiscuity of binding). The receptors of any modified signaling agents, e.g. one of the cytokines, growth factors, and hormones as described herein, are known in the art.

Illustrative mutations which provide reduced affinity and/or activity (e.g. agonistic) at a receptor are found in WO 2013/107791 and PCT/EP2017/061544 (e.g. with regard to interferons), WO 2015/007542 (e.g. with regard to interleukins), and WO 2015/007903 (e.g. with regard to TNF), the entire contents of each of which are hereby incorporated by reference. Illustrative mutations which provide reduced affinity and/or activity (e.g. antagonistic) at a therapeutic receptor are found in WO 2015/007520, the entire contents of which are hereby incorporated by reference.

In some embodiments, the modified signaling agent comprises one or more mutations that cause the signaling agent to have reduced affinity and/or activity for a type I cytokine receptor, a type II cytokine receptor, a chemokine receptor, a receptor in the Tumor Necrosis Factor Receptor (TNFR) superfamily, TGF-beta Receptors, a receptor in the immunoglobulin (Ig) superfamily, and/or a receptor in the tyrosine kinase superfamily.

In various embodiments, the receptor for the signaling agent is a Type I cytokine receptor. Type I cytokine receptors are known in the art and include, but are not limited to receptors for IL2 (beta-subunit), IL3, IL4, IL5, IL6, IL7, IL9, IL11, IL12, GM-CSF, G-CSF, LIF, CNTF, and also the receptors for Thrombopoietin (TPO), Prolactin, and Growth hormone. Illustrative type I cytokine receptors include, but are not limited to, GM-CSF receptor, G-CSF receptor, LIF receptor, CNTF receptor, TPO receptor, and type I IL receptors.

In various embodiments, the receptor for the signaling agent is a Type II cytokine receptor. Type II cytokine receptors are multimeric receptors composed of heterologous subunits, and are receptors mainly for interferons. This family of receptors includes, but is not limited to, receptors for interferon-α, interferon-β and interferon-γ, IL10, IL22, and tissue factor. Illustrative type II cytokine receptors include, but are not limited to, IFN-α receptor (e.g. IFNAR1 and IFNAR2), IFN-β receptor, IFN-γ receptor (e.g. IFNGR1 and IFNGR2), and type II IL receptors.

In various embodiments, the receptor for the signaling agent is a G protein-coupled receptor. Chemokine receptors are G protein-coupled receptors with seven transmembrane structure and coupled to G-protein for signal transduction. Chemokine receptors include, but are not limited to, CC chemokine receptors, CXC chemokine receptors, CX3C chemokine receptors, and XC chemokine receptor (XCR1). Exemplary chemokine receptors include, but are not limited to, CCR1, CCR2, CCR3, CCR4, CCR5, CCR6, CCR7, CCR8, CCR9, CCR10, CXCR1, CXCR2, CXCR3, CXCR3B, CXCR4, CXCR5, CSCR6, CXCR7, XCR1, and CX3CR1.

In various embodiments, the receptor for the signaling agent is a TNFR family member. Tumor necrosis factor receptor (TNFR) family members share a cysteine-rich domain (CRD) formed of three disulfide bonds surrounding a core motif of CXXCXXC creating an elongated molecule. Exemplary tumor necrosis factor receptor family members include: CDI 20a (TNFRSFIA), CD 120b (TNFRSFIB), Lymphotoxin beta receptor (LTBR, TNFRSF3), CD 134 (TNFRSF4), CD40 (CD40, TNFRSF5), FAS (FAS, TNFRSF6), TNFRSF6B (TNFRSF6B), CD27 (CD27, TNFRSF7), CD30 (TNFRSF8), CD137 (TNFRSF9), TNFRSFIOA (TNFRSFIOA), TNFRSFIOB, (TNFRSFIOB), TNFRSFIOC (TNFRSFIOC), TNFRSFIOD (TNFRSFIOD), RANK (TNFRSFI IA), Osteoprotegerin (TNFRSFI IB), TNFRSF12A (TNFRSF12A), TNFRSF13B (TNFRSF13B), TNFRSF13C (TNFRSF13C), TNFRSF14 (TNFRSF14), Nerve growth factor receptor (NGFR, TNFRSF16), TNFRSF17 (TNFRSF17), TNFRSF18 (TNFRSF18), TNFRSF19 (TNFRSF19), TNFRSF21 (TNFRSF21), and TNFRSF25 (TNFRSF25). In an embodiment, the TNFR family member is CD120a (TNFRSF1A) or TNF-R1. In another embodiment, the TNFR family member is CD 120b (TNFRSFIB) or TNF-R2.

In various embodiments, the receptor for the signaling agent is a TGF-beta receptor. TGF-beta receptors are single pass serine/threonine kinase receptors. TGF-beta receptors include, but are not limited to, TGFBR1, TGFBR2, and TGFBR3.

In various embodiments, the receptor for the signaling agent is an Ig superfamily receptor. Receptors in the immunoglobulin (Ig) superfamily share structural homology with immunoglobulins. Receptors in the Ig superfamily include, but are not limited to, interleukin-1 receptors, CSF-1R, PDGFR (e.g. PDGFRA and PDGFRB), and SCFR.

In various embodiments, the receptor for the signaling agent is a tyrosine kinase superfamily receptor. Receptors in the tyrosine kinase superfamily are well known in the art. There are about 58 known receptor tyrosine kinases (RTKs), grouped into 20 subfamilies. Receptors in the tyrosine kinase superfamily include, but are not limited to, FGF receptors and their various isoforms such as FGFR1, FGFR2, FGFR3, FGFR4, and FGFR5.

In an embodiment, the modified signaling agent is interferon α. In such embodiments, the modified IFN-α agent has reduced affinity and/or activity for the IFN-α/β receptor (IFNAR), i.e., IFNAR1 and/or IFNAR2 chains. In some embodiments, the modified IFN-α agent has substantially reduced or ablated affinity and/or activity for the IFN-α/β receptor (IFNAR), i.e., IFNAR1 and/or IFNAR2 chains.

Mutant forms of interferon α are known to the person skilled in the art. In an illustrative embodiment, the modified signaling agent is the allelic form IFN-α2a having the amino acid sequence of IFN-α2a (SEQ ID NO:288).

In an illustrative embodiment, the modified signaling agent is the allelic form IFN-α2b having the amino acid sequence of (which differs from IFN-α2a at amino acid position 23) IFN-α2b (SEQ ID NO:289).

In some embodiments, said IFN-α2 mutant (IFN-α2a or IFN-α2b) is mutated atone or more amino acids at positions 144-154, such as amino acid positions 148, 149 and/or 153. In some embodiments, the IFN-α2 mutant comprises one or more mutations selected from L153A, R149A, and M148A. Such mutants are described, for example, in WO2013/107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wild type IFN-α2 activity. In such embodiments, said mutant IFN-α2 has reduced affinity and/or activity for IFNAR1 while affinity and/or activity of IFNR2 is retained.

In some embodiments, the human IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In an embodiment, the human IFN-α2 mutant comprises R120E and L153A.

In some embodiments, the human IFN-α2 mutant comprises one or more mutations selected from, L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885. In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885.

In an embodiment, the modified signaling agent is interferon β. In such embodiments, the modified interferon β agent has reduced affinity and/or activity for the IFN-α/β receptor (IFNAR), i.e., IFNAR1 and/or IFNAR2 chains. In some embodiments, the modified interferon β agent has substantially reduced or ablated affinity and/or activity for the IFN-α/β receptor (IFNAR), i.e., IFNAR1 and/or IFNAR2 chains.

In an illustrative embodiment, the modified signaling agent is IFN-β. In various embodiments, the IFN-β encompasses functional derivatives, analogs, precursors, isoforms, splice variants, or fragments of IFN-β. In various embodiments, the IFN-β encompasses IFN-β derived from any species. In an embodiment, the chimeric protein comprises a modified version of mouse IFN-β. In another embodiment, the chimeric protein comprises a modified version of human IFN-β. Human IFN-β is a polypeptide with a molecular weight of about 22 kDa comprising 166 amino acid residues. The amino acid sequence of human IFN-β is SEQ ID NO:290.

In some embodiments, the human IFN-β is IFN-β-1a which is a glycosylated form of human IFN-β. In some embodiments, the human IFN-β is IFN-β-1b which is a non-glycosylated form of human IFN-β that has a Met-1 deletion and a Cys-17 to Ser mutation.

In various embodiments, the modified IFN-β has one or more mutations that reduce its binding to or its affinity for the IFNAR1 subunit of IFNAR. In one embodiment, the modified IFN-β has reduced affinity and/or activity at IFNAR1. In various embodiments, the modified IFN-β is human IFN-β and has one or more mutations at positions F67, R71, L88, Y92, 195, N96, K123, and R124. In some embodiments, the one or more mutations are substitutions selected from F67G, F67S, R71A, L88G, L88S, Y92G, Y92S, I95A, N96G, K123G, and R124G. In an embodiment, the modified IFN-β comprises the F67G mutation. In an embodiment, the modified IFN-β comprises the K123G mutation. In an embodiment, the modified IFN-β comprises the F67G and R71A mutations. In an embodiment, the modified IFN-β comprises the L88G and Y92G mutations. In an embodiment, the modified IFN-β comprises the Y92G, I95A, and N96G mutations. In an embodiment, the modified IFN-β comprises the K123G and R124G mutations. In an embodiment, the modified IFN-β comprises the F67G, L88G, and Y92G mutations. In an embodiment, the modified IFN-β comprises the F67S, L88S, and Y92S mutations.

In some embodiments, the modified IFN-β has one or more mutations that reduce its binding to or its affinity for the IFNAR2 subunit of IFNAR. In one embodiment, the modified IFN-β has reduced affinity and/or activity at IFNAR2. In various embodiments, the modified IFN-β is human IFN-β and has one or more mutations at positions W22, R27, L32, R35, V148, L151, R152, and Y155. In some embodiments, the one or more mutations are substitutions selected from W22G, R27G, L32A, L32G, R35A, R35G, V148G, L151G, R152A, R152G, and Y155G. In an embodiment, the modified IFN-β comprises the W22G mutation. In an embodiment, the modified IFN-β comprises the L32A mutation. In an embodiment, the modified IFN-β comprises the L32G mutation. In an embodiment, the modified IFN-β comprises the R35A mutation. In an embodiment, the modified IFN-β comprises the R35G mutation. In an embodiment, the modified IFN-β comprises the V148G mutation. In an embodiment, the modified IFN-β comprises the R152A mutation. In an embodiment, the modified IFN-β comprises the R152G mutation. In an embodiment, the modified IFN-β comprises the Y155G mutation. In an embodiment, the modified IFN-β comprises the W22G and R27G mutations. In an embodiment, the modified IFN-β comprises the L32A and R35A mutation. In an embodiment, the modified IFN-β comprises the L151G and R152A mutations. In an embodiment, the modified IFN-β comprises the V148G and R152A mutations.

In some embodiments, the modified IFN-β has one or more of the following mutations: R35A, R35T, E42K, M621, G78S, A141Y, A142T, E149K, and R152H. In some embodiments, the modified IFN-β has one or more of the following mutations: R35A, R35T, E42K, M621, G78S, A141Y, A142T, E149K, and R152H in combination with C17S or C17A.

In some embodiments, the modified IFN-β has one or more of the following mutations: R35A, R35T, E42K, M621, G78S, A141Y, A142T, E149K, and R152H in combination with any of the other IFN-β mutations described herein.

The crystal structure of human IFN-β is known and is described in Karpusas et al., (1998) PNAS, 94(22): 11813-11818. Specifically, the structure of human IFN-β has been shown to include five α-helices (i.e., A, B, C, D, and E) and four loop regions that connect these helices (i.e., AB, BC, CD, and DE loops). In various embodiments, the modified IFN-β has one or more mutations in the A, B, C, D, E helices and/or the AB, BC, CD, and DE loops which reduce its binding affinity or activity at a therapeutic receptor such as IFNAR. Exemplary mutations are described in WO2000/023114 and US20150011732, the entire contents of which are hereby incorporated by reference. In an exemplary embodiment, the modified IFN-β is human IFN-β comprising alanine substitutions at amino acid positions 15, 16, 18, 19, 22, and/or 23. In an exemplary embodiment, the modified IFN-β is human IFN-β comprising alanine substitutions at amino acid positions 28-30, 32, and 33. In an exemplary embodiment, the modified IFN-β is human IFN-β comprising alanine substitutions at amino acid positions 36, 37, 39, and 42. In an exemplary embodiment, the modified IFN-β is human IFN-β comprising alanine substitutions at amino acid positions 64 and 67 and a serine substitution at position 68. In an exemplary embodiment, the modified IFN-β is human IFN-β comprising alanine substitutions at amino acid positions 71-73. In an exemplary embodiment, the modified IFN-β is human IFN-β comprising alanine substitutions at amino acid positions 92, 96, 99, and 100. In an exemplary embodiment, the modified IFN-β is human IFN-β comprising alanine substitutions at amino acid positions 128, 130, 131, and 134. In an exemplary embodiment, the modified IFN-β is human IFN-β comprising alanine substitutions at amino acid positions 149, 153, 156, and 159. In some embodiments, the mutant IFNβ comprises SEQ ID NO: 290 and a mutation at W22, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at R27, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at W22, the mutation being an aliphatic hydrophobic residue selected from glycine (G), alanine (A), leucine (L), isoleucine (I), methionine (M), and valine (V) and a mutation at R27, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at L32, the mutation being an aliphatic hydrophobic residue selected from glycine (G), alanine (A), isoleucine (I), methionine (M), and valine (V).

In some embodiments, the mutant IFNβ comprises SEQ ID NO:290 and a mutation at R35, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at L32, the mutation being an aliphatic hydrophobic residue selected from glycine (G), alanine (A), isoleucine (I), methionine (M), and valine (V) and a mutation at R35, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at F67, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at R71, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at F67, the mutation being an aliphatic hydrophobic residue selected from glycine (G), alanine (A), leucine (L), isoleucine (I), methionine (M), and valine (V) and a mutation at R71, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at L88, the mutation being an aliphatic hydrophobic residue selected from glycine (G), alanine (A), isoleucine (I), methionine (M), and valine (V).

In some embodiments, the mutant IFNβ comprises SEQ ID NO:290 and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at F67, the mutation being an aliphatic hydrophobic residue selected from glycine (G), alanine (A), leucine (L), isoleucine (I), methionine (M), and valine (V) and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at L88, the mutation being an aliphatic hydrophobic residue selected from glycine (G), alanine (A), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at I95, the mutation being an aliphatic hydrophobic residue selected from glycine (G), alanine (A), leucine (L), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at N96, the mutation being an aliphatic hydrophobic residue selected from glycine (G), alanine (A), leucine (L), isoleucine (I), methionine (M), and valine (V) and a mutation at Y92, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at Y92, the mutation being an aliphatic hydrophobic residue selected from glycine (G), alanine (A), leucine (L), isoleucine (I), methionine (M), and valine (V) and a mutation at I95, the mutation being an aliphatic hydrophobic residue selected from glycine (G), alanine (A), leucine (L), methionine (M), and valine (V) and a mutation at N96, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at K123, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at R124, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at K123, the mutation being an aliphatic hydrophobic residue selected from glycine (G), alanine (A), leucine (L), isoleucine (I), methionine (M), and valine (V) and a mutation at R124, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at L151, the mutation being an aliphatic hydrophobic residue selected from glycine (G), alanine (A), isoleucine (I), methionine (M), and valine (V).

In some embodiments, the mutant IFNβ comprises SEQ ID NO:290 and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at L151, the mutation being an aliphatic hydrophobic residue selected from glycine (G), alanine (A), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at V148, the mutation being an aliphatic hydrophobic residue selected from glycine (G), alanine (A), leucine (L), isoleucine (I), and methionine (M).

In some embodiments, the mutant IFNβ comprises SEQ ID NO:290 and a mutation at V148, the mutation being an aliphatic hydrophobic residue selected from glycine (G), alanine (A), leucine (L), isoleucine (I), methionine (M), and valine (V) and a mutation at R152, the mutation being an aliphatic hydrophobic residue selected from glycine (G), alanine (A), leucine (L), isoleucine (I), methionine (M), and valine (V).

In some embodiments, the mutant IFNβ comprises SEQ ID NO:290 and a mutation at Y155, the mutation being an aliphatic hydrophobic residue selected from glycine (G), alanine (A), leucine (L), isoleucine (I), methionine (M), and valine (V).

In some embodiments, the present invention relates to a chimeric protein comprising: (a) a modified IFN-β, having the amino acid sequence of SEQ ID NO:290 and a mutation at position W22, wherein the mutation is an aliphatic hydrophobic residue; and (b) one or more targeting moieties, said targeting moieties comprising recognition domains which specifically bind to antigens or receptors of interest (e.g., CD8), the modified IFN-β and the one or more targeting moieties are optionally connected with one or more linkers. In various embodiments the mutation at position W22 is aliphatic hydrophobic residue is selected from G, A, L, I, M, and V. In various embodiments the mutation at position W22 is G.

Additional exemplary IFNβ mutants are provided in PCT/EP2017/061544, the entire disclosure of which is incorporated by reference herein.

In an embodiment, the modified signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

In some embodiments, the modified signaling agent is vascular endothelial growth factor (VEGF). VEGF is a potent growth factor that plays major roles in physiological but also pathological angiogenesis, regulates vascular permeability and can act as a growth factor on cells expressing VEGF receptors. Additional functions include, among others, stimulation of cell migration in macrophage lineage and endothelial cells. Several members of the VEGF family of growth factors exist, as well as at least three receptors (VEGFR-1, VEGFR-2, and VEGFR-3).

Members of the VEGF family can bind and activate more than one VEGFR type. For example, VEGF-A binds VEGFR-1 and -2, while VEGF-C can bind VEGFR-2 and -3. VEGFR-1 and -2 activation regulates angiogenesis while VEGFR-3 activation is associated with lymphangiogenesis. The major pro-angiogenic signal is generated from activation of VEGFR-2. VEGFR-1 activation has been reported to be possibly associated with negative role in angiogenesis. It has also been reported that VEGFR-1 signaling is important for progression of tumors in vivo via bone marrow-derived VEGFR-1 positive cells (contributing to formation of premetastatic niche in the bone). Several therapies based on VEGF-A directed/neutralizing therapeutic antibodies have been developed, primarily for use in treatment of various human tumors relying on angiogenesis. These are not without side effects though. This may not be surprising considering that these operate as general, non-cell/tissue specific VEGF/VEGFR interaction inhibitors. Hence, it would be desirable to restrict VEGF (e.g. VEGF-A)/VEGFR-2 inhibition to specific target cells (e.g. tumor vasculature endothelial cells).

In some embodiments, the VEGF is VEGF-A, VEGF-B, VEFG-C, VEGF-D, or VEGF-E and isoforms thereof including the various isoforms of VEGF-A such as $VEGF_{121}$, $VEGF_{121}b$, $VEGF_{145}$, $VEGF_{165}$, $VEGF_{16}b$, $VEGF_{189}$, and $VEGF_{206}$. In some embodiments, the modified signaling agent has reduced affinity and/or activity for VEGFR-1 (Flt-1) and/or VEGFR-2 (KDR/Flk-1). In some embodiments, the modified signaling agent has substantially reduced or ablated affinity and/or activity for VEGFR-1 (Flt-1) and/or VEGFR-2 (KDR/Flk-1). In an embodiment, the modified signaling agent has reduced affinity and/or activity for VEGFR-2 (KDR/Flk-1) and/or substantially reduced or ablated affinity and/or activity for VEGFR-1 (Flt-1). Such an embodiment finds use, for example, in wound healing methods or treatment of ischemia-related diseases (without wishing to be bound by theory, mediated by VEGFR-2's effects on endothelial cell function and angiogenesis). In various embodiments, binding to VEGFR-1 (Flt-1), which is linked to cancers and pro-inflammatory activities, is avoided. In various embodiments, VEGFR-1 (Flt-1) acts a decoy receptor and therefore substantially reduces or ablates affinity at this receptor avoids sequestration of the therapeutic agent. In an embodiment, the modified signaling agent has substantially reduced or ablated affinity and/or activity for VEGFR-1 (Flt-1) and/or substantially reduced or ablated affinity and/or activity for VEGFR-2 (KDR/Flk-1). In some embodiments, the VEGF is VEGF-C or VEGF-D. In such embodiments, the modified signaling agent has reduced affinity and/or activity for VEGFR-3. Alternatively, the modified signaling agent has substantially reduced or ablated affinity and/or activity for VEGFR-3.

Proangiogenic therapies are also important in various diseases (e.g. ischemic heart disease, bleeding etc.), and include VEGF-based therapeutics. Activation of VEGFR-2 is proangiogenic (acting on endothelial cells). Activation of VEFGR-1 can cause stimulation of migration of inflammatory cells (including, for example, macrophages) and lead to inflammation associated hypervascular permeability. Activation of VEFGR-1 can also promote bone marrow associated tumor niche formation. Thus, VEGF based therapeutic selective for VEGFR-2 activation would be desirable in this case. In addition, cell specific targeting, e.g. to endothelial cells, would be desirable.

In some embodiments, the modified signaling agent has reduced affinity and/or activity (e.g. antagonistic) for VEGFR-2 and/or has substantially reduced or ablated affinity and/or activity for VEGFR-1. When targeted to tumor vasculature endothelial cells via a targeting moiety that binds to a tumor endothelial cell marker (e.g. PSMA and others), such construct inhibits VEGFR-2 activation specifically on such marker-positive cells, while not activating VEGFR-1 en route and on target cells (if activity ablated), thus eliminating induction of inflammatory responses, for example. This would provide a more selective and safe anti-angiogenic therapy for many tumor types as compared to VEGF-A neutralizing therapies.

In some embodiments, the modified signaling agent has reduced affinity and/or activity (e.g. agonistic) for VEGFR-2 and/or has substantially reduced or ablated affinity and/or activity for VEGFR-1. Through targeting to vascular endothelial cells, such construct, in some embodiments, promotes angiogenesis without causing VEGFR-1 associated induction of inflammatory responses. Hence, such a construct would have targeted proangiogenic effects with substantially reduced risk of side effects caused by systemic activation of VEGFR-2 as well as VEGFR-1.

In an illustrative embodiment, the modified signaling agent is $VEGF_{165}$, which has the amino acid sequence SEQ ID NO:291.

In another illustrative embodiment, the modified signaling agent is $VEGF_{165b}$, which has the amino acid sequence SEQ ID NO:292.

In these embodiments, the modified signaling agent has a mutation at amino acid 183 (e.g., a substitution mutation at I83, e.g., I83K, I83R, or I83H). Without wishing to be bound by theory, it is believed that such mutations may result in reduced receptor binding affinity. See, for example, U.S. Pat. No. 9,078,860, the entire contents of which are hereby incorporated by reference.

In an embodiment, the modified signaling agent is TNF-α. TNF is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFkB pathway). Administration of TNF is systemically toxic, and this is largely due to TNFR1 engagement. However, it should be noted that activation of TNFR2 is also associated with a broad range of activities and, as with TNFR1, in the context of developing TNF based therapeutics, control over TNF targeting and activity is important.

In some embodiments, the modified signaling agent has reduced affinity and/or activity for TNFR1 and/or TNFR2. In some embodiments, the modified signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly, in embodiments directed to methods of treating cancer, the modified signaling agent has reduced affinity and/or activity for TNFR1 and/or substantially reduced or ablated affinity and/or activity for TNFR2. In these embodiments, the chimeric proteins may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified signaling agent has reduced affinity and/or activity for TNFR2 and/or substantially reduced or ablated affinity and/or activity for TNFR1. Stated another way, the present chimeric proteins, in some embodiments, comprise modified TNF-α agent that allows of favoring either death or survival signals.

In some embodiments, the chimeric protein has a modified TNF having reduced affinity and/or activity for TNFR1 and/or substantially reduced or ablated affinity and/or activity for TNFR2. Such a chimera, in some embodiments, is a more potent inducer of apoptosis as compared to a wild type TNF and/or a chimera bearing only mutation(s) causing reduced affinity and/or activity for TNFR1. Such a chimera, in some embodiments, finds use in inducing tumor cell death or a tumor vasculature endothelial cell death (e.g. in the treatment of cancers). Also, in some embodiments, these chimeras avoid or reduce activation of $T_{reg}$ cells via TNFR2, for example, thus further supporting TNFR1-mediated antitumor activity in vivo.

In some embodiments, the chimeric protein has a modified TNF having reduced affinity and/or activity for TNFR2 and/or substantially reduced or ablated affinity and/or activity for TNFR1. Such a chimera, in some embodiments, is a more potent activator of cell survival in some cell types, which may be a specific therapeutic objective in various disease settings, including without limitation, stimulation of neurogenesis. In addition, such a TNFR2-favoring chimeras also are useful in the treatment of autoimmune diseases (e.g. Crohn's, diabetes, MS, colitis etc. and many others described herein). In some embodiments, the chimera is targeted to auto-reactive T cells. In some embodiments, the chimera promotes $T_{reg}$ cell activation and indirect suppression of cytotoxic T cells.

In some embodiments, the chimera causes the death of auto-reactive T cells, e.g. by activation of TNFR2 and/or avoidance of TNFR1 (e.g. a modified TNF having reduced affinity and/or activity for TNFR2 and/or substantially reduced or ablated affinity and/or activity for TNFR1).

Without wishing to be bound by theory these auto-reactive T cells, have their apoptosis/survival signals altered e.g. by NFkB pathway activity/signaling alterations. In some embodiments, the chimera causes the death of autoreactive T cells having lesions or modifications in the NFkB pathway, which underlie an imbalance of their cell death (apoptosis)/survival signaling properties and, optionally, altered susceptibility to certain death-inducing signals (e.g., TNFR2 activation).

In some embodiments, a TNFR2 based chimera has additional therapeutic applications in diseases, including various autoimmune diseases, heart disease, de-myelinating and neurodegenerative disorders, and infectious disease, among others.

In an embodiment, the wild type TNF-α has the amino acid sequence of SEQ ID NO:293.

In such embodiments, the modified TNF-α agent has mutations at one or more amino acid positions 29, 31, 32, 84, 85, 86, 87, 88, 89, 145, 146 and 147 which produces a modified TNF-α with reduced receptor binding affinity. See, for example, U.S. Pat. No. 7,993,636, the entire contents of which are hereby incorporated by reference.

In some embodiments, the modified human TNF-α moiety has mutations at one or more amino acid positions R32, N34, Q67, H73, L75, T77, S86, Y87, V91, I97, T105, P106, A109, P113, Y115, E127, N137, D143, A145, and E146 as described, for example, in WO/2015/007903, the entire contents of which is hereby incorporated by reference (numbering according to the human TNF sequence, Genbank accession number BAG70306, version BAG70306.1 GI: 197692685). In some embodiments, the modified human TNF-α moiety has substitution mutations selected from L29S, R32G, R32W, N34G, Q67G, H73G, L75G, L75A, L75S, T77A, S86G, S86T, Y87Q, Y87L, Y87A, Y87F, Y87H, V91G, V91A, I97A, I97Q, I97S, T105G, P106G, A109Y, P113G, Y115G, Y115A, E127G, N137G, D143N, A145G, A145R, A145T, E146D, E146K, and S147D. In an embodiment, the human TNF-α moiety has a mutation selected from Y87Q, Y87L, Y87A, Y87F, and Y87H. In another embodiment, the human TNF-α moiety has a mutation selected from I97A, I97Q, and I97S. In a further embodiment, the human TNF-α moiety has a mutation selected from Y115A and Y115G. In an embodiment, the human TNF-α moiety has an E146K mutation. In an embodiment, the human TNF-α moiety has an Y87H and an E146K mutation. In an embodiment, the human TNF-α moiety has an Y87H and an A145R mutation. In an embodiment, the human TNF-α moiety has a R32W and a S86T mutation. In an embodiment, the human TNF-α moiety has a R32W and an E146K mutation. In an embodiment, the human TNF-α moiety has a L29S and a R32W mutation. In an embodiment, the human TNF-α moiety has a D143N and an A145R mutation. In an embodiment, the human TNF-α moiety has a D143N and an A145R mutation. In an embodiment, the human TNF-α moiety has an A145T, an E146D, and a S147D mutation. In an embodiment, the human TNF-α moiety has an A145T and a S147D mutation.

In some embodiments, the modified TNF-α agent has one or more mutations selected from N39Y, S147Y, and Y87H, as described in WO2008/124086, the entire contents of which is hereby incorporated by reference.

In some embodiments, the modified human TNF-α moiety has mutations that provide receptor selectivity as described in PCT/IB2016/001668, the entire contents of which are hereby incorporated by reference. In some embodiments, the mutations to TNF are TNF-R1 selective. In some embodiments, the mutations to TNF which are TNF-R1 selective are at one or more of positions R32, S86, and E146. In some embodiments, the mutations to TNF which are TNF-R1 selective are one or more of R32W, S86T, and E146K. In some embodiments, the mutations to TNF which are TNF-R1 selective are one or more of R32W, R32W/S86T, R32W/E146K and E146K. In some embodiments, the mutations to TNF are TNF-R2 selective. In some embodiments, the mutations to TNF which are TNF-R2 selective are at one or more of positions A145, E146, and S147. In some embodiments, the mutations to TNF which are TNF-R2 selective are one or more of A145T, A145R, E146D, and S147D. In some embodiments, the mutations to TNF which are TNF-R2 selective are one or more of A145R, A145T/S147D, and A145T/E146D/S147D.

In an embodiment, the modified signaling agent is TNF-β. TNF-β can form a homotrimer or a heterotrimer with LT-β (LT-α1β2). In some embodiments, the modified signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of TNF-beta SEQ ID NO:294.

In such embodiments, the modified soluble agent may comprise mutations at one or more amino acids at positions 106-113, which produce a modified TNF-β with reduced receptor binding affinity to TNFR2. In an embodiment, the modified soluble agent has one or more substitution mutations at amino acid positions 106-113. In illustrative embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified soluble agent has an insertion of about 1 to about 3 amino acids at positions 106-113.

In some embodiments, the modified agent is a TNF family member (e.g. TNF-alpha, TNF-beta) which can be a single chain trimeric version as described in WO 2015/007903, the entire contents of which are incorporated by reference.

In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified agent is a TNF family member (e.g. TNF-alpha, TNF-beta) which also, optionally, has substantially reduced or ablated affinity and/or activity for TNFR2. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2. In these embodiments, the modified agent is a TNF family member (e.g. TNF-alpha, TNF-beta) which also, optionally, has substantially reduced or ablated affinity and/or activity for TNFR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In an embodiment, the modified signaling agent is TRAIL. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of TRAIL SEQ ID NO:295.

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP 003801, version 10 NP_003801.1, GI: 4507593; see above).

In some embodiments, the modified TRAIL agent may comprise one or more mutations that substantially reduce its affinity and/or activity for TRAIL-R1. In such embodiments, the modified TRAIL agent may specifically bind to TRIL-R2. Exemplary mutations include mutations at one or more amino acid positions Y189, R191, Q193, H264, I266, and D267. For example the mutations may be one or more of Y189Q, R191K, Q193R, H264R, I266L and D267Q. In an embodiment, the modified TRAIL agent comprises the mutations Y189Q, R191K, Q193R, H264R, I266L and D267Q.

In some embodiments, the modified TRAIL agent may comprise one or more mutations that substantially reduce its affinity and/or activity for TRAIL-R2. In such embodiments, the modified TRAIL agent may specifically bind to TRIL-R1. Exemplary mutations include mutations at one or more amino acid positions G131, R149, S159, N199, K201, and S215. For example, the mutations may be one or more of G131R, R1491, S159R, N199R, K201H, and S215D. In an embodiment, the modified TRAIL agent comprises the mutations G131R, R1491, S159R, N199R, K201H, and S215D. Additional TRAIL mutations are described in, for example, Trebing et al., (2014) Cell Death and Disease, 5:e1035, the entire disclosure of which is hereby incorporated by reference.

In an embodiment, the modified signaling agent is TGFα. In such embodiments, the modified TGFα agent has reduced affinity and/or activity for the epidermal growth factor receptor (EGFR). In some embodiments, the modified TGFα agent has substantially reduced or ablated affinity and/or activity for the epidermal growth factor receptor (EGFR).

In an embodiment, the modified signaling agent is TGFβ. In such embodiments, the modified signaling agent has reduced affinity and/or activity for TGFBR1 and/or TGFBR2. In some embodiments, the modified signaling agent has substantially reduced or ablated affinity and/or activity for TGFBR1 and/or TGFBR2. In some embodiments, the modified signaling agent optionally has reduced or substantially reduced or ablated affinity and/or activity for TGFBR3 which, without wishing to be bound by theory, may act as a reservoir of ligand for TGF-beta receptors. In some embodiments, the TGFβ may favor TGFBR1 over TGFBR2 or TGFBR2 over TGFBR1. Similarly, LAP, without wishing to be bound by theory, may act as a reservoir of ligand for TGF-beta receptors. In some embodiments, the modified signaling agent has reduced affinity and/or activity for TGFBR1 and/or TGFBR2 and/or substantially reduced or ablated affinity and/or activity for Latency Associated Peptide (LAP). In some embodiments, such chimeras find use in Camurati-Engelmann disease, or other diseases associated with inappropriate TGFβ signaling.

In some embodiments, the modified agent is a TGF family member (e.g. TGFα, TGFβ) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at one or more of TGFBR1, TGFBR2, TGFBR3. In these embodiments, the modified agent is a TGF family member (e.g. TGFα, TGFβ) which also, optionally, has substantially reduced or ablated affinity and/or activity at one or more of TGFBR1, TGFBR2, TGFBR3.

In some embodiments, the modified agent is a TGF family member (e.g. TGFα, TGFβ) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TGFBR1 and/or TGFBR2. In these embodiments, the modified agent is a TGF family member (e.g. TGFα, TGFβ) which also, optionally, has substantially reduced or ablated affinity and/or activity at TGFBR3.

In an embodiment, the modified signaling agent is an interleukin. In an embodiment, the modified signaling agent is IL-1. In an embodiment, the modified signaling agent is IL-1a or IL-1p. In some embodiments, the modified signaling agent has reduced affinity and/or activity for IL-1R1 and/or IL-1RAcP. In some embodiments, the modified signaling agent has substantially reduced or ablated affinity and/or activity for IL-1R1 and/or IL-1RAcP. In some embodiments, the modified signaling agent has reduced affinity and/or activity for IL-1R2. In some embodiments, the modified signaling agent has substantially reduced or ablated affinity and/or activity for IL-1R2. For instance, in some embodiments, the present modified IL-1 agents avoid interaction at IL-1R2 and therefore substantially reduce its function as a decoy and/or sink for therapeutic agents.

In an embodiment, the wild type IL-1β has the amino acid sequence of SEQ ID NO:296.

IL1 is a proinflammatory cytokine and an important immune system regulator. It is a potent activator of CD4 T cell responses, increases proportion of Th17 cells and expansion of IFNγ and IL-4 producing cells. IL-1 is also a potent regulator of $CD8^+$ T cells, enhancing antigen-specific $CD8^+$ T cell expansion, differentiation, migration to periphery and memory. IL-1 receptors comprise IL-1R1 and IL-1R2. Binding to and signaling through the IL-1R1 constitutes the mechanism whereby IL-1 mediates many of its biological (and pathological) activities. IL1-R2 can function as a decoy receptor, thereby reducing IL-1 availability for interaction and signaling through the IL-1R1.

In some embodiments, the modified IL-1 has reduced affinity and/or activity (e.g. agonistic activity) for IL-1R1. In some embodiments, the modified IL-1 has substantially reduced or ablated affinity and/or activity for IL-1R2. In such embodiments, there is restorable IL-1/IL-1R1 signaling and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating cancer, including, for example, stimulating the immune system to mount an anti-cancer response.

In some embodiments, the modified IL-1 has reduced affinity and/or activity (e.g. antagonistic activity, e.g. natural antagonistic activity or antagonistic activity that is the result of one or more mutations, see, e.g., WO 2015/007520, the entire contents of which are hereby incorporated by reference) for IL-1R1. In some embodiments, the modified IL-1 has substantially reduced or ablated affinity and/or activity for IL-1R2. In such embodiments, there is the IL-1/IL-1R1 signaling is not restorable and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating autoimmune diseases, including, for example, suppressing the immune system.

In such embodiments, the modified signaling agent has a deletion of amino acids 52-54 which produces a modified human IL-1β with reduced binding affinity for type I IL-1R and reduced biological activity. See, for example, WO 1994/000491, the entire contents of which are hereby incorporated by reference. In some embodiments, the modified human IL-1β has one or more substitution mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, I172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO2015/007542 and WO/2015/007536, the entire contents of which is hereby incorporated by reference (numbering base on the human IL-1β sequence, Genbank accession number NP_000567, version NP-000567.1, GI: 10835145). In some embodiments, the modified human IL-1β may have one or more mutations selected from R120A, R120G, Q130A, Q130W, H146A, H146G, H146E, H146N, H146R, Q148E, Q148G, Q148L, K209A, K209D, K219S, K219Q, E221S and E221K. In an embodiment, the modified human IL-1β comprises the mutations Q131G and Q148G. In an embodiment, the modified human IL-1β comprises the mutations Q148G and K208E. In an embodiment, the modified human IL-1β comprises the mutations R120G and Q131G. In an embodiment, the modified human IL-1β comprises the mutations R120G and H146A. In an embodiment, the modified human IL-1β comprises the mutations R120G and H146N. In an embodiment, the modified human IL-1β comprises the mutations R120G and H146R. In an embodiment, the modified human IL-1p comprises the mutations R120G and H146E. In an embodiment, the modified human IL-1β comprises the mutations R120G and H146G. In an embodiment, the modified human IL-1β comprises the mutations R120G and K208E. In an embodiment, the modified human IL-1β comprises the mutations R120G, F162A, and Q164E.

In an embodiment, the modified signaling agent is IL-2. In such an embodiment, the modified signaling agent has reduced affinity and/or activity for IL-2Rα and/or IL-2Rβ and/or IL-2Rγ. In some embodiments, the modified signaling agent has reduced affinity and/or activity for IL-2Rβ and/or IL-2Rγ. In some embodiments, the modified signaling agent has substantially reduced or ablated affinity and/or activity for IL-2Rα. Such embodiments may be relevant for treatment of cancer, for instance when the modified IL-2 is agonistic at IL-2Rβ and/or IL-2Rγ. For instance, the present constructs may favor attenuated activation of $CD8^+$ T cells (which can provide an anti-tumor effect), which have IL2 receptors β and γ and disfavor $T_{regs}$ (which can provide an immune suppressive, pro-tumor effect), which have IL2 receptors α, β, and γ. Further, in some embodiments, the preferences for IL-2Rβ and/or IL-2Rγ over IL-2Rα avoid IL-2 side effects such as pulmonary edema. Also, IL-2-based chimeras are useful for the treatment of autoimmune diseases, for instance when the modified IL-2 is antagonistic (e.g. natural antagonistic activity or antagonistic activity that is the result of one or more mutations, see, e.g., WO 2015/007520, the entire contents of which are hereby incorporated by reference) at IL-2Rβ and/or IL-2Rγ. For instance, the present constructs may favor attenuated suppression of $CD8^+$ T cells (and therefore dampen the immune response), which have IL2 receptors β and γ and disfavor $T_{regs}$ which have IL2 receptors α, β, and γ. Alternatively, in some embodiments, the chimeras bearing IL-2 favor the activation of $T_{regs}$, and therefore immune suppression, and activation of disfavor of $CD8^+$ T cells. For instance, these constructs find use in the treatment of diseases or diseases that would benefit from immune suppression, e.g. autoimmune disorders.

In some embodiments, the chimeric protein has targeting moieties as described herein directed to $CD8^+$ T cells as well as a modified IL-2 agent having reduced affinity and/or activity for IL-2Rβ and/or IL-2Rγ and/or substantially reduced or ablated affinity and/or activity for IL-2Rα. In some embodiments, these constructs provide targeted $CD8^+$ T cell activity and are generally inactive (or have substantially reduced activity) towards $T_{reg}$ cells. In some embodiments, such constructs have enhanced immune stimulatory effect compared to wild type IL-2 (e.g., without wishing to be bound by theory, by not stimulating Tregs), whilst eliminating or reducing the systemic toxicity associated with IL-2.

In an embodiment, the wild type IL-2 has the amino acid sequence of SEQ ID NO:297.

In such embodiments, the modified IL-2 agent has one or more mutations at amino acids L72 (L72G, L72A, L72S, L72T, L72Q, L72E, L72N, L72D, L72R, or L72K), F42 (F42A, F42G, F42S, F42T, F42Q, F42E, F42N, F42D, F42R, or F42K) and Y45 (Y45A, Y45G, Y45S, Y45T, Y45Q, Y45E, Y45N, Y45D, Y45R or Y45K). Without wishing to be bound by theory, it is believed that these modified IL-2 agents have reduced affinity for the high-affinity IL-2 receptor and preserves affinity to the intermediate-affinity IL-2 receptor, as compared to the wild-type IL-2. See, for example, US Patent Publication No. 2012/0244112, the entire contents of which are hereby incorporated by reference.

In some embodiments, the modified IL-2 agent has one or more mutations at amino acids R38, F42, Y45, and E62. For example, the modified IL-2 agent may comprise one or more of R38A, F42A, Y45A, and E62A. In some embodiments, the modified IL-2 agent may comprise a mutation at C125. For example, the mutation may be C125S. In such embodiments, the modified IL-2 agent may have substantially reduced affinity and/or activity for IL-2Rα, as described in, for example, Carmenate et al. (2013) The Journal of Immunology, 190:6230-6238, the entire disclosure of which is hereby incorporated by reference. In some embodiments, the modified IL-2 agent with mutations at R38, F42, Y45, and/or E62 is able to induce an expansion of effector cells including $CD8^+$ T cells and NK cells but not Treg cells. In some embodiments, the modified IL-2 agent with mutations at R38, F42, Y45, and/or E62 is less toxic than wildtype IL-2 agents. A chimeric protein comprising the modified IL-2 agent with substantially reduced affinity and/or activity for IL-2Rα may find application in oncology for example.

In other embodiments, the modified IL-2 agent may have substantially reduced affinity and/or activity for IL-2Rβ, as described in, for example, WO2016/025385, the entire disclosure of which is hereby incorporated by reference. In such embodiments, the modified IL-2 agent may induce an expansion of Treg cells but not effector cells such as $CD8^+$ T cells and NK cells. A chimeric protein comprising the modified IL-2 agent with substantially reduced affinity and/or activity for IL-2Rβ may find application in the treatment of autoimmune disease for example. In some embodiments, the modified IL-2 agent may comprise one or more mutations at amino acids N88, D20, and/r A126. For example, the modified IL-2 agent may comprise one or more of N88R, N88I, N88G, D20H, Q126L, and Q126F.

In various embodiments, the modified IL-2 agent may comprise a mutation at D109 or C125. For example, the mutation may be D109C or C125S. In some embodiments, the modified IL-2 with a mutation at D109 or C125 may be utilized for attachment to a PEG moiety.

In an embodiment, the modified signaling agent is IL-3. In some embodiments, the modified signaling agent has reduced affinity and/or activity for the IL-3 receptor, which is a heterodimer with a unique alpha chain paired with the common beta (beta c or CD131) subunit. In some embodiments, the modified signaling agent has substantially reduced or ablated affinity and/or activity for the IL-3 receptor, which is a heterodimer with a unique alpha chain paired with the common beta (beta c or CD131) subunit.

In an embodiment, the modified signaling agent is IL-4. In such an embodiment, the modified signaling agent has reduced affinity and/or activity for type 1 and/or type 2 IL-4 receptors. In such an embodiment, the modified signaling agent has substantially reduced or ablated affinity and/or activity for type 1 and/or type 2 IL-4 receptors. Type 1 IL-4 receptors are composed of the IL-4Rα subunit with a common γ chain and specifically bind IL-4. Type 2 IL-4 receptors include an IL-4Rα subunit bound to a different subunit known as IL-13Rα1. In some embodiments, the modified signaling agent has substantially reduced or ablated affinity and/or activity the type 2 IL-4 receptors.

In an embodiment, the wild type IL-4 has the amino acid sequence of SEQ ID NO:298.

In such embodiments, the modified IL-4 agent has one or more mutations at amino acids R121 (R121A, R121D, R121E, R121F, R121H, R1211, R121K, R121N, R121P, R121T, R121W), E122 (E122F), Y124 (Y124A, Y124Q, Y124R, Y124S, Y124T) and S125 (S125A). Without wishing to be bound by theory, it is believed that these modified IL-4 agents maintain the activity mediated by the type I receptor, but significantly reduces the biological activity mediated by the other receptors. See, for example, U.S. Pat. No. 6,433,157, the entire contents of which are hereby incorporated by reference.

In an embodiment, the modified signaling agent is IL-6. IL-6 signals through a cell-surface type I cytokine receptor complex including the ligand-binding IL-6R chain (CD126), and the signal-transducing component gp130. IL-6 may also bind to a soluble form of IL-6R (sIL-6R), which is the extracellular portion of IL-6R. The sIL-6R/IL-6 complex may be involved in neurites outgrowth and survival of neurons and, hence, may be important in nerve regeneration through remyelination. Accordingly, in some embodiments, the modified signaling agent has reduced affinity and/or activity for IL-6R/gp130 and/or sIL-6R. In some embodiments, the modified signaling agent has substantially reduced or ablated affinity and/or activity for IL-6R/gp130 and/or sIL-6R.

In an embodiment, the wild type IL-6 has the amino acid sequence of IL-6 (mature form, wild type) (SEQ ID NO:299).

In such embodiments, the modified signaling agent has one or more mutations at amino acids 58, 160, 163, 171 or 177. Without wishing to be bound by theory, it is believed that these modified IL-6 agents exhibit reduced binding affinity to IL-6Ralpha and reduced biological activity. See, for example, WO 97/10338, the entire contents of which are hereby incorporated by reference.

In an embodiment, the modified signaling agent is IL-10. In such an embodiment, the modified signaling agent has reduced affinity and/or activity for IL-10 receptor-1 and IL-10 receptor-2. In some embodiments, the modified signaling agent has substantially reduced or ablated affinity and/or activity for IL-10 receptor-1 and IL-10 receptor-2

In an embodiment, the modified signaling agent is IL-11. In such an embodiment, the modified signaling agent has reduced affinity and/or activity for IL-11Rα and/or IL-11Rβ and/or gp130. In such an embodiment, the modified signaling agent has substantially reduced or ablated affinity and/or activity for IL-11Rα and/or IL-11Rβ and/or gp130.

In an embodiment, the modified signaling agent is IL-12. In such an embodiment, the modified signaling agent has reduced affinity and/or activity for IL-12Rβ1 and/or IL-12Rβ2. In such an embodiment, the modified signaling agent has substantially reduced or ablated affinity and/or activity for IL-12Rβ1 and/or IL-12Rβ2.

In an embodiment, the modified signaling agent is IL-13. In such an embodiment, the modified signaling agent has reduced affinity and/or activity for the IL-4 receptor (IL-4Rα) and IL-13Rα1. In some embodiments, the modified signaling agent has substantially reduced or ablated affinity and/or activity for IL-4 receptor (IL-4Rα) or IL-13Rα1.

In an embodiment, the wild type IL-13 has the amino acid sequence of IL-13 (mature form, wild type) (SEQ ID NO:300).

In such embodiments, the modified IL-13 agent has one or more mutations at amino acids 13, 16, 17, 66, 69, 99, 102, 104, 105, 106, 107, 108, 109, 112, 113 and 114. Without wishing to be bound by theory, it is believed that these modified IL-13 agents exhibit reduced biological activity. See, for example, WO 2002/018422, the entire contents of which are hereby incorporated by reference.

In an embodiment, the modified signaling agent is IL-18. In some embodiments, the modified signaling agent has reduced affinity and/or activity for IL-18Rα and/or IL-18Rβ. In some embodiments, the modified signaling agent has substantially reduced or ablated affinity and/or activity for IL-18Rα and/or IL-18Rβ. In some embodiments, the modified signaling agent has substantially reduced or ablated affinity and/or activity for IL-18Rα type II, which is an isoform of IL-18Rα that lacks the TIR domain required for signaling.

In an embodiment, the wild type IL-18 has the amino acid sequence of IL-18 (wild type) (SEQ ID NO:301).

In such embodiments, the modified IL-18 agent may comprise one or more mutations in amino acids or amino acid regions selected from Y37-K44, R49-Q54, D59-R63, E67-C74, R80, M87-A97, N 127-K129, Q139-M149, K165-K171, R183 and Q190-N191, as described in WO/2015/007542, the entire contents of which are hereby incorporated by reference (numbering based on the human IL-18 sequence, Genbank accession number AAV38697, version AAV38697.1, GI: 54696650).

In an embodiment, the modified signaling agent is IL-33. In such an embodiment, the modified signaling agent has reduced affinity and/or activity for the ST-2 receptor and IL-1RAcP. In some embodiments, the modified signaling agent has substantially reduced or ablated affinity and/or activity for the ST-2 receptor and IL-1RAcP.

In an embodiment, the wild type IL-33 has the amino acid sequence of SEQ ID NO:302.

In such embodiments, the modified IL-33 agent may comprise one or more mutations in amino acids or amino acid regions selected from I113-Y122, S127-E139, E144-D157, Y163-M183, E200, Q215, L220-C227 and T260-E269, as described in WO/2015/007542, the entire contents of which are hereby incorporated by reference (numbering based on the human sequence, Genbank accession number NP_254274, version NP_254274.1, GI:15559209).

In an embodiment, the modified signaling agent is epidermal growth factor (EGF). EGF is a member of a family of potent growth factors. Members include EGF, HB-EGF, and others such as TGF alpha, amphiregulin, neuregulins, epiregulin, betacellulin. EGF family receptors include EGFR (ErbB1), ErbB2, ErbB3 and ErbB4. These may function as homodimeric and for heterodimeric receptor subtypes. The different EGF family members exhibit differential selectivity for the various receptor subtypes. For example, EGF associates with ErbB1/ErbB1, ErbB1/ErbB2, ErbB4/ErbB2 and some other heterodimeric subtypes. HB-EGF has a similar pattern, although it also associates with ErbB4/4. Modulation of EGF (EGF-like) growth factor signaling, positively or negatively, is of considerable therapeutic interest. For example, inhibition of EGFRs signaling is of interest in the treatment of various cancers where EGFR signaling constitutes a major growth promoting signal. Alternatively, stimulation of EGFRs signaling is of therapeutic interest in, for example, promoting wound healing (acute and chronic), oral mucositis (a major side-effect of various cancer therapies, including, without limitation radiation therapy).

In some embodiments, the modified signaling agent has reduced affinity and/or activity for ErbB1, ErbB2, ErbB3, and/or ErbB4. Such embodiments find use, for example, in methods of treating wounds. In some embodiments, the modified signaling agent binds to one or more ErbB1, ErbB2, ErbB3, and ErbB4 and antagonizes the activity of the receptor. In such embodiments, the modified signaling agent has reduced affinity and/or activity for ErbB1, ErbB2, ErbB3, and/or ErbB4 which allows for the activity of the receptor to be antagonized in an attenuated fashion.

Such embodiments find use in, for example, treatments of cancer. In an embodiment, the modified signaling agent has reduced affinity and/or activity for ErbB1. ErbB1 is the therapeutic target of kinase inhibitors—most have side effects because they are not very selective (e.g., gefitinib, erlotinib, afatinib, brigatinib and icotinib). In some embodiments, attenuated antagonistic ErbB1 signaling is more on-target and has less side effects than other agents targeting receptors for EGF.

In some embodiments, the modified signaling agent has reduced affinity and/or activity (e.g. antagonistic e.g. natural antagonistic activity or antagonistic activity that is the result of one or more mutations, see, e.g., WO 2015/007520, the entire contents of which are hereby incorporated by reference) for ErbB1 and/or substantially reduced or ablated affinity and/or activity for ErbB4 or other subtypes it may interact with. Through specific targeting via the targeting moiety, cell-selective suppression (antagonism e.g. natural antagonistic activity or antagonistic activity that is the result of one or more mutations, see, e.g., WO 2015/007520, the entire contents of which are hereby incorporated by reference) of ErbB1/ErbB1 receptor activation would be achieved—while not engaging other receptor subtypes potentially associated with inhibition-associated side effects. Hence, in contrast to EGFR kinase inhibitors, which inhibit EGFR activity in all cell types in the body, such a construct would provide a cell-selective (e.g., tumor cell with activated EGFR signaling due to amplification of receptor, overexpression etc.) anti-EGFR (ErbB1) drug effect with reduced side effects.

In some embodiments, the modified signaling agent has reduced affinity and/or activity (e.g. agonistic) for ErbB4 and/or other subtypes it may interact with. Through targeting to specific target cells through the targeting moiety, a selective activation of ErbB1 signaling is achieved (e.g. epithelial cells). Such a construct finds use, in some embodiments, in the treatment of wounds (promoting would healing) with reduced side effects, especially for treatment of chronic conditions and application other than topical application of a therapeutic (e.g. systemic wound healing).

In an embodiment, the modified signaling agent is insulin or insulin analogs. In some embodiments, the modified insulin or insulin analog has reduced affinity and/or activity for the insulin receptor and/or IGF1 or IGF2 receptor.

In some embodiments, the modified insulin or insulin analog has substantially reduced or ablated affinity and/or activity for the insulin receptor and/or IGF1 or IGF2 receptor. Attenuated response at the insulin receptor allows for the control of diabetes, obesity, metabolic disorders and the like while directing away from IGF1 or IGF2 receptor avoids pro-cancer effects.

In an embodiment, the modified signaling agent is insulin-like growth factor-I or insulin-like growth factor-II (IGF-1 or IGF-2). In an embodiment, the modified signaling agent is IGF-1. In such an embodiment, the modified signaling agent has reduced affinity and/or activity for the insulin receptor and/or IGF1 receptor. In an embodiment, the modified signaling agent may bind to the IGF1 receptor and antagonize the activity of the receptor. In such an embodiment, the modified signaling agent has reduced affinity and/or activity for IGF1 receptor which allows for the activity of the receptor to be antagonized in an attenuated fashion. In some embodiments, the modified signaling agent has substantially reduced or ablated affinity and/or activity for the insulin receptor and/or IGF1 receptor. In some embodiments, the modified signaling agent has reduced affinity and/or activity for IGF2 receptor which allows for the activity of the receptor to be antagonized in an attenuated fashion. In an embodiment, the modified signaling agent has substantially reduced or ablated affinity and/or activity for the insulin receptor and accordingly does not interfere with insulin signaling. In various embodiments, this applies to cancer treatment. In various embodiments, the present agents may prevent IR isoform A from causing resistance to cancer treatments.

In one embodiment, the present chimeric protein has (i) a CD8 binding agent and (ii) a targeting moiety which is directed against a tumor cell, along with any of the modified (e.g. mutant) form signaling agents described herein. In an embodiment, the present chimeric protein has a targeting moiety directed against CD8 on T cells and a second targeting moiety directed against PD-L1 or PD-L2 on tumor cells.

In various embodiments, the signaling agent is a toxin or toxic enzyme. In some embodiments, the toxin or toxic enzyme is derived from plants and bacteria. Illustrative toxins or toxic enzymes include, but are not limited to, the diphtheria toxin, *Pseudomonas* toxin, anthrax toxin, ribosome-inactivating proteins (RIPs) such as ricin and saporin, modeccin, abrin, gelonin, and poke weed antiviral protein. Additional toxins include those disclosed in Mathew et al., (2009) Cancer Sci 100(8): 1359-65, the entire disclosures are hereby incorporated by reference. In such embodiments, the chimeric proteins of the invention may be utilized to induce cell death in cell-type specific manner. In such embodiments, the toxin may be modified, e.g. mutated, to reduce affinity and/or activity of the toxin for an attenuated effect, as described with other signaling agents herein.

Multi-Specific Chimeras and Fusions with Signaling Agents

In various embodiments, the CD8 binding agent of the invention is part of a chimera or fusion with one or more signaling agents as described herein and/or one or more additional targeting moieties. Accordingly, the present invention provides for chimeric or fusion proteins that include one or more signaling agents and a targeting moiety against CD8 and/or one or more additional targeting moieties.

In various embodiments, the CD8 binding agent of the invention is multispecific, i.e., the CD8 binding agent comprises two or more targeting moieties having recognition domains that recognize and bind two or more targets, e.g. antigens, or receptors, or epitopes. In such embodiments, the CD8 binding agent of the invention may comprise two more targeting moieties having recognition domains that recognize and bind two or more epitopes on the same antigen or on different antigens. In various embodiments, such multispecific CD8 binding agents exhibit advantageous properties such as increased avidity and/or improved selectivity. In an embodiment, the CD8 binding agent of the invention comprises two targeting moieties and is bispecific, i.e., binds and recognizes two epitopes on the same antigen or on different antigens.

In various embodiments, the multispecific CD8 binding agent of the invention comprises two or more targeting moieties with each targeting moiety being an antibody or an antibody derivative as described herein. In an embodiment, the multispecific CD8 binding agent of the invention comprises at least one VHH comprising an antigen recognition domain against CD8 and one antibody or antibody derivative comprising an antigen recognition domain against a tumor antigen.

In various embodiments, the present multispecific CD8 binding agents have two or more targeting moieties that target different antigens or receptors, and one targeting moiety may be attenuated for its antigen or receptor, e.g. the targeting moiety binds its antigen or receptor with a low affinity or avidity (including, for example, at an affinity or avidity that is less than the affinity or avidity the other targeting moiety has for its for its antigen or receptor, for instance the difference between the binding affinities may be about 10-fold, or 25-fold, or 50-fold, or 100-fold, or 300-fold, or 500-fold, or 1000-fold, or 5000-fold; for instance the lower affinity or avidity targeting moiety may bind its antigen or receptor at a $K_D$ in the mid- to high-nM or low- to mid-NM range while the higher affinity or avidity targeting moiety may bind its antigen or receptor at a $K_D$ in the mid- to high-pM or low- to mid-nM range). For instance, in some embodiments, the present multispecific CD8 binding agents comprises an attenuated targeting moiety that is directed against a promiscuous antigen or receptor, which may improve targeting to a cell of interest (e.g. via the other targeting moiety) and prevent effects across multiple types of cells, including those not being targeted for therapy (e.g. by binding promiscuous antigen or receptor at a higher affinity than what is provided in these embodiments). In various embodiments, the present chimeric proteins have one or more targeting moieties that target different antigens or receptors with low affinities or avidities and can enhance binding of the other, e.g. cooperatively.

The multispecific CD8 binding agent of the invention may be constructed using methods known in the art, see for example, U.S. Pat. No. 9,067,991, U.S. Patent Publication No. 20110262348 and WO 2004/041862, the entire contents of which are hereby incorporated by reference. In an illustrative embodiment, the multispecific CD8 binding agent of the invention comprising two or more targeting moieties may be constructed by chemical crosslinking, for example, by reacting amino acid residues with an organic derivatizing agent as described by Blattler et al., Biochemistry 24, 1517-1524 and EP294703, the entire contents of which are hereby incorporated by reference. In another illustrative embodiment, the multispecific CD8 binding agent comprising two or more targeting moieties is constructed by genetic fusion, i.e., constructing a single polypeptide which includes the polypeptides of the individual targeting moieties. For example, a single polypeptide construct may be formed which encodes a first VHH with an antigen recognition domain against CD8 and a second antibody or antibody derivative with an antigen recognition domain against a tumor antigen. A method for producing bivalent or multivalent VHH polypeptide constructs is disclosed in PCT patent application WO 96/34103, the entire contents of which is hereby incorporated by reference. In a further illustrative embodiment, the multispecific CD8 binding agent of the invention may be constructed by using linkers. For example, the carboxy-terminus of a first VHH with an antigen recognition domain against CD8 may be linked to the amino-terminus of a second antibody or antibody derivative with an antigen recognition domain against a tumor antigen (or vice versa). Exemplary linkers that may be used are described herein. In some embodiments, the components of the multispecific CD8 binding agent of the invention are directly linked to each other without the use of linkers.

In various embodiments, the multi-specific CD8 binding agent of the invention recognizes and binds to CD8 and one or more antigens found on one or more immune cells, which can include, without limitation, megakaryocytes, thrombocytes, erythrocytes, mast cells, basophils, neutrophils, eosinophils, monocytes, macrophages, natural killer cells, T lymphocytes (e.g., cytotoxic T lymphocytes, T helper cells, natural killer T cells), B lymphocytes, plasma cells, dendritic cells, or subsets thereof. In some embodiments, the CD8 binding agent specifically binds to an antigen of interest and effectively directly or indirectly recruits one of more immune cells.

In various embodiments, the multi-specific CD8 binding agent of the invention recognizes and binds to CD8 and one or more antigens found on tumor cells. In these embodiments, the present CD8 binding agents may directly or indirectly recruit an immune cell to a tumor cell or the tumor microenvironment. In some embodiments, the present CD8 binding agents may directly or indirectly recruit an immune cell, e.g. an immune cell that can kill and/or suppress a tumor cell (e.g., a CTL), to a site of action (such as, by way of non-limiting example, the tumor microenvironment).

In some embodiments, the present CD8 binding agents are capable of, or find use in methods involving, shifting the balance of immune cells in favor of immune attack of a tumor. For instance, the present CD8 binding agents can shift the ratio of immune cells at a site of clinical importance in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), neutrophils, B cells, dendritic cells or subsets thereof and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present CD8 binding agent is capable of increasing a ratio of effector T cells to regulatory T cells.

In some embodiments, the multi-specific CD8 binding agent of the invention comprises a targeting moiety having an antigen recognition domain that specifically binds to an antigen associated with tumor cells. In some embodiments, the targeting moiety directly or indirectly recruits tumor cells. For instance, in some embodiments, the recruitment of the tumor cell is to one or more effector cell (e.g. an immune cell as described herein) that can kill and/or suppress the tumor cell. In some embodiments, the targeting moiety directly or indirectly recruits T cells to a tumor cell, for example, by virtue of the two targeting moieties interacting with their respective antigens on a tumor and CD8-positive immune cell (e.g. T cell).

Tumor cells, or cancer cells refer to an uncontrolled growth of cells or tissues and/or an abnormal increased in cell survival and/or inhibition of apoptosis which interferes with the normal functioning of bodily organs and systems. For example, tumor cells include benign and malignant cancers, polyps, hyperplasia, as well as dormant tumors or micrometastases. Illustrative tumor cells include, but are not limited to cells of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Tumor cells, or cancer cells also include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative tumor antigens include, but are not limited to, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel17, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD56, CD70, CD74, CD138, AGS16, MUC1, GPNMB, Ep-CAM, PD-L1, PD-L2, PMSA, and BCMA (TNFRSF17). In various embodiments, the CD8 binding agent comprises a targeting moiety that binds one or more of these tumor antigens.

In some embodiments, the present multi-specific CD8 binding agent recognizes and binds to CD8 as well as an antigen on a tumor cell. In some embodiments, the multi-specific CD8 binding agent directly or indirectly recruits CTLs to the tumor cell or tumor microenvironment.

In various embodiments, the present multi-specific CD8 binding agent has targeting moieties which target two different cells (e.g. to make a synapse) or the same cell (e.g. to get a more concentrated signaling agent effect).

In some embodiments, the multi-specific CD8 binding agent of the invention comprises a targeting moiety having an antigen recognition domain that specifically binds to a target (e.g. antigen, receptor) associated with T cells. In some embodiments, the targeting moiety recruits directly or indirectly T cells. In an embodiment, the antigen recognition domains specifically bind to effector T cells. In some embodiments, the antigen recognition domain directly or indirectly recruits effector T cells, e.g., in some embodiments, to a therapeutic site (e.g. a locus with one or more disease cell or cell to be modulated for a therapeutic effect). Illustrative effector T cells include cytotoxic T cells (e.g. αβ TCR, $CD3^+$, $CD8^+$, $CD45RO^+$); $CD4^+$ effector T cells (e.g. αβ TCR, $CD3^+$, $CD4^+$, $CCR7^+$, CD62Lhi, IL-7R/$CD127^+$); $CD8^+$ effector T cells (e.g. αβ TCR, $CD3^+$, $CD8^+$, $CCR7^+$, CD62Lhi, IL-7R/$CD127^+$); effector memory T cells (e.g. CD62Llow, $CD44^+$, TCR, $CD3^+$, IL-7R/$CD127^+$, IL-$15R^+$, CCR7low); central memory T cells (e.g. $CCR7^+$, $CD62L^+$, $CD27^+$; or CCR7hi, $CD44^+$, CD62Lhi, TCR, $CD3^+$, IL-7R/$CD127^+$, IL-$15R^+$); $CD62L^+$ effector T cells; $CD8^+$ effector memory T cells (TEM) including early effector memory T cells ($CD27^+$ $CD62L^-$) and late effector memory T cells ($CD27^-$ $CD62L^-$) (TemE and TemL, respectively); CD127 ($^+$)CD25(low/−) effector T cells; CD127($^-$) CD25($^-$) effector T cells; $CD8^+$ stem cell memory effector cells (TSCM) (e.g. CD44(low)CD62L(high)CD122(high)sca($^+$)); TH1 effector T-cells (e.g. $CXCR3^+$, $CXCR6^+$ and $CCR5^+$; or αβ TCR, $CD3^+$, $CD4^+$, IL-$12R^+$, IFNγ$R^+$, $CXCR3^+$), TH2 effector T cells (e.g. $CCR3^+$, $CCR4^+$ and $CCR8^+$; or αβ TCR, $CD3^+$, $CD4^+$, IL-$4R^+$, IL-$33R^+$, $CCR4^+$, IL-$17RB^+$, $CRTH2^+$); TH9 effector T cells (e.g. αβ TCR, $CD3^+$, $CD4^+$); TH17 effector T cells (e.g. αβ TCR, $CD3^+$, $CD4^+$, IL-$23R^+$, $CCR6^+$, IL-$1R^+$); $CD4^+$ $CD45RO^+CCR7^+$ effector T cells, $ICOS^+$ effector T cells; $CD4^+CD45RO^+$CCR7($^-$) effector T cells; and effector T cells secreting IL-2, IL-4 and/or IFN-γ.

Illustrative T cell antigens of interest include, for example (and inclusive of the extracellular domains, where applicable): CD8, CD3, SLAMF4, IL-2Rα, 4-1BB/TNFRSF9, IL-2 R β, ALCAM, B7-1, IL-4 R, B7-H3, BLAME/SLAMFS, CEACAM1, IL-6 R, CCR3, IL-7 R α, CCR4, CXCRI/IL-S RA, CCR5, CCR6, IL-10R α, CCR7, IL-I 0 R β, CCRS, IL-12 R β 1, CCR9, IL-12 R β 2, CD2, IL-13 R α 1, IL-13, CD3, CD4, ILT2/CDS5j, ILT3/CDS5k, ILT4/CDS5d, ILT5/CDS5a, lutegrin α 4/CD49d, CDS, Integrin α E/CD103, CD6, Integrin α M/CD 11 b, CDS, Integrin α X/CD11c, Integrin β 2/CDIS, KIR/CD15S, CD27/TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP β 1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1 and TSLP R. In various embodiments, the CD8 binding agent comprises a targeting moiety that binds one or more of these illustrative T cell antigens.

In some embodiments, the multi-specific CD8 binding agent of the invention comprises a targeting moiety having an antigen recognition domain that specifically binds to a target (e.g. antigen, receptor) associated with B cells. In some embodiments, the targeting moiety directly or indirectly recruits B cells, e.g., in some embodiments, to a therapeutic site (e.g. a locus with one or more disease cell or cell to be modulated for a therapeutic effect).

Illustrative B cell antigens of interest include, for example, CD10, CD19, CD20, CD21, CD22, CD23, CD24, CD37, CD38, CD39, CD40, CD70, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138, CDw150, and B-cell maturation antigen (BCMA). In various embodiments, the CD8 binding agent comprises a targeting moiety that binds one or more of these illustrative B cell antigens.

In some embodiments, the multi-specific CD8 binding agent of the invention comprises a targeting moiety having an antigen recognition domain that specifically bind to a target (e.g. antigen, receptor) associated with Natural Killer cells. In some embodiments, the targeting moiety directly or indirectly recruits Natural Killer cells, e.g., in some embodiments, to a therapeutic site (e.g. a locus with one or more disease cell or cell to be modulated for a therapeutic effect). Illustrative Natural Killer cell antigens of interest include, for example TIGIT, 2B4/SLAMF4, KIR2DS4, CD155/PVR, KIR3DL1, CD94, LMIR1/CD300A, CD69, LMIR2/CD300c, CRACC/SLAMF7, LMIR3/CD300LF, Kir1alpha, DNAM-1, LMIR5/CD300LB, Fc-epsilon RII, LMIR6/CD300LE, Fc-γ RI/CD64, MICA, Fc-γ RIIB/CD32b, MICB, Fc-γ RIIC/CD32c, MULT-1, Fc-γ RIIA/CD32a, Nectin-2/CD112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAMF6, Rae-1, Rae-1 α, Rae-1 β, Rae-1 delta, H60, Rae-1 epsilon, ILT2/CD85j, Rae-1 γ, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d and ULBP-3. In various embodiments, the CD8 binding agent comprises a targeting moiety that binds one or more of these illustrative NK cell antigens.

In some embodiments, the multi-specific CD8 binding agent of the invention comprises a targeting moiety having an antigen recognition domain that specifically binds to a target (e.g. antigen, receptor) associated with macrophages/monocytes. In some embodiments, the targeting moiety directly or indirectly recruits macrophages/monocytes, e.g., in some embodiments, to a therapeutic site (e.g. a locus with one or more disease cell or cell to be modulated for a therapeutic effect). Illustrative macrophages/monocyte antigens of interest include, for example SIRP1a, B7-1/CD80, ILT4/CD85d, B7-H1, ILT5/CD85a, Common β Chain, Integrin α 4/CD49d, BLAME/SLAMF8, Integrin α X/CDIIc, CCL6/C10, Integrin β 2/CD18, CD155/PVR, Integrin β 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R α, TCCR/WSX-1, ICAM-2/CD102, TLR3, IFN-γ RI, TLR4, IFN-gannna R2, TREM-1, IL-I RII, TREM-2, ILT2/CD85j, TREM-3, ILT3/CD85k, TREML1/TLT-1, 2B4/SLAMF 4, IL-10 R α, ALCAM, IL-10 R β, AminopeptidaseN/ANPEP, ILT2/CD85j, Common β Chain, ILT3/CD85k, Clq R1/CD93, ILT4/CD85d, CCR1, ILT5/CD85a, CCR2, CD206, Integrin α 4/CD49d, CCR5, Integrin α M/CDII b, CCR8, Integrin α X/CDIIc, CD155/PVR, Integrin β 2/CD18, CD14, Integrin β 3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF R α, Siglec-3/CD33, HVEM/TNFRSF14, SLAM, ICAM-1/CD54, TCCR/WSX-1, ICAM-2/CD102, TREM-I, IL-6 R, TREM-2, CXCRI/IL-8 RA, TREM-3 and TREMLI/TLT-1. In various embodiments, the CD8 binding agent comprises a targeting moiety that binds one or more of these illustrative macrophage/monocyte antigens.

In some embodiments, the multi-specific CD8 binding agent of the invention comprises a targeting moiety having an antigen recognition domain that specifically binds to a target (e.g. antigen, receptor) associated with dendritic cells. In some embodiments, the targeting moiety directly or indirectly recruits dendritic cells, e.g., in some embodiments, to a therapeutic site (e.g. a locus with one or more disease cell or cell to be modulated for a therapeutic effect). Illustrative dendritic cell antigens of interest include, for example, CLEC9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin α 4/CD49d, Aag, Integrin β 2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, CLEC-8, Siglec-2/CD22, CRACC/SLAMF7, Siglec-3/CD33, DC-SIGN, DEC-205, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCR/WSX-1, Fc-γ R1/CD64, TLR3, Fc-γ RIIB/CD32b, TREM-1, Fc-γ RIIC/CD32c, TREM-2, Fc-γ RIIA/CD32a, TREM-3, Fc-γ RII/CD16, TREML1/TLT-1, ICAM-2/CD102, DEC205, and Vanilloid R1. In various embodiments, the CD8 binding agent comprises a targeting moiety that binds one or more of these illustrative DC antigens.

In some embodiments, the multi-specific CD8 binding agent of the invention comprises a targeting moiety against Clec9A which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the multi-specific CD8 binding agent of the invention comprises a VHH against Clec9A having a variable domain comprising at least one CDR1, CDR2, and/or CDR3 sequences.

In exemplary embodiments, the CDR1 sequence is selected from SEQ ID NO: 303 to SEQ NO: 322.

In exemplary embodiments, the CDR2 sequence is selected from SEQ ID NO: 323 to SEQ ID NO: 344.

In exemplary embodiments, the CDR3 sequence is selected from SEQ ID NO: 345 to SEQ ID NO: 359; or LGR; or VIK.

In various embodiments, the Clec9A targeting moiety comprises an amino acid sequence selected from the following sequences: R2CHCL8 (SEQ ID NO:360); R1CHCL50 (SEQ ID NO:361); R1CHCL21 (SEQ ID NO:362); R2CHCL87 (SEQ ID NO:363); R2CHCL24 (SEQ ID NO:364); R2CHCL38 (SEQ ID NO:365); R1CHCL16 (SEQ ID NO:366); R2CHCL10 (SEQ ID NO:367); R1CHCL34 (SEQ ID NO:368); R1CHCL82 (SEQ ID NO:369); R2CHCL3 (SEQ ID NO:370); R2CHCL69 (SEQ ID NO:371); R1CHCL56 (SEQ ID NO:372); R2CHCL32 (SEQ ID NO:373); R2CHCL49 (SEQ ID NO:374); R2CHCL53 (SEQ ID NO:375); R2CHCL22 (SEQ ID NO:376); R2CHCL25 (SEQ ID NO:377); R2CHCL18 (SEQ ID NO:378); R1CHCL23 (SEQ ID NO:379); R1CHCL27 (SEQ ID NO:380); R2CHCL13 (SEQ ID NO:381); R2CHCL14 (SEQ ID NO:382); R2CHCL42 (SEQ ID NO:383); R2CHCL41 (SEQ ID NO:384); R2CHCL94 (SEQ ID NO:385); or R2CHCL27 (SEQ ID NO:386).

In various embodiments, the Clec9A targeting moiety comprises a VHH having a variable domain comprising at least one CDR1, CDR2, and/or CDR3 sequences as described below.

In some embodiments, the CDR1 sequence is selected from SEQ ID NO: 387 to SEQ ID NO: 452.

In some embodiments, the CDR2 sequence is selected from SEQ ID NO: 453 to SEQ ID NO: 518.

In some embodiments, the CDR3 sequence is selected from SEQ ID NO: 519 to SEQ ID NO: 584.

In various exemplary embodiments, the Clec9A targeting moiety comprises an amino acid sequence selected from the following sequences: 1LEC 7 (SEQ ID NO:585) or 1LEC 9 (SEQ ID NO:586) or 1LEC 26 (SEQ ID NO:587) or 1LEC 27 (SEQ ID NO:588) or 1LEC 28 (SEQ ID NO:589) or 1LEC 30 (SEQ ID NO:590) or 1LEC 38 (SEQ ID NO:591) or 1LEC 42 (SEQ ID NO:592) or 1LEC 51 (SEQ ID NO:593) or 1LEC 61 (SEQ ID NO:594) or 1LEC 62 (SEQ ID NO:595) or 1LEC 63 (SEQ ID NO:596) or 1LEC 64 (SEQ ID NO:597) or 1LEC 70 (SEQ ID NO:598) or 1LEC 84 (SEQ ID NO:599) or 1LEC 88 (SEQ ID NO:600) or 1LEC 91 (SEQ ID NO:601) or 1LEC 92 (SEQ ID NO:602) or 1LEC 94 (SEQ ID NO:603) or 2LEC 6 (SEQ ID NO:604) or 2LEC 13 (SEQ ID NO:605) or 2LEC 16 (SEQ ID NO:606) or 2LEC 20 (SEQ ID NO:607) or 2LEC 23 (SEQ ID NO:608) or 2LEC 24 (SEQ ID NO:609) or 2LEC 26 (SEQ ID NO:610) or 2LEC 38 (SEQ ID NO:611) or 2LEC 48 (SEQ ID NO:612) or 2LEC 53 (SEQ ID NO:613) or 2LEC 54 (SEQ ID NO:614) or 2LEC 55 (SEQ ID NO:615) or 2LEC 59 (SEQ ID NO:616) or 2LEC 60 (SEQ ID NO:617) or 2LEC 61 (SEQ ID NO:618) or 2LEC 62 (SEQ ID NO:619) or 2LEC 63 (SEQ ID NO:620) or 2LEC 67 (SEQ ID NO:621) or 2LEC 68 (SEQ ID NO:622) or 2LEC 76 (SEQ ID NO:623) or 2LEC 83 (SEQ ID NO:624) or 2LEC 88 (SEQ ID NO:625) or 2LEC 89 (SEQ ID NO:626) or 2LEC 90 (SEQ ID NO:627) or 2LEC 93 (SEQ ID NO:628) or 2LEC 95 (SEQ ID NO:629) or 3LEC 4 (SEQ ID NO:630) or 3LEC 6 (SEQ ID NO:631) or 3LEC 9 (SEQ ID NO:632) or 3LEC 11 (SEQ ID NO:633) or 3LEC 13 (SEQ ID NO:634) or 3LEC 15 (SEQ ID NO:635) or 3LEC 22 (SEQ ID NO:636) or 3LEC 23 (SEQ ID NO:637) or 3LEC 27 (SEQ ID NO:638) or 3LEC 30 (SEQ ID NO:639) or 3LEC 36 (SEQ ID NO:640) or 3LEC 55 (SEQ ID NO:641) or 3LEC 57 (SEQ ID NO:642) or 3LEC 61 (SEQ ID NO:643) or 3LEC 62 (SEQ ID NO:644) or 3LEC 66 (SEQ ID NO:645) or 3LEC 69 (SEQ ID NO:646) or 3LEC 76 (SEQ ID NO:647) or 3LEC 82 (SEQ ID NO:648) or 3LEC 89 (SEQ ID NO:649) or 3LEC 94 (SEQ ID NO:650). In various exemplary embodiments, the Clec9A targeting moiety comprises an amino acid sequence selected from any one of the above sequences without the terminal histidine tag sequence (i.e., HHHHHH, SEQ ID NO: 1213).

In some embodiments, the Clec9A targeting moiety comprises an amino acid sequence selected from any one of the above sequences without the HA tag (i.e., YPYDVPDYGS; SEQ ID NO: 1214).

In some embodiments, the Clec9A targeting moiety comprises an amino acid sequence selected from any one of the above sequences without the AAA linker.

In some embodiments, the Clec9A targeting moiety comprises an amino acid sequence selected from any one of the above sequences without the AAA linker, HA tag, and terminal histidine tag sequence (i.e.,

AAAYPYDVPDYGSHHHHHH; SEQ ID NO: 1215).

In an embodiment, the targeting moiety comprises the anti-Clec9A antibody as disclosed in Tullett et al., JCI Insight. 2016; 1(7):e87102, the entire disclosures of which are hereby incorporated by reference.

In various embodiments, the present invention contemplates the use of any natural or synthetic analogs, mutants, variants, alleles, homologs and orthologs (herein collectively referred to as "analogs") of the targeting moiety directed against Clec9A as described herein. In various embodiments, the amino acid sequence of the targeting moiety directed against Clec9A further includes an amino acid analog, an amino acid derivative, or other non-classical amino acids.

In various embodiments, the present chimeric protein comprises a targeting moiety comprising an amino acid sequence that is at least 60% identical to any one of the sequences disclosed herein. For example, the chimeric protein may comprise a targeting moiety comprising an amino acid sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any one of the sequences discloses herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the sequences disclosed herein).

In some embodiments, the multi-specific CD8 binding agent of the invention comprises a targeting moiety having an antigen recognition domain that specifically binds a target (e.g. antigen, receptor) on immune cells selected from, but not limited to, megakaryocytes, thrombocytes, erythrocytes, mast cells, basophils, neutrophils, and eosinophils. In some embodiments, the antigen recognition domains directly or indirectly recruit megakaryocytes, thrombocytes, erythrocytes, mast cells, basophils, neutrophils, and eosinophil, e.g., in some embodiments, to a therapeutic site (e.g. a locus with one or more disease cell or cell to be modulated for a therapeutic effect).

In some embodiments, the multi-specific CD8 binding agent of the invention comprises a targeting moiety having an antigen recognition domain that specifically binds to a target (e.g. antigen, receptor) associated with megakaryocytes and/or thrombocytes. Illustrative megakaryocyte and/or thrombocyte antigens of interest include, for example, GP IIb/IIIa, GPIb, vWF, PF4, and TSP. In various embodiments, the CD8 binding agent comprises a targeting moiety that binds one or more of these illustrative megakaryocyte and/or thrombocyte antigens.

In some embodiments, the multi-specific CD8 binding agent of the invention comprises a targeting moiety having an antigen recognition domain that specifically binds to a target (e.g. antigen, receptor) associated with erythrocytes. Illustrative erythrocyte antigens of interest include, for example, CD34, CD36, CD38, CD41a (platelet glycoprotein IIb/IIIa), CD41b (GPIIb), CD71 (transferrin receptor), CD105, glycophorin A, glycophorin C, c-kit, HLA-DR, H2 (MHC-II), and Rhesus antigens. In various embodiments, the CD8 binding agent comprises a targeting moiety that binds one or more of these illustrative erythrocyte antigens.

In some embodiments, the multi-specific CD8 binding agent of the invention comprises a targeting moiety having an antigen recognition domain that specifically binds to a target (e.g. antigen, receptor) associated with mast cells. Illustrative mast cells antigens of interest include, for example, SCFR/CD117, $Fc_{\varepsilon}RI$, CD2, CD25, CD35, CD88, CD203c, C5R1, CMAI, FCERIA, FCER2, TPSABI. In various embodiments, the CD8 binding agent comprises a targeting moiety that binds one or more of these mast cell antigens.

In some embodiments, the multi-specific CD8 binding agent of the invention comprises a targeting moiety having an antigen recognition domain that specifically binds to a target (e.g. antigen, receptor) associated with basophils. Illustrative basophils antigens of interest include, for example, $Fc_{\varepsilon}RI$, CD203c, CD123, CD13, CD107a, CD107b, and CD164. In various embodiments, the CD8 binding agent comprises a targeting moiety that binds one or more of these basophil antigens.

In some embodiments, the multi-specific CD8 binding agent of the invention comprises a targeting moiety having an antigen recognition domain that specifically binds to a target (e.g. antigen, receptor) associated with neutrophils. Illustrative neutrophils antigens of interest include, for example, 7D5, CD10/CALLA, CD13, CD16 (FcRIII), CD18 proteins (LFA-1, CR3, and p150, 95), CD45, CD67, and CD177. In various embodiments, the CD8 binding agent comprises a targeting moiety that binds one or more of these neutrophil antigens.

In some embodiments, the multi-specific CD8 binding agent of the invention comprises a targeting moiety having an antigen recognition domain that specifically binds to a target (e.g. antigen, receptor) associated with eosinophils. Illustrative eosinophils antigens of interest include, for example, CD35, CD44 and CD69. In various embodiments, the CD8 binding agent comprises a targeting moiety that binds one or more of these eosinophil antigens.

In various embodiments, the multi-specific CD8 binding agent of the invention comprises a targeting moiety having an antigen recognition domain that specifically binds to any appropriate antigen or receptor or cell surface markers known by the skilled artisan. In some embodiments, the antigen or cell surface marker is a tissue-specific marker. Illustrative tissue-specific markers include, but are not limited to, endothelial cell surface markers such as ACE, CD14, CD34, CDH5, ENG, ICAM2, MCAM, NOS3, PECAMI, PROCR, SELE, SELP, TEK, THBD, VCAMI, VWF; smooth muscle cell surface markers such as ACTA2, MYHIO, MYHI 1, MYH9, MYOCD; fibroblast (stromal) cell surface markers such as ALCAM, CD34, COLIAI, COL1A2, COL3A1, FAP, PH-4; epithelial cell surface markers such as CDID, K6IRS2, KRTIO, KRT13, KRT17, KRT18, KRT19, KRT4, KRT5, KRT8, MUCI, TACSTDI; neovasculature markers such as CD13, TFNA, Alpha-v beta-3 ($\alpha_v\beta_3$), E-selectin; and adipocyte surface markers such as ADIPOQ, FABP4, and RETN. In various embodiments, the CD8 binding agent comprises a targeting moiety that binds one or more of these antigens.

In various embodiments, the multi-specific CD8 binding agent of the invention comprises a targeting moiety having an antigen recognition domain that specifically binds to a checkpoint marker expressed on a T cell, e.g. one or more of PD-1, CD28, CTLA4, ICOS, BTLA, KIR, LAG3, CD137, OX40, CD27, CD40L, TIM3, and A2aR.

In various embodiments, the multi-specific CD8 binding agent of the invention comprises a targeting moiety having an antigen recognition domain that specifically binds to a checkpoint marker, e.g. one or more of PD-1/PD-L1 or PD-L2, CD28/CD80 or CD86, CTLA4/CD80 or CD86, ICOS/ICOSL or B7RP1, BTLA/HVEM, KIR, LAG3, CD137/CD137L, OX40/OX40L, CD27, CD40L, TIM3/Gal9, and A2aR.

By way of non-limiting example, in various embodiments, the present multispecific CD8 binding agent comprises a targeting moiety directed against (i) CD8; (ii) a checkpoint marker expressed on a T cell, e.g. one or more of PD-1, CD28, CTLA4, ICOS, BTLA, KIR, LAG3, CD137, OX40, Cd27, CD40L, TIM3, and A2aR and/or (iii) a targeting moiety is directed against a tumor cell, along with any of the modified (e.g. mutant) signaling agents described herein.

In various embodiments, the present multi-specific CD8 binding agent has one or more targeting moieties directed against PD-1. In some embodiments, the CD8 binding agent has one or more targeting moieties which selectively bind a PD-1 polypeptide. In some embodiments, the CD8 binding agent comprises one or more antibodies, antibody derivatives or formats, peptides or polypeptides, or fusion proteins that selectively bind a PD-1 polypeptide.

In various embodiments, the multi-specific CD8 binding agent of the invention comprises a VHH against PD1 having a variable domain comprising at least one CDR1, CDR2, and/or CDR3 sequences.

In some embodiments, the CDR1 sequence is selected from SEQ ID NO: 651 to SEQ ID NO: 664.

In some embodiments, the CDR2 sequence is selected from SEQ ID NOL 665 to SEQ ID NO: 678.

In some embodiments, the CDR3 sequence is selected from SEQ ID NO: 679 to SEQ ID NO: 692.

In various exemplary embodiments, the PD1 targeting moiety comprises an amino acid sequence selected from the following sequences: 2PD23 (SEQ ID NO: 693); or 2PD26 (SEQ ID NO: 694); or 2PD90 (SEQ ID NO: 695); or 2PD106 (SEQ ID NO: 696); or 2PD16 (SEQ ID NO: 697); or 2PD71 (SEQ ID NO: 698); or 2PD152 (SEQ ID NO: 699); or 2PD12 (SEQ ID NO: 700); or 3PD55 (SEQ ID NO: 701); or 3PD82 (SEQ ID NO: 702); or 2PD8 (SEQ ID NO: 703); or 2PD27 (SEQ ID NO: 704); or 2PD82 (SEQ ID NO: 705); or 3PD36 (SEQ ID NO: 706).

In various exemplary embodiments, the PD1 targeting moiety comprises an amino acid sequence selected from any one of the above without the terminal histidine tag sequence (i.e., HHHHHH, SEQ ID NO: 1213).

In some embodiments, the PD1 targeting moiety comprises an amino acid sequence selected from any one of the above sequences without the HA tag (i.e., YPYDVPDYGS; SEQ ID NO: 1214).

In some embodiments, the PD1 targeting moiety comprises an amino acid sequence selected from any one of the above sequences without the AAA linker.

In some embodiments, the PD1 targeting moiety comprises an amino acid sequence selected from any one of the above sequences without the AAA linker, HA tag, and terminal histidine tag sequence (i.e.,

```
AAAYPYDVPDYGSHHHHHH; SEQ ID NO: 1215).
```

In an embodiment, the targeting moiety comprises the anti-PD-1 antibody pembrolizumab (aka MK-3475, KEYTRUDA), or fragments thereof. Pembrolizumab and other humanized anti-PD-1 antibodies are disclosed in Hamid, et al. (2013) New England Journal of Medicine 369 (2): 134-44, U.S. Pat. No. 8,354,509, and WO 2009/114335, the entire disclosures of which are hereby incorporated by reference. In illustrative embodiments, pembrolizumab or an antigen-binding fragment thereof for use in the methods provided herein comprises a heavy chain comprising the amino acid sequence of SEQ ID NO:707; and/or a light chain comprising the amino acid sequence of SEQ ID NO:708.

In an embodiment, the targeting moiety comprises the anti-PD-1 antibody, nivolumab (aka BMS-936558, MDX-1106, ONO-4538, OPDIVO), or fragments thereof. Nivolumab (clone 5C4) and other human monoclonal antibodies that specifically bind to PD-1 are disclosed in U.S. Pat. No. 8,008,449 and WO 2006/121168, the entire disclosures of which are hereby incorporated by reference. In illustrative embodiments, nivolumab or an antigen-binding fragment thereof comprises a heavy chain comprising the amino acid sequence of SEQ ID NO:709; and/or a light chain comprising the amino acid sequence of SEQ ID NO:710.

In an embodiment, the targeting moiety comprises the anti-PD-1 antibody pidilizumab (aka CT-011, hBAT or hBAT-1), or fragments thereof. Pidilizumab and other humanized anti-PD-I monoclonal antibodies are disclosed in US 2008/0025980 and WO 2009/101611, the entire disclosures of which are hereby incorporated by reference. In illustrative embodiments, the anti-PD-1 antibody or an antigen-binding fragment thereof for use in the methods provided herein comprises a light chain variable regions comprising an amino acid sequence selected from SEQ ID NOS: 15-18 of US 2008/0025980: SEQ ID NO: 15 of US 2008/0025980 (SEQ ID NO:711); SEQ ID NO: 16 of US 2008/0025980 (SEQ ID NO:712); SEQ ID NO: 17 of US 2008/0025980 (SEQ ID NO:713); SEQ ID NO: 18 of US 2008/0025980 (SEQ ID NO:714); and/or a heavy chain comprising an amino acid sequence selected from SEQ ID NOS: 20-24 of US 2008/0025980: SEQ ID NO: 20 of US 2008/0025980 (SEQ ID NO:715); SEQ ID NO: 21 of US 2008/0025980 (SEQ ID NO:716); SEQ ID NO: 22 of US 2008/0025980 (SEQ ID NO:717); SEQ ID NO: 23 of US 2008/0025980 (SEQ ID NO:718); or SEQ ID NO: 24 of US 2008/0025980 (SEQ ID NO:719).

In an embodiment, the targeting moiety comprises a light chain comprising SEQ ID NO:18 of US 2008/0025980 and a heavy chain comprising SEQ ID NO:22 of US 2008/0025980.

In an embodiment, the targeting moiety comprises AMP-514 (aka MEDI-0680).

In an embodiment, the targeting moiety comprises the PD-L2-Fc fusion protein AMP-224, which is disclosed in WO2010/027827 and WO 2011/066342, the entire disclosures of which are hereby incorporated by reference. In such an embodiment, the targeting moiety may include a targeting domain which comprises SEQ ID NO:4 of WO2010/027827 (SEQ ID NO:720) and/or the B7-DC fusion protein which comprises SEQ ID NO:83 of WO2010/027827 (SEQ ID NO:721).

In an embodiment, the targeting moiety comprises the peptide AUNP 12 or any of the other peptides disclosed in US 2011/0318373 or 8,907,053. For example, the targeting moiety may comprise AUNP 12 (i.e., Compound 8 or SEQ ID NO:49 of US 2011/0318373) which has the sequence of SEQ ID NO:722:

SNTSESFK (SNTSESF) FRVTQLAPKAQIKE—NH2

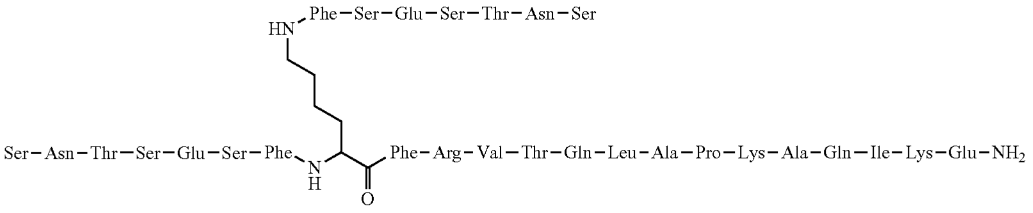

or:

SNTSESF—NH
|
SNTSESFKFRVTQLAPKAQIKE—$NH_2$

In an embodiment, the targeting moiety comprises the anti-PD-1 antibody 1E3, or fragments thereof, as disclosed in US 2014/0044738, the entire disclosures of which are hereby incorporated by reference. In illustrative embodiments, 1E3 or an antigen-binding fragment thereof for use in the methods provided herein comprises a heavy chain variable region comprising the amino acid sequence of SEQ ID NO:723; and/or alight chain variable region comprising the amino acid sequence of SEQ ID NO:724.

In an embodiment, the targeting moiety comprises the anti-PD-1 antibody 1E8, or fragments thereof, as disclosed in US 2014/0044738, the entire disclosures of which are hereby incorporated by reference. In illustrative embodiments, 1E8 or an antigen-binding fragment thereof for use in the methods provided herein comprises a heavy chain variable region comprising the amino acid sequence of SEQ ID NO:725; and/or alight chain variable region comprising the amino acid sequence of SEQ ID NO:726.

In an embodiment, the targeting moiety comprises the anti-PD-1 antibody 1H3, or fragments thereof, as disclosed in US 2014/0044738, the entire disclosures of which are hereby incorporated by reference. In illustrative embodiments, 1H3 or an antigen-binding fragment thereof for use in the methods provided herein comprises a heavy chain variable region comprising the amino acid sequence of SEQ ID NO:727; and/or light chain variable region comprising the amino acid sequence of SEQ ID NO:728.

In an embodiment, the targeting moiety comprises a VHH directed against PD-1 as disclosed, for example, in U.S. Pat. No. 8,907,065 and WO 2008/071447, the entire disclosures of which are hereby incorporated by reference. In illustrative embodiments, the VHHs against PD-1 comprise SEQ ID NOS: 347-351 of U.S. Pat. No. 8,907,065: SEQ ID NO: 347 of U.S. Pat. No. 8,907,065 (SEQ ID NO:729); SEQ ID NO: 348 of U.S. Pat. No. 8,907,065 (SEQ ID NO:730); SEQ ID NO: 349 of U.S. Pat. No. 8,907,065 (SEQ ID NO:731); SEQ ID NO: 350 of U.S. Pat. No. 8,907,065 (SEQ ID NO:732); or SEQ ID NO: 351 of U.S. Pat. No. 8,907,065 (SEQ ID NO:733).

In an embodiment, the targeting moiety comprises any one of the anti-PD-1 antibodies, or fragments thereof, as disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID NOS: 25-29 of US2011/0271358: SEQ ID NO: 25 of US2011/0271358 (SEQ ID NO:734); SEQ ID NO: 26 of US2011/0271358 (SEQ ID NO:735); SEQ ID NO: 27 of US2011/0271358 (SEQ ID NO:736); SEQ ID NO: 28 of US2011/0271358 (SEQ ID NO:737); SEQ ID NO: 29 of US2011/0271358 (SEQ ID NO:738); and/or alight chain comprising an amino acid sequence selected from SEQ ID NOS: 30-33 of US2011/0271358: SEQ ID NO: 30 of US2011/0271358 (SEQ ID NO:739); SEQ ID NO: 31 of US2011/0271358 (SEQ ID NO:740); SEQ ID NO: 32 of US2011/0271358 (SEQ ID NO:741); or SEQ ID NO: 33 of US2011/0271358 (SEQ ID NO:742).

In various embodiments, the present multi-specific CD8 binding agent comprises one or more antibodies directed against PD-1, or antibody fragments thereof, selected from TSR-042 (Tesaro, Inc.), REGN2810 (Regeneron Pharmaceuticals, Inc.), PDR001 (Novartis Pharmaceuticals), and BGB-A317 (BeiGene Ltd.)

In various embodiments, the present multi-specific CD8 binding agent has one or more targeting moieties directed against PD-L1. In some embodiments, the CD8 binding agent has one or more targeting moieties which selectively bind a PD-L1 polypeptide. In some embodiments, the CD8 binding agent comprises one or more antibodies, antibody derivatives or formats, peptides or polypeptides, or fusion proteins that selectively bind a PD-L1 polypeptide.

In various embodiments, the multi-specific CD8 binding agent of the invention comprises a VHH against PD-L1 having a variable domain comprising at least one CDR1, CDR2, and/or CDR3 sequences.

In some embodiments, the CDR1 sequence is selected from SEQ ID NO: 743 to SEQ ID NO: 773.

In some embodiments, the CDR2 sequence is selected from SEQ ID NO: 774 to SEQ ID NO: 804.

In some embodiments, the CDR3 sequence is selected from SEQ ID NO: 805 to SEQ ID NO: 835.

In various exemplary embodiments, the PD-L1 targeting moiety comprises an amino acid sequence selected from the following sequences: 2LIG2 (SEQ ID NO: 836); or 2LIG3 (SEQ ID NO: 837); or 2LIG16 (SEQ ID NO: 838) or 2LIG22 (SEQ ID NO: 839) or 2LIG27 (SEQ ID NO: 840) or 2LIG29 (SEQ ID NO: 841) or 2LIG30 (SEQ ID NO: 842) or 2LIG34 (SEQ ID NO: 843) or 2LIG35 (SEQ ID NO: 844) or 2LIG48 (SEQ ID NO: 845) or 2LIG65 (SEQ ID NO: 846) or 2LIG85 (SEQ ID NO: 847) or 2LIG86 (SEQ ID NO: 848) or 2LIG89 (SEQ ID NO: 849) or 2LIG97 (SEQ ID NO: 850) or 2LIG99 (SEQ ID NO: 851) or 2LIG109 (SEQ ID NO: 852) or 2LIG127 (SEQ ID NO: 853) or 2LIG139 (SEQ ID NO: 854) or 2LIG176 (SEQ ID NO: 855) or 2LIG189 (SEQ ID NO: 856) or 3LIG3 (SEQ ID NO: 857) or 3LIG7 (SEQ ID NO: 858) or 3LIG8 (SEQ ID NO: 859) or 3LIG9 (SEQ ID NO: 860) or 3LIG18 (SEQ ID NO: 861) or 3LIG20 (SEQ ID NO: 862) or 3LIG28 (SEQ ID NO: 863) or 3LIG29 (SEQ ID NO: 864) or 3LIG30 (SEQ ID NO: 865) or 3LIG33 (SEQ ID NO: 866).

In various exemplary embodiments, the PD-L1 targeting moiety comprises an amino acid sequence selected from any one of the above sequences without the terminal histidine tag sequence (i.e., HHHHHH, SEQ ID NO: 1213).

In some embodiments, the PD-L1 targeting moiety comprises an amino acid sequence selected from any one of the above sequences without the HA tag (i.e., YPYDVPDYGS; SEQ ID NO: 1214).

In some embodiments, the PD-L1 targeting moiety comprises an amino acid sequence selected from any one of the above sequences without the AAA linker.

In some embodiments, the PD-L1 targeting moiety comprises an amino acid sequence selected from any one of the above sequences without the AAA linker, HA tag, and terminal histidine tag sequence (i.e.,

AAAYPYDVPDYGSHHHHHH; SEQ ID NO: 1215).

In an embodiment, the targeting moiety comprises the anti-PD-L1 antibody MEDI4736 (aka durvalumab), or fragments thereof. MEDI4736 is selective for PD-L1 and blocks the binding of PD-L1 to the PD-1 and CD80 receptors. MEDI4736 and antigen-binding fragments thereof for use in the methods provided herein comprises a heavy chain and a light chain or a heavy chain variable region and a light chain variable region. The sequence of MEDI4736 is disclosed in WO/2016/06272, the entire contents of which are hereby incorporated by reference. In illustrative embodiments, MEDI4736 or an antigen-binding fragment thereof for use in the methods provided herein comprises a heavy chain comprising the amino acid sequence of (SEQ ID NO:867); and/or a light chain comprising the amino acid sequence of (SEQ ID NO:868).

In illustrative embodiments, the MEDI4736 or an antigen-binding fragment thereof for use in the methods provided herein comprises a heavy chain variable region comprising the amino acid sequence of SEQ ID NO:4 of WO/2016/06272 (SEQ ID NO:869); and/or a light chain variable region comprising the amino acid sequence of SEQ ID NO:3 of WO/2016/06272 (SEQ ID NO:870).

In an embodiment, the targeting moiety comprises the anti-PD-L1 antibody atezolizumab (aka MPDL3280A, RG7446), or fragments thereof. In illustrative embodiments, atezolizumab or an antigen-binding fragment thereof for use in the methods provided herein comprises a heavy chain comprising the amino acid sequence of: SEQ ID NO:871); and/or a light chain comprising the amino acid sequence of SEQ ID NO:872.

In an embodiment, the targeting moiety comprises the anti-PD-L1 antibody avelumab (aka MSB0010718C), or fragments thereof. In illustrative embodiments, avelumab or an antigen-binding fragment thereof for use in the methods provided herein comprises a heavy chain comprising the amino acid sequence of SEQ ID NO:873; and/or a light chain comprising the amino acid sequence of SEQ ID NO:874.

In an embodiment, the targeting moiety comprises the anti-PD-L1 antibody BMS-936559 (aka 12A4, MDX-1105), or fragments thereof, as disclosed in US 2013/0309250 and WO2007/005874, the entire disclosures of which are hereby incorporated by reference. In illustrative embodiments, BMS-936559 or an antigen-binding fragment thereof for use in the methods provided herein comprises a heavy chain variable region comprising the amino acid sequence of SEQ ID NO:875; and/or a light chain variable region comprising the amino acid sequence of SEQ ID NO:876.

In an embodiment, the targeting moiety comprises the anti-PD-L1 antibody 3G10, or fragments thereof, as disclosed in US 2013/0309250 and WO2007/005874, the entire disclosures of which are hereby incorporated by reference. In illustrative embodiments, 3G10 or an antigen-binding fragment thereof for use in the methods provided herein comprises a heavy chain variable region comprising the amino acid sequence of SEQ ID NO:877; and/or a light chain variable region comprising the amino acid sequence of SEQ ID NO:878.

In an embodiment, the targeting moiety comprises the anti-PD-L1 antibody 10A5, or fragments thereof, as disclosed in US 2013/0309250 and WO2007/005874, the entire disclosures of which are hereby incorporated by reference. In illustrative embodiments, 10A5 or an antigen-binding fragment thereof for use in the methods provided herein comprises a heavy chain variable region comprising the amino acid sequence of SEQ ID NO:879; and/or a light chain variable region comprising the amino acid sequence of SEQ ID NO:880.

In an embodiment, the targeting moiety comprises the anti-PD-L1 antibody 5F8, or fragments thereof, as disclosed in US 2013/0309250 and WO2007/005874, the entire disclosures of which are hereby incorporated by reference. In illustrative embodiments, 5F8 or an antigen-binding fragment thereof for use in the methods provided herein comprises a heavy chain variable region comprising the amino acid sequence of SEQ ID NO:881; and/or a light chain variable region comprising the amino acid sequence of SEQ ID NO:882.

In an embodiment, the targeting moiety comprises the anti-PD-L1 antibody 10H10, or fragments thereof, as disclosed in US 2013/0309250 and WO2007/005874, the entire disclosures of which are hereby incorporated by reference. In illustrative embodiments, 10H10 or an antigen-binding fragment thereof for use in the methods provided herein comprises a heavy chain variable region comprising the amino acid sequence of SEQ ID NO:883); and/or a light chain variable region comprising the amino acid sequence of SEQ ID NO:884.

In an embodiment, the targeting moiety comprises the anti-PD-L1 antibody 1B12, or fragments thereof, as disclosed in US 2013/0309250 and WO2007/005874, the entire disclosures of which are hereby incorporated by reference. In illustrative embodiments, 1B12 or an antigen-binding fragment thereof for use in the methods provided herein comprises a heavy chain variable region comprising the amino acid sequence of SEQ ID NO:885; and/or a light chain variable region comprising the amino acid sequence of SEQ ID NO:886.

In an embodiment, the targeting moiety comprises the anti-PD-L1 antibody 7H1, or fragments thereof, as disclosed in US 2013/0309250 and WO2007/005874, the entire disclosures of which are hereby incorporated by reference. In illustrative embodiments, 7H1 or an antigen-binding fragment thereof for use in the methods provided herein comprises a heavy chain variable region comprising the amino acid sequence of SEQ ID NO:887; and/or a light chain variable region comprising the amino acid sequence of SEQ ID NO:888.

In an embodiment, the targeting moiety comprises the anti-PD-L1 antibody 11E6, or fragments thereof, as disclosed in US 2013/0309250 and WO2007/005874, the entire disclosures of which are hereby incorporated by reference. In illustrative embodiments, 11E6 or an antigen-binding fragment thereof for use in the methods provided herein comprises a heavy chain variable region comprising the amino acid sequence of SEQ ID NO:889; and/or a light chain variable region comprising the amino acid sequence of SEQ ID NO:890.

In an embodiment, the targeting moiety comprises the anti-PD-L1 antibody 12B7, or fragments thereof, as disclosed in US 2013/0309250 and WO2007/005874, the entire disclosures of which are hereby incorporated by reference. In illustrative embodiments, 12B7 or an antigen-binding fragment thereof for use in the methods provided herein comprises a heavy chain variable region comprising the amino acid sequence of SEQ ID NO:891; and/or a light chain variable region comprising the amino acid sequence of SEQ ID NO:892.

In an embodiment, the targeting moiety comprises the anti-PD-L1 antibody 13G4, or fragments thereof, as disclosed in US 2013/0309250 and WO2007/005874, the entire disclosures of which are hereby incorporated by reference. In illustrative embodiments, 13G4 or an antigen-binding fragment thereof for use in the methods provided herein comprises a heavy chain variable region comprising the amino acid sequence of SEQ ID NO:893; and/or a light chain variable region comprising the amino acid sequence of SEQ ID NO:894.

In an embodiment, the targeting moiety comprises the anti-PD-L1 antibody 1E12, or fragments thereof, as disclosed in US 2014/0044738, the entire disclosures of which are hereby incorporated by reference. In illustrative embodiments, 1E12 or an antigen-binding fragment thereof for use in the methods provided herein comprises a heavy chain variable region comprising the amino acid sequence of SEQ ID NO:895; and/or alight chain variable region comprising the amino acid sequence of SEQ ID NO:896.

In an embodiment, the targeting moiety comprises the anti-PD-L1 antibody 1F4, or fragments thereof, as disclosed in US 2014/0044738, the entire disclosures of which are hereby incorporated by reference. In illustrative embodiments, 1F4 or an antigen-binding fragment thereof for use in the methods provided herein comprises a heavy chain variable region comprising the amino acid sequence of SEQ ID NO:897; and/or alight chain variable region comprising the amino acid sequence of SEQ ID NO:898.

In an embodiment, the targeting moiety comprises the anti-PD-L1 antibody 2G11, or fragments thereof, as disclosed in US 2014/0044738, the entire disclosures of which are hereby incorporated by reference. In illustrative embodiments, 2G11 or an antigen-binding fragment thereof for use in the methods provided herein comprises a heavy chain variable region comprising the amino acid sequence of SEQ ID NO:899; and/or alight chain variable region comprising the amino acid sequence of SEQ ID NO:900.

In an embodiment, the targeting moiety comprises the anti-PD-L1 antibody 3B6, or fragments thereof, as disclosed in US 2014/0044738, the entire disclosures of which are hereby incorporated by reference. In illustrative embodiments, 3B6 or an antigen-binding fragment thereof for use in the methods provided herein comprises a heavy chain variable region comprising the amino acid sequence of SEQ ID NO:901; and/or alight chain variable region comprising the amino acid sequence of SEQ ID NO:902.

In an embodiment, the targeting moiety comprises the anti-PD-L1 antibody 3D10, or fragments thereof, as disclosed in US 2014/0044738 and WO2012/145493, the entire disclosures of which are hereby incorporated by reference. In illustrative embodiments, 3D10 or an antigen-binding fragment thereof for use in the methods provided herein comprises a heavy chain variable region comprising the amino acid sequence of SEQ ID NO:903; and/or a light chain variable region comprising the amino acid sequence of SEQ ID NO:904.

In an embodiment, the targeting moiety comprises any one of the anti-PD-L1 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID NOs: 34-38 of US2011/0271358: SEQ ID NO: 34 of US2011/0271358 (SEQ ID NO:905); SEQ ID NO: 35 of US2011/0271358 (SEQ ID NO:906); SEQ ID NO: 36 of US2011/0271358 (SEQ ID NO:907); SEQ ID NO: 37 of US2011/0271358 (SEQ ID NO:908); SEQ ID NO: 38 of US2011/0271358 (SEQ ID NO:909); and/or alight chain comprising an amino acid sequence selected from SEQ ID NOs: 39-42 of US2011/0271358: SEQ ID NO: 39 of US2011/0271358 (SEQ ID NO:910); SEQ ID NO: 40 of US2011/0271358 (SEQ ID NO:911); SEQ ID NO: 41 of US2011/0271358 (SEQ ID NO:912); or SEQ ID NO: 42 of US2011/0271358 (SEQ ID NO:913).

In an embodiment, the targeting moiety comprises the anti-PD-L1 antibody 2.7A4, or fragments thereof, as disclosed in WO 2011/066389, U.S. Pat. No. 8,779,108, and US2014/0356353, the entire disclosures of which are hereby incorporated by reference. In illustrative embodiments, 2.7A4 or an antigen-binding fragment thereof for use in the methods provided herein comprises a heavy chain variable region comprising the amino acid sequence of: SEQ ID NO: 2 of WO 2011/066389 (SEQ ID NO:914); and/or a light chain variable region comprising the amino acid sequence of SEQ ID NO: 7 of WO 2011/066389 (SEQ ID NO:915).

In an embodiment, the targeting moiety comprises the anti-PD-L1 antibody 2.9D10, or fragments thereof, as disclosed in WO 2011/066389, U.S. Pat. No. 8,779,108, and US2014/0356353, the entire disclosures of which are hereby incorporated by reference. In illustrative embodiments, 2.9D10 or an antigen-binding fragment thereof for use in the methods provided herein comprises a heavy chain variable region comprising the amino acid sequence of SEQ ID NO: 12 of WO 2011/066389 (SEQ ID NO:916); and/or a light chain variable region comprising the amino acid sequence of SEQ ID NO: 17 of WO 2011/066389 (SEQ ID NO:917).

In an embodiment, the targeting moiety comprises the anti-PD-L1 antibody 2.14H9, or fragments thereof, as disclosed in WO 2011/066389, U.S. Pat. No. 8,779,108, and US2014/0356353, the entire disclosures of which are hereby incorporated by reference. In illustrative embodiments, 2.14H9 or an antigen-binding fragment thereof for use in the methods provided herein comprises a heavy chain variable region comprising the amino acid sequence of SEQ ID NO: 22 of WO 2011/066389 (SEQ ID NO:918); and/or a light chain variable region comprising the amino acid sequence of SEQ ID NO: 27 of WO 2011/066389 (SEQ ID NO:919).

In an embodiment, the targeting moiety comprises the anti-PD-L1 antibody 2.20A8, or fragments thereof, as disclosed in WO 2011/066389, U.S. Pat. No. 8,779,108, and US2014/0356353, the entire disclosures of which are hereby incorporated by reference. In illustrative embodiments, 2.20A8 or an antigen-binding fragment thereof for use in the methods provided herein comprises a heavy chain variable region comprising the amino acid sequence of SEQ ID NO: 32 of WO 2011/066389 (SEQ ID NO:920); and/or a light chain variable region comprising the amino acid sequence of SEQ ID NO: 37 of WO 2011/066389 (SEQ ID NO:921).

In an embodiment, the targeting moiety comprises the anti-PD-L1 antibody 3.15G8, or fragments thereof, as disclosed in WO 2011/066389, U.S. Pat. No. 8,779,108, and US2014/0356353, the entire disclosures of which are hereby incorporated by reference. In illustrative embodiments, 3.15G8 or an antigen-binding fragment thereof for use in the methods provided herein comprises a heavy chain variable region comprising the amino acid sequence of SEQ ID NO: 42 of WO 2011/066389 (SEQ ID NO:922); and/or a light chain variable region comprising the amino acid sequence of SEQ ID NO:923.

In an embodiment, the targeting moiety comprises the anti-PD-L1 antibody 3.18G1, or fragments thereof, as disclosed in WO 2011/066389, U.S. Pat. No. 8,779,108, and US2014/0356353, the entire disclosures of which are hereby incorporated by reference. In illustrative embodiments, 3.18G1 or an antigen-binding fragment thereof for use in the methods provided herein comprises a heavy chain variable region comprising the amino acid sequence of SEQ ID NO: 52 of WO 2011/066389 (SEQ ID NO:924); and/or a light chain variable region comprising the amino acid sequence of SEQ ID NO: 57 of WO 2011/066389 (SEQ ID NO:925).

In an embodiment, the targeting moiety comprises the anti-PD-L1 antibody 2.7A40PT, or fragments thereof, as disclosed in WO 2011/066389, U.S. Pat. No. 8,779,108, and US2014/0356353, and US2014/0356353, the entire disclosures of which are hereby incorporated by reference. In illustrative embodiments, 2.7A40PT or an antigen-binding fragment thereof for use in the methods provided herein comprises a heavy chain variable region comprising the amino acid sequence of SEQ ID NO: 62 of WO 2011/066389 (SEQ ID NO:926); and/or a light chain variable region comprising the amino acid sequence of SEQ ID NO: 67 of WO 2011/066389 (SEQ ID NO:927).

In an embodiment, the targeting moiety comprises the anti-PD-L1 antibody 2.14H90PT, or fragments thereof, as disclosed in WO 2011/066389, U.S. Pat. No. 8,779,108, and US2014/0356353, the entire disclosures of which are hereby incorporated by reference. In illustrative embodiments, 2.14H90PT or an antigen-binding fragment thereof for use in the methods provided herein comprises a heavy chain variable region comprising the amino acid sequence of SEQ ID NO: 72 of WO 2011/066389 (SEQ ID NO:928); and/or a light chain variable region comprising the amino acid sequence of SEQ ID NO: 77 of WO 2011/066389 (SEQ ID NO:929).

In an embodiment, the targeting moiety comprises any one of the anti-PD-L1 antibodies disclosed in WO2016/061142, the entire contents of which are hereby incorporated by reference. In illustrative embodiments, the antibody or an antigen-binding fragment thereof for use in the methods provided herein comprises a heavy chain comprising an amino acid sequence selected from SEQ ID NOs: 18, 30, 38, 46, 50, 54, 62, 70, and 78 of WO2016/061142: SEQ ID NO: 18 of WO2016/061142 (SEQ ID NO:930); SEQ ID NO: 30 of WO2016/061142 (SEQ ID NO:931); SEQ ID NO: 38 of WO2016/061142 (SEQ ID NO:932); SEQ ID NO: 46 of WO2016/061142 (SEQ ID NO:933); SEQ ID NO: 50 of WO2016/061142 (SEQ ID NO:934); SEQ ID NO: 54 of WO2016/061142 (SEQ ID NO:935); SEQ ID NO: 62 of WO2016/061142 (SEQ ID NO:936); SEQ ID NO: 70 of WO2016/061142 (SEQ ID NO:937); SEQ ID NO: 78 of WO2016/061142 (SEQ ID NO:938); and/or a light chain comprising an amino acid sequence selected from SEQ ID NOs: 22, 26, 34, 42, 58, 66, 74, 82, and 86 of WO2016/061142: SEQ ID NO: 22 of WO2016/061142 (SEQ ID NO:939); SEQ ID NO: 26 of WO2016/061142 (SEQ ID NO:940); SEQ ID NO: 34 of WO2016/061142 (SEQ ID NO:941); SEQ ID NO: 42 of WO2016/061142 (SEQ ID NO:942); SEQ ID NO: 58 of WO2016/061142 (SEQ ID NO:943); SEQ ID NO: 66 of WO2016/061142 (SEQ ID NO:944); SEQ ID NO: 74 of WO2016/061142 (SEQ ID NO:945); SEQ ID NO: 82 of WO2016/061142 (SEQ ID NO:946); or SEQ ID NO: 86 of WO2016/061142 (SEQ ID NO:947).

In an embodiment, the targeting moiety comprises any one of the anti-PD-L1 antibodies disclosed in WO2016/022630, the entire contents of which are hereby incorporated by reference. In illustrative embodiments, the antibody or an antigen-binding fragment thereof for use in the methods provided herein comprises a heavy chain comprising an amino acid sequence selected from SEQ ID NOs: 2, 6, 10, 14, 18, 22, 26, 30, 34, 38, 42, and 46 of WO2016/022630: SEQ ID NO: 2 of WO2016/022630 (SEQ ID NO:948); SEQ ID NO: 6 of WO2016/022630 (SEQ ID NO:949); SEQ ID NO: 10 of WO2016/022630 (SEQ ID NO:950); SEQ ID NO: 14 of WO2016/022630 (SEQ ID NO:951); SEQ ID NO: 18 of WO2016/022630 (SEQ ID NO:952); SEQ ID NO: 22 of WO2016/022630 (SEQ ID NO:953); SEQ ID NO: 26 of WO2016/022630 (SEQ ID NO:954); SEQ ID NO: 30 of WO2016/022630 (SEQ ID NO:955); SEQ ID NO: 34 of WO2016/022630 (SEQ ID NO:956); SEQ ID NO: 38 of WO2016/022630 (SEQ ID NO:957); SEQ ID NO: 42 of WO2016/022630 (SEQ ID NO:958); or SEQ ID NO: 46 of WO2016/022630 (SEQ ID NO:959); and/or a light chain comprising an amino acid sequence selected from SEQ ID NOs: 4, 8, 12, 16, 20, 24, 28, 32, 36, 40, 44, and 48 of WO2016/022630: SEQ ID NO: 4 of WO2016/022630 (SEQ ID NO:960); SEQ ID NO: 8 of WO2016/022630 (SEQ ID NO:961); SEQ ID NO: 12 of WO2016/022630 (SEQ ID NO:962); SEQ ID NO: 16 of WO2016/022630 (SEQ ID NO:963); SEQ ID NO: 20 of WO2016/022630 (SEQ ID NO:964); SEQ ID NO: 24 of WO2016/022630 (SEQ ID NO:965); SEQ ID NO: 28 of WO2016/022630 (SEQ ID NO:966); SEQ ID NO: 32 of WO2016/022630 (SEQ ID NO:967); SEQ ID NO: 36 of WO2016/

022630 (SEQ ID NO:968); SEQ ID NO: 40 of WO2016/022630 (SEQ ID NO:969); SEQ ID NO: 44 of WO2016/022630 (SEQ ID NO:970); or SEQ ID NO: 48 of WO2016/022630 (SEQ ID NO:971).

In an embodiment, the targeting moiety comprises any one of the anti-PD-L1 antibodies disclosed in WO2015/112900, the entire contents of which are hereby incorporated by reference. In illustrative embodiments, the antibody or an antigen-binding fragment thereof for use in the methods provided herein comprises a heavy chain comprising an amino acid sequence selected from SEQ ID NOs: 38, 50, 82, and 86 of WO 2015/112900: SEQ ID NO: 38 of WO2015/112900 (SEQ ID NO:972); SEQ ID NO: 50 of WO 2015/112900 (SEQ ID NO:973); SEQ ID NO: 82 of WO 2015/112900 (SEQ ID NO:974); or SEQ ID NO: 86 of WO 2015/112900 (SEQ ID NO:975); and/or a light chain comprising an amino acid sequence selected from SEQ ID NOs: 42, 46, 54, 58, 62, 66, 70, 74, and 78 of WO 2015/112900: SEQ ID NO: 42 of WO2015/112900 (SEQ ID NO:976); SEQ ID NO: 46 of WO 2015/112900 (SEQ ID NO:977); SEQ ID NO: 54 of WO 2015/112900 (SEQ ID NO:978); SEQ ID NO: 58 of WO 2015/112900 (SEQ ID NO:979); SEQ ID NO: 62 of WO 2015/112900 (SEQ ID NO:980); SEQ ID NO: 66 of WO 2015/112900 (SEQ ID NO:981); SEQ ID NO: 70 of WO 2015/112900 (SEQ ID NO:982); SEQ ID NO: 74 of WO 2015/112900 (SEQ ID NO:983); SEQ ID NO: 78 of WO 2015/112900 (SEQ ID NO:984).

In an embodiment, the targeting moiety comprises any one of the anti-PD-L1 antibodies disclosed in WO 2010/077634 and U.S. Pat. No. 8,217,149, the entire disclosures of which are hereby incorporated by reference. In illustrative embodiments, the anti-PD-L1 antibody or an antigen-binding fragment thereof for use in the methods provided herein comprises a heavy chain region comprising the amino acid sequence of: SEQ ID NO: 20 of WO 2010/077634 (SEQ ID NO:985); and/or a light chain variable region comprising the amino acid sequence of SEQ ID NO: 21 of WO 2010/077634 (SEQ ID NO:986).

In an embodiment, the targeting moiety comprises any one of the anti-PD-L1 antibodies obtainable from the hybridoma accessible under CNCM deposit numbers CNCM I-4122, CNCM I-4080 and CNCM I-4081 as disclosed in US 20120039906, the entire disclosures of which are hereby incorporated by reference.

In an embodiment, the targeting moiety comprises a VHH directed against PD-L1 as disclosed, for example, in U.S. Pat. No. 8,907,065 and WO 2008/071447, the entire disclosures of which are hereby incorporated by reference. In illustrative embodiments, the VHHs against PD-L1 comprise SEQ ID NOS: 394-399 of U.S. Pat. No. 8,907,065: SEQ ID NO: 394 of U.S. Pat. No. 8,907,065 (SEQ ID NO:987); SEQ ID NO: 395 of U.S. Pat. No. 8,907,065 (SEQ ID NO:988); SEQ ID NO: 396 of U.S. Pat. No. 8,907,065 (SEQ ID NO:989); SEQ ID NO: 397 of U.S. Pat. No. 8,907,065 (SEQ ID NO:990); SEQ ID NO: 398 of U.S. Pat. No. 8,907,065 (SEQ ID NO:991); or SEQ ID NO: 399 of U.S. Pat. No. 8,907,065 (SEQ ID NO:992).

In various embodiments, the present multi-specific CD8 binding agent has one or more targeting moieties directed against PD-L2. In some embodiments, the CD8 binding agent has one or more targeting moieties which selectively bind a PD-L2 polypeptide. In some embodiments, the CD8 binding agent comprises one or more antibodies, antibody derivatives or formats, peptides or polypeptides, or fusion proteins that selectively bind a PD-L2 polypeptide.

In an embodiment, the targeting moiety comprises a VHH directed against PD-L2 as disclosed, for example, in U.S. Pat. No. 8,907,065 and WO 2008/071447, the entire disclosures of which are hereby incorporated by reference. In illustrative embodiments, the VHHs against PD-1 comprise SEQ ID NOs: 449-455 of U.S. Pat. No. 8,907,065: SEQ ID NO: 449 of U.S. Pat. No. 8,907,065 (SEQ ID NO:993); SEQ ID NO: 450 of U.S. Pat. No. 8,907,065 (SEQ ID NO:994); SEQ ID NO: 451 of U.S. Pat. No. 8,907,065 (SEQ ID NO:995); SEQ ID NO: 452 of U.S. Pat. No. 8,907,065 (SEQ ID NO:996); SEQ ID NO: 453 of U.S. Pat. No. 8,907,065 (SEQ ID NO:997); SEQ ID NO: 454 of U.S. Pat. No. 8,907,065 (SEQ ID NO:998); SEQ ID NO: 455 of U.S. Pat. No. 8,907,065 (SEQ ID NO:999).

In an embodiment, the targeting moiety comprises any one of the anti-PD-L2 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID NOs: 43-47 of US2011/0271358: SEQ ID NO: 43 of US2011/0271358 (SEQ ID NO:1000); SEQ ID NO: 44 of US2011/0271358 (SEQ ID NO:1001); SEQ ID NO: 45 of US2011/0271358 (SEQ ID NO:1002); SEQ ID NO: 46 of US2011/0271358 (SEQ ID NO:1003); SEQ ID NO: 47 of US2011/0271358 (SEQ ID NO:1004); and/or a light chain comprising an amino acid sequence selected from SEQ ID NOs: 48-51 of US2011/0271358: SEQ ID NO: 48 of US2011/0271358 (SEQ ID NO:1005); SEQ ID NO: 49 of US2011/0271358 (SEQ ID NO:1006); SEQ ID NO: 50 of US2011/0271358 (SEQ ID NO:1007); or SEQ ID NO: 51 of US2011/0271358 (SEQ ID NO:1008).

In various embodiments, the targeting moieties of the invention may comprise a sequence that targets PD-1, PD-L1, and/or PD-L2 which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity with any of the sequences disclosed herein).

In various embodiments, the targeting moieties of the invention may comprise any combination of heavy chain, light chain, heavy chain variable region, light chain variable region, complementarity determining region (CDR), and framework region sequences that target PD-1, PD-L1, and/or PD-L2 as disclosed herein.

Additional antibodies, antibody derivatives or formats, peptides or polypeptides, or fusion proteins that selectively bind or target PD-1, PD-L1 and/or PD-L2 are disclosed in WO 2011/066389, US 2008/0025980, US 2013/0034559, U.S. Pat. No. 8,779,108, US 2014/0356353, U.S. Pat. No. 8,609,089, US 2010/028330, US 2012/0114649, WO 2010/027827, WO 2011/066342, U.S. Pat. No. 8,907,065, WO 2016/062722, WO 2009/101611, WO2010/027827, WO 2011/066342, WO 2007/005874, WO 2001/014556, US2011/0271358, WO 2010/036959, WO 2010/077634, U.S. Pat. No. 8,217,149, US 2012/0039906, WO 2012/145493, US 2011/0318373, U.S. Pat. No. 8,779,108, US 20140044738, WO 2009/089149, WO 2007/00587, WO 2016061142, WO 2016,02263, WO 2010/077634, and WO 2015/112900, the entire disclosures of which are hereby incorporated by reference.

In various embodiments, the multi-specific CD8 binding agent of the invention comprises a targeting moiety having an antigen recognition domain that specifically binds to XCR1, e.g. on DCs. In various embodiments, the multi-specific CD8 binding agent of the invention comprises a targeting moiety having an antigen recognition domain that comprise all of or part of XCL1.

In various embodiments, the multi-specific CD8 binding agents have targeting moieties having recognition domains which specifically bind to a target (e.g. antigen, receptor) which is part of a non-cellular structure. In some embodiments, the antigen or receptor is not an integral component of an intact cell or cellular structure. In some embodiments, the antigen or receptor is an extracellular antigen or receptor. In some embodiments, the target is a non-proteinaceous, non-cellular marker, including, without limitation, nucleic acids, inclusive of DNA or RNA, such as, for example, DNA released from necrotic tumor cells or extracellular deposits such as cholesterol.

In some embodiments, the target (e.g. antigen, receptor) of interest is part of the non-cellular component of the stroma or the extracellular matrix (ECM) or the markers associated therewith. As used herein, stroma refers to the connective and supportive framework of a tissue or organ. Stroma may include a compilation of cells such as fibroblasts/myofibroblasts, glial, epithelia, fat, immune, vascular, smooth muscle, and immune cells along with the extracellular matrix (ECM) and extracellular molecules. In various embodiments, the target (e.g. antigen, receptor) of interest is part of the non-cellular component of the stroma such as the extracellular matrix and extracellular molecules. As used herein, the ECM refers to the non-cellular components present within all tissues and organs. The ECM is composed of a large collection of biochemically distinct components including, without limitation, proteins, glycoproteins, proteoglycans, and polysaccharides. These components of the ECM are usually produced by adjacent cells and secreted into the ECM via exocytosis. Once secreted, the ECM components often aggregate to form a complex network of macromolecules. In various embodiments, the chimeric protein of the invention comprises a targeting moiety that recognizes a target (e.g., an antigen or receptor or non-proteinaceous molecule) located on any component of the ECM. Illustrative components of the ECM include, without limitation, the proteoglycans, the non-proteoglycan polysaccharides, fibers, and other ECM proteins or ECM non-proteins, e.g. polysaccharides and/or lipids, or ECM associated molecules (e.g. proteins or non-proteins, e.g. polysaccharides, nucleic acids and/or lipids).

In some embodiments, the targeting moiety recognizes a target (e.g. antigen, receptor) on ECM proteoglycans. Proteoglycans are glycosylated proteins. The basic proteoglycan unit includes a core protein with one or more covalently attached glycosaminoglycan (GAG) chains. Proteoglycans have a net negative charge that attracts positively charged sodium ions (Na+), which attracts water molecules via osmosis, keeping the ECM and resident cells hydrated. Proteoglycans may also help to trap and store growth factors within the ECM. Illustrative proteoglycans that may be targeted by the chimeric proteins of the invention include, but are not limited to, heparan sulfate, chondroitin sulfate, and keratan sulfate. In an embodiment, the targeting moiety recognizes a target (e.g. antigen, receptor) on non-proteoglycan polysaccharides such as hyaluronic acid.

In some embodiments, the targeting moiety recognizes a target (e.g. antigen, receptor) on ECM fibers. ECM fibers include collagen fibers and elastin fibers. In some embodiments, the targeting moiety recognizes one or more epitopes on collagens or collagen fibers. Collagens are the most abundant proteins in the ECM. Collagens are present in the ECM as fibrillar proteins and provide structural support to resident cells. In one or more embodiments, the targeting moiety recognizes and binds to various types of collagens present within the ECM including, without limitation, fibrillar collagens (types I, II, III, V, XI), facit collagens (types IX, XII, XIV), short chain collagens (types VIII, X), basement membrane collagens (type IV), and/or collagen types VI, VII, or XIII. Elastin fibers provide elasticity to tissues, allowing them to stretch when needed and then return to their original state. In some embodiments, the target moiety recognizes one or more epitopes on elastins or elastin fibers.

In some embodiments, the targeting moiety recognizes one or more ECM proteins including, but not limited to, a tenascin, a fibronectin, a fibrin, a laminin, or a nidogen/entactin.

In an embodiment, the targeting moiety recognizes and binds to tenascin. The tenascin (TN) family of glycoproteins includes at least four members, tenascin-C, tenascin-R, tenascin-X, and tenascin W. The primary structures of tenascin proteins include several common motifs ordered in the same consecutive sequence: amino-terminal heptad repeats, epidermal growth factor (EGF)-like repeats, fibronectin type III domain repeats, and a carboxyl-terminal fibrinogen-like globular domain. Each protein member is associated with typical variations in the number and nature of EGF-like and fibronectin type III repeats. Isoform variants also exist particularly with respect to tenascin-C. Over 27 splice variants and/or isoforms of tenascin-C are known. In a particular embodiment, the targeting moiety recognizes and binds to tenascin-CA1. Similarly, tenascin-R also has various splice variants and isoforms. Tenascin-R usually exists as dimers or trimers. Tenascin-X is the largest member of the tenascin family and is known to exist as trimers. Tenascin-W exists as trimers. In some embodiments, the targeting moiety recognizes one or more epitopes on a tenascin protein. In some embodiments, the targeting moiety recognizes the monomeric and/or the dimeric and/or the trimeric and/or the hexameric forms of a tenascin protein.

In an embodiment, the targeting moieties recognize and bind to fibronectin. Fibronectins are glycoproteins that connect cells with collagen fibers in the ECM, allowing cells to move through the ECM. Upon binding to integrins, fibronectins unfolds to form functional dimers. In some embodiments, the targeting moiety recognizes the monomeric and/or the dimeric forms of fibronectin. In some embodiments, the targeting moiety recognizes one or more epitopes on fibronectin. In illustrative embodiments, the targeting moiety recognizes fibronectin extracellular domain A (EDA) or fibronectin extracellular domain B (EDB). Elevated levels of EDA are associated with various diseases and disorders including psoriasis, rheumatoid arthritis, diabetes, and cancer. In some embodiments, the targeting moiety recognizes fibronectin that contains the EDA isoform and may be utilized to target the chimeric protein to diseased cells including cancer cells. In some embodiments, the targeting moiety recognizes fibronectin that contains the EDB isoform. In various embodiments, such targeting moieties may be utilized to target the chimeric protein to tumor cells including the tumor neovasculature.

In an embodiment, the targeting moiety recognizes and binds to fibrin. Fibrin is another protein substance often found in the matrix network of the ECM. Fibrin is formed by the action of the protease thrombin on fibrinogen which causes the fibrin to polymerize. In some embodiments, the targeting moiety recognizes one or more epitopes on fibrin. In some embodiments, the targeting moiety recognizes the monomeric as well as the polymerized forms of fibrin.

In an embodiment, the targeting moiety recognizes and binds to laminin. Laminin is a major component of the basal lamina, which is a protein network foundation for cells and organs. Laminins are heterotrimeric proteins that contain an α-chain, a β-chain, and a γ-chain. In some embodiments, the targeting moiety recognizes one or more epitopes on laminin. In some embodiments, the targeting moiety recognizes the monomeric, the dimeric as well as the trimeric forms of laminin.

In an embodiment, the targeting moiety recognizes and binds to a nidogen or entactin. Nidogens/entactins are a family of highly conserved, sulfated glycoproteins. They make up the major structural component of the basement membranes and function to link laminin and collagen IV networks in basement membranes. Members of this family include nidogen-1 and nidogen-2. In various embodiments, the targeting moiety recognizes an epitope on nidogen-1 and/or nidogen-2.

In various embodiments, the targeting moiety comprises an antigen recognition domain that recognizes an epitope present on any of the targets (e.g., ECM proteins) described herein. In an embodiment, the antigen-recognition domain recognizes one or more linear epitopes present on the protein. As used herein, a linear epitope refers to any continuous sequence of amino acids present on the protein. In another embodiment, the antigen-recognition domain recognizes one or more conformational epitopes present on the protein. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the targeting moiety may bind to the full-length and/or mature forms and/or isoforms and/or splice variants and/or fragments and/or any other naturally occurring or synthetic analogs, variants, or mutants of any of the targets (e.g., ECM proteins) described herein. In various embodiments, the targeting moiety may bind to any forms of the proteins described herein, including monomeric, dimeric, trimeric, tetrameric, heterodimeric, multimeric and associated forms. In various embodiments, the targeting moiety may bind to any post-translationally modified forms of the proteins described herein, such as glycosylated and/or phosphorylated forms.

In various embodiments, the targeting moiety comprises an antigen recognition domain that recognizes extracellular molecules such as DNA. In some embodiments, the targeting moiety comprises an antigen recognition domain that recognizes DNA. In an embodiment, the DNA is shed into the extracellular space from necrotic or apoptotic tumor cells or other diseased cells.

In various embodiments, the targeting moiety comprises an antigen recognition domain that recognizes one or more non-cellular structures associated with atherosclerotic plaques. Two types of atherosclerotic plaques are known. The fibro-lipid (fibro-fatty) plaque is characterized by an accumulation of lipid-laden cells underneath the intima of the arteries. Beneath the endothelium there is a fibrous cap covering the atheromatous core of the plaque.

The core includes lipid-laden cells (macrophages and smooth muscle cells) with elevated tissue cholesterol and cholesterol ester content, fibrin, proteoglycans, collagen, elastin, and cellular debris. In advanced plaques, the central core of the plaque usually contains extracellular cholesterol deposits (released from dead cells), which form areas of cholesterol crystals with empty, needle-like clefts. At the periphery of the plaque are younger foamy cells and capillaries. A fibrous plaque is also localized under the intima, within the wall of the artery resulting in thickening and expansion of the wall and, sometimes, spotty localized narrowing of the lumen with some atrophy of the muscular layer. The fibrous plaque contains collagen fibers (eosinophilic), precipitates of calcium (hematoxylinophilic) and lipid-laden cells. In some embodiments, the targeting moiety recognizes and binds to one or more of the non-cellular components of these plaques such as the fibrin, proteoglycans, collagen, elastin, cellular debris, and calcium or other mineral deposits or precipitates. In some embodiments, the cellular debris is a nucleic acid, e.g. DNA or RNA, released from dead cells.

In various embodiments, the targeting moiety comprises an antigen recognition domain that recognizes one or more non-cellular structures found in the brain plaques associated with neurodegenerative diseases. In some embodiments, the targeting moiety recognizes and binds to one or more non-cellular structures located in the amyloid plaques found in the brains of patients with Alzheimer's disease. For example, the targeting moiety may recognize and bind to the peptide amyloid beta, which is a major component of the amyloid plaques. In some embodiments, the targeting moiety recognizes and binds to one or more non-cellular structures located in the brains plaques found in patients with Huntington's disease. In various embodiments, the targeting moiety recognizes and binds to one or more non-cellular structures found in plaques associated with other neurodegenerative or musculoskeletal diseases such as Lewy body dementia and inclusion body myositis.

Linkers and Functional Groups

In various embodiments, the CD8 binding agent may include one or more functional groups, residues, or moieties. In various embodiments, the one or more functional groups, residues, or moieties are attached or genetically fused to any of the signaling agents or targeting moieties described herein. In some embodiments, such functional groups, residues or moieties confer one or more desired properties or functionalities to the CD8 binding agent of the invention. Examples of such functional groups and of techniques for introducing them into the CD8 binding agent are known in the art, for example, see Remington's Pharmaceutical Sciences, 16th ed., Mack Publishing Co., Easton, Pa. (1980).

In various embodiments, the CD8 binding agent may by conjugated and/or fused with another agent to extend half-life or otherwise improve pharmacodynamic and pharmacokinetic properties. In some embodiments, the CD8 binding agent may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In some embodiments, the CD8 binding agent may be fused or conjugated with an antibody or an antibody fragment such as an Fc fragment. For example, the chimeric protein may be fused to either the N-terminus or the C-terminus of the Fc domain of human immunoglobulin (Ig) G. In various embodiments, each of the individual chimeric proteins is fused to one or more of the agents described in BioDrugs (2015) 29:215-239, the entire contents of which are hereby incorporated by reference.

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG). In some embodiments, attachment of the PEG moiety increases the half-life and/or reduces the immunogenicity of the CD8 binding protein. Generally, any suitable form of pegylation can be used, such as the pegylation used in the art for antibodies and antibody fragments (including but not limited to single domain antibodies such as VHHs); see, for example, Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). For example, for this purpose, PEG may be attached to a cysteine residue that naturally occurs in the CD8 binding agent of the invention. In some embodiments, the CD8 binding agent of the invention is modified so as to suitably introduce one or more cysteine residues for attachment of PEG, or an amino acid sequence comprising one or more cysteine residues for attachment of PEG may be fused to the amino- and/or carboxy-terminus of the CD8 binding agent, using techniques known in the art. In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VHHs and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the CD8 binding agent. In some embodiments, the CD8 binding agent may include a single tag or multiple tags. The tag for example is a peptide, sugar, or DNA molecule that does not inhibit or prevent binding of the CD8 binding agent to CD8 or any other antigen of interest such as tumor antigens. In various embodiments, the tag is at least about: three to five amino acids long, five to eight amino acids long, eight to twelve amino acids long, twelve to fifteen amino acids long, or fifteen to twenty amino acids long. Exemplary tags are described for example, in U.S. Patent Publication No. US2013/0058962. In some embodiment, the tag is an affinity tag such as glutathione-S-transferase (GST) and histidine (His) tag. In an embodiment, the CD8 binding agent comprises a His tag.

In some embodiments, the functional groups, residues, or moieties comprise a chelating group, for example, to chelate one of the metals or metallic cations. Suitable chelating groups, for example, include, without limitation, diethylenetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the CD8 binding agent of the invention to another protein, polypeptide or chemical compound that is bound to the other half of the binding pair, i.e., through formation of the binding pair. For example, a CD8 binding agent of the invention may be conjugated to biotin, and linked to another protein, polypeptide, compound or carrier conjugated to avidin or streptavidin. For example, such a conjugated CD8 binding agent may be used as a reporter, for example, in a diagnostic system where a detectable signal-producing agent is conjugated to avidin or streptavidin. Such binding pairs may, for example, also be used to bind the CD8 binding agent to a carrier, including carriers suitable for pharmaceutical purposes. One non-limiting example are the liposomal formulations described by Cao and Suresh, *Journal of Drug Targeting,* 8, 4, 257 (2000). Such binding pairs may also be used to link a therapeutically active agent to the CD8 binding agent of the invention.

In some embodiments, the present CD8 binding agent optionally comprises one or more linkers. In some embodiments, the present CD8 binding agent comprises a linker connecting the targeting moiety and the signaling agent. In some embodiments, the present chimeric protein comprises a linker within the signaling agent (e.g. in the case of single chain TNF, which can comprise two linkers to yield a trimer).

In some embodiments, the CD8 binding agent includes a linker that connects each binding region and/or targeting moieties. In some embodiments, the linker may be utilized to link various functional groups, residues, or moieties as described herein to the CD8 binding agent. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present CD8 binding agent.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the e is flexible. In another embodiment, the linker is rigid.

In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8 (SEQ ID NOs: 1009-1016). In an embodiment, the linker sequence is GGSGGSGGGGSGGGGS (SEQ ID NO:1017). Additional illustrative linkers include, but are not limited to, linkers having the sequence LE, GGGGS (SEQ ID NO:1009), $(GGGGS)_n$ (n=1-4) (SEQ ID NOs:1009-1012), $(Gly)_8$(SEQ ID NO:1018), $(Gly)_6$ (SEQ ID NO:1019), $(EAAAK)_n$ (n=1-3) (SEQ ID NOs:1020-1022), $A(EAAAK)_nA$ (n=2-5) (SEQ ID NOs:1023-1026), AEAAAKEAAAKA (SEQ ID NO:1027), $A(EAAAK)_4ALEA(EAAAK)_4A$ (SEQ ID NO:1028), PAPAP (SEQ ID NO:1029), KESGSVSSEQLAQFRSLD (SEQ ID NO:1030), EGKSSGSGSESKST (SEQ ID NO:1031), GSAGSAAGSGEF (SEQ ID NO:1032), and $(XP)_n$, with X designating any amino acid, e.g., Ala, Lys, or Glu. In various embodiments, the linker is (GGS)n (n=1-20) (SEQ ID NO: 1176-SEQ ID NO: 1195). In some embodiments, the linker is G. In some embodiments, the linker is AAA. In some embodiments, the linker is (GGGGS)n (n=9-20) (SEQ ID NO: 1196-SEQ ID NO: 1207).

In some embodiments, the linker is one or more of GGGSE (SEQ ID NO: 1208), GSESG (SEQ ID NO: 1209), GSEGS (SEQ ID NO: 1210), GEGGSGEGSSGEGSSSEGGGSEGGGSEGGGSEGGS (SEQ ID NO: 1211), and a linker of randomly placed G, S, and E every 4 amino acid intervals.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of $C_H1$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys (SEQ ID NO: 1212) which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites. In various embodiments, the linker is a hinge-CH2-CH3 domain of a human IgG4 antibody.

If desired, the present CD8 binding agent can be linked to an antibody Fc region, comprising one or both of $C_{H2}$ and $C_{H3}$ domains, and optionally a hinge region. For example, vectors encoding the present CD8 binding agents linked as a single nucleotide sequence to an Fc region can be used to prepare such polypeptides.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present CD8 binding agent. In another example, the linker may function to target the CD8 binding agent to a particular cell type or location.

Modifications and Production of CD8 Binding Agents

In various embodiments, the CD8 binding agent comprises a targeting moiety that is a VHH. In various embodiments, the VHH is not limited to a specific biological source or to a specific method of preparation. For example, the VHH can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the CD8 binding agent comprises a VHH that corresponds to the $V_HH$ domains of naturally occurring heavy chain antibodies directed against human CD8. In some embodiments, such $V_HH$ sequences can generally be generated or obtained by suitably immunizing a species of Camelid with a CD8 molecule, (i.e., so as to raise an immune response and/or heavy chain antibodies directed against CD8), by obtaining a suitable biological sample from the Camelid (such as a blood sample, or any sample of B-cells), and by generating $V_HH$ sequences directed against CD8, starting from the sample, using any suitable known techniques. In some embodiments, naturally occurring $V_HH$ domains against CD8 can be obtained from naive libraries of Camelid $V_HH$ sequences, for example, by screening such a library using CD8 or at least one part, fragment, antigenic determinant or epitope thereof using one or more screening techniques known in the art. Such libraries and techniques are, for example, described in WO9937681, WO0190190, WO03025020 and WO03035694, the entire contents of which are hereby incorporated by reference. In some embodiments, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as for example, described in WO0043507, the entire contents of which are hereby incorporated by reference. In some embodiments, another technique for obtaining $V_HH$ sequences directed against a CD8 involves suitably immunizing a transgenic mammal that is capable of expressing heavy chain antibodies (i.e., so as to raise an immune response and/or heavy chain antibodies directed against CD8), obtaining a suitable biological sample from the transgenic mammal (such as a blood sample, or any sample of B-cells), and then generating $V_HH$ sequences directed against CD8 starting from the sample, using any suitable known techniques. For example, for this purpose, the heavy chain antibody-expressing mice and the further methods and techniques described in WO02085945 and in WO04049794 (the entire contents of which are hereby incorporated by reference) can be used.

In an embodiment, the CD8 binding agent comprises a VHH that has been "humanized" i.e., by replacing one or more amino acid residues in the amino acid sequence of the naturally occurring $V_HH$ sequence (and in particular in the framework sequences) by one or more of the amino acid residues that occur at the corresponding position(s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the invention may become more "human-like," while still retaining favorable properties such as a reduced immunogenicity, compared to the corresponding naturally occurring $V_HH$ domains. In various embodiments, the humanized VHHs of the invention can be obtained in any suitable manner known in the art and thus are not strictly limited to polypeptides that have been obtained using a polypeptide that comprises a naturally occurring $V_HH$ domain as a starting material.

In an embodiment, the CD8 binding agent comprises a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a $V_HH$ domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In various embodiments, the camelized VHHs can be obtained in any suitable manner known in the art (i.e., as indicated under points (1)-(8) above) and thus are not strictly limited to polypeptides that have been obtained using a polypeptide that comprises a naturally occurring VH domain as a starting material.

In various embodiments, both "humanization" and "camelization" can be performed by providing a nucleotide sequence that encodes a naturally occurring $V_H$H domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the invention. Alternatively, based on the amino acid sequence of a naturally occurring $V_H$H domain or VH domain, respectively, the amino acid sequence of the desired humanized or camelized VHH of the invention, respectively, can be designed and then synthesized de novo using techniques for peptide synthesis known in the art. Also, based on the amino acid sequence or nucleotide sequence of a naturally occurring $V_H$H domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the invention. Other suitable methods and techniques for obtaining the VHHs of the invention and/or nucleic acids encoding the same, starting from naturally occurring VH sequences or $V_H$H sequences, are known in the art, and may, for example, comprise combining one or more parts of one or more naturally occurring VH sequences (such as one or more FR sequences and/or CDR sequences), one or more parts of one or more naturally occurring $V_H$H sequences (such as one or more FR sequences or CDR sequences), and/or one or more synthetic or semi-synthetic sequences, in a suitable manner, so as to provide a VHH of the invention or a nucleotide sequence or nucleic acid encoding the same.

Methods for producing the CD8 binding agents of the invention are described herein. For example, DNA sequences encoding the CD8 binding agents of the invention can be chemically synthesized using methods known in the art. Synthetic DNA sequences can be ligated to other appropriate nucleotide sequences, including, e.g., expression control sequences, to produce gene expression constructs encoding the desired CD8 binding agents. Accordingly, in various embodiments, the present invention provides for isolated nucleic acids comprising a nucleotide sequence encoding the CD8 binding agent of the invention.

Nucleic acids encoding the CD8 binding agent of the invention can be incorporated (ligated) into expression vectors, which can be introduced into host cells through transfection, transformation, or transduction techniques. For example, nucleic acids encoding the CD8 binding agent of the invention can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the CD8 binding agent of the invention. Accordingly, in various embodiments, the present invention provides expression vectors comprising nucleic acids that encode the CD8 binding agent of the invention. In various embodiments, the present invention additional provides host cells comprising such expression vectors.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The CD8 binding agent of the invention can be produced by growing a host cell transfected with an expression vector encoding the CD8 binding agent under conditions that permit expression of the protein. Following expression, the protein can be harvested and purified using techniques well known in the art, e.g., affinity tags such as glutathione-S-transferase (GST) and histidine (His) tags or by chromatography. In an embodiment, the CD8 binding agent comprises a His tag (which is optionally cleavable via an engineered proteolytic cleavage site).

Accordingly, in various embodiments, the present invention provides for a nucleic acid encoding a CD8 binding agent of the present invention. In various embodiments, the present invention provides for a host cell comprising a nucleic acid encoding a CD8 binding agent of the present invention.

In various embodiments, the present CD8 binding agent or chimeric protein comprising the same may be expressed in vivo, for instance, in a patient. For example, in various embodiments, the present CD8 binding agent or chimeric protein comprising the same may administered in the form of nucleic acid which encodes the present CD8 binding agents or chimeric proteins comprising the same. In various embodiments, the nucleic acid is DNA or RNA. In some embodiments, present CD8 binding agent or chimeric protein comprising the same is encoded by a modified mRNA, i.e. an mRNA comprising one or more modified nucleotides. In some embodiments, the modified mRNA comprises one or modifications found in U.S. Pat. No. 8,278,036, the entire contents of which are hereby incorporated by reference. In some embodiments, the modified mRNA comprises one or more of m5C, m5U, m6A, s2U, Ψ, and 2'-O-methyl-U. In some embodiments, the present invention relates to administering a modified mRNA encoding one or more of the present chimeric proteins. In some embodiments, the present invention relates to gene therapy vectors comprising the same. In some embodiments, the present invention relates to gene therapy methods comprising the same. In various embodiments, the nucleic acid is in the form of an oncolytic virus, e.g. an adenovirus, reovirus, measles, herpes simplex, Newcastle disease virus or vaccinia.

Pharmaceutically Acceptable Salts and Excipients

The CD8 binding agents described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The*

*Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to pharmaceutical compositions comprising the CD8 binding agents described herein and a pharmaceutically acceptable carrier or excipient. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the CD8 binding agent described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any CD8 binding agents described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, Science 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the CD8 binding agent to be administered according to the present invention will vary according to the particular dosage form, and the mode of administration. Many factors that may modify the action of the CD8 binding agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the CD8 binding agent is in a range of about 0.01 mg/kg to about 10 g/kg of body weight of the subject, about 0.01 mg/kg to about 1 g/kg of body weight of the subject, about 0.01 mg/kg to about 100 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 100 mg/kg body weight, about 1 g/kg of body weight, about 10 g/kg of body weight, inclusive of all values and ranges therebetween.

Individual doses of the CD8 binding agent can be administered in unit dosage forms containing, for example, from about 0.01 mg to about 100 g, from about 0.01 mg to about 75 g, from about 0.01 mg to about 50 g, from about 0.01 mg to about 25 g, about 0.01 mg to about 10 g, about 0.01 mg to about 7.5 g, about 0.01 mg to about 5 g, about 0.01 mg to about 2.5 g, about 0.01 mg to about 1 g, about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 10 g, about 25 g, about 50 g, about 75 g, about 100 g, inclusive of all values and ranges therebetween.

In one embodiment, the CD8 binding agent is administered at an amount of from about 0.01 mg to about 100 g daily, from about 0.01 mg to about 75 g daily, from about 0.01 mg to about 50 g daily, from about 0.01 mg to about 25 g daily, from about 0.01 mg to about 10 g daily, from about 0.01 mg to about 7.5 g daily, from about 0.01 mg to about 5 g daily, from about 0.01 mg to about 2.5 g daily, from about 0.01 mg to about 1 g daily, from about 0.01 mg to about 100 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the CD8 binding agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 7.5 g, about 10 g, about 25 g, about 50 g, about 75 g, about 100 g, inclusive of all values and ranges therebetween.

In accordance with certain embodiments of the invention, the pharmaceutical composition comprising the CD8 binding agent may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year.

Combination Therapy and Additional Therapeutic Agents

In various embodiments, the pharmaceutical composition of the present invention is co-administered in conjunction with additional therapeutic agent(s). Co-administration can be simultaneous or sequential.

In one embodiment, the additional therapeutic agent and the CD8 binding agent of the present invention are administered to a subject simultaneously. The term "simultaneously" as used herein, means that the additional therapeutic agent and the CD8 binding agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the CD8 binding agent can be by simultaneous administration of a single formulation (e.g., a formulation comprising the additional therapeutic agent and the CD8 binding agent) or of separate formulations (e.g., a first formulation including the additional therapeutic agent and a second formulation including the CD8 binding agent).

Co-administration does not require the therapeutic agents to be administered simultaneously, if the timing of their administration is such that the pharmacological activities of the additional therapeutic agent and the CD8 binding agent overlap in time, thereby exerting a combined therapeutic effect. For example, the additional therapeutic agent and the CD8 binding agent can be administered sequentially. The term "sequentially" as used herein means that the additional therapeutic agent and the CD8 binding agent are administered with a time separation of more than about 60 minutes. For example, the time between the sequential administration of the additional therapeutic agent and the CD8 binding agent can be more than about 60 minutes, more than about 2 hours, more than about 5 hours, more than about 10 hours, more than about 1 day, more than about 2 days, more than about 3 days, more than about 1 week apart, more than about 2 weeks apart, or more than about one month apart. The optimal administration times will depend on the rates of metabolism, excretion, and/or the pharmacodynamic activity of the additional therapeutic agent and the CD8 binding agent being administered. Either the additional therapeutic agent or the CD8 binding agent cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the CD8 binding agent described herein acts synergistically when co-administered with another therapeutic agent. In such embodiments, the CD8 binding agent and the additional therapeutic agent may be administered at doses that are lower than the doses employed when the agents are used in the context of monotherapy.

In some embodiments, the present invention pertains to chemotherapeutic agents as additional therapeutic agents. For example, without limitation, such combination of the present CD8 binding agents and chemotherapeutic agent find use in the treatment of cancers, as described elsewhere herein. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegalI (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, inclusive of, without limitation, infectious disease applications, the present invention pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmmune applications, the additional therapeutic agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosuppressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin). Additional anti-inflammatory agents are described, for example, in U.S. Pat. No. 4,537,776, the entire contents of which is incorporated by reference herein.

In some embodiments, the present invention relates to combination therapy with one or more immune-modulating agents, for example, without limitation, agents that modulate immune checkpoint. In various embodiments, the immune-modulating agent targets one or more of PD-1, PD-L1, and PD-L2. In various embodiments, the immune-modulating agent is PD-1 inhibitor. In various embodiments, the immune-modulating agent is an antibody specific for one or more of PD-1, PD-L1, and PD-L2. For instance, in some embodiments, the immune-modulating agent is an antibody such as, by way of non-limitation, nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE). In some embodiments, the immune-modulating agent targets one or more of CD137 or CD137L. In various embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the present CD8 binding agent is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an agent that targets one or more of CTLA-4, AP2M1, CD80, CD86, SHP-2, and PPP2R5A. In various embodiments, the immune-modulating agent is an antibody specific for one or more of CTLA-4, AP2M1, CD80, CD86, SHP-2, and PPP2R5A. For instance, in some embodiments, the immune-modulating agent is an antibody such as, by way of non-limitation, ipilimumab (MDX-010, MDX-101, Yervoy, BMS) and/or tremelimumab (Pfizer). In some embodiments, the present CD8 binding agent is combined with ipilimumab (optionally with bavituximab) for the treatment of one or more of melanoma, prostate cancer, and lung cancer. In various embodiments, the immune-modulating agent targets CD20. In various embodiments, the immune-modulating agent is an antibody specific CD20. For instance, in some embodiments, the immune-modulating agent is an antibody such as, by way of non-limitation, Ofatumumab (GENMAB), obinutuzumab (GAZYVA), AME-133v (APPLIED MOLECULAR EVOLUTION), Ocrelizumab (GENENTECH), TRU-015 (TRUBION/EMERGENT), veltuzumab (IMMU-106).

In some embodiments, the present invention relates to combination therapy with one or more chimeric agents described in WO 2013/10779, WO 2015/007536, WO 2015/007520, WO 2015/007542, and WO 2015/007903, the entire contents of which are hereby incorporated by reference in their entireties.

In some embodiments, the CD8 binding agent described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the CD8 binding agent described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The CD8 binding agent described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and Pseudomonas toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the CD8 binding agent, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment

Methods and compositions described herein have application to treating various diseases and disorders, including, but not limited to cancer, infections, immune disorders, inflammatory diseases or conditions, and autoimmune diseases.

Further, any of the present agents may be for use in the treating, or the manufacture of a medicament for treating, various diseases and disorders, including, but not limited to cancer, infections, immune disorders, inflammatory diseases or conditions, and autoimmune diseases.

In some embodiments, the present invention relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

In some embodiments, the present invention relates to the treatment of, or a patient having a microbial infection and/or chronic infection. Illustrative infections include, but are not limited to, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

In various embodiments, the present compositions are used to treat or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In various embodiments, the present compositions are used to treat or prevent one or more autoimmune diseases or conditions, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

Kits

The present invention also provides kits for the administration of any CD8 binding agent described herein (e.g. with or without additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired therapeutic outcome, such as to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A “pharmacologically effective amount,” “pharmacologically effective dose,” “therapeutically effective amount,” or “effective amount” refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, “methods of treatment” are equally applicable to use of a composition for treating the diseases or disorders described herein and/or compositions for use and/or uses in the manufacture of a medicaments for treating the diseases or disorders described herein.

EXAMPLES

Example 1. Construction and Evaluation of VHHs Specific for Human CD8

Isolation of Antigen-Specific VHHs

A VHH library was constructed from an immunized llama. Three consecutive rounds of panning of a VHH library were performed in solution using stably transfected CHO-K1 cells expressing human CD8. The enrichment for antigen-specific phages was assessed after each round of panning by comparing the number of phagemid particles eluted from transfected cells (output) with the number of phagemid particles used for panning (input). The phage output increased about $10^2$-fold in the $2^{nd}$ round and about $10^3$-fold in the $3^{rd}$ round, as compared to the output from the $1^{st}$ round. The input phage was always about $10^{11}$ and the output from first round was about $10^7$ phage particles. 285 randomly selected colonies from the $1^{st}$, $2^{nd}$ and $3^{rd}$ panning rounds (95 from each round) were sequenced and then grouped based on CDR3 sequences. Using crude periplasmic extracts including VHHs, 89 unique sequences were analyzed by flow cytometry for specificity to human CD8 using CHO-K1 cells stably transfected with human CD8. The parental non-transfected CHO-K1 cells served as negative control cell. An irrelevant VHH was used as negative Nanobody control. Flow cytometry experiments revealed that 69 different VHHs, belonging to 31 different groups (see FIG. 3), were specific for human CD8. The table below provides a description of 69 clones representing the 69 different anti-human CD8 VHH genes. *E. coli* TG1 harboring recombinant phagemid pMECS containing anti-human CD8A VHH sequences was generated and stored at −80° C. The vector pMECS codes for ampicillin resistance.

| *E. coli* strain + Vector | VHH (Nb) | NSF Glycerol Stock No. |
|---|---|---|
| TG1, pMECS | 1CDA 7 | 4757 |
| TG1, pMECS | 1CDA 12 | 4758 |
| TG1, pMECS | 1CDA 14 | 4759 |
| TG1, pMECS | 1CDA 15 | 4760 |
| TG1, pMECS | 1CDA 17 | 4761 |
| TG1, pMECS | 1CDA 18 | 4762 |
| TG1, pMECS | 1CDA 19 | 4763 |
| TG1, pMECS | 1CDA 24 | 4764 |
| TG1, pMECS | 1CDA 26 | 4765 |
| TG1, pMECS | 1CDA 28 | 4766 |
| TG1, pMECS | 1CDA 37 | 4767 |
| TG1, pMECS | 1CDA 43 | 4768 |
| TG1, pMECS | 1CDA 45 | 4769 |
| TG1, pMECS | 1CDA 47 | 4770 |
| TG1, pMECS | 1CDA 48 | 4771 |
| TG1, pMECS | 1CDA 58 | 4772 |
| TG1, pMECS | 1CDA 65 | 4773 |
| TG1, pMECS | 1CDA 68 | 4774 |
| TG1, pMECS | 1CDA 73 | 4775 |
| TG1, pMECS | 1CDA 75 | 4776 |
| TG1, pMECS | 1CDA 86 | 4777 |
| TG1, pMECS | 1CDA 87 | 4778 |
| TG1, pMECS | 1CDA 88 | 4779 |
| TG1, pMECS | 1CDA 89 | 4780 |
| TG1, pMECS | 1CDA 92 | 4781 |
| TG1, pMECS | 1CDA 93 | 4782 |
| TG1, pMECS | 2CDA 1 | 4783 |
| TG1, pMECS | 2CDA 5 | 4784 |
| TG1, pMECS | 2CDA 22 | 4785 |
| TG1, pMECS | 2CDA 28 | 4786 |
| TG1, pMECS | 2CDA 62 | 4787 |
| TG1, pMECS | 2CDA 68 | 4788 |
| TG1, pMECS | 2CDA 73 | 4789 |
| TG1, pMECS | 2CDA 74 | 4790 |
| TG1, pMECS | 2CDA 75 | 4791 |
| TG1, pMECS | 2CDA 77 | 4792 |
| TG1, pMECS | 2CDA 81 | 4793 |
| TG1, pMECS | 2CDA 87 | 4794 |
| TG1, pMECS | 2CDA 88 | 4795 |
| TG1, pMECS | 2CDA 89 | 4796 |
| TG1, pMECS | 2CDA 91 | 4797 |
| TG1, pMECS | 2CDA 92 | 4798 |
| TG1, pMECS | 2CDA 93 | 4799 |
| TG1, pMECS | 2CDA 94 | 4800 |
| TG1, pMECS | 2CDA 95 | 4801 |
| TG1, pMECS | 3CDA 3 | 4802 |

-continued

| *E. coli* strain + Vector | VHH (Nb) | NSF Glycerol Stock No. |
|---|---|---|
| TG1, pMECS | 3CDA 8 | 4803 |
| TG1, pMECS | 3CDA 11 | 4804 |
| TG1, pMECS | 3CDA 18 | 4805 |
| TG1, pMECS | 3CDA 19 | 4806 |
| TG1, pMECS | 3CDA 21 | 4807 |
| TG1, pMECS | 3CDA 24 | 4808 |
| TG1, pMECS | 3CDA 28 | 4809 |
| TG1, pMECS | 3CDA 29 | 4810 |
| TG1, pMECS | 3CDA 31 | 4811 |
| TG1, pMECS | 3CDA 32 | 4812 |
| TG1, pMECS | 3CDA 33 | 4813 |
| TG1, pMECS | 3CDA 37 | 4814 |
| TG1, pMECS | 3CDA 40 | 4815 |
| TG1, pMECS | 3CDA 41 | 4816 |
| TG1, pMECS | 3CDA 48 | 4817 |
| TG1, pMECS | 3CDA 57 | 4818 |
| TG1, pMECS | 3CDA 65 | 4819 |
| TG1, pMECS | 3CDA 70 | 4820 |
| TG1, pMECS | 3CDA 73 | 4821 |
| TG1, pMECS | 3CDA 83 | 4822 |
| TG1, pMECS | 3CDA 86 | 4823 |
| TG1, pMECS | 3CDA 88 | 4824 |
| TG1, pMECS | 3CDA 90 | 4825 |

Transformation of Non-Suppressor Strain (e.g. WK6) with Recombinant pMECS

The VHH gene cloned in pMECS vector contained PelB signal sequence at the N-terminus and HA tag and $His_6$ tag at the C-terminus (PelB leader-VHH-HA-$His_6$). The PelB leader sequence directed the VHH to the periplasmic space of the *E. coli*, and the HA and $His_6$ tags was used for the purification and detection of VHH (e.g. in ELISA, Western Blot, etc.).

In pMECS vector, the $His_6$ tag was followed by an amber stop codon (TAG) and this amber stop codon was followed by gene III of M13 phage. In suppressor *E. coli* strains (e.g. TG1), the amber stop codon was read as glutamine and therefore the VHH was expressed as fusion protein with protein III of the phage which allowed the display of the VHH on the phage coat for panning. In TG1 suppressor strains, the efficiency of suppression is not 100% and therefore the expression of VHHs in suppressor strains led to two different types of VHH molecules, fused to protein III and without protein III). In non-suppressor *E. coli* strains (e. g., WK6), the amber stop codon was read as stop codon and therefore the resulting VHH was not fused to protein III.

In order to express and purify VHHs cloned in pMECS vector, pMECS was prepared containing the gene of the VHH of interest, and the plasmid was transformed into a non-suppressor strain (e.g., WK6). The VHH of the resulting clone was sequenced using the MP057 primer (5'-TTATGCTTCCGGCTCGTATG-3') (SEQ ID NO:1033) to verify the identity of the clone. Antigen binding capacity was retested by ELISA or any other appropriate assay. The non-suppressor strain (e.g., WK6) containing the recombinant pMECS vector with the VHH gene was used for the expression and purification of the VHH.

In pMECS vector, the $His_6$ tag was cleaved off upon storage of the VHH. Accordingly, the VHH gene was recloned from pMECS into pHEN6c vector, if the $His_6$ tag was to be used for detection, etc. Specifically, the VHH gene was amplified by PCR using recombinant pMECS harboring the VHH gene as template and primers A6E and PMCF. Primers A6E and PMCF were framework1 and framework4 primers, respectively. The primer sequences were as follows:

```
Primer A6E
                                        (SEQ ID NO: 1034)
(5' GAT GTG CAG CTG CAG GAG TCT GGR* GGA GG 3').

Primer PMCF
                                        (SEQ ID NO: 1035)
(5' CTA GTG CGG CCG CTG AGG AGA CGG TGA CCT GGG

T 3').

Universal reverse primer
                                        (SEQ ID NO: 1036)
(5' TCA CAC AGG AAA CAG CTA TGA C 3').

Universal forward primer
                                        (SEQ ID NO: 1037)
(5' CGC CAG GGT TTT CCC AGT CAC GAC 3').
```

*R stands for A or G. PstI, NotI and BstEII (Eco91I) recognition sequences are shown in bold, italic and underline, respectively.

The amplification protocol included about 30 cycles of PCR, each cycle included 30 seconds at 94° C., 30 seconds at 55° C. and 45 seconds at 72° C., followed by 10 minutes extension at 72° C. at the end of PCR. A fragment of about 400 bp was amplified.

The PCR product was purified (e.g. by Qiaquick PCR purification kit from Qiagen) and digested overnight with PstI. The purified PCR product was digested with BstEII overnight (or with Eco91I from Fermentas). The temperature used for digestion varied. For example, digestion with BstEII was done at 50° C. or 60° C. depending on the supplier of the enzyme.

For ligation, the PCR product was purified. The pHEN6c vector was digested with PstI for 3 hours, purified as described above, and then digested with BstEII for 2 to 3 hours. Alternatively, digestion was carried out using Eco91I from Fermentas. The digested vector was ran on 1% agarose gel, with the vector band excised out of the gel and purified (e.g. by Qiaquick gel extraction kit from Qiagen). The PCR fragment was subsequently ligated to the vector.

Electrocompetent WK6 cells were transformed with the ligation reaction, and transformants were selected using LB/agar/ampicillin (100 μg/ml)/glucose (1-2%) plates. Positive clones were screened by PCR using universal reverse and universal forward primers. A fragment of about 550 bp was amplified, if the insert was present. To verify the identity of the clones, at least 2 clones per each VHH were sequenced using universal reverse primers. Antigen binding capacity was retested by ELISA or any other appropriate assay.

Following the above protocol, the VHH gene cloned in pHEN6c vector was generated which contained PelB signal sequence at the N-terminus and Hiss-tail at the C-terminus. The PelB leader sequence directed the VHH to the periplasmic space of the *E. coli*, and the His-tag was used for the purification and detection of VHH (e.g. in ELISA, Western Blot, etc.).

Expression and Purification of VHHs

Expression and purification of VHHs were carried out. Specifically, on day 1, 10-20 ml of LB+ampicillin (100 μg/ml)+glucose (1%) were innoculated with a freshly transformed WK6 colony. This pre-culture was incubated at 37° C. overnight with shaking at 200-250 rpm. On day 2, a TB medium was used for expressing the VHHs. The TB medium included, per liter: 2.3 g $KH_2PO_4$, 16.4 g $K_2HPO_4·3H_2O$, 12 g Tryptone (Duchefa Biochemie), 24 g Yeast (Duchefa Biochemie), and 4 ml 100% glycerol (Duchefa Biochemie)

A baffled shaker flask of 1 liter was filled with 330 ml TB and autoclaved. $KH_2PO_4$ and $K_2HPO_4.3H_2O$ were not autoclaved. Instead, $KH_2PO_4$ and $K_2HPO_4.3H_2O$ were prepared, filter sterilized, and then added to the rest of the medium that was already autoclaved. About 1 ml of the pre-culture was added to 330 ml of TB supplemented with 100 μg/ml Ampicillin, 2 mM $MgCl_2$ and 0.1% glucose and subsequently grew at 37° C. with shaking (200-250 rpm) until an $OD_{600}$ of 0.6-0.9 was reached. IPTG (final concentration of 1 mM) was added to induce VHH expression. The culture was incubated at 28° C. with shaking overnight (about 16-18 hours). The $OD_{600}$ after overnight induction was usually between 25 and 30. At least 1 liter of culture (3 bottles) per clone was prepared with an average yield of between 1 and 15 mg/I.

Extraction of the VHHs from the periplasm of *E. coli* was carried out on day 3. The solutions used included: TES: 0.2 M Tris pH 8.0, 0.5 mM EDTA, 0.5 M sucrose, TES/4: TES diluted 4 times in water.

The overnight induced cultures were centrifuged for 8 minutes at 8000 rpm. The cell pellets from 1 liter culture were resuspended in 12 ml TES by pipetting up and down and shaken for 1 hour on ice. Per each 12 ml TES used, about 18 ml TES/4 were added and incubated on ice for an additional hour with shaking followed by centrifuge for 30 minutes at 8000 rpm at 4° C. The supernatant which contained proteins extracted from the periplasmic spaced was transferred to fresh falcon tubes.

The VHHs were subsequently purified by IMAC which utilized the following solution: HIS-select (SIGMA), PBS, and 50 mM NaAcetate pH 4.6.

His-select was equilibrated with PBS. Specifically, per periplasmic extract derived from 1 liter culture, 1 ml of Resin (about 2 ml His-select solution) was added to a 50 ml falcon tube. PBS was also added to final volume of 50 ml and mixed. Centrifugation was carried out at 2000 rpm for 2 minutes, and the supernatant was discarded. The resin was washed with PBS twice as described above. The periplasmic extract was added to the resin, incubated for 30 minutes to 1 hour at room temperature with gentle shaking. The samples were loaded on PD-10 columns with a filter at the bottom (GE healthcare, cat. No. 17-0435-01) and washed with 50 to 100 ml PBS (50-100 ml PBS per 1 ml resin used). Elution was carried out for 3 times, each time with 1 ml PBS/0.5 M imidazole per 1 ml resin used (for efficient elution, resuspend the beads and leave overnight at 4° C. with the bottom of the column closed). Dialysis was performed overnight at 4° C. against PBS (cutoff 3500 daltons) to remove imidazole. For efficient dialysis, the dialysis buffer (PBS) was changed 2-3 times. Alternatively, instead of elution with imidazole, the bound VHHs could be eluted with 10 ml 50 mM Na-acetate pH 4.6. If 50 mM Na-acetate pH 4.6 was used to elute VHHs, the eluted VHHs was immediately neutralized with 1M Tris pH 8.0, and no dialysis was required.

The amount of protein was estimated by $OD_{280}$ measurement of eluted sample. Extinction coefficient of each clone was determined by protParam tool under primary structure analysis at the Expasy proteomics server. Further purification of VHHs could be achieved by different methods. For example, the samples could be concentrated (Vivaspin 5000 MW cutoff, Vivascience) by centrifuging at 2000 rpm at 4° C. until an appropriate volume for loading on a Superdex 75 16/60 was obtained (max. 4 ml). The concentrated sample was loaded on a Superdex 75 16/60 column equilibrated with PBS. Peak fractions were pooled, and $OD_{280}$ measurements were performed for quantification. In general, VHHs eluted after 85-95 minutes when run at 1 ml/min. Aliquots of concentrated VHH samples were stored at −20° C. at a concentration of about 1 mg/ml.

Example 2. Functional Characterization of Human CD8 Binding VHHs

Figure 4:
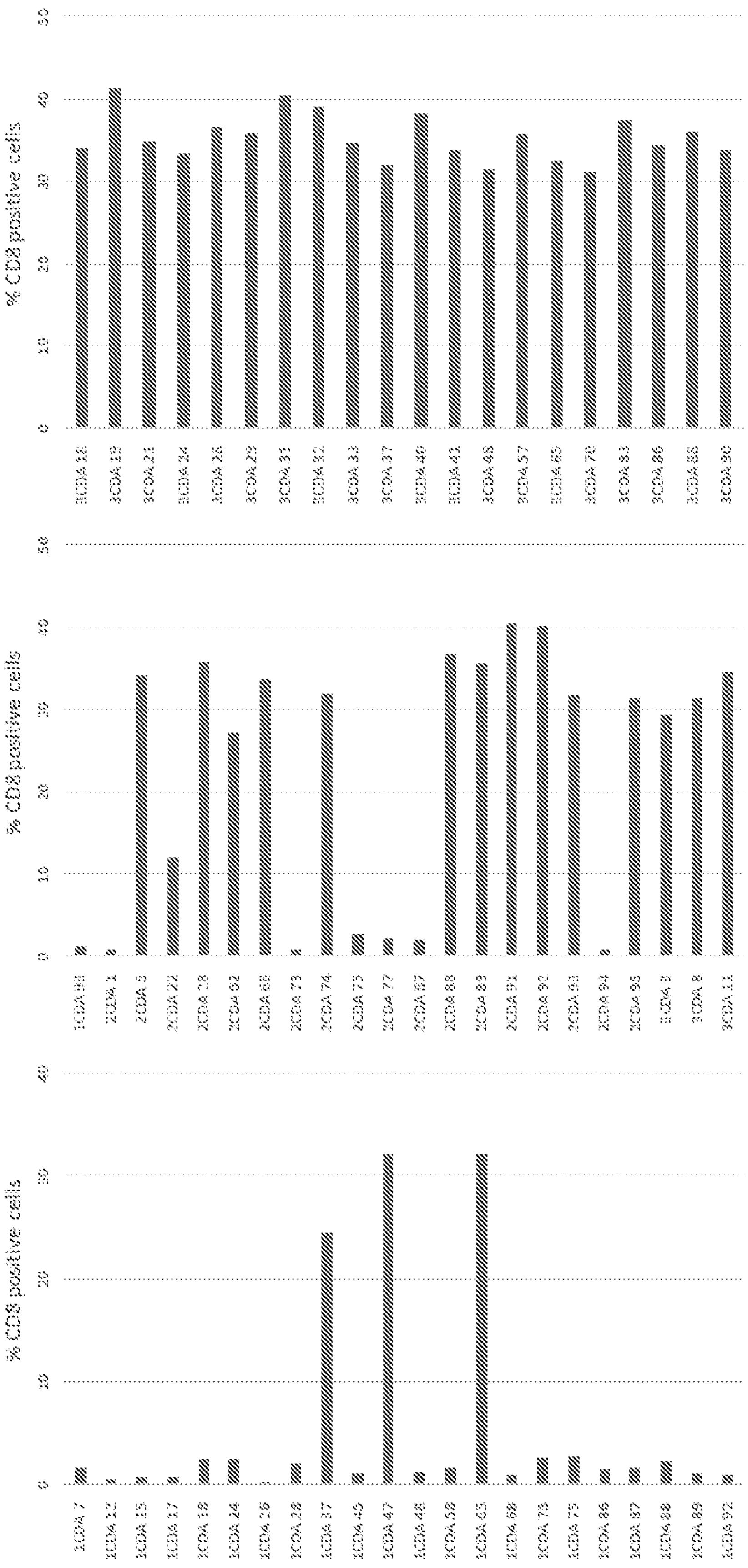
FIG. 4 shows the binding of various VHHs to Hek293 T cells transfected with human CD8.

The binding characteristics of various VHHs (as described in Example 1) were tested by flow cytometry. HEK293-T cells were transfected with a human CD8α expression plasmid and stained with the His-tagged VHHs at 2 μg/ml, followed by staining with an anti-His Fitc conjugated antibody. Binding was measured by detecting cellular fluorescence via flow cytometry. Results as shown in FIG. 4 show that the VHHs bound to CD8.

Example 3. pSTAT Signaling Induced by Anti-Human CD8 VHH Chimeras

The term "AcTaferon" (AFN) is used herein to reference an interferon-based chimera. In the following example, unless noted, mutations to IFN are relative to human IFN-α2 (SEQ ID NO:12).

A pSTAT signaling assay was undertaken in CD8 positive and CD8 negative cells. Chimeras studied were anti-human CD8 VHH/human IFN R149A fusions.

Based on FACS analysis of binding to CD8 and on sequence similarities, six CD8 VHH's were selected for further analysis: 3CDA19, 3CDA65, 3CDA33, 3CDA28, 3CDA31, and 2CDA5. These VHH's were cloned into an AcTaferon (AFN) context in the pMTW vector for eukaryotic expression as follows: pmTW-SIgK-hCD8_VHH-$(GGS)_{20}$-hIFNa2_R149A-GGS-$(His)_9$. Resulting proteins were produced in Hek293F cells with 25K PEI (polyethylenimine) according to standard protocols. Medium was harvested, cells removed by centrifugation and filter-sterilized. Recombinant proteins were purified using Ni Excel resin (GE Healthcare) according to the manufacturer's instructions and imidazole removed from the samples with PD10 columns (GE Healthcare).

PBMCs from buffy coats of healthy donors were isolated using density gradient centrifugation with Ficoll-Paque (GE Healthcare). Cells were washed twice with FACS buffer (2% FBS, 1 mM EDTA in PBS) and stained with anti-human CD8 APC (clone REA734; Miltenyi Biotec) for 20 minutes at 4° C. After two washes, cells were stimulated with a serial dilution CD8-AcTaferons for 15 minutes at 37° C. After fixation (10 minutes, 37° C., Fix Buffer I; BD Biosciences) and permeabilization (30 minutes, on ice, Perm III Buffer I; BD Biosciences) and washing, cells were stained with anti-STAT1 pY701 Ab (BD Biosciences). Samples were acquired with a FACSCalibur (BD Biosciences), with the CellQuest Pro Version 4.0.2 software (BD Biosciences).

Figure 5A:
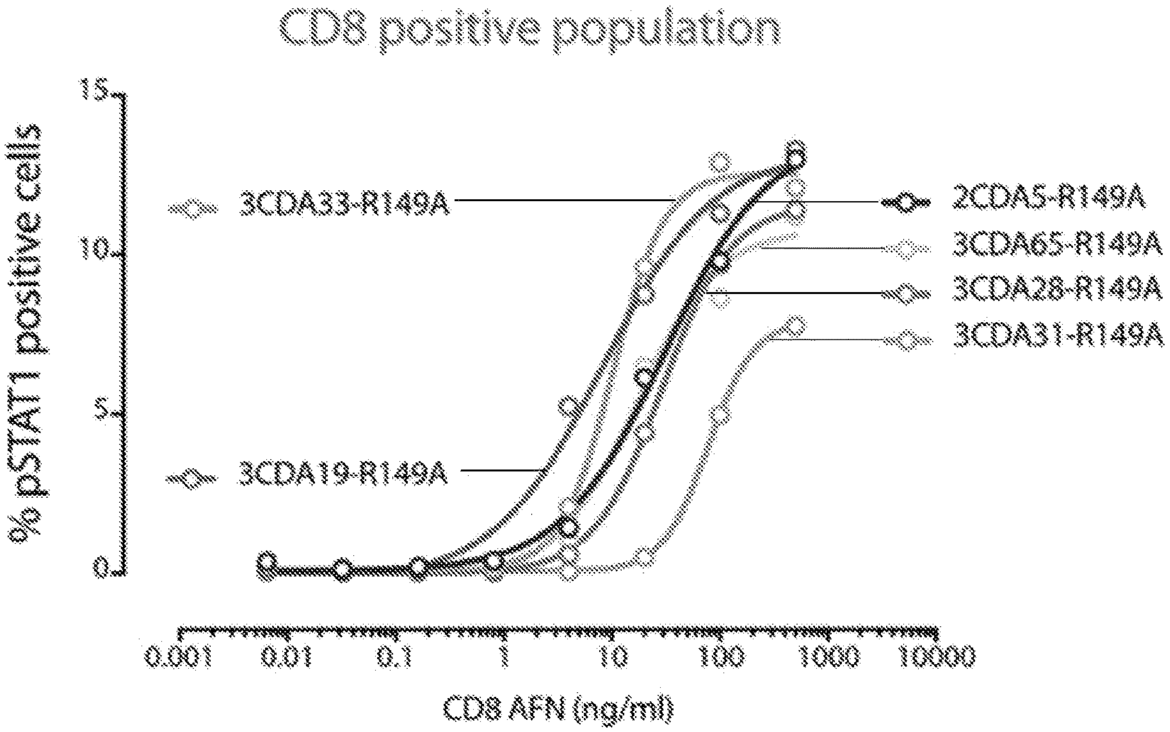
FIGS. 5A-B shows pSTAT1 signaling assay in CD8 positive (FIG. 5A) and CD8 negative cells (FIG. 5B). Chimeras studied were anti-human CD8 VHH/human IFN R149A (i.e., CD8 VHH-AFN). Peripheral blood mononuclear cells (PBMCs) from healthy donors were stained with CD8 antibody and stimulated with CD8 VHH-AFN's for 15 minutes. After fixation and permeabilisation, cells were stained with a pSTAT1 antibody. Data are plotted as percentage of pSTAT1 positive cells.
Figure 5B:
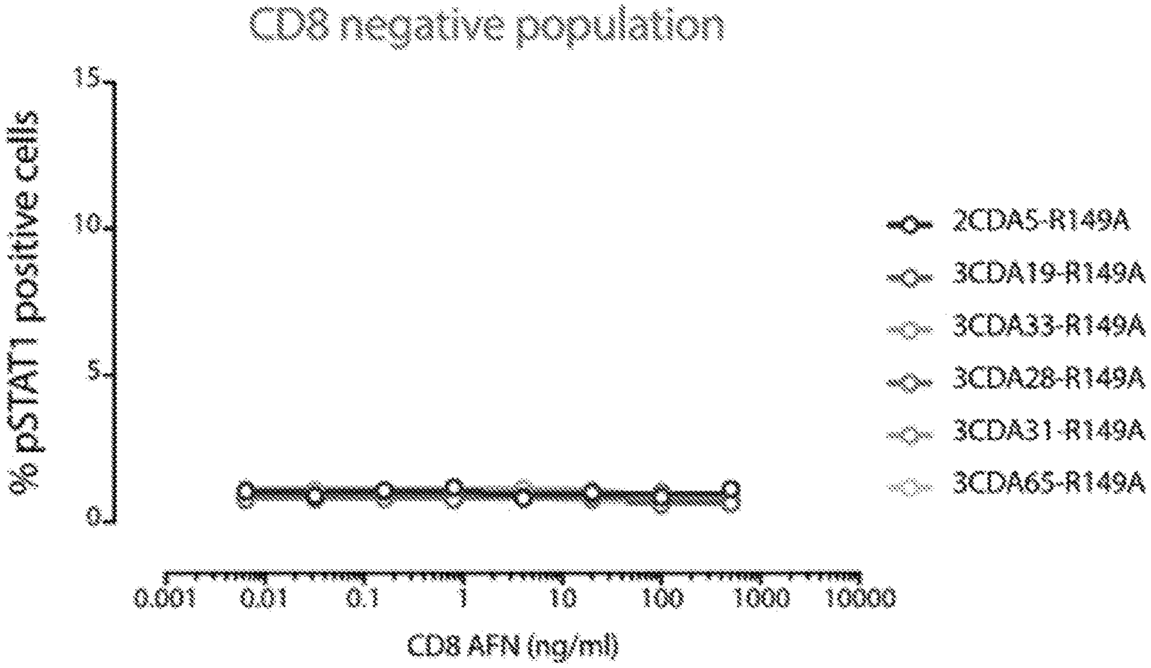
Figure 6B:
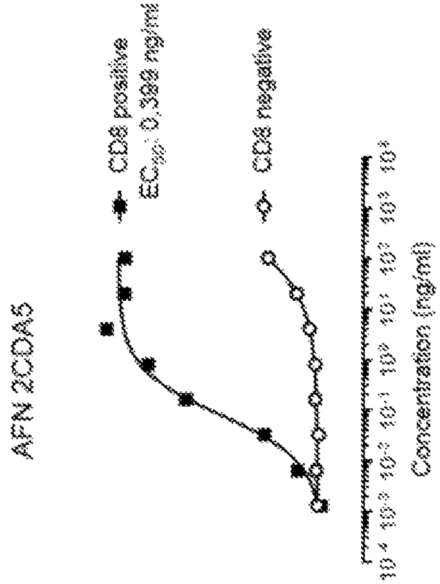
FIGS. 6A-F are graphs showing CD8 VHH AcTaferons (AFNs) stimulation of STAT phosphorylation in PBMC's from healthy donors. PBMC's from healthy donors were stained with CD8 Ab and stimulated with wild type IFNα2 (FIG. 6A) or CD8 VHH AFN's (i.e., AFN 2CDA5 (FIG. 6B), AFN 3CDA19 (FIG. 6C), AFN 1CDA65 (FIG. 6D), AFN 2CDA74 (C50S) (FIG. 6E), or AFN 2CDA68 (FIG. 6F)) for 15 minutes. After fixation and permeabilization, cells were stained with a pSTAT1 Ab. The data is plotted as increase over baseline STAT1 phosphorylation.
Figure 6A:
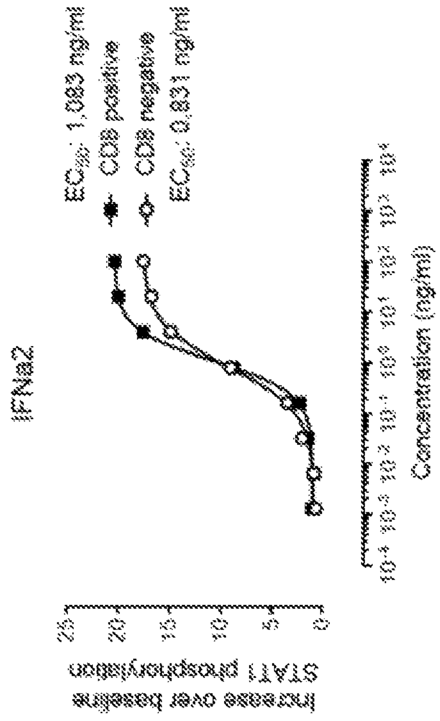
Figure 6D:
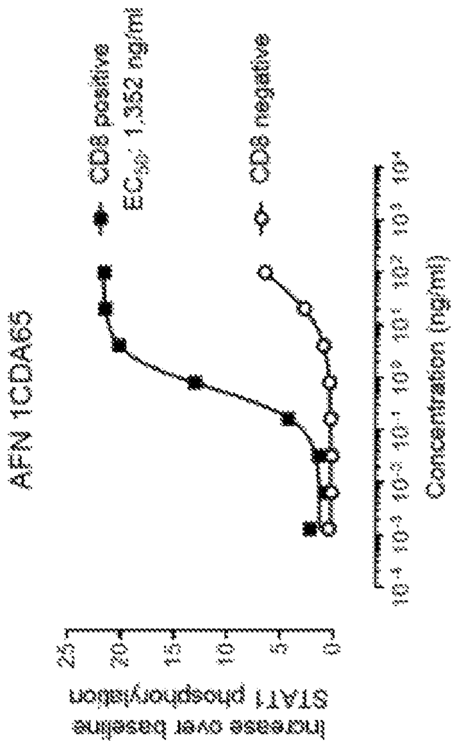
Figure 6C:
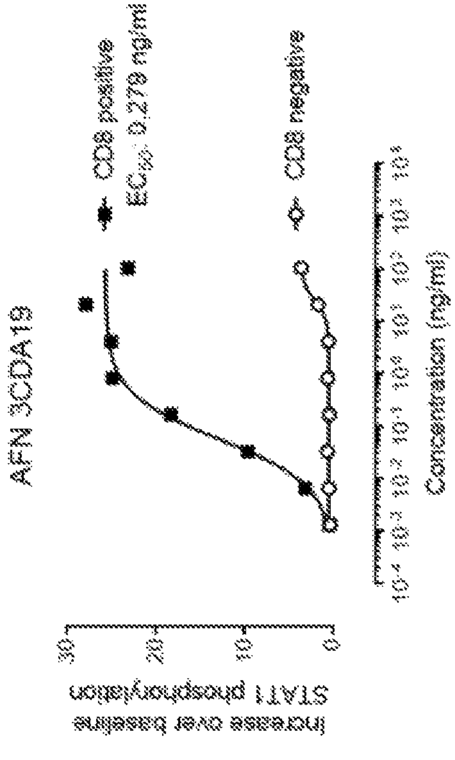
Figure 6E:
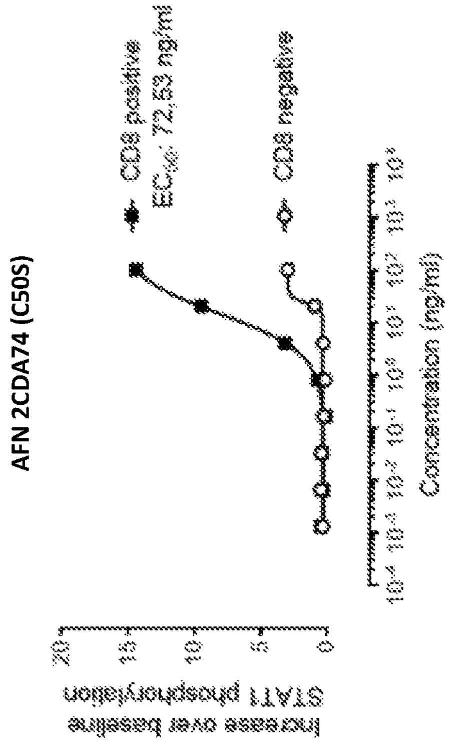
Figure 6F:
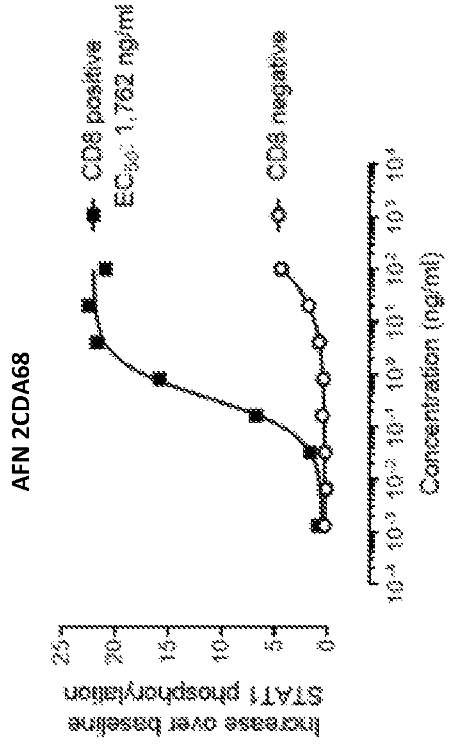
Figure 7B:
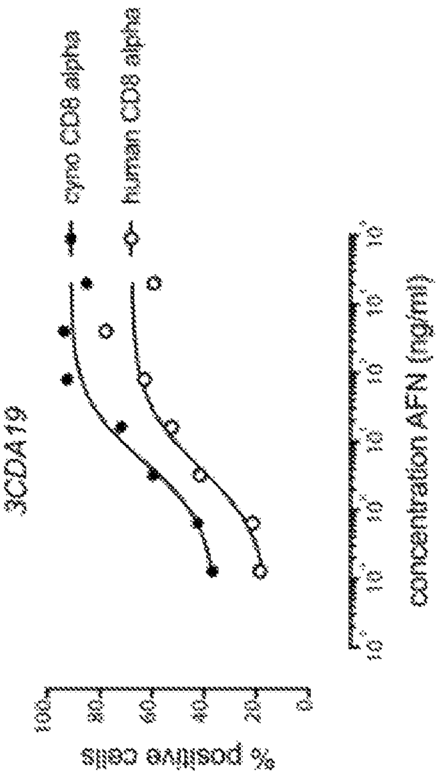
FIGS. 7A-E are graphs showing that CD8 VHHs (i.e., 2CDA5 (FIG. 7A), 3CDA19 (FIG. 7B), 1CDA65 (FIG. 7C), 2CDA74 (C50S) (FIG. 7D), and 2CDA68 (FIG. 7E)) bind equally as well to human and cynomolgus CD8 alpha in FACs.
Figure 7A:
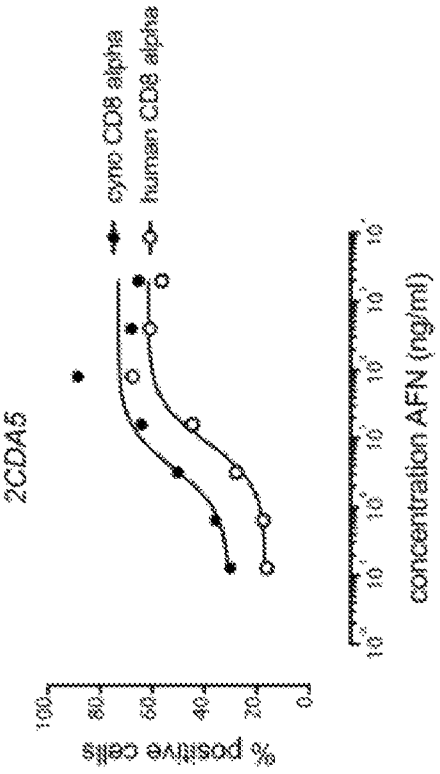
Figure 7D:
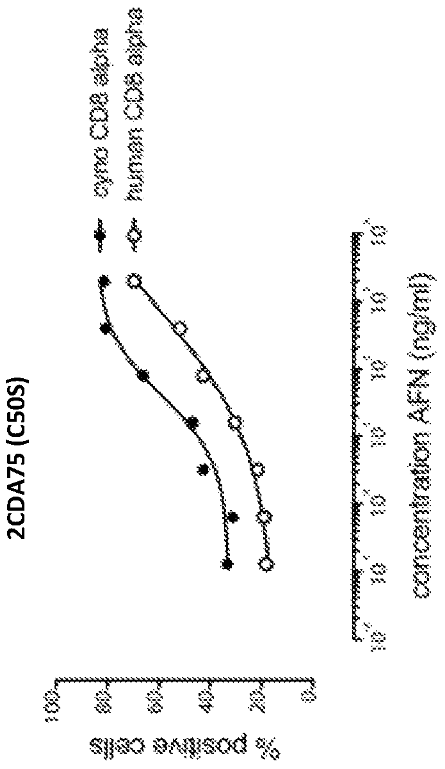
Figure 7C:
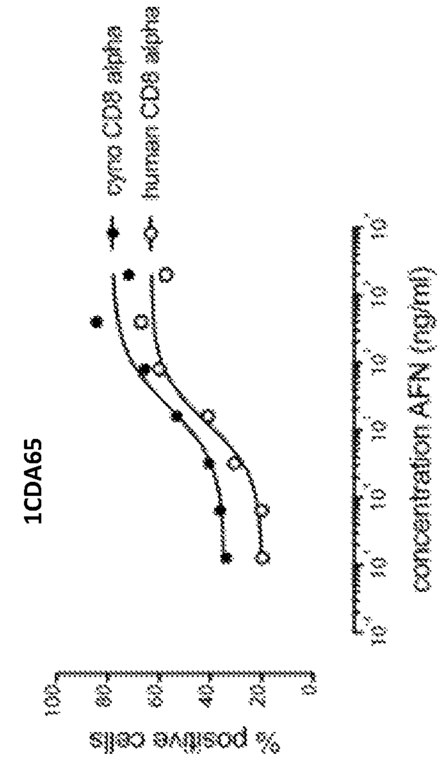
Figure 7E:
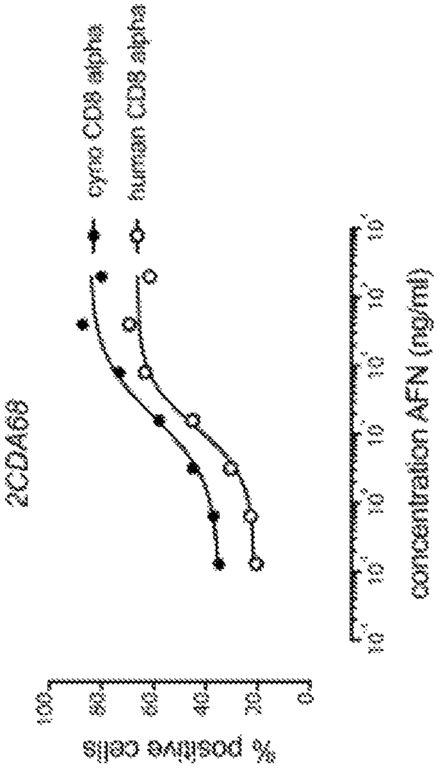

As shown in FIGS. 5A-B, CD8 VHH targeted mutant IFN (i.e., R149A) was able to phosphorylate STAT1 in CD8 positive (FIG. 5A) but not CD8 negative cells (FIG. 5B) indicating efficient CD8 targeting.

Example 4. pSTAT1 Signaling Induced by Additional Anti-Human CD8 VHH AcTaferons In Example 3, CD8 VHHs were selected from the larger sequence groups 1, 2, and 15 as defined in FIG. 3. Based on binding to CD8 in FACS (see Example 2 and FIG. 4) additional sequence groups, including group 3, 4, 22, and 30, showed strong binding to CD8. These CD8 VHHs were selected for further evaluation of their efficiency of human CD8 targeting of AcTaferons by quantification of STAT1 phosphorylation in CD8-positive and CD8-negative peripheral blood mononuclear cells (PBMCs) in FACS. Sequence groups 3 and 4 were considered similar and the stronger binding VHH 2CDA74 was selected as representative member. The sequence of 2CDA74 contains a free cysteine in CDR2 at position 50. This residue was mutated to serine to avoid disulfide-based dimer formation. The mutation resulted in 2CDA74 having a CDR2 sequence of SSISRSDGSTY (SEQ ID NO: 1221).

The affinities of CD8 VHH's 1CDA65, 2CDA5, 2CDA68, 2CDA74 (C50S), and 3CDA19 (sequences provided below) were measured (see Table 1). Affinities of the CD8 VHH's were measured using bio-layer interferometry an Octet RED96 system (ForteBio): biotinylated CD8 (Sino Biological) was immobilized on streptavidin biosensors (ForteBio) and dipped in a serial dilution CD8 AFN's. Affinities were calculated with the Octet software (ForteBio).

```
1CDA65
                                      (SEQ ID NO: 1217)
QVQLQESGGGLVQPGGSLRLSCAASGSIFSINVMGWYRQTPGKERELVAK

ITNFGITSYADSAQGRFTISRGNAKNTVYLQMNSLKPEDTAVYYCNLDTT

GWGPPPYQYWGQGTQVTVSS.

2CDA5
                                      (SEQ ID NO: 1218)
QVQLQESGGGLVQAGDSLRLTCTASGRTFSNYGIGWFRQAPGKEREFVAG

INWSGESADYADSVKGRFTISRDNAKNTVYLQMNSLKPEDTAVYYCAAGE

SGVWVGGLDYWXQGTQVTVSS.

2CDA68
                                      (SEQ ID NO: 1219)
QVQLQESGGGLVQAGGSLRLSCAASGRTFSSYVMGWFRQAPGKEREFVAQ

ISWSAGSIYYADSVKGRFTISNDNAKRTVYLQMNSLKPEDTAVYYCAERG

YAYCSDDGCQRTQDYDYWGQGTQVTVSS.

2CDA74(C50S)
                                      (SEQ ID NO: 1216)
QVQLQESGGGLVQAGGSLRLSCAVSGFTFDNYAIGWFRQAPGKEREGVSS

ISRSDGSTYYADSVRGRFTISSDNAKNTVYLQMNSLKPEDTAVYYCAAET

SADSGEFRFGWVLKPSLYDYWGQGTQVTVSS.

3CDA19
                                      (SEQ ID NO: 1220)
QVQLQESGGGLVQAGGSLRLSCAASGFSSDDYTIGWFRQAPGKEREGISC

FSSSDGSTGFADSVKGRFTISSDNATNTVYLEMNSLKPEDTAVYYCAADF

NVWSPPICGSRWYGPPPGGMEYWGKGTQVTVSS.
```

TABLE 1

| | KD (M) | KD Error | kon(1/Ms) | kon Error | kdis (1/s) | kdis Error |
|---|---|---|---|---|---|---|
| 2CDA5 | 2.01E−08 | 3.41E−10 | 1.02E+05 | 1.43E+03 | 2.04E−03 | 1.95E−05 |
| 3CDA19 | 2.60E−09 | 3.29E−11 | 2.07E+05 | 1.10E+03 | 5.37E−04 | 6.17E−06 |
| 1CDA65 | 3.09E−09 | 1.87E−11 | 3.13E+05 | 1.18E+03 | 9.65E−04 | 4.59E−06 |
| 2CDA74 (C50S) | 1.94E−08 | 9.55E−10 | 4.97E+03 | 5.44E+01 | 9.67E−05 | 4.63E−06 |
| 2CDA68 | 9.30E−09 | 1.32−10 | 3.24E+05 | 4.10E+03 | 3.01E−03 | 1.93E−05 |

The CD8 VHH's 1CDA65, 2CDA5, 2CDA68, 2CDA74 (C50S), and 3CDA19 were cloned into an AFN in the pMTW vector for eukaryotic expression as follows: pmTW-SIgK-hCD8_VHH-$(GGS)_{20}$-hIFNa2_R149A-GGS-$(His)_9$. Resulting CD8 VHH AFN proteins (i.e., AFN 1CDA65, AFN 2CDA5, AFN 2CDA68, AFN 2CDA74 (C50S), and AFN 3CDA19) were produced in ExpiCHO cells (Thermo Fisher) according to the manufacturers guidelines. Medium was harvested, cells removed by centrifugation and filter-sterilized. Recombinant proteins were purified using HisPur Cobalt beads (Thermo Fisher) and imidazole removed from the samples with PD10 columns (GE Healthcare).

To test the biological activity of the resulting CD8 VHH AFN's, PBMCs were isolated from buffy coats of healthy donors using density gradient centrifugation with Ficoll-Paque (GE Healthcare). Cells were washed twice with FACS buffer (2% FBS, 1 mM EDTA in PBS) and stained with anti-human CD8-FITC (clone REA734; Miltenyi Biotec) for 20 minutes at 4° C. After two washes, cells were stimulated with serial dilutions of a CD8 VHH AFN (i.e., AFN 1CDA65, AFN 2CDA5, AFN 2CDA68, AFN 2CDA74 (C50S), or AFN 3CDA19) or wild type IFNα2 (positive control) for 15 minutes at 37° C. After fixation (10 minutes, 37° C., Fix Buffer I; BD Biosciences) and permeabilization (30 minutes, on ice, Perm III Buffer I; BD Biosciences) and washing, cells were stained with anti-STAT1 pY701 Ab (BD Biosciences). Samples were acquired with a FACS Calibur (BD Biosciences), with the CellQuest Pro Version 4.0.2 software (BD Biosciences) and analyzed using the FlowJo software (FlowJo).

FIGS. 6A-F show that treatment with CD8 VHH AFNs lead to greater phosphorylation of STAT1 in CD8 positive cells as compared to CD8 negative cells (data plotted as increase over baseline STAT1 phosphorylation).

Example 5. Cross-Reactivity with Cynomolgus CD8

The ability of the CD8 VHH's from Example 4 to bind to human and cynomolgus CD8 alpha in FACS was tested.

Hek293T cells were transiently transfected with expression plasmids encoding human or cynomolgus CD8 alpha using standard calcium phosphate transfection. Two days later, cells were resuspended and sequentially incubated with serial dilutions CD8 AFN's and FITC coupled THE HIS Ab (Genscript). Samples were acquired with a FACS Calibur (BD Biosciences), with the CellQuest Pro Version 4.0.2 software (BD Biosciences) and analyzed using the FlowJo software (FlowJo).

FIGS. 7A-E show that all five CD8 VHHs bind equally as well to human and cynomolgus CD8 alpha.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

The following are hereby incorporated by reference in their entireties.

Artyomov M N, Lis M, Devadas S, Davis M M, Chakraborty A K, 2010. CD4 and CD8 binding to MHC molecules primarily acts to enhance Lck delivery. *Proceedings of the National Academy of Sciences of the United States of America* 107, 16916-21.

Cole D K, Dunn S M, Sami M, Boulter J M, Jakobsen B K, Sewell A K, 2008. T cell receptor engagement of peptide-major histocompatibility complex class I does not modify CD8 binding. *Molecular Immunology* 45, 2700-9.

Cole D K, Pumphrey N J, Boulter J M, et al., 2007. Human TCR-binding affinity is governed by MHC class restriction. *Journal of Immunology* 178, 5727-34.

Janeway C A, Jr., 1992. The T cell receptor as a multicomponent signalling machine: CD4/CD8 coreceptors and CD45 in T cell activation. *Annual Review of Immunology* 10, 645-74.

Jiang N, Huang J, Edwards L J, et al., 2011. Two-stage cooperative T cell receptor-peptide major histocompatibility complex-CD8 trimolecular interactions amplify antigen discrimination. *Immunity* 34, 13-23.

Laugel B, Price D A, Milicic A, Sewell A K, 2007a. CD8 exerts differential effects on the deployment of cytotoxic T lymphocyte effector functions. *European Journal of Immunology* 37, 905-13.

Laugel B, Van Den Berg H A, Gostick E, et al., 2007b. Different T cell receptor affinity thresholds and CD8 coreceptor dependence govern cytotoxic T lymphocyte activation and tetramer binding properties. *The Journal of Biological Chemistry* 282, 23799-810.

Li Y, Yin Y, Mariuzza R A, 2013. Structural and biophysical insights into the role of CD4 and CD8 in T cell activation. *Frontiers in Immunology* 4, 206.

Moebius U, Kober G, Griscelli A L, Hercend T, Meuer S C, 1991. Expression of different CD8 isoforms on distinct human lymphocyte subpopulations. *European Journal of Immunology* 21, 1793-800.

Purbhoo M A, Boulter J M, Price D A, et al., 2001. The human CD8 coreceptor effects cytotoxic T cell activation and antigen sensitivity primarily by mediating complete phosphorylation of the T cell receptor zeta chain. *The Journal of Biological Chemistry* 276, 32786-92.

Singer A, Bosselut R, 2004. CD4/CD8 coreceptors in thymocyte development, selection, and lineage commitment: analysis of the CD4/CD8 lineage decision. *Advances in Immunology* 83, 91-131.

Turner J M, Brodsky M H, Irving B A, Levin S D, Perlmutter R M, Littman D R, 1990. Interaction of the unique N-terminal region of tyrosine kinase p56lck with cytoplasmic domains of CD4 and CD8 is mediated by cysteine motifs. *Cell* 60, 755-65.

Van Der Merwe P A, Davis S J, 2003. Molecular interactions mediating T cell antigen recognition. *Annual Review of Immunology* 21, 659-84.

Veillette A, Bookman M A, Horak E M, Bolen J B, 1988. The CD4 and CD8 T cell surface antigens are associated with the internal membrane tyrosine-protein kinase p56lck. *Cell* 55, 301-8.

Wyer J R, Willcox B E, Gao G F, et al., 1999. T cell receptor and coreceptor CD8 alphaalpha bind peptide-MHC independently and with distinct kinetics. *Immunity* 10, 219-25.

Zamoyska R, 1998. CD4 and CD8: modulators of T-cell receptor recognition of antigen and of immune responses? *Current Opinion in Immunology* 10, 82-7.

What is claimed is:

1. A chimeric protein comprising a CD8 binding agent comprising:

(a) a targeting moiety having (i) an amino acid sequence having at least 90% identity with SEQ ID NO: 1217 and having a CDR3 consisting of the amino acid sequence of SEQ ID NO: 166; (ii) an amino acid sequence having at least 90% identity with SEQ ID NO: 1218 and having a CDR3 consisting of the amino acid sequence of SEQ ID NO: 177; (ii) an amino acid sequence having at least 90% identity with SEQ ID NO: 1219 and having a CDR3 consisting of the amino acid sequence of SEQ ID NO: 181; (iv) an amino acid sequence having at least 90% identity with SEQ ID NO: 1220 and having a CDR3 consisting of the amino acid sequence of SEQ ID NO: 199; or (v) an amino acid sequence having at least 90% identity with SEQ ID NO: 1216 and having a CDR3 consisting of the amino acid sequence of SEQ ID NO: 183, and (b) a modified human interferon alpha 2 (IFN-α2) molecule having the amino acid sequence of SEQ ID NO: 288 or 289 and comprising a R149A mutation, relative to SEQ ID NO: 288 or 289, that confers reduced affinity or activity for its receptor, wherein the reduced affinity or activity at the receptor is restorable by attachment with the CD8 binding agent.

2. The chimeric protein of claim 1, further comprising one or more additional targeting moieties.

3. The chimeric protein of claim 2, wherein the one or more additional targeting moieties recognize a tumor antigen.

4. The chimeric protein of claim 2, wherein the one or more additional targeting moieties modulate a tumor antigen.

5. The chimeric protein of claim 2, wherein the one or more additional targeting moieties recognize an antigen on an immune cell.

6. The chimeric protein of claim 2, wherein the one or more additional targeting moieties modulate an antigen on an immune cell.

7. The chimeric protein of claim 6, wherein the immune cell is selected from a T cell, a B cell, a dendritic cell, a macrophage, neutrophil, and a NK cell.

8. The chimeric protein of claim 1, wherein the chimeric CD8 binding agent recruits cytotoxic T cells to tumor cells or to the tumor environment.

9. The chimeric protein of claim 1, wherein the modified human IFN-α2 further comprises one or more mutations selected from R120E, A145G, M148A, and L153A, relative to SEQ ID NO: 288 or 289.

10. The chimeric protein of claim 1, wherein the targeting moiety has an amino acid sequence having at least 90% identity with SEQ ID NO: 1217 and having a CDR3 consisting of the amino acid sequence of SEQ ID NO: 166.

11. The chimeric protein of claim 1, wherein the targeting moiety has an amino acid sequence having at least 92% identity with SEQ ID NO: 1217.

12. A recombinant nucleic acid encoding the chimeric protein of claim 1.

13. A host cell comprising the recombinant nucleic acid of claim 12.

14. A method for treating or preventing cancer, comprising administering to a patient in need thereof an effective amount of the chimeric protein of claim 1.

* * * * *

SEQUENCE LISTING

```
Sequence total quantity: 1221
SEQ ID NO: 1            moltype = AA  length = 235
FEATURE                 Location/Qualifiers
REGION                  1..235
                        note = Synthetic polymer
source                  1..235
                        mol_type = protein
                        organism = synthetic construct
SEQUENCE: 1
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARYV       235

SEQ ID NO: 2            moltype = AA  length = 198
FEATURE                 Location/Qualifiers
REGION                  1..198
                        note = Synthetic polymer
source                  1..198
```

-continued

```
                      mol_type = protein
                      organism = synthetic construct
SEQUENCE: 2
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AGNRRRVCKC  180
PRPVVKSGDK PSLSARYV                                               198

SEQ ID NO: 3          moltype = AA  length = 276
FEATURE               Location/Qualifiers
REGION                1..276
                      note = Synthetic polymer
source                1..276
                      mol_type = protein
                      organism = synthetic construct
SEQUENCE: 3
MRNQAPGRPK GATFPPRRPT GSRAPPLAPE LRAKQRPGER VMALPVTALL LPLALLLHAA  60
RPSQFRVSPL DRTWNLGETV ELKCQVLLSN PTSGCSWLFQ PRGAAASPTF LLYLSQNKPK  120
AAEGLDTQRF SGKRLGDTFV LTLSDFRREN EGYYFCSALS NSIMYFSHFV PVFLPAKPTT  180
TPAPRPPTPA PTIASQPLSL RPEACRPAAG GAVHTRGLDF ACDIYIWAPL AGTCGVLLLS  240
LVITLYCNHR NRRRVCKCPR PVVKSGDKPS LSARYV                           276

SEQ ID NO: 4          moltype = AA  length = 210
FEATURE               Location/Qualifiers
REGION                1..210
                      note = Synthetic polymer
source                1..210
                      mol_type = protein
                      organism = synthetic construct
SEQUENCE: 4
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQFYK                                  210

SEQ ID NO: 5          moltype = AA  length = 221
FEATURE               Location/Qualifiers
REGION                1..221
                      note = Synthetic polymer
source                1..221
                      mol_type = protein
                      organism = synthetic construct
SEQUENCE: 5
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQLRL HPLEKCSRMD Y                     221

SEQ ID NO: 6          moltype = AA  length = 213
FEATURE               Location/Qualifiers
REGION                1..213
                      note = Synthetic polymer
source                1..213
                      mol_type = protein
                      organism = synthetic construct
SEQUENCE: 6
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGRRRRA RLRFMKQPQG  180
EGISGTFVPQ CLHGYYSNTT TSQKLLNPWI LKT                              213

SEQ ID NO: 7          moltype = AA  length = 246
FEATURE               Location/Qualifiers
REGION                1..246
                      note = Synthetic polymer
source                1..246
                      mol_type = protein
                      organism = synthetic construct
SEQUENCE: 7
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQKFN IVCLKISGFT TCCCFQILQI SREYGFGVLL  240
QKDIGQ                                                            246

SEQ ID NO: 8          moltype = AA  length = 243
FEATURE               Location/Qualifiers
REGION                1..243
                      note = Synthetic polymer
```

```
source                  1..243
                        mol_type = protein
                        organism = synthetic construct
SEQUENCE: 8
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQPQG EGISGTFVPQ CLHGYYSNTT TSQKLLNPWI  240
LKT                                                               243

SEQ ID NO: 9            moltype = AA  length = 180
FEATURE                 Location/Qualifiers
REGION                  1..180
                        note = Synthetic polymer
source                  1..180
                        mol_type = protein
                        organism = synthetic construct
SEQUENCE: 9
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGRRRRA RLRFMKQFYK  180

SEQ ID NO: 10           moltype = AA  length = 206
FEATURE                 Location/Qualifiers
REGION                  1..206
                        note = Synthetic polymer
source                  1..206
                        mol_type = protein
                        organism = synthetic construct
SEQUENCE: 10
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKDFTNKQ RIGFWCPATK  180
RHRSVMSTMW KNERRDTFNP GEFNGC                                      206

SEQ ID NO: 11           moltype = AA  length = 198
FEATURE                 Location/Qualifiers
REGION                  1..198
                        note = Synthetic polymer
source                  1..198
                        mol_type = protein
                        organism = synthetic construct
SEQUENCE: 11
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGLKGKV YQEPLSPNAC  180
MDTTAILQPH RSCLTHGS                                               198

SEQ ID NO: 12           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 12
GRSFSSYTLA                                                        10

SEQ ID NO: 13           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 13
GRTFSSYTMG                                                        10

SEQ ID NO: 14           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 14
GRTFSSYIMG                                                        10

SEQ ID NO: 15           moltype = AA  length = 10
```

```
FEATURE                Location/Qualifiers
REGION                 1..10
                       note = Synthetic polymer
source                 1..10
                       mol_type = protein
                       organism = synthetic construct
SEQUENCE: 15
GRTFSSYTMG                                                            10

SEQ ID NO: 16          moltype = AA  length = 14
FEATURE                Location/Qualifiers
REGION                 1..14
                       note = Synthetic polymer
source                 1..14
                       mol_type = protein
                       organism = synthetic construct
SEQUENCE: 16
GRTSGRTFSS YTMG                                                       14

SEQ ID NO: 17          moltype = AA  length = 10
FEATURE                Location/Qualifiers
REGION                 1..10
                       note = Synthetic polymer
source                 1..10
                       mol_type = protein
                       organism = synthetic construct
SEQUENCE: 17
GRTFSSYAMG                                                            10

SEQ ID NO: 18          moltype = AA  length = 10
FEATURE                Location/Qualifiers
REGION                 1..10
                       note = Synthetic polymer
source                 1..10
                       mol_type = protein
                       organism = synthetic construct
SEQUENCE: 18
GLTFSNYIMG                                                            10

SEQ ID NO: 19          moltype = AA  length = 10
FEATURE                Location/Qualifiers
REGION                 1..10
                       note = Synthetic polymer
source                 1..10
                       mol_type = protein
                       organism = synthetic construct
SEQUENCE: 19
GRTFSSYTMG                                                            10

SEQ ID NO: 20          moltype = AA  length = 10
FEATURE                Location/Qualifiers
REGION                 1..10
                       note = Synthetic polymer
source                 1..10
                       mol_type = protein
                       organism = synthetic construct
SEQUENCE: 20
GRTFSSDTMG                                                            10

SEQ ID NO: 21          moltype = AA  length = 10
FEATURE                Location/Qualifiers
REGION                 1..10
                       note = Synthetic polymer
source                 1..10
                       mol_type = protein
                       organism = synthetic construct
SEQUENCE: 21
GLTFSNYIMG                                                            10

SEQ ID NO: 22          moltype = AA  length = 10
FEATURE                Location/Qualifiers
REGION                 1..10
                       note = Synthetic polymer
source                 1..10
                       mol_type = protein
                       organism = synthetic construct
SEQUENCE: 22
GFTLDYYGIG                                                            10
```

-continued

```
SEQ ID NO: 23          moltype = AA  length = 10
FEATURE                Location/Qualifiers
REGION                 1..10
                       note = Synthetic polymer
source                 1..10
                       mol_type = protein
                       organism = synthetic construct
SEQUENCE: 23
GHTFSSYTMG                                                            10

SEQ ID NO: 24          moltype = AA  length = 10
FEATURE                Location/Qualifiers
REGION                 1..10
                       note = Synthetic polymer
source                 1..10
                       mol_type = protein
                       organism = synthetic construct
SEQUENCE: 24
GRTFSSYVIG                                                            10

SEQ ID NO: 25          moltype = AA  length = 10
FEATURE                Location/Qualifiers
REGION                 1..10
                       note = Synthetic polymer
source                 1..10
                       mol_type = protein
                       organism = synthetic construct
SEQUENCE: 25
GFAFDGYAIG                                                            10

SEQ ID NO: 26          moltype = AA  length = 10
FEATURE                Location/Qualifiers
REGION                 1..10
                       note = Synthetic polymer
source                 1..10
                       mol_type = protein
                       organism = synthetic construct
SEQUENCE: 26
GFAFGFFDMT                                                            10

SEQ ID NO: 27          moltype = AA  length = 10
FEATURE                Location/Qualifiers
REGION                 1..10
                       note = Synthetic polymer
source                 1..10
                       mol_type = protein
                       organism = synthetic construct
SEQUENCE: 27
GRTFSNYVIG                                                            10

SEQ ID NO: 28          moltype = AA  length = 10
FEATURE                Location/Qualifiers
REGION                 1..10
                       note = Synthetic polymer
source                 1..10
                       mol_type = protein
                       organism = synthetic construct
SEQUENCE: 28
GSIFSINVMG                                                            10

SEQ ID NO: 29          moltype = AA  length = 10
FEATURE                Location/Qualifiers
REGION                 1..10
                       note = Synthetic polymer
source                 1..10
                       mol_type = protein
                       organism = synthetic construct
SEQUENCE: 29
GRTFSNYNVG                                                            10

SEQ ID NO: 30          moltype = AA  length = 10
FEATURE                Location/Qualifiers
REGION                 1..10
                       note = Synthetic polymer
source                 1..10
                       mol_type = protein
                       organism = synthetic construct
SEQUENCE: 30
GHTFSSYTMG                                                            10
```

```
SEQ ID NO: 31           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 31
GRTFSTYPVG                                                            10

SEQ ID NO: 32           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 32
GRTFSNYAMG                                                            10

SEQ ID NO: 33           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 33
GRTFSDYRMG                                                            10

SEQ ID NO: 34           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 34
GLTFSNYIMA                                                            10

SEQ ID NO: 35           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 35
GRTFSNSVMG                                                            10

SEQ ID NO: 36           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 36
GRTFSSYIIG                                                            10

SEQ ID NO: 37           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 37
GRTFSSYVMG                                                            10

SEQ ID NO: 38           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 38
```

-continued

```
GGTFSNYVMG                                                              10

SEQ ID NO: 39          moltype = AA  length = 10
FEATURE                Location/Qualifiers
REGION                 1..10
                       note = Synthetic polymer
source                 1..10
                       mol_type = protein
                       organism = synthetic construct
SEQUENCE: 39
GRTFSNYGIG                                                              10

SEQ ID NO: 40          moltype = AA  length = 10
FEATURE                Location/Qualifiers
REGION                 1..10
                       note = Synthetic polymer
source                 1..10
                       mol_type = protein
                       organism = synthetic construct
SEQUENCE: 40
GFTFDDYAIA                                                              10

SEQ ID NO: 41          moltype = AA  length = 10
FEATURE                Location/Qualifiers
REGION                 1..10
                       note = Synthetic polymer
source                 1..10
                       mol_type = protein
                       organism = synthetic construct
SEQUENCE: 41
GRTFSSYTVA                                                              10

SEQ ID NO: 42          moltype = AA  length = 10
FEATURE                Location/Qualifiers
REGION                 1..10
                       note = Synthetic polymer
source                 1..10
                       mol_type = protein
                       organism = synthetic construct
SEQUENCE: 42
GFPFDDYAIA                                                              10

SEQ ID NO: 43          moltype = AA  length = 10
FEATURE                Location/Qualifiers
REGION                 1..10
                       note = Synthetic polymer
source                 1..10
                       mol_type = protein
                       organism = synthetic construct
SEQUENCE: 43
GRTFSSYVMG                                                              10

SEQ ID NO: 44          moltype = AA  length = 10
FEATURE                Location/Qualifiers
REGION                 1..10
                       note = Synthetic polymer
source                 1..10
                       mol_type = protein
                       organism = synthetic construct
SEQUENCE: 44
GRTLSSNPMA                                                              10

SEQ ID NO: 45          moltype = AA  length = 10
FEATURE                Location/Qualifiers
REGION                 1..10
                       note = Synthetic polymer
source                 1..10
                       mol_type = protein
                       organism = synthetic construct
SEQUENCE: 45
GFTFDNYAIG                                                              10

SEQ ID NO: 46          moltype = AA  length = 10
FEATURE                Location/Qualifiers
REGION                 1..10
                       note = Synthetic polymer
source                 1..10
                       mol_type = protein
                       organism = synthetic construct
```

-continued

```
SEQUENCE: 46
GRAFSSYFMG                                                            10

SEQ ID NO: 47          moltype = AA  length = 10
FEATURE                Location/Qualifiers
REGION                 1..10
                       note = Synthetic polymer
source                 1..10
                       mol_type = protein
                       organism = synthetic construct
SEQUENCE: 47
TPTFSSYNMG                                                            10

SEQ ID NO: 48          moltype = AA  length = 10
FEATURE                Location/Qualifiers
REGION                 1..10
                       note = Synthetic polymer
source                 1..10
                       mol_type = protein
                       organism = synthetic construct
SEQUENCE: 48
GFTFDDYAIA                                                            10

SEQ ID NO: 49          moltype = AA  length = 10
FEATURE                Location/Qualifiers
REGION                 1..10
                       note = Synthetic polymer
source                 1..10
                       mol_type = protein
                       organism = synthetic construct
SEQUENCE: 49
GGTFSGYIMG                                                            10

SEQ ID NO: 50          moltype = AA  length = 10
FEATURE                Location/Qualifiers
REGION                 1..10
                       note = Synthetic polymer
source                 1..10
                       mol_type = protein
                       organism = synthetic construct
SEQUENCE: 50
GRSFSSYTIA                                                            10

SEQ ID NO: 51          moltype = AA  length = 10
FEATURE                Location/Qualifiers
REGION                 1..10
                       note = Synthetic polymer
source                 1..10
                       mol_type = protein
                       organism = synthetic construct
SEQUENCE: 51
GFSSDDYTIG                                                            10

SEQ ID NO: 52          moltype = AA  length = 10
FEATURE                Location/Qualifiers
REGION                 1..10
                       note = Synthetic polymer
source                 1..10
                       mol_type = protein
                       organism = synthetic construct
SEQUENCE: 52
GFTFDDYTIG                                                            10

SEQ ID NO: 53          moltype = AA  length = 10
FEATURE                Location/Qualifiers
REGION                 1..10
                       note = Synthetic polymer
source                 1..10
                       mol_type = protein
                       organism = synthetic construct
SEQUENCE: 53
GFSSDDYTIG                                                            10

SEQ ID NO: 54          moltype = AA  length = 10
FEATURE                Location/Qualifiers
REGION                 1..10
                       note = Synthetic polymer
source                 1..10
                       mol_type = protein
```

```
                      organism = synthetic construct
SEQUENCE: 54
GFTFDQYTIA                                                    10

SEQ ID NO: 55         moltype = AA  length = 10
FEATURE               Location/Qualifiers
REGION                1..10
                      note = Synthetic polymer
source                1..10
                      mol_type = protein
                      organism = synthetic construct
SEQUENCE: 55
GRTFSSYAMA                                                    10

SEQ ID NO: 56         moltype = AA  length = 10
FEATURE               Location/Qualifiers
REGION                1..10
                      note = Synthetic polymer
source                1..10
                      mol_type = protein
                      organism = synthetic construct
SEQUENCE: 56
GFAFDGYAIG                                                    10

SEQ ID NO: 57         moltype = AA  length = 10
FEATURE               Location/Qualifiers
REGION                1..10
                      note = Synthetic polymer
source                1..10
                      mol_type = protein
                      organism = synthetic construct
SEQUENCE: 57
GFSSDDYTIA                                                    10

SEQ ID NO: 58         moltype = AA  length = 10
FEATURE               Location/Qualifiers
REGION                1..10
                      note = Synthetic polymer
source                1..10
                      mol_type = protein
                      organism = synthetic construct
SEQUENCE: 58
GFSSDDYTIG                                                    10

SEQ ID NO: 59         moltype = AA  length = 10
FEATURE               Location/Qualifiers
REGION                1..10
                      note = Synthetic polymer
source                1..10
                      mol_type = protein
                      organism = synthetic construct
SEQUENCE: 59
GFTFDDYTIG                                                    10

SEQ ID NO: 60         moltype = AA  length = 10
FEATURE               Location/Qualifiers
REGION                1..10
                      note = Synthetic polymer
source                1..10
                      mol_type = protein
                      organism = synthetic construct
SEQUENCE: 60
GFSSDDYTIG                                                    10

SEQ ID NO: 61         moltype = AA  length = 10
FEATURE               Location/Qualifiers
REGION                1..10
                      note = Synthetic polymer
source                1..10
                      mol_type = protein
                      organism = synthetic construct
SEQUENCE: 61
GFSSDDYTIG                                                    10

SEQ ID NO: 62         moltype = AA  length = 10
FEATURE               Location/Qualifiers
REGION                1..10
                      note = Synthetic polymer
source                1..10
```

```
                        mol_type = protein
                        organism = synthetic construct
SEQUENCE: 62
GFSFDDYAIA                                                  10

SEQ ID NO: 63           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 63
GFSSDDYTIG                                                  10

SEQ ID NO: 64           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 64
GFTGNDLAIG                                                  10

SEQ ID NO: 65           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 65
GFSSDDYTIA                                                  10

SEQ ID NO: 66           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 66
EGTLSSYGIG                                                  10

SEQ ID NO: 67           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 67
GFSSDDYTIA                                                  10

SEQ ID NO: 68           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 68
GFTFDDYAIA                                                  10

SEQ ID NO: 69           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 69
GLSSDDYTIG                                                  10

SEQ ID NO: 70           moltype = AA  length = 10
FEATURE                 Location/Qualifiers
REGION                  1..10
                        note = Synthetic polymer
```

```
source                  1..10
                        mol_type = protein
                        organism = synthetic construct
SEQUENCE: 70
GLSSDDYTIG                                                         10

SEQ ID NO: 71           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 71
GFSSDDYTIG                                                         10

SEQ ID NO: 72           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 72
GFSFDDYTIG                                                         10

SEQ ID NO: 73           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 73
GFTFDDYAIA                                                         10

SEQ ID NO: 74           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 74
GFTFDDYAIG                                                         10

SEQ ID NO: 75           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 75
GFTFGDYTIG                                                         10

SEQ ID NO: 76           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 76
EGTFSSYGIG                                                         10

SEQ ID NO: 77           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 77
GFSSDDYTIG                                                         10

SEQ ID NO: 78           moltype = AA  length = 10
FEATURE                 Location/Qualifiers
REGION                  1..10
```

```
                        note = Synthetic polymer
source                  1..10
                        mol_type = protein
                        organism = synthetic construct
SEQUENCE: 78
GVSIGDYNIG                                                  10

SEQ ID NO: 79           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 79
GFTFDDYTIA                                                  10

SEQ ID NO: 80           moltype = AA  length = 10
FEATURE                 Location/Qualifiers
REGION                  1..10
                        note = Synthetic polymer
source                  1..10
                        mol_type = protein
                        organism = synthetic construct
SEQUENCE: 80
GFTFDDYTIA                                                  10

SEQ ID NO: 81           moltype = AA  length = 11
FEATURE                 Location/Qualifiers
REGION                  1..11
                        note = Synthetic polymer
source                  1..11
                        mol_type = protein
                        organism = synthetic construct
SEQUENCE: 81
ASITWGGGNT Y                                                11

SEQ ID NO: 82           moltype = AA  length = 11
FEATURE                 Location/Qualifiers
REGION                  1..11
                        note = Synthetic polymer
source                  1..11
                        mol_type = protein
                        organism = synthetic construct
SEQUENCE: 82
AATVWTGAGT V                                                11

SEQ ID NO: 83           moltype = AA  length = 11
FEATURE                 Location/Qualifiers
REGION                  1..11
                        note = Synthetic polymer
source                  1..11
                        mol_type = protein
                        organism = synthetic construct
SEQUENCE: 83
AAIGWSADIT V                                                11

SEQ ID NO: 84           moltype = AA  length = 11
FEATURE                 Location/Qualifiers
REGION                  1..11
                        note = Synthetic polymer
source                  1..11
                        mol_type = protein
                        organism = synthetic construct
SEQUENCE: 84
AFIDWSGGGT Y                                                11

SEQ ID NO: 85           moltype = AA  length = 11
FEATURE                 Location/Qualifiers
REGION                  1..11
                        note = Synthetic polymer
source                  1..11
                        mol_type = protein
                        organism = synthetic construct
SEQUENCE: 85
ATITWGGGST Y                                                11

SEQ ID NO: 86           moltype = AA  length = 11
FEATURE                 Location/Qualifiers
```

-continued

```
REGION              1..11
                    note = Synthetic polymer
source              1..11
                    mol_type = protein
                    organism = synthetic construct
SEQUENCE: 86
AAISWSGGPT V                                                  11

SEQ ID NO: 87       moltype = AA  length = 11
FEATURE             Location/Qualifiers
REGION              1..11
                    note = Synthetic polymer
source              1..11
                    mol_type = protein
                    organism = synthetic construct
SEQUENCE: 87
AAITWGGGST V                                                  11

SEQ ID NO: 88       moltype = AA  length = 11
FEATURE             Location/Qualifiers
REGION              1..11
                    note = Synthetic polymer
source              1..11
                    mol_type = protein
                    organism = synthetic construct
SEQUENCE: 88
AAITWSGVST V                                                  11

SEQ ID NO: 89       moltype = AA  length = 11
FEATURE             Location/Qualifiers
REGION              1..11
                    note = Synthetic polymer
source              1..11
                    mol_type = protein
                    organism = synthetic construct
SEQUENCE: 89
GAIMWSGAFT H                                                  11

SEQ ID NO: 90       moltype = AA  length = 11
FEATURE             Location/Qualifiers
REGION              1..11
                    note = Synthetic polymer
source              1..11
                    mol_type = protein
                    organism = synthetic construct
SEQUENCE: 90
AAITWGGGST V                                                  11

SEQ ID NO: 91       moltype = AA  length = 11
FEATURE             Location/Qualifiers
REGION              1..11
                    note = Synthetic polymer
source              1..11
                    mol_type = protein
                    organism = synthetic construct
SEQUENCE: 91
SCISSSDRNT Y                                                  11

SEQ ID NO: 92       moltype = AA  length = 11
FEATURE             Location/Qualifiers
REGION              1..11
                    note = Synthetic polymer
source              1..11
                    mol_type = protein
                    organism = synthetic construct
SEQUENCE: 92
AFIDWSGGGT Y                                                  11

SEQ ID NO: 93       moltype = AA  length = 11
FEATURE             Location/Qualifiers
REGION              1..11
                    note = Synthetic polymer
source              1..11
                    mol_type = protein
                    organism = synthetic construct
SEQUENCE: 93
AVITWSGDST Y                                                  11

SEQ ID NO: 94       moltype = AA  length = 11
```

-continued

```
FEATURE                Location/Qualifiers
REGION                 1..11
                       note = Synthetic polymer
source                 1..11
                       mol_type = protein
                       organism = synthetic construct
SEQUENCE: 94
ACISSKDGST Y                                                       11

SEQ ID NO: 95          moltype = AA  length = 11
FEATURE                Location/Qualifiers
REGION                 1..11
                       note = Synthetic polymer
source                 1..11
                       mol_type = protein
                       organism = synthetic construct
SEQUENCE: 95
SGINSIGGST T                                                       11

SEQ ID NO: 96          moltype = AA  length = 11
FEATURE                Location/Qualifiers
REGION                 1..11
                       note = Synthetic polymer
source                 1..11
                       mol_type = protein
                       organism = synthetic construct
SEQUENCE: 96
AVVTWSGDST Y                                                       11

SEQ ID NO: 97          moltype = AA  length = 10
FEATURE                Location/Qualifiers
REGION                 1..10
                       note = Synthetic polymer
source                 1..10
                       mol_type = protein
                       organism = synthetic construct
SEQUENCE: 97
AKITNFGITS                                                         10

SEQ ID NO: 98          moltype = AA  length = 11
FEATURE                Location/Qualifiers
REGION                 1..11
                       note = Synthetic polymer
source                 1..11
                       mol_type = protein
                       organism = synthetic construct
SEQUENCE: 98
SFISWISDIT Y                                                       11

SEQ ID NO: 99          moltype = AA  length = 11
FEATURE                Location/Qualifiers
REGION                 1..11
                       note = Synthetic polymer
source                 1..11
                       mol_type = protein
                       organism = synthetic construct
SEQUENCE: 99
AFIDWSGGGT Y                                                       11

SEQ ID NO: 100         moltype = AA  length = 11
FEATURE                Location/Qualifiers
REGION                 1..11
                       note = Synthetic polymer
source                 1..11
                       mol_type = protein
                       organism = synthetic construct
SEQUENCE: 100
AVILWSGVST Y                                                       11

SEQ ID NO: 101         moltype = AA  length = 11
FEATURE                Location/Qualifiers
REGION                 1..11
                       note = Synthetic polymer
source                 1..11
                       mol_type = protein
                       organism = synthetic construct
SEQUENCE: 101
AAIVWSGGST Y                                                       11
```

```
SEQ ID NO: 102          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 102
AAISSSGYHT Y                                                    11

SEQ ID NO: 103          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 103
SCISSPDGST Y                                                    11

SEQ ID NO: 104          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 104
AAVLWSGVST A                                                    11

SEQ ID NO: 105          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 105
VAITWDGSAT T                                                    11

SEQ ID NO: 106          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 106
AAIGWNGGIT Y                                                    11

SEQ ID NO: 107          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 107
GFITWSGAST Y                                                    11

SEQ ID NO: 108          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 108
AGINWSGESA D                                                    11

SEQ ID NO: 109          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 109
SCIERSDGST Y                                                    11
```

```
SEQ ID NO: 110          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 110
SCISNTDSST Y                                                      11

SEQ ID NO: 111          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 111
SCISNTDSST Y                                                      11

SEQ ID NO: 112          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 112
AQISWSAGSI Y                                                      11

SEQ ID NO: 113          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 113
AGMSWNPGPA V                                                      11

SEQ ID NO: 114          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 114
SCISRSDGST Y                                                      11

SEQ ID NO: 115          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 115
ANIGWTGDMT Y                                                      11

SEQ ID NO: 116          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 116
AAIIWSGSMT Y                                                      11

SEQ ID NO: 117          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 117
```

```
SCISNTDSST Y                                                        11

SEQ ID NO: 118          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 118
AANTWSGGPT Y                                                        11

SEQ ID NO: 119          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 119
SCISSDGSTG                                                          10

SEQ ID NO: 120          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 120
SCYSSSDGST G                                                        11

SEQ ID NO: 121          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 121
SCISSDGSTG                                                          10

SEQ ID NO: 122          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 122
GCIKSSDGTT G                                                        11

SEQ ID NO: 123          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 123
SCISNTDSST Y                                                        11

SEQ ID NO: 124          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 124
AAIAWSAGST Y                                                        11

SEQ ID NO: 125          moltype = AA  length = 11
FEATURE                 Location/Qualifiers
REGION                  1..11
                        note = Synthetic polymer
source                  1..11
                        mol_type = protein
                        organism = synthetic construct
```

```
SEQUENCE: 125
SCISSKEGST Y                                                    11

SEQ ID NO: 126          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 126
SCISSSDGST G                                                    11

SEQ ID NO: 127          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 127
SCYSSRDGTT G                                                    11

SEQ ID NO: 128          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 128
SCISSDGSTG                                                      10

SEQ ID NO: 129          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 129
SCYSSSDGST G                                                    11

SEQ ID NO: 130          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 130
SCFSSSDGST G                                                    11

SEQ ID NO: 131          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 131
SCISNTDSST F                                                    11

SEQ ID NO: 132          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 132
SCYSSSDGST G                                                    11

SEQ ID NO: 133          moltype = AA  length = 11
FEATURE                 Location/Qualifiers
REGION                  1..11
                        note = Synthetic polymer
source                  1..11
                        mol_type = protein
```

```
                        organism = synthetic construct
SEQUENCE: 133
SCISNTDSST Y                                                         11

SEQ ID NO: 134          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 134
SCISSSDGST G                                                         11

SEQ ID NO: 135          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 135
GGINWSGDST D                                                         11

SEQ ID NO: 136          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 136
SCFSSSDGSA G                                                         11

SEQ ID NO: 137          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 137
SCISNTDSST Y                                                         11

SEQ ID NO: 138          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 138
SCFSTRDGNA G                                                         11

SEQ ID NO: 139          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 139
SCFSSRDGST G                                                         11

SEQ ID NO: 140          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 140
SCFSSRDGST G                                                         11

SEQ ID NO: 141          moltype = AA  length = 10
FEATURE                 Location/Qualifiers
REGION                  1..10
                        note = Synthetic polymer
source                  1..10
```

```
                        mol_type = protein
                        organism = synthetic construct
SEQUENCE: 141
SCISSDGSTG                                              10

SEQ ID NO: 142          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 142
SCISNTDSST Y                                            11

SEQ ID NO: 143          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 143
SCISSPDGST Y                                            11

SEQ ID NO: 144          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 144
SCYSSSDGNT G                                            11

SEQ ID NO: 145          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 145
GGINWSGDST D                                            11

SEQ ID NO: 146          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 146
SCFSSSDGST G                                            11

SEQ ID NO: 147          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 147
SCISSGDGTT Y                                            11

SEQ ID NO: 148          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 148
SCISSDGSTG                                              10

SEQ ID NO: 149          moltype = AA  length = 10
FEATURE                 Location/Qualifiers
REGION                  1..10
                        note = Synthetic polymer
```

```
source                  1..10
                        mol_type = protein
                        organism = synthetic construct
SEQUENCE: 149
SCISSDGSTG                                                        10

SEQ ID NO: 150          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 150
AKGLRNSDWD LRRGYEYDY                                              19

SEQ ID NO: 151          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 151
ADQASVPPPY GSERYDIASP SEYDY                                       25

SEQ ID NO: 152          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 152
ANSRAYYSSS YDLGRLASYD Y                                           21

SEQ ID NO: 153          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 153
AAQRLGSVTD YTKYDY                                                 16

SEQ ID NO: 154          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 154
ASVKVVAGSG IDISGSRNYD Y                                           21

SEQ ID NO: 155          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 155
AKRLDYSATD KGVDLSDEYD Y                                           21

SEQ ID NO: 156          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 156
AAGGSGRLRD LKVGQNYDY                                              19

SEQ ID NO: 157          moltype = AA  length = 23
FEATURE                 Location/Qualifiers
REGION                  1..23
```

```
                        note = Synthetic polymer
source                  1..23
                        mol_type = protein
                        organism = synthetic construct
SEQUENCE: 157
ADSPPRTYSS GSVNLEDGSE YDY                                             23

SEQ ID NO: 158          moltype = AA  length = 21
FEATURE                 Location/Qualifiers
REGION                  1..21
                        note = Synthetic polymer
source                  1..21
                        mol_type = protein
                        organism = synthetic construct
SEQUENCE: 158
VIPGRGSALP IDVGKSDEYE Y                                               21

SEQ ID NO: 159          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 159
AAGASGRLRD LKVGQNYDY                                                  19

SEQ ID NO: 160          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 160
ADGNVWSPPI CGSAGPPPGG MDY                                             23

SEQ ID NO: 161          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 161
AAQRLGSVTD YTKYDY                                                     16

SEQ ID NO: 162          moltype = AA  length = 22
FEATURE                 Location/Qualifiers
REGION                  1..22
                        note = Synthetic polymer
source                  1..22
                        mol_type = protein
                        organism = synthetic construct
SEQUENCE: 162
AIPPRAYSGG SYSLKDQSKY EY                                              22

SEQ ID NO: 163          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 163
ADGNVWSPPI CSSAGPPPGG MDY                                             23

SEQ ID NO: 164          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 164
KSRSSYSNN                                                             9

SEQ ID NO: 165          moltype = AA  length = 22
FEATURE                 Location/Qualifiers
```

```
REGION                  1..22
                        note = Synthetic polymer
source                  1..22
                        mol_type = protein
                        organism = synthetic construct
SEQUENCE: 165
AMPPRAYTGR SVSLKDQSKY EY                                          22

SEQ ID NO: 166          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 166
LDTTGWGPPP YQY                                                    13

SEQ ID NO: 167          moltype = AA  length = 22
FEATURE                 Location/Qualifiers
REGION                  1..22
                        note = Synthetic polymer
source                  1..22
                        mol_type = protein
                        organism = synthetic construct
SEQUENCE: 167
AHPPDPSRGG EWRLQTPSEY DY                                          22

SEQ ID NO: 168          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 168
AAQRLGSVTD YTKYDY                                                 16

SEQ ID NO: 169          moltype = AA  length = 24
FEATURE                 Location/Qualifiers
REGION                  1..24
                        note = Synthetic polymer
source                  1..24
                        mol_type = protein
                        organism = synthetic construct
SEQUENCE: 169
VPRSHFTTAQ DMGQDMGAPS WYEY                                        24

SEQ ID NO: 170          moltype = AA  length = 22
FEATURE                 Location/Qualifiers
REGION                  1..22
                        note = Synthetic polymer
source                  1..22
                        mol_type = protein
                        organism = synthetic construct
SEQUENCE: 170
AVLIRYYSGG YQGLSDANEY DY                                          22

SEQ ID NO: 171          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 171
VVKYLSGSYS YAGQYNF                                                17

SEQ ID NO: 172          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 172
ADFNVWSPPI CGSVGPPPGG MDY                                         23

SEQ ID NO: 173          moltype = AA  length = 21
```

```
FEATURE               Location/Qualifiers
REGION                1..21
                      note = Synthetic polymer
source                1..21
                      mol_type = protein
                      organism = synthetic construct
SEQUENCE: 173
AHESTYYSGT YYLTDPRRYV Y                                                21

SEQ ID NO: 174        moltype = AA  length = 19
FEATURE               Location/Qualifiers
REGION                1..19
                      note = Synthetic polymer
source                1..19
                      mol_type = protein
                      organism = synthetic construct
SEQUENCE: 174
AVPARGLTMD LENSDIYDH                                                   19

SEQ ID NO: 175        moltype = AA  length = 22
FEATURE               Location/Qualifiers
REGION                1..22
                      note = Synthetic polymer
source                1..22
                      mol_type = protein
                      organism = synthetic construct
SEQUENCE: 175
AATLQVTGSY YLDLSTVDIY DN                                               22

SEQ ID NO: 176        moltype = AA  length = 20
FEATURE               Location/Qualifiers
REGION                1..20
                      note = Synthetic polymer
source                1..20
                      mol_type = protein
                      organism = synthetic construct
SEQUENCE: 176
ATLFRSNGPK DLSSGYEYDY                                                  20

SEQ ID NO: 177        moltype = AA  length = 13
FEATURE               Location/Qualifiers
REGION                1..13
                      note = Synthetic polymer
source                1..13
                      mol_type = protein
                      organism = synthetic construct
SEQUENCE: 177
AGESGVWVGG LDY                                                         13

SEQ ID NO: 178        moltype = AA  length = 22
FEATURE               Location/Qualifiers
REGION                1..22
                      note = Synthetic polymer
source                1..22
                      mol_type = protein
                      organism = synthetic construct
SEQUENCE: 178
VGSANSGEFR FGWVLKPDLY NY                                               22

SEQ ID NO: 179        moltype = AA  length = 23
FEATURE               Location/Qualifiers
REGION                1..23
                      note = Synthetic polymer
source                1..23
                      mol_type = protein
                      organism = synthetic construct
SEQUENCE: 179
ADGNVWSPPI CGSAGPPPGG MDY                                              23

SEQ ID NO: 180        moltype = AA  length = 23
FEATURE               Location/Qualifiers
REGION                1..23
                      note = Synthetic polymer
source                1..23
                      mol_type = protein
                      organism = synthetic construct
SEQUENCE: 180
ADGNVWSPPI CGSAGPPPGG MDY                                              23
```

-continued

```
SEQ ID NO: 181         moltype = AA  length = 20
FEATURE                Location/Qualifiers
REGION                 1..20
                       note = Synthetic polymer
source                 1..20
                       mol_type = protein
                       organism = synthetic construct
SEQUENCE: 181
ERGYAYCSDD GCQRTQDYDY                                          20

SEQ ID NO: 182         moltype = AA  length = 21
FEATURE                Location/Qualifiers
REGION                 1..21
                       note = Synthetic polymer
source                 1..21
                       mol_type = protein
                       organism = synthetic construct
SEQUENCE: 182
GAARAWWSGS YDYTRMNNYD Y                                        21

SEQ ID NO: 183         moltype = AA  length = 23
FEATURE                Location/Qualifiers
REGION                 1..23
                       note = Synthetic polymer
source                 1..23
                       mol_type = protein
                       organism = synthetic construct
SEQUENCE: 183
AETSADSGEF RFGWVLKPSL YDY                                      23

SEQ ID NO: 184         moltype = AA  length = 21
FEATURE                Location/Qualifiers
REGION                 1..21
                       note = Synthetic polymer
source                 1..21
                       mol_type = protein
                       organism = synthetic construct
SEQUENCE: 184
AAGSAYSGSY WNITMAANYD Y                                        21

SEQ ID NO: 185         moltype = AA  length = 18
FEATURE                Location/Qualifiers
REGION                 1..18
                       note = Synthetic polymer
source                 1..18
                       mol_type = protein
                       organism = synthetic construct
SEQUENCE: 185
AQRIFGAQPM DLSGDYEY                                            18

SEQ ID NO: 186         moltype = AA  length = 23
FEATURE                Location/Qualifiers
REGION                 1..23
                       note = Synthetic polymer
source                 1..23
                       mol_type = protein
                       organism = synthetic construct
SEQUENCE: 186
ADGNVWSPPI CGSAGPPPGG MDY                                      23

SEQ ID NO: 187         moltype = AA  length = 18
FEATURE                Location/Qualifiers
REGION                 1..18
                       note = Synthetic polymer
source                 1..18
                       mol_type = protein
                       organism = synthetic construct
SEQUENCE: 187
ARDYRGIKDL DLKGDYDY                                            18

SEQ ID NO: 188         moltype = AA  length = 25
FEATURE                Location/Qualifiers
REGION                 1..25
                       note = Synthetic polymer
source                 1..25
                       mol_type = protein
                       organism = synthetic construct
SEQUENCE: 188
ADFNVWSPPI CGSIWYGPPP RGMDY                                    25
```

```
SEQ ID NO: 189          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 189
ADSNVWSPPI CGSRWYGPPP GGMAY                                            25

SEQ ID NO: 190          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 190
ADFNVWSPPI CGSNWYGPPP GGMDY                                            25

SEQ ID NO: 191          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 191
ADFNVWSPPI CGSIWYGPPP GGMDY                                            25

SEQ ID NO: 192          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 192
ADGNVWSPPI CGSAGPPPGG MDY                                              23

SEQ ID NO: 193          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 193
ARIITVATMR LDSDYDY                                                     17

SEQ ID NO: 194          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 194
ADGNVWSPPI CGSAGPPPGG MDY                                              23

SEQ ID NO: 195          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 195
ADSNVWSPPI CGRTWYGPPP GGMDY                                            25

SEQ ID NO: 196          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 196
```

```
ADFNVWSPPI CGSIWYGPPP GGMAY                                          25

SEQ ID NO: 197          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 197
ADFNVWSPPI CGSNWYGPPP GGMDY                                          25

SEQ ID NO: 198          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 198
ADFNVWSPPI CGSSWYGPPP GGMDY                                          25

SEQ ID NO: 199          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 199
ADFNVWSPPI CGSRWYGPPP GGMEY                                          25

SEQ ID NO: 200          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 200
ADGNVWSPPI CGSAGPPPGG MDY                                            23

SEQ ID NO: 201          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 201
ADFNVWSPPI CGSRWYGPPP GGMAY                                          25

SEQ ID NO: 202          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 202
ADGNVWSPPI CGSAGPPPGG MDY                                            23

SEQ ID NO: 203          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 203
ADSNVWSPPI CGKTWYGPPP GGMDY                                          25

SEQ ID NO: 204          moltype = AA  length = 13
FEATURE                 Location/Qualifiers
REGION                  1..13
                        note = Synthetic polymer
source                  1..13
                        mol_type = protein
                        organism = synthetic construct
```

SEQUENCE: 204
AGESGVWVGG LDY 13

SEQ ID NO: 205 moltype = AA length = 25
FEATURE Location/Qualifiers
REGION 1..25
note = Synthetic polymer
source 1..25
mol_type = protein
organism = synthetic construct
SEQUENCE: 205
ADSNVWSPPI CGSTWYGPPP GGMAY 25

SEQ ID NO: 206 moltype = AA length = 23
FEATURE Location/Qualifiers
REGION 1..23
note = Synthetic polymer
source 1..23
mol_type = protein
organism = synthetic construct
SEQUENCE: 206
ADGNVWSPPI CGSAGPPPGG MDY 23

SEQ ID NO: 207 moltype = AA length = 25
FEATURE Location/Qualifiers
REGION 1..25
note = Synthetic polymer
source 1..25
mol_type = protein
organism = synthetic construct
SEQUENCE: 207
ADFNVWSPPI CGSRWYGPPP GGMDY 25

SEQ ID NO: 208 moltype = AA length = 25
FEATURE Location/Qualifiers
REGION 1..25
note = Synthetic polymer
source 1..25
mol_type = protein
organism = synthetic construct
SEQUENCE: 208
ADFNVWSPPI CGSRWYGPPP GGMDY 25

SEQ ID NO: 209 moltype = AA length = 25
FEATURE Location/Qualifiers
REGION 1..25
note = Synthetic polymer
source 1..25
mol_type = protein
organism = synthetic construct
SEQUENCE: 209
ADFNVWSPPI CGSRWYGPPP GGMDY 25

SEQ ID NO: 210 moltype = AA length = 25
FEATURE Location/Qualifiers
REGION 1..25
note = Synthetic polymer
source 1..25
mol_type = protein
organism = synthetic construct
SEQUENCE: 210
ADFNVWSPPI CGSIWYGPPP GGMDY 25

SEQ ID NO: 211 moltype = AA length = 23
FEATURE Location/Qualifiers
REGION 1..23
note = Synthetic polymer
source 1..23
mol_type = protein
organism = synthetic construct
SEQUENCE: 211
ADGNVWSPPI CGSAGPPPGG MDY 23

SEQ ID NO: 212 moltype = AA length = 23
FEATURE Location/Qualifiers
REGION 1..23
note = Synthetic polymer
source 1..23
mol_type = protein

```
                        organism = synthetic construct
SEQUENCE: 212
ADFNVWSPPI CGSVGPPPGG MDY                                         23

SEQ ID NO: 213          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 213
ADFNVWSPPI CGSSWYGPPP GGMAY                                       25

SEQ ID NO: 214          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 214
AGESGVWVGG LDY                                                    13

SEQ ID NO: 215          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 215
ADFNVWSPPI CGSSWYGPPP GGMEY                                       25

SEQ ID NO: 216          moltype = AA  length = 23
FEATURE                 Location/Qualifiers
REGION                  1..23
                        note = Synthetic polymer
source                  1..23
                        mol_type = protein
                        organism = synthetic construct
SEQUENCE: 216
ADGNVWSPPI CGSAGPPPGG MDY                                         23

SEQ ID NO: 217          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 217
ADFNVWSPPI CSSNWYGPPP RGMDY                                       25

SEQ ID NO: 218          moltype = AA  length = 25
FEATURE                 Location/Qualifiers
REGION                  1..25
                        note = Synthetic polymer
source                  1..25
                        mol_type = protein
                        organism = synthetic construct
SEQUENCE: 218
ADFNVWSPPI CGSIWYGPPP RGMDY                                       25

SEQ ID NO: 219          moltype = AA  length = 146
FEATURE                 Location/Qualifiers
REGION                  1..146
                        note = Synthetic polymer
source                  1..146
                        mol_type = protein
                        organism = synthetic construct
SEQUENCE: 219
QVQLQESGGG LVQAGGSLRL SCAASGRSFS SYTLAWFRQA PGKEREFVAS ITWGGGNTYY  60
PDSVKGRFTI SRDDAKNTVY LQMNSLKPED TAVYYCAAKG LRNSDWDLRR GYEYDYWGQG  120
TQVTVSSAAA YPYDVPDYGS HHHHHH                                      146

SEQ ID NO: 220          moltype = AA  length = 152
FEATURE                 Location/Qualifiers
REGION                  1..152
```

```
                        note = Synthetic polymer
source                  1..152
                        mol_type = protein
                        organism = synthetic construct
SEQUENCE: 220
QVQLQESGGG LVQDGGSLRL SCAFSGRTFS SYTMGWFRQG PGKEREFVAA TVWTGAGTVY  60
ADSVKGRFTI SRDNAKNTVY LQMNSLRPED TAVYYCAADQ ASVPPPYGSE RYDIASPSEY  120
DYWGQGTQVT VSSAAAYPYD VPDYGSHHHH HH                                152

SEQ ID NO: 221          moltype = AA  length = 148
FEATURE                 Location/Qualifiers
REGION                  1..148
                        note = Synthetic polymer
source                  1..148
                        mol_type = protein
                        organism = synthetic construct
SEQUENCE: 221
QVQLQESGGG LVQAGASLRL SCAASGRTFS SYIMGWFRQA PGKEREFVAA IGWSADITVY  60
ADSVKGRFTI SRDNAENMVY LQMNSLNPED TAVYYCAANS RAYYSSSYDL GRLASYDYWG  120
QGTQVTVSSA AAYPYDVPDY GSHHHHHH                                     148

SEQ ID NO: 222          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 222
QVQLQESGGG LVQAGGSLRL SCAASGRTFS SYTMGWFRQA PGKEREFVAF IDWSGGGTYY  60
DDSVKGRFTI SRDNAENTVY LQMNNLEPED TAVYYCAAAQ RLGSVTDYTK YDYWGQGTQV  120
TVSSAAAYPY DVPDYGSHHH HHH                                          143

SEQ ID NO: 223          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 223
QVQLQESGGG LVQAGGSLRL SCAASGRTSG RTFSSYTMGW FRQAPGKERE FVATITWGGG  60
STYYADSVKG RFTISRDNAN NTVYLQMNSL KPEDTAVYYC AASVKVVAGS GIDISGSRNY  120
DYWGQGTQVT VSSAAAYPYD VPDYGSHHHH HH                                152

SEQ ID NO: 224          moltype = AA  length = 148
FEATURE                 Location/Qualifiers
REGION                  1..148
                        note = Synthetic polymer
source                  1..148
                        mol_type = protein
                        organism = synthetic construct
SEQUENCE: 224
QVQLQESGGG LVQPGGSLRL SCLASGRTFS SYAMGWFRQA PGKEREFVAA ISWSGGPTVY  60
ADHVKGRFTI SRDNAKNTVY LQVNSLKPED TADYYCAAKR LDYSATDKGV DLSDEYDYWG  120
QGTQVTVSSA AAYPYDVPDY GSHHHHHH                                     148

SEQ ID NO: 225          moltype = AA  length = 146
FEATURE                 Location/Qualifiers
REGION                  1..146
                        note = Synthetic polymer
source                  1..146
                        mol_type = protein
                        organism = synthetic construct
SEQUENCE: 225
QVQLQESGGG LVQAGDSLRL SCAASGLTFS NYIMGWFRQA PGKEREFVAA ITWGGGSTVY  60
ADSVEGRFTI SRDGTKNTVS LQMNSLLPED TAVYYCAAAG GSGRLRDLKV GQNYDYWGQG  120
TQVTVSSAAA YPYDVPDYGS HHHHHH                                       146

SEQ ID NO: 226          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 226
QVQLQESGGG LVQAGGSLRL SCAASGRTFS SYTMGWFRQA PGREREFVAA ITWSGVSTVY  60
TDSVKGRFTV SRDNAKNTVY LQMNSLKPED TAVYYCAADS PPRTYSSGSV NLEDGSEYDY  120
```

```
WGQGTQVTVS SAAAYPYDVP DYGSHHHHHH                            150

SEQ ID NO: 227          moltype = AA  length = 148
FEATURE                 Location/Qualifiers
REGION                  1..148
                        note = Synthetic polymer
source                  1..148
                        mol_type = protein
                        organism = synthetic construct
SEQUENCE: 227
QVQLQESGGG LVQAGGSLRL SCAASGRTFS SDTMGWFRQA PGKEREFVGA IMWSGAFTHY  60
ADSVKGRFTI SRDNAKNTVY LQMNALKPED TAVYYCAVIP GRGSALPIDV GKSDEYEYWG  120
QGTQVTVSSA AAYPYDVPDY GSHHHHHH                              148

SEQ ID NO: 228          moltype = AA  length = 146
FEATURE                 Location/Qualifiers
REGION                  1..146
                        note = Synthetic polymer
source                  1..146
                        mol_type = protein
                        organism = synthetic construct
SEQUENCE: 228
QVQLQESGGG LVQAGDSLRL SCAASGLTFS NYIMGWFRQA PGKEREFVAA ITWGGGSTVY  60
ADSVEGRFTI SRDGTKNTVS LQMNSLQPED TAVYYCAAAG ASGRLRDLKV GQNYDYWGQG  120
TQVTVSSAAA YPYDVPDYGS HHHHHH                                146

SEQ ID NO: 229          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 229
QVQLQESGGG LVQAGGSLRL SCAGSGFTLD YYGIGWFRQA PGKEREGVSC ISSSDRNTYY  60
ADSVKGRFTI SGDNAKNTVY LQMNNLKPED TAVYYCAADG NVWSPPICGS AGPPPGGMDY  120
WGKGTQVTVS SAAAYPYDVP DYGSHHHHHH                            150

SEQ ID NO: 230          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 230
QVQLQESGGG LVQAGGSLRL SCVASGHTFS SYTMGWFRQA PGKEREFVAF IDWSGGGTYY  60
ANSVKGRFTI SRDNAENTVY LQMNNLKPED TAVYYCAAAQ RLGSVTDYTK YDYWGQGTQV  120
TVSSAAAYPY DVPDYGSHHH HHH                                   143

SEQ ID NO: 231          moltype = AA  length = 149
FEATURE                 Location/Qualifiers
REGION                  1..149
                        note = Synthetic polymer
source                  1..149
                        mol_type = protein
                        organism = synthetic construct
SEQUENCE: 231
QVQLQESGGG LVQAGGSLRL SCAASGRTFS SYVIGWFRQA PGKEREFVAV ITWSGDSTYS  60
SDSLKGRFTI SRDNAKNTVY LQMNALNPED TAVYYCAAIP PRAYSGGSYS LKDQSKYEYW  120
GQGTQVTVSS AAAYPYDVPD YGSHHHHHH                             149

SEQ ID NO: 232          moltype = AA  length = 149
FEATURE                 Location/Qualifiers
REGION                  1..149
                        note = Synthetic polymer
source                  1..149
                        mol_type = protein
                        organism = synthetic construct
SEQUENCE: 232
QVQLQESGGG LVQAEGSLKL SCISGFAFDG YAIGWFRQAP GKEREGVACI SSKDGSTYYA  60
DSVKGRFTMS VDKTKNTVYL QMSSLKPEDT AVYYCAADGN VWSPPICSSA GPPPGGMDYW  120
GKGTQVTVSS AAAYPYDVPD YGSHHHHHH                             149

SEQ ID NO: 233          moltype = AA  length = 139
FEATURE                 Location/Qualifiers
REGION                  1..139
                        note = Synthetic polymer
source                  1..139
```

-continued

```
                         mol_type = protein
                         organism = synthetic construct
SEQUENCE: 233
QVQLQESGGG LVQPGGSLTL SCAASGFAFG FFDMTWVRQA PGKGLEWVSG INSIGGSTTY  60
ADSVKGRFTI SRDNAKNELY LQMNSLKPDD TAVYYCAKSR SSYSNNWRPP GQGTQVTVSS  120
AAAYPYDVPD YGSHHHHHH                                              139

SEQ ID NO: 234           moltype = AA  length = 149
FEATURE                  Location/Qualifiers
REGION                   1..149
                         note = Synthetic polymer
source                   1..149
                         mol_type = protein
                         organism = synthetic construct
SEQUENCE: 234
QVQLQESGGG LVQARGSLTL SCAASGRTFS NYVIGWFRQA PGEEREFVAV VTWSGDSTYS  60
SDSLKGRFTI SRDNAKNTVY LQMNNLNPED TAVYYCAAMP PRAYTGRSVS LKDQSKYEYW  120
GQGTQVTVSS AAAYPYDVPD YGSHHHHHH                                   149

SEQ ID NO: 235           moltype = AA  length = 139
FEATURE                  Location/Qualifiers
REGION                   1..139
                         note = Synthetic polymer
source                   1..139
                         mol_type = protein
                         organism = synthetic construct
SEQUENCE: 235
QVQLQESGGG LVQPGGSLRL SCAASGSIFS INVMGWYRQT PGKERELVAK ITNFGITSYA  60
DSAQGRFTIS RGNAKNTVYL QMNSLKPEDT AVYYCNLDTT GWGPPPYQYW GQGTQVTVSS  120
AAAYPYDVPD YGSHHHHHH                                              139

SEQ ID NO: 236           moltype = AA  length = 149
FEATURE                  Location/Qualifiers
REGION                   1..149
                         note = Synthetic polymer
source                   1..149
                         mol_type = protein
                         organism = synthetic construct
SEQUENCE: 236
QVQLQESGGG LVQAGASLRL SCAASGRTFS NYNVGWFRQA PGKEREFVSF ISWISDITYY  60
SDSVKGRFII SRDNAKNMVY LQMNSLKPED TAVYYCAAHP PDPSRGGEWR LQTPSEYDYW  120
GQGTQVTVSS AAAYPYDVPD YGSHHHHHH                                   149

SEQ ID NO: 237           moltype = AA  length = 143
FEATURE                  Location/Qualifiers
REGION                   1..143
                         note = Synthetic polymer
source                   1..143
                         mol_type = protein
                         organism = synthetic construct
SEQUENCE: 237
QVQLQESGGG LVQAGGSLRL SCAASGHTFS SYTMGWFRQA PGKEREFVAF IDWSGGGTYY  60
ADSVKGRFTI SRDNAENTVY LQMNNLKPED TAVYYCAAAQ RLGSVTDYTK YDYWGQGTQV  120
TVSSAAAYPY DVPDYGSHHH HHH                                         143

SEQ ID NO: 238           moltype = AA  length = 151
FEATURE                  Location/Qualifiers
REGION                   1..151
                         note = Synthetic polymer
source                   1..151
                         mol_type = protein
                         organism = synthetic construct
SEQUENCE: 238
QVQLQESGGG LVQAGGSLRL SCAASGRTFS TYPVGWFRQA PGKEREFVAV ILWSGVSTYY  60
ADSVKGRFTI SRDNAQNTVY LQMDSLKPED TAVYYCAVPR SHFTTAQDMG QDMGAPSWYE  120
YWGQGTQVTV SSAAAYPYDV PDYGSHHHHH H                                151

SEQ ID NO: 239           moltype = AA  length = 149
FEATURE                  Location/Qualifiers
REGION                   1..149
                         note = Synthetic polymer
source                   1..149
                         mol_type = protein
                         organism = synthetic construct
SEQUENCE: 239
QVQLQESGGG LVQAGGSLRL SCAASGRTFS NYAMGWFRQA PGKEREFVAA IVWSGGSTYY  60
ADSVKGRFTI SRDNAKNTVY LQMNSLKPED TAVYYCAAVL IRYYSGGYQG LSDANEYDYW  120
GQGTQVTVSS AAAYPYDVPD YGSHHHHHH                                   149
```

-continued

```
SEQ ID NO: 240          moltype = AA  length = 144
FEATURE                 Location/Qualifiers
REGION                  1..144
                        note = Synthetic polymer
source                  1..144
                        mol_type = protein
                        organism = synthetic construct
SEQUENCE: 240
QVQLQESGGG LVQAGASLRL SCSASGRTFS DYRMGWFRQA PGKEREWVAA ISSSGYHTYY  60
ADSVKGRFTI SRDNAKNTGY LQMSSLKPED TAVYYCAVVK YLSGSYSYAG QYNFWGQGTQ  120
VTVSSAAAYP YDVPDYGSHH HHHH                                        144

SEQ ID NO: 241          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 241
QVQLQESGGG LVQAGDSLKL SCAASGLTFS NYIMAWFRQA PGKEREGVSC ISSPDGSTYY  60
ADSVKGRFTI SSDNAKNTVY LQMNSLKPED TAVYYCAADF NVWSPPICGS VGPPPGGMDY  120
WGKGTQVTVS SAAAYPYDVP DYGSHHHHHH                                  150

SEQ ID NO: 242          moltype = AA  length = 148
FEATURE                 Location/Qualifiers
REGION                  1..148
                        note = Synthetic polymer
source                  1..148
                        mol_type = protein
                        organism = synthetic construct
SEQUENCE: 242
QVQLQESGGG LVQAGGSLRL SCAASGRTFS NSVMGWFRQP PGKEREFVAA VLWSGVSTAY  60
ADSVKGRFTI SRDNAKNTVY LQMNNLKPDD TAVYYCAAHE STYYSGTYYL TDPRRYVYWG  120
QGTQVTVSSA AAYPYDVPDY GSHHHHHH                                    148

SEQ ID NO: 243          moltype = AA  length = 146
FEATURE                 Location/Qualifiers
REGION                  1..146
                        note = Synthetic polymer
source                  1..146
                        mol_type = protein
                        organism = synthetic construct
SEQUENCE: 243
QVQLQESGGG LVQAGGSLRL SCVGDGRTFS SYIIGWFRQA PGNEREFVVA ITWDGSATTY  60
ADSVKGRFTV SRDSAKNTAY LQMNSLKPED TAVYYCAAVP ARGLTMDLEN SDIYDHWGRG  120
TQVTVSSAAA YPYDVPDYGS HHHHHH                                      146

SEQ ID NO: 244          moltype = AA  length = 149
FEATURE                 Location/Qualifiers
REGION                  1..149
                        note = Synthetic polymer
source                  1..149
                        mol_type = protein
                        organism = synthetic construct
SEQUENCE: 244
QVQLQESGGG LVQAGGSLRL SCAASGRTFS SYVMGWFRQA LGKEREFVAA IGWNGGITYY  60
ADSVKGRFAI SRDNAKNTVY LQMNSLKPED TAVYYCAAAT LQVTGSYYLD LSTVDIYDNW  120
GQGTQVTVSS AAAYPYDVPD YGSHHHHHH                                   149

SEQ ID NO: 245          moltype = AA  length = 147
FEATURE                 Location/Qualifiers
REGION                  1..147
                        note = Synthetic polymer
source                  1..147
                        mol_type = protein
                        organism = synthetic construct
SEQUENCE: 245
QVQLQESGGG LVQAGGSLRL SCAASGGTFS NYVMGWFRQA PGKEREFVGF ITWSGASTYY  60
ADSVKGRFTI SRDNAENTVY LQMNSLKPED TAVYYCAATL FRSNGPKDLS SGYEYDYWGQ  120
GTQVTVSSAA AYPYDVPDYG SHHHHHH                                     147

SEQ ID NO: 246          moltype = AA  length = 140
FEATURE                 Location/Qualifiers
REGION                  1..140
                        note = Synthetic polymer
SITE                    112
                        note = misc_feature - Xaa can be any naturally occurring
                         amino acid
```

```
source                  1..140
                        mol_type = protein
                        organism = synthetic construct
SEQUENCE: 246
QVQLQESGGG LVQAGDSLRL TCTASGRTFS NYGIGWFRQA PGKEREFVAG INWSGESADY  60
ADSVKGRFTI SRDNAKNTVY LQMNSLKPED TAVYYCAAGE SGVWVGGLDY WXQGTQVTVS  120
SAAAYPYDVP DYGSHHHHHH                                              140

SEQ ID NO: 247          moltype = AA  length = 149
FEATURE                 Location/Qualifiers
REGION                  1..149
                        note = Synthetic polymer
source                  1..149
                        mol_type = protein
                        organism = synthetic construct
SEQUENCE: 247
QVQLQESGGG LVQAGGSLRL SCAASGFTFD DYAIAWFRQA PGKEREGVSC IERSDGSTYY  60
ADSVKGRFTI SSDNAKNTVY LQMNSLKPED TAVYYCAVGS ANSGEFRFGW VLKPDLYNYW  120
GQGTQVTVSS AAAYPYDVPD YGSHHHHHH                                    149

SEQ ID NO: 248          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 248
QVQLQESGGG LVQAGGSLRL SCTASGRTFS SYTVAWFRQS PGKEREGISC ISNTDSSTYY  60
ADSVKGRFTI SSDNAKSTVH LQMSSLKPED TAVYYCAADG NVWSPPICGS AGPPPGGMDY  120
WGKGTQVTVS SAAAYPYDVP DYGSHHHHHH                                   150

SEQ ID NO: 249          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 249
QVQLQESGGG LVQPGGSLRL SCATFGFPFD DYAIAWFRQA PGKEREGVSC ISNTDSSTYY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH                                   150

SEQ ID NO: 250          moltype = AA  length = 147
FEATURE                 Location/Qualifiers
REGION                  1..147
                        note = Synthetic polymer
source                  1..147
                        mol_type = protein
                        organism = synthetic construct
SEQUENCE: 250
QVQLQESGGG LVQAGGSLRL SCAASGRTFS SYVMGWFRQA PGKEREFVAQ ISWSAGSIYY  60
ADSVKGRFTI SNDNAKRTVY LQMNSLKPED TAVYYCAERG YAYCSDDGCQ RTQDYDYWGQ  120
GTQVTVSSAA AYPYDVPDYG SHHHHHH                                      147

SEQ ID NO: 251          moltype = AA  length = 148
FEATURE                 Location/Qualifiers
REGION                  1..148
                        note = Synthetic polymer
source                  1..148
                        mol_type = protein
                        organism = synthetic construct
SEQUENCE: 251
QVQLQESGGG LVQAGGSLRL SCAASGRTLS SNPMAWFRQA AGKEREFVAG MSWNPGPAVY  60
ADSVKGRFTI SRDSAENTVY LQMNSLKPED TAVYYCAGAA RAWWSGSYDY TRMNNYDYWG  120
PGTQVTVSSA AAYPYDVPDY GSHHHHHH                                     148

SEQ ID NO: 252          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 252
QVQLQESGGG LVQAGGSLRL SCAVSGFTFD NYAIGWFRQA PGKEREGVSC ISRSDGSTYY  60
ADSVRGRFTI SSDNAKNTVY LQMNSLKPED TAVYYCAAET SADSGEFRFG WVLKPSLYDY  120
WGQGTQVTVS SAAAYPYDVP DYGSHHHHHH                                   150
```

-continued

```
SEQ ID NO: 253         moltype = AA  length = 148
FEATURE                Location/Qualifiers
REGION                 1..148
                       note = Synthetic polymer
source                 1..148
                       mol_type = protein
                       organism = synthetic construct
SEQUENCE: 253
QVQLQESGGG LVQAGGSLRL SCAASGRAFS SYFMGWFRQT PGKEREFVAN IGWTGDMTYY  60
ADSVKGRFTI SRDNAKNTVY LQMNSLKPED TAVYYCAAAG SAYSGSYWNI TMAANYDYWG  120
QGTQVTVSSA AAYPYDVPDY GSHHHHHH                                     148

SEQ ID NO: 254         moltype = AA  length = 145
FEATURE                Location/Qualifiers
REGION                 1..145
                       note = Synthetic polymer
source                 1..145
                       mol_type = protein
                       organism = synthetic construct
SEQUENCE: 254
QVQLQESGGG LVQAGGSLRL SCAASTPTFS SYNMGWFRQA PGKEREFVAA IIWSGSMTYY  60
ADSMKGRFTV SIDNAKNTVY LQMNSLKPED TAVYYCAAQR IFGAQPMDLS GDYEYWGQGT  120
QVTVSSAAAY PYDVPDYGSH HHHHH                                        145

SEQ ID NO: 255         moltype = AA  length = 150
FEATURE                Location/Qualifiers
REGION                 1..150
                       note = Synthetic polymer
source                 1..150
                       mol_type = protein
                       organism = synthetic construct
SEQUENCE: 255
QVQLQESGGG LVQAGGSLRL SCATFGFTFD DYAIAWFRQA PGKEREGISC ISNTDSSTYY  60
ADSVKGRFTI SSDSAKNTVH LQMSSLKPED TAVYYCAADG NVWSPPICGS AGPPPGGMDY  120
WGKGTQVTVS SAAAYPYDVP DYGSHHHHHH                                   150

SEQ ID NO: 256         moltype = AA  length = 145
FEATURE                Location/Qualifiers
REGION                 1..145
                       note = Synthetic polymer
source                 1..145
                       mol_type = protein
                       organism = synthetic construct
SEQUENCE: 256
QVQLQESGGG LVQAGGSLRL SCKASGGTFS GYIMGWFRQA PGKEREFVAA NTWSGGPTYY  60
SDSVKGRFTI SRDNAKNTVY LQMNTLKPED TAVYQCAARD YRGIKDLDLK GDYDYWGQGT  120
QVTVSSAAAY PYDVPDYGSH HHHHH                                        145

SEQ ID NO: 257         moltype = AA  length = 151
FEATURE                Location/Qualifiers
REGION                 1..151
                       note = Synthetic polymer
source                 1..151
                       mol_type = protein
                       organism = synthetic construct
SEQUENCE: 257
QVQLQESGGG LVQAGDSLKL SCATSGRSFS SYTIAWFRQA PGKEREGISC ISSDGSTGYA  60
DSVRGRFTIS SDNAKNTVYL QMNSLKPEDT AVYYCAADFN VWSPPICGSI WYGPPPRGMD  120
YWGKGTQVTV SSAAAYPYDV PDYGSHHHHH H                                 151

SEQ ID NO: 258         moltype = AA  length = 152
FEATURE                Location/Qualifiers
REGION                 1..152
                       note = Synthetic polymer
source                 1..152
                       mol_type = protein
                       organism = synthetic construct
SEQUENCE: 258
QVQLQESGGG LVQAGGYLRL SCAASGFSSD DYTIGWFRQA PGKEREGISC YSSSDGSTGF  60
ADSVKGRFTI SSDNAKNTVY LQMNNLRPED TAVYYCAADS NVWSPPICGS RWYGPPPGGM  120
AYWGKGTQVT VSSAAAYPYD VPDYGSHHHH HH                                152

SEQ ID NO: 259         moltype = AA  length = 151
FEATURE                Location/Qualifiers
REGION                 1..151
                       note = Synthetic polymer
source                 1..151
                       mol_type = protein
```

```
                        organism = synthetic construct
SEQUENCE: 259
QVQLQESGGG LAQVGGSLRL SCTASGFTFD DYTIGWFRQA PGKEREGISC ISSDGSTGYA  60
DSVKGRFTIS SDNAKNTVYL QMNSLKPEDT AVYYCAADFN VWSPPICGSN WYGPPPGGMD  120
YWGKGTQVTV SSAAAYPYDV PDYGSHHHHH H                                151

SEQ ID NO: 260          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 260
QVQLQESGGG LVQAGGSLRL SCAASGFSSD DYTIGWFRQA PGKEREGIGC IKSSDGTTGY  60
ADSVKGRFTI SSDNAKNTVY LQMNSLKPED TAVYYCAADF NVWSPPICGS IWYGPPPGGM  120
DYWGKGTQVT VSSAAAYPYD VPDYGSHHHH HH                               152

SEQ ID NO: 261          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 261
QVQLQESGGG LAQAGGSLRL SCAASGFTFD QYTIAWFRQA PGKEREGVSC ISNTDSSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH                                  150

SEQ ID NO: 262          moltype = AA  length = 144
FEATURE                 Location/Qualifiers
REGION                  1..144
                        note = Synthetic polymer
source                  1..144
                        mol_type = protein
                        organism = synthetic construct
SEQUENCE: 262
QVQLQESGGG LVQAGGSLRL SCAASGRTFS SYAMAWFRQA PGKEREFVAA IAWSAGSTYY  60
ADSVKGRFAI SRDNAENTVY LQMNSLKPED TAVYYCAARI ITVATMRLDS DYDYWGQGTQ  120
VTVSSAAAYP YDVPDYGSHH HHHH                                        144

SEQ ID NO: 263          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 263
QVQLQESGGG LVQAGGSLRL SCAASGFAFD GYAIGWFRQA PGKEREGVSC ISSKEGSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH                                  150

SEQ ID NO: 264          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 264
QVQLQESGGG LVQAGGSLRL SCAASGFSSD DYTIAWFRRA PGKEREGISC ISSSDGSTGY  60
ADSVKGRFTI TSDSAKNTVY LQMNSLKPED TAVYYCAADS NVWSPPICGR TWYGPPPGGM  120
DYWGKGTQVT VSSAAAYPYD VPDYGSHHHH HH                               152

SEQ ID NO: 265          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 265
QVQLQESGGG LVQPGGSLRL SCAASGFSSD DYTIGWFRQA PGKEREGISC YSSRDGTTGY  60
ADSVKGRFTI SSDNAKNTVY LQMNSLKPED TAVYYCAADF NVWSPPICGS IWYGPPPGGM  120
AYWGQGTQVT VSSAAAYPYD VPDYGSHHHH HH                               152

SEQ ID NO: 266          moltype = AA  length = 151
```

```
FEATURE                 Location/Qualifiers
REGION                  1..151
                        note = Synthetic polymer
source                  1..151
                        mol_type = protein
                        organism = synthetic construct
SEQUENCE: 266
QVQLQESGGG LVQAGGSLRL SCAASGFTFD DYTIGWFRQA PGKEREGISC ISSDGSTGYA  60
DSVKGRFTIS SDNAKNTVYL QMNSLKPEDT AVYYCAADFN VWSPPICGSN WYGPPPGGMD  120
YWGKGTQVTV SSAAAYPYDV PDYGSHHHHH H                                 151

SEQ ID NO: 267          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 267
QVQLQESGGG LVQAGGSLRL SCAASGFSSD DYTIGWFRQA PGKEREGISC YSSSDGSTGY  60
ADSVKGRFTI SSDNAKNTVY LQMNSLKPED TAVYYCAADF NVWSPPICGS SWYGPPPGGM  120
DYWGKGTQVT VSSAAAYPYD VPDYGSHHHH HH                                152

SEQ ID NO: 268          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 268
QVQLQESGGG LVQAGGSLRL SCAASGFSSD DYTIGWFRQA PGKEREGISC FSSSDGSTGF  60
ADSVKGRFTI SSDNATNTVY LEMNSLKPED TAVYYCAADF NVWSPPICGS RWYGPPPGGM  120
EYWGKGTQVT VSSAAAYPYD VPDYGSHHHH HH                                152

SEQ ID NO: 269          moltype = AA  length = 150
FEATURE                 Location/Qualifiers
REGION                  1..150
                        note = Synthetic polymer
source                  1..150
                        mol_type = protein
                        organism = synthetic construct
SEQUENCE: 269
QVQLQESGGG LVQAGGSLRL SCATFGFSFD DYAIAWFRQA PGKEREGISC ISNTDSSTFY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH                                   150

SEQ ID NO: 270          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 270
QVQLQESGGG LVQAGGSLRL SCAASGFSSD DYTIGWFRQA PGKEREGISC YSSSDGSTGF  60
ADSVKGRFTI SSDNAKNTVY LQMNSLRPED TAVYYCAADF NVWSPPICGS RWYGPPPGGM  120
AYWGKGTQVT VSSAAAYPYD VPDYGSHHHH HH                                152

SEQ ID NO: 271          moltype = AA  length = 151
FEATURE                 Location/Qualifiers
REGION                  1..151
                        note = Synthetic polymer
source                  1..151
                        mol_type = protein
                        organism = synthetic construct
SEQUENCE: 271
QVQLQESGGG LVQVGGSLRL SCTISGFTGN DLAIGWFRQA PGKDQREGIS CISNTDSSTY  60
YADSVKGRFT ISSDNAKNTV HLQMSSLKPE DTAVYYCAAD GNVWSPPICG SAGPPPGGMD  120
YWGKGTQVTV SSAAAYPYDV PDYGSHHHHH H                                 151

SEQ ID NO: 272          moltype = AA  length = 152
FEATURE                 Location/Qualifiers
REGION                  1..152
                        note = Synthetic polymer
source                  1..152
                        mol_type = protein
                        organism = synthetic construct
SEQUENCE: 272
```

-continued

```
QVQLQESGGG LVQAGGSLRL SCAASGFSSD DYTIAWFRRA PGKEREGISC ISSSDGSTGY  60
ADSVKGRFTI SSDNAKNTVY LQMTSLKPED TAVYYCAADS NVWSPPICGK TWYGPPPGGM  120
DYWGKGTQVT VSSAAAYPYD VPDYGSHHHH HH                                152

SEQ ID NO: 273         moltype = AA  length = 140
FEATURE                Location/Qualifiers
REGION                 1..140
                       note = Synthetic polymer
source                 1..140
                       mol_type = protein
                       organism = synthetic construct
SEQUENCE: 273
QVQLQESGGG LVQAGDSLRL SCAGSEGTLS SYGIGWFRQA PGKEREFVGG INWSGDSTDY  60
ADSVKGRFTI SRDSAKNTVY LQMNSLKPED TAVYYCAAGE SGVWVGGLDY WGQGTQVTVS  120
SAAAYPYDVP DYGSHHHHHH                                              140

SEQ ID NO: 274         moltype = AA  length = 152
FEATURE                Location/Qualifiers
REGION                 1..152
                       note = Synthetic polymer
source                 1..152
                       mol_type = protein
                       organism = synthetic construct
SEQUENCE: 274
QVQLQESGGG LVQAGGSLRL SCAASGFSSD DYTIAWFRRA PGKEREGISC FSSSDGSAGY  60
ADSVKGRFTV SSDNAKNTVY LQMNSLKPED TAVYYCAADS NVWSPPICGS TWYGPPPGGM  120
AYWGKGTQVT VSSAAAYPYD VPDYGSHHHH HH                                152

SEQ ID NO: 275         moltype = AA  length = 150
FEATURE                Location/Qualifiers
REGION                 1..150
                       note = Synthetic polymer
source                 1..150
                       mol_type = protein
                       organism = synthetic construct
SEQUENCE: 275
QVQLQESGGG LVQAGGSLRL SCATSGFTFD DYAIAWFRQA PGKEREGVSC ISNTDSSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH                                   150

SEQ ID NO: 276         moltype = AA  length = 152
FEATURE                Location/Qualifiers
REGION                 1..152
                       note = Synthetic polymer
source                 1..152
                       mol_type = protein
                       organism = synthetic construct
SEQUENCE: 276
QVQLQESGGG LVQAGGSLRL SCEVSGLSSD DYTIGWFRQA PGKEREGFSC FSTRDGNAGY  60
ADSVKGRFTI SSDNAKNTVY LQMNNLKPED TAVYYCAADF NVWSPPICGS RWYGPPPGGM  120
DYWGKGTQVT VSSAAAYPYD VPDYGSHHHH HH                                152

SEQ ID NO: 277         moltype = AA  length = 152
FEATURE                Location/Qualifiers
REGION                 1..152
                       note = Synthetic polymer
source                 1..152
                       mol_type = protein
                       organism = synthetic construct
SEQUENCE: 277
QVQLQESGGG LVQAGGSLRL SCEVSGLSSD DYTIGWFRQA PGKKREGFSC FSSRDGSTGY  60
ADSVKGRFTI SSDNAKNTVY LQMNSLKPED TAVYYCAADF NVWSPPICGS RWYGPPPGGM  120
DYWGKGTQVT VSSAAAYPYD VPDYGSHHHH HH                                152

SEQ ID NO: 278         moltype = AA  length = 152
FEATURE                Location/Qualifiers
REGION                 1..152
                       note = Synthetic polymer
source                 1..152
                       mol_type = protein
                       organism = synthetic construct
SEQUENCE: 278
QVQLQESGGG LVQAGGSLRL SCAASGFSSD DYTIGWFRQA PGKEREGFSC FSSRDGSTGY  60
ADSVKGRFTI SSDNAKNTVY LQMNSLKPED TAVYYCAADF NVWSPPICGS RWYGPPPGGM  120
DYWGKGTQVT VSSAAAYPYD VPDYGSHHHH HH                                152

SEQ ID NO: 279         moltype = AA  length = 151
FEATURE                Location/Qualifiers
REGION                 1..151
```

```
                         note = Synthetic polymer
source                   1..151
                         mol_type = protein
                         organism = synthetic construct
SEQUENCE: 279
QVQLQESGGG LVQAGGSLRL SCAASGFSFD DYTIGWFRQV PGKEREGISC ISSDGSTGYA  60
DSVKGRFTIS SDNAKNTVYL QINSLKPEDT AVYYCAADFN VWSPPICGSI WYGPPPGGMD  120
YWGKGTQVTV SSAAAYPYDV PDYGSHHHHH H                                 151

SEQ ID NO: 280           moltype = AA  length = 150
FEATURE                  Location/Qualifiers
REGION                   1..150
                         note = Synthetic polymer
source                   1..150
                         mol_type = protein
                         organism = synthetic construct
SEQUENCE: 280
QVQLQESGGG LVQAGGSLRL SCATFGFTFD DYAIAWFRQA PGKEREGISC ISNTDSSTYY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH                                   150

SEQ ID NO: 281           moltype = AA  length = 150
FEATURE                  Location/Qualifiers
REGION                   1..150
                         note = Synthetic polymer
SITE                     19
                         note = misc_feature - Xaa can be any naturally occurring
                          amino acid
source                   1..150
                         mol_type = protein
                         organism = synthetic construct
SEQUENCE: 281
QVQLQESGGG LVQAGGSLXL SCAASGFTFD DYAIGWFRQA PGKEREGVSC ISSPDGSTYY  60
ADSVKGRFTI SSDNAKNTVY LQMNSLKPED TAVYYCAADF NVWSPPICGS VGPPPGGMDY  120
WGKGTQVTVS SAAAYPYDVP DYGSHHHHHH                                   150

SEQ ID NO: 282           moltype = AA  length = 152
FEATURE                  Location/Qualifiers
REGION                   1..152
                         note = Synthetic polymer
source                   1..152
                         mol_type = protein
                         organism = synthetic construct
SEQUENCE: 282
QVQLQESGGG LVQAGASLRL SCKASGFTFG DYTIGWFRQA PGKEREGISC YSSSDGNTGY  60
ADSVKGRFTI SSDNAKNTVY LQMNSLRPED TAVYYCAADF NVWSPPICGS SWYGPPPGGM  120
AYWGKGTQVT VSSAAAYPYD VPDYGSHHHH HH                                152

SEQ ID NO: 283           moltype = AA  length = 140
FEATURE                  Location/Qualifiers
REGION                   1..140
                         note = Synthetic polymer
source                   1..140
                         mol_type = protein
                         organism = synthetic construct
SEQUENCE: 283
QVQLQESGGG LVQAGDSLRL SCAGSEGTFS SYGIGWFRQA PGKEREFVGG INWSGDSTDY  60
ADSVKGRFTI SRDNAKNTVY LQMNSLKPED TAVYYCAAGE SGVWVGGLDY WGQGTQVTVS  120
SAAAYPYDVP DYGSHHHHHH                                              140

SEQ ID NO: 284           moltype = AA  length = 152
FEATURE                  Location/Qualifiers
REGION                   1..152
                         note = Synthetic polymer
source                   1..152
                         mol_type = protein
                         organism = synthetic construct
SEQUENCE: 284
QVQLQESGGG LVQAGGSLRL SCAASGFSSD DYTIGWFRQA PGKEREGISC FSSSDGSTGF  60
ADSVKGRFTI SSDNATNTVY LQMNSLKPED TAVYYCAADF NVWSPPICGS SWYGPPPGGM  120
EYWGKGTQVT VSSAAAYPYD VPDYGSHHHH HH                                152

SEQ ID NO: 285           moltype = AA  length = 150
FEATURE                  Location/Qualifiers
REGION                   1..150
                         note = Synthetic polymer
source                   1..150
                         mol_type = protein
                         organism = synthetic construct
```

-continued

```
SEQUENCE: 285
QVQLQESGGG LVQAGDSLRL SCTASGVSIG DYNIGWFRQA PGKEREGVSC ISSGDGTTYY  60
TDSVKGRFTI STDNAKNTVY LQMNSLKPED TAVYYCAADG NVWSPPICGS AGPPPGGMDY  120
WGKGTQVTVS SAAAYPYDVP DYGSHHHHHH                                   150

SEQ ID NO: 286         moltype = AA  length = 152
FEATURE                Location/Qualifiers
REGION                 1..152
                       note = Synthetic polymer
source                 1..152
                       mol_type = protein
                       organism = synthetic construct
SEQUENCE: 286
QVQLQESGGG LVQAGGSLRL SCAASGFTFD DYTIAWFRQA PGGKEREGIS CISSDGSTGY  60
ADSVKGRFTI SSDNAKNMVY LQMNSLKPED TALYYCAADF NVWSPPICSS NWYGPPPRGM  120
DYWGKGTQVT VSSAAAYPYD VPDYGSHHHH HH                                152

SEQ ID NO: 287         moltype = AA  length = 151
FEATURE                Location/Qualifiers
REGION                 1..151
                       note = Synthetic polymer
source                 1..151
                       mol_type = protein
                       organism = synthetic construct
SEQUENCE: 287
QVQLQESGGG LVQAGGSLRL SCAASGFTFD DYTIAWFRQA PGKEREGISC ISSDGSTGYA  60
DSVRGRFTIS SDNAKNTVYL QMNSLKPEDT AVYYCAADFN VWSPPICGSI WYGPPPRGMD  120
YWGKGTQVTV SSAAAYPYDV PDYGSHHHHH H                                 151

SEQ ID NO: 288         moltype = AA  length = 165
FEATURE                Location/Qualifiers
REGION                 1..165
                       note = Synthetic polymer
source                 1..165
                       mol_type = protein
                       organism = synthetic construct
SEQUENCE: 288
CDLPQTHSLG SRRTLMLLAQ MRKISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 289         moltype = AA  length = 165
FEATURE                Location/Qualifiers
REGION                 1..165
                       note = Synthetic polymer
source                 1..165
                       mol_type = protein
                       organism = synthetic construct
SEQUENCE: 289
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 290         moltype = AA  length = 166
FEATURE                Location/Qualifiers
REGION                 1..166
                       note = Synthetic polymer
source                 1..166
                       mol_type = protein
                       organism = synthetic construct
SEQUENCE: 290
MSYNLLGFLQ RSSNFQCQKL LWQLNGRLEY CLKDRMNFDI PEEIKQLQQF QKEDAALTIY  60
EMLQNIFAIF RQDSSSTGWN ETIVENLLAN VYHQINHLKT VLEEKLEKED FTRGKLMSSL  120
HLKRYYGRIL HYLKAKEYSH CAWTIVRVEI LRNFYFINRL TGYLRN                 166

SEQ ID NO: 291         moltype = AA  length = 165
FEATURE                Location/Qualifiers
REGION                 1..165
                       note = Synthetic polymer
source                 1..165
                       mol_type = protein
                       organism = synthetic construct
SEQUENCE: 291
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRC DKPRR                  165

SEQ ID NO: 292         moltype = AA  length = 165
FEATURE                Location/Qualifiers
```

```
REGION                  1..165
                        note = Synthetic polymer
source                  1..165
                        mol_type = protein
                        organism = synthetic construct
SEQUENCE: 292
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRS LTRKD                  165

SEQ ID NO: 293          moltype = AA  length = 157
FEATURE                 Location/Qualifiers
REGION                  1..157
                        note = Synthetic polymer
source                  1..157
                        mol_type = protein
                        organism = synthetic construct
SEQUENCE: 293
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL  120
GGVFQLEKGD RLSAEINRPD YLDFAESGQV YFGIIAL                           157

SEQ ID NO: 294          moltype = AA  length = 171
FEATURE                 Location/Qualifiers
REGION                  1..171
                        note = Synthetic polymer
source                  1..171
                        mol_type = protein
                        organism = synthetic construct
SEQUENCE: 294
LPGVGLTPSA AQTARQHPKM HLAHSNLKPA AHLIGDPSKQ NSLLWRANTD RAFLQDGFSL  60
SNNSLLVPTS GIYFVYSQVV FSGKAYSPKA TSSPLYLAHE VQLFSSQYPF HVPLLSSQKM  120
VYPGLQEPWL HSMYHGAAFQ LTQGDQLSTH TDGIPHLVLS PSTVFFGAFA L            171

SEQ ID NO: 295          moltype = AA  length = 281
FEATURE                 Location/Qualifiers
REGION                  1..281
                        note = Synthetic polymer
source                  1..281
                        mol_type = protein
                        organism = synthetic construct
SEQUENCE: 295
MAMMEVQGGP SLGQTCVLIV IFTVLLQSLC VAVTYVYFTN ELKQMQDKYS KSGIACFLKE  60
DDSYWDPNDE ESMNSPCWQV KWQLRQLVRK MILRTSEETI STVQEKQQNI SPLVRERGPQ  120
RVAAHITGTR GRSNTLSSPN SKNEKALGRK INSWESSRSG HSFLSNLHLR NGELVIHEKG  180
FYYIYSQTYF RFQEEIKENT KNDKQMVQYI YKYTSYPDPI LLMKSARNSC WSKDAEYGLY  240
SIYQGGIFEL KENDRIFVSV TNEHLIDMDH EASFFGAFLV G                      281

SEQ ID NO: 296          moltype = AA  length = 153
FEATURE                 Location/Qualifiers
REGION                  1..153
                        note = Synthetic polymer
source                  1..153
                        mol_type = protein
                        organism = synthetic construct
SEQUENCE: 296
APVRSLNCTL RDSQQKSLVM SGPYELKALH LQGQDMEQQV VFSMSFVQGE ESNDKIPVAL  60
GLKEKNLYLS CVLKDDKPTL QLESVDPKNY PKKKMEKRFV FNKIEINNKL EFESAQFPNW  120
YISTSQAENM PVFLGGTKGG QDITDFTMQF VSS                               153

SEQ ID NO: 297          moltype = AA  length = 133
FEATURE                 Location/Qualifiers
REGION                  1..133
                        note = Synthetic polymer
source                  1..133
                        mol_type = protein
                        organism = synthetic construct
SEQUENCE: 297
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 298          moltype = AA  length = 129
FEATURE                 Location/Qualifiers
REGION                  1..129
                        note = Synthetic polymer
source                  1..129
                        mol_type = protein
                        organism = synthetic construct
```

-continued

```
SEQUENCE: 298
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
REKYSKCSS                                                          129

SEQ ID NO: 299         moltype = AA  length = 185
FEATURE                Location/Qualifiers
REGION                 1..185
                       note = Synthetic polymer
source                 1..185
                       mol_type = protein
                       organism = synthetic construct
SEQUENCE: 299
APVPPGEDSK DVAAPHRQPL TSSERIDKQI RYILDGISAL RKETCNKSNM CESSKEALAE  60
NNLNLPKMAE KDGCFQSGFN EETCLVKIIT GLLEFEVYLE YLQNRFESSE EQARAVQMST  120
KVLIQFLQKK AKNLDAITTP DPTTNASLTT KLQAQNQWLQ DMTTHLILRS FKEFLQSSLR  180
ALRQM                                                              185

SEQ ID NO: 300         moltype = AA  length = 114
FEATURE                Location/Qualifiers
REGION                 1..114
                       note = Synthetic polymer
source                 1..114
                       mol_type = protein
                       organism = synthetic construct
SEQUENCE: 300
SPGPVPPSTA LRELIEELVN ITQNQKAPLC NGSMVWSINL TAGMYCAALE SLINVSGCSA  60
IEKTQRMLSG FCPHKVSAGQ FSSLHVRDTK IEVAQFVKDL LLHLKKLFRE GRFN        114

SEQ ID NO: 301         moltype = AA  length = 194
FEATURE                Location/Qualifiers
REGION                 1..194
                       note = Synthetic polymer
source                 1..194
                       mol_type = protein
                       organism = synthetic construct
SEQUENCE: 301
MAAEPVEDNC INFVAMKFID NTLYFIAEDD ENLESDYFGK LESKLSVIRN LNDQVLFIDQ  60
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NEDL                                                    194

SEQ ID NO: 302         moltype = AA  length = 270
FEATURE                Location/Qualifiers
REGION                 1..270
                       note = Synthetic polymer
source                 1..270
                       mol_type = protein
                       organism = synthetic construct
SEQUENCE: 302
MKPKMKYSTN KISTAKWKNT ASKALCFKLG KSQQKAKEVC PMYFMKLRSG LMIKKEACYF  60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
GVKDNHLALI KVDSSENLCT ENILFKLSET                                   270

SEQ ID NO: 303         moltype = AA  length = 10
FEATURE                Location/Qualifiers
REGION                 1..10
                       note = Synthetic polymer
source                 1..10
                       mol_type = protein
                       organism = synthetic construct
SEQUENCE: 303
GSISSINVMG                                                         10

SEQ ID NO: 304         moltype = AA  length = 10
FEATURE                Location/Qualifiers
REGION                 1..10
                       note = Synthetic polymer
source                 1..10
                       mol_type = protein
                       organism = synthetic construct
SEQUENCE: 304
GSFSSINVMG                                                         10

SEQ ID NO: 305         moltype = AA  length = 10
FEATURE                Location/Qualifiers
REGION                 1..10
```

```
                         note = Synthetic polymer
source                   1..10
                         mol_type = protein
                         organism = synthetic construct
SEQUENCE: 305
GSISSINIMG                                                           10

SEQ ID NO: 306           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 306
GSISSINIMG                                                           10

SEQ ID NO: 307           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 307
VSIFSINAMG                                                           10

SEQ ID NO: 308           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 308
GSIFSLNAMG                                                           10

SEQ ID NO: 309           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 309
GRTISNYDMA                                                           10

SEQ ID NO: 310           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 310
GRTFTTSLMQ                                                           10

SEQ ID NO: 311           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 311
ERNLRIYDMA                                                           10

SEQ ID NO: 312           moltype = AA  length = 10
FEATURE                  Location/Qualifiers
REGION                   1..10
                         note = Synthetic polymer
source                   1..10
                         mol_type = protein
                         organism = synthetic construct
SEQUENCE: 312
ERNLRSYDMA                                                           10

SEQ ID NO: 313           moltype = AA  length = 10
FEATURE                  Location/Qualifiers
```

```
REGION                  1..10
                        note = Synthetic polymer
source                  1..10
                        mol_type = protein
                        organism = synthetic construct
SEQUENCE: 313
GLTFSNYHMG                                                                  10

SEQ ID NO: 314          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 314
GLTFSSYHMG                                                                  10

SEQ ID NO: 315          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 315
GLTFSRYHMG                                                                  10

SEQ ID NO: 316          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 316
GLTLSSYYIA                                                                  10

SEQ ID NO: 317          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 317
GLTFSSYYTG                                                                  10

SEQ ID NO: 318          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 318
GLTLSSYHMG                                                                  10

SEQ ID NO: 319          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 319
GRTSSPYVTG                                                                  10

SEQ ID NO: 320          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 320
GFTFSGYVMS                                                                  10

SEQ ID NO: 321          moltype = AA  length = 10
```

-continued

```
FEATURE                Location/Qualifiers
REGION                 1..10
                       note = Synthetic polymer
source                 1..10
                       mol_type = protein
                       organism = synthetic construct
SEQUENCE: 321
GFTFSGYVMT                                                            10

SEQ ID NO: 322         moltype = AA  length = 10
FEATURE                Location/Qualifiers
REGION                 1..10
                       note = Synthetic polymer
source                 1..10
                       mol_type = protein
                       organism = synthetic construct
SEQUENCE: 322
GFTFSGYLMS                                                            10

SEQ ID NO: 323         moltype = AA  length = 16
FEATURE                Location/Qualifiers
REGION                 1..16
                       note = Synthetic polymer
source                 1..16
                       mol_type = protein
                       organism = synthetic construct
SEQUENCE: 323
RITNLGLPNY ADWLKD                                                     16

SEQ ID NO: 324         moltype = AA  length = 16
FEATURE                Location/Qualifiers
REGION                 1..16
                       note = Synthetic polymer
source                 1..16
                       mol_type = protein
                       organism = synthetic construct
SEQUENCE: 324
RITNLGLPNY ADSVTG                                                     16

SEQ ID NO: 325         moltype = AA  length = 16
FEATURE                Location/Qualifiers
REGION                 1..16
                       note = Synthetic polymer
source                 1..16
                       mol_type = protein
                       organism = synthetic construct
SEQUENCE: 325
RITNIGLPNY ADSVKG                                                     16

SEQ ID NO: 326         moltype = AA  length = 16
FEATURE                Location/Qualifiers
REGION                 1..16
                       note = Synthetic polymer
source                 1..16
                       mol_type = protein
                       organism = synthetic construct
SEQUENCE: 326
RITNLGLPNY ADSVEG                                                     16

SEQ ID NO: 327         moltype = AA  length = 16
FEATURE                Location/Qualifiers
REGION                 1..16
                       note = Synthetic polymer
source                 1..16
                       mol_type = protein
                       organism = synthetic construct
SEQUENCE: 327
AITSGGRVVY SDSVKG                                                     16

SEQ ID NO: 328         moltype = AA  length = 16
FEATURE                Location/Qualifiers
REGION                 1..16
                       note = Synthetic polymer
source                 1..16
                       mol_type = protein
                       organism = synthetic construct
SEQUENCE: 328
AITSGGRTAY ADSVKG                                                     16
```

```
SEQ ID NO: 329          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 329
HITSDGRIVY ADPVKG                                                 16

SEQ ID NO: 330          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 330
RISGSGDRTD YADSVKG                                                17

SEQ ID NO: 331          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 331
SITWSTGNTH YADSVKG                                                17

SEQ ID NO: 332          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 332
VISSSGDSTH YSDFVKG                                                17

SEQ ID NO: 333          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 333
VITSSGDSTH YSDFVKG                                                17

SEQ ID NO: 334          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 334
QITWSDASIY YAGSVKG                                                17

SEQ ID NO: 335          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 335
QITWSDTSIY YAGSVKG                                                17

SEQ ID NO: 336          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 336
QITWSDGTTY YPGSVKG                                                17
```

```
SEQ ID NO: 337          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 337
QIRWSDDSTY YPGSVKG                                                 17

SEQ ID NO: 338          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 338
QISWSDDSTY YADSVKG                                                 17

SEQ ID NO: 339          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 339
TVSWGGVTYY ADSVKG                                                  16

SEQ ID NO: 340          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 340
SIGSGGGYPS YTDSVEG                                                 17

SEQ ID NO: 341          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 341
SIGSGGGYPS YTGSVEG                                                 17

SEQ ID NO: 342          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 342
HIGSGGGYPS YTDSVQG                                                 17

SEQ ID NO: 343          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 343
HIGSGGGHAT YTDSVEG                                                 17

SEQ ID NO: 344          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 344
```

```
TIGSGGGITS YADSVKG                                          17

SEQ ID NO: 345          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 345
VALSAEY                                                     7

SEQ ID NO: 346          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 346
VALKAEY                                                     7

SEQ ID NO: 347          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 347
VGLKAEY                                                     7

SEQ ID NO: 348          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 348
KTKSAVLFGG MDY                                              13

SEQ ID NO: 349          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 349
YIRGEDY                                                     7

SEQ ID NO: 350          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 350
KHYASNY                                                     7

SEQ ID NO: 351          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 351
QDFGSPSF                                                    8

SEQ ID NO: 352          moltype = AA  length = 8
FEATURE                 Location/Qualifiers
REGION                  1..8
                        note = Synthetic polymer
source                  1..8
                        mol_type = protein
                        organism = synthetic construct
```

```
SEQUENCE: 352
QDFRSPDF                                                             8

SEQ ID NO: 353          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 353
QIFGSPNF                                                             8

SEQ ID NO: 354          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 354
LAIHGDY                                                              7

SEQ ID NO: 355          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 355
NQIRQWP                                                              7

SEQ ID NO: 356          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 356
NSIRQWP                                                              7

SEQ ID NO: 357          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 357
NAIRQWP                                                              7

SEQ ID NO: 358          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 358
RKVGGPDY                                                             8

SEQ ID NO: 359          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 359
NTFGNVY                                                              7

SEQ ID NO: 360          moltype = AA  length = 115
FEATURE                 Location/Qualifiers
REGION                  1..115
                        note = Synthetic polymer
source                  1..115
                        mol_type = protein
```

```
                         organism = synthetic construct
SEQUENCE: 360
QVQLVESGGG LVHPGGSLRL SCAASGSISS INVMGWYRQA PGKERELVAR ITNLGLPNYA  60
DWLKDRFTIS RDNAKNTVYL QMNSLKPEDT AVYYCYLVAL SAEYWGQGTQ VTVSS       115

SEQ ID NO: 361           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 361
QVQLVESGGG LVHPGGSLRL SCAASGSFSS INVMGWYRQA PGKERELVAR ITNLGLPNYA  60
DSVTGRFTIS RDNAKNTVYL QMNSLKPEDT AVYYCYLVAL KAEYWGQGTQ VTVSS       115

SEQ ID NO: 362           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 362
QVQLVESGGG LVHRGGSLRL SCAASGSISS INIMGWYRQA PGKERELVAR ITNIGLPNYA  60
DSVKGRFTIS RDNAKSTVYL QMNSLNAEDT AVYYCYLVAL KAEYWGQGTQ VTVSS       115

SEQ ID NO: 363           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 363
QVQLVESGGG LVQPGGSLRL SCAASGSISS INVMGWYRQA PGKERELVAR ITNLGLPNYA  60
DSVEGRFTIS RDKDENTVYL EMNTLKPEDT AVYYCYLVGL KAEYWGQGTQ VTVSS       115

SEQ ID NO: 364           moltype = AA  length = 121
FEATURE                  Location/Qualifiers
REGION                   1..121
                         note = Synthetic polymer
source                   1..121
                         mol_type = protein
                         organism = synthetic construct
SEQUENCE: 364
QVQLVESGGG LVQPGGSLRL SCAASGSSDS INAMGWYRQA PGKERELVAA ITSGGRVVYS  60
DSVKGRGTIS RDNAKNTVYL QIASLKPEDT AVYYCNVKTK SAVLFGGMDY WGKGTQVTVS  120
S                                                                  121

SEQ ID NO: 365           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 365
QVQLVESGGG LVQPGGSLRL SCAASVSIFS INAMGWYRQA PGKERELVAA ITSGGRTAYA  60
DSVKGRFTIS RDNSKNTVYL QMDSLKPEDT DVYYCKAYIR GEDYWGKGTQ VTVSS       115

SEQ ID NO: 366           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 366
DVQLVESGGG LVQPGGSLRL SCAASGSIFS LNAMGWYRQA PGKERELVAH ITSDGRIVYA  60
DPVKGRFTIS RVDGKNMVTL QMNSLKPEDT AVYYCNAKHY ASNYWGQGTQ VTVSS       115

SEQ ID NO: 367           moltype = AA  length = 117
FEATURE                  Location/Qualifiers
REGION                   1..117
                         note = Synthetic polymer
source                   1..117
                         mol_type = protein
                         organism = synthetic construct
```

```
SEQUENCE: 367
QVQLVESGGG SVQAGGSLRL SCAASGRTIS NYDMAWSRQA PGKEREFVAR ISGSGDRTDY  60
ADSVKGRFTI SRDNAKNTVY LQMNSLKPED TAIYYCQIQD FGSPSFSGQG TQVTVSS     117

SEQ ID NO: 368         moltype = AA  length = 117
FEATURE                Location/Qualifiers
REGION                 1..117
                       note = Synthetic polymer
source                 1..117
                       mol_type = protein
                       organism = synthetic construct
SEQUENCE: 368
DVQLVESGGG SVQAGGSLRL SCAASGRTIS NYDMAWSRQA PGKEREFVAR ISGSGDRTDY  60
ADSVKGRFTI SRDNAKNTVY LQMNSLKPED TAIYYCQIQD FRSPDFWSQG TQVTVSS     117

SEQ ID NO: 369         moltype = AA  length = 117
FEATURE                Location/Qualifiers
REGION                 1..117
                       note = Synthetic polymer
source                 1..117
                       mol_type = protein
                       organism = synthetic construct
SEQUENCE: 369
QVQLVESGGE SVQAGGSLRL SCAASGRTIS NYDMAWSRQA PGKEREFVAR ISGSGDRTDY  60
ADSVKGRFTI SRDNAKNTVY LQMNSLKPED TAIYNCQTQI FGSPNFSGQG TQVTVSS     117

SEQ ID NO: 370         moltype = AA  length = 116
FEATURE                Location/Qualifiers
REGION                 1..116
                       note = Synthetic polymer
source                 1..116
                       mol_type = protein
                       organism = synthetic construct
SEQUENCE: 370
QVQLVESGGG LVQAGDSLRL SCAASGRTFT TSLMQWHRQA PGKEREFVAS ITWSTGNTHY  60
ADSVKGRFTI SRDNARNTVY LQMNSLKPED TAIYTCRVLA IHGDYWGQGT QVTVSS      116

SEQ ID NO: 371         moltype = AA  length = 116
FEATURE                Location/Qualifiers
REGION                 1..116
                       note = Synthetic polymer
source                 1..116
                       mol_type = protein
                       organism = synthetic construct
SEQUENCE: 371
DVQLVESGGG LVQAGDSLRL SCAASERNLR IYDMAWYRQA PGKEREYVAV ISSSGDSTHY  60
SDFVKGRFTI SRDNAKNTVS LQMDSLKPED TAFYYCNVNQ IRQWPWGQGT QVTVSS      116

SEQ ID NO: 372         moltype = AA  length = 116
FEATURE                Location/Qualifiers
REGION                 1..116
                       note = Synthetic polymer
source                 1..116
                       mol_type = protein
                       organism = synthetic construct
SEQUENCE: 372
QVQLVESGGG LVQAGDSLRL SCAASERNLR IYDMAWYRQA PGKEREYVAV ISSSGDSTHY  60
SDFVKGRFTI SRDNAKNTVS LQMDSLKPED TAFYYCNVNS IRQWPWGQGT QVTVSS      116

SEQ ID NO: 373         moltype = AA  length = 116
FEATURE                Location/Qualifiers
REGION                 1..116
                       note = Synthetic polymer
source                 1..116
                       mol_type = protein
                       organism = synthetic construct
SEQUENCE: 373
QVQLVESGGG LVQAGDSLRL SCTASERNLR SYDMAWWRQA PGKEREYVAV ITSSGDSTHY  60
SDFVKGRFTI SRDNAKNTVS LQMDSLKPED TASYYCNVNA IRQWPWGQGT QVTVSS      116

SEQ ID NO: 374         moltype = AA  length = 117
FEATURE                Location/Qualifiers
REGION                 1..117
                       note = Synthetic polymer
source                 1..117
                       mol_type = protein
                       organism = synthetic construct
SEQUENCE: 374
DVQLVESGGG SVQAGGSLRL SCAISGLTFS NYHMGWYRQA PGREREFVAQ ITWSDASIYY  60
```

```
AGSVKGRFTI SRDNVKNIVY LQIDNLKPED TAIYYCDARK VGGPDYWGQG TQVTVSS     117

SEQ ID NO: 375         moltype = AA  length = 117
FEATURE                Location/Qualifiers
REGION                 1..117
                       note = Synthetic polymer
source                 1..117
                       mol_type = protein
                       organism = synthetic construct
SEQUENCE: 375
QVQLVESGGG LVQAGGSLTL SCAISGLTFS SYHMGWYRQA PGREREFVAQ ITWSDTSIYY  60
AGSVKGRFTI SRDNVKNIVY LQIDNLKPED TAIYYCDARK VGGPDYWGQG TQVTVSS     117

SEQ ID NO: 376         moltype = AA  length = 117
FEATURE                Location/Qualifiers
REGION                 1..117
                       note = Synthetic polymer
source                 1..117
                       mol_type = protein
                       organism = synthetic construct
SEQUENCE: 376
DVQLVESGGG LVQAGGSLRL SCAISGLTFS RYHMGWYRQA PGREREFVAQ ITWSDGTTYY  60
PGSVKGRFTI SRDNARNTVY LQIDNLKPED TAIYYCDARK VGGPDYWGQG TQVTVSS     117

SEQ ID NO: 377         moltype = AA  length = 117
FEATURE                Location/Qualifiers
REGION                 1..117
                       note = Synthetic polymer
source                 1..117
                       mol_type = protein
                       organism = synthetic construct
SEQUENCE: 377
QVQLVESGGG LVQAGGSLRL SCATSGLTLS SYYIAWYRQA PGREREFVAQ IRWSDDSTYY  60
PGSVKGRFTI SRDNARNTVY LRMDNLKPED TARYYCDARK VGGPDYWGQG TQVTVSS     117

SEQ ID NO: 378         moltype = AA  length = 117
FEATURE                Location/Qualifiers
REGION                 1..117
                       note = Synthetic polymer
source                 1..117
                       mol_type = protein
                       organism = synthetic construct
SEQUENCE: 378
DVQLVESGGG LVQAGGSLRL SCATSGLTFS SYYTGWYRQA PGREREFVAQ ISWSDDSTYY  60
ADSVKGRFTI SRDNARNTVY LQMNNLKPGD TAIYYCDARK VGGPDYWGQG TQVTVSS     117

SEQ ID NO: 379         moltype = AA  length = 117
FEATURE                Location/Qualifiers
REGION                 1..117
                       note = Synthetic polymer
source                 1..117
                       mol_type = protein
                       organism = synthetic construct
SEQUENCE: 379
DVQLVESGGG LVQAGGSLRL SCATSGLTLS SYHMGWYRQA PGREREFVAQ ISWSDDSTYY  60
ADSVKGRFTI SRDNARNTVY LQMNNLKPED TAIYYCDARK VGGPDYWGQG TQVTVSS     117

SEQ ID NO: 380         moltype = AA  length = 115
FEATURE                Location/Qualifiers
REGION                 1..115
                       note = Synthetic polymer
source                 1..115
                       mol_type = protein
                       organism = synthetic construct
SEQUENCE: 380
DVQLVESGGG LVQAGGSLRL SCAASGRTSS PYVTGWYRQT PGKEREPVAT VSWGGVTYYA  60
DSVKGRFTIS RDNAKNTVYL QMNALKPEDT AIYYCNVNTF GNVYWGQGTQ VTVSS       115

SEQ ID NO: 381         moltype = AA  length = 112
FEATURE                Location/Qualifiers
REGION                 1..112
                       note = Synthetic polymer
source                 1..112
                       mol_type = protein
                       organism = synthetic construct
SEQUENCE: 381
QVQLVESGGG LVQPGGSLRL SCAASGFTFS GYVMSWVRQA PGKGLEWVAS IGSGGGYPSY  60
TDSVEGRFTI SRDNAKNTLY LLMDNLKPDD TAVYYCEMLG RRGQGTQVTV SS          112
```

```
SEQ ID NO: 382         moltype = AA  length = 112
FEATURE                Location/Qualifiers
REGION                 1..112
                       note = Synthetic polymer
source                 1..112
                       mol_type = protein
                       organism = synthetic construct
SEQUENCE: 382
QVQLVESGGG LVQPGGSLRL SCAASGFTFS GYVMSWVRQA PGKGLEWVAS IGSGGGYPSY  60
TDSVEGRFTI SRDNAKNTLY LQMNNLKPDD TAVYYCEMLG RRGQGTQVTV SS          112

SEQ ID NO: 383         moltype = AA  length = 112
FEATURE                Location/Qualifiers
REGION                 1..112
                       note = Synthetic polymer
source                 1..112
                       mol_type = protein
                       organism = synthetic construct
SEQUENCE: 383
QVQLVESGGG LVQPGGSLRL SCAASGFTFS GYVMSWVRQA PGKGLEWVAS IGSGGGYPSY  60
TGSVEGRFTI SRDNAKNTLY LLMNNLKPDD TAVYYCEMLG RRGQGTQVTV SS          112

SEQ ID NO: 384         moltype = AA  length = 112
FEATURE                Location/Qualifiers
REGION                 1..112
                       note = Synthetic polymer
source                 1..112
                       mol_type = protein
                       organism = synthetic construct
SEQUENCE: 384
QVQLVESGGG LVQPGGSLRL SCAASGFTFS GYVMSWVRQA PGKGLEWVAH IGSGGGYPSY  60
TDSVQGRFTI SRDNAKNTLY LQMNNLKPED TAVYYCEMLG RRGQGTQVTV SS          112

SEQ ID NO: 385         moltype = AA  length = 112
FEATURE                Location/Qualifiers
REGION                 1..112
                       note = Synthetic polymer
source                 1..112
                       mol_type = protein
                       organism = synthetic construct
SEQUENCE: 385
QVQLVESGGG LVQPGGSLRL SCAASGFTFS GYVMTWVRQA PGKGLEWVAH IGSGGGHATY  60
TDSVEGRFTI SRDNAKNTLY LQMNNLKAED TAVYYCEFLG RRGQGTQVTV SS          112

SEQ ID NO: 386         moltype = AA  length = 112
FEATURE                Location/Qualifiers
REGION                 1..112
                       note = Synthetic polymer
source                 1..112
                       mol_type = protein
                       organism = synthetic construct
SEQUENCE: 386
QVQLVESGGG LVQPGGSLRL SCAASGFTFS GYLMSWVRQA PGKGLEWVAT IGSGGGITSY  60
ADSVKGRFTI SRDNAKNTLY LQMNNLKHED TAVYYCETVI KRGQGTQVTV SS          112

SEQ ID NO: 387         moltype = AA  length = 10
FEATURE                Location/Qualifiers
REGION                 1..10
                       note = Synthetic polymer
source                 1..10
                       mol_type = protein
                       organism = synthetic construct
SEQUENCE: 387
GRISSINSMG                                                         10

SEQ ID NO: 388         moltype = AA  length = 10
FEATURE                Location/Qualifiers
REGION                 1..10
                       note = Synthetic polymer
source                 1..10
                       mol_type = protein
                       organism = synthetic construct
SEQUENCE: 388
GSITSINAMG                                                         10

SEQ ID NO: 389         moltype = AA  length = 10
FEATURE                Location/Qualifiers
REGION                 1..10
                       note = Synthetic polymer
```

```
source                  1..10
                        mol_type = protein
                        organism = synthetic construct
SEQUENCE: 389
GRFFRVNAMG                                                      10

SEQ ID NO: 390          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 390
GSSDSINAMG                                                      10

SEQ ID NO: 391          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 391
GSVFSINAWG                                                      10

SEQ ID NO: 392          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 392
GSILSINSMG                                                      10

SEQ ID NO: 393          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 393
VSISSINSMG                                                      10

SEQ ID NO: 394          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 394
GRVFSINAMG                                                      10

SEQ ID NO: 395          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 395
VNIDTLNSMA                                                      10

SEQ ID NO: 396          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 396
GGISSINSMG                                                      10

SEQ ID NO: 397          moltype = AA  length = 10
FEATURE                 Location/Qualifiers
REGION                  1..10
```

-continued

```
                        note = Synthetic polymer
source                  1..10
                        mol_type = protein
                        organism = synthetic construct
SEQUENCE: 397
GSMHSVNSMA                                                        10

SEQ ID NO: 398          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 398
GDISSINAMG                                                        10

SEQ ID NO: 399          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 399
GSIFSIDAMG                                                        10

SEQ ID NO: 400          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 400
GSIFSINAMG                                                        10

SEQ ID NO: 401          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 401
GSIFSIAAMG                                                        10

SEQ ID NO: 402          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 402
GNIASITAMG                                                        10

SEQ ID NO: 403          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 403
GFTFDDYAIG                                                        10

SEQ ID NO: 404          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 404
GSISSINAMG                                                        10

SEQ ID NO: 405          moltype = AA  length = 10
FEATURE                 Location/Qualifiers
```

-continued

```
REGION                  1..10
                        note = Synthetic polymer
source                  1..10
                        mol_type = protein
                        organism = synthetic construct
SEQUENCE: 405
VSIFRSYFMG                                                           10

SEQ ID NO: 406          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 406
GSIVSINAIG                                                           10

SEQ ID NO: 407          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 407
GSIFSINAMG                                                           10

SEQ ID NO: 408          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 408
RSFSSFNAMG                                                           10

SEQ ID NO: 409          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 409
GSFSSINAMG                                                           10

SEQ ID NO: 410          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 410
GTSFSINGMA                                                           10

SEQ ID NO: 411          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 411
GRTFSTYAMG                                                           10

SEQ ID NO: 412          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 412
GSIFSINAMG                                                           10

SEQ ID NO: 413          moltype = AA  length = 10
```

-continued

```
FEATURE                Location/Qualifiers
REGION                 1..10
                       note = Synthetic polymer
source                 1..10
                       mol_type = protein
                       organism = synthetic construct
SEQUENCE: 413
GRIFDINAMG                                                                10

SEQ ID NO: 414         moltype = AA  length = 10
FEATURE                Location/Qualifiers
REGION                 1..10
                       note = Synthetic polymer
source                 1..10
                       mol_type = protein
                       organism = synthetic construct
SEQUENCE: 414
GTLFSINGMA                                                                10

SEQ ID NO: 415         moltype = AA  length = 10
FEATURE                Location/Qualifiers
REGION                 1..10
                       note = Synthetic polymer
source                 1..10
                       mol_type = protein
                       organism = synthetic construct
SEQUENCE: 415
GSIDSINAMG                                                                10

SEQ ID NO: 416         moltype = AA  length = 10
FEATURE                Location/Qualifiers
REGION                 1..10
                       note = Synthetic polymer
source                 1..10
                       mol_type = protein
                       organism = synthetic construct
SEQUENCE: 416
GRAFSTNSMG                                                                10

SEQ ID NO: 417         moltype = AA  length = 10
FEATURE                Location/Qualifiers
REGION                 1..10
                       note = Synthetic polymer
source                 1..10
                       mol_type = protein
                       organism = synthetic construct
SEQUENCE: 417
GSIISINSMG                                                                10

SEQ ID NO: 418         moltype = AA  length = 10
FEATURE                Location/Qualifiers
REGION                 1..10
                       note = Synthetic polymer
source                 1..10
                       mol_type = protein
                       organism = synthetic construct
SEQUENCE: 418
RNFFSINAMG                                                                10

SEQ ID NO: 419         moltype = AA  length = 10
FEATURE                Location/Qualifiers
REGION                 1..10
                       note = Synthetic polymer
source                 1..10
                       mol_type = protein
                       organism = synthetic construct
SEQUENCE: 419
GRFFRVNAMG                                                                10

SEQ ID NO: 420         moltype = AA  length = 10
FEATURE                Location/Qualifiers
REGION                 1..10
                       note = Synthetic polymer
source                 1..10
                       mol_type = protein
                       organism = synthetic construct
SEQUENCE: 420
GSIVSINSMG                                                                10
```

```
SEQ ID NO: 421          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 421
GSIFSINAMG                                                            10

SEQ ID NO: 422          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 422
GSIIGINSMG                                                            10

SEQ ID NO: 423          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 423
GRTFPGYVMA                                                            10

SEQ ID NO: 424          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 424
GSIFSINAMG                                                            10

SEQ ID NO: 425          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 425
GRTFSINAMG                                                            10

SEQ ID NO: 426          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 426
GRTLSSYTIG                                                            10

SEQ ID NO: 427          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 427
GSFFSINAMG                                                            10

SEQ ID NO: 428          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 428
GSIFSINSMG                                                            10
```

```
SEQ ID NO: 429          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 429
GSIFSFNAMG                                                         10

SEQ ID NO: 430          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 430
GSIFSINAMG                                                         10

SEQ ID NO: 431          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 431
GRTFSTYAMA                                                         10

SEQ ID NO: 432          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 432
GSFFSINAMG                                                         10

SEQ ID NO: 433          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 433
VNIGSLNSMV                                                         10

SEQ ID NO: 434          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 434
GRTLSNYAVG                                                         10

SEQ ID NO: 435          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 435
GSISSINAMG                                                         10

SEQ ID NO: 436          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 436
```

```
GRFFRVNAMG                                                          10

SEQ ID NO: 437          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 437
GSVFSINAMG                                                          10

SEQ ID NO: 438          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 438
GSIFEINSIG                                                          10

SEQ ID NO: 439          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 439
GSIFNINSMG                                                          10

SEQ ID NO: 440          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 440
VNIGTLNSMA                                                          10

SEQ ID NO: 441          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 441
GSIFSINSMG                                                          10

SEQ ID NO: 442          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 442
GRIGSINSMG                                                          10

SEQ ID NO: 443          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 443
GSIFSFNAMG                                                          10

SEQ ID NO: 444          moltype = AA  length = 10
FEATURE                 Location/Qualifiers
REGION                  1..10
                        note = Synthetic polymer
source                  1..10
                        mol_type = protein
                        organism = synthetic construct
```

```
SEQUENCE: 444
GRISSINSMG                                                           10

SEQ ID NO: 445          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 445
GRTLSNYAVA                                                           10

SEQ ID NO: 446          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 446
GRIGSINSMG                                                           10

SEQ ID NO: 447          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 447
RSFFSFNAMG                                                           10

SEQ ID NO: 448          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 448
GRFFRVNAMG                                                           10

SEQ ID NO: 449          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 449
GIIFSINAMG                                                           10

SEQ ID NO: 450          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 450
GRTLSNYAVA                                                           10

SEQ ID NO: 451          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 451
GRIFSVNAMG                                                           10

SEQ ID NO: 452          moltype = AA  length = 10
FEATURE                 Location/Qualifiers
REGION                  1..10
                        note = Synthetic polymer
source                  1..10
                        mol_type = protein
```

```
                        organism = synthetic construct
SEQUENCE: 452
GRTFSSYAMA                                                          10

SEQ ID NO: 453          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 453
AITNGGAKTY ADSVKG                                                   16

SEQ ID NO: 454          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 454
AITSGGRLSY ADSVKG                                                   16

SEQ ID NO: 455          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 455
AITNGGQTAY ADSVKG                                                   16

SEQ ID NO: 456          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 456
AITSGGRSTY IDSAKG                                                   16

SEQ ID NO: 457          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 457
AITNQGRIAY APSVNG                                                   16

SEQ ID NO: 458          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 458
AITNDGRTTY VDSVKG                                                   16

SEQ ID NO: 459          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 459
AVTVGGRYAY ADSAKN                                                   16

SEQ ID NO: 460          moltype = AA  length = 16
FEATURE                 Location/Qualifiers
REGION                  1..16
                        note = Synthetic polymer
source                  1..16
```

```
                        mol_type = protein
                        organism = synthetic construct
SEQUENCE: 460
AITNQGATTY ADSVKG                                                   16

SEQ ID NO: 461          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 461
GITGSGQITY ANSVRG                                                   16

SEQ ID NO: 462          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 462
AITNGGRTVY GDSVKG                                                   16

SEQ ID NO: 463          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 463
AITSGGRLAY APSVNG                                                   16

SEQ ID NO: 464          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 464
AITNGGRTTY VDSVKG                                                   16

SEQ ID NO: 465          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 465
AITTGGRTTY VDSVKG                                                   16

SEQ ID NO: 466          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 466
AITNQGRLTY ADSVKG                                                   16

SEQ ID NO: 467          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 467
AITSGGRRAY ADSVKG                                                   16

SEQ ID NO: 468          moltype = AA  length = 18
FEATURE                 Location/Qualifiers
REGION                  1..18
                        note = Synthetic polymer
```

```
source                  1..18
                        mol_type = protein
                        organism = synthetic construct
SEQUENCE: 468
AITSASASRT TYADSVKG                                                   18

SEQ ID NO: 469          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 469
CISRSDGSTY YDDSVKG                                                    17

SEQ ID NO: 470          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 470
AITNQGRVTY ADSVKG                                                     16

SEQ ID NO: 471          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 471
AITDGGRLAY ADSAKG                                                     16

SEQ ID NO: 472          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 472
SITNQGIRNY STSVMG                                                     16

SEQ ID NO: 473          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 473
AITNQGRTTY ADSVKG                                                     16

SEQ ID NO: 474          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 474
AITNGGRIAY GIAVNG                                                     16

SEQ ID NO: 475          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 475
AITNGGRIAY SDSAKG                                                     16

SEQ ID NO: 476          moltype = AA  length = 16
FEATURE                 Location/Qualifiers
REGION                  1..16
```

```
                        note = Synthetic polymer
source                  1..16
                        mol_type = protein
                        organism = synthetic construct
SEQUENCE: 476
GITSDGSTGY ADSVKG                                                   16

SEQ ID NO: 477          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 477
AISWSGGSTY YADSVKG                                                  17

SEQ ID NO: 478          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 478
AITDQGRLAY ADSAKG                                                   16

SEQ ID NO: 479          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 479
AITNGGQTTY ADSVKG                                                   16

SEQ ID NO: 480          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 480
GITSDGSTGY ADSVKG                                                   16

SEQ ID NO: 481          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 481
AITTGGRTAY VDSVKG                                                   16

SEQ ID NO: 482          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 482
AITSQGRITL ADSVKG                                                   16

SEQ ID NO: 483          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 483
AITVDGRLAY ADSAKH                                                   16

SEQ ID NO: 484          moltype = AA  length = 16
FEATURE                 Location/Qualifiers
```

-continued

```
REGION                 1..16
                       note = Synthetic polymer
source                 1..16
                       mol_type = protein
                       organism = synthetic construct
SEQUENCE: 484
AITNGGRIAY GTSVMG                                                   16

SEQ ID NO: 485         moltype = AA  length = 16
FEATURE                Location/Qualifiers
REGION                 1..16
                       note = Synthetic polymer
source                 1..16
                       mol_type = protein
                       organism = synthetic construct
SEQUENCE: 485
AITNGGQIAY ADSVKG                                                   16

SEQ ID NO: 486         moltype = AA  length = 16
FEATURE                Location/Qualifiers
REGION                 1..16
                       note = Synthetic polymer
source                 1..16
                       mol_type = protein
                       organism = synthetic construct
SEQUENCE: 486
AITDQGRTTY ADSVKG                                                   16

SEQ ID NO: 487         moltype = AA  length = 16
FEATURE                Location/Qualifiers
REGION                 1..16
                       note = Synthetic polymer
source                 1..16
                       mol_type = protein
                       organism = synthetic construct
SEQUENCE: 487
GITTQGRITY GNSVRG                                                   16

SEQ ID NO: 488         moltype = AA  length = 16
FEATURE                Location/Qualifiers
REGION                 1..16
                       note = Synthetic polymer
source                 1..16
                       mol_type = protein
                       organism = synthetic construct
SEQUENCE: 488
AITSGGRTTY VDSVKG                                                   16

SEQ ID NO: 489         moltype = AA  length = 17
FEATURE                Location/Qualifiers
REGION                 1..17
                       note = Synthetic polymer
source                 1..17
                       mol_type = protein
                       organism = synthetic construct
SEQUENCE: 489
AINWRGGDTY YADSVKG                                                  17

SEQ ID NO: 490         moltype = AA  length = 16
FEATURE                Location/Qualifiers
REGION                 1..16
                       note = Synthetic polymer
source                 1..16
                       mol_type = protein
                       organism = synthetic construct
SEQUENCE: 490
AITDGGAKTY ADSVKG                                                   16

SEQ ID NO: 491         moltype = AA  length = 16
FEATURE                Location/Qualifiers
REGION                 1..16
                       note = Synthetic polymer
source                 1..16
                       mol_type = protein
                       organism = synthetic construct
SEQUENCE: 491
AITNQGRLSY VDSVKG                                                   16

SEQ ID NO: 492         moltype = AA  length = 16
```

```
FEATURE                Location/Qualifiers
REGION                 1..16
                       note = Synthetic polymer
source                 1..16
                       mol_type = protein
                       organism = synthetic construct
SEQUENCE: 492
AITNQGRRTY ADSVKG                                                         16

SEQ ID NO: 493         moltype = AA  length = 16
FEATURE                Location/Qualifiers
REGION                 1..16
                       note = Synthetic polymer
source                 1..16
                       mol_type = protein
                       organism = synthetic construct
SEQUENCE: 493
AITNGGRIAY TDSVKG                                                         16

SEQ ID NO: 494         moltype = AA  length = 16
FEATURE                Location/Qualifiers
REGION                 1..16
                       note = Synthetic polymer
source                 1..16
                       mol_type = protein
                       organism = synthetic construct
SEQUENCE: 494
AITNGGRTTY ADSVKG                                                         16

SEQ ID NO: 495         moltype = AA  length = 16
FEATURE                Location/Qualifiers
REGION                 1..16
                       note = Synthetic polymer
source                 1..16
                       mol_type = protein
                       organism = synthetic construct
SEQUENCE: 495
AITDGGRLTY ADSAKG                                                         16

SEQ ID NO: 496         moltype = AA  length = 16
FEATURE                Location/Qualifiers
REGION                 1..16
                       note = Synthetic polymer
source                 1..16
                       mol_type = protein
                       organism = synthetic construct
SEQUENCE: 496
AITTGGRTTY VDSVKG                                                         16

SEQ ID NO: 497         moltype = AA  length = 17
FEATURE                Location/Qualifiers
REGION                 1..17
                       note = Synthetic polymer
source                 1..17
                       mol_type = protein
                       organism = synthetic construct
SEQUENCE: 497
AISWSGGSTE YHDSVKG                                                        17

SEQ ID NO: 498         moltype = AA  length = 16
FEATURE                Location/Qualifiers
REGION                 1..16
                       note = Synthetic polymer
source                 1..16
                       mol_type = protein
                       organism = synthetic construct
SEQUENCE: 498
AITNQGRIAY ADSVKG                                                         16

SEQ ID NO: 499         moltype = AA  length = 16
FEATURE                Location/Qualifiers
REGION                 1..16
                       note = Synthetic polymer
source                 1..16
                       mol_type = protein
                       organism = synthetic construct
SEQUENCE: 499
GITGSGQITY ANSVRG                                                         16
```

```
SEQ ID NO: 500          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 500
AINWSSGGIS YSNSAKG                                              17

SEQ ID NO: 501          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 501
AITGQGRTTY ADSVKG                                               16

SEQ ID NO: 502          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 502
AITNGGQIVY ADSVKG                                               16

SEQ ID NO: 503          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 503
AITTQGRTTY EDSVKG                                               16

SEQ ID NO: 504          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 504
AITSGGITNY ANSVQG                                               16

SEQ ID NO: 505          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 505
AITVGGRLAY ADSAKG                                               16

SEQ ID NO: 506          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 506
GITGGGQITY ANSVRG                                               16

SEQ ID NO: 507          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 507
AITSQGRSTY ADSAKG                                               16
```

```
SEQ ID NO: 508          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 508
AITNGGATVY ADSVKG                                                   16

SEQ ID NO: 509          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 509
AITDGGRLTY ADSAKN                                                   16

SEQ ID NO: 510          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 510
AITNGGAKTY ADSVKG                                                   16

SEQ ID NO: 511          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 511
AINWSSGGIS YSNAAKG                                                  17

SEQ ID NO: 512          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 512
AITNGGATVY ADSVKG                                                   16

SEQ ID NO: 513          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 513
AITNGGRIAY GTSVMG                                                   16

SEQ ID NO: 514          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 514
AITNGGQTAY ADSVKG                                                   16

SEQ ID NO: 515          moltype = AA  length = 16
FEATURE                 Location/Qualifiers
REGION                  1..16
                        note = Synthetic polymer
SITE                    5
                        note = misc_feature - Xaa can be any naturally occurring
                         amino acid
source                  1..16
```

```
                         mol_type = protein
                         organism = synthetic construct
SEQUENCE: 515
AITNXGRTTY ADSVKG                                                  16

SEQ ID NO: 516           moltype = AA  length = 17
FEATURE                  Location/Qualifiers
REGION                   1..17
                         note = Synthetic polymer
source                   1..17
                         mol_type = protein
                         organism = synthetic construct
SEQUENCE: 516
AIWWASGGIS YANSAKG                                                 17

SEQ ID NO: 517           moltype = AA  length = 16
FEATURE                  Location/Qualifiers
REGION                   1..16
                         note = Synthetic polymer
source                   1..16
                         mol_type = protein
                         organism = synthetic construct
SEQUENCE: 517
AITNQGAPTY ADSVKG                                                  16

SEQ ID NO: 518           moltype = AA  length = 17
FEATURE                  Location/Qualifiers
REGION                   1..17
                         note = Synthetic polymer
source                   1..17
                         mol_type = protein
                         organism = synthetic construct
SEQUENCE: 518
AISWSGGSTY YADSVKG                                                 17

SEQ ID NO: 519           moltype = AA  length = 7
FEATURE                  Location/Qualifiers
REGION                   1..7
                         note = Synthetic polymer
source                   1..7
                         mol_type = protein
                         organism = synthetic construct
SEQUENCE: 519
FTRRDDY                                                            7

SEQ ID NO: 520           moltype = AA  length = 7
FEATURE                  Location/Qualifiers
REGION                   1..7
                         note = Synthetic polymer
source                   1..7
                         mol_type = protein
                         organism = synthetic construct
SEQUENCE: 520
FQSSGID                                                            7

SEQ ID NO: 521           moltype = AA  length = 8
FEATURE                  Location/Qualifiers
REGION                   1..8
                         note = Synthetic polymer
source                   1..8
                         mol_type = protein
                         organism = synthetic construct
SEQUENCE: 521
WAADYQQY                                                           8

SEQ ID NO: 522           moltype = AA  length = 8
FEATURE                  Location/Qualifiers
REGION                   1..8
                         note = Synthetic polymer
source                   1..8
                         mol_type = protein
                         organism = synthetic construct
SEQUENCE: 522
WNRDRQQY                                                           8

SEQ ID NO: 523           moltype = AA  length = 13
FEATURE                  Location/Qualifiers
REGION                   1..13
                         note = Synthetic polymer
```

```
source                 1..13
                       mol_type = protein
                       organism = synthetic construct
SEQUENCE: 523
KPTPVYGSTV GDY                                                 13

SEQ ID NO: 524         moltype = AA  length = 7
FEATURE                Location/Qualifiers
REGION                 1..7
                       note = Synthetic polymer
source                 1..7
                       mol_type = protein
                       organism = synthetic construct
SEQUENCE: 524
FTRDKDY                                                        7

SEQ ID NO: 525         moltype = AA  length = 8
FEATURE                Location/Qualifiers
REGION                 1..8
                       note = Synthetic polymer
source                 1..8
                       mol_type = protein
                       organism = synthetic construct
SEQUENCE: 525
WDRDRQQY                                                       8

SEQ ID NO: 526         moltype = AA  length = 7
FEATURE                Location/Qualifiers
REGION                 1..7
                       note = Synthetic polymer
source                 1..7
                       mol_type = protein
                       organism = synthetic construct
SEQUENCE: 526
FTRTDDY                                                        7

SEQ ID NO: 527         moltype = AA  length = 8
FEATURE                Location/Qualifiers
REGION                 1..8
                       note = Synthetic polymer
source                 1..8
                       mol_type = protein
                       organism = synthetic construct
SEQUENCE: 527
YDRSSTPY                                                       8

SEQ ID NO: 528         moltype = AA  length = 7
FEATURE                Location/Qualifiers
REGION                 1..7
                       note = Synthetic polymer
source                 1..7
                       mol_type = protein
                       organism = synthetic construct
SEQUENCE: 528
FTRGDDY                                                        7

SEQ ID NO: 529         moltype = AA  length = 7
FEATURE                Location/Qualifiers
REGION                 1..7
                       note = Synthetic polymer
source                 1..7
                       mol_type = protein
                       organism = synthetic construct
SEQUENCE: 529
LNSATTY                                                        7

SEQ ID NO: 530         moltype = AA  length = 7
FEATURE                Location/Qualifiers
REGION                 1..7
                       note = Synthetic polymer
source                 1..7
                       mol_type = protein
                       organism = synthetic construct
SEQUENCE: 530
YTRDEDY                                                        7

SEQ ID NO: 531         moltype = AA  length = 7
FEATURE                Location/Qualifiers
REGION                 1..7
```

```
                        note = Synthetic polymer
source                  1..7
                        mol_type = protein
                        organism = synthetic construct
SEQUENCE: 531
FTRDEDY                                                            7

SEQ ID NO: 532          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 532
KWYDPLVIEY YDN                                                     13

SEQ ID NO: 533          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 533
KADHNDY                                                            7

SEQ ID NO: 534          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 534
FRSGADDY                                                           8

SEQ ID NO: 535          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 535
EVPSTYSCSG FREDY                                                   15

SEQ ID NO: 536          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 536
FAASGMEY                                                           8

SEQ ID NO: 537          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 537
WTTDRQQY                                                           8

SEQ ID NO: 538          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 538
FAGWGKEDY                                                          9

SEQ ID NO: 539          moltype = AA  length = 7
FEATURE                 Location/Qualifiers
```

```
REGION               1..7
                     note = Synthetic polymer
source               1..7
                     mol_type = protein
                     organism = synthetic construct
SEQUENCE: 539
FSPTGDY                                                       7

SEQ ID NO: 540       moltype = AA  length = 13
FEATURE              Location/Qualifiers
REGION               1..13
                     note = Synthetic polymer
source               1..13
                     mol_type = protein
                     organism = synthetic construct
SEQUENCE: 540
KPTPVYGSTV GDY                                                13

SEQ ID NO: 541       moltype = AA  length = 13
FEATURE              Location/Qualifiers
REGION               1..13
                     note = Synthetic polymer
source               1..13
                     mol_type = protein
                     organism = synthetic construct
SEQUENCE: 541
KASPVYGSTV EDY                                                13

SEQ ID NO: 542       moltype = AA  length = 8
FEATURE              Location/Qualifiers
REGION               1..8
                     note = Synthetic polymer
source               1..8
                     mol_type = protein
                     organism = synthetic construct
SEQUENCE: 542
STPRGDSY                                                      8

SEQ ID NO: 543       moltype = AA  length = 15
FEATURE              Location/Qualifiers
REGION               1..15
                     note = Synthetic polymer
source               1..15
                     mol_type = protein
                     organism = synthetic construct
SEQUENCE: 543
EAEGSGREGN FYERS                                              15

SEQ ID NO: 544       moltype = AA  length = 8
FEATURE              Location/Qualifiers
REGION               1..8
                     note = Synthetic polymer
source               1..8
                     mol_type = protein
                     organism = synthetic construct
SEQUENCE: 544
WDRDRQQY                                                      8

SEQ ID NO: 545       moltype = AA  length = 7
FEATURE              Location/Qualifiers
REGION               1..7
                     note = Synthetic polymer
source               1..7
                     mol_type = protein
                     organism = synthetic construct
SEQUENCE: 545
FTRSDDY                                                       7

SEQ ID NO: 546       moltype = AA  length = 8
FEATURE              Location/Qualifiers
REGION               1..8
                     note = Synthetic polymer
source               1..8
                     mol_type = protein
                     organism = synthetic construct
SEQUENCE: 546
STPRGDSY                                                      8

SEQ ID NO: 547       moltype = AA  length = 7
```

-continued

```
FEATURE                 Location/Qualifiers
REGION                  1..7
                        note = Synthetic polymer
source                  1..7
                        mol_type = protein
                        organism = synthetic construct
SEQUENCE: 547
FTRDTDY                                                                   7

SEQ ID NO: 548          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 548
WTTLGTF                                                                   7

SEQ ID NO: 549          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 549
WVRDGQQY                                                                  8

SEQ ID NO: 550          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 550
KAIPVYGSTV EDY                                                            13

SEQ ID NO: 551          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 551
KAAATHLSTV ADY                                                            13

SEQ ID NO: 552          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 552
FGRFDDY                                                                   7

SEQ ID NO: 553          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 553
WGVKTGPESG SGTL                                                           14

SEQ ID NO: 554          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 554
FTRDEDY                                                                   7
```

-continued

```
SEQ ID NO: 555          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 555
RLTTEYDYAY                                                          10

SEQ ID NO: 556          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 556
FTRGNDY                                                             7

SEQ ID NO: 557          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 557
FQSSGID                                                             7

SEQ ID NO: 558          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 558
FSPTDDF                                                             7

SEQ ID NO: 559          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 559
KAIPIYGSTA EDY                                                      13

SEQ ID NO: 560          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 560
FSLTDDY                                                             7

SEQ ID NO: 561          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 561
WTRDRQQY                                                            8

SEQ ID NO: 562          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 562
FTRDEDF                                                             7
```

```
SEQ ID NO: 563          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 563
EVEGSGREGN FYGA                                                   14

SEQ ID NO: 564          moltype = AA  length = 5
FEATURE                 Location/Qualifiers
REGION                  1..5
                        note = Synthetic polymer
source                  1..5
                        mol_type = protein
                        organism = synthetic construct
SEQUENCE: 564
PGWDY                                                             5

SEQ ID NO: 565          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 565
YDRSATAY                                                          8

SEQ ID NO: 566          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 566
ASSVLSGTVD Y                                                      11

SEQ ID NO: 567          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 567
FAADGMEY                                                          8

SEQ ID NO: 568          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 568
KAAASYVSTV ADY                                                    13

SEQ ID NO: 569          moltype = AA  length = 6
FEATURE                 Location/Qualifiers
REGION                  1..6
                        note = Synthetic polymer
source                  1..6
                        mol_type = protein
                        organism = synthetic construct
SEQUENCE: 569
TAKDDY                                                            6

SEQ ID NO: 570          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 570
```

```
FTGWGKEDY                                                        9

SEQ ID NO: 571          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 571
WAADYQQY                                                         8

SEQ ID NO: 572          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 572
YDRSATPY                                                         8

SEQ ID NO: 573          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 573
WARDRQQY                                                         8

SEQ ID NO: 574          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 574
FTRGDDY                                                          7

SEQ ID NO: 575          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 575
WTKDRQQY                                                         8

SEQ ID NO: 576          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 576
FTRTYDY                                                          7

SEQ ID NO: 577          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 577
ASSILSGTVD Y                                                     11

SEQ ID NO: 578          moltype = AA  length = 8
FEATURE                 Location/Qualifiers
REGION                  1..8
                        note = Synthetic polymer
source                  1..8
                        mol_type = protein
                        organism = synthetic construct
```

```
SEQUENCE: 578
WAADYQQY                                                 8

SEQ ID NO: 579          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 579
KPAPVYGSTV GDY                                           13

SEQ ID NO: 580          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 580
FAADGMEY                                                 8

SEQ ID NO: 581          moltype = AA  length = 6
FEATURE                 Location/Qualifiers
REGION                  1..6
                        note = Synthetic polymer
source                  1..6
                        mol_type = protein
                        organism = synthetic construct
SEQUENCE: 581
FGSGGG                                                   6

SEQ ID NO: 582          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 582
ASSVLSGTAD Y                                             11

SEQ ID NO: 583          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 583
FTRGDDY                                                  7

SEQ ID NO: 584          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 584
EAEGSGREGN FYERS                                         15

SEQ ID NO: 585          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 585
QVQLQESGGG LVQPGGSLRL SCAASGRISS INSMGWYRQA PGNQRELVAA ITNGGAKTYA  60
DSVKGRFTIS TDNAGNTVYL QMDSLRPEDT AVYYCKAFTR RDDYWGQGTQ ITVSSAAAYP  120
YDVPDYGSHH HHHH                                          134

SEQ ID NO: 586          moltype = AA  length = 134
FEATURE                 Location/Qualifiers
REGION                  1..134
                        note = Synthetic polymer
```

-continued

```
source                  1..134
                        mol_type = protein
                        organism = synthetic construct
SEQUENCE: 586
QVQLQESGGG LVQAGGSLRL SCAASGSITS INAMGWYRQA PGKQRELVAA ITSGGRLSYA  60
DSVKGRFTIS RDNAESTVAL QMNSLKPEDT AVYSCAAFQS SGIDWGQGTQ VTVSSAAAYP  120
YDVPDYGSHH HHHH                                                   134

SEQ ID NO: 587          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 587
QVQLQESGGG LVQPGGSLRL SCAASGRFFR VNAMGWYRQA PGKQRELVAA ITNGGQTAYA  60
DSVKGRFTIS KESARNTVHL QMSSLKPEDT AVYYCTIWAA DYQQYWGQGT QVTVSSAAAY  120
PYDVPDYGSH HHHHH                                                  135

SEQ ID NO: 588          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 588
QVQLQESGGG LVQAGESLRL SCAASGSSDS INAMGWYRQA PGKQRELVAA ITSGGRSTYI  60
DSAKGRATIS RDNARNTAYL QMSSLKAEDT AVYYCTIWNR DRQQYWGQGT QVTVSSAAAY  120
PYDVPDYGSH HHHHH                                                  135

SEQ ID NO: 589          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 589
QVQLQESGGG LVQSGGSLRL SCAASGSVFS INAWGWYRQA PGKQRELVAA ITNQGRIAYA  60
PSVNGRFTIS RDSAKNTVYL QMNSLKPEDT AVYYCNAKPT PVYGSTVGDY WGQGTQVTVS  120
SAAAYPYDVP DYGSHHHHHH                                             140

SEQ ID NO: 590          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 590
QVQLQESGGG LVQAGGSLRL SCAASGSILS INSMGWYRPA LGNQRELVAA ITNDGRTTYV  60
DSVKGRFTIS RDNAKNTVYL QMNSLKPEDT AVYWCKAFTR DKDYWGQGTQ VTVSSAAAYP  120
YDVPDYGSHH HHHH                                                   134

SEQ ID NO: 591          moltype = AA  length = 135
FEATURE                 Location/Qualifiers
REGION                  1..135
                        note = Synthetic polymer
SITE                    108
                        note = misc_feature - Xaa can be any naturally occurring
                         amino acid
source                  1..135
                        mol_type = protein
                        organism = synthetic construct
SEQUENCE: 591
QVQLQESGGG LVQTGGSLRL SCAASVSISS INSMGWYRQA PGKERELVAA VTVGGRYAYA  60
DSAKNRFTIS RDDAQNTVHL QMSSLRAEDT AVYYCTIWDR DRQQYWGXGT QVTVSSAAAY  120
PYDVPDYGSH HHHHH                                                  135

SEQ ID NO: 592          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 592
```

-continued

```
QVQLQESGGG LVQPGGSLRL SCAASGRVFS INAMGWYRQA PGKQRELVAA ITNQGATTYA  60
DSVKGRFTIS RDTAGNTVYL QMNSLRPEDT AVHYCKAFTR TDDYWGQGTQ VTVSSAAAYP  120
YDVPDYGSHH HHHH                                                   134

SEQ ID NO: 593         moltype = AA  length = 135
FEATURE                Location/Qualifiers
REGION                 1..135
                       note = Synthetic polymer
source                 1..135
                       mol_type = protein
                       organism = synthetic construct
SEQUENCE: 593
QVQLQESGGG LVQAGGSLRL SCAASVNIDT LNSMAWYRQA PGKQRELVAG ITGSGQITYA  60
NSVRGRFTVS RDNAKSTVYL QMNTLQPEDT AVYYCAAYDR SSTPYWGQGT QVTVSSAAAY  120
PYDVPDYGSH HHHHH                                                  135

SEQ ID NO: 594         moltype = AA  length = 134
FEATURE                Location/Qualifiers
REGION                 1..134
                       note = Synthetic polymer
source                 1..134
                       mol_type = protein
                       organism = synthetic construct
SEQUENCE: 594
QVQLQESGGG LVQPGGSLRL SCAASGGISS INSMGWYRQA PGNQRELVAA ITNGGRTVYG  60
DSVKGRFTIS RDSAGNTVHL QMDSLRPEDT GVYYCKAFTR GDDYWGQGTQ VTVSSAAAYP  120
YDVPDYGSHH HHHH                                                   134

SEQ ID NO: 595         moltype = AA  length = 134
FEATURE                Location/Qualifiers
REGION                 1..134
                       note = Synthetic polymer
source                 1..134
                       mol_type = protein
                       organism = synthetic construct
SEQUENCE: 595
QVQLQESGGG LVQPGGFLSL SCAASGSMHS VNSMAWYRQV PGKQRELVAA ITSGGRLAYA  60
PSVNGRFTIS RDYAKNTIHL QMNSLEPEDT AVYYCAALNS ATTYWGQGTQ VTVSSAAAYP  120
YDVPDYGSHH HHHH                                                   134

SEQ ID NO: 596         moltype = AA  length = 134
FEATURE                Location/Qualifiers
REGION                 1..134
                       note = Synthetic polymer
source                 1..134
                       mol_type = protein
                       organism = synthetic construct
SEQUENCE: 596
QVQLQESGGG LVQAGGSLRL SCAATGDISS INAMGWHRPA RGNERELVAA ITNGGRTTYV  60
DSVKGRFTIS RDNAKNTVYL QMNSLKPEDT AVYFCKAYTR DEDYWGQGTQ VTVSSAAAYP  120
YDVPDYGSHH HHHH                                                   134

SEQ ID NO: 597         moltype = AA  length = 134
FEATURE                Location/Qualifiers
REGION                 1..134
                       note = Synthetic polymer
source                 1..134
                       mol_type = protein
                       organism = synthetic construct
SEQUENCE: 597
QVQLQESGGG LVRAGGSLRL SCAASGSIFS IDAMGWYRPA HGEQRELVAA ITTGGRTTYV  60
DSVKGRFTIS RDNAKNTVYL QMNSLKPEDT AVYFCKAFTR DEDYWGQGTQ VTVSSAAAYP  120
YDVPDYGSHH HHHH                                                   134

SEQ ID NO: 598         moltype = AA  length = 140
FEATURE                Location/Qualifiers
REGION                 1..140
                       note = Synthetic polymer
source                 1..140
                       mol_type = protein
                       organism = synthetic construct
SEQUENCE: 598
QVQLQESGGG LVQPGGSLRL SCAASGSIFS INAMGWYRQA PGKQRELVAA ITNQGRLTYA  60
DSVKGRFTIS RDNAKNTVFL QMDSLKPEDT AVYYCNAKWY DPLVIEYYDN WGQGTQVTVS  120
SAAAYPYDVP DYGSHHHHHH                                             140

SEQ ID NO: 599         moltype = AA  length = 134
FEATURE                Location/Qualifiers
REGION                 1..134
```

```
                        note = Synthetic polymer
source                  1..134
                        mol_type = protein
                        organism = synthetic construct
SEQUENCE: 599
QVQLQESGGG LVQPGGSLRL SCAASGSIFS IAAMGWYRQA PGKQRELVAA ITSGGRRAYA  60
DSVKGRFTIS RDNDENTVAL QMNSLKPEDT DVYYCNAKAD HNDYWGQGTQ ITVSSAAAYP  120
YDVPDYGSHH HHHH                                                   134

SEQ ID NO: 600          moltype = AA  length = 137
FEATURE                 Location/Qualifiers
REGION                  1..137
                        note = Synthetic polymer
source                  1..137
                        mol_type = protein
                        organism = synthetic construct
SEQUENCE: 600
QVQLQESGGG LVQPGGSLRL SCAAIGNIAS ITAMGWYRQA PGKQRELVAA ITSASASRTT  60
YADSVKGRFT ISRDNAKNTV YLQMNSLQPE DTAVYYCKGF RSGADDYWGQ GTQVTVSSAA  120
AYPYDVPDYG SHHHHHH                                                137

SEQ ID NO: 601          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 601
QVQLQESGGG LVQPGGSLRL SCAASGFTFD DYAIGWFRQA PGKEHEGVSC ISRSDGSTYY  60
DDSVKGRFTI SSDNAKNTVY LQMNSLKPED TAVYYCAAEV PSTYSCSGFR EDYKGKGTQV  120
TVSSAAAYPY DVPDYGSHHH HHH                                         143

SEQ ID NO: 602          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 602
QVQLQESGGG LVQPGGSLRL SCAASGSISS INAMGWYRQA PGNQRELVAA ITNQGRVTYA  60
DSVKGRFTIS RDGAKNTVYL QMNSLKPEDT AVYYCKVFAA SGMEYWGKGT QVTVSSAAAY  120
PYDVPDYGSH HHHHH                                                  135

SEQ ID NO: 603          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 603
QVQLQESGGG LVQAGESLRL SCAASVSIFR SYFMGWYRQA PGKQRELVAA ITDGGRLAYA  60
DSAKGRFTIS REDTRNTVHL QMSSLKAEDT AVYYCTIWTT DRQQYWGQGT QVTVSSAAAY  120
PYDVPDYGSH HHHHH                                                  135

SEQ ID NO: 604          moltype = AA  length = 136
FEATURE                 Location/Qualifiers
REGION                  1..136
                        note = Synthetic polymer
source                  1..136
                        mol_type = protein
                        organism = synthetic construct
SEQUENCE: 604
QVQLQESGGG WVQPGGSLRL SCAATGSIVS INAIGWYRQA PGKQRELVAS ITNQGIRNYS  60
TSVMGRFTIS RDDVKNTVSL QMNSLKPEDS AVYYCKGFAG WGKEDYWGQG TQVTVSSAAA  120
YPYDVPDYGS HHHHHH                                                 136

SEQ ID NO: 605          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 605
QVQLQESGGG LVQAGASLRL SCAASGSIFS INAMGWYRQA PGKQRELVAA ITNQGRTTYA  60
DSVKGRFTIS RDNAKNTVYL QMDSLEPEDT AIYYCKGFSP TGDYWGQGTQ VTVSSAAAYP  120
```

-continued

```
YDVPDYGSHH HHHH                                                     134

SEQ ID NO: 606          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 606
QVQLQESGGG LVQPGGSLRL SCLASRSFSS FNAMGWYRQA PGKERELVAA ITNGGRIAYG  60
IAVNGRFTIS RDNAKNTVYL QMNSLKPEDT AVYYCNAKPT PVYGSTVGDY WGQGTQVTVS  120
SAAAYPYDVP DYGSHHHHHH                                               140

SEQ ID NO: 607          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 607
QVQLQESGGG LVQAGGSLTL SCAASGSFSS INAMGYYRQA PGKQRELVAA ITNGGRIAYS  60
DSAKGRFTIS RDSAKNTMYL QMNSLKPEDT DVYYCNAKAS PVYGSTVEDY WGQGTQVTVS  120
SAAAYPYDVP DYGSHHHHHH                                               140

SEQ ID NO: 608          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 608
QVQLQESGGG LVQPGGSLRL SCAASGTSFS INGMAWYRQA PGGQRELVGG ITSDGSTGYA  60
DSVKGRFTVS RDNAKNTVYL QMNRLKPEDT AVYYCGTSTP RGDSYWGQGT QVTVSSAAAY  120
PYDVPDYGSH HHHHH                                                    135

SEQ ID NO: 609          moltype = AA  length = 145
FEATURE                 Location/Qualifiers
REGION                  1..145
                        note = Synthetic polymer
source                  1..145
                        mol_type = protein
                        organism = synthetic construct
SEQUENCE: 609
QVQLQESGGG LVQAGGSLRL SCAASGRTFS TYAMGWFRQA PGKERGLVAA ISWSGGSTYY  60
ADSVKGRFTI FRDNAENTVY LQMNSLKPED TAVYYCAAEA EGSGREGNFY ERSWYQGQGT  120
QVTVSSAAAY PYDVPDYGSH HHHHH                                         145

SEQ ID NO: 610          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 610
QVQLQESGGG LVETGGSLRL SCAASGSIFS INAMGWYRQA PGKQRELVAA ITDQGRLAYA  60
DSAKGRFTIS RENARNTLHL QMSSLKAEDT AVYYCTIWDR DRQQYWGQGT QVTVSSAAAY  120
PYDVPDYGSH HHHHH                                                    135

SEQ ID NO: 611          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 611
QVQLQESGGG LVQPGGSLRL SCAASGRIFD INAMGWYRQA PGKQRELVAA ITNGGQTTYA  60
DSVKGRFTIS RDNAGNTVYL QMNSLRPEDT AVYYCKAFTR SDDYWGQGTQ VTVSSAAAYP  120
YDVPDYGSHH HHHH                                                     134

SEQ ID NO: 612          moltype = AA  length = 135
FEATURE                 Location/Qualifiers
REGION                  1..135
                        note = Synthetic polymer
source                  1..135
```

```
                        mol_type = protein
                        organism = synthetic construct
SEQUENCE: 612
QVQLQESGGG LVQAGGSLRL SCAASGTLFS INGMAWYRQA PGKRRELVGG ITSDGSTGYA  60
DSVKGRFTIS RDNAKNTAYL QMNSLKPEDT AVYYCGTSTP RGDSYWGQGT QVTVSSAAAY  120
PYDVPDYGSH HHHHH                                                  135

SEQ ID NO: 613          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 613
QVQLQESGGG LVQAGGSLRL SCAASGSIDS INAMGWYRPA LGEQRELVAA ITTGGRTAYV  60
DSVKGRFTIS RDAAKNTVYL QMNSLKPEDT AVYSCKAFTR DTDYWGQGTQ VTVSSAAAYP  120
YDVPDYGSHH HHHH                                                   134

SEQ ID NO: 614          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 614
QVQLQESGGG LAQPGGSLQL SCAASGRAFS TNSMGWYRQA SGKQRELVAA ITSQGRITLA  60
DSVKGRFTIS SDNTKNTVFL QMNSLKPEDT AVYYCNAWTT LGTFGGQGTQ VTVSSAAAYP  120
YDVPDYGSHH HHHH                                                   134

SEQ ID NO: 615          moltype = AA  length = 136
FEATURE                 Location/Qualifiers
REGION                  1..136
                        note = Synthetic polymer
source                  1..136
                        mol_type = protein
                        organism = synthetic construct
SEQUENCE: 615
QVQLQESGGG LVQTGESLSL SCAVASGSII SINSMGWYRQ APEKQRELVA AITVDGRLAY  60
ADSAKHRFTI SKESARNTVH LHMSSLKPED TAVYYCTIWV RDGQQYWGQG TQVTVSSAAA  120
YPYDVPDYGS HHHHHH                                                 136

SEQ ID NO: 616          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 616
QVQLQESGGG LVQPGGSLRL SCAVSRNFFS INAMGWYRQA PGKQRELVAA ITNGGRIAYG  60
TSVMGRFTIS RDDAKNTVDL QMNSLRPEDT AVYYCNAKAI PVYGSTVEDY WGQGTQVTVS  120
SAAAYPYDVP DYGSHHHHHH                                             140

SEQ ID NO: 617          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 617
QVQLQESGGG LVQPGGSLRL SCAASGRFFR VNAMGWYRQV PGKQRELVAA ITNGGQIAYA  60
DSVKGRFTIS RDSAKNTVYL QMNSLKSEDT DVYYCNAKAA ATHLSTVADY WGQGTQVTVS  120
SAAAYPYDVP DYGSHHHHHH                                             140

SEQ ID NO: 618          moltype = AA  length = 136
FEATURE                 Location/Qualifiers
REGION                  1..136
                        note = Synthetic polymer
source                  1..136
                        mol_type = protein
                        organism = synthetic construct
SEQUENCE: 618
QVQLQESGGG LVQPGGSLRL SCAASGSIVS INSMGWYRQA PGKQRELVAA ITDQGRTTYA  60
DSVKGRFTIS RDDAKNKNTV YLQMNSLKAE DTAVYACKAF GRFDDYWGQG TQVTVSSAAA  120
YPYDVPDYGS HHHHHH                                                 136
```

-continued

```
SEQ ID NO: 619         moltype = AA  length = 141
FEATURE                Location/Qualifiers
REGION                 1..141
                       note = Synthetic polymer
source                 1..141
                       mol_type = protein
                       organism = synthetic construct
SEQUENCE: 619
QVQLQESGGG LVQPGGSLRL SCAAYGSIFS INAMGWYRQA PGKERELVAG ITTQGRITYG  60
NSVRGRFTIS GDNAKNTVYL QMKSLKPEDT AVYYCSAWGV KTGPESGSGT LEGQGTQVTV  120
SSAAAYPYDV PDYGSHHHHH H                                            141

SEQ ID NO: 620         moltype = AA  length = 134
FEATURE                Location/Qualifiers
REGION                 1..134
                       note = Synthetic polymer
source                 1..134
                       mol_type = protein
                       organism = synthetic construct
SEQUENCE: 620
QVQLQESGGG LVQAGGSLRL SCAASGSIIG INSMGYYRTA PGKQRELVAA ITSGGRTTYV  60
DSVKGRFTIS RDNAKNTVYL QMNSLKPEDT AVYFCKAFTR DEDYWGQGTQ VTVSSAAAYP  120
YDVPDYGSHH HHHH                                                    134

SEQ ID NO: 621         moltype = AA  length = 138
FEATURE                Location/Qualifiers
REGION                 1..138
                       note = Synthetic polymer
source                 1..138
                       mol_type = protein
                       organism = synthetic construct
SEQUENCE: 621
QVQLQESGGG LVQAGGSLRL SCAASGRTFP GYVMAWFRQS PGQEREFAAA INWRGGDTYY  60
ADSVKGRFTI SRDNVKNTVF LQMNSLKPED TAVYFCAARL TTEYDYAYWG QGTQVTVSSA  120
AAYPYDVPDY GSHHHHHH                                                138

SEQ ID NO: 622         moltype = AA  length = 134
FEATURE                Location/Qualifiers
REGION                 1..134
                       note = Synthetic polymer
source                 1..134
                       mol_type = protein
                       organism = synthetic construct
SEQUENCE: 622
QVQLQESGGG LVQPGESLRL SCAASGSIFS INAMGWYRQA PGKQRELVAA ITDGGAKTYA  60
DSVKGRFTIS TDNAGNTVYL QMDSLRPEDT AVYYCKAFTR GNDYWGQGTQ VTVSSAAAYP  120
YDVPDYGSHH HHHH                                                    134

SEQ ID NO: 623         moltype = AA  length = 134
FEATURE                Location/Qualifiers
REGION                 1..134
                       note = Synthetic polymer
source                 1..134
                       mol_type = protein
                       organism = synthetic construct
SEQUENCE: 623
QVQLQESGGG LVQAGESLRL SCVVSGRTFS INAMGWYRQA PGKQRELVAA ITNQGRLSYV  60
DSVKGRFTIS RDNAANTVYL QMNSLKPEDT AVYYCAAFQS SGIDWGQGTQ VTVSSAAAYP  120
YDVPDYGSHH HHHH                                                    134

SEQ ID NO: 624         moltype = AA  length = 134
FEATURE                Location/Qualifiers
REGION                 1..134
                       note = Synthetic polymer
source                 1..134
                       mol_type = protein
                       organism = synthetic construct
SEQUENCE: 624
QVQLQESGGG LVQAGGSLRL SCAASGRTLS SYTIGWYRQA PGKQRELVAA ITNQGRRTYA  60
DSVKGRFTIS RDNAKNTVYL QMDSLKSEDT AVYYCKGFSP TDDFWGQGTQ VTVSSAAAYP  120
YDVPDYGSHH HHHH                                                    134

SEQ ID NO: 625         moltype = AA  length = 140
FEATURE                Location/Qualifiers
REGION                 1..140
                       note = Synthetic polymer
source                 1..140
                       mol_type = protein
                       organism = synthetic construct
```

```
SEQUENCE: 625
QVQLQESGGG LVQPGGSLRL SCTASGSFFS INAMGWYRQA PGNQRELVAA ITNGGRIAYT  60
DSVKGRFTIS NDNAKNTVYL QMNSLKPEDT DVYYCNAKAI PIYGSTAEDY WGQGTQVTVS  120
SAAAYPYDVP DYGSHHHHHH                                              140

SEQ ID NO: 626          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 626
QVQLQESGGG LVQAGGSLRL SCAASGSIFS INSMGWYRQA PGKQRELVAA ITNGGRTTYA  60
DSVKGRFTIS RDNAKNTVYL QMDSLKPEDT AVYYCKGFSL TDDYWGQGTQ VTVSSAAAYP  120
YDVPDYGSHH HHHH                                                    134

SEQ ID NO: 627          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 627
QVQLQESGGG LVQTGGSLRL SCAASGSIFS FNAMGWYRQA PGKQRELVAA ITDGGRLTYA  60
DSAKGRFTIS RENTRNTVHL QMSSLKAEDT ADYYCTIWTR DRQQYWGQGT QVTVSSAAAY  120
PYDVPDYGSH HHHHH                                                   135

SEQ ID NO: 628          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 628
QVQLQESGGG LVQAGGSLRL SCAASGSIFS INAMGWYRPA LGEQRELVAA ITTGGRTTYV  60
DSVKGRFSIS RDNAKNTVYL QMNSLKPEDT AVYFCKAFTR DEDFWGQGTQ VTVSSAAAYP  120
YDVPDYGSHH HHHH                                                    134

SEQ ID NO: 629          moltype = AA  length = 145
FEATURE                 Location/Qualifiers
REGION                  1..145
                        note = Synthetic polymer
source                  1..145
                        mol_type = protein
                        organism = synthetic construct
SEQUENCE: 629
QVQLQESGGG LVQAGGSLRL SCEASGRTFS TYAMAWFRQA PGKERDLVAA ISWSGGSTEY  60
HDSVKGRFTI SRDNTKNTVY LQMNSLKAED TAVYYCAAEV EGSGREGNFY GASWYPGQGT  120
QVTVSSAAAY PYDVPDYGSH HHHHH                                        145

SEQ ID NO: 630          moltype = AA  length = 132
FEATURE                 Location/Qualifiers
REGION                  1..132
                        note = Synthetic polymer
source                  1..132
                        mol_type = protein
                        organism = synthetic construct
SEQUENCE: 630
QVQLQESGGG LVQPGGSLRL SCAASGSFFS INAMGWYRQA PGKQRELVAA ITNQGRIAYA  60
DSVKGRFTIS RDNAKNTVYL QMNSLKPEDT AVYYCGRPGW DYWGQGTQVT VSSAAAYPYD  120
VPDYGSHHHH HH                                                      132

SEQ ID NO: 631          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 631
QVQLQESGGG LVQAGGSLRL SCVASVNIGS LNSMVWYRQS PGKQRELVAG ITGSGQITYA  60
NSVRGRFTVS RDIAKSTAYL QMNTLKPEDT AVYYCAAYDR SATAYWGQGT QVTVSSAAAY  120
PYDVPDYGSH HHHHH                                                   135

SEQ ID NO: 632          moltype = AA  length = 139
FEATURE                 Location/Qualifiers
```

-continued

```
REGION                 1..139
                       note = Synthetic polymer
source                 1..139
                       mol_type = protein
                       organism = synthetic construct
SEQUENCE: 632
QVQLQESGGG LVQAGGSLRV SCAASGRTLS NYAVGWWRQA PGKQREFVAA INWSSGGISY  60
SNSAKGRFAL SRDNAKNTVY LQMDSLKPED TAVYYCAAAS SVLSGTVDYW GQGTQVTVSS  120
AAAYPYDVPD YGSHHHHHH                                               139

SEQ ID NO: 633         moltype = AA  length = 135
FEATURE                Location/Qualifiers
REGION                 1..135
                       note = Synthetic polymer
source                 1..135
                       mol_type = protein
                       organism = synthetic construct
SEQUENCE: 633
QVQLQESGGG LVQPGGSLRL SCAASGSISS INAMGWYRQA PGKQRELVAA ITGQGRTTYA  60
DSVKGRFTIS RDGAKNTVYL QMNSLKPEDT AVYYCKVFAA DGMEYWGKGT QVTVSSAAAY  120
PYDVPDYGSH HHHHH                                                   135

SEQ ID NO: 634         moltype = AA  length = 140
FEATURE                Location/Qualifiers
REGION                 1..140
                       note = Synthetic polymer
source                 1..140
                       mol_type = protein
                       organism = synthetic construct
SEQUENCE: 634
QVQLQESGGG LVQPGGSLRL SCAASGRFFR VNAMGWYRQA PGKQRELVAA ITNGGQIVYA  60
DSVKGRFTIS RDSAKNTVYL QMNSLKSEDT AVYYCNAKAA ASYVSTVADY WGQGTQVTVS  120
SAAAYPYDVP DYGSHHHHHH                                              140

SEQ ID NO: 635         moltype = AA  length = 134
FEATURE                Location/Qualifiers
REGION                 1..134
                       note = Synthetic polymer
source                 1..134
                       mol_type = protein
                       organism = synthetic construct
SEQUENCE: 635
QVQLQESGGG LVQAGGSLRL SCAASGSVFS INAMGWYRQA PEKQRELVAA ITTQGRTTYE  60
DSVKGRFTIS RDGAQNTVYL QMDSLKPEDT AVYYCKAWTA KDDYWGKGTQ VTVSSAAAYP  120
YDVPDYGSHH HHHH                                                    134

SEQ ID NO: 636         moltype = AA  length = 136
FEATURE                Location/Qualifiers
REGION                 1..136
                       note = Synthetic polymer
source                 1..136
                       mol_type = protein
                       organism = synthetic construct
SEQUENCE: 636
QVQLQESGGG RVQPGGSLRL SCAAIGSIFE INSIGWYRQA PGKQRELVAA ITSGGITNYA  60
NSVQGRSTIS RDNVNNTVYL QMNSLKPEDS AVYYCKGFTG WGKEDYWGQG TQVTVSSAAA  120
YPYDVPDYGS HHHHHH                                                  136

SEQ ID NO: 637         moltype = AA  length = 135
FEATURE                Location/Qualifiers
REGION                 1..135
                       note = Synthetic polymer
source                 1..135
                       mol_type = protein
                       organism = synthetic construct
SEQUENCE: 637
QVQLQESGGG LVQTGGSLRL SCAASGSIFN INSMGWYRQA PGKQRELVAA ITVGGRLAYA  60
DSAKGRFTIS KESARNTVHL QMSSLKPEDT AVYYCTIWAA DYQQYWGQGT QVTVSSAAAY  120
PYDVPDYGSH HHHHH                                                   135

SEQ ID NO: 638         moltype = AA  length = 135
FEATURE                Location/Qualifiers
REGION                 1..135
                       note = Synthetic polymer
source                 1..135
                       mol_type = protein
                       organism = synthetic construct
SEQUENCE: 638
QVQLQESGGG LVQAGGSLRL SCAASVNIGT LNSMAWYREA PGKQRELVAG ITGGGQITYA  60
```

-continued

```
NSVRGRFTVS RDIAKSTAYL QMNTLKPEDT AVYYCAAYDR SATPYWGQGT QVTVSSAAAY  120
PYDVPDYGSH HHHHH                                                   135

SEQ ID NO: 639         moltype = AA  length = 135
FEATURE                Location/Qualifiers
REGION                 1..135
                       note = Synthetic polymer
source                 1..135
                       mol_type = protein
                       organism = synthetic construct
SEQUENCE: 639
QVQLQESGGG LVQTGGSLRL SCAASGSIFS INSMGWYRQA PGKQRELVAA ITSQGRSTYA  60
DSAKGRFTIS LGNARNTVNL QMSSLKTEDT AVYYCTIWAR DRQQYWGQGT QVTVSSAAAY  120
PYDVPDYGSH HHHHH                                                   135

SEQ ID NO: 640         moltype = AA  length = 134
FEATURE                Location/Qualifiers
REGION                 1..134
                       note = Synthetic polymer
source                 1..134
                       mol_type = protein
                       organism = synthetic construct
SEQUENCE: 640
QVQLQESGGG LVQPGGSLRL SCAASGRIGS INSMGWYRQA PGKQREMVAA ITNGGATVYA  60
DSVKGRFTIS RDNAGNTVDL HMNSLRPEDS AVYYCKAFTR GDDYWGQGTQ VTVSSAAAYP  120
YDVPDYGSHH HHHH                                                    134

SEQ ID NO: 641         moltype = AA  length = 135
FEATURE                Location/Qualifiers
REGION                 1..135
                       note = Synthetic polymer
source                 1..135
                       mol_type = protein
                       organism = synthetic construct
SEQUENCE: 641
QVQLQESGGG LVQPGGSLKL SCAASGSIFS FNAMGWYRQA PGKQRELVAA ITDGGRLTYA  60
DSAKNRFTIS RENTRNTVHL QMSSLKAEDT AVYYCTIWTK DRQQYWGQGT QVTVSSAAAY  120
PYDVPDYGSH HHHHH                                                   135

SEQ ID NO: 642         moltype = AA  length = 134
FEATURE                Location/Qualifiers
REGION                 1..134
                       note = Synthetic polymer
source                 1..134
                       mol_type = protein
                       organism = synthetic construct
SEQUENCE: 642
QVQLQESGGG LVQPGGSLRL SCAASGRISS INSMGWYRQA PGKQRELVAA ITNGGAKTYA  60
DSVKGRFTIS RDGAGNTVYL QMDNLRPEDT AVYYCKAFTR TYDYWGQGTQ VTVSSAAAYP  120
YDVPDYGSHH HHHH                                                    134

SEQ ID NO: 643         moltype = AA  length = 139
FEATURE                Location/Qualifiers
REGION                 1..139
                       note = Synthetic polymer
source                 1..139
                       mol_type = protein
                       organism = synthetic construct
SEQUENCE: 643
QVQLQESGGG LVQAGGSLRV SCAASGRTLS NYAVAWFRQA PGKQREFVAA INWSSGGISY  60
SNAAKGRFAL SRDNAKNTVY LQMDSLKPED TAVYYCAAAS SILSGTVDYW GQGTQVTVSS  120
AAAYPYDVPD YGSHHHHHH                                               139

SEQ ID NO: 644         moltype = AA  length = 135
FEATURE                Location/Qualifiers
REGION                 1..135
                       note = Synthetic polymer
source                 1..135
                       mol_type = protein
                       organism = synthetic construct
SEQUENCE: 644
QVQLQESGGG LVQPGGSLRL SCAASGRIGS INSMGWYRQA PGKQREMVAA ITNGGATVYA  60
DSVKGRFTIS RDNAGNTVDL HMNSLRPEDS AVYYCTIWAA DYQQYWGQGT QVTVSSAAAY  120
PYDVPDYGSH HHHHH                                                   135

SEQ ID NO: 645         moltype = AA  length = 140
FEATURE                Location/Qualifiers
REGION                 1..140
                       note = Synthetic polymer
```

```
source                  1..140
                        mol_type = protein
                        organism = synthetic construct
SEQUENCE: 645
QVQLQESGGG LVQPGGSLRL SCAASRSFFS FNAMGWYRQA PGKQRELVAA ITNGGRIAYG  60
TSVMGRFTIS RDNAKNTVYL QMDSLKPEDT AVYYCNAKPA PVYGSTVGDY WGQGTQVTVS  120
SAAAYPYDVP DYGSHHHHHH                                             140

SEQ ID NO: 646          moltype = AA  length = 135
FEATURE                 Location/Qualifiers
REGION                  1..135
                        note = Synthetic polymer
source                  1..135
                        mol_type = protein
                        organism = synthetic construct
SEQUENCE: 646
QVQLQESGGG LVQPGGSPRL SCAASGRFFR VNAMGWYRQA PGKQRELVAA ITNGGQTAYA  60
DSVKGRFTIS RDSAKNTVYL QMNSLKSEDT AVYYCKVFAA DGMEYWGKGT QVTVSSAAAY  120
PYDVPDYGSH HHHHH                                                  135

SEQ ID NO: 647          moltype = AA  length = 133
FEATURE                 Location/Qualifiers
REGION                  1..133
                        note = Synthetic polymer
SITE                    54
                        note = misc_feature - Xaa can be any naturally occurring
                         amino acid
source                  1..133
                        mol_type = protein
                        organism = synthetic construct
SEQUENCE: 647
QVQLQESGGG LVQPGESLRL SCAASGIIFS INAMGWYRQA PGKQRELVAA ITNXGRTTYA  60
DSVKGRFTIS RDNAKNTVTL QMNSLKPEDT AVYYCNAFGS GGGVGQGTQV TVSSAAAYPY  120
DVPDYGSHHH HHH                                                    133

SEQ ID NO: 648          moltype = AA  length = 139
FEATURE                 Location/Qualifiers
REGION                  1..139
                        note = Synthetic polymer
source                  1..139
                        mol_type = protein
                        organism = synthetic construct
SEQUENCE: 648
QVQLQESGGG LVQAGGSLRL SCAASGRTLS NYAVAWFRQA PGKQRELVAA IWWASGGISY  60
ANSAKGRFVL SRDNAKNTVY LQMDSLKPED TAVYYCAAAS SVLSGTADYW GQGTQVTVSS  120
AAAYPYDVPD YGSHHHHHH                                              139

SEQ ID NO: 649          moltype = AA  length = 134
FEATURE                 Location/Qualifiers
REGION                  1..134
                        note = Synthetic polymer
source                  1..134
                        mol_type = protein
                        organism = synthetic construct
SEQUENCE: 649
QVQLQESGGG LVQPGGSLRL SCAASGRIFS VNAMGWYRQA PGKQRELVAA ITNQGAPTYA  60
DSVKGRFTIS RDNAGNTVYL QMNSLRPEDT AVYYCKAFTR GDDYWGQGTQ VTVSSAAAYP  120
YDVPDYGSHH HHHH                                                   134

SEQ ID NO: 650          moltype = AA  length = 145
FEATURE                 Location/Qualifiers
REGION                  1..145
                        note = Synthetic polymer
source                  1..145
                        mol_type = protein
                        organism = synthetic construct
SEQUENCE: 650
QVQLQESGGG SVQAGGSLRL SCAASGRTFS SYAMAWFRQA PGMERELVAA ISWSGGSTYY  60
ADSVKGRFTI SRDNAENTVY LQMNSLKPED TAVYYCAAEA EGSGREGNFY ERSWYQGQGT  120
QVTVSSAAAY PYDVPDYGSH HHHHH                                       145

SEQ ID NO: 651          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 651
```

```
GFSMDYYAIA                                                      10

SEQ ID NO: 652          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 652
GFSMDYYAIA                                                      10

SEQ ID NO: 653          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 653
GFSVDYYAIA                                                      10

SEQ ID NO: 654          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 654
GFSMDYYAIA                                                      10

SEQ ID NO: 655          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 655
GGFNRVSYMG                                                      10

SEQ ID NO: 656          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 656
GGFNRVSYMG                                                      10

SEQ ID NO: 657          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 657
GIIKSINFMG                                                      10

SEQ ID NO: 658          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 658
GFILDYYGIG                                                      10

SEQ ID NO: 659          moltype = AA  length = 10
FEATURE                 Location/Qualifiers
REGION                  1..10
                        note = Synthetic polymer
source                  1..10
                        mol_type = protein
                        organism = synthetic construct
```

```
SEQUENCE: 659
GLSLDYDGVG                                                        10

SEQ ID NO: 660          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 660
GFILDYYGIG                                                        10

SEQ ID NO: 661          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 661
GRTFSSLGMG                                                        10

SEQ ID NO: 662          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 662
GRTFSSLGMG                                                        10

SEQ ID NO: 663          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 663
GFAFGSYDMG                                                        10

SEQ ID NO: 664          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 664
GFSFGNNDMS                                                        10

SEQ ID NO: 665          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 665
CITGSDFMVD T                                                      11

SEQ ID NO: 666          moltype = AA  length = 11
FEATURE                 Location/Qualifiers
REGION                  1..11
                        note = Synthetic polymer
source                  1..11
                        mol_type = protein
                        organism = synthetic construct
SEQUENCE: 666
CITGSDFMVD T                                                      11

SEQ ID NO: 667          moltype = AA  length = 11
FEATURE                 Location/Qualifiers
REGION                  1..11
                        note = Synthetic polymer
source                  1..11
                        mol_type = protein
```

```
                       organism = synthetic construct
SEQUENCE: 667
CITGSDFMVD T                                                       11

SEQ ID NO: 668         moltype = AA  length = 11
FEATURE                Location/Qualifiers
REGION                 1..11
                       note = Synthetic polymer
source                 1..11
                       mol_type = protein
                       organism = synthetic construct
SEQUENCE: 668
CITGSDFMVD T                                                       11

SEQ ID NO: 669         moltype = AA  length = 8
FEATURE                Location/Qualifiers
REGION                 1..8
                       note = Synthetic polymer
source                 1..8
                       mol_type = protein
                       organism = synthetic construct
SEQUENCE: 669
SVTSGGEI                                                           8

SEQ ID NO: 670         moltype = AA  length = 8
FEATURE                Location/Qualifiers
REGION                 1..8
                       note = Synthetic polymer
source                 1..8
                       mol_type = protein
                       organism = synthetic construct
SEQUENCE: 670
SVTSGGEI                                                           8

SEQ ID NO: 671         moltype = AA  length = 8
FEATURE                Location/Qualifiers
REGION                 1..8
                       note = Synthetic polymer
source                 1..8
                       mol_type = protein
                       organism = synthetic construct
SEQUENCE: 671
STTSDGRT                                                           8

SEQ ID NO: 672         moltype = AA  length = 9
FEATURE                Location/Qualifiers
REGION                 1..9
                       note = Synthetic polymer
source                 1..9
                       mol_type = protein
                       organism = synthetic construct
SEQUENCE: 672
CISSSDGST                                                          9

SEQ ID NO: 673         moltype = AA  length = 9
FEATURE                Location/Qualifiers
REGION                 1..9
                       note = Synthetic polymer
source                 1..9
                       mol_type = protein
                       organism = synthetic construct
SEQUENCE: 673
CISSSDGST                                                          9

SEQ ID NO: 674         moltype = AA  length = 9
FEATURE                Location/Qualifiers
REGION                 1..9
                       note = Synthetic polymer
source                 1..9
                       mol_type = protein
                       organism = synthetic construct
SEQUENCE: 674
CISSSDGST                                                          9

SEQ ID NO: 675         moltype = AA  length = 9
FEATURE                Location/Qualifiers
REGION                 1..9
                       note = Synthetic polymer
source                 1..9
```

```
                        mol_type = protein
                        organism = synthetic construct
SEQUENCE: 675
AIAWNGAST                                                9

SEQ ID NO: 676          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 676
AIAWNGAST                                                9

SEQ ID NO: 677          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 677
GINSGGRIT                                                9

SEQ ID NO: 678          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 678
AINSGGGST                                                9

SEQ ID NO: 679          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 679
AVRSTANTLC PSHYSVMDY                                     19

SEQ ID NO: 680          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 680
AVRSTANTLC PSHYSVMDY                                     19

SEQ ID NO: 681          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 681
AVRSTANTLC PSHYSIMDY                                     19

SEQ ID NO: 682          moltype = AA  length = 19
FEATURE                 Location/Qualifiers
REGION                  1..19
                        note = Synthetic polymer
source                  1..19
                        mol_type = protein
                        organism = synthetic construct
SEQUENCE: 682
AVRSTANTLC PSHYSVMDY                                     19

SEQ ID NO: 683          moltype = AA  length = 14
FEATURE                 Location/Qualifiers
REGION                  1..14
                        note = Synthetic polymer
```

```
source                  1..14
                        mol_type = protein
                        organism = synthetic construct
SEQUENCE: 683
NADIWVSDAR MYNY                                                  14

SEQ ID NO: 684          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 684
NADIWVSDAR MYNY                                                  14

SEQ ID NO: 685          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 685
NADIWLPSDR MYNY                                                  14

SEQ ID NO: 686          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 686
ATATLCDGGI WGY                                                   13

SEQ ID NO: 687          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 687
ATATLCDGGI WGY                                                   13

SEQ ID NO: 688          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 688
ATATLCDGGI WGY                                                   13

SEQ ID NO: 689          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 689
AASGLGSVVV TANEYDY                                               17

SEQ ID NO: 690          moltype = AA  length = 17
FEATURE                 Location/Qualifiers
REGION                  1..17
                        note = Synthetic polymer
source                  1..17
                        mol_type = protein
                        organism = synthetic construct
SEQUENCE: 690
AASGLGSVVV TANEYDY                                               17

SEQ ID NO: 691          moltype = AA  length = 15
FEATURE                 Location/Qualifiers
REGION                  1..15
```

```
                        note = Synthetic polymer
source                  1..15
                        mol_type = protein
                        organism = synthetic construct
SEQUENCE: 691
AQGDRSSWHY YGMDY                                                  15

SEQ ID NO: 692          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 692
ATKSDPMTNE YDL                                                    13

SEQ ID NO: 693          moltype = AA  length = 147
FEATURE                 Location/Qualifiers
REGION                  1..147
                        note = Synthetic polymer
source                  1..147
                        mol_type = protein
                        organism = synthetic construct
SEQUENCE: 693
QVQLQESGGG LVQPGGSLRL SCAASGFSMD YYAIAWFRQA PGKEREEISC ITGSDFMVDT  60
YYVASVKGRF TISRDNAENT AYLQMNNLKP EDTGVYFCAV RSTANTLCPS HYSVMDYWGK  120
GTQVTVSSAA AYPYDVPDYG SHHHHHH                                     147

SEQ ID NO: 694          moltype = AA  length = 147
FEATURE                 Location/Qualifiers
REGION                  1..147
                        note = Synthetic polymer
source                  1..147
                        mol_type = protein
                        organism = synthetic construct
SEQUENCE: 694
QVQLQESGGG LVQAGGSLRL SCAASGFSMD YYAIAWFRQA PGKEREEISC ITGSDFMVDT  60
YYVASVKGRF TISRDNAENT AYLQMNNLKP EDTGVYFCAV RSTANTLCPS HYSVMDYWGK  120
GTQVTVSSAA AYPYDVPDYG SHHHHHH                                     147

SEQ ID NO: 695          moltype = AA  length = 146
FEATURE                 Location/Qualifiers
REGION                  1..146
                        note = Synthetic polymer
source                  1..146
                        mol_type = protein
                        organism = synthetic construct
SEQUENCE: 695
QVQLQESGGG LVQPGGSLRL SCSASGFSVD YYAIAWFRQA PGKEREEISC ITGSDFMVDT  60
YYVASVKGRF TISRDNAKNT AYLQMNSLKP EDTGVYFCAV RSTANTLCPS HYSIMDYWGK  120
GTQVTVSSAA AYPYDVPDYG SHHHHH                                      146

SEQ ID NO: 696          moltype = AA  length = 147
FEATURE                 Location/Qualifiers
REGION                  1..147
                        note = Synthetic polymer
source                  1..147
                        mol_type = protein
                        organism = synthetic construct
SEQUENCE: 696
QVQLQESGGG LVQPGGSLRL SCSASGFSMD YYAIAWFRQA PGKEREEISC ITGSDFMVDT  60
YYVASVKGRF TISRDNAKNT AHLQMNSLKP EDTGVYFCAV RSTANTLCPS HYSVMDYWGK  120
GTQVTVSSAA AYPYDVPDYG SHHHHHH                                     147

SEQ ID NO: 697          moltype = AA  length = 139
FEATURE                 Location/Qualifiers
REGION                  1..139
                        note = Synthetic polymer
source                  1..139
                        mol_type = protein
                        organism = synthetic construct
SEQUENCE: 697
QVQLQESGGG LVQAGGSLRL SCAASGGFNR VSYMGWYRQA PGTKRELVAS VTSGGEITIA  60
DSVKGRFTVS RDNSKNTLYL QMNGLKPEDG ATYWCNADIW VSDARMYNYW GQGTQVTVSS  120
AAAYPYDVPD YGSHHHHHH                                              139

SEQ ID NO: 698          moltype = AA  length = 139
FEATURE                 Location/Qualifiers
```

```
REGION                  1..139
                        note = Synthetic polymer
source                  1..139
                        mol_type = protein
                        organism = synthetic construct
SEQUENCE: 698
QVQLQESGGG LVQTGESLRL SCAASGGFNR VSYMGWYRQA PGSKRELVAS VTSGGEITVA  60
DSVKGRFTVS RDNNKNTLYL QMNGLKPEDG ATYWCNADIW VSDARMYNYW GQGTQVTVSS  120
AAAYPYDVPD YGSHHHHHH                                               139

SEQ ID NO: 699          moltype = AA  length = 139
FEATURE                 Location/Qualifiers
REGION                  1..139
                        note = Synthetic polymer
source                  1..139
                        mol_type = protein
                        organism = synthetic construct
SEQUENCE: 699
QVQLQESGGG LVQTGESLRL SCAASGIIKS INFMGWYRQP PGTKRELVAS TTSDGRTTVA  60
DSVKGRFTIS RDNAKNTIYL EMSSLKPEDT ATYWCNADIW LPSDRMYNYW GQGTQVTVSS  120
AAAYPYDVPD YGSHHHHHH                                               139

SEQ ID NO: 700          moltype = AA  length = 139
FEATURE                 Location/Qualifiers
REGION                  1..139
                        note = Synthetic polymer
source                  1..139
                        mol_type = protein
                        organism = synthetic construct
SEQUENCE: 700
QVQLQESGGG LVQAGGSLRL SCAVSGFILD YYGIGWFRQA PGKEREAVSC ISSSDGSTYY  60
ADSVKGRFTI SRDNALNTLY LQMNSLKPED TAVYHCATAT LCDGGIWGYW GQGTQVTVSS  120
AAAYPYDVPD YGSHHHHHH                                               139

SEQ ID NO: 701          moltype = AA  length = 139
FEATURE                 Location/Qualifiers
REGION                  1..139
                        note = Synthetic polymer
source                  1..139
                        mol_type = protein
                        organism = synthetic construct
SEQUENCE: 701
QVQLQESGGG LAQAGGSLRL SCEGSGLSLD YDGVGWFRQA PGKEREAVSC ISSSDGSTYY  60
ADSVKGRFTI SRGNALNTLY LQMNSLKPED TAVYYCATAT LCDGGIWGYW GQGTQVTVSS  120
AAAYPYDVPD YGSHHHHHH                                               139

SEQ ID NO: 702          moltype = AA  length = 139
FEATURE                 Location/Qualifiers
REGION                  1..139
                        note = Synthetic polymer
source                  1..139
                        mol_type = protein
                        organism = synthetic construct
SEQUENCE: 702
QVQLQESGGG SVQPGGSLRL SCAVSGFILD YYGIGWFRQA PGKEREAVSC ISSSDGSTYY  60
ADSVKGRFTI SRDNALNTLY LQMNSLKPED TAVYYCATAT LCDGGIWGYW GQGTQVTVSS  120
AAAYPYDVPD YGSHHHHHH                                               139

SEQ ID NO: 703          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 703
QVQLQESGGG SVQAGDSLRL SCTASGRTFS SLGMGWFRQA PGKEREFVSA IAWNGASTYY  60
TESVKGRFTI SRDDAKNTVY LQMNSLKPTD TAVYFCAASG LGSVVVTANE YDYWGQGTQV  120
TVSSAAAYPY DVPDYGSHHH HHH                                          143

SEQ ID NO: 704          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 704
QVQLQESGGG SVQPGKSLRL SCAASGRTFS SLGMGWFRQA PGKEREFVSA IAWNGASTYY  60
```

```
TESVKGRFTI SRDDAKNTVY LQMNSLKPTD TAVYFCAASG LGSVVVTANE YDYWGQGTQV  120
TVSSAAAYPY DVPDYGSHHH HHH                                         143

SEQ ID NO: 705         moltype = AA  length = 141
FEATURE                Location/Qualifiers
REGION                 1..141
                       note = Synthetic polymer
source                 1..141
                       mol_type = protein
                       organism = synthetic construct
SEQUENCE: 705
QVQLQESGGG LVQPGGSLRL SCTTSGFAFG SYDMGWVRQA PGKGPEWVSG INSGGRITDY  60
ADSVTGRFTI SRDNAKNTLY LQMNSLKPED TAVYYCAQGD RSSWHYYGMD YWGKGTQVTV  120
SSAAAYPYDV PDYGSHHHHH H                                           141

SEQ ID NO: 706         moltype = AA  length = 139
FEATURE                Location/Qualifiers
REGION                 1..139
                       note = Synthetic polymer
SITE                   112
                       note = misc_feature - Xaa can be any naturally occurring
                        amino acid
source                 1..139
                       mol_type = protein
                       organism = synthetic construct
SEQUENCE: 706
QVQLQESGGG LVQPGGSLRL SCAASGFSFG NNDMSWVRQA PGKGPEWVSA INSGGGSTYY  60
ADSVKGRFTI SRDNAKNTLY LQMNSLKPED TAVYYCATKS DPMTNEYDLW GXGTQVTVSS  120
AAAYPYDVPD YGSHHHHHH                                              139

SEQ ID NO: 707         moltype = AA  length = 447
FEATURE                Location/Qualifiers
REGION                 1..447
                       note = Synthetic polymer
source                 1..447
                       mol_type = protein
                       organism = synthetic construct
SEQUENCE: 707
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 708         moltype = AA  length = 218
FEATURE                Location/Qualifiers
REGION                 1..218
                       note = Synthetic polymer
source                 1..218
                       mol_type = protein
                       organism = synthetic construct
SEQUENCE: 708
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 709         moltype = AA  length = 440
FEATURE                Location/Qualifiers
REGION                 1..440
                       note = Synthetic polymer
source                 1..440
                       mol_type = protein
                       organism = synthetic construct
SEQUENCE: 709
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                             440

SEQ ID NO: 710         moltype = AA  length = 214
FEATURE                Location/Qualifiers
```

```
REGION                  1..214
                        note = Synthetic polymer
source                  1..214
                        mol_type = protein
                        organism = synthetic construct
SEQUENCE: 710
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 711          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 711
EIVLTQSPSS LSASVGDRVT ITCSARSSVS YMHWYQQKPG KAPKLLIYRT SNLASGVPSR  60
FSGSGSGTDF TLTINSLQPE DFATYYCQQR SSFPLTFGGG TKLEIK                 106

SEQ ID NO: 712          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 712
EIVLTQSPSS LSASVGDRVT ITCSARSSVS YMHWFQQKPG KAPKLWIYRT SNLASGVPSR  60
FSGSGSGTDY TLTINSLQPE DFATYYCQQR SSFPLTFGGG TKLEIK                 106

SEQ ID NO: 713          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 713
EIVLTQSPSS LSASVGDRVT ITCSARSSVS YMHWFQQKPG KAPKLWIYRT SNLASGVPSR  60
FSGSGSGTDY CLTINSLQPE DFATYYCQQR SSFPLTFGGG TKLEIK                 106

SEQ ID NO: 714          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 714
EIVLTQSPSS LSASVGDRVT ITCSARSSVS YMHWFQQKPG KAPKLWIYRT SNLASGVPSR  60
FSGSGSGTSY CLTINSLQPE DFATYYCQQR SSFPLTFGGG TKLEIK                 106

SEQ ID NO: 715          moltype = AA  length = 117
FEATURE                 Location/Qualifiers
REGION                  1..117
                        note = Synthetic polymer
source                  1..117
                        mol_type = protein
                        organism = synthetic construct
SEQUENCE: 715
QVQLVQSGSE LKKPGASVKI SCKASGYSFS NYGMNWVRQA PGQGLQWMGW INTDSGESTY  60
AEEFKGRFVF SLDTSVSTAY LQITSLTAED TGMYFCAKVG YDALDYWGQG TLVTVSS     117

SEQ ID NO: 716          moltype = AA  length = 60
FEATURE                 Location/Qualifiers
REGION                  1..60
                        note = Synthetic polymer
source                  1..60
                        mol_type = protein
                        organism = synthetic construct
SEQUENCE: 716
QVQLVQSGSE LKKPGASVKI SCKASGYTFT NYGMNWVRQA PGQGLQWMGW INTDSGESTY  60

SEQ ID NO: 717          moltype = AA  length = 117
FEATURE                 Location/Qualifiers
REGION                  1..117
```

-continued

```
                        note = Synthetic polymer
source                  1..117
                        mol_type = protein
                        organism = synthetic construct
SEQUENCE: 717
QVQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 718          moltype = AA  length = 117
FEATURE                 Location/Qualifiers
REGION                  1..117
                        note = Synthetic polymer
source                  1..117
                        mol_type = protein
                        organism = synthetic construct
SEQUENCE: 718
QIQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 719          moltype = AA  length = 117
FEATURE                 Location/Qualifiers
REGION                  1..117
                        note = Synthetic polymer
source                  1..117
                        mol_type = protein
                        organism = synthetic construct
SEQUENCE: 719
QIQLVQSGSE LKKPGASVKI SCKASGYTFT NYGMNWVKQA PGQGLKWMGW INTDSGESTY  60
AEEFKGRFAF SLDTSVNTAY LQITSLNAED TGMYFCVRVG YDALDYWGQG TLVTVSS     117

SEQ ID NO: 720          moltype = AA  length = 254
FEATURE                 Location/Qualifiers
REGION                  1..254
                        note = Synthetic polymer
source                  1..254
                        mol_type = protein
                        organism = synthetic construct
SEQUENCE: 720
LFTVTVPKEL YIIEHGSNVT LECNFDTGSH VNLGAITASL QKVENDTSPH RERATLLEEQ  60
LPLGKASFHI PQVQVRDEGQ YQCIIIYGVA WDYKYLTLKV KASYRKINTH ILKVPETDEV  120
ELTCQATGYP LAEVSWPNVS VPANTSHSRT PEGLYQVTSV LRLKPPPGRN FSCVFWNTHV  180
RELTLASIDL QSQMEPRTHP TWLLHIFIPF CIIAFIFIAT VIALRKQLCQ KLYSSKDTTK  240
RPVTTTKREV NSAI                                                    254

SEQ ID NO: 721          moltype = AA  length = 453
FEATURE                 Location/Qualifiers
REGION                  1..453
                        note = Synthetic polymer
source                  1..453
                        mol_type = protein
                        organism = synthetic construct
SEQUENCE: 721
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT WEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                                453

SEQ ID NO: 722          moltype = AA  length = 29
FEATURE                 Location/Qualifiers
REGION                  1..29
                        note = Synthetic polymer
source                  1..29
                        mol_type = protein
                        organism = synthetic construct
SEQUENCE: 722
SNTSESFKSN TSESFFRVTQ LAPKAQIKE                                     29

SEQ ID NO: 723          moltype = AA  length = 119
FEATURE                 Location/Qualifiers
REGION                  1..119
                        note = Synthetic polymer
source                  1..119
                        mol_type = protein
                        organism = synthetic construct
SEQUENCE: 723
```

-continued

```
EVQLQQSGPV LVKPGASVKM SCKASGYTFT DYYMNWVKQS HGKSLEWIGN INPYNGGTTY  60
NQKFKGKATL TVDKSSRTAY MEINSLTSED SAVYYCARGR IYDGSLDYWG QGTALTVSS   119

SEQ ID NO: 724         moltype = AA  length = 106
FEATURE                Location/Qualifiers
REGION                 1..106
                       note = Synthetic polymer
source                 1..106
                       mol_type = protein
                       organism = synthetic construct
SEQUENCE: 724
DIQMTQFPSS LCASQGGKVT VTCKASQDIN NYMAWYQHKP GKGPRLLIHY TSTLLSGIPS  60
RFSGSGSGRD YSFSISNLEP EDIATYYCLQ YDNLWTFGGG TKLEIK                106

SEQ ID NO: 725         moltype = AA  length = 116
FEATURE                Location/Qualifiers
REGION                 1..116
                       note = Synthetic polymer
source                 1..116
                       mol_type = protein
                       organism = synthetic construct
SEQUENCE: 725
QVQLQQSGAE LAKPGASVRL SCKASGYTFT NYWMHWVKQR PGQGLEWIGH INPSSGFTTY  60
NQNFKDKATL TADKSSNTAY MQLSSLTYED SAVYFCARED YDVDYWGQGT TLTVSS     116

SEQ ID NO: 726         moltype = AA  length = 107
FEATURE                Location/Qualifiers
REGION                 1..107
                       note = Synthetic polymer
source                 1..107
                       mol_type = protein
                       organism = synthetic construct
SEQUENCE: 726
DIVMTQSQKF MSTSVGDRVS VTCKASQSVD TNVAWYQQKP GQSPKALIFS ASYRYSGVPD  60
RFTGSGSGTD FTLTINSVQS EDLAEYFCQQ YNSYPYTFGS GTKLEIK               107

SEQ ID NO: 727         moltype = AA  length = 122
FEATURE                Location/Qualifiers
REGION                 1..122
                       note = Synthetic polymer
source                 1..122
                       mol_type = protein
                       organism = synthetic construct
SEQUENCE: 727
EVQLVESGGG LVKPGGSLKL SCAASGFTFS DYGMHWVRQA PEKGLEWVAY ISSGSYTIYY  60
TDTVKGRFTI SRDNAKNTLF LQMTSLRSED TAMYYCARRG YGSFYEYYFD YWGQGTTLTV  120
SS                                                                122

SEQ ID NO: 728         moltype = AA  length = 106
FEATURE                Location/Qualifiers
REGION                 1..106
                       note = Synthetic polymer
source                 1..106
                       mol_type = protein
                       organism = synthetic construct
SEQUENCE: 728
QIVLTQSPAL MSASPGEKVT MTCSASSSVS YMYWYQQKPR SSPKPWIYLT SNLASGVPAR  60
FSGSGSGTSY SLTISSMEAE DAATYYCQQW SSNPFTFGSG TKLEIK                106

SEQ ID NO: 729         moltype = AA  length = 119
FEATURE                Location/Qualifiers
REGION                 1..119
                       note = Synthetic polymer
source                 1..119
                       mol_type = protein
                       organism = synthetic construct
SEQUENCE: 729
EVQLVESGGG LVQAGKSLRL SCAASGSIFS IHAMGWFRQA PGKEREFVAA ITWSGGITYY  60
EDSVKGRFTI SRDNAKNTVY LQMNSLKPED TAIYYCAADR AESSWYDYWG QGTQVTVSS   119

SEQ ID NO: 730         moltype = AA  length = 119
FEATURE                Location/Qualifiers
REGION                 1..119
                       note = Synthetic polymer
source                 1..119
                       mol_type = protein
                       organism = synthetic construct
SEQUENCE: 730
EVQLVESGGG LVQAGGSLRL SCAASGSIAS IHAMGWFRQA PGKEREFVAV ITWSGGITYY  60
```

```
ADSVKGRFTI SRDNAKNTVY LQMNSLKPED TAIYYCAGDK HQSSWYDYWG QGTQVTVSS   119

SEQ ID NO: 731         moltype = AA  length = 119
FEATURE                Location/Qualifiers
REGION                 1..119
                       note = Synthetic polymer
source                 1..119
                       mol_type = protein
                       organism = synthetic construct
SEQUENCE: 731
EVQLVESGGG LVQAGGSLRL SCAASGSISS IHAMGWFRQA PGKEREFVAA ITWSGGITYY  60
ADSLKGRFTI SRDNAKNTGY LQMNSLKPED TAIYYCAADR AQSSWYDYWG QGTQVTVSS   119

SEQ ID NO: 732         moltype = AA  length = 119
FEATURE                Location/Qualifiers
REGION                 1..119
                       note = Synthetic polymer
source                 1..119
                       mol_type = protein
                       organism = synthetic construct
SEQUENCE: 732
EVQLVESGGG LVQAGGSLGL SCAASGSIFS INAMAWFRQA PGKEREFVAL ISWSGGSTYY  60
EDSVKGRFTI SRDNAKNTVY LQMNSLKPED TAIYYCAADR VDSNWYDYWG QGTQVTVSS   119

SEQ ID NO: 733         moltype = AA  length = 120
FEATURE                Location/Qualifiers
REGION                 1..120
                       note = Synthetic polymer
source                 1..120
                       mol_type = protein
                       organism = synthetic construct
SEQUENCE: 733
EVQLVESGGG LVQAGGSLRL SCAASGRAFS SGTMGWFRRA PGKEREFVAS IPWSGGRIYY  60
ADSVKGRFTI SRDNAQNTVY LQMNSLKPED TAVYYCAVKE RSTGWDFASW GQCTQVTVSS  120

SEQ ID NO: 734         moltype = AA  length = 121
FEATURE                Location/Qualifiers
REGION                 1..121
                       note = Synthetic polymer
source                 1..121
                       mol_type = protein
                       organism = synthetic construct
SEQUENCE: 734
QVQLVQSGAE LKQPGASVKM SCKASGYSFT SSWIHWVKQA PGQGLEWIGY IYPSTGFTEY  60
NQKFKDRATL TADKSTSTAY MELSSLRSED SAVYYCARWR DSSGYHAMDY WGQGTSVTVS  120
S                                                                  121

SEQ ID NO: 735         moltype = AA  length = 121
FEATURE                Location/Qualifiers
REGION                 1..121
                       note = Synthetic polymer
source                 1..121
                       mol_type = protein
                       organism = synthetic construct
SEQUENCE: 735
QVQLVQSGAE VKQPGASVKM SCKASGYSFT SSWIHWVKQA PGQGLEWIGY IYPSTGFTEY  60
NQKFKDRATL TADKSTSTAY MELSSLRSED TAVYYCARWR DSSGYHAMDY WGQGTSVTVS  120
S                                                                  121

SEQ ID NO: 736         moltype = AA  length = 121
FEATURE                Location/Qualifiers
REGION                 1..121
                       note = Synthetic polymer
source                 1..121
                       mol_type = protein
                       organism = synthetic construct
SEQUENCE: 736
QVQLVQSGHE VKQPGASVKM SCKASGYSFT SSWIHWVKQA PGQGLEWIGY IYPSTGFTEY  60
NQKFKDRATL TADKSTSTAY MELSSLRSED TAVYYCARWR DSSGYHAMDY WGQGTLVTVS  120
S                                                                  121

SEQ ID NO: 737         moltype = AA  length = 121
FEATURE                Location/Qualifiers
REGION                 1..121
                       note = Synthetic polymer
source                 1..121
                       mol_type = protein
                       organism = synthetic construct
SEQUENCE: 737
```

-continued

```
QVQLVQSGHE VKQPGASVKM SCKASGYSFT SSWIHWVRQA PGQGLEWIGY IYPSTGFTEY  60
NQKFKDRATL TADKSTSTAY MELSSLRSED TAVYYCARWR DSSGYHAMDY WGQGTLVTVS  120
S                                                                 121

SEQ ID NO: 738          moltype = AA  length = 121
FEATURE                 Location/Qualifiers
REGION                  1..121
                        note = Synthetic polymer
source                  1..121
                        mol_type = protein
                        organism = synthetic construct
SEQUENCE: 738
QVQLVQSGHE VKQPGASVKV SCKASGYSFT SSWIHWVRQA PGQGLEWIGY IYPSTGFTEY  60
NQKFKDRATI TADKSTSTAY MELSSLRSED TAVYYCARWR DSSGYHAMDY WGQGTLVTVS  120
S                                                                 121

SEQ ID NO: 739          moltype = AA  length = 111
FEATURE                 Location/Qualifiers
REGION                  1..111
                        note = Synthetic polymer
source                  1..111
                        mol_type = protein
                        organism = synthetic construct
SEQUENCE: 739
DIVLTQSPAS LTLSPGQRLT ISCRASQSVS TSGYSYMHWY QQKPDQSPKL LIKFGSNLES  60
GIPARFSGSG SGTDFTLTIS SLEEEDFATY YCQHSWEIPY TFGQGTKLEI K          111

SEQ ID NO: 740          moltype = AA  length = 111
FEATURE                 Location/Qualifiers
REGION                  1..111
                        note = Synthetic polymer
source                  1..111
                        mol_type = protein
                        organism = synthetic construct
SEQUENCE: 740
DIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K          111

SEQ ID NO: 741          moltype = AA  length = 111
FEATURE                 Location/Qualifiers
REGION                  1..111
                        note = Synthetic polymer
source                  1..111
                        mol_type = protein
                        organism = synthetic construct
SEQUENCE: 741
EIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K          111

SEQ ID NO: 742          moltype = AA  length = 111
FEATURE                 Location/Qualifiers
REGION                  1..111
                        note = Synthetic polymer
source                  1..111
                        mol_type = protein
                        organism = synthetic construct
SEQUENCE: 742
DIVLTQSPAT LSLSPGQRLT ISCRASQSVS TSGYSYMHWY QQKPDQSPKL LIKFGSNLES  60
GIPARFSGSG SGTDFTLTIS SLEPEDFAVY YCQHSWEIPY TFGQGTKLEI K          111

SEQ ID NO: 743          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 743
GFTLDYYAIG                                                        10

SEQ ID NO: 744          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 744
GTIFSINHMD                                                        10
```

```
SEQ ID NO: 745          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 745
GFTFDDYGMS                                                            10

SEQ ID NO: 746          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 746
GFTLDYYAIN                                                            10

SEQ ID NO: 747          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 747
GTIFSINRMD                                                            10

SEQ ID NO: 748          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 748
GFTFSSYGMS                                                            10

SEQ ID NO: 749          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 749
GKIFSGNDMG                                                            10

SEQ ID NO: 750          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 750
GTIFSINRMD                                                            10

SEQ ID NO: 751          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 751
GFTFSSYGMS                                                            10

SEQ ID NO: 752          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 752
```

-continued

```
GFTFNDYAMS                                                              10

SEQ ID NO: 753          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 753
GFNLDPYAIA                                                              10

SEQ ID NO: 754          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 754
GFTFTAYAMS                                                              10

SEQ ID NO: 755          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 755
GFTFDYYAIG                                                              10

SEQ ID NO: 756          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 756
GFNLDPYAIA                                                              10

SEQ ID NO: 757          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 757
GTIFSINRMD                                                              10

SEQ ID NO: 758          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 758
GTIFSINRMD                                                              10

SEQ ID NO: 759          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 759
GFTFSSYGMS                                                              10

SEQ ID NO: 760          moltype = AA  length = 10
FEATURE                 Location/Qualifiers
REGION                  1..10
                        note = Synthetic polymer
source                  1..10
                        mol_type = protein
                        organism = synthetic construct
```

```
SEQUENCE: 760
GFNLDPYAIG                                                      10

SEQ ID NO: 761          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 761
GFNLDPYAIA                                                      10

SEQ ID NO: 762          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 762
ESIFSIEAMG                                                      10

SEQ ID NO: 763          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 763
GKIFSGNDMG                                                      10

SEQ ID NO: 764          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 764
GFTLDYYAIG                                                      10

SEQ ID NO: 765          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 765
GFTFSSYGMS                                                      10

SEQ ID NO: 766          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 766
GTIFSINRMD                                                      10

SEQ ID NO: 767          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 767
GFTFSSYGMS                                                      10

SEQ ID NO: 768          moltype = AA  length = 10
FEATURE                 Location/Qualifiers
REGION                  1..10
                        note = Synthetic polymer
source                  1..10
                        mol_type = protein
```

```
                        organism = synthetic construct
SEQUENCE: 768
GFNLDPYAIA                                                                  10

SEQ ID NO: 769          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 769
GRTFSISAMG                                                                  10

SEQ ID NO: 770          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 770
GFTLDYYAIN                                                                  10

SEQ ID NO: 771          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 771
GFTFSSYGMS                                                                  10

SEQ ID NO: 772          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 772
GFTFNDYAMS                                                                  10

SEQ ID NO: 773          moltype = AA  length = 10
FEATURE                 Location/Qualifiers
REGION                  1..10
                        note = Synthetic polymer
source                  1..10
                        mol_type = protein
                        organism = synthetic construct
SEQUENCE: 773
GFTLDYYAIG                                                                  10

SEQ ID NO: 774          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 774
ISSSDGSTY                                                                   9

SEQ ID NO: 775          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 775
ITSDGFPT                                                                    8

SEQ ID NO: 776          moltype = AA  length = 9
FEATURE                 Location/Qualifiers
REGION                  1..9
                        note = Synthetic polymer
source                  1..9
```

```
                        mol_type = protein
                        organism = synthetic construct
SEQUENCE: 776
IRWNGGSTN                                                                9

SEQ ID NO: 777          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 777
ISSSDGSTY                                                                9

SEQ ID NO: 778          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 778
ITSDGTPT                                                                 8

SEQ ID NO: 779          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 779
IDSGGGSTS                                                                9

SEQ ID NO: 780          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 780
ITSGGITD                                                                 8

SEQ ID NO: 781          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 781
ITSDGTPT                                                                 8

SEQ ID NO: 782          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 782
IDSGGGSTS                                                                9

SEQ ID NO: 783          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 783
IRSNGGYTN                                                                9

SEQ ID NO: 784          moltype = AA  length = 9
FEATURE                 Location/Qualifiers
REGION                  1..9
                        note = Synthetic polymer
```

```
source                  1..9
                        mol_type = protein
                        organism = synthetic construct
SEQUENCE: 784
ISSSDVGTY                                                                   9

SEQ ID NO: 785          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 785
INSSDGSTY                                                                   9

SEQ ID NO: 786          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 786
ISGSDSSTY                                                                   9

SEQ ID NO: 787          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 787
ISSSDVGTY                                                                   9

SEQ ID NO: 788          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 788
ITSDGTPT                                                                    8

SEQ ID NO: 789          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 789
ITSDGTPA                                                                    8

SEQ ID NO: 790          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 790
IDSGGGSTS                                                                   9

SEQ ID NO: 791          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 791
ISSGDGSKY                                                                   9

SEQ ID NO: 792          moltype = AA  length = 9
FEATURE                 Location/Qualifiers
REGION                  1..9
```

```
                        note = Synthetic polymer
source                  1..9
                        mol_type = protein
                        organism = synthetic construct
SEQUENCE: 792
ISSSDVGTY                                                        9

SEQ ID NO: 793          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 793
IFGGGFTN                                                         8

SEQ ID NO: 794          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 794
ITSGGITD                                                         8

SEQ ID NO: 795          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 795
ISSSDGSTY                                                        9

SEQ ID NO: 796          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 796
IDSGGGSTS                                                        9

SEQ ID NO: 797          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 797
ITSDGTPT                                                         8

SEQ ID NO: 798          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 798
IDSGGGSTS                                                        9

SEQ ID NO: 799          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 799
ISSSDVGTY                                                        9

SEQ ID NO: 800          moltype = AA  length = 9
FEATURE                 Location/Qualifiers
```

```
REGION                  1..9
                        note = Synthetic polymer
source                  1..9
                        mol_type = protein
                        organism = synthetic construct
SEQUENCE: 800
ITWSGGSTS                                                    9

SEQ ID NO: 801          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 801
ISSSDGSTY                                                    9

SEQ ID NO: 802          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 802
IDSGGGSTS                                                    9

SEQ ID NO: 803          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 803
IRSNGGYTN                                                    9

SEQ ID NO: 804          moltype = AA  length = 9
FEATURE                 Location/Qualifiers
REGION                  1..9
                        note = Synthetic polymer
source                  1..9
                        mol_type = protein
                        organism = synthetic construct
SEQUENCE: 804
ISSSDGSTY                                                    9

SEQ ID NO: 805          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 805
DGWSSCRHGI NEYLYW                                            16

SEQ ID NO: 806          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 806
SSGVYNYW                                                     8

SEQ ID NO: 807          moltype = AA  length = 12
FEATURE                 Location/Qualifiers
REGION                  1..12
                        note = Synthetic polymer
source                  1..12
                        mol_type = protein
                        organism = synthetic construct
SEQUENCE: 807
QGYYCSGYGC PR                                                12

SEQ ID NO: 808          moltype = AA  length = 17
```

-continued

```
FEATURE                Location/Qualifiers
REGION                 1..17
                       note = Synthetic polymer
source                 1..17
                       mol_type = protein
                       organism = synthetic construct
SEQUENCE: 808
SGWRLCRPTD EYDYSYW                                                  17

SEQ ID NO: 809         moltype = AA  length = 8
FEATURE                Location/Qualifiers
REGION                 1..8
                       note = Synthetic polymer
source                 1..8
                       mol_type = protein
                       organism = synthetic construct
SEQUENCE: 809
SSGVYNYW                                                            8

SEQ ID NO: 810         moltype = AA  length = 14
FEATURE                Location/Qualifiers
REGION                 1..14
                       note = Synthetic polymer
source                 1..14
                       mol_type = protein
                       organism = synthetic construct
SEQUENCE: 810
QGYYCSGYGC SDYW                                                     14

SEQ ID NO: 811         moltype = AA  length = 7
FEATURE                Location/Qualifiers
REGION                 1..7
                       note = Synthetic polymer
source                 1..7
                       mol_type = protein
                       organism = synthetic construct
SEQUENCE: 811
RDRTIWW                                                             7

SEQ ID NO: 812         moltype = AA  length = 8
FEATURE                Location/Qualifiers
REGION                 1..8
                       note = Synthetic polymer
source                 1..8
                       mol_type = protein
                       organism = synthetic construct
SEQUENCE: 812
SSGVYNYW                                                            8

SEQ ID NO: 813         moltype = AA  length = 14
FEATURE                Location/Qualifiers
REGION                 1..14
                       note = Synthetic polymer
source                 1..14
                       mol_type = protein
                       organism = synthetic construct
SEQUENCE: 813
QGYYCSGYGC SDYW                                                     14

SEQ ID NO: 814         moltype = AA  length = 12
FEATURE                Location/Qualifiers
REGION                 1..12
                       note = Synthetic polymer
source                 1..12
                       mol_type = protein
                       organism = synthetic construct
SEQUENCE: 814
QGYYCSGYGC YP                                                       12

SEQ ID NO: 815         moltype = AA  length = 15
FEATURE                Location/Qualifiers
REGION                 1..15
                       note = Synthetic polymer
source                 1..15
                       mol_type = protein
                       organism = synthetic construct
SEQUENCE: 815
DGYYYCSDYP HPLYW                                                    15
```

-continued

```
SEQ ID NO: 816          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 816
DGWRDCTWSN EYAYW                                                    15

SEQ ID NO: 817          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 817
TGWRTCRGLN EYDYW                                                    15

SEQ ID NO: 818          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 818
DGYYYCSDYP HPLYW                                                    15

SEQ ID NO: 819          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 819
SSGVYNYW                                                            8

SEQ ID NO: 820          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 820
SSGVYNYW                                                            8

SEQ ID NO: 821          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 821
QGYYCSGYGC SDYW                                                     14

SEQ ID NO: 822          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 822
DGYYYCSDYP HPLYW                                                    15

SEQ ID NO: 823          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 823
DGYYYCSDYP HPLYW                                                    15
```

```
SEQ ID NO: 824          moltype = AA  length = 13
FEATURE                 Location/Qualifiers
REGION                  1..13
                        note = Synthetic polymer
source                  1..13
                        mol_type = protein
                        organism = synthetic construct
SEQUENCE: 824
DLVSGSSRLY DYW                                                      13

SEQ ID NO: 825          moltype = AA  length = 7
FEATURE                 Location/Qualifiers
REGION                  1..7
                        note = Synthetic polymer
source                  1..7
                        mol_type = protein
                        organism = synthetic construct
SEQUENCE: 825
RDRTIWW                                                             7

SEQ ID NO: 826          moltype = AA  length = 16
FEATURE                 Location/Qualifiers
REGION                  1..16
                        note = Synthetic polymer
source                  1..16
                        mol_type = protein
                        organism = synthetic construct
SEQUENCE: 826
DGWSSCRHGI NEYLYW                                                   16

SEQ ID NO: 827          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 827
QGYYCSGYGC SDYW                                                     14

SEQ ID NO: 828          moltype = AA  length = 8
FEATURE                 Location/Qualifiers
REGION                  1..8
                        note = Synthetic polymer
source                  1..8
                        mol_type = protein
                        organism = synthetic construct
SEQUENCE: 828
SSGVYNYW                                                            8

SEQ ID NO: 829          moltype = AA  length = 14
FEATURE                 Location/Qualifiers
REGION                  1..14
                        note = Synthetic polymer
source                  1..14
                        mol_type = protein
                        organism = synthetic construct
SEQUENCE: 829
QGYYCSGYGC SDYW                                                     14

SEQ ID NO: 830          moltype = AA  length = 15
FEATURE                 Location/Qualifiers
REGION                  1..15
                        note = Synthetic polymer
source                  1..15
                        mol_type = protein
                        organism = synthetic construct
SEQUENCE: 830
DGYYYCSDYP HPLYW                                                    15

SEQ ID NO: 831          moltype = AA  length = 18
FEATURE                 Location/Qualifiers
REGION                  1..18
                        note = Synthetic polymer
source                  1..18
                        mol_type = protein
                        organism = synthetic construct
SEQUENCE: 831
```

-continued

```
MGRTNYGVIY DPNMYNYW                                                18

SEQ ID NO: 832         moltype = AA  length = 17
FEATURE                Location/Qualifiers
REGION                 1..17
                       note = Synthetic polymer
source                 1..17
                       mol_type = protein
                       organism = synthetic construct
SEQUENCE: 832
SGWRLCRPTD EYDYLYW                                                 17

SEQ ID NO: 833         moltype = AA  length = 14
FEATURE                Location/Qualifiers
REGION                 1..14
                       note = Synthetic polymer
source                 1..14
                       mol_type = protein
                       organism = synthetic construct
SEQUENCE: 833
QGYYCSGYGC SDYW                                                    14

SEQ ID NO: 834         moltype = AA  length = 12
FEATURE                Location/Qualifiers
REGION                 1..12
                       note = Synthetic polymer
source                 1..12
                       mol_type = protein
                       organism = synthetic construct
SEQUENCE: 834
QGYYCSGYGC YP                                                      12

SEQ ID NO: 835         moltype = AA  length = 16
FEATURE                Location/Qualifiers
REGION                 1..16
                       note = Synthetic polymer
source                 1..16
                       mol_type = protein
                       organism = synthetic construct
SEQUENCE: 835
DGWSSCRHGI NEYLYW                                                  16

SEQ ID NO: 836         moltype = AA  length = 143
FEATURE                Location/Qualifiers
REGION                 1..143
                       note = Synthetic polymer
source                 1..143
                       mol_type = protein
                       organism = synthetic construct
SEQUENCE: 836
QVQLQESGGG LVQAGGSLRL SCAASGFTLD YYAIGWFRQA PGKEREEVSC ISSSDGSTYY  60
ADSVKGRFTI SRDNAKNTVN LQMNSLKPED TAVYYCATDG WSSCRHGINE YLYWGQGTQV  120
TVSSAAAYPY DVPDYGSHHH HHH                                          143

SEQ ID NO: 837         moltype = AA  length = 134
FEATURE                Location/Qualifiers
REGION                 1..134
                       note = Synthetic polymer
source                 1..134
                       mol_type = protein
                       organism = synthetic construct
SEQUENCE: 837
QVQLQESGGG LVQAGGSLRL SCTASGTIFS INHMDWFRQA PGKQRELVAL ITSDGFPTYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 838         moltype = AA  length = 138
FEATURE                Location/Qualifiers
REGION                 1..138
                       note = Synthetic polymer
source                 1..138
                       mol_type = protein
                       organism = synthetic construct
SEQUENCE: 838
QVQLQESGGG LVQPGGSLRL SCAASGFTFD DYGMSWVRQA PGKGLEWVSA IRWNGGSTNY  60
ADSVKGRFTI SRDNAKNTLY LQMNSLKSED TAVYYCAQGY YCSGYGCPRG QGTQVTVSSA  120
AAYPYDVPDY GSHHHHHH                                                138

SEQ ID NO: 839         moltype = AA  length = 144
```

```
FEATURE                Location/Qualifiers
REGION                 1..144
                       note = Synthetic polymer
source                 1..144
                       mol_type = protein
                       organism = synthetic construct
SEQUENCE: 839
QVQLQESGGG LVQPGGSLRL SCAASGFTLD YYAINWFRQA PGKEREEVSC ISSSDGSTYY  60
ADSVKGRFTI SRDNAKNTVY LQMNSLKPED TAVYYCATSG WRLCRPTDEY DYSYWGQGTQ  120
VTVSSAAAYP YDVPDYGSHH HHHH                                         144

SEQ ID NO: 840         moltype = AA  length = 134
FEATURE                Location/Qualifiers
REGION                 1..134
                       note = Synthetic polymer
source                 1..134
                       mol_type = protein
                       organism = synthetic construct
SEQUENCE: 840
QVQLQESGGG VVQAGGSLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 841         moltype = AA  length = 140
FEATURE                Location/Qualifiers
REGION                 1..140
                       note = Synthetic polymer
source                 1..140
                       mol_type = protein
                       organism = synthetic construct
SEQUENCE: 841
QVQLQESGGG LVQTGGSLRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 842         moltype = AA  length = 133
FEATURE                Location/Qualifiers
REGION                 1..133
                       note = Synthetic polymer
source                 1..133
                       mol_type = protein
                       organism = synthetic construct
SEQUENCE: 842
QVQLQESGGG LVQPGGSLRL SCAASGKIFS GNDMGWYRQA PGKQRELVGI ITSGGITDYA  60
DAVKGRFTIS RDNAKNMMYL QMNSLKPEDT AVYYCNMRDR TIWWGQGTQV TVSSAAAYPY  120
DVPDYGSHHH HHH                                                     133

SEQ ID NO: 843         moltype = AA  length = 134
FEATURE                Location/Qualifiers
REGION                 1..134
                       note = Synthetic polymer
source                 1..134
                       mol_type = protein
                       organism = synthetic construct
SEQUENCE: 843
QVQLQESGGG SVQAGGSLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 844         moltype = AA  length = 140
FEATURE                Location/Qualifiers
REGION                 1..140
                       note = Synthetic polymer
source                 1..140
                       mol_type = protein
                       organism = synthetic construct
SEQUENCE: 844
QVQLQESGGG LVQPGGSLRL SCAASGFTFS SYGMSWVRQT PGKGPEWVSA IDSGGGSTSY  60
ADSVKGRFTT SRDNAKNTLY LQMNSLKPED TAVYYCAQGY YCSGYGCSDY WGQGTQVTVS  120
SAAAYPYDVP DYGSHHHHHH                                              140

SEQ ID NO: 845         moltype = AA  length = 138
FEATURE                Location/Qualifiers
REGION                 1..138
                       note = Synthetic polymer
source                 1..138
                       mol_type = protein
                       organism = synthetic construct
SEQUENCE: 845
```

-continued

```
QVQLQESGGG LVQPGGSLRL SCAASGFTFN DYAMSWVRQA PGKGLEWVSG IRSNGGYTNY  60
ADSVKGRFTI SRDNAKNTLY LQMNSLKSED TAVYYCAQGY YCSGYGCYPG QGTQVTVSSA  120
AAYPYDVPDY GSHHHHHH                                                138

SEQ ID NO: 846         moltype = AA  length = 142
FEATURE                Location/Qualifiers
REGION                 1..142
                       note = Synthetic polymer
source                 1..142
                       mol_type = protein
                       organism = synthetic construct
SEQUENCE: 846
QVQLQESGGG LVQAGGSLRL SCAASGFNLD PYAIAWFRQA PGKEREEVSC ISSSDVGTYY  60
ADSVKGRFTI SRDNAKKTVY LQMNSLKPED TAVYYCATDG YYYCSDYPHP LYWGQGTQVT  120
VSSAAAYPYD VPDYGSHHHH HH                                           142

SEQ ID NO: 847         moltype = AA  length = 142
FEATURE                Location/Qualifiers
REGION                 1..142
                       note = Synthetic polymer
source                 1..142
                       mol_type = protein
                       organism = synthetic construct
SEQUENCE: 847
QVQLQESGGG LVQPGGSLRL SCAASGFTFT AYAMSWFRQA PGKEREEVSC INSSDGSTYY  60
ADSVKGRFTI SRDNAKNTVY LQMNSLKPED TAVYHCATDG WRDCTWSNEY AYWGQGTQVT  120
VSSAAAYPYD VPDYGSHHHH HH                                           142

SEQ ID NO: 848         moltype = AA  length = 142
FEATURE                Location/Qualifiers
REGION                 1..142
                       note = Synthetic polymer
source                 1..142
                       mol_type = protein
                       organism = synthetic construct
SEQUENCE: 848
QVQLQESGGG LVQPGGSLRL SCAASGFTFD YYAIGWFRQA PGKEREEVSC ISGSDSSTYY  60
ADSVKGRFTI VRDNAQNTVY LQMNSLKPED TAIYYCAVTG WRTCRGLNEY DYWGQGTQVT  120
VSSAAAYPYD VPDYGSHHHH HH                                           142

SEQ ID NO: 849         moltype = AA  length = 142
FEATURE                Location/Qualifiers
REGION                 1..142
                       note = Synthetic polymer
source                 1..142
                       mol_type = protein
                       organism = synthetic construct
SEQUENCE: 849
QVQLQESGGG LVQPGGSLRL SCAASGFNLD PYAIAWFRQA PGKEREEVSC ISSSDVGTYY  60
ADSVKGRFTI SRDNTKKTVY LQMNSLKPED TAVYYCATDG YYYCSDYPHP LYWGQGTQVT  120
VSSAAAYPYD VPDYGSHHHH HH                                           142

SEQ ID NO: 850         moltype = AA  length = 134
FEATURE                Location/Qualifiers
REGION                 1..134
                       note = Synthetic polymer
source                 1..134
                       mol_type = protein
                       organism = synthetic construct
SEQUENCE: 850
QVQLQESGGG LVQAGESLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 851         moltype = AA  length = 134
FEATURE                Location/Qualifiers
REGION                 1..134
                       note = Synthetic polymer
source                 1..134
                       mol_type = protein
                       organism = synthetic construct
SEQUENCE: 851
QVQLQESGGG LVQAGGSLRL SCTASGTIFS INRMDWFRQA PGKQRELVAL ITSDGTPAYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 852         moltype = AA  length = 140
FEATURE                Location/Qualifiers
REGION                 1..140
```

-continued

```
                        note = Synthetic polymer
source                  1..140
                        mol_type = protein
                        organism = synthetic construct
SEQUENCE: 852
QVQLQESGGG LVQSGGSLRL SCKTSGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 853          moltype = AA  length = 142
FEATURE                 Location/Qualifiers
REGION                  1..142
                        note = Synthetic polymer
source                  1..142
                        mol_type = protein
                        organism = synthetic construct
SEQUENCE: 853
QVQLQESGGG LVQPGGSLRL SCAASGFNLD PYAIGWFRQA PGKEREEVSC ISSGDGSKYY  60
ADSVKGRFTM SRDNAKKTVY LQMNSLKPED TAVYYCATDG YYYCSDYPHP LYWGQGTQVT  120
VSSAAAYPYD VPDYGSHHHH HH                                           142

SEQ ID NO: 854          moltype = AA  length = 142
FEATURE                 Location/Qualifiers
REGION                  1..142
                        note = Synthetic polymer
source                  1..142
                        mol_type = protein
                        organism = synthetic construct
SEQUENCE: 854
QVQLQESGGG LVQPGGSLRL SCAVSGFNLD PYAIAWFRQA PGKEREEVSC ISSSDVGTYY  60
ADSVKGRFTI SRDNAKKTVY LQMNSLKPED TAVYYCATDG YYYCSDYPHP LYWGQGTQVT  120
VSSAAAYPYD VPDYGSHHHH HH                                           142

SEQ ID NO: 855          moltype = AA  length = 139
FEATURE                 Location/Qualifiers
REGION                  1..139
                        note = Synthetic polymer
source                  1..139
                        mol_type = protein
                        organism = synthetic construct
SEQUENCE: 855
QVQLQESGGG LVQAGGSLRL SCAASESIFS IEAMGWYRQA PGKQRELVAA IFGGGFTNYA  60
DSVKGRFTIS RDNANRTVYL QMNSLKPEDT AVYYCNADLV SGSSRLYDYW GQGTQVTVSS  120
AAAYPYDVPD YGSHHHHHH                                               139

SEQ ID NO: 856          moltype = AA  length = 133
FEATURE                 Location/Qualifiers
REGION                  1..133
                        note = Synthetic polymer
source                  1..133
                        mol_type = protein
                        organism = synthetic construct
SEQUENCE: 856
QVQLQESGGG LVQAGGSLRL SCAASGKIFS GNDMGWYRQA PGKQRELVGI ITSGGITDYA  60
DAVKGRFTIS RDNAKNMMYL QMNSLKPEDT AVYYCNMRDR TIWWGQGTQV TVSSAAAYPY  120
DVPDYGSHHH HHH                                                     133

SEQ ID NO: 857          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 857
QVQLQESGGG LVQPGGSLRL SCAASGFTLD YYAIGWFRQA PGKEREEVSC ISSSDGSTYY  60
ADSVKGRFTI SRDNAKNTVN LQMNSLKPED TAVYYCATDG WSSCRHGINE YLYWGQGTQV  120
TVSSAAAYPY DVPDYGSHHH HHH                                          143

SEQ ID NO: 858          moltype = AA  length = 140
FEATURE                 Location/Qualifiers
REGION                  1..140
                        note = Synthetic polymer
source                  1..140
                        mol_type = protein
                        organism = synthetic construct
SEQUENCE: 858
QVQLQESGGG LVQAGGSLRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
```

```
SAAAYPYDVP DYGSHHHHHH                                              140

SEQ ID NO: 859         moltype = AA  length = 134
FEATURE                Location/Qualifiers
REGION                 1..134
                       note = Synthetic polymer
source                 1..134
                       mol_type = protein
                       organism = synthetic construct
SEQUENCE: 859
QVQLQESGGG LVQPGGSLRL SCTASGTIFS INRMDWFRQA PGKQRELVAL ITSDGTPTYA  60
DSAKGRFTIS RDNTKKTVSL QMNSLKPEDT AVYYCHVSSG VYNYWGQGTQ VTVSSAAAYP  120
YDVPDYGSHH HHHH                                                    134

SEQ ID NO: 860         moltype = AA  length = 140
FEATURE                Location/Qualifiers
REGION                 1..140
                       note = Synthetic polymer
source                 1..140
                       mol_type = protein
                       organism = synthetic construct
SEQUENCE: 860
QVQLQESGGG LVQPGGSLRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 861         moltype = AA  length = 142
FEATURE                Location/Qualifiers
REGION                 1..142
                       note = Synthetic polymer
source                 1..142
                       mol_type = protein
                       organism = synthetic construct
SEQUENCE: 861
QVQLQESGGG LVQPGGSLRL SCAASGFNLD PYAIAWFRQA PGKEREEVSC ISSSDVGTYY  60
ADSVKGRFTI SRDNAKKTVY LQMNSLKPED TAVYYCATDG YYYCSDYPHP LYWGQGTQVT  120
VSSAAAYPYD VPDYGSHHHH HH                                           142

SEQ ID NO: 862         moltype = AA  length = 145
FEATURE                Location/Qualifiers
REGION                 1..145
                       note = Synthetic polymer
SITE                   13
                       note = misc_feature - Xaa can be any naturally occurring
                        amino acid
source                 1..145
                       mol_type = protein
                       organism = synthetic construct
SEQUENCE: 862
QVQLQESGGG LVXAGGSLRL SCAASGRTFS ISAMGWFRQA PGKEREFVAA ITWSGGSTSY  60
TDSVKGRFTI SRDNAKNTLY LQMNSLKPED TAIYYCAAMG RTNYGVIYDP NMYNYWGQGT  120
QVTVSSAAAY PYDVPDYGSH HHHHH                                        145

SEQ ID NO: 863         moltype = AA  length = 144
FEATURE                Location/Qualifiers
REGION                 1..144
                       note = Synthetic polymer
source                 1..144
                       mol_type = protein
                       organism = synthetic construct
SEQUENCE: 863
QVQLQESGGG LVQPGGSLRL SCAASGFTLD YYAINWFRQA PGKEREEVSC ISSSDGSTYY  60
ADSVKGRFTI SRDNAKNTVY LQMNSLKPED TAVYYCATSG WRLCRPTDEY DYLYWGQGTQ  120
VTVSSAAAYP YDVPDYGSHH HHHH                                         144

SEQ ID NO: 864         moltype = AA  length = 140
FEATURE                Location/Qualifiers
REGION                 1..140
                       note = Synthetic polymer
source                 1..140
                       mol_type = protein
                       organism = synthetic construct
SEQUENCE: 864
QVQLQESGGG LVQAGGSMRL SCAASGFTFS SYGMSWVRQT PGKGPEWVSA IDSGGGSTSY  60
ADSVKGRFTI SRDNAKNTLY LQMNSLKPED TAVYYCAQGY YCSGYGCSDY WGQGTQVTVS  120
SAAAYPYDVP DYGSHHHHHH                                              140

SEQ ID NO: 865         moltype = AA  length = 138
FEATURE                Location/Qualifiers
```

```
REGION                  1..138
                        note = Synthetic polymer
source                  1..138
                        mol_type = protein
                        organism = synthetic construct
SEQUENCE: 865
QVQLQESGGG TVQAGGSLRL SCAASGFTFN DYAMSWVRQA PGKGLEWVSG IRSNGGYTNY  60
ADSVKGRFTI SRDNAKNTLY LQMNSLKSED TAVYYCAQGY YCSGYGCYPG QGTQVTVSSA  120
AAYPYDVPDY GSHHHHHH                                                138

SEQ ID NO: 866          moltype = AA  length = 143
FEATURE                 Location/Qualifiers
REGION                  1..143
                        note = Synthetic polymer
source                  1..143
                        mol_type = protein
                        organism = synthetic construct
SEQUENCE: 866
QVQLQESGGG LVQPGTSLRL SCAASGFTLD YYAIGWFRQA PGKEREEVSC ISSSDGSTYY  60
ADSVKGRFTI SRDNAKNTVN LQMNSLKPED TAVYYCATDG WSSCRHGINE YLYWGQGTQV  120
TVSSAAAYPY DVPDYGSHHH HHH                                          143

SEQ ID NO: 867          moltype = AA  length = 451
FEATURE                 Location/Qualifiers
REGION                  1..451
                        note = Synthetic polymer
source                  1..451
                        mol_type = protein
                        organism = synthetic construct
SEQUENCE: 867
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                  451

SEQ ID NO: 868          moltype = AA  length = 215
FEATURE                 Location/Qualifiers
REGION                  1..215
                        note = Synthetic polymer
source                  1..215
                        mol_type = protein
                        organism = synthetic construct
SEQUENCE: 868
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 869          moltype = AA  length = 121
FEATURE                 Location/Qualifiers
REGION                  1..121
                        note = Synthetic polymer
source                  1..121
                        mol_type = protein
                        organism = synthetic construct
SEQUENCE: 869
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 870          moltype = AA  length = 108
FEATURE                 Location/Qualifiers
REGION                  1..108
                        note = Synthetic polymer
source                  1..108
                        mol_type = protein
                        organism = synthetic construct
SEQUENCE: 870
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK               108

SEQ ID NO: 871          moltype = AA  length = 448
FEATURE                 Location/Qualifiers
REGION                  1..448
                        note = Synthetic polymer
```

```
source                  1..448
                        mol_type = protein
                        organism = synthetic construct
SEQUENCE: 871
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 872          moltype = AA  length = 214
FEATURE                 Location/Qualifiers
REGION                  1..214
                        note = Synthetic polymer
source                  1..214
                        mol_type = protein
                        organism = synthetic construct
SEQUENCE: 872
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 873          moltype = AA  length = 450
FEATURE                 Location/Qualifiers
REGION                  1..450
                        note = Synthetic polymer
source                  1..450
                        mol_type = protein
                        organism = synthetic construct
SEQUENCE: 873
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 874          moltype = AA  length = 216
FEATURE                 Location/Qualifiers
REGION                  1..216
                        note = Synthetic polymer
source                  1..216
                        mol_type = protein
                        organism = synthetic construct
SEQUENCE: 874
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 875          moltype = AA  length = 123
FEATURE                 Location/Qualifiers
REGION                  1..123
                        note = Synthetic polymer
source                  1..123
                        mol_type = protein
                        organism = synthetic construct
SEQUENCE: 875
QVQLVQSGAE VKKPGSSVKV SCKTSGDTFS TYAISWVRQA PGQGLEWMGG IIPIFGKAHY  60
AQKFQGRVTI TADESTSTAY MELSSLRSED TAVYFCARKF HFVSGSPFGM DVWGQGTTVT  120
VSS                                                               123

SEQ ID NO: 876          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 876
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106
```

```
SEQ ID NO: 877          moltype = AA  length = 117
FEATURE                 Location/Qualifiers
REGION                  1..117
                        note = Synthetic polymer
source                  1..117
                        mol_type = protein
                        organism = synthetic construct
SEQUENCE: 877
QVQLVQSGAE VKKPGASVKV SCKASGYTFT DYGFSWVRQA PGQGLEWMGW ITAYNGNTNY  60
AQKLQGRVTM TTDTSTSTVY MELRSLRSDD TAVYYCARDY FYGMDVWGQG TTVTVSS     117

SEQ ID NO: 878          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 878
EIVLTQSPAT LSLSPGERAT LSCRASQSVS SYLVWYQQKP GQAPRLLIYD ASNRATGIPA  60
RFSGSGSGTD FTLTISSLEP EDFAVYYCQQ RSNWPRTFGQ GTKVEIK                107

SEQ ID NO: 879          moltype = AA  length = 118
FEATURE                 Location/Qualifiers
REGION                  1..118
                        note = Synthetic polymer
source                  1..118
                        mol_type = protein
                        organism = synthetic construct
SEQUENCE: 879
QVQLVQSGAE VKKPGASVKV SCKASGYTFT SYDVHWVRQA PGQRLEWMGW LHADTGITKF  60
SQKFQGRVTI TRDTSASTAY MELSSLRSED TAVYYCARER IQLWFDYWGQ GTLVTVSS    118

SEQ ID NO: 880          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 880
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK                107

SEQ ID NO: 881          moltype = AA  length = 120
FEATURE                 Location/Qualifiers
REGION                  1..120
                        note = Synthetic polymer
source                  1..120
                        mol_type = protein
                        organism = synthetic construct
SEQUENCE: 881
QVQLVQSGAE VKKPGSSVKV SCKVSGGIFS TYAINWVRQA PGQGLEWMGG IIPIFGTANH  60
AQKFQGRVTI TADESTSTAY MELSSLRSED TAVYYCARDQ GIAAALFDYW GQGTLVTVSS  120

SEQ ID NO: 882          moltype = AA  length = 108
FEATURE                 Location/Qualifiers
REGION                  1..108
                        note = Synthetic polymer
source                  1..108
                        mol_type = protein
                        organism = synthetic construct
SEQUENCE: 882
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK               108

SEQ ID NO: 883          moltype = AA  length = 113
FEATURE                 Location/Qualifiers
REGION                  1..113
                        note = Synthetic polymer
source                  1..113
                        mol_type = protein
                        organism = synthetic construct
SEQUENCE: 883
EVQLVESGGG LVQPGRSLRL SCAVSGFTFD DYVVHWVRQA PGKGLEWVSG ISGNSGNIGY  60
ADSVKGRFTI SRDNAKNSLY LQMNSLRAED TALYYCAVPF DYWGQGTLVT VSS         113

SEQ ID NO: 884          moltype = AA  length = 107
FEATURE                 Location/Qualifiers
```

```
REGION                  1..107
                        note = Synthetic polymer
source                  1..107
                        mol_type = protein
                        organism = synthetic construct
SEQUENCE: 884
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK               107

SEQ ID NO: 885          moltype = AA  length = 123
FEATURE                 Location/Qualifiers
REGION                  1..123
                        note = Synthetic polymer
source                  1..123
                        mol_type = protein
                        organism = synthetic construct
SEQUENCE: 885
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HFVSGSPFGM DVWGQGTTVT  120
VSS                                                               123

SEQ ID NO: 886          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 886
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 887          moltype = AA  length = 123
FEATURE                 Location/Qualifiers
REGION                  1..123
                        note = Synthetic polymer
source                  1..123
                        mol_type = protein
                        organism = synthetic construct
SEQUENCE: 887
QVQLVQSGAE VKKPGSSVKV SCKTSGGTFS SYAISWVRQA PGQGLEWMGG IIPIFGKAHY  60
AQKFQGRVTI TADESTTTAY MELSSLRSED TAVYYCARKY DYVSGSPFGM DVWGQGTTVT  120
VSS                                                               123

SEQ ID NO: 888          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 888
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 889          moltype = AA  length = 121
FEATURE                 Location/Qualifiers
REGION                  1..121
                        note = Synthetic polymer
source                  1..121
                        mol_type = protein
                        organism = synthetic construct
SEQUENCE: 889
QVQLVQSGAE VKKPGSSVKV SCKASGGTFS SYAINWVRQA PGQGLEWMGG IIPIFGSANY  60
AQKFQDRVTI TADESTSAAY MELSSLRSED TAVYYCARDS SGWSRYYMDV WGQGTTVTVS  120
S                                                                 121

SEQ ID NO: 890          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 890
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPFGGG TKVEIK                106

SEQ ID NO: 891          moltype = AA  length = 123
```

-continued

```
FEATURE                Location/Qualifiers
REGION                 1..123
                       note = Synthetic polymer
source                 1..123
                       mol_type = protein
                       organism = synthetic construct
SEQUENCE: 891
QVQLVQSGAE VKEPGSSVKV SCKASGGTFN SYAISWVRQA PGQGLEWMGG IIPLFGIAHY  60
AQKFQGRVTI TADESTNTAY MDLSSLRSED TAVYYCARKY SYVSGSPFGM DVWGQGTTVT  120
VSS                                                                123

SEQ ID NO: 892         moltype = AA  length = 106
FEATURE                Location/Qualifiers
REGION                 1..106
                       note = Synthetic polymer
source                 1..106
                       mol_type = protein
                       organism = synthetic construct
SEQUENCE: 892
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TRLEIK                 106

SEQ ID NO: 893         moltype = AA  length = 121
FEATURE                Location/Qualifiers
REGION                 1..121
                       note = Synthetic polymer
source                 1..121
                       mol_type = protein
                       organism = synthetic construct
SEQUENCE: 893
EVQLVESGGG LVQPGRSLRL SCAASGITFD DYGMHWVRQA PGKGLEWVSG ISWNRGRIEY  60
ADSVKGRFTI SRDNAKNSLY LQMNSLRAED TALYYCAKGR FRYFDWFLDY WGQGTLVTVS  120
S                                                                  121

SEQ ID NO: 894         moltype = AA  length = 107
FEATURE                Location/Qualifiers
REGION                 1..107
                       note = Synthetic polymer
source                 1..107
                       mol_type = protein
                       organism = synthetic construct
SEQUENCE: 894
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPFTFGP GTKVDIK                107

SEQ ID NO: 895         moltype = AA  length = 118
FEATURE                Location/Qualifiers
REGION                 1..118
                       note = Synthetic polymer
source                 1..118
                       mol_type = protein
                       organism = synthetic construct
SEQUENCE: 895
EVKLQESGPS LVKPSQTLSL TCSVTGYSIT SDYWNWIRKF PGNKLEYVGY ISYTGSTYYN  60
PSLKSRISIT RDTSKNQYYL QLNSVTSEDT ATYYCARYGG WLSPFDYWGQ GTTLTVSS    118

SEQ ID NO: 896         moltype = AA  length = 107
FEATURE                Location/Qualifiers
REGION                 1..107
                       note = Synthetic polymer
source                 1..107
                       mol_type = protein
                       organism = synthetic construct
SEQUENCE: 896
DIVMTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK                107

SEQ ID NO: 897         moltype = AA  length = 120
FEATURE                Location/Qualifiers
REGION                 1..120
                       note = Synthetic polymer
source                 1..120
                       mol_type = protein
                       organism = synthetic construct
SEQUENCE: 897
EVQLQESGPG LVAPSQSLSI TCTVSGFSLT TYSINWIRQP PGKGLEWLGV MWAGGGTNSN  60
SVLKSRLIIS KDNSKSQVFL KMNSLQTDDT ARYYCARYYG NSPYYAIDYW GQGTSVTVSS  120

SEQ ID NO: 898         moltype = AA  length = 107
```

```
FEATURE                Location/Qualifiers
REGION                 1..107
                       note = Synthetic polymer
source                 1..107
                       mol_type = protein
                       organism = synthetic construct
SEQUENCE: 898
DIVTTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK                107

SEQ ID NO: 899         moltype = AA  length = 118
FEATURE                Location/Qualifiers
REGION                 1..118
                       note = Synthetic polymer
source                 1..118
                       mol_type = protein
                       organism = synthetic construct
SEQUENCE: 899
EVKLQESGPS LVKPSQTLSL TCSVTGYSII SDYWNWIRKF PGNKLEYLGY ISYTGSTYYN  60
PSLKSRISIT RDTSKNQYYL QLNSVTTEDT ATYYCARRGG WLLPFDYWGQ GTTLTVSS    118

SEQ ID NO: 900         moltype = AA  length = 113
FEATURE                Location/Qualifiers
REGION                 1..113
                       note = Synthetic polymer
source                 1..113
                       mol_type = protein
                       organism = synthetic construct
SEQUENCE: 900
DIVMTQSPSS LAVSVGEKVS MGCKSSQSLL YSSNQKNSLA WYQQKPGQSP KLLIDWASTR  60
ESGVPDRFTG SGSGTDFTLT ISSVKAEDLA VYYCQQYYGY PLTFGAGTKL ELK         113

SEQ ID NO: 901         moltype = AA  length = 118
FEATURE                Location/Qualifiers
REGION                 1..118
                       note = Synthetic polymer
source                 1..118
                       mol_type = protein
                       organism = synthetic construct
SEQUENCE: 901
EVKLQESGPS LVKPGASVKL SCKASGYTFT SYDINWVKQR PGQGLEWIGW IFPRDNNTKY  60
NENFKGKATL TVDTSSTTAY MELHSLTSED SAVYFCTKEN WVGDFDYWGQ GTTLTLSS    118

SEQ ID NO: 902         moltype = AA  length = 106
FEATURE                Location/Qualifiers
REGION                 1..106
                       note = Synthetic polymer
source                 1..106
                       mol_type = protein
                       organism = synthetic construct
SEQUENCE: 902
DIVMTQSPAI MSASPGEKVT MTCSASSSIR YMHWYQQKPG TSPKRWISDT SKLTSGVPAR  60
FSGSGSGTSY ALTISSMEAE DAATYYCHQR SSYPWTFGGG TKLEIK                 106

SEQ ID NO: 903         moltype = AA  length = 114
FEATURE                Location/Qualifiers
REGION                 1..114
                       note = Synthetic polymer
source                 1..114
                       mol_type = protein
                       organism = synthetic construct
SEQUENCE: 903
EVQLQQSGPD LVTPGASVRI SCQASGYTFP DYYMNWVKQS HGKSLEWIGD IDPNYGGTTY  60
NQKFKGKAIL TVDRSSSTAY MELRSLTSED SAVYYCARGA LTDWGQGTSL TVSS        114

SEQ ID NO: 904         moltype = AA  length = 106
FEATURE                Location/Qualifiers
REGION                 1..106
                       note = Synthetic polymer
source                 1..106
                       mol_type = protein
                       organism = synthetic construct
SEQUENCE: 904
QIVLSQSPAI LSASPGEKVT MTCRASSSVS YIYWFQQKPG SSPKPWIYAT FNLASGVPAR  60
FSGSGSGTSY SLTISRVETE DAATYYCQQW SNNPLTFGAG TKLELK                 106

SEQ ID NO: 905         moltype = AA  length = 115
FEATURE                Location/Qualifiers
REGION                 1..115
```

```
                         note = Synthetic polymer
source                   1..115
                         mol_type = protein
                         organism = synthetic construct
SEQUENCE: 905
EVQLVQSGPE LKKPGASVKM SCKASGYTFT SYVMHWVKQA PGQRLEWIGY VNPFNDGTKY  60
NEMFKGRATL TSDKSTSTAY MELSSLRSED SAVYYCARQA WGYPWGQGTL VTVSS       115

SEQ ID NO: 906           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 906
EVQLVQSGAE VKKPGASVKM SCKASGYTFT SYVMHWVKQA PGQRLEWIGY VNPFNDGTKY  60
NEMFKGRATL TSDKSTSTAY MELSSLRSED TAVYYCARQA WGYPWGQGTL VTVSS       115

SEQ ID NO: 907           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 907
EVQLVQSGAE VKKPGASVKM SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 908           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 908
EVQLVQSGAE VKKPGASVKV SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 909           moltype = AA  length = 115
FEATURE                  Location/Qualifiers
REGION                   1..115
                         note = Synthetic polymer
source                   1..115
                         mol_type = protein
                         organism = synthetic construct
SEQUENCE: 909
EVQLVQSGAE VKKPGASVKV SCKASGYTFT SYVMHWVRQA PGQRLEWIGY VNPFNDGTKY  60
NEMFKGRATI TSDKSTSTAY MELSSLRSED TAVYYCARQA WGYPWGQGTL VTVSS       115

SEQ ID NO: 910           moltype = AA  length = 111
FEATURE                  Location/Qualifiers
REGION                   1..111
                         note = Synthetic polymer
source                   1..111
                         mol_type = protein
                         organism = synthetic construct
SEQUENCE: 910
DIVLTQSPAS LALSPGERAT LSCRATESVE YYGTSLVQWY QQKPGQPPKL LIYAASSVDS  60
GVPSRFSGSG SGTDFTLTIN SLEEEDAAMY FCQQSRRVPY TFGQGTKLEI K           111

SEQ ID NO: 911           moltype = AA  length = 111
FEATURE                  Location/Qualifiers
REGION                   1..111
                         note = Synthetic polymer
source                   1..111
                         mol_type = protein
                         organism = synthetic construct
SEQUENCE: 911
DIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 912           moltype = AA  length = 111
FEATURE                  Location/Qualifiers
REGION                   1..111
                         note = Synthetic polymer
source                   1..111
```

```
                         mol_type = protein
                         organism = synthetic construct
SEQUENCE: 912
EIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 913           moltype = AA  length = 111
FEATURE                  Location/Qualifiers
REGION                   1..111
                         note = Synthetic polymer
source                   1..111
                         mol_type = protein
                         organism = synthetic construct
SEQUENCE: 913
DIVLTQSPAT LSLSPGERAT LSCRATESVE YYGTSLVQWY QQKPGQPPKL LIYAASSVDS  60
GVPSRFSGSG SGTDFTLTIN SLEAEDAATY FCQQSRRVPY TFGQGTKLEI K           111

SEQ ID NO: 914           moltype = AA  length = 120
FEATURE                  Location/Qualifiers
REGION                   1..120
                         note = Synthetic polymer
source                   1..120
                         mol_type = protein
                         organism = synthetic construct
SEQUENCE: 914
EVQLVESGGG LVKPGGSLRL SCAASGFTFS TYSMNWVRQA PGKGLEWVSS ISSSGDYIYY  60
ADSVKGRFTI SRDNAKNSLF LQMNSLKAED TAVYYCARDL VTSMVAFDYW GQGTLVTVSS  120

SEQ ID NO: 915           moltype = AA  length = 108
FEATURE                  Location/Qualifiers
REGION                   1..108
                         note = Synthetic polymer
source                   1..108
                         mol_type = protein
                         organism = synthetic construct
SEQUENCE: 915
SYELTQPPSV SVSPGQAARI TCSGDALPQK YVFWYQQKSG QAPVLVIYED SKRPSGIPER  60
FSGSSSGTMA TLTISGAQVE DEADYYCYST DRSGNHRVFG GGTRLTVL               108

SEQ ID NO: 916           moltype = AA  length = 120
FEATURE                  Location/Qualifiers
REGION                   1..120
                         note = Synthetic polymer
source                   1..120
                         mol_type = protein
                         organism = synthetic construct
SEQUENCE: 916
EVQLVESGGG LVQPGGSLRL SCAASGFTFS SYWMSWVRQA PGKGLEWVAN IKQDGGEQYY  60
VDSVKGRFTI SRDNAKNSLY LQMNSLRAED TAVYYCARDW NYGYYDMDVW GQGTTVTVSS  120

SEQ ID NO: 917           moltype = AA  length = 108
FEATURE                  Location/Qualifiers
REGION                   1..108
                         note = Synthetic polymer
source                   1..108
                         mol_type = protein
                         organism = synthetic construct
SEQUENCE: 917
EIVLTQSPGT LSLSPGERAT LSCRASQSVS SNYLAWFQQK PGQAPRLLIF GTSSRATGIP  60
DRFSGSGSGT DFTLTISRLE PEDFAVYYCQ QYGSSIFTFG PGTKVDIK               108

SEQ ID NO: 918           moltype = AA  length = 121
FEATURE                  Location/Qualifiers
REGION                   1..121
                         note = Synthetic polymer
source                   1..121
                         mol_type = protein
                         organism = synthetic construct
SEQUENCE: 918
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 919           moltype = AA  length = 108
FEATURE                  Location/Qualifiers
REGION                   1..108
                         note = Synthetic polymer
source                   1..108
                         mol_type = protein
```

```
                         organism = synthetic construct
SEQUENCE: 919
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTEVEIK              108

SEQ ID NO: 920           moltype = AA  length = 121
FEATURE                  Location/Qualifiers
REGION                   1..121
                         note = Synthetic polymer
source                   1..121
                         mol_type = protein
                         organism = synthetic construct
SEQUENCE: 920
EVQLLESGGG LVQPGGSLRL SCAASGFTFS NYAMSWVRQA PGKGLEWVSA IRGSGGSTYY  60
ADSVKGRFTI SRDNSKNTLY LQMNSLRAED TAVYYCAKDL HYDSSGYLDY WGQGTLVTVS  120
S                                                                 121

SEQ ID NO: 921           moltype = AA  length = 107
FEATURE                  Location/Qualifiers
REGION                   1..107
                         note = Synthetic polymer
source                   1..107
                         mol_type = protein
                         organism = synthetic construct
SEQUENCE: 921
DIQMTQSPSS VSASVGDRVT ITCRASQGIR SWLAWYQQKP GKAPKLLIYA ISRLQSGVPS  60
RFSGSGSGTD FTLTISSLQP EDFATYYCQQ ANSFPLTFGG GTKVEIK               107

SEQ ID NO: 922           moltype = AA  length = 119
FEATURE                  Location/Qualifiers
REGION                   1..119
                         note = Synthetic polymer
source                   1..119
                         mol_type = protein
                         organism = synthetic construct
SEQUENCE: 922
EVQLVESGGG LVQPGGSLRL SCAASGFTFS SYWMSWVRQA PGKGLEWVAN IKQDGGEKYY  60
VDSVKGRFTI SRDNAKNSLF LQMNSLRAED TAVYYCARVQ LYSDYFDYWG QGTLVTVSS   119

SEQ ID NO: 923           moltype = AA  length = 107
FEATURE                  Location/Qualifiers
REGION                   1..107
                         note = Synthetic polymer
source                   1..107
                         mol_type = protein
                         organism = synthetic construct
SEQUENCE: 923
DIQMTQSPSS VSASVGDRVT ITCRASQGIS SWLAWYQQKS GKAPKLLIYA ASGLQSGVPS  60
RFSGSGSGTD FTLTISSLQP EDLATYYCQQ SHSLPPTFGQ GTKVEIK               107

SEQ ID NO: 924           moltype = AA  length = 121
FEATURE                  Location/Qualifiers
REGION                   1..121
                         note = Synthetic polymer
source                   1..121
                         mol_type = protein
                         organism = synthetic construct
SEQUENCE: 924
EVQLLESGGD LVQPGGSLRL SCAASGFTFN SYAMSWVRQA PGKGLEWVST ISGSGGFTFS  60
ADSVKGRFTI SRDNSKNTLF LQMNSLRVED SAVYSCAKVL VGFNNGCWDY WGQGTLVTVS  120
S                                                                 121

SEQ ID NO: 925           moltype = AA  length = 108
FEATURE                  Location/Qualifiers
REGION                   1..108
                         note = Synthetic polymer
source                   1..108
                         mol_type = protein
                         organism = synthetic construct
SEQUENCE: 925
SYVLTQPPSV SVAPGQTARI TCGGNNIGSK SVHWYQQKPG QAPVLVVYDD SDRPSGIPER  60
FSGSNSGNTA TLTISRVEAG DEADYYCQVW DSSNDHVVFG GGTKLTVL              108

SEQ ID NO: 926           moltype = AA  length = 120
FEATURE                  Location/Qualifiers
REGION                   1..120
                         note = Synthetic polymer
source                   1..120
                         mol_type = protein
```

```
                         organism = synthetic construct
SEQUENCE: 926
EVQLVESGGG LVKPGGSLRL SCAASGFTFS TYSMNWVRQA PGKGLEWVSS ISSSGDYIYY  60
ADSVKGRFTI SRDNAKNSLY LQMNSLRAED TAVYYCARDL VTSMVAFDYW GQGTLVTVSS  120

SEQ ID NO: 927           moltype = AA  length = 108
FEATURE                  Location/Qualifiers
REGION                   1..108
                         note = Synthetic polymer
source                   1..108
                         mol_type = protein
                         organism = synthetic construct
SEQUENCE: 927
SYELTQPPSV SVSPGQTARI TCSGDALPQK YVFWYQQKSG QAPVLVIYED SKRPSGIPER  60
FSGSSSGTMA TLTISGAQVE DEADYYCYST DRSGNHRVFG GGTKLTVL              108

SEQ ID NO: 928           moltype = AA  length = 121
FEATURE                  Location/Qualifiers
REGION                   1..121
                         note = Synthetic polymer
source                   1..121
                         mol_type = protein
                         organism = synthetic construct
SEQUENCE: 928
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 929           moltype = AA  length = 108
FEATURE                  Location/Qualifiers
REGION                   1..108
                         note = Synthetic polymer
source                   1..108
                         mol_type = protein
                         organism = synthetic construct
SEQUENCE: 929
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK              108

SEQ ID NO: 930           moltype = AA  length = 120
FEATURE                  Location/Qualifiers
REGION                   1..120
                         note = Synthetic polymer
source                   1..120
                         mol_type = protein
                         organism = synthetic construct
SEQUENCE: 930
QVQLVQSGAE VKKPGASVKV SCKASGYTFT SYWMYWVRQA TGQGLEWMGR IDPNSGSTKY  60
NEKFKNRFTI SRDDSKNTAY LQMNSLKTED TAVYYCARDY RKGLYAMDYW GQGTTVTVSS  120

SEQ ID NO: 931           moltype = AA  length = 120
FEATURE                  Location/Qualifiers
REGION                   1..120
                         note = Synthetic polymer
source                   1..120
                         mol_type = protein
                         organism = synthetic construct
SEQUENCE: 931
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120

SEQ ID NO: 932           moltype = AA  length = 120
FEATURE                  Location/Qualifiers
REGION                   1..120
                         note = Synthetic polymer
source                   1..120
                         mol_type = protein
                         organism = synthetic construct
SEQUENCE: 932
EVQLVQSGAE VKKPGESLRI SCKGSGYTFT SYWMYWVRQA PGQGLEWMGR IDPNSGSTKY  60
NEKFKNRVTI SVDTSKNQFS LKLSSVTAAD TAVYYCARDY RKGLYAMDYW GQGTTVTVSS  120

SEQ ID NO: 933           moltype = AA  length = 120
FEATURE                  Location/Qualifiers
REGION                   1..120
                         note = Synthetic polymer
source                   1..120
                         mol_type = protein
                         organism = synthetic construct
```

```
SEQUENCE: 933
EVQLVQSGAE VKKPGATVKI SCKVSGYTFT SYWMYWIRQS PSRGLEWLGR IDPNSGSTKY  60
NEKFKNRLTI SKDTSKNQVV LTMTNMDPVD TATYYCARDY RKGLYAMDYW GQGTTVTVSS  120

SEQ ID NO: 934         moltype = AA  length = 120
FEATURE                Location/Qualifiers
REGION                 1..120
                       note = Synthetic polymer
source                 1..120
                       mol_type = protein
                       organism = synthetic construct
SEQUENCE: 934
EVQLVQSGAE VKKPGESLRI SCKGSGYTFT SYWMYWIRQP PGKGLEWIGR IDPNSGSTKY  60
NEKFKNRVTI TADKSTSTAY MELSSLRSED TAVYYCARDY RKGLYAMDYW GQGTTVTVSS  120

SEQ ID NO: 935         moltype = AA  length = 120
FEATURE                Location/Qualifiers
REGION                 1..120
                       note = Synthetic polymer
source                 1..120
                       mol_type = protein
                       organism = synthetic construct
SEQUENCE: 935
QVQLVQSGAE VKKPGASVKV SCKASGYTFT SYWMYWIRQS PSRGLEWLGR IDPNSGSTKY  60
NEKFKNRFTI SRDDSKNTAY LQMNSLKTED TAVYYCARDY RKGLYAMDYW GQGTTVTVSS  120

SEQ ID NO: 936         moltype = AA  length = 120
FEATURE                Location/Qualifiers
REGION                 1..120
                       note = Synthetic polymer
source                 1..120
                       mol_type = protein
                       organism = synthetic construct
SEQUENCE: 936
EVQLVQSGAE VKKPGESLRI SCKGSGYTFT SYWMYWVRQA RGQRLEWIGR IDPNSGSTKY  60
NEKFKNRLTI SKDTSKNQVV LTMTNMDPVD TATYYCARDY RKGLYAMDYW GQGTTVTVSS  120

SEQ ID NO: 937         moltype = AA  length = 120
FEATURE                Location/Qualifiers
REGION                 1..120
                       note = Synthetic polymer
source                 1..120
                       mol_type = protein
                       organism = synthetic construct
SEQUENCE: 937
QITLKESGPT LVKPTQTLTL TCTFSGYTFT SYWMYWVRQA PGKGLEWVSR IDPNSGSTKY  60
NEKFKNRVTI TADKSTSTAY MELSSLRSED TAVYYCARDY RKGLYAMDYW GQGTTVTVSS  120

SEQ ID NO: 938         moltype = AA  length = 120
FEATURE                Location/Qualifiers
REGION                 1..120
                       note = Synthetic polymer
source                 1..120
                       mol_type = protein
                       organism = synthetic construct
SEQUENCE: 938
EVQLVQSGAE VKKPGATVKI SCKVSGYTFT SYWMYWVRQA RGQRLEWIGR IDPNSGSTKY  60
NEKFKNRFTI SRDNSKNTLY LQMNSLRAED TAVYYCARDY RKGLYAMDYW GQGTTVTVSS  120

SEQ ID NO: 939         moltype = AA  length = 107
FEATURE                Location/Qualifiers
REGION                 1..107
                       note = Synthetic polymer
source                 1..107
                       mol_type = protein
                       organism = synthetic construct
SEQUENCE: 939
DIVMTQTPLS LPVTPGEPAS ISCKASQDVG TAVAWYLQKP GQSPQLLIYW ASTRHTGIPA  60
RFSGSGSGTE FTLTISSLQS EDFAVYYCQQ YNSYPLTFGQ GTKVEIK                107

SEQ ID NO: 940         moltype = AA  length = 107
FEATURE                Location/Qualifiers
REGION                 1..107
                       note = Synthetic polymer
source                 1..107
                       mol_type = protein
                       organism = synthetic construct
SEQUENCE: 940
DIQMTQSPSS LSASVGDRVT ITCKASQDVG TAVAWYLQKP GQSPQLLIYW ASTRHTGVPS  60
```

```
RFSGSGSGTD FTLTISSLQP EDFATYYCQQ YNSYPLTFGQ GTKVEIK                107

SEQ ID NO: 941          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 941
EIVLTQSPDF QSVTPKEKVT ITCKASQDVG TAVAWYLQKP GQSPQLLIYW ASTRHTGVPD  60
RFSGSGSGTD FTLKISRVEA EDVGVYYCQQ YNSYPLTFGQ GTKVEIK                107

SEQ ID NO: 942          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 942
EIVLTQSPDF QSVTPKEKVT ITCKASQDVG TAVAWYLQKP GQSPQLLIYW ASTRHTGVPS  60
RFSGSGSGTD FTFTISSLQP EDIATYYCQQ YNSYPLTFGQ GTKVEIK                107

SEQ ID NO: 943          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 943
EIVLTQSPAT LSLSPGERAT LSCKASQDVG TAVAWYLQKP GQSPQLLIYW ASTRHTGIPP  60
RFSGSGYGTD FTLTINNIES EDAAYYFCQQ YNSYPLTFGQ GTKVEIK                107

SEQ ID NO: 944          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 944
DVVMTQSPLS LPVTLGQPAS ISCKASQDVG TAVAWYQQKP GQAPRLLIYW ASTRHTGVPS  60
RFSGSGSGTE FTLTISSLQP DDFATYYCQQ YNSYPLTFGQ GTKVEIK                107

SEQ ID NO: 945          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 945
DIQMTQSPSS LSASVGDRVT ITCKASQDVG TAVAWYQQKP GQAPRLLIYW ASTRHTGVPS  60
RFSGSGSGTD FTFTISSLQP EDIATYYCQQ YNSYPLTFGQ GTKVEIK                107

SEQ ID NO: 946          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 946
AIQLTQSPSS LSASVGDRVT ITCKASQDVG TAVAWYLQKP GQSPQLLIYW ASTRHTGVPS  60
RFSGSGSGTD FTFTISSLEA EDAATYYCQQ YNSYPLTFGQ GTKVEIK                107

SEQ ID NO: 947          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 947
EIVLTQSPDF QSVTPKEKVT ITCKASQDVG TAVAWYQQKP GQAPRLLIYW ASTRHTGVPS  60
RFSGSGSGTE FTLTISSLQP DDFATYYCQQ YNSYPLTFGQ GTKVEIK                107
```

```
SEQ ID NO: 948         moltype = AA  length = 116
FEATURE                Location/Qualifiers
REGION                 1..116
                       note = Synthetic polymer
source                 1..116
                       mol_type = protein
                       organism = synthetic construct
SEQUENCE: 948
EVKLVESGGG LVKPGGSLKL SCAASGFIFR SYGMSWVRQT PEKRLEWVAS ISSGGSTYYP  60
DSVKGRFTIS RDNARNILYL QMSSLRSEDT AMYDCARGYD SGFAYWGQGT LVTVSE      116

SEQ ID NO: 949         moltype = AA  length = 116
FEATURE                Location/Qualifiers
REGION                 1..116
                       note = Synthetic polymer
source                 1..116
                       mol_type = protein
                       organism = synthetic construct
SEQUENCE: 949
EVKLVESGGG LVKPGGSLKL SCAASGFTFR SYGMSWVRQT PEKRLEWVAS ISSGGTTYYP  60
DSVKGRFIIS RDNARNILYL QMSSLRSEDT AMYYCAKGYD SGFAYWGQGT LVIVSA      116

SEQ ID NO: 950         moltype = AA  length = 116
FEATURE                Location/Qualifiers
REGION                 1..116
                       note = Synthetic polymer
source                 1..116
                       mol_type = protein
                       organism = synthetic construct
SEQUENCE: 950
QVQLKQSGPG LVQPSQSLSI TCTVSGFSLT TYGVHWVRQS PGKGLEWLGV IWRGVTTDYN  60
AAFMSRLTIT KDNSKSQVFF KMNSLQANDT AIYYCARLGF YAMDYWGQGT SVTVSS      116

SEQ ID NO: 951         moltype = AA  length = 116
FEATURE                Location/Qualifiers
REGION                 1..116
                       note = Synthetic polymer
source                 1..116
                       mol_type = protein
                       organism = synthetic construct
SEQUENCE: 951
QVQLKQSGPG LVQPSQSLSI TCTVSGFSLT SYGVHWVRQS PGKGLEWLGV IWSGGVTDYN  60
AAFISRLSIS KDNSKSQVFF KMNSLQANDT AIYYCARLGF YAMDYWGQGT SVTVSS      116

SEQ ID NO: 952         moltype = AA  length = 119
FEATURE                Location/Qualifiers
REGION                 1..119
                       note = Synthetic polymer
source                 1..119
                       mol_type = protein
                       organism = synthetic construct
SEQUENCE: 952
EVKLFESGGG LVQPGGSLKL SCVASGFDFS TYWMHWVRQA PGQGLEWIGQ INPDSTTINY  60
APSLKDRFII SRDNAKNTLF LQMSKVRSED TALYYCAKPG DYGYDFDCWG QGTTLTVSS   119

SEQ ID NO: 953         moltype = AA  length = 119
FEATURE                Location/Qualifiers
REGION                 1..119
                       note = Synthetic polymer
source                 1..119
                       mol_type = protein
                       organism = synthetic construct
SEQUENCE: 953
EVQLQESGPS LVKPSQTLSL TCSVTGDSIT SGYWNWIRKF PGNKLEYMGY ISYSGSTYYN  60
PSLKSRISIT RDTSKNQYYL QLNSVTTEDT ATYYCARSLL WFSTGFAYWG QGTLVTVSA   119

SEQ ID NO: 954         moltype = AA  length = 116
FEATURE                Location/Qualifiers
REGION                 1..116
                       note = Synthetic polymer
source                 1..116
                       mol_type = protein
                       organism = synthetic construct
SEQUENCE: 954
QVQLKQSGPG LVQPSQSLSI TCTVSGFSLT SYGVHWVRQS PGKGLEWLGV IWSGGITDYN  60
AAFKSRLSIS KDNSKSQVFF KMNSLQANDT AIYFCARLGF YAMDYWGQGT SVTVSS      116

SEQ ID NO: 955         moltype = AA  length = 116
FEATURE                Location/Qualifiers
```

```
REGION                  1..116
                        note = Synthetic polymer
source                  1..116
                        mol_type = protein
                        organism = synthetic construct
SEQUENCE: 955
EVKLVESGGG LVKPGGSLKL SCAASGFTFR SYGMSWARQI PEKRLEWVAS ISSGGTTYYL  60
GSVQGRFTIS RDNARNILYL QMSSLRSEDT AMYYCARGYD AGFAYWGQGT LVSVSE      116

SEQ ID NO: 956          moltype = AA  length = 117
FEATURE                 Location/Qualifiers
REGION                  1..117
                        note = Synthetic polymer
source                  1..117
                        mol_type = protein
                        organism = synthetic construct
SEQUENCE: 956
EVQLQESGPS LVKPSQTLSL TCSVTGDSIT SGYWTWIRKF PGNKLEYMGY ISYTGSTYYN  60
PSLKSRISIS RDTSKSQYYL QLNSVTTEDT ATYYCARQRD WLGFAYWGQG TLVTVSA     117

SEQ ID NO: 957          moltype = AA  length = 116
FEATURE                 Location/Qualifiers
REGION                  1..116
                        note = Synthetic polymer
source                  1..116
                        mol_type = protein
                        organism = synthetic construct
SEQUENCE: 957
EEKLVESGGG LVKPGGSLKL SCAASGFSFS SYGMSWVRQT PEKRLEWVAS ISSGGSIYYP  60
DSVKGRFTIS RDNARNILYL QMSSLRSEDT AMYYCARGYD AGFAFWGQGT LVTASA      116

SEQ ID NO: 958          moltype = AA  length = 116
FEATURE                 Location/Qualifiers
REGION                  1..116
                        note = Synthetic polymer
source                  1..116
                        mol_type = protein
                        organism = synthetic construct
SEQUENCE: 958
QITLKESGPT LVKPTQTLTL TCTVSGFSLS TYGVHWIRQP PGKALEWLGV IWRGVTTDYN  60
AAFMSRLTIT KDNSKNQVVL TMNNMDPVDT ATYYCARLGF YAMDYWGQGT LVTVSS      116

SEQ ID NO: 959          moltype = AA  length = 116
FEATURE                 Location/Qualifiers
REGION                  1..116
                        note = Synthetic polymer
source                  1..116
                        mol_type = protein
                        organism = synthetic construct
SEQUENCE: 959
EVQLVESGGG LVKPGGSLRL SCAASGFIFR SYGMSWVRQA PGKGLEWVAS ISSGGSTYYP  60
DSVKGRFTIS RDNAKNSLYL QMNSLRAEDT AVYDCARGYD SGFAYWGQGT LVTVSS      116

SEQ ID NO: 960          moltype = AA  length = 112
FEATURE                 Location/Qualifiers
REGION                  1..112
                        note = Synthetic polymer
source                  1..112
                        mol_type = protein
                        organism = synthetic construct
SEQUENCE: 960
DIVLTQSPAS LAVSLGQRAT ISCRASQSVS TSSSSFMHWY QQKPGQPPKL LIKYASNLES  60
GVPARFSGSG SGTDFTLNIH PVEEEDTATY YCQHSWEIPY TFGGGTKLEI KR          112

SEQ ID NO: 961          moltype = AA  length = 111
FEATURE                 Location/Qualifiers
REGION                  1..111
                        note = Synthetic polymer
source                  1..111
                        mol_type = protein
                        organism = synthetic construct
SEQUENCE: 961
DIVLTQSPPS LAVSLGQRAT ISCRASQSVS TSSSSYMHWY QQKPGQPPKL LIKYASNLES  60
GVPARFSGSG SGTDFTLNIH PVEEEDTATY YCQHSWEIPY TFGGGTKLEI K           111

SEQ ID NO: 962          moltype = AA  length = 107
FEATURE                 Location/Qualifiers
REGION                  1..107
                        note = Synthetic polymer
```

```
source                  1..107
                        mol_type = protein
                        organism = synthetic construct
SEQUENCE: 962
SIVMTQTPKF LLVSAGDRVT ITCKASQSVS NDVAWYQQKP GQSPKLLIYY AANRYTGVPD  60
RFTGSGYGTD FTFTISIVQA EDLAVYFCQQ DYTSPYTFGG GTKLEIK               107

SEQ ID NO: 963          moltype = AA  length = 107
FEATURE                 Location/Qualifiers
REGION                  1..107
                        note = Synthetic polymer
source                  1..107
                        mol_type = protein
                        organism = synthetic construct
SEQUENCE: 963
SIVMTQTPKF LLVSAGDRVT ITCKASQSVS NDVGWYQQKP GQSPKLLIYY ASNRYSGVPD  60
RFTGSGYGTD FTFTISTVQA EDLAVYFCQQ DYTSPYTFGG GTKLEIK               107

SEQ ID NO: 964          moltype = AA  length = 112
FEATURE                 Location/Qualifiers
REGION                  1..112
                        note = Synthetic polymer
source                  1..112
                        mol_type = protein
                        organism = synthetic construct
SEQUENCE: 964
DVLMTQTPLY LPVSLGDQAS ISCRSSQIIV HSNANTYLEW FLQKPGQSPK LLIYKVSNRF  60
SGVPDRFSGS GSGTDFTLKI SRVEAEDLGV YYCFQGSHVP YTFGGGTKLE IK         112

SEQ ID NO: 965          moltype = AA  length = 108
FEATURE                 Location/Qualifiers
REGION                  1..108
                        note = Synthetic polymer
source                  1..108
                        mol_type = protein
                        organism = synthetic construct
SEQUENCE: 965
QIVLTQSPAI MSASPGEKVT LTCSASSSVS SSYLYWNQQK PGSSPKVWIY NTSNLASGVP  60
ARFSGSGSGT SYSLTISSME AEDAASYFCH QWRSYPPTLG AGTKLELK              108

SEQ ID NO: 966          moltype = AA  length = 106
FEATURE                 Location/Qualifiers
REGION                  1..106
                        note = Synthetic polymer
source                  1..106
                        mol_type = protein
                        organism = synthetic construct
SEQUENCE: 966
QIVLTQSPAI MSASPGEKVT MTCSANSSVS YMHWYQQKSG TSPKRWIYDT SKLASGVPAR  60
FSGSGSGTSY SLTISSMGAE DAATYYCQQW SSNPWTFGGG TKLEIK                106

SEQ ID NO: 967          moltype = AA  length = 111
FEATURE                 Location/Qualifiers
REGION                  1..111
                        note = Synthetic polymer
source                  1..111
                        mol_type = protein
                        organism = synthetic construct
SEQUENCE: 967
DIVLTQSPAS LAVSLGQRAT ISCRASQSVS TSSYSYMHWY QQKPGQPPKL LIKYASNLES  60
GVPARFSGSG SGTDFTLNIH PVEEEDTATY YCQNSWEIPY TFGGGTKLEI K          111

SEQ ID NO: 968          moltype = AA  length = 113
FEATURE                 Location/Qualifiers
REGION                  1..113
                        note = Synthetic polymer
source                  1..113
                        mol_type = protein
                        organism = synthetic construct
SEQUENCE: 968
DIVMTQTPSS LAVSLGEKVT MSCKSSQSLL YSSNQKNSLA WYQQKPGQSP KLLIYWASNR  60
ESGVPDRFTG SSSGTDFTLT ISSVKAEDLA VYYCQQYYSY PLTFGAGTKL ELK        113

SEQ ID NO: 969          moltype = AA  length = 111
FEATURE                 Location/Qualifiers
REGION                  1..111
                        note = Synthetic polymer
source                  1..111
                        mol_type = protein
```

```
                       organism = synthetic construct
SEQUENCE: 969
DIVLTQSPAS LAVSLGQRAT ISCRASQSVS TSSYSYVHWY QQKPGQPPKL LIKYASNLES  60
GVPARFSGSG SGTDFTLNIH PVEEEDTATY YCQHSWEIPY TFGGGTKLEI K           111

SEQ ID NO: 970         moltype = AA  length = 107
FEATURE                Location/Qualifiers
REGION                 1..107
                       note = Synthetic polymer
source                 1..107
                       mol_type = protein
                       organism = synthetic construct
SEQUENCE: 970
DIQMTQSPSS LSASVGDRVT ITCKASQSVS NDVAWYQQKP GKAPKLLIYY AANRYTGVPD  60
RFSGSGYGTD FTFTISSLQP EDIATYFCQQ DYTSPYTFGQ GTKLEIK               107

SEQ ID NO: 971         moltype = AA  length = 111
FEATURE                Location/Qualifiers
REGION                 1..111
                       note = Synthetic polymer
source                 1..111
                       mol_type = protein
                       organism = synthetic construct
SEQUENCE: 971
DIVLTQSPAS LAVSPGQRAT ITCRASQSVS TSSSSFMHWY QQKPGQPPKL LIKYASNLES  60
GVPARFSGSG SGTDFTLTIN PVEANDTANY YCQHSWEIPY TFGQGTKLEI K           111

SEQ ID NO: 972         moltype = AA  length = 117
FEATURE                Location/Qualifiers
REGION                 1..117
                       note = Synthetic polymer
source                 1..117
                       mol_type = protein
                       organism = synthetic construct
SEQUENCE: 972
EVQLVQSGAE VKKPGESLRI SCKGSGYTFT TYWMHWVRQA TGQGLEWMGN IYPGTGGSNF  60
DEKFKNRVTI TADKSTSTAY MELSSLRSED TAVYYCTRWT TGTGAYWGQG TTVTVSS     117

SEQ ID NO: 973         moltype = AA  length = 117
FEATURE                Location/Qualifiers
REGION                 1..117
                       note = Synthetic polymer
source                 1..117
                       mol_type = protein
                       organism = synthetic construct
SEQUENCE: 973
EVQLVQSGAE VKKPGESLRI SCKGSGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 974         moltype = AA  length = 117
FEATURE                Location/Qualifiers
REGION                 1..117
                       note = Synthetic polymer
source                 1..117
                       mol_type = protein
                       organism = synthetic construct
SEQUENCE: 974
QVQLVQSGAE VKKPGASVKV SCKASGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 975         moltype = AA  length = 117
FEATURE                Location/Qualifiers
REGION                 1..117
                       note = Synthetic polymer
source                 1..117
                       mol_type = protein
                       organism = synthetic construct
SEQUENCE: 975
EVQLVQSGAE VKKPGESLRI SCKGSGYTFT TYWMHWVRQA PGQGLEWMGN IYPGTGGSNF  60
DEKFKNRFTI SRDNSKNTLY LQMNSLRAED TAVYYCTRWT TGTGAYWGQG TTVTVSS     117

SEQ ID NO: 976         moltype = AA  length = 113
FEATURE                Location/Qualifiers
REGION                 1..113
                       note = Synthetic polymer
source                 1..113
                       mol_type = protein
                       organism = synthetic construct
SEQUENCE: 976
```

-continued

```
EIVLTQSPAT LSLSPGERAT LSCKSSQSLL DSGNQKNFLT WYQQKPGQAP RLLIYWASTR  60
ESGVPSRFSG SGSGTEFTLT ISSLQPDDFA TYYCQNDYSY PYTFGQGTKV EIK         113

SEQ ID NO: 977         moltype = AA  length = 113
FEATURE                Location/Qualifiers
REGION                 1..113
                       note = Synthetic polymer
source                 1..113
                       mol_type = protein
                       organism = synthetic construct
SEQUENCE: 977
DIQMTQSPSS LSASVGDRVT ITCKSSQSLL DSGNQKNFLT WYQQKPGQAP RLLIYWASTR  60
ESGIPPRFSG SGYGTDFTLT INNIESEDAA YYFCQNDYSY PYTFGQGTKV EIK         113

SEQ ID NO: 978         moltype = AA  length = 113
FEATURE                Location/Qualifiers
REGION                 1..113
                       note = Synthetic polymer
source                 1..113
                       mol_type = protein
                       organism = synthetic construct
SEQUENCE: 978
EIVLTQSPAT LSLSPGERAT LSCKSSQSLL DSGNQKNFLT WYQQKPGKAP KLLIYWASTR  60
ESGVPSRFSG SGSGTDFTFT ISSLQPEDIA TYYCQNDYSY PYTFGQGTKV EIK         113

SEQ ID NO: 979         moltype = AA  length = 113
FEATURE                Location/Qualifiers
REGION                 1..113
                       note = Synthetic polymer
source                 1..113
                       mol_type = protein
                       organism = synthetic construct
SEQUENCE: 979
DIVMTQTPLS LPVTPGEPAS ISCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 980         moltype = AA  length = 113
FEATURE                Location/Qualifiers
REGION                 1..113
                       note = Synthetic polymer
source                 1..113
                       mol_type = protein
                       organism = synthetic construct
SEQUENCE: 980
EIVLTQSPAT LSLSPGERAT LSCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113

SEQ ID NO: 981         moltype = AA  length = 113
FEATURE                Location/Qualifiers
REGION                 1..113
                       note = Synthetic polymer
source                 1..113
                       mol_type = protein
                       organism = synthetic construct
SEQUENCE: 981
EIVLTQSPDF QSVTPKEKVT ITCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 982         moltype = AA  length = 113
FEATURE                Location/Qualifiers
REGION                 1..113
                       note = Synthetic polymer
source                 1..113
                       mol_type = protein
                       organism = synthetic construct
SEQUENCE: 982
EIVLTQSPAT LSLSPGERAT LSCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 983         moltype = AA  length = 113
FEATURE                Location/Qualifiers
REGION                 1..113
                       note = Synthetic polymer
source                 1..113
                       mol_type = protein
                       organism = synthetic construct
SEQUENCE: 983
DIQMTQSPSS LSASVGDRVT ITCKSSQSLL DSGNQKNFLT WYLQKPGQSP QLLIYWASTR  60
ESGVPSRFSG SGSGTDFTFT ISSLEAEDAA TYYCQNDYSY PYTFGQGTKV EIK         113
```

```
SEQ ID NO: 984          moltype = AA  length = 113
FEATURE                 Location/Qualifiers
REGION                  1..113
                        note = Synthetic polymer
source                  1..113
                        mol_type = protein
                        organism = synthetic construct
SEQUENCE: 984
DVVMTQSPLS LPVTLGQPAS ISCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113

SEQ ID NO: 985          moltype = AA  length = 118
FEATURE                 Location/Qualifiers
REGION                  1..118
                        note = Synthetic polymer
source                  1..118
                        mol_type = protein
                        organism = synthetic construct
SEQUENCE: 985
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSA    118

SEQ ID NO: 986          moltype = AA  length = 108
FEATURE                 Location/Qualifiers
REGION                  1..108
                        note = Synthetic polymer
source                  1..108
                        mol_type = protein
                        organism = synthetic construct
SEQUENCE: 986
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR              108

SEQ ID NO: 987          moltype = AA  length = 126
FEATURE                 Location/Qualifiers
REGION                  1..126
                        note = Synthetic polymer
source                  1..126
                        mol_type = protein
                        organism = synthetic construct
SEQUENCE: 987
EVQLVESGGG LVQPGGSLRL SCAASGFTLD YYAIGWFRQA PGKEREWASS ISSSDGSTYY  60
ADSVKGRFTI SRDNAKNTVF LQMNSLKPED TAVYSCAASQ APITIATMMK PFYDYWGQGT  120
QVTVSS                                                            126

SEQ ID NO: 988          moltype = AA  length = 123
FEATURE                 Location/Qualifiers
REGION                  1..123
                        note = Synthetic polymer
source                  1..123
                        mol_type = protein
                        organism = synthetic construct
SEQUENCE: 988
EVQLVESGGG LVQPGGSLRL SCAASGFTLD YYAKCWFRQA PGKEREWVSC ISSSDGSTYY  60
ADSVKGRFTI SRDNAKNTVY LQMNSLKPED TAVYFCAARH GGPLTVEYFF DYWGQGTQVT  120
VSS                                                               123

SEQ ID NO: 989          moltype = AA  length = 124
FEATURE                 Location/Qualifiers
REGION                  1..124
                        note = Synthetic polymer
source                  1..124
                        mol_type = protein
                        organism = synthetic construct
SEQUENCE: 989
EVQLVESGGG LVQPGGSLRL SCAASGFTFD YYAIGWFRQA PGKAREGVSC ISGGDNSTYY  60
ADSVKGRFTI SRDNAKNTVY LQMNSLKPED TAVYYCATGG WKYCSGYDPE YIYWGQGTQV  120
TVSS                                                              124

SEQ ID NO: 990          moltype = AA  length = 115
FEATURE                 Location/Qualifiers
REGION                  1..115
                        note = Synthetic polymer
source                  1..115
                        mol_type = protein
                        organism = synthetic construct
SEQUENCE: 990
EVQLVESGGG LVQAGGSLRL SCAASGSTFS QYDVGWYRQA PGKQRELVAF SSSGGRTIYP  60
```

```
DSVKGRFTFS RDNTKNTVYL QMTSLKPEDT AVYYCKIDWY LNSYWGQGTQ VTVSS       115

SEQ ID NO: 991         moltype = AA  length = 114
FEATURE                Location/Qualifiers
REGION                 1..114
                       note = Synthetic polymer
source                 1..114
                       mol_type = protein
                       organism = synthetic construct
SEQUENCE: 991
EVQLVESGGG LVQAGGSLRL SCAASGVDAS NSAMGWYRQA PGKQREWVAR ITGGGLIAYT  60
DSVKGRFTIS RDNAKSTVYL QMNSLEPEDT AVYYCNTINS RDGWGQGTQV TVSS        114

SEQ ID NO: 992         moltype = AA  length = 111
FEATURE                Location/Qualifiers
REGION                 1..111
                       note = Synthetic polymer
source                 1..111
                       mol_type = protein
                       organism = synthetic construct
SEQUENCE: 992
EVQLVESGGG LVQAGGSLTI SCAASGITFS DSIVSWYRRA RGKQREWVAG ISNGGTTKYA  60
ESVLGRFTIS RDNAKNNVYL QMNGLNPEDT AVYLCKVRQY WGQGTQVTVS S           111

SEQ ID NO: 993         moltype = AA  length = 130
FEATURE                Location/Qualifiers
REGION                 1..130
                       note = Synthetic polymer
source                 1..130
                       mol_type = protein
                       organism = synthetic construct
SEQUENCE: 993
EVQLVESGGG LVQAGGSLRL SCAASESTVL INAMGWYRQA PGKQRELVAS ISSGGSTNYA  60
DSVKGRFTIS RDNAKNTVYL QMNSLKPEDT AVYYCNADVY PQDYGLGYVE GKVYYGHDYW  120
GTGTLVTVSS                                                         130

SEQ ID NO: 994         moltype = AA  length = 119
FEATURE                Location/Qualifiers
REGION                 1..119
                       note = Synthetic polymer
source                 1..119
                       mol_type = protein
                       organism = synthetic construct
SEQUENCE: 994
EVQLVESGGG LVQAGGSLRL SCAASGSTFS NYVSNYAMGW GRQAPGTQRE LVASISNGDT  60
TNYADSVKGR FTISRDNAKN TVYLQMNSLK PEDTAVYYCF EHQVAGLTWG QGTQVTVSS   119

SEQ ID NO: 995         moltype = AA  length = 118
FEATURE                Location/Qualifiers
REGION                 1..118
                       note = Synthetic polymer
SITE                   27
                       note = misc_feature - Xaa can be any naturally occurring
                        amino acid
SITE                   32
                       note = misc_feature - Xaa can be any naturally occurring
                        amino acid
SITE                   75
                       note = misc_feature - Xaa can be any naturally occurring
                        amino acid
source                 1..118
                       mol_type = protein
                       organism = synthetic construct
SEQUENCE: 995
EVQLVESGGG LVQAGGSLRL SCVASGXALK IXVMGWYRQA PGKQRELVAA ITSGGRTNYS  60
DSVKGRFTIS GDNAXNTVYL QMNSLKSEDT AVYYCREWNS GYPPVDYWGQ GTQVTVSS    118

SEQ ID NO: 996         moltype = AA  length = 120
FEATURE                Location/Qualifiers
REGION                 1..120
                       note = Synthetic polymer
source                 1..120
                       mol_type = protein
                       organism = synthetic construct
SEQUENCE: 996
EVQLVESGGG LVQAGGSLRL SCAASGRTFS SGTMGWFRRA PGKEREFVAS IPWSGGRTYY  60
ADSVKDRFTI SRDNAQNTVF LQMNSLKPED TAVYYCAFKE RSTGWDFASW GQGIQVTVSS  120

SEQ ID NO: 997         moltype = AA  length = 127
```

```
FEATURE                Location/Qualifiers
REGION                 1..127
                       note = Synthetic polymer
source                 1..127
                       mol_type = protein
                       organism = synthetic construct
SEQUENCE: 997
EVQLVESGGG LVQTGGSLRL SCAASGFTLD YYGIGWFRQA PGKEREGVSF ISGSDGSTYY  60
AESVKGRFTI SRDKAKNTVY LQMNSLKPED TAVYYCAADP WGPPSIATMT SYEYKHWGQG  120
TQVTVSS                                                            127

SEQ ID NO: 998         moltype = AA  length = 113
FEATURE                Location/Qualifiers
REGION                 1..113
                       note = Synthetic polymer
source                 1..113
                       mol_type = protein
                       organism = synthetic construct
SEQUENCE: 998
EVQLVESGGG LVQPGGSLRL SCAASGFTFS TYTMIWLRRA PGKGFEWVST IDKDGNTNYV  60
DSVKGRFAVS RDNTKNTLYL QMNSLKPEDT AMYYCTKHGS SARGQGTRVT VSS         113

SEQ ID NO: 999         moltype = AA  length = 114
FEATURE                Location/Qualifiers
REGION                 1..114
                       note = Synthetic polymer
source                 1..114
                       mol_type = protein
                       organism = synthetic construct
SEQUENCE: 999
EVQLVESGGG LVEPGGSLRL SCVASGFTFS SYDMSWVRQA PGKGLEWVST INSGGGITYR  60
GSVKGRFTIS RDNAKNTLYL QMNSLKPEDT AVYYCENGGS SYRRGQGTQV TVSS        114

SEQ ID NO: 1000        moltype = AA  length = 114
FEATURE                Location/Qualifiers
REGION                 1..114
                       note = Synthetic polymer
source                 1..114
                       mol_type = protein
                       organism = synthetic construct
SEQUENCE: 1000
QVQLVQSGAE LKKPGASVKM SCKASGYTFT GYTMHWVKQA PGQGLEWIGY INPRSGYTEY  60
NQKFKDRTTL TADKSTSTAY MELSSLRSED SAVYYCARPW FAYWGQGTLV TVSS        114

SEQ ID NO: 1001        moltype = AA  length = 114
FEATURE                Location/Qualifiers
REGION                 1..114
                       note = Synthetic polymer
source                 1..114
                       mol_type = protein
                       organism = synthetic construct
SEQUENCE: 1001
QVQLVQSGAE VKKPGASVKM SCKASGYTFT GYTMHWVKQA PGQGLEWIGY INPRSGYTEY  60
NQKFKDRTTL TADKSTSTAY MELSSLRSED TAVYYCARPW FAYWGQGTLV TVSS        114

SEQ ID NO: 1002        moltype = AA  length = 114
FEATURE                Location/Qualifiers
REGION                 1..114
                       note = Synthetic polymer
source                 1..114
                       mol_type = protein
                       organism = synthetic construct
SEQUENCE: 1002
QVQLVQSGAE VKKPGASVKM SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 1003        moltype = AA  length = 114
FEATURE                Location/Qualifiers
REGION                 1..114
                       note = Synthetic polymer
source                 1..114
                       mol_type = protein
                       organism = synthetic construct
SEQUENCE: 1003
QVQLVQSGAE VKKPGASVKV SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 1004        moltype = AA  length = 114
FEATURE                Location/Qualifiers
```

```
REGION                  1..114
                        note = Synthetic polymer
source                  1..114
                        mol_type = protein
                        organism = synthetic construct
SEQUENCE: 1004
QVQLVQSGAE VKKPGASVKV SCKASGYTFT GYTMHWVRQA PGQGLEWIGY INPRSGYTEY  60
NQKFKDRTTI TADKSTSTAY MELSSLRSED TAVYYCARPW FAYWGQGTLV TVSS        114

SEQ ID NO: 1005         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1005
DIVMTQSPAS LTVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 1006         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1006
DIVMTQSPAS LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 1007         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1007
DIVMTQSPAF LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 1008         moltype = AA  length = 113
FEATURE                 Location/Qualifiers
REGION                  1..113
                        note = Synthetic polymer
source                  1..113
                        mol_type = protein
                        organism = synthetic construct
SEQUENCE: 1008
DIVMTQSPAF LSVTPGEKVT ITCKSSQSLL NSGNQKNYLT WYQQKPGQPP KLLIYWASTR  60
ESGVPDRFSG SGSGTDFTLT ISSLQAEDVA VYYCQNDYSY PLTFGQGTKL EIK         113

SEQ ID NO: 1009         moltype = AA  length = 5
FEATURE                 Location/Qualifiers
REGION                  1..5
                        note = Synthetic polymer
source                  1..5
                        mol_type = protein
                        organism = synthetic construct
SEQUENCE: 1009
GGGGS                                                              5

SEQ ID NO: 1010         moltype = AA  length = 10
FEATURE                 Location/Qualifiers
REGION                  1..10
                        note = Synthetic polymer
source                  1..10
                        mol_type = protein
                        organism = synthetic construct
SEQUENCE: 1010
GGGGSGGGGS                                                         10

SEQ ID NO: 1011         moltype = AA  length = 15
FEATURE                 Location/Qualifiers
REGION                  1..15
                        note = Synthetic polymer
source                  1..15
                        mol_type = protein
```

```
                        organism = synthetic construct
SEQUENCE: 1011
GGGGSGGGGS GGGGS                                                   15

SEQ ID NO: 1012         moltype = AA  length = 20
FEATURE                 Location/Qualifiers
REGION                  1..20
                        note = Synthetic polymer
source                  1..20
                        mol_type = protein
                        organism = synthetic construct
SEQUENCE: 1012
GGGGSGGGGS GGGGSGGGGS                                              20

SEQ ID NO: 1013         moltype = AA  length = 25
FEATURE                 Location/Qualifiers
REGION                  1..25
                        note = Synthetic polymer
source                  1..25
                        mol_type = protein
                        organism = synthetic construct
SEQUENCE: 1013
GGGGSGGGGS GGGGSGGGGS GGGGS                                        25

SEQ ID NO: 1014         moltype = AA  length = 30
FEATURE                 Location/Qualifiers
REGION                  1..30
                        note = Synthetic polymer
source                  1..30
                        mol_type = protein
                        organism = synthetic construct
SEQUENCE: 1014
GGGGSGGGGS GGGGSGGGGS GGGGSGGGGS                                   30

SEQ ID NO: 1015         moltype = AA  length = 35
FEATURE                 Location/Qualifiers
REGION                  1..35
                        note = Synthetic polymer
source                  1..35
                        mol_type = protein
                        organism = synthetic construct
SEQUENCE: 1015
GGGGSGGGGS GGGGSGGGGS GGGGSGGGGS GGGGS                             35

SEQ ID NO: 1016         moltype = AA  length = 40
FEATURE                 Location/Qualifiers
REGION                  1..40
                        note = Synthetic polymer
source                  1..40
                        mol_type = protein
                        organism = synthetic construct
SEQUENCE: 1016
GGGGSGGGGS GGGGSGGGGS GGGGSGGGGS GGGGSGGGGS                        40

SEQ ID NO: 1017         moltype = AA  length = 16
FEATURE                 Location/Qualifiers
REGION                  1..16
                        note = Synthetic polymer
source                  1..16
                        mol_type = protein
                        organism = synthetic construct
SEQUENCE: 1017
GGSGGSGGGG SGGGGS                                                  16

SEQ ID NO: 1018         moltype = AA  length = 8
FEATURE                 Location/Qualifiers
REGION                  1..8
                        note = Synthetic polymer
source                  1..8
                        mol_type = protein
                        organism = synthetic construct
SEQUENCE: 1018
GGGGGGGG                                                           8

SEQ ID NO: 1019         moltype = AA  length = 6
FEATURE                 Location/Qualifiers
REGION                  1..6
                        note = Synthetic polymer
source                  1..6
```

```
                        mol_type = protein
                        organism = synthetic construct
SEQUENCE: 1019
GGGGGG                                                        6

SEQ ID NO: 1020         moltype = AA  length = 5
FEATURE                 Location/Qualifiers
REGION                  1..5
                        note = Synthetic polymer
source                  1..5
                        mol_type = protein
                        organism = synthetic construct
SEQUENCE: 1020
EAAAK                                                         5

SEQ ID NO: 1021         moltype = AA  length = 10
FEATURE                 Location/Qualifiers
REGION                  1..10
                        note = Synthetic polymer
source                  1..10
                        mol_type = protein
                        organism = synthetic construct
SEQUENCE: 1021
EAAAKEAAAK                                                    10

SEQ ID NO: 1022         moltype = AA  length = 15
FEATURE                 Location/Qualifiers
REGION                  1..15
                        note = Synthetic polymer
source                  1..15
                        mol_type = protein
                        organism = synthetic construct
SEQUENCE: 1022
EAAAKEAAAK EAAAK                                              15

SEQ ID NO: 1023         moltype = AA  length = 12
FEATURE                 Location/Qualifiers
REGION                  1..12
                        note = Synthetic polymer
source                  1..12
                        mol_type = protein
                        organism = synthetic construct
SEQUENCE: 1023
AEAAAKEAAA KA                                                 12

SEQ ID NO: 1024         moltype = AA  length = 17
FEATURE                 Location/Qualifiers
REGION                  1..17
                        note = Synthetic polymer
source                  1..17
                        mol_type = protein
                        organism = synthetic construct
SEQUENCE: 1024
AEAAAKEAAA KEAAAKA                                            17

SEQ ID NO: 1025         moltype = AA  length = 22
FEATURE                 Location/Qualifiers
REGION                  1..22
                        note = Synthetic polymer
source                  1..22
                        mol_type = protein
                        organism = synthetic construct
SEQUENCE: 1025
AEAAAKEAAA KEAAAKEAAA KA                                      22

SEQ ID NO: 1026         moltype = AA  length = 27
FEATURE                 Location/Qualifiers
REGION                  1..27
                        note = Synthetic polymer
source                  1..27
                        mol_type = protein
                        organism = synthetic construct
SEQUENCE: 1026
AEAAAKEAAA KEAAAKEAAA KEAAAKA                                 27

SEQ ID NO: 1027         moltype = AA  length = 12
FEATURE                 Location/Qualifiers
REGION                  1..12
                        note = Synthetic polymer
```

```
source                  1..12
                        mol_type = protein
                        organism = synthetic construct
SEQUENCE: 1027
AEAAAKEAAA KA                                                         12

SEQ ID NO: 1028         moltype = AA  length = 46
FEATURE                 Location/Qualifiers
REGION                  1..46
                        note = Synthetic polymer
source                  1..46
                        mol_type = protein
                        organism = synthetic construct
SEQUENCE: 1028
AEAAAKEAAA KEAAAKEAAA KALEAEAAAK EAAAKEAAAK EAAAKA                    46

SEQ ID NO: 1029         moltype = AA  length = 5
FEATURE                 Location/Qualifiers
REGION                  1..5
                        note = Synthetic polymer
source                  1..5
                        mol_type = protein
                        organism = synthetic construct
SEQUENCE: 1029
PAPAP                                                                 5

SEQ ID NO: 1030         moltype = AA  length = 18
FEATURE                 Location/Qualifiers
REGION                  1..18
                        note = Synthetic polymer
source                  1..18
                        mol_type = protein
                        organism = synthetic construct
SEQUENCE: 1030
KESGSVSSEQ LAQFRSLD                                                   18

SEQ ID NO: 1031         moltype = AA  length = 14
FEATURE                 Location/Qualifiers
REGION                  1..14
                        note = Synthetic polymer
source                  1..14
                        mol_type = protein
                        organism = synthetic construct
SEQUENCE: 1031
EGKSSGSGSE SKST                                                       14

SEQ ID NO: 1032         moltype = AA  length = 12
FEATURE                 Location/Qualifiers
REGION                  1..12
                        note = Synthetic polymer
source                  1..12
                        mol_type = protein
                        organism = synthetic construct
SEQUENCE: 1032
GSAGSAAGSG EF                                                         12

SEQ ID NO: 1033         moltype = DNA  length = 20
FEATURE                 Location/Qualifiers
misc_feature            1..20
                        note = Synthetic polymer
source                  1..20
                        mol_type = other DNA
                        organism = synthetic construct
SEQUENCE: 1033
ttatgcttcc ggctcgtatg                                                 20

SEQ ID NO: 1034         moltype = DNA  length = 29
FEATURE                 Location/Qualifiers
misc_feature            1..29
                        note = Synthetic polymer
misc_feature            24
                        note = r is A or G
source                  1..29
                        mol_type = other DNA
                        organism = synthetic construct
SEQUENCE: 1034
gatgtgcagc tgcaggagtc tggrggagg                                       29

SEQ ID NO: 1035         moltype = DNA  length = 34
```

```
FEATURE                Location/Qualifiers
misc_feature           1..34
                       note = Synthetic polymer
source                 1..34
                       mol_type = other DNA
                       organism = synthetic construct
SEQUENCE: 1035
ctagtgcggc cgctgaggag acggtgacct gggt                              34

SEQ ID NO: 1036        moltype = DNA  length = 22
FEATURE                Location/Qualifiers
misc_feature           1..22
                       note = Synthetic polymer
source                 1..22
                       mol_type = other DNA
                       organism = synthetic construct
SEQUENCE: 1036
tcacacagga aacagctatg ac                                           22

SEQ ID NO: 1037        moltype = DNA  length = 24
FEATURE                Location/Qualifiers
misc_feature           1..24
                       note = Synthetic polymer
source                 1..24
                       mol_type = other DNA
                       organism = synthetic construct
SEQUENCE: 1037
cgccagggtt ttcccagtca cgac                                         24

SEQ ID NO: 1038        moltype = DNA  length = 456
FEATURE                Location/Qualifiers
misc_feature           1..456
                       note = Synthetic polymer
source                 1..456
                       mol_type = other DNA
                       organism = synthetic construct
SEQUENCE: 1038
caggtgcagc tgcaggagtc tggggggaggc ttggtgcagg ctggggggtc tctgagactc  60
tcctgtgcag cctctggatt caccttcgat gattatacca taggctggtt ccgccaggcc  120
ccagggaagg agcgtgaggg aatctcatgt attagtagtg atggtagcac aggctatgca  180
gactccgtga agggccgatt caccatctcc agtgacaacg ccaagaacac ggtatatctg  240
caaatgaaca gcctgaaacc tgaggacacg gccgtttatt actgtgcagc agatttcaac  300
gtgtggtccc cccccatctg cggtagtaat tggtacgggc cgccaccggg gggcatggac  360
tactggggca aagggaccca ggtcaccgtc tcctcagcgg ccgcataccc gtacgacgtt  420
ccggactacg gttcccacca ccatcaccat cactag                            456

SEQ ID NO: 1039        moltype = DNA  length = 456
FEATURE                Location/Qualifiers
misc_feature           1..456
                       note = Synthetic polymer
source                 1..456
                       mol_type = other DNA
                       organism = synthetic construct
SEQUENCE: 1039
caggtgcagc tgcaggagtc tggggggaggc ttggtgcagg ctggggggtc tctgagactc  60
tcctgtgcag cctctggatt cagtttcgat gattatacca taggctggtt ccgccaggtc  120
ccagggaagg agcgtgaggg aatctcatgt attagtagtg atggtagcac aggctatgca  180
gactccgtga agggccgatt caccatttcc agtgacaacg ccaagaacac ggtatatctg  240
caaatcaaca gcctgaaacc tgaggacacg gccgtttatt actgtgcagc agatttcaac  300
gtgtggtccc cccccatctg cggtagtatt tggtacgggc cgccaccggg gggcatggac  360
tactggggca aagggaccca ggtcaccgtc tcctcagcgg ccgcataccc gtacgacgtt  420
ccggactacg gttcccacca ccatcaccat cactag                            456

SEQ ID NO: 1040        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1040
caggtgcagc tgcaggagtc tggggggaggc ttggtgcagg ctggggggtc tctgagactc  60
tcctgtgcag cctctggatt cactttcgat gattatacca tagcctggtt ccgccaggcc  120
ccaggggggga aggagcgtga gggaatctca tgtattagta gtgatggtag cacaggctat  180
gcagactccg tgaagggccg attcaccatc tccagtgaca acgccaagaa catggtatat  240
ctgcaaatga acagcctgaa acctgaggac acggcccttt attactgtgc agcagatttc  300
aacgtgtggt cccccccccat ctgtagtagt aactggtacg ggccgccacc gcggggcatg  360
gactactggg gcaaagggac ccaggtcacc gtctcctcag cggccgcata cccgtacgac  420
gttccggact acggttccca ccaccatcac catcactag                         459
```

```
SEQ ID NO: 1041        moltype = DNA  length = 456
FEATURE                Location/Qualifiers
misc_feature           1..456
                       note = Synthetic polymer
source                 1..456
                       mol_type = other DNA
                       organism = synthetic construct
SEQUENCE: 1041
caggtgcagc tgcaggagtc tggggaggc ttggcgcagg ttggggggtc tctgagactc  60
tcctgtacag cctctggatt cactttcgat gattatacca taggctggtt ccgccaggcc  120
ccagggaagg agcgtgaggg aatctcatgt attagtagtg atggtagcac aggctatgca  180
gactccgtga agggccgatt caccatctcc agtgacaacg ccaagaacac ggtatatctg  240
caaatgaaca gcctgaaacc tgaggacacg gccgtttatt actgtgcagc agatttcaac  300
gtgtggtccc cccccatctg cggtagtaat tggtacgggc cgccaccggg gggcatggac  360
tactggggca aagggaccca ggtcaccgtc tcctctgcgg ccgcataccc gtacgacgtt  420
ccggactacg gttcccacca ccatcaccat cactag                           456

SEQ ID NO: 1042        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1042
caggtgcagc tgcaggagtc tggaggaggc ttggtgcagg ctggggggtc tctgagactc  60
tcctgtgcag cctctggatt cagttccgat gattatacca taggctggtt ccgccaggcc  120
ccagggaagg agcgtgaggg aattggatgt attaaaagta gtgatggtac cacaggctat  180
gcagactccg tgaagggccg attcaccatc tccagtgaca acgccaagaa cacggtatat  240
ctgcaaatga acagcctgaa acctgaggac acggccgttt attactgtgc agcagatttc  300
aacgtgtggt cccccccat ctgcggtagt atttggtacg ggccgccacc ggggggcatg  360
gactactggg gcaaagggac ccaggtcacc gtctcctcag cggccgcata cccgtacgac  420
gttccggact acggttccca ccaccatcac catcactag                        459

SEQ ID NO: 1043        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1043
caggtgcagc tgcaggagtc tggggggagga ttggtgcagg ctggggggtc tctgagactc  60
tcctgtgcag cctctggatt cagttccgat gattatacca taggctggtt ccgccaggcc  120
ccagggaagg agcgtgaggg aatctcatgt tatagtagta gtgatggtag cacaggctat  180
gcagactccg tgaagggccg attcaccatc tccagtgaca acgccaagaa cacggtatat  240
ctgcaaatga acagcctgaa acctgaggac acggccgttt attactgtgc agcagatttc  300
aacgtgtggt cccccccat ctgcggtagt agctggtacg ggccgccacc ggggggcatg  360
gactactggg gcaaagggac ccaggtcacc gtctcctcag cggccgcata cccgtacgac  420
gttccggact acggttccca ccaccatcac catcactag                        459

SEQ ID NO: 1044        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1044
caggtgcagc tgcaggagtc tggggggagga ttggtgcagg ctggggggtc tctgagactc  60
tcctgtgcag cctctggatt cagttccgat gattatacca taggctggtt ccgccaggcc  120
ccagggaagg agcgtgaggg aatctcatgc tatagtagta gtgatggtag cacaggcttt  180
gcagactccg tgaagggccg attcaccatc tccagtgaca acgccaagaa cacggtatat  240
ctgcaaatga acagcctgag acctgaggac acggccgttt attactgtgc agcagatttc  300
aacgtgtggt cccccccat ctgcggtagt aggtggtacg ggccgccacc ggggggcatg  360
gcctactggg gcaaaggaac ccaggtcacc gtctcctcag cggccgcata cccgtacgac  420
gttccggact acggttccca ccaccatcac catcactag                        459

SEQ ID NO: 1045        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1045
caggtgcagc tgcaggagtc tggggggagga ttggtgcagg ctggggcctc tctgagactc  60
tcctgtaaag cctctggatt cacgttcgga gattatacca taggctggtt ccgccaggcc  120
```

```
ccagggaagg agcgtgaggg aatctcatgt tatagtagta gtgatggtaa cacaggctat  180
gcagactccg tgaagggccg attcaccatc tccagtgaca acgccaagaa cacggtatat  240
ctgcaaatga acagcctgag acctgaggac acggccgttt attactgtgc agcagatttc  300
aacgtgtggt cccccccat ctgcggtagt agctggtacg ggccgccacc gggggcatg  360
gcctactggg gcaaagggac ccaggtcacc gtctcctcag cggccgcata cccgtacgac  420
gttccggact acggttccca ccaccatcac catcactag                        459

SEQ ID NO: 1046        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1046
caggtgcagc tgcaggagtc tgggggaggc ttggtgcagg ctgggggta tctgagactc  60
tcctgtgcag cctctggatt cagttccgat gattatacca taggctggtt ccgccaggcc  120
ccagggaagg agcgtgaggg aatctcatgt tatagtagta gtgatggtag cacagggttt  180
gcagactccg tgaagggccg attcaccatc tccagtgaca acgccaagaa cacggtatat  240
ctgcaaatga acaacctgag acctgaggac acggccgttt attactgtgc agcagattcc  300
aacgtgtggt cccccccat ctgcggtagt aggtggtacg ggccgccacc gggggcatg  360
gcctactggg gcaaagggac ccaggtcacc gtctcctcag cggccgcata cccgtacgac  420
gttccggact acggttccca ccaccatcac catcactag                        459

SEQ ID NO: 1047        moltype = DNA  length = 456
FEATURE                Location/Qualifiers
misc_feature           1..456
                       note = Synthetic polymer
source                 1..456
                       mol_type = other DNA
                       organism = synthetic construct
SEQUENCE: 1047
caggtgcagc tgcaggagtc tgggggaggc ttggtgcagg ctgggggtc tctgagactc  60
tcctgtgcag cctctggatt cactttcgat gattatacca tagcctggtt ccgccaggcc  120
ccagggaagg agcgtgaggg aatctcatgt attagtagtg atggtagcac aggctatgca  180
gattccgtgc ggggccgatt caccatctcc agtgacaacg ccaagaacac ggtatatctg  240
caaatgaaca gcctgaaacc tgaggacacg gccgtttatt actgtgcagc agatttcaac  300
gtgtggtccc cccccatttg cggtagtatt tggtacgggc cgccaccgcg gggcatggac  360
tactggggca aagggaccca ggtcaccgtc tcctcagcgg ccgcataccc gtacgacgtt  420
ccggactacg gttcccacca ccatcaccat cactag                           456

SEQ ID NO: 1048        moltype = DNA  length = 456
FEATURE                Location/Qualifiers
misc_feature           1..456
                       note = Synthetic polymer
source                 1..456
                       mol_type = other DNA
                       organism = synthetic construct
SEQUENCE: 1048
caggtgcagc tgcaggagtc tgggggagga ttggtgcagg ctggggactc tctgaaactc  60
tcctgtgcaa cctctggacg gagcttcagt agctatacca tagcctggtt ccgccaggcc  120
ccagggaagg agcgtgaggg aatctcatgt attagtagtg atggtagcac aggctatgca  180
gattccgtgc ggggccgatt caccatctcc agtgacaacg ccaagaacac ggtatatctg  240
caaatgaaca gcctgaaacc tgaggacacg gccgtttatt actgtgcagc agatttcaac  300
gtgtggtccc cccccatttg cggtagtatt tggtacgggc cgccaccgcg gggcatggac  360
tactggggca aagggaccca ggtcaccgtc tcctcagcgg ccgcataccc gtacgacgtt  420
ccggactacg gttcccacca ccatcaccat cactag                           456

SEQ ID NO: 1049        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1049
caggtgcagc tgcaggagtc tgggggaggc ttggtgcagg ctgggggtc tctgagactc  60
tcctgtgaag tctctgggct cagttccgat gattatacca taggctggtt ccgccaggcc  120
ccagggaagg agcgtgaggg attctcatgc tttagtacgc gtgatggtaa cgctggctat  180
gcagactccg tgaagggccg attcaccatc tccagtgaca acgccaagaa cacggtatat  240
ctgcaaatga acaacctgaa acctgaggac acggccgttt attattgtgc agcagatttc  300
aacgtgtggt cccccccat ctgcggtagt cgctggtacg ggccgccacc gggggcatg  360
gactactggg gcaaagggac ccaggtcacc gtctcctcag cggccgcata cccgtacgac  420
gttccggact acggttccca ccaccatcac catcactag                        459

SEQ ID NO: 1050        moltype = DNA  length = 459
FEATURE                Location/Qualifiers
misc_feature           1..459
                       note = Synthetic polymer
```

```
source                  1..459
                        mol_type = other DNA
                        organism = synthetic construct
SEQUENCE: 1050
caggtgcagc tgcaggagtc tgggggaggc ttggtgcagg ctgggggtc tctgagactc  60
tcctgtgaag tctctgggct cagttccgat gattatacca taggctggtt ccgccaggcc  120
ccagggaaga agcgtgaggg attctcatgt tttagtagtc gtgatggtag cactggctat  180
gcagactccg tgaagggccg attcaccatc tccagtgaca acgccaagaa cacggtatat  240
ctgcaaatga acagcctgaa acctgaggac acggccgttt attattgtgc agcagatttc  300
aacgtgtggt cccccccat ctgcggtagt cgctggtacg ggccgccacc gggggcatg  360
gactactggg gcaaagggac ccaggtcacc gtctcctcag cggccgcata cccgtacgac  420
gttccggact acggttccca ccaccatcac catcactag                        459

SEQ ID NO: 1051         moltype = DNA  length = 459
FEATURE                 Location/Qualifiers
misc_feature            1..459
                        note = Synthetic polymer
source                  1..459
                        mol_type = other DNA
                        organism = synthetic construct
SEQUENCE: 1051
caggtgcagc tgcaggagtc tggaggaggc ttggtgcagg ctgggggtc tctgagactc  60
tcctgtgcag cctctggatt cagttccgat gattatacca taggctggtt ccgccaggcc  120
ccagggaagg agcgtgaggg attctcatgt tttagtagtc gtgatggtag cacaggctat  180
gcagactccg tgaagggccg attcaccatc tccagtgaca acgccaagaa cacggtatat  240
ctgcaaatga acagcctgaa acctgaggac acggccgttt attattgtgc agcagatttc  300
aacgtgtggt cccccccat ctgcggtagt cgctggtacg ggccgccacc gggggcatg  360
gactactggg gcaaagggac ccaggtcacc gtctcctcag cggccgcata cccgtacgac  420
gttccggact acggttccca ccaccatcac catcactag                        459

SEQ ID NO: 1052         moltype = DNA  length = 459
FEATURE                 Location/Qualifiers
misc_feature            1..459
                        note = Synthetic polymer
source                  1..459
                        mol_type = other DNA
                        organism = synthetic construct
SEQUENCE: 1052
caggtgcagc tgcaggagtc tgggggaggc ttggtgcagg ctgggggtc tctgagactc  60
tcctgtgcag cctctggatt cagttccgat gattatacca tagcctggtt ccgccgggcc  120
ccagggaagg agcgtgaggg aatctcatgt attagtagta gtgatggtag cacaggttat  180
gcagactccg tgaagggccg attcaccatc accagtgaca gcgccaagaa cacggtttat  240
ctgcaaatga acagcctgaa acctgaggac acggccgttt attactgtgc agcagattcc  300
aacgtgtggt cccccccat ctgcggtcgt acctggtacg ggccgccacc gggggcatg  360
gactactggg gcaaagggac ccaggtcacc gtctcctcag cggccgcata cccgtacgac  420
gttccggact acggttccca ccaccatcac catcactag                        459

SEQ ID NO: 1053         moltype = DNA  length = 459
FEATURE                 Location/Qualifiers
misc_feature            1..459
                        note = Synthetic polymer
source                  1..459
                        mol_type = other DNA
                        organism = synthetic construct
SEQUENCE: 1053
caggtgcagc tgcaggagtc tgggggaggc ttggtgcagg ctgggggtc tctgagactc  60
tcctgtgcag cctctggatt cagttccgat gattatacca tagcctggtt ccgccgggcc  120
ccagggaagg agcgtgaggg aatctcatgt attagtagta gtgatggtag cacaggttat  180
gcagactccg tgaagggccg attcaccatc tccagtgaca acgccaagaa cacggtatat  240
ctgcaaatga ccagtctgaa acctgaggac acggccgttt attactgtgc agcagattcc  300
aacgtgtggt cccccccat ctgcggtaaa acctggtacg ggccgccacc agggggcatg  360
gactactggg gcaaagggac ccaggtcacc gtctcctcag cggccgcata cccgtacgac  420
gttccggact acggttccca ccaccatcac catcactag                        459

SEQ ID NO: 1054         moltype = DNA  length = 459
FEATURE                 Location/Qualifiers
misc_feature            1..459
                        note = Synthetic polymer
source                  1..459
                        mol_type = other DNA
                        organism = synthetic construct
SEQUENCE: 1054
caggtgcagc tgcaggagtc tgggggaggc ttggtgcagg ctgggggtc tctgagactc  60
tcctgtgcag cctctggatt cagttccgat gattatacca tagcctggtt ccgccgggcc  120
ccagggaagg agcgtgaggg catctcatgt tttagtagta gtgatggtag cgcaggctat  180
gcagactccg tgaagggccg attcaccgtc tccagtgaca acgccaagaa cacggtatat  240
ctgcaaatga acagcctgaa acctgaggac acggccgttt attactgtgc agcagattcc  300
aacgtgtggt cccccccat ctgcggtagt acctggtacg ggccgccacc gggggcatg  360
gcctactggg gcaaagggac ccaggtcacc gtctcctcag cggccgcata cccgtacgac  420
```

-continued

```
gttccggact acggttccca ccaccatcac catcactag                        459

SEQ ID NO: 1055        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1055
caggtgcagc tgcaggagtc tgggggaggc ttggtgcagc ctgggggggtc tctgagactc  60
tcctgtgcag cctctggatt cagttccgat gattatacca taggctggtt ccgtcaggcc  120
ccagggaagg agcgtgaggg aatctcatgt tatagtagcc gtgatggtac cacaggctat  180
gcagactccg tgaagggccg attcaccatc tccagtgaca acgccaagaa cacggtatat  240
ctgcaaatga acagcctgaa acctgaggac acggccgttt attactgtgc agcagatttc  300
aatgtgtggt cccccccat ctgcggtagt atctggtacg ggccgccacc ggggggcatg  360
gcctactggg gccaggggac ccaggtcacc gtctcctcag cggccgcata cccgtacgac  420
gttccggact acggttccca ccaccatcac catcactag                        459

SEQ ID NO: 1056        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1056
caggtgcagc tgcaggagtc tggaggaggc ttggtgcagg ctgggggggtc tctgaractc  60
tcctgtgcag cctctggatt cactttcgat gattatgcca taggctggtt ccgccaggcc  120
ccagggaagg agcgtgaggg ggtctcatgt attagtagtc cggatggtag cacatactat  180
gcagactccg tgaagggccg attcaccatc tccagtgaca acgccaagaa cacggtgtat  240
ctgcaaatga acagcctgaa acctgaggac acggccgttt attactgtgc agcagatttc  300
aacgtgtggt cccccccat ctgcggtagt gtagggccgc caccgggggg catggactac  360
tggggcaaag ggacccaggt caccgtctcc tcagcggccg catacccgta cgacgttccg  420
gactacggtt cccaccacca tcaccatcac tag                              453

SEQ ID NO: 1057        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1057
caggtgcagc tgcaggagtc tgggggaggc ttggtgcagg ctgggggggtc tctgagactc  60
tcctgtgcag cctctggatt cagttccgat gattatacca taggctggtt ccgccaggcc  120
ccagggaagg agcgtgaggg aatctcgtgt ttcagtagta gtgatggtag cacaggcttt  180
gcagactccg tgaagggccg gttcaccatc tccagtgaca acgccacgaa cacggtatat  240
ctggaaatga acagcctgaa acctgaggac acggccgttt attactgtgc agcagatttc  300
aacgtgtggt cccccccat ttgcggtagt aggtggtacg ggccgccacc ggggggcatg  360
gagtactggg gcaaagggac ccaggtcacc gtctcctcag cggccgcata cccgtacgac  420
gttccggact acggttccca ccaccatcac catcactag                        459

SEQ ID NO: 1058        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1058
caggtgcagc tgcaggagtc tgggggaggc ttggtgcagg ctgggggggtc tctgagactc  60
tcctgtgcag cctctggatt cagttccgat gattatacca taggctggtt ccgccaggcc  120
ccagggaagg agcgtgaggg aatctcgtgt ttcagtagta gtgatggtag cacaggcttt  180
gcagactccg tgaagggccg gttcaccatc tccagtgaca acgccacgaa cacggtatat  240
ctgcaaatga acagcctgaa acctgaggac acggccgttt attactgtgc agcagatttc  300
aacgtgtggt cccccccat ttgcggtagt agctggtacg ggccgccacc ggggggtatg  360
gaatactggg gcaaagggac ccaggtcacc gtctcctcag cggccgcata cccgtacgac  420
gttccggact acggttccca ccaccatcac catcactag                        459

SEQ ID NO: 1059        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1059
caggtgcagc tgcaggagtc tggaggaggc ttggtgcagg ctgggggatc tctgagactc  60
```

```
tcctgtgcag cctctggatt cgctttcgat ggttatgcca taggctggtt ccggcaggcc  120
ccagggaagg agcgtgaggg cgtctcatgt attagtagta aggagggtag cacatactat  180
gcagactccg tgaagggccg attcaccatc tccagtgaca acgccaagaa cacggtgtat  240
ctgcaaatga gcagcctgaa acctgaggac acggccgtct attactgcgc agcagatggt  300
aacgtgtggt cccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                                453

SEQ ID NO: 1060        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1060
caggtgcagc tgcaggagtc tggggggaggg ttggtgcagg ctggggactc tctgaaactc  60
tcctgtgcag cctctggcct caccttcagt aactatatca tggcctggtt ccgccaggct  120
ccagggaagg agcgtgaggg ggtctcatgt attagtagtc cggatggtag cacatactat  180
gcagactccg tgaagggccg attcaccatc tccagtgaca acgccaagaa cacggtgtat  240
ctgcaaatga acagcctgaa acctgaggac acggccgttt attactgtgc agcagatttc  300
aacgtgtggt cccccccat ctgcggtagt gtagggccgc caccgggggg catggactac  360
tggggcaaag ggacccaggt caccgtctcc tcagcggccg catacccgta cgacgttccg  420
gactacggtt cccaccacca tcaccatcac tag                                453

SEQ ID NO: 1061        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1061
caggtgcagc tgcaggagtc tgggggaggc ttggtgcagg ctgggggggtc tctgagactc  60
tcctgtgcaa cctttggatt cacttttgat gattatgcca tagcctggtt ccgccaggcc  120
ccagggaagg agcgtgaggg gatctcctgt attagtaata cggatagtag cacatactat  180
gcagactccg tgaagggccg attcaccatc tccagtgaca gcgccaagaa cacggtgcat  240
ctgcaaatga gcagcctgaa acctgaggac acggccgtct attactgcgc agcagatggc  300
aacgtgtggt cccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                                453

SEQ ID NO: 1062        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1062
caggtgcagc tgcaggagtc tgggggaggc ttggtgcagg ctgggggggtc tctgagactc  60
tcctgtgcaa cctttggatt cagttttgat gattatgcca tagcctggtt ccgccaggcc  120
ccagggaagg agcgtgaggg gatctcctgt attagtaata cggatagtag cacattctat  180
gcagactccg tgaagggccg attcaccatc tccagtgaca acgccaagaa cacggtgcat  240
ctgcagatga gcagcctgaa acctgaggac acggccgtct attactgcgc agcagatggc  300
aacgtgtggt cccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                                453

SEQ ID NO: 1063        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1063
caggtgcagc tgcaggagtc tgggggaggc ttggtgcagg ctgggggggtc tctgagactc  60
tcctgtgcaa cctttggatt cacttttgat gattatgcca tagcctggtt ccgccaggcc  120
ccagggaagg agcgtgaggg gatctcctgt attagtaata cggatagtag cacatactat  180
gcagactccg tcaagggccg attcaccatc tccagtgaca acgccaagaa cacggtgcat  240
ctgcaaatga gcagcctgaa acctgaggac acggccgtct attactgcgc agcagatggc  300
aacgtgtggt cccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                                453

SEQ ID NO: 1064        moltype = DNA  length = 453
FEATURE                Location/Qualifiers
misc_feature           1..453
```

```
                        note = Synthetic polymer
source                  1..453
                        mol_type = other DNA
                        organism = synthetic construct
SEQUENCE: 1064
caggtgcagc tgcaggagtc tgggggaggc ttggtgcagg ctgggggtc tctgagactc  60
tcctgtgcaa cctctggatt cactttcgat gattatgcca tagcctggtt ccgccaggcc  120
ccggggaagg agcgtgaggg ggtctcctgt attagtaata cggatagtag cacatactat  180
gcagactccg taaagggccg attcaccatc tccagtgaca acgccaagaa cacggtgtat  240
ctgcaaatga gcagcctgaa acctgaggac acggccgtct attactgcgc agcagatggt  300
aacgtgtggt ccccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                              453

SEQ ID NO: 1065         moltype = DNA  length = 453
FEATURE                 Location/Qualifiers
misc_feature            1..453
                        note = Synthetic polymer
source                  1..453
                        mol_type = other DNA
                        organism = synthetic construct
SEQUENCE: 1065
caggtgcagc tgcaggagtc tgggggaggc ttggtgcagc ctgggggtc tctgagactc  60
tcctgtgcaa cctttggatt ccctttcgat gattatgcca tagcctggtt ccgccaggcc  120
ccagggaagg agcgtgaggg ggtctcctgt attagtaata cggatagtag cacatactat  180
gcagactccg tgaagggccg gttcaccatc tccagtgaca acgccaagaa cacggtgcat  240
ctgcaaatga gcagcctgaa acccgaggac acggccgtct attactgcgc agcagatggc  300
aacgtgtggt ccccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                              453

SEQ ID NO: 1066         moltype = DNA  length = 453
FEATURE                 Location/Qualifiers
misc_feature            1..453
                        note = Synthetic polymer
source                  1..453
                        mol_type = other DNA
                        organism = synthetic construct
SEQUENCE: 1066
caggtgcagc tgcaggagtc tgggggaggc ttggcgcagg ctgggggtc tctgagactc  60
tcttgtgcag cctctggatt cactttcgat cagtatacca tagcctggtt ccgccaggcc  120
ccagggaagg agcgtgaggg ggtctcctgt attagtaata cggatagtag cacatactat  180
gcagactccg tgaagggccg attcaccatc tccagtgaca acgccaagaa cacggtgtat  240
ctgcaaatga gcagcctgaa acctgaggac acggccgtct attactgcgc agcagatggt  300
aacgtgtggt ccccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                              453

SEQ ID NO: 1067         moltype = DNA  length = 456
FEATURE                 Location/Qualifiers
misc_feature            1..456
                        note = Synthetic polymer
source                  1..456
                        mol_type = other DNA
                        organism = synthetic construct
SEQUENCE: 1067
caggtgcagc tgcaggagtc tggaggaggc ttggtgcagg ttggggggatc tctgagactc  60
tcctgtacaa tttctggatt cactgggaat gatcttgcca taggctggtt tcgccaggcc  120
ccagggaagg accagcgtga gggtatctcc tgtattagta atacggatag tagcacatac  180
tatgcagact ccgtgaaggg ccgattcacc atctccagtg acaacgccaa gaacacggtg  240
catctgcaaa tgagcagcct gaaacctgag gacacggccg tctattactg cgcagcagat  300
ggcaacgtgt ggtccccccc catctgcggt agtgccgggc cgccaccggg gggcatggac  360
tactggggca aagggaccca ggtcaccgtc tcctcagcgg ccgcataccc gtacgacgtt  420
ccggactacg gttcccacca ccatcaccat cactag                           456

SEQ ID NO: 1068         moltype = DNA  length = 453
FEATURE                 Location/Qualifiers
misc_feature            1..453
                        note = Synthetic polymer
source                  1..453
                        mol_type = other DNA
                        organism = synthetic construct
SEQUENCE: 1068
caggtgcagc tgcaggagtc tgggggaggc ttggtgcagg ctgggggtc tctgagactc  60
tcctgtgcag gctctggatt cactttggat tattatggca taggctggtt ccgccaggcc  120
ccagggaagg agcgcgaggg ggtctcatgt attagtagta gtgatcgtaa cacatactat  180
gcagactccg tgaagggccg attcaccatc tccggtgaca atgccaagaa cacggtgtat  240
ctgcaaatga acaacctgaa acctgaggac acggccgttt attactgcgc agcagatggc  300
aacgtgtggt ccccccccat ctgcggtagt gccgggccgc caccgggggg catggactac  360
```

```
tggggcaaag ggacccaggt caccgtctcc tcagcggccg catacccgta cgacgttccg  420
gactacggtt cccaccacca tcaccatcac tag                               453

SEQ ID NO: 1069        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1069
caggtgcagc tgcaggagtc tggaggagga ttggtgcagg ctgggggctc tctgagactc  60
tcgtgtacag cctctggacg caccttcagt agctataccg tggcctggtt ccgccagtct  120
ccagggaagg agcgtgaggg gatctcctgt attagtaata cggatagtag cacatactat  180
gcagactccg tgaagggccg attcaccatc tccagtgaca acgccaagag cacggtgcat  240
ctgcaaatga gcagcctgaa acctgaggac acggccgtct attactgcgc cgcagatggc  300
aacgtgtggt cccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                               453

SEQ ID NO: 1070        moltype = DNA  length = 450
FEATURE                Location/Qualifiers
misc_feature           1..450
                       note = Synthetic polymer
source                 1..450
                       mol_type = other DNA
                       organism = synthetic construct
SEQUENCE: 1070
caggtgcagc tgcaggagtc tgggggaggc ttggtgcagg ctgaggggtc tctgaaactc  60
tcctgtattt ctggattcgc tttcgatggt tatgccatag gttggttccg ccaggcccca  120
gggaaggagc gtgagggggt cgcatgtatt agtagtaaag atggtagcac atactatgca  180
gactccgtga agggccgctt caccatgtcc gtagacaaga ccaagaacac ggtgtatctg  240
cagatgagca gcctgaaacc tgaggacacg gccgtctatt actgcgcagc agatggcaac  300
gtgtggtccc cccccatctg cagtagtgcc gggccgccac cggggggcat ggactactgg  360
ggcaaaggga cccaggtcac cgtctcctca gcggccgcat acccgtacga cgttccggac  420
tacggttccc accaccatca ccatcactag                                   450

SEQ ID NO: 1071        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1071
caggtgcagc tgcaggagtc tggaggaggc ttggtgcagg ctggggactc tctgagactc  60
tcctgtacag cctctggcgt ctcaattggc gattataaca tcggctggtt ccgccaggcc  120
ccaggaaagg agcgtgaggg ggtttcatgt attagtagtg gagatggtac cacatactat  180
acagactccg tgaagggccg attcaccatc tccaccgaca acgccaagaa cacggtgtat  240
ctgcaaatga acagcctgaa acctgaggac acggccgtct attactgcgc agcagatggc  300
aacgtgtggt cccccccat ctgcggtagt gccgggccgc caccgggggg catggactac  360
tggggcaaag ggacccaggt caccgtctcc tcagcggccg catacccgta cgacgttccg  420
gactacggtt cccaccacca tcaccatcac tag                               453

SEQ ID NO: 1072        moltype = DNA  length = 450
FEATURE                Location/Qualifiers
misc_feature           1..450
                       note = Synthetic polymer
source                 1..450
                       mol_type = other DNA
                       organism = synthetic construct
SEQUENCE: 1072
caggtgcagc tgcaggagtc tgggggaggc ttggtgcagg ctggggggtc tctgagactc  60
tcctgtgcgg cctctggatt cactttcgat gattatgcca tagcctggtt ccgccaggcc  120
ccagggaagg agcgtgaggg ggtctcatgt attgaaagaa gtgatggtag cacatactat  180
gcagactccg tgaagggccg attcaccatc tccagtgaca acgccaagaa cacggtatat  240
ctacaaatga acagcctgaa acctgaggac acggccgttt attactgtgc agtagggtcc  300
gccaattcag gagagtttcg attcggttgg gtacttaaac ctgacctcta taactactgg  360
ggccagggga cccaggtcac cgtctcctca gcggccgcat acccgtacga cgttccggac  420
tacggttccc accaccatca ccatcactag                                   450

SEQ ID NO: 1073        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1073
```

```
caggtgcagc tgcaggagtc tgggggaggc ttggtgcagg ctggggggtc tctgagactc  60
tcctgtgcag tctctggatt cactttcgat aattatgcca taggctggtt ccgccaggcc  120
ccagggaagg agcgtgaggg ggtctcatgt attagcagga gtgatggtag cacatactat  180
gcagactccg tcaggggccg attcaccatc tccagtgaca acgccaagaa cacggtgtat  240
ctacaaatga acagcctcaa acctgaggac acggccgttt attactgtgc agcagagacg  300
tccgccgatt caggagagtt tcgattcggt tgggtactta aacctagtct ctatgactac  360
tggggccagg ggacccaggt caccgtctcc tcagcggccg catacccgta cgacgttccg  420
gactacggtt cccaccacca tcaccatcac tag                               453

SEQ ID NO: 1074        moltype = DNA  length = 450
FEATURE                Location/Qualifiers
misc_feature           1..450
                       note = Synthetic polymer
source                 1..450
                       mol_type = other DNA
                       organism = synthetic construct
SEQUENCE: 1074
caggtgcagc tgcaggagtc tggggggagga ttggtgcagg ctgggggctc tctgagactc  60
tcctgtgcag cctctggacg caccttcagt aactatgcca tgggctggtt ccgccaggct  120
ccagggaagg agcgtgagtt tgtagcagct attgtctgga gtggtggtag cacatactat  180
gcagactccg tgaagggccg attcaccatc tccagagaca acgccaagaa cacggtgtat  240
ctgcaaatga acagcctgaa acctgaggac acggccgttt attactgtgc agcagtactc  300
atacgatact atagtggtgg ttaccagggg ctctcggacg cgaatgagta tgactactgg  360
ggccagggga cccaggtcac cgtctcctca gcggccgcat acccgtacga cgttccggac  420
tacggttccc accaccatca ccatcactag                                   450

SEQ ID NO: 1075        moltype = DNA  length = 435
FEATURE                Location/Qualifiers
misc_feature           1..435
                       note = Synthetic polymer
source                 1..435
                       mol_type = other DNA
                       organism = synthetic construct
SEQUENCE: 1075
caggtgcagc tgcaggagtc tgggggaggc ttggtgcagg ctggggggtc tctgagactc  60
tcctgtgcag cctctggacg caccttcagt agctatgcca tggcctggtt ccgccaggct  120
ccagggaagg agcgtgagtt tgtagcagct attgcctgga gtgctggtag cacatactat  180
gcagactccg tgaagggccg attcgccatc tccagagaca acgccgagaa cacggtgtat  240
ctgcaaatga acagcctgaa acctgaggac acggccgttt attactgtgc agcacgtata  300
attactgtag cgactatgag actcgacagc gattatgact actggggcca ggggacccag  360
gtcaccgtct cctcagcggc cgcatacccg tacgacgttc cggactacgg ttcccaccac  420
catcaccatc actag                                                   435

SEQ ID NO: 1076        moltype = DNA  length = 447
FEATURE                Location/Qualifiers
misc_feature           1..447
                       note = Synthetic polymer
source                 1..447
                       mol_type = other DNA
                       organism = synthetic construct
SEQUENCE: 1076
caggtgcagc tgcaggagtc tggggggagga ttggtgcagg ctgggggctc tctgagactc  60
tcctgtgcag cctctggacg caccttcagt aacagtgtca tgggctggtt ccgccagcct  120
ccagggaagg agcgtgagtt tgtagcagct gtgttgtggt ctggtgttag tacagcctat  180
gcagactccg tgaagggccg attcaccatc tccagagaca acgccaagaa cacggtgtat  240
ctgcagatga acaacctgaa acctgatgac acggccgttt attactgtgc agcccacgag  300
agtacatact atagtggtac ttactacctc accgaccctc ggagatatgt ctactggggc  360
caggggaccc aggtcaccgt ctcctcagcg gccgcatacc cgtacgacgt tccggactac  420
ggttcccacc accatcacca tcactag                                      447

SEQ ID NO: 1077        moltype = DNA  length = 453
FEATURE                Location/Qualifiers
misc_feature           1..453
                       note = Synthetic polymer
source                 1..453
                       mol_type = other DNA
                       organism = synthetic construct
SEQUENCE: 1077
caggtgcagc tgcaggagtc tgggggaggc ttggtgcagg ctgggggctc cctgagactc  60
tcctgtgcag cctctggacg caccttcagt agttatacca tgggctggtt ccgccaggct  120
ccagggaggg agcgtgagtt tgtagcagct attacatgga gtggtgttag cactgtctat  180
acagactccg tgaagggccg attcaccgtc tccagagaca acgccaagaa cacggtgtat  240
ctgcaaatga acagcctgaa acctgaggac acggctgttt attactgtgc agcagatagt  300
ccccccagga catactcgag tggtagtgtg aacctggaag acgggagtga gtatgactac  360
tggggccagg ggacccaggt caccgtctcc tcagcggccg catacccgta cgacgttccg  420
gactacggtt cccaccacca tcaccatcac tag                               453

SEQ ID NO: 1078        moltype = DNA  length = 447
FEATURE                Location/Qualifiers
```

```
misc_feature            1..447
                        note = Synthetic polymer
source                  1..447
                        mol_type = other DNA
                        organism = synthetic construct
SEQUENCE: 1078
caggtgcagc tgcaggagtc tgggggagga ttggtgcagg ctggggcctc tctgagactc  60
tcctgtgcag cctctggacg caccttcagt agctatatca tgggctggtt ccgccaggct  120
ccagggaagg agcgtgagtt tgtagcagct attggctgga gtgctgatat cacagtctat  180
gcagactccg tgaagggccg attcaccatc tccagagaca acgccgagaa tatggtgtat  240
ctgcaaatga acagtctgaa ccctgaggac acggccgttt attactgtgc agcaaattca  300
cgtgcatatt atagcagtag ttacgactta gggcgacttg cctcgtatga ctactggggc  360
cagggcaccc aggtcaccgt ctcctcagcg gccgcatacc cgtacgacgt tccggactac  420
ggttcccacc accatcacca tcactag                                     447

SEQ ID NO: 1079         moltype = DNA  length = 450
FEATURE                 Location/Qualifiers
misc_feature            1..450
                        note = Synthetic polymer
source                  1..450
                        mol_type = other DNA
                        organism = synthetic construct
SEQUENCE: 1079
caggtgcagc tgcaggagtc tgggggagga ttggtgcagg ctgggggctc tctgagactc  60
tcctgtgcag cctctggacg caccttcagt agctatgtca tgggctggtt ccgccaggct  120
ctagggaagg agcgtgagtt tgtagcagct atcggctgga atggtggtat cacatactat  180
gcagactccg tgaagggccg attcgccatc tccagagaca acgccaagaa cacggtgtat  240
ctgcaaatga acagcctgaa acctgaggac acggccgttt attactgtgc agccgctacc  300
cttcaagtta ctggtagtta ctacttagac ctatccaccg tggacatata tgacaactgg  360
ggccagggga cccaggtcac cgtctcctca gcggccgcat acccgtacga cgttccggac  420
tacggttccc accaccatca ccatcactag                                  450

SEQ ID NO: 1080         moltype = DNA  length = 444
FEATURE                 Location/Qualifiers
misc_feature            1..444
                        note = Synthetic polymer
source                  1..444
                        mol_type = other DNA
                        organism = synthetic construct
SEQUENCE: 1080
caggtgcagc tgcaggagtc tgggggagga ttggtgcagg ctgggggctc cctgagactc  60
tcctgtgcag cctctggagg caccttcagt aattatgtca tgggctggtt ccgccaggct  120
ccagggaagg agcgtgagtt tgtaggtttt attacctgga gtggtgctag tacatactat  180
gcagattccg tgaagggccg attcactatc tccagagaca acgccgagaa cacggtgtat  240
ctgcaaatga acagcctgaa acctgaggac acggccgttt attactgtgc agccactcta  300
tttaggtcca acggcccgaa agacctatct tcgggctatg agtatgacta ctggggccag  360
gggacccagg tcaccgtctc ctcagcggcc gcatacccgt acgacgttcc ggactacggt  420
tcccaccacc atcaccatca ctag                                        444

SEQ ID NO: 1081         moltype = DNA  length = 438
FEATURE                 Location/Qualifiers
misc_feature            1..438
                        note = Synthetic polymer
source                  1..438
                        mol_type = other DNA
                        organism = synthetic construct
SEQUENCE: 1081
caggtgcagc tgcaggagtc tgggggagga ttggtgcagg ctgggggctc tctgagactc  60
tcctgtgcag cctctacacc caccttcagt agctataaca tgggctggtt ccgccaggct  120
ccagggaagg agcgtgagtt tgtagcagct attatctgga gtggtagtat gacatactat  180
gcagactcca tgaagggccg attcaccgtt tggagctcag cctatggacc tttctgggga  240
ttatgagtac tggggccagg ggacccaggt caccgtctcc tcagcggccg catacccgta  300
cgacgttccg gactccatag acaacgccaa gaacacggtg tatctgcaaa tgaacagcct  360
gaaacctgag gacacggccg tttattactg tgcagcacaa cggatatcta cggttcccac  420
caccatcacc atcactag                                               438

SEQ ID NO: 1082         moltype = DNA  length = 447
FEATURE                 Location/Qualifiers
misc_feature            1..447
                        note = Synthetic polymer
source                  1..447
                        mol_type = other DNA
                        organism = synthetic construct
SEQUENCE: 1082
caggtgcagc tgcaggagtc tgggggagga ttggtgcagg ctgggggctc tctgagactc  60
tcctgtgcag cctctggacg cgccttcagt agctatttca tgggctggtt ccgccagact  120
ccagggaagg agcgggagtt tgtagcaaat attggctgga ctggtgatat gacatactat  180
gcagactccg tgaagggccg attcaccatc tcgcgagaca acgccaagaa cacggtgtat  240
ctgcaaatga acagcctgaa acctgaggac acggccgttt attattgtgc agcagcgggc  300
```

```
agcgcatata gcggtagtta ctggaacata acgatggcgg ccaattatga ctactggggc  360
caggggaccc aggtcaccgt ctcctcagcg gccgcatacc cgtacgacgt tccggactac  420
ggttcccacc accatcacca tcactag                                       447

SEQ ID NO: 1083        moltype = DNA  length = 456
FEATURE                Location/Qualifiers
misc_feature           1..456
                       note = Synthetic polymer
source                 1..456
                       mol_type = other DNA
                       organism = synthetic construct
SEQUENCE: 1083
caggtgcagc tgcaggagtc tggggggagga ttggtgcagg ctgggggctc tctgagactc  60
tcctgtgcag cctctggacg caccttcagt acctatcccg tgggctggtt ccgccaggct  120
ccagggaagg agcgtgagtt tgtcgcagtt attctctgga gtggtgttag cacatactat  180
gcagactccg tgaagggccg attcaccatc tccagagaca acgcacagaa cacggtgtat  240
ctgcaaatgg acagtctgaa acctgaggac acggccgttt attactgtgc agtccccagg  300
tctcacttta ctactgctca agacatgggt caagacatgg gtgccccttc gtggtatgag  360
tactggggcc aggggaccca ggtcaccgtc tcctcagcgg ccgcataccc gtacgacgtt  420
ccggactacg gttcccacca ccatcaccat cactag                             456

SEQ ID NO: 1084        moltype = DNA  length = 444
FEATURE                Location/Qualifiers
misc_feature           1..444
                       note = Synthetic polymer
source                 1..444
                       mol_type = other DNA
                       organism = synthetic construct
SEQUENCE: 1084
caggtgcagc tgcaggagtc tggggggagga ttggtgcagg ctgggggctc tctgagactc  60
tcctgtgcag cctctggacg caccttcagt agctatgtca tgggctggtt ccgccaggct  120
ccagggaagg agcgtgaatt tgtagcgcaa attagctgga gtgctggtag catatactat  180
gcagactccg tgaagggccg attcaccatc tccaatgaca acgccaagcg tacggtgtat  240
ctgcaaatga acagcctgaa acctgaggac acggccgttt attactgtgc cgagcggggc  300
tatgcttact gctcagacga tggctgtcag aggacccaag actatgacta ctggggccag  360
gggacccagg tcaccgtctc ctcagcggcc gcatacccgt acgacgttcc ggactacggt  420
tcccaccacc atcaccatca ctag                                          444

SEQ ID NO: 1085        moltype = DNA  length = 432
FEATURE                Location/Qualifiers
misc_feature           1..432
                       note = Synthetic polymer
source                 1..432
                       mol_type = other DNA
                       organism = synthetic construct
SEQUENCE: 1085
caggtgcagc tgcaggagtc tggggggagga ttggtgcagg ctgggggctc tctgagactc  60
tcctgtgtag cctctgggca caccttcagt agctatacca tgggctggtt ccgccaggct  120
ccagggaagg agcgtgagtt tgtagcattt attgactgga gtggtggtgg tacatattat  180
gccaactccg tgaagggccg attcaccatc tccagagaca acgccgagaa cacggtgtat  240
ctgcaaatga acaacctgaa acctgaggac acggccgttt attactgtgc agcagctcag  300
cgccttggat ctgtcacgga ctatactaag tatgactact ggggccaggg gacccaggtc  360
accgtctcct cagcggccgc atacccgtac gacgttccgg actacggttc ccaccaccat  420
caccatcact ag                                                       432

SEQ ID NO: 1086        moltype = DNA  length = 432
FEATURE                Location/Qualifiers
misc_feature           1..432
                       note = Synthetic polymer
source                 1..432
                       mol_type = other DNA
                       organism = synthetic construct
SEQUENCE: 1086
caggtgcagc tgcaggagtc tggggggagga ttggtgcagg ctgggggctc tctgagactc  60
tcctgtgcag cctctgggca caccttcagt agctatacaa tgggctggtt ccgccaggct  120
ccagggaagg agcgtgagtt tgtagcattt attgactgga gtggtggtgg tacatattat  180
gccgactccg tgaagggccg attcaccatc tccagagaca acgccgagaa cacggtgtat  240
ctgcaaatga acaacctgaa acctgaggac acggccgttt attactgtgc agcagctcag  300
cgccttggat ctgtcacgga ctatactaag tatgactact ggggccaggg gacccaggtc  360
accgtctcct cagcggccgc atacccgtac gacgttccgg actacggttc ccaccaccat  420
caccatcact ag                                                       432

SEQ ID NO: 1087        moltype = DNA  length = 432
FEATURE                Location/Qualifiers
misc_feature           1..432
                       note = Synthetic polymer
source                 1..432
                       mol_type = other DNA
                       organism = synthetic construct
```

```
SEQUENCE: 1087
caggtgcagc tgcaggagtc tggggggagga ttggtgcagg ctgggggctc tctgagactc  60
tcctgtgcag cctctgggcg caccttcagt agctatacca tgggctggtt ccgccaggct  120
ccagggaagg agcgtgagtt tgtagcattt attgactgga gtggtggtgg tacatattat  180
gacgactccg tgaagggccg attcaccatc tccagagaca acgccgagaa cacggtgtat  240
ctgcaaatga acaacctgga acctgaggac acggccgttt attactgtgc agcagctcag  300
cgccttggat ccgtcacgga ctatactaag tatgactact ggggccaggg gacccaggtc  360
accgtctcct cagcggccgc atacccgtac gacgttccgg actacggttc ccaccaccat  420
caccatcact ag                                                       432

SEQ ID NO: 1088        moltype = DNA  length = 441
FEATURE                Location/Qualifiers
misc_feature           1..441
                       note = Synthetic polymer
source                 1..441
                       mol_type = other DNA
                       organism = synthetic construct
SEQUENCE: 1088
caggtgcagc tgcaggagtc tggggggagga ttggtgcagg ctgggggctc tctgagactc  60
tcctgcgcag cctctggacg cagctttagt agctataccc tggcctggtt ccgccaggct  120
ccagggaagg agcgtgagtt tgtagcaagt attacctggg gtggtggtaa cacatactat  180
ccagactccg tgaagggccg attcaccatc tccagagacg acgccaagaa cacggtgtat  240
ctgcaaatga acagcctgaa acctgaggac acggccgttt attactgtgc agccaaaggc  300
cttcgtaata gcgactggga tctccggcgg gggtatgaat atgactactg gggccagggg  360
acccaggtca ccgtctcctc agcggccgca tacccgtacg acgttccgga ctacggttcc  420
caccaccatc accatcacta g                                             441

SEQ ID NO: 1089        moltype = DNA  length = 459
FEATURE                Location/Qualifiers
misc_feature           1..459
                       note = Synthetic polymer
source                 1..459
                       mol_type = other DNA
                       organism = synthetic construct
SEQUENCE: 1089
caggtgcagc tgcaggagtc tggggggagga ttggtgcagg ctgggggctc tctgagactc  60
tcctgtgcag cctctggacg cacctctgga cgcaccttta gtagctatac tatgggctgg  120
ttccgccagg ctccagggaa ggagcgtgag tttgtagcaa ctattacctg gggtggtgga  180
agtacatatt atgctgactc cgtgaagggc cgattcacca tctccagaga caacgccaac  240
aacacggtgt atctgcaaat gaacagcctg aaacctgagg acacggccgt ttattactgc  300
gcagcctcag tcaaggtagt agctggttca ggaatcgata tatctggatc cagaaattat  360
gactactggg gccaggggac ccaggtcacc gtctcctcag cggccgcata cccgtacgac  420
gttccggact acggttccca ccaccatcac catcactag                          459

SEQ ID NO: 1090        moltype = DNA  length = 447
FEATURE                Location/Qualifiers
misc_feature           1..447
                       note = Synthetic polymer
source                 1..447
                       mol_type = other DNA
                       organism = synthetic construct
SEQUENCE: 1090
caggtgcagc tgcaggagtc tggggggaggc ttggtgcagc ctggggggtc tctgagactc  60
tcctgtttag cctctggacg caccttcagt agctatgcca tgggctggtt ccgccaggct  120
ccagggaagg agcgtgagtt tgtagcagct attagctgga gtggtggtcc cactgtctat  180
gcagaccacg taaagggccg attcaccatc tccagggaca acgccaagaa cacggtgtat  240
ctgcaagtga acagcctgaa acctgaggac acggccgatt attactgtgc agctaagaga  300
cttgactata gcgccactga caagggcgtt gacttgtcag atgagtatga ctactggggc  360
caggggaccc aggtcaccgt ctcctcagcg gccgcatacc cgtacgacgt tccggactac  420
ggttcccacc accatcacca tcactag                                       447

SEQ ID NO: 1091        moltype = DNA  length = 447
FEATURE                Location/Qualifiers
misc_feature           1..447
                       note = Synthetic polymer
source                 1..447
                       mol_type = other DNA
                       organism = synthetic construct
SEQUENCE: 1091
caggtgcagc tgcaggagtc tggggggagga ttggtgcagg ctgggggctc tctgagactc  60
tcctgtgcag cctctggacg taccttcagt agcgacacca tgggctggtt ccgccaggct  120
ccagggaagg agcgtgagtt tgtaggagcg attatgtgga gtggtgcatt tacacactat  180
gcagactccg tgaagggccg attcaccatt tccagagaca acgcaaagaa cacggtgtat  240
ctgcaaatga acgcgctgaa accggaggac acggccgttt attactgtgc agtaattccg  300
ggcagaggta gtgccttacc catagacgtg gggaagagcg atgagtatga gtattggggc  360
caggggaccc aggtcaccgt ctcctcagcg gccgcatacc cgtacgacgt tccggactac  420
ggttcccacc accatcacca tcactag                                       447

SEQ ID NO: 1092        moltype = DNA  length = 450
```

```
FEATURE                 Location/Qualifiers
misc_feature            1..450
                        note = Synthetic polymer
source                  1..450
                        mol_type = other DNA
                        organism = synthetic construct
SEQUENCE: 1092
caggtgcagc tgcaggagtc tggggggagga ttggtgcagg ctggtgcctc tctgagactc  60
tcctgtgcag cctctggacg caccttcagt aattataacg tgggctggtt ccgccaggct  120
ccgggtaagg agcgtgagtt tgtctcattt attagctgga taagtgacat cacatactat  180
tcagactccg tgaagggccg attcatcatc tccagagaca acgccaagaa tatggtgtat  240
ctgcaaatga acagcctgaa acctgaggac acggccgttt attactgtgc agcgcatcct  300
ccagacccat ctcgtggggg agagtggcgc ttgcaaactc cgtcggaata tgactactgg  360
ggccagggga cccaggtcac cgtctcctca gcggccgcat acccgtacga cgttccggac  420
tacggttccc accaccatca ccatcactag                                  450

SEQ ID NO: 1093         moltype = DNA  length = 423
FEATURE                 Location/Qualifiers
misc_feature            1..423
                        note = Synthetic polymer
source                  1..423
                        mol_type = other DNA
                        organism = synthetic construct
SEQUENCE: 1093
caggtgcagc tgcaggagtc tgggggagga ttggtgcagg ctggggactc tctgagactc  60
tcctgtgcag gctctgaagg caccctcagt agctatggca ttggctggtt ccgccaggct  120
ccagggaagg agcgtgagtt tgtaggaggt attaactgga gtggcgatag cacagactat  180
gcagactccg tgaagggccg attcaccatc tccagagaca gcgccaagaa cacggtgtat  240
ctgcaaatga acagcctgaa acctgaggac acggccgttt attactgtgc agccggtgaa  300
agtggtgttt gggtaggggg cttggactac tggggccagg ggacccaggt caccgtctcc  360
tcagcggccg catacccgta cgacgttccg gactacggtt cccaccacca tcaccatcac  420
tag                                                               423

SEQ ID NO: 1094         moltype = DNA  length = 423
FEATURE                 Location/Qualifiers
misc_feature            1..423
                        note = Synthetic polymer
source                  1..423
                        mol_type = other DNA
                        organism = synthetic construct
SEQUENCE: 1094
caggtgcagc tgcaggagtc tggaggagga ttggtgcagg ctggggactc tctgagactc  60
tcctgtgcag gctctgaagg caccttcagt agctatggca ttggctggtt ccgccaggct  120
ccagggaagg agcgtgagtt tgtaggaggt attaactgga gtggcgatag cacagactat  180
gcagactccg tgaagggccg attcaccatc tccagagaca acgccaagaa cacggtgtat  240
ctgcaaatga acagcctgaa acctgaggac acggccgttt attactgtgc agccggtgaa  300
agtggtgttt gggtaggggg cttggactac tggggccagg ggacccaggt caccgtctcc  360
tcagcggccg catacccgta cgacgttccg gactacggtt cccaccacca tcaccatcac  420
tag                                                               423

SEQ ID NO: 1095         moltype = DNA  length = 423
FEATURE                 Location/Qualifiers
misc_feature            1..423
                        note = Synthetic polymer
source                  1..423
                        mol_type = other DNA
                        organism = synthetic construct
SEQUENCE: 1095
caggtgcagc tgcaggagtc tgggggagga ttggtgcagg ctggggactc tctgagactc  60
acctgtacag cctctggacg caccttcagt aactatggca taggctggtt ccgccaggct  120
ccagggaagg agcgtgaatt tgtagcaggt attaactgga gtggcgaaag cgccgactat  180
gcagactccg tgaagggccg attcaccatc tccagagaca acgccaagaa cacggtgtat  240
ctgcaaatga acagcctgaa acctgaggac acggccgttt attactgtgc agccggtgaa  300
agtggtgttt gggtaggggg cttggactac tgggkccagg ggacccaggt caccgtctcc  360
tcagcggccg catacccgta cgacgttccg gactacggtt cccaccacca tcaccatcac  420
tag                                                               423

SEQ ID NO: 1096         moltype = DNA  length = 438
FEATURE                 Location/Qualifiers
misc_feature            1..438
                        note = Synthetic polymer
source                  1..438
                        mol_type = other DNA
                        organism = synthetic construct
SEQUENCE: 1096
caggtgcagc tgcaggagtc tgggggagga ttggtgcagg ctgggggctc tctgagactc  60
tcctgtaaag cctctggagg caccttcagt ggctatatca tgggctggtt ccgccaggct  120
ccagggaagg agcgtgagtt tgtagcagct aatacttgga gtggtggtcc cacatactat  180
tcagactccg tgaagggccg attcaccatt tccagagaca acgccaagaa cacggtgtat  240
```

```
ctgcaaatga acaccctgaa acctgaagac acggccgttt atcaatgtgc agcacgagac  300
tatcgtggta ttaaagacct cgatctaaag ggggattatg actactgggg ccaggggacc  360
caggtcaccg tctcctcagc ggccgcatac ccgtacgacg ttccggacta cggttcccac  420
caccatcacc atcactag                                                438

SEQ ID NO: 1097        moltype = DNA  length = 450
FEATURE                Location/Qualifiers
misc_feature           1..450
                       note = Synthetic polymer
source                 1..450
                       mol_type = other DNA
                       organism = synthetic construct
SEQUENCE: 1097
caggtgcagc tgcaggagtc tggggggagga ttggtgcaag ctgggggctc tctgagactc  60
tcctgtgcag cctctggacg caccttcagt agctatgtga tagggtggtt ccgccaggct  120
ccagggaagg agcgtgagtt tgtcgcagtt attacttgga gtggtgatag cacatactct  180
tcagactccc tgaagggccg attcaccatc tccagagaca acgccaagaa cacagtctat  240
ctacaaatga acgccctgaa ccctgaggac acggccgttt attactgtgc agctatacct  300
cccagagcct actccggtgg gagttactcc ttaaaggacc aatcgaagta tgaatactgg  360
ggccagggga cccaggtcac cgtctcctca gcggccgcat acccgtacga cgttccggac  420
tacggttccc accaccatca ccatcactag                                   450

SEQ ID NO: 1098        moltype = DNA  length = 450
FEATURE                Location/Qualifiers
misc_feature           1..450
                       note = Synthetic polymer
source                 1..450
                       mol_type = other DNA
                       organism = synthetic construct
SEQUENCE: 1098
caggtgcagc tgcaggagtc tggaggagga ttggtgcaag ctaggggctc tctgacgctc  60
tcctgtgcag cctctggacg caccttcagt aactatgtaa taggctggtt ccgccaggct  120
ccaggggagg agcgtgagtt tgtcgcagtt gttacctgga gtggtgatag cacatactct  180
tcagactccc tgaagggccg attcaccatc tccagagaca acgccaagaa cacagtctat  240
ctacaaatga acaacctgaa ccctgaggac acggccgttt attactgtgc ggctatgccc  300
cccagggcct acaccggtag gagtgtctcc ttaaaggacc aatcgaagta tgaatactgg  360
ggccagggga cccaggtcac cgtctcctca gcggccgcat acccgtacga cgttccggac  420
tacggttccc accaccatca ccatcactag                                   450

SEQ ID NO: 1099        moltype = DNA  length = 435
FEATURE                Location/Qualifiers
misc_feature           1..435
                       note = Synthetic polymer
source                 1..435
                       mol_type = other DNA
                       organism = synthetic construct
SEQUENCE: 1099
caggtgcagc tgcaggagtc tggaggagga ttggtgcagg ctggggcctc tctgagactc  60
tcctgttcag cctctggacg caccttcagt gactatcgca tgggctggtt ccgccaggcg  120
ccagggaagg agcgtgagtg ggtagcagct attagctcga gtggttatca cacatactat  180
gcagactccg tgaagggccg attcaccatc tccagagaca acgccaagaa cacagggtat  240
ctgcagatga gcagcctgaa acctgaggac acggccgttt attattgtgc agtcgttaaa  300
tacttgagtg gtagttactc ctatgccgga cagtataact tctggggcca ggggacccag  360
gtcaccgtct cctcagcggc cgcatacccg tacgacgttc cggactacgg ttcccaccac  420
catcaccatc actag                                                   435

SEQ ID NO: 1100        moltype = DNA  length = 441
FEATURE                Location/Qualifiers
misc_feature           1..441
                       note = Synthetic polymer
source                 1..441
                       mol_type = other DNA
                       organism = synthetic construct
SEQUENCE: 1100
caggtgcagc tgcaggagtc tggggggagga ttggtgcagg ctgggggctc tctgagactc  60
tcctgtgtag gcgacggacg caccttcagt agttatatta tcggctggtt ccgccaggct  120
ccagggaacg agcgtgagtt tgtagtcgct attacctggg atggtagcgc tacaacctat  180
gcagactccg tgaagggccg gttcaccgtc tccagagaca gcgccaagaa cacggcgtat  240
ctgcaaatga acagtctgaa acctgaggac acggccgttt attactgtgc agcagtaccg  300
gcccgaggcc tgacaatgga tctagaaaat agcgacatat atgaccactg ggccgggggg  360
acccaggtca ccgtctcctc agcggccgca tacccgtacg acgttccgga ctacggttcc  420
caccaccatc accatcacta g                                            441

SEQ ID NO: 1101        moltype = DNA  length = 447
FEATURE                Location/Qualifiers
misc_feature           1..447
                       note = Synthetic polymer
source                 1..447
                       mol_type = other DNA
```

```
                         organism = synthetic construct
SEQUENCE: 1101
caggtgcagc tgcaggagtc tgggggaggg ttggtgcagg ctgggggctc tctgagactc  60
tcctgtgcag cctctggacg caccttaagt agcaatccga tggcctggtt ccgccaggct  120
gccgggaagg agcgtgagtt tgtagcaggt atgtcgtgga atcctggtcc cgcagtctat  180
gcagactccg tgaagggccg attcaccatc tccagagaca gcgccgagaa cacggtgtat  240
ctgcaaatga acagcctgaa accagaagac acggccgttt attactgtgc aggagcggct  300
cgagcatggt ggagtggtag ttacgactac acccgtatga ataattatga ctactggggc  360
ccggggaccc aggtcaccgt ctcctcagcg gccgcatacc cgtacgacgt tccggactac  420
ggttcccacc accatcacca tcactag                                      447

SEQ ID NO: 1102          moltype = DNA  length = 459
FEATURE                  Location/Qualifiers
misc_feature             1..459
                         note = Synthetic polymer
source                   1..459
                         mol_type = other DNA
                         organism = synthetic construct
SEQUENCE: 1102
caggtgcagc tgcaggagtc tggaggagga ttggtgcagg atgggggctc tctgagactc  60
tcctgtgcat tctctggacg cacctttagt agttatacta tgggctggtt ccgccagggt  120
ccagggaagg agcgtgagtt tgtagcagct actgtctgga ctggtgctgg tacagtttat  180
gctgactccg tgaagggccg attcaccatc tccagagaca acgccaagaa cacggtgtat  240
cttcaaatga acagcctgag gcctgaggac acggccgttt attactgtgc agcggatcaa  300
gcaagtgtac cccctccgta cggtagtgaa cggtacgaca tcgcgagtcc tagtgaatat  360
gactattggg gccaggggac ccaggtcacc gtctcctcag cggccgcata cccgtacgac  420
gttccggact acggttccca ccaccatcac catcactag                         459

SEQ ID NO: 1103          moltype = DNA  length = 441
FEATURE                  Location/Qualifiers
misc_feature             1..441
                         note = Synthetic polymer
source                   1..441
                         mol_type = other DNA
                         organism = synthetic construct
SEQUENCE: 1103
caggtgcagc tgcaggagtc tgggggagga ttggtgcagg ctggggactc tctgagactc  60
tcctgtgcag cctctggact taccttcagt aactatataa tgggctggtt ccgtcaggcc  120
ccagggaagg agcgtgagtt tgtagcagct attacctggg gtggtggtag cacagtctat  180
gcagactccg tagagggccg attcaccatc tccagagacg gcaccaagaa cacggtgtct  240
ctacagatga acagcctact acctgaggac acggccgttt actactgtgc agccgccggg  300
ggttcggggc ggcttcgtga tctaaaagtg ggtcagaact atgactactg gggccagggg  360
acccaggtca ccgtctcctc agcggccgca tacccgtacg acgttccgga ctacggttcc  420
caccaccatc accatcacta g                                            441

SEQ ID NO: 1104          moltype = DNA  length = 441
FEATURE                  Location/Qualifiers
misc_feature             1..441
                         note = Synthetic polymer
source                   1..441
                         mol_type = other DNA
                         organism = synthetic construct
SEQUENCE: 1104
caggtgcagc tgcaggagtc tgggggagga ttggtgcagg ctggggactc tctgagactc  60
tcctgtgcag cctctggact taccttcagc aactatataa tgggctggtt ccgtcaggcc  120
ccagggaagg agcgtgaatt tgtagcagct attacctggg gtggtggtag cacagtctat  180
gcagactccg tagagggccg attcaccatc tccagagacg gcaccaagaa cacggtgtct  240
ctacagatga acagcctaca gcctgaggac acggccgttt actactgtgc agccgccggg  300
gcttcggggc ggcttcgtga tctaaaagtg ggtcagaact atgactactg gggccagggg  360
acccaggtca ccgtctcctc agcggccgca tacccgtacg acgttccgga ctacggttcc  420
caccaccatc accatcacta g                                            441

SEQ ID NO: 1105          moltype = DNA  length = 420
FEATURE                  Location/Qualifiers
misc_feature             1..420
                         note = Synthetic polymer
source                   1..420
                         mol_type = other DNA
                         organism = synthetic construct
SEQUENCE: 1105
caggtgcagc tgcaggagtc tggaggaggc ttggtgcagc ctggggggtc tctgagactc  60
tcctgtgcag cctctggaag tatcttcagt atcaatgtca tgggctggta ccgccagact  120
ccagggaagg agcgcgagtt ggtcgcaaaa attactaatt ttggtattac aagctatgca  180
gattccgcac agggccgatt caccatctcc agaggcaacg ccaagaacac ggtgtatctg  240
caaatgaaca gcctgaaacc tgaggacacg gccgtctatt attgtaattt agacactacg  300
ggttggggtc cgcccccgta tcagtactgg ggccagggga cccaggtcac cgtctcctca  360
gcggccgcat acccgtacga cgttccggac tacggttccc accaccatca ccatcactag  420

SEQ ID NO: 1106          moltype = DNA  length = 420
```

-continued

```
FEATURE                Location/Qualifiers
misc_feature           1..420
                       note = Synthetic polymer
source                 1..420
                       mol_type = other DNA
                       organism = synthetic construct
SEQUENCE: 1106
caggtgcagc tgcaggagtc tggggggaggc ttggtgcagc ctggggggtc tctgacactc  60
tcctgtgcag cctctggatt cgccttcggt ttcttcgaca tgacctgggt ccgccaggct  120
ccaggaaagg ggctcgaatg ggtctcaggt attaatagta ttggtggtag cacaacctat  180
gcagactccg tgaagggccg attcaccatc tccagagaca acgccaagaa cgagctgtat  240
ctgcaaatga acagcctgaa acctgacgac acggccgtgt attactgtgc gaaatctaga  300
agctcctaca gtaataactg gcgccccccg ggccagggga cccaggtcac cgtctcctca  360
gcggccgcat acccgtacga cgttccggac tacggttccc accaccatca ccatcactag  420

SEQ ID NO: 1107        moltype = AA  length = 152
FEATURE                Location/Qualifiers
REGION                 1..152
                       note = Synthetic polymer
SITE                   152
                       note = misc_feature - Xaa can be any naturally occurring
                        amino acid
source                 1..152
                       mol_type = protein
                       organism = synthetic construct
SEQUENCE: 1107
QVQLQESGGG LVQAGGSLRL SCAASGFTFD DYTIGWFRQA PGKEREGISC ISSDGSTGYA  60
DSVKGRFTIS SDNAKNTVYL QMNSLKPEDT AVYYCAADFN VWSPPICGSN WYGPPPGGMD  120
YWGKGTQVTV SSAAAYPYDV PDYGSHHHHH HX                               152

SEQ ID NO: 1108        moltype = AA  length = 153
FEATURE                Location/Qualifiers
REGION                 1..153
                       note = Synthetic polymer
SITE                   153
                       note = misc_feature - Xaa can be any naturally occurring
                        amino acid
source                 1..153
                       mol_type = protein
                       organism = synthetic construct
SEQUENCE: 1108
QVQLQESGGG LVQAGGSLRL SCAASGFSSD DYTIGWFRQA PGKEREGISC YSSSDGSTGY  60
ADSVKGRFTI SSDNAKNTVY LQMNSLKPED TAVYYCAADF NVWSPPICGS SWYGPPPGGM  120
DYWGKGTQVT VSSAAAYPYD VPDYGSHHHH HHX                              153

SEQ ID NO: 1109        moltype = AA  length = 152
FEATURE                Location/Qualifiers
REGION                 1..152
                       note = Synthetic polymer
SITE                   152
                       note = misc_feature - Xaa can be any naturally occurring
                        amino acid
source                 1..152
                       mol_type = protein
                       organism = synthetic construct
SEQUENCE: 1109
QVQLQESGGG LVQAGGSLRL SCAASGFSFD DYTIGWFRQV PGKEREGISC ISSDGSTGYA  60
DSVKGRFTIS SDNAKNTVYL QINSLKPEDT AVYYCAADFN VWSPPICGSI WYGPPPGGMD  120
YWGKGTQVTV SSAAAYPYDV PDYGSHHHHH HX                               152

SEQ ID NO: 1110        moltype = AA  length = 152
FEATURE                Location/Qualifiers
REGION                 1..152
                       note = Synthetic polymer
SITE                   152
                       note = misc_feature - Xaa can be any naturally occurring
                        amino acid
source                 1..152
                       mol_type = protein
                       organism = synthetic construct
SEQUENCE: 1110
QVQLQESGGG LAQVGGSLRL SCTASGFTFD DYTIGWFRQA PGKEREGISC ISSDGSTGYA  60
DSVKGRFTIS SDNAKNTVYL QMNSLKPEDT AVYYCAADFN VWSPPICGSN WYGPPPGGMD  120
YWGKGTQVTV SSAAAYPYDV PDYGSHHHHH HX                               152

SEQ ID NO: 1111        moltype = AA  length = 152
FEATURE                Location/Qualifiers
REGION                 1..152
                       note = Synthetic polymer
```

```
SITE                    152
                        note = misc_feature - Xaa can be any naturally occurring
                         amino acid
source                  1..152
                        mol_type = protein
                        organism = synthetic construct
SEQUENCE: 1111
QVQLQESGGG LVQAGGSLRL SCAASGFTFD DYTIAWFRQA PGKEREGISC ISSDGSTGYA  60
DSVRGRFTIS SDNAKNTVYL QMNSLKPEDT AVYYCAADFN VWSPPICGSI WYGPPPRGMD  120
YWGKGTQVTV SSAAAYPYDV PDYGSHHHHH HX                                152

SEQ ID NO: 1112         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1112
QVQLQESGGG LVQAGGSLRL SCAASGFTFD DYTIAWFRQA PGGKEREGIS CISSDGSTGY  60
ADSVKGRFTI SSDNAKNMVY LQMNSLKPED TALYYCAADF NVWSPPICSS NWYGPPPRGM  120
DYWGKGTQVT VSSAAAYPYD VPDYGSHHHH HHX                               153

SEQ ID NO: 1113         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1113
QVQLQESGGG LVQAGGSLRL SCAASGFSSD DYTIGWFRQA PGKEREGIGC IKSSDGTTGY  60
ADSVKGRFTI SSDNAKNTVY LQMNSLKPED TAVYYCAADF NVWSPPICGS IWYGPPPGGM  120
DYWGKGTQVT VSSAAAYPYD VPDYGSHHHH HHX                               153

SEQ ID NO: 1114         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1114
QVQLQESGGG LVQAGGSLRL SCAASGFSSD DYTIGWFRQA PGKEREGISC FSSSDGSTGF  60
ADSVKGRFTI SSDNATNTVY LEMNSLKPED TAVYYCAADF NVWSPPICGS RWYGPPPGGM  120
EYWGKGTQVT VSSAAAYPYD VPDYGSHHHH HHX                               153

SEQ ID NO: 1115         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1115
QVQLQESGGG LVQAGGSLRL SCAASGFSSD DYTIGWFRQA PGKEREGISC FSSSDGSTGF  60
ADSVKGRFTI SSDNATNTVY LQMNSLKPED TAVYYCAADF NVWSPPICGS SWYGPPPGGM  120
EYWGKGTQVT VSSAAAYPYD VPDYGSHHHH HHX                               153

SEQ ID NO: 1116         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
```

```
                       mol_type = protein
                       organism = synthetic construct
SEQUENCE: 1116
QVQLQESGGG LVQAGGSLRL SCEVSGLSSD DYTIGWFRQA PGKKREGFSC FSSRDGSTGY  60
ADSVKGRFTI SSDNAKNTVY LQMNSLKPED TAVYYCAADF NVWSPPICGS RWYGPPPGGM  120
DYWGKGTQVT VSSAAAYPYD VPDYGSHHHH HHX                               153

SEQ ID NO: 1117        moltype = AA  length = 153
FEATURE                Location/Qualifiers
REGION                 1..153
                       note = Synthetic polymer
SITE                   153
                       note = misc_feature - Xaa can be any naturally occurring
                        amino acid
source                 1..153
                       mol_type = protein
                       organism = synthetic construct
SEQUENCE: 1117
QVQLQESGGG LVQAGGSLRL SCAASGFSSD DYTIGWFRQA PGKEREGFSC FSSRDGSTGY  60
ADSVKGRFTI SSDNAKNTVY LQMNSLKPED TAVYYCAADF NVWSPPICGS RWYGPPPGGM  120
DYWGKGTQVT VSSAAAYPYD VPDYGSHHHH HHX                               153

SEQ ID NO: 1118        moltype = AA  length = 153
FEATURE                Location/Qualifiers
REGION                 1..153
                       note = Synthetic polymer
SITE                   153
                       note = misc_feature - Xaa can be any naturally occurring
                        amino acid
source                 1..153
                       mol_type = protein
                       organism = synthetic construct
SEQUENCE: 1118
QVQLQESGGG LVQAGGSLRL SCEVSGLSSD DYTIGWFRQA PGKEREGFSC FSTRDGNAGY  60
ADSVKGRFTI SSDNAKNTVY LQMNNLKPED TAVYYCAADF NVWSPPICGS RWYGPPPGGM  120
DYWGKGTQVT VSSAAAYPYD VPDYGSHHHH HHX                               153

SEQ ID NO: 1119        moltype = AA  length = 153
FEATURE                Location/Qualifiers
REGION                 1..153
                       note = Synthetic polymer
SITE                   153
                       note = misc_feature - Xaa can be any naturally occurring
                        amino acid
source                 1..153
                       mol_type = protein
                       organism = synthetic construct
SEQUENCE: 1119
QVQLQESGGG LVQAGGSLRL SCAASGFSSD DYTIAWFRRA PGKEREGISC ISSSDGSTGY  60
ADSVKGRFTI TSDSAKNTVY LQMNSLKPED TAVYYCAADS NVWSPPICGR TWYGPPPGGM  120
DYWGKGTQVT VSSAAAYPYD VPDYGSHHHH HHX                               153

SEQ ID NO: 1120        moltype = AA  length = 153
FEATURE                Location/Qualifiers
REGION                 1..153
                       note = Synthetic polymer
SITE                   153
                       note = misc_feature - Xaa can be any naturally occurring
                        amino acid
source                 1..153
                       mol_type = protein
                       organism = synthetic construct
SEQUENCE: 1120
QVQLQESGGG LVQAGGSLRL SCAASGFSSD DYTIAWFRRA PGKEREGISC ISSSDGSTGY  60
ADSVKGRFTI SSDNAKNTVY LQMTSLKPED TAVYYCAADS NVWSPPICGK TWYGPPPGGM  120
DYWGKGTQVT VSSAAAYPYD VPDYGSHHHH HHX                               153

SEQ ID NO: 1121        moltype = AA  length = 151
FEATURE                Location/Qualifiers
REGION                 1..151
                       note = Synthetic polymer
SITE                   19
                       note = misc_feature - Xaa can be any naturally occurring
                        amino acid
SITE                   151
                       note = misc_feature - Xaa can be any naturally occurring
                        amino acid
source                 1..151
                       mol_type = protein
```

```
                        organism = synthetic construct
SEQUENCE: 1121
QVQLQESGGG LVQAGGSLXL SCAASGFTFD DYAIGWFRQA PGKEREGVSC ISSPDGSTYY  60
ADSVKGRFTI SSDNAKNTVY LQMNSLKPED TAVYYCAADF NVWSPPICGS VGPPPGGMDY  120
WGKGTQVTVS SAAAYPYDVP DYGSHHHHHH X                                151

SEQ ID NO: 1122         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1122
QVQLQESGGG LVQPGGSLRL SCAASGFSSD DYTIGWFRQA PGKEREGISC YSSRDGTTGY  60
ADSVKGRFTI SSDNAKNTVY LQMNSLKPED TAVYYCAADF NVWSPPICGS IWYGPPPGGM  120
AYWGQGTQVT VSSAAAYPYD VPDYGSHHHH HHX                              153

SEQ ID NO: 1123         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1123
QVQLQESGGG LVQAGGSLRL SCAASGFSSD DYTIGWFRQA PGKEREGISC YSSSDGSTGF  60
ADSVKGRFTI SSDNAKNTVY LQMNSLRPED TAVYYCAADF NVWSPPICGS RWYGPPPGGM  120
AYWGKGTQVT VSSAAAYPYD VPDYGSHHHH HHX                              153

SEQ ID NO: 1124         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1124
QVQLQESGGG LVQAGGYLRL SCAASGFSSD DYTIGWFRQA PGKEREGISC YSSSDGSTGF  60
ADSVKGRFTI SSDNAKNTVY LQMNNLRPED TAVYYCAADS NVWSPPICGS RWYGPPPGGM  120
AYWGKGTQVT VSSAAAYPYD VPDYGSHHHH HHX                              153

SEQ ID NO: 1125         moltype = AA  length = 152
FEATURE                 Location/Qualifiers
REGION                  1..152
                        note = Synthetic polymer
SITE                    152
                        note = misc_feature - Xaa can be any naturally occurring
                         amino acid
source                  1..152
                        mol_type = protein
                        organism = synthetic construct
SEQUENCE: 1125
QVQLQESGGG LVQAGDSLKL SCATSGRSFS SYTIAWFRQA PGKEREGISC ISSDGSTGYA  60
DSVRGRFTIS SDNAKNTVYL QMNSLKPEDT AVYYCAADFN VWSPPICGSI WYGPPPRGMD  120
YWGKGTQVTV SSAAAYPYDV PDYGSHHHHH HX                               152

SEQ ID NO: 1126         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1126
QVQLQESGGG LVQAGASLRL SCKASGFTFG DYTIGWFRQA PGKEREGISC YSSSDGNTGY  60
ADSVKGRFTI SSDNAKNTVY LQMNSLRPED TAVYYCAADF NVWSPPICGS SWYGPPPGGM  120
```

```
AYWGKGTQVT VSSAAAYPYD VPDYGSHHHH HHX                          153

SEQ ID NO: 1127        moltype = AA  length = 153
FEATURE                Location/Qualifiers
REGION                 1..153
                       note = Synthetic polymer
SITE                   153
                       note = misc_feature - Xaa can be any naturally occurring
                        amino acid
source                 1..153
                       mol_type = protein
                       organism = synthetic construct
SEQUENCE: 1127
QVQLQESGGG LVQAGGSLRL SCAASGFSSD DYTIAWFRRA PGKEREGISC FSSSDGSAGY  60
ADSVKGRFTV SSDNAKNTVY LQMNSLKPED TAVYYCAADS NVWSPPICGS TWYGPPPGGM  120
AYWGKGTQVT VSSAAAYPYD VPDYGSHHHH HHX                          153

SEQ ID NO: 1128        moltype = AA  length = 151
FEATURE                Location/Qualifiers
REGION                 1..151
                       note = Synthetic polymer
SITE                   151
                       note = misc_feature - Xaa can be any naturally occurring
                        amino acid
source                 1..151
                       mol_type = protein
                       organism = synthetic construct
SEQUENCE: 1128
QVQLQESGGG LVQAGGSLRL SCAASGFAFD GYAIGWFRQA PGKEREGVSC ISSKEGSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH X                            151

SEQ ID NO: 1129        moltype = AA  length = 151
FEATURE                Location/Qualifiers
REGION                 1..151
                       note = Synthetic polymer
SITE                   151
                       note = misc_feature - Xaa can be any naturally occurring
                        amino acid
source                 1..151
                       mol_type = protein
                       organism = synthetic construct
SEQUENCE: 1129
QVQLQESGGG LVQAGDSLKL SCAASGLTFS NYIMAWFRQA PGKEREGVSC ISSPDGSTYY  60
ADSVKGRFTI SSDNAKNTVY LQMNSLKPED TAVYYCAADF NVWSPPICGS VGPPPGGMDY  120
WGKGTQVTVS SAAAYPYDVP DYGSHHHHHH X                            151

SEQ ID NO: 1130        moltype = AA  length = 151
FEATURE                Location/Qualifiers
REGION                 1..151
                       note = Synthetic polymer
SITE                   151
                       note = misc_feature - Xaa can be any naturally occurring
                        amino acid
source                 1..151
                       mol_type = protein
                       organism = synthetic construct
SEQUENCE: 1130
QVQLQESGGG LVQAGGSLRL SCATFGFTFD DYAIAWFRQA PGKEREGISC ISNTDSSTYY  60
ADSVKGRFTI SSDSAKNTVH LQMSSLKPED TAVYYCAADG NVWSPPICGS AGPPPGGMDY  120
WGKGTQVTVS SAAAYPYDVP DYGSHHHHHH X                            151

SEQ ID NO: 1131        moltype = AA  length = 151
FEATURE                Location/Qualifiers
REGION                 1..151
                       note = Synthetic polymer
SITE                   151
                       note = misc_feature - Xaa can be any naturally occurring
                        amino acid
source                 1..151
                       mol_type = protein
                       organism = synthetic construct
SEQUENCE: 1131
QVQLQESGGG LVQAGGSLRL SCATFGFTFD DYAIAWFRQA PGKEREGISC ISNTDSSTYY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH X                            151

SEQ ID NO: 1132        moltype = AA  length = 151
FEATURE                Location/Qualifiers
```

```
REGION                  1..151
                        note = Synthetic polymer
SITE                    151
                        note = misc_feature - Xaa can be any naturally occurring
                         amino acid
source                  1..151
                        mol_type = protein
                        organism = synthetic construct
SEQUENCE: 1132
QVQLQESGGG LVQAGGSLRL SCATFGFSFD DYAIAWFRQA PGKEREGISC ISNTDSSTFY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH X                                151

SEQ ID NO: 1133         moltype = AA  length = 151
FEATURE                 Location/Qualifiers
REGION                  1..151
                        note = Synthetic polymer
SITE                    151
                        note = misc_feature - Xaa can be any naturally occurring
                         amino acid
source                  1..151
                        mol_type = protein
                        organism = synthetic construct
SEQUENCE: 1133
QVQLQESGGG LVQAGGSLRL SCATSGFTFD DYAIAWFRQA PGKEREGVSC ISNTDSSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH X                                151

SEQ ID NO: 1134         moltype = AA  length = 151
FEATURE                 Location/Qualifiers
REGION                  1..151
                        note = Synthetic polymer
SITE                    151
                        note = misc_feature - Xaa can be any naturally occurring
                         amino acid
source                  1..151
                        mol_type = protein
                        organism = synthetic construct
SEQUENCE: 1134
QVQLQESGGG LVQPGGSLRL SCATFGFPFD DYAIAWFRQA PGKEREGVSC ISNTDSSTYY  60
ADSVKGRFTI SSDNAKNTVH LQMSSLKPED TAVYYCAADG NVWSPPICGS AGPPPGGMDY  120
WGKGTQVTVS SAAAYPYDVP DYGSHHHHHH X                                151

SEQ ID NO: 1135         moltype = AA  length = 151
FEATURE                 Location/Qualifiers
REGION                  1..151
                        note = Synthetic polymer
SITE                    151
                        note = misc_feature - Xaa can be any naturally occurring
                         amino acid
source                  1..151
                        mol_type = protein
                        organism = synthetic construct
SEQUENCE: 1135
QVQLQESGGG LAQAGGSLRL SCAASGFTFD QYTIAWFRQA PGKEREGVSC ISNTDSSTYY  60
ADSVKGRFTI SSDNAKNTVY LQMSSLKPED TAVYYCAADG NVWSPPICGS AGPPPGGMDY  120
WGKGTQVTVS SAAAYPYDVP DYGSHHHHHH X                                151

SEQ ID NO: 1136         moltype = AA  length = 152
FEATURE                 Location/Qualifiers
REGION                  1..152
                        note = Synthetic polymer
SITE                    152
                        note = misc_feature - Xaa can be any naturally occurring
                         amino acid
source                  1..152
                        mol_type = protein
                        organism = synthetic construct
SEQUENCE: 1136
QVQLQESGGG LVQVGGSLRL SCTISGFTGN DLAIGWFRQA PGKDQREGIS CISNTDSSTY  60
YADSVKGRFT ISSDNAKNTV HLQMSSLKPE DTAVYYCAAD GNVWSPPICG SAGPPPGGMD  120
YWGKGTQVTV SSAAAYPYDV PDYGSHHHHH HX                               152

SEQ ID NO: 1137         moltype = AA  length = 151
FEATURE                 Location/Qualifiers
REGION                  1..151
                        note = Synthetic polymer
SITE                    151
                        note = misc_feature - Xaa can be any naturally occurring
```

```
                         amino acid
source                  1..151
                        mol_type = protein
                        organism = synthetic construct
SEQUENCE: 1137
QVQLQESGGG LVQAGGSLRL SCTASGRTFS SYTVAWFRQS PGKEREGISC ISNTDSSTYY  60
ADSVKGRFTI SSDNAKSTVH LQMSSLKPED TAVYYCAADG NVWSPPICGS AGPPPGGMDY  120
WGKGTQVTVS SAAAYPYDVP DYGSHHHHHH X                                 151

SEQ ID NO: 1138         moltype = AA  length = 150
FEATURE                 Location/Qualifiers
REGION                  1..150
                        note = Synthetic polymer
SITE                    150
                        note = misc_feature - Xaa can be any naturally occurring
                         amino acid
source                  1..150
                        mol_type = protein
                        organism = synthetic construct
SEQUENCE: 1138
QVQLQESGGG LVQAEGSLKL SCISGFAFDG YAIGWFRQAP GKEREGVACI SSKDGSTYYA  60
DSVKGRFTMS VDKTKNTVYL QMSSLKPEDT AVYYCAADGN VWSPPICSSA GPPPGGMDYW  120
GKGTQVTVSS AAAYPYDVPD YGSHHHHHHX                                  150

SEQ ID NO: 1139         moltype = AA  length = 151
FEATURE                 Location/Qualifiers
REGION                  1..151
                        note = Synthetic polymer
SITE                    151
                        note = misc_feature - Xaa can be any naturally occurring
                         amino acid
source                  1..151
                        mol_type = protein
                        organism = synthetic construct
SEQUENCE: 1139
QVQLQESGGG LVQAGDSLRL SCTASGVSIG DYNIGWFRQA PGKEREGVSC ISSGDGTTYY  60
TDSVKGRFTI STDNAKNTVY LQMNSLKPED TAVYYCAADG NVWSPPICGS AGPPPGGMDY  120
WGKGTQVTVS SAAAYPYDVP DYGSHHHHHH X                                 151

SEQ ID NO: 1140         moltype = AA  length = 151
FEATURE                 Location/Qualifiers
REGION                  1..151
                        note = Synthetic polymer
SITE                    151
                        note = misc_feature - Xaa can be any naturally occurring
                         amino acid
source                  1..151
                        mol_type = protein
                        organism = synthetic construct
SEQUENCE: 1140
QVQLQESGGG LVQAGGSLRL SCAGSGFTLD YYGIGWFRQA PGKEREGVSC ISSSDRNTYY  60
ADSVKGRFTI SGDNAKNTVY LQMNNLKPED TAVYYCAADG NVWSPPICGS AGPPPGGMDY  120
WGKGTQVTVS SAAAYPYDVP DYGSHHHHHH X                                 151

SEQ ID NO: 1141         moltype = AA  length = 150
FEATURE                 Location/Qualifiers
REGION                  1..150
                        note = Synthetic polymer
SITE                    150
                        note = misc_feature - Xaa can be any naturally occurring
                         amino acid
source                  1..150
                        mol_type = protein
                        organism = synthetic construct
SEQUENCE: 1141
QVQLQESGGG LVQAGGSLRL SCAASGFTFD DYAIAWFRQA PGKEREGVSC IERSDGSTYY  60
ADSVKGRFTI SSDNAKNTVY LQMNSLKPED TAVYYCAVGS ANSGEFRFGW VLKPDLYNYW  120
GQGTQVTVSS AAAYPYDVPD YGSHHHHHHX                                  150

SEQ ID NO: 1142         moltype = AA  length = 151
FEATURE                 Location/Qualifiers
REGION                  1..151
                        note = Synthetic polymer
SITE                    151
                        note = misc_feature - Xaa can be any naturally occurring
                         amino acid
source                  1..151
                        mol_type = protein
                        organism = synthetic construct
```

```
SEQUENCE: 1142
QVQLQESGGG LVQAGGSLRL SCAVSGFTFD NYAIGWFRQA PGKEREGVSC ISRSDGSTYY  60
ADSVRGRFTI SSDNAKNTVY LQMNSLKPED TAVYYCAAET SADSGEFRFG WVLKPSLYDY  120
WGQGTQVTVS SAAAYPYDVP DYGSHHHHHH X                               151

SEQ ID NO: 1143        moltype = AA  length = 150
FEATURE                Location/Qualifiers
REGION                 1..150
                       note = Synthetic polymer
SITE                   150
                       note = misc_feature - Xaa can be any naturally occurring
                        amino acid
source                 1..150
                       mol_type = protein
                       organism = synthetic construct
SEQUENCE: 1143
QVQLQESGGG LVQAGGSLRL SCAASGRTFS NYAMGWFRQA PGKEREFVAA IVWSGGSTYY  60
ADSVKGRFTI SRDNAKNTVY LQMNSLKPED TAVYYCAAVL IRYYSGGYQG LSDANEYDYW  120
GQGTQVTVSS AAAYPYDVPD YGSHHHHHHX                                150

SEQ ID NO: 1144        moltype = AA  length = 145
FEATURE                Location/Qualifiers
REGION                 1..145
                       note = Synthetic polymer
SITE                   145
                       note = misc_feature - Xaa can be any naturally occurring
                        amino acid
source                 1..145
                       mol_type = protein
                       organism = synthetic construct
SEQUENCE: 1144
QVQLQESGGG LVQAGGSLRL SCAASGRTFS SYAMAWFRQA PGKEREFVAA IAWSAGSTYY  60
ADSVKGRFAI SRDNAENTVY LQMNSLKPED TAVYYCAARI ITVATMRLDS DYDYWGQGTQ  120
VTVSSAAAYP YDVPDYGSHH HHHHX                                     145

SEQ ID NO: 1145        moltype = AA  length = 153
FEATURE                Location/Qualifiers
REGION                 1..153
                       note = Synthetic polymer
SITE                   153
                       note = misc_feature - Xaa can be any naturally occurring
                        amino acid
source                 1..153
                       mol_type = protein
                       organism = synthetic construct
SEQUENCE: 1145
QVQLQESGGG LVQAGGSLRL SCAASGRTSG RTFSSYTMGW FRQAPGKERE FVATITWGGG  60
STYYADSVKG RFTISRDNAN NTVYLQMNSL KPEDTAVYYC AASVKVVAGS GIDISGSRNY  120
DYWGQGTQVT VSSAAAYPYD VPDYGSHHHH HHX                            153

SEQ ID NO: 1146        moltype = AA  length = 149
FEATURE                Location/Qualifiers
REGION                 1..149
                       note = Synthetic polymer
SITE                   149
                       note = misc_feature - Xaa can be any naturally occurring
                        amino acid
source                 1..149
                       mol_type = protein
                       organism = synthetic construct
SEQUENCE: 1146
QVQLQESGGG LVQAGGSLRL SCAASGRTFS NSVMGWFRQP PGKEREFVAA VLWSGVSTAY  60
ADSVKGRFTI SRDNAKNTVY LQMNNLKPDD TAVYYCAAHE STYYSGTYYL TDPRRYVYWG  120
QGTQVTVSSA AAYPYDVPDY GSHHHHHHX                                 149

SEQ ID NO: 1147        moltype = AA  length = 148
FEATURE                Location/Qualifiers
REGION                 1..148
                       note = Synthetic polymer
SITE                   148
                       note = misc_feature - Xaa can be any naturally occurring
                        amino acid
source                 1..148
                       mol_type = protein
                       organism = synthetic construct
SEQUENCE: 1147
QVQLQESGGG LVQAGGSLRL SCAASGGTFS NYVMGWFRQA PGKEREFVGF ITWSGASTYY  60
ADSVKGRFTI SRDNAENTVY LQMNSLKPED TAVYYCAATL FRSNGPKDLS SGYEYDYWGQ  120
GTQVTVSSAA AYPYDVPDYG SHHHHHHX                                  148
```

```
SEQ ID NO: 1148        moltype = AA  length = 149
FEATURE                Location/Qualifiers
REGION                 1..149
                       note = Synthetic polymer
SITE                   149
                       note = misc_feature - Xaa can be any naturally occurring
                        amino acid
source                 1..149
                       mol_type = protein
                       organism = synthetic construct
SEQUENCE: 1148
QVQLQESGGG LVQAGGSLRL SCAASGRAFS SYFMGWFRQT PGKEREFVAN IGWTGDMTYY  60
ADSVKGRFTI SRDNAKNTVY LQMNSLKPED TAVYYCAAAG SAYSGSYWNI TMAANYDYWG  120
QGTQVTVSSA AAYPYDVPDY GSHHHHHHX                                   149

SEQ ID NO: 1149        moltype = AA  length = 144
FEATURE                Location/Qualifiers
REGION                 1..144
                       note = Synthetic polymer
SITE                   144
                       note = misc_feature - Xaa can be any naturally occurring
                        amino acid
source                 1..144
                       mol_type = protein
                       organism = synthetic construct
SEQUENCE: 1149
QVQLQESGGG LVQAGGSLRL SCVASGHTFS SYTMGWFRQA PGKEREFVAF IDWSGGGTYY  60
ANSVKGRFTI SRDNAENTVY LQMNNLKPED TAVYYCAAAQ RLGSVTDYTK YDYWGQGTQV  120
TVSSAAAYPY DVPDYGSHHH HHHX                                        144

SEQ ID NO: 1150        moltype = AA  length = 144
FEATURE                Location/Qualifiers
REGION                 1..144
                       note = Synthetic polymer
SITE                   144
                       note = misc_feature - Xaa can be any naturally occurring
                        amino acid
source                 1..144
                       mol_type = protein
                       organism = synthetic construct
SEQUENCE: 1150
QVQLQESGGG LVQAGGSLRL SCAASGHTFS SYTMGWFRQA PGKEREFVAF IDWSGGGTYY  60
ADSVKGRFTI SRDNAENTVY LQMNNLKPED TAVYYCAAAQ RLGSVTDYTK YDYWGQGTQV  120
TVSSAAAYPY DVPDYGSHHH HHHX                                        144

SEQ ID NO: 1151        moltype = AA  length = 144
FEATURE                Location/Qualifiers
REGION                 1..144
                       note = Synthetic polymer
SITE                   144
                       note = misc_feature - Xaa can be any naturally occurring
                        amino acid
source                 1..144
                       mol_type = protein
                       organism = synthetic construct
SEQUENCE: 1151
QVQLQESGGG LVQAGGSLRL SCAASGRTFS SYTMGWFRQA PGKEREFVAF IDWSGGGTYY  60
DDSVKGRFTI SRDNAENTVY LQMNNLEPED TAVYYCAAAQ RLGSVTDYTK YDYWGQGTQV  120
TVSSAAAYPY DVPDYGSHHH HHHX                                        144

SEQ ID NO: 1152        moltype = AA  length = 151
FEATURE                Location/Qualifiers
REGION                 1..151
                       note = Synthetic polymer
SITE                   151
                       note = misc_feature - Xaa can be any naturally occurring
                        amino acid
source                 1..151
                       mol_type = protein
                       organism = synthetic construct
SEQUENCE: 1152
QVQLQESGGG LVQAGGSLRL SCAASGRTFS SYTMGWFRQA PGREREFVAA ITWSGVSTVY  60
TDSVKGRFTV SRDNAKNTVY LQMNSLKPED TAVYYCAADS PPRTYSSGSV NLEDGSEYDY  120
WGQGTQVTVS SAAAYPYDVP DYGSHHHHHH X                                151

SEQ ID NO: 1153        moltype = AA  length = 152
FEATURE                Location/Qualifiers
REGION                 1..152
```

```
                        note = Synthetic polymer
SITE                    152
                        note = misc_feature - Xaa can be any naturally occurring
                         amino acid
source                  1..152
                        mol_type = protein
                        organism = synthetic construct
SEQUENCE: 1153
QVQLQESGGG LVQAGGSLRL SCAASGRTFS TYPVGWFRQA PGKEREFVAV ILWSGVSTYY  60
ADSVKGRFTI SRDNAQNTVY LQMDSLKPED TAVYYCAVPR SHFTTAQDMG QDMGAPSWYE  120
YWGQGTQVTV SSAAAYPYDV PDYGSHHHHH HX                                152

SEQ ID NO: 1154         moltype = AA  length = 149
FEATURE                 Location/Qualifiers
REGION                  1..149
                        note = Synthetic polymer
SITE                    149
                        note = misc_feature - Xaa can be any naturally occurring
                         amino acid
source                  1..149
                        mol_type = protein
                        organism = synthetic construct
SEQUENCE: 1154
QVQLQESGGG LVQAGGSLRL SCAASGRTFS SDTMGWFRQA PGKEREFVGA IMWSGAFTHY  60
ADSVKGRFTI SRDNAKNTVY LQMNALKPED TAVYYCAVIP GRGSALPIDV GKSDEYEYWG  120
QGTQVTVSSA AAYPYDVPDY GSHHHHHHX                                    149

SEQ ID NO: 1155         moltype = AA  length = 141
FEATURE                 Location/Qualifiers
REGION                  1..141
                        note = Synthetic polymer
SITE                    141
                        note = misc_feature - Xaa can be any naturally occurring
                         amino acid
source                  1..141
                        mol_type = protein
                        organism = synthetic construct
SEQUENCE: 1155
QVQLQESGGG LVQAGDSLRL SCAGSEGTLS SYGIGWFRQA PGKEREFVGG INWSGDSTDY  60
ADSVKGRFTI SRDSAKNTVY LQMNSLKPED TAVYYCAAGE SGVWVGGLDY WGQGTQVTVS  120
SAAAYPYDVP DYGSHHHHHH X                                            141

SEQ ID NO: 1156         moltype = AA  length = 141
FEATURE                 Location/Qualifiers
REGION                  1..141
                        note = Synthetic polymer
SITE                    141
                        note = misc_feature - Xaa can be any naturally occurring
                         amino acid
source                  1..141
                        mol_type = protein
                        organism = synthetic construct
SEQUENCE: 1156
QVQLQESGGG LVQAGDSLRL SCAGSEGTFS SYGIGWFRQA PGKEREFVGG INWSGDSTDY  60
ADSVKGRFTI SRDNAKNTVY LQMNSLKPED TAVYYCAAGE SGVWVGGLDY WGQGTQVTVS  120
SAAAYPYDVP DYGSHHHHHH X                                            141

SEQ ID NO: 1157         moltype = AA  length = 141
FEATURE                 Location/Qualifiers
REGION                  1..141
                        note = Synthetic polymer
SITE                    112
                        note = misc_feature - Xaa can be any naturally occurring
                         amino acid
SITE                    141
                        note = misc_feature - Xaa can be any naturally occurring
                         amino acid
source                  1..141
                        mol_type = protein
                        organism = synthetic construct
SEQUENCE: 1157
QVQLQESGGG LVQAGDSLRL TCTASGRTFS NYGIGWFRQA PGKEREFVAG INWSGESADY  60
ADSVKGRFTI SRDNAKNTVY LQMNSLKPED TAVYYCAAGE SGVWVGGLDY WXQGTQVTVS  120
SAAAYPYDVP DYGSHHHHHH X                                            141

SEQ ID NO: 1158         moltype = AA  length = 146
FEATURE                 Location/Qualifiers
REGION                  1..146
                        note = Synthetic polymer
```

-continued

```
SITE                    146
                        note = misc_feature - Xaa can be any naturally occurring
                         amino acid
source                  1..146
                        mol_type = protein
                        organism = synthetic construct
SEQUENCE: 1158
QVQLQESGGG LVQAGGSLRL SCKASGGTFS GYIMGWFRQA PGKEREFVAA NTWSGGPTYY  60
SDSVKGRFTI SRDNAKNTVY LQMNTLKPED TAVYQCAARD YRGIKDLDLK GDYDYWGQGT  120
QVTVSSAAAY PYDVPDYGSH HHHHX                                       146

SEQ ID NO: 1159         moltype = AA  length = 153
FEATURE                 Location/Qualifiers
REGION                  1..153
                        note = Synthetic polymer
SITE                    153
                        note = misc_feature - Xaa can be any naturally occurring
                         amino acid
source                  1..153
                        mol_type = protein
                        organism = synthetic construct
SEQUENCE: 1159
QVQLQESGGG LVQDGGSLRL SCAFSGRTFS SYTMGWFRQG PGKEREFVAA TVWTGAGTVY  60
ADSVKGRFTI SRDNAKNTVY LQMNSLRPED TAVYYCAADQ ASVPPPYGSE RYDIASPSEY  120
DYWGQGTQVT VSSAAAYPYD VPDYGSHHHH HHX                              153

SEQ ID NO: 1160         moltype = AA  length = 150
FEATURE                 Location/Qualifiers
REGION                  1..150
                        note = Synthetic polymer
SITE                    150
                        note = misc_feature - Xaa can be any naturally occurring
                         amino acid
source                  1..150
                        mol_type = protein
                        organism = synthetic construct
SEQUENCE: 1160
QVQLQESGGG LVQAGGSLRL SCAASGRTFS SYVMGWFRQA LGKEREFVAA IGWNGGITYY  60
ADSVKGRFAI SRDNAKNTVY LQMNSLKPED TAVYYCAAAT LQVTGSYYLD LSTVDIYDNW  120
GQGTQVTVSS AAAYPYDVPD YGSHHHHHHX                                  150

SEQ ID NO: 1161         moltype = AA  length = 146
FEATURE                 Location/Qualifiers
REGION                  1..146
                        note = Synthetic polymer
SITE                    146
                        note = misc_feature - Xaa can be any naturally occurring
                         amino acid
source                  1..146
                        mol_type = protein
                        organism = synthetic construct
SEQUENCE: 1161
QVQLQESGGG LVQAGGSLRL SCAASTPTFS SYNMGWFRQA PGKEREFVAA IIWSGSMTYY  60
ADSMKGRFTV SIDNAKNTVY LQMNSLKPED TAVYYCAAQR IFGAQPMDLS GDYEYWGQGT  120
QVTVSSAAAY PYDVPDYGSH HHHHX                                       146

SEQ ID NO: 1162         moltype = AA  length = 147
FEATURE                 Location/Qualifiers
REGION                  1..147
                        note = Synthetic polymer
SITE                    147
                        note = misc_feature - Xaa can be any naturally occurring
                         amino acid
source                  1..147
                        mol_type = protein
                        organism = synthetic construct
SEQUENCE: 1162
QVQLQESGGG LVQAGGSLRL SCAASGRSFS SYTLAWFRQA PGKEREFVAS ITWGGGNTYY  60
PDSVKGRFTI SRDDAKNTVY LQMNSLKPED TAVYYCAAKG LRNSDWDLRR GYEYDYWGQG  120
TQVTVSSAAA YPYDVPDYGS HHHHHHX                                     147

SEQ ID NO: 1163         moltype = AA  length = 149
FEATURE                 Location/Qualifiers
REGION                  1..149
                        note = Synthetic polymer
SITE                    149
                        note = misc_feature - Xaa can be any naturally occurring
                         amino acid
source                  1..149
```

```
                        mol_type = protein
                        organism = synthetic construct
SEQUENCE: 1163
QVQLQESGGG LVQAGASLRL SCAASGRTFS SYIMGWFRQA PGKEREFVAA IGWSADITVY  60
ADSVKGRFTI SRDNAENMVY LQMNSLNPED TAVYYCAANS RAYYSSSYDL GRLASYDYWG  120
QGTQVTVSSA AAYPYDVPDY GSHHHHHHX                                   149

SEQ ID NO: 1164         moltype = AA  length = 148
FEATURE                 Location/Qualifiers
REGION                  1..148
                        note = Synthetic polymer
SITE                    148
                        note = misc_feature - Xaa can be any naturally occurring
                         amino acid
source                  1..148
                        mol_type = protein
                        organism = synthetic construct
SEQUENCE: 1164
QVQLQESGGG LVQAGGSLRL SCAASGRTFS SYVMGWFRQA PGKEREFVAQ ISWSAGSIYY  60
ADSVKGRFTI SNDNAKRTVY LQMNSLKPED TAVYYCAERG YAYCSDDGCQ RTQDYDYWGQ  120
GTQVTVSSAA AYPYDVPDYG SHHHHHHX                                    148

SEQ ID NO: 1165         moltype = AA  length = 149
FEATURE                 Location/Qualifiers
REGION                  1..149
                        note = Synthetic polymer
SITE                    149
                        note = misc_feature - Xaa can be any naturally occurring
                         amino acid
source                  1..149
                        mol_type = protein
                        organism = synthetic construct
SEQUENCE: 1165
QVQLQESGGG LVQPGGSLRL SCLASGRTFS SYAMGWFRQA PGKEREFVAA ISWSGGPTVY  60
ADHVKGRFTI SRDNAKNTVY LQVNSLKPED TADYYCAAKR LDYSATDKGV DLSDEYDYWG  120
QGTQVTVSSA AAYPYDVPDY GSHHHHHHX                                   149

SEQ ID NO: 1166         moltype = AA  length = 150
FEATURE                 Location/Qualifiers
REGION                  1..150
                        note = Synthetic polymer
SITE                    150
                        note = misc_feature - Xaa can be any naturally occurring
                         amino acid
source                  1..150
                        mol_type = protein
                        organism = synthetic construct
SEQUENCE: 1166
QVQLQESGGG LVQAGGSLRL SCAASGRTFS SYVIGWFRQA PGKEREFVAV ITWSGDSTYS  60
SDSLKGRFTI SRDNAKNTVY LQMNALNPED TAVYYCAAIP PRAYSGGSYS LKDQSKYEYW  120
GQGTQVTVSS AAAYPYDVPD YGSHHHHHHX                                  150

SEQ ID NO: 1167         moltype = AA  length = 150
FEATURE                 Location/Qualifiers
REGION                  1..150
                        note = Synthetic polymer
SITE                    150
                        note = misc_feature - Xaa can be any naturally occurring
                         amino acid
source                  1..150
                        mol_type = protein
                        organism = synthetic construct
SEQUENCE: 1167
QVQLQESGGG LVQARGSLTL SCAASGRTFS NYVIGWFRQA PGEEREFVAV VTWSGDSTYS  60
SDSLKGRFTI SRDNAKNTVY LQMNNLNPED TAVYYCAAMP PRAYTGRSVS LKDQSKYEYW  120
GQGTQVTVSS AAAYPYDVPD YGSHHHHHHX                                  150

SEQ ID NO: 1168         moltype = AA  length = 150
FEATURE                 Location/Qualifiers
REGION                  1..150
                        note = Synthetic polymer
SITE                    150
                        note = misc_feature - Xaa can be any naturally occurring
                         amino acid
source                  1..150
                        mol_type = protein
                        organism = synthetic construct
SEQUENCE: 1168
QVQLQESGGG LVQAGASLRL SCAASGRTFS NYNVGWFRQA PGKEREFVSF ISWISDITYY  60
```

-continued

```
SDSVKGRFII SRDNAKNMVY LQMNSLKPED TAVYYCAAHP PDPSRGGEWR LQTPSEYDYW  120
GQGTQVTVSS AAAYPYDVPD YGSHHHHHHX                                  150

SEQ ID NO: 1169        moltype = AA  length = 145
FEATURE                Location/Qualifiers
REGION                 1..145
                       note = Synthetic polymer
SITE                   145
                       note = misc_feature - Xaa can be any naturally occurring
                        amino acid
source                 1..145
                       mol_type = protein
                       organism = synthetic construct
SEQUENCE: 1169
QVQLQESGGG LVQAGASLRL SCSASGRTFS DYRMGWFRQA PGKEREWVAA ISSSGYHTYY  60
ADSVKGRFTI SRDNAKNTGY LQMSSLKPED TAVYYCAVVK YLSGSYSYAG QYNFWGQGTQ  120
VTVSSAAAYP YDVPDYGSHH HHHX                                        145

SEQ ID NO: 1170        moltype = AA  length = 147
FEATURE                Location/Qualifiers
REGION                 1..147
                       note = Synthetic polymer
SITE                   147
                       note = misc_feature - Xaa can be any naturally occurring
                        amino acid
source                 1..147
                       mol_type = protein
                       organism = synthetic construct
SEQUENCE: 1170
QVQLQESGGG LVQAGDSLRL SCAASGLTFS NYIMGWFRQA PGKEREFVAA ITWGGGSTVY  60
ADSVEGRFTI SRDGTKNTVS LQMNSLLPED TAVYYCAAAG GSGRLRDLKV GQNYDYWGQG  120
TQVTVSSAAA YPYDVPDYGS HHHHHHX                                     147

SEQ ID NO: 1171        moltype = AA  length = 147
FEATURE                Location/Qualifiers
REGION                 1..147
                       note = Synthetic polymer
SITE                   147
                       note = misc_feature - Xaa can be any naturally occurring
                        amino acid
source                 1..147
                       mol_type = protein
                       organism = synthetic construct
SEQUENCE: 1171
QVQLQESGGG LVQAGDSLRL SCAASGLTFS NYIMGWFRQA PGKEREFVAA ITWGGGSTVY  60
ADSVEGRFTI SRDGTKNTVS LQMNSLQPED TAVYYCAAAG ASGRLRDLKV GQNYDYWGQG  120
TQVTVSSAAA YPYDVPDYGS HHHHHHX                                     147

SEQ ID NO: 1172        moltype = AA  length = 149
FEATURE                Location/Qualifiers
REGION                 1..149
                       note = Synthetic polymer
SITE                   149
                       note = misc_feature - Xaa can be any naturally occurring
                        amino acid
source                 1..149
                       mol_type = protein
                       organism = synthetic construct
SEQUENCE: 1172
QVQLQESGGG LVQAGGSLRL SCAASGRTLS SNPMAWFRQA AGKEREFVAG MSWNPGPAVY  60
ADSVKGRFTI SRDSAENTVY LQMNSLKPED TAVYYCAGAA RAWWSGSYDY TRMNNYDYWG  120
PGTQVTVSSA AAYPYDVPDY GSHHHHHHX                                   149

SEQ ID NO: 1173        moltype = AA  length = 147
FEATURE                Location/Qualifiers
REGION                 1..147
                       note = Synthetic polymer
SITE                   147
                       note = misc_feature - Xaa can be any naturally occurring
                        amino acid
source                 1..147
                       mol_type = protein
                       organism = synthetic construct
SEQUENCE: 1173
QVQLQESGGG LVQAGGSLRL SCVGDGRTFS SYIIGWFRQA PGNEREFVVA ITWDGSATTY  60
ADSVKGRFTV SRDSAKNTAY LQMNSLKPED TAVYYCAAVP ARGLTMDLEN SDIYDHWGRG  120
TQVTVSSAAA YPYDVPDYGS HHHHHHX                                     147

SEQ ID NO: 1174        moltype = AA  length = 140
```

-continued

```
FEATURE                Location/Qualifiers
REGION                 1..140
                       note = Synthetic polymer
SITE                   140
                       note = misc_feature - Xaa can be any naturally occurring
                        amino acid
source                 1..140
                       mol_type = protein
                       organism = synthetic construct
SEQUENCE: 1174
QVQLQESGGG LVQPGGSLRL SCAASGSIFS INVMGWYRQT PGKERELVAK ITNFGITSYA  60
DSAQGRFTIS RGNAKNTVYL QMNSLKPEDT AVYYCNLDTT GWGPPPYQYW GQGTQVTVSS  120
AAAYPYDVPD YGSHHHHHHX                                              140

SEQ ID NO: 1175        moltype = AA  length = 140
FEATURE                Location/Qualifiers
REGION                 1..140
                       note = Synthetic polymer
SITE                   140
                       note = misc_feature - Xaa can be any naturally occurring
                        amino acid
source                 1..140
                       mol_type = protein
                       organism = synthetic construct
SEQUENCE: 1175
QVQLQESGGG LVQPGGSLTL SCAASGFAFG FFDMTWVRQA PGKGLEWVSG INSIGGSTTY  60
ADSVKGRFTI SRDNAKNELY LQMNSLKPDD TAVYYCAKSR SSYSNNWRPP GQGTQVTVSS  120
AAAYPYDVPD YGSHHHHHHX                                              140

SEQ ID NO: 1176        moltype =   length =
SEQUENCE: 1176
000

SEQ ID NO: 1177        moltype = AA  length = 6
FEATURE                Location/Qualifiers
REGION                 1..6
                       note = Synthetic polymer.
source                 1..6
                       mol_type = protein
                       organism = synthetic construct
SEQUENCE: 1177
GGSGGS                                                             6

SEQ ID NO: 1178        moltype = AA  length = 9
FEATURE                Location/Qualifiers
REGION                 1..9
                       note = Synthetic polymer.
source                 1..9
                       mol_type = protein
                       organism = synthetic construct
SEQUENCE: 1178
GGSGGSGGS                                                          9

SEQ ID NO: 1179        moltype = AA  length = 12
FEATURE                Location/Qualifiers
REGION                 1..12
                       note = Synthetic polymer.
source                 1..12
                       mol_type = protein
                       organism = synthetic construct
SEQUENCE: 1179
GGSGGSGGSG GS                                                      12

SEQ ID NO: 1180        moltype = AA  length = 15
FEATURE                Location/Qualifiers
REGION                 1..15
                       note = Synthetic polymer.
source                 1..15
                       mol_type = protein
                       organism = synthetic construct
SEQUENCE: 1180
GGSGGSGGSG GSGGS                                                   15

SEQ ID NO: 1181        moltype = AA  length = 18
FEATURE                Location/Qualifiers
REGION                 1..18
                       note = Synthetic polymer.
source                 1..18
                       mol_type = protein
```

```
                         organism = synthetic construct
SEQUENCE: 1181
GGSGGSGGSG GSGGSGGS                                                    18

SEQ ID NO: 1182          moltype = AA  length = 21
FEATURE                  Location/Qualifiers
REGION                   1..21
                         note = Synthetic polymer.
source                   1..21
                         mol_type = protein
                         organism = synthetic construct
SEQUENCE: 1182
GGSGGSGGSG GSGGSGGSGG S                                                21

SEQ ID NO: 1183          moltype = AA  length = 24
FEATURE                  Location/Qualifiers
REGION                   1..24
                         note = Synthetic polymer.
source                   1..24
                         mol_type = protein
                         organism = synthetic construct
SEQUENCE: 1183
GGSGGSGGSG GSGGSGGSGG SGGS                                             24

SEQ ID NO: 1184          moltype = AA  length = 27
FEATURE                  Location/Qualifiers
REGION                   1..27
                         note = Synthetic polymer.
source                   1..27
                         mol_type = protein
                         organism = synthetic construct
SEQUENCE: 1184
GGSGGSGGSG GSGGSGGSGG SGGSGGS                                          27

SEQ ID NO: 1185          moltype = AA  length = 30
FEATURE                  Location/Qualifiers
REGION                   1..30
                         note = Synthetic polymer.
source                   1..30
                         mol_type = protein
                         organism = synthetic construct
SEQUENCE: 1185
GGSGGSGGSG GSGGSGGSGG SGGSGGSGGS                                       30

SEQ ID NO: 1186          moltype = AA  length = 33
FEATURE                  Location/Qualifiers
REGION                   1..33
                         note = Synthetic polymer.
source                   1..33
                         mol_type = protein
                         organism = synthetic construct
SEQUENCE: 1186
GGSGGSGGSG GSGGSGGSGG SGGSGGSGGS GGS                                   33

SEQ ID NO: 1187          moltype = AA  length = 36
FEATURE                  Location/Qualifiers
REGION                   1..36
                         note = Synthetic polymer.
source                   1..36
                         mol_type = protein
                         organism = synthetic construct
SEQUENCE: 1187
GGSGGSGGSG GSGGSGGSGG SGGSGGSGGS GGSGGS                                36

SEQ ID NO: 1188          moltype = AA  length = 39
FEATURE                  Location/Qualifiers
REGION                   1..39
                         note = Synthetic polymer.
source                   1..39
                         mol_type = protein
                         organism = synthetic construct
SEQUENCE: 1188
GGSGGSGGSG GSGGSGGSGG SGGSGGSGGS GGSGGSGGS                             39

SEQ ID NO: 1189          moltype = AA  length = 42
FEATURE                  Location/Qualifiers
REGION                   1..42
                         note = Synthetic polymer.
source                   1..42
```

```
                         mol_type = protein
                         organism = synthetic construct
SEQUENCE: 1189
GGSGGSGGSG GSGGSGGSGG SGGSGGSGGS GGSGGSGGSG GS                    42

SEQ ID NO: 1190          moltype = AA  length = 45
FEATURE                  Location/Qualifiers
REGION                   1..45
                         note = Synthetic polymer.
source                   1..45
                         mol_type = protein
                         organism = synthetic construct
SEQUENCE: 1190
GGSGGSGGSG GSGGSGGSGG SGGSGGSGGS GGSGGSGGSG GSGGS                 45

SEQ ID NO: 1191          moltype = AA  length = 48
FEATURE                  Location/Qualifiers
REGION                   1..48
                         note = Synthetic polymer.
source                   1..48
                         mol_type = protein
                         organism = synthetic construct
SEQUENCE: 1191
GGSGGSGGSG GSGGSGGSGG SGGSGGSGGS GGSGGSGGSG GSGGSGGS              48

SEQ ID NO: 1192          moltype = AA  length = 51
FEATURE                  Location/Qualifiers
REGION                   1..51
                         note = Synthetic polymer.
source                   1..51
                         mol_type = protein
                         organism = synthetic construct
SEQUENCE: 1192
GGSGGSGGSG GSGGSGGSGG SGGSGGSGGS GGSGGSGGSG GSGGSGGSGG S          51

SEQ ID NO: 1193          moltype = AA  length = 54
FEATURE                  Location/Qualifiers
REGION                   1..54
                         note = Synthetic polymer.
source                   1..54
                         mol_type = protein
                         organism = synthetic construct
SEQUENCE: 1193
GGSGGSGGSG GSGGSGGSGG SGGSGGSGGS GGSGGSGGSG GSGGSGGSGG SGGS       54

SEQ ID NO: 1194          moltype = AA  length = 57
FEATURE                  Location/Qualifiers
REGION                   1..57
                         note = Synthetic polymer.
source                   1..57
                         mol_type = protein
                         organism = synthetic construct
SEQUENCE: 1194
GGSGGSGGSG GSGGSGGSGG SGGSGGSGGS GGSGGSGGSG GSGGSGGSGG SGGSGGS    57

SEQ ID NO: 1195          moltype = AA  length = 60
FEATURE                  Location/Qualifiers
REGION                   1..60
                         note = Synthetic polymer.
source                   1..60
                         mol_type = protein
                         organism = synthetic construct
SEQUENCE: 1195
GGSGGSGGSG GSGGSGGSGG SGGSGGSGGS GGSGGSGGSG GSGGSGGSGG SGGSGGSGGS 60

SEQ ID NO: 1196          moltype = AA  length = 45
FEATURE                  Location/Qualifiers
REGION                   1..45
                         note = Synthetic polymer.
source                   1..45
                         mol_type = protein
                         organism = synthetic construct
SEQUENCE: 1196
GGGGSGGGGS GGGGSGGGGS GGGGSGGGGS GGGGSGGGGS GGGGS                 45

SEQ ID NO: 1197          moltype = AA  length = 50
FEATURE                  Location/Qualifiers
REGION                   1..50
                         note = Synthetic polymer.
```

```
source                  1..50
                        mol_type = protein
                        organism = synthetic construct
SEQUENCE: 1197
GGGGSGGGGS GGGGSGGGGS GGGGSGGGGS GGGGSGGGGS GGGGSGGGGS             50

SEQ ID NO: 1198         moltype = AA  length = 55
FEATURE                 Location/Qualifiers
REGION                  1..55
                        note = Synthetic polymer.
source                  1..55
                        mol_type = protein
                        organism = synthetic construct
SEQUENCE: 1198
GGGGSGGGGS GGGGSGGGGS GGGGSGGGGS GGGGSGGGGS GGGGSGGGGS GGGGS       55

SEQ ID NO: 1199         moltype = AA  length = 60
FEATURE                 Location/Qualifiers
REGION                  1..60
                        note = Synthetic polymer.
source                  1..60
                        mol_type = protein
                        organism = synthetic construct
SEQUENCE: 1199
GGGGSGGGGS GGGGSGGGGS GGGGSGGGGS GGGGSGGGGS GGGGSGGGGS GGGGSGGGGS  60

SEQ ID NO: 1200         moltype = AA  length = 65
FEATURE                 Location/Qualifiers
REGION                  1..65
                        note = Synthetic polymer.
source                  1..65
                        mol_type = protein
                        organism = synthetic construct
SEQUENCE: 1200
GGGGSGGGGS GGGGSGGGGS GGGGSGGGGS GGGGSGGGGS GGGGSGGGGS GGGGSGGGGS  60
GGGGS                                                              65

SEQ ID NO: 1201         moltype = AA  length = 70
FEATURE                 Location/Qualifiers
REGION                  1..70
                        note = Synthetic polymer.
source                  1..70
                        mol_type = protein
                        organism = synthetic construct
SEQUENCE: 1201
GGGGSGGGGS GGGGSGGGGS GGGGSGGGGS GGGGSGGGGS GGGGSGGGGS GGGGSGGGGS  60
GGGGSGGGGS                                                         70

SEQ ID NO: 1202         moltype = AA  length = 75
FEATURE                 Location/Qualifiers
REGION                  1..75
                        note = Synthetic polymer.
source                  1..75
                        mol_type = protein
                        organism = synthetic construct
SEQUENCE: 1202
GGGGSGGGGS GGGGSGGGGS GGGGSGGGGS GGGGSGGGGS GGGGSGGGGS GGGGSGGGGS  60
GGGGSGGGGS GGGGS                                                   75

SEQ ID NO: 1203         moltype = AA  length = 80
FEATURE                 Location/Qualifiers
REGION                  1..80
                        note = Synthetic polymer.
source                  1..80
                        mol_type = protein
                        organism = synthetic construct
SEQUENCE: 1203
GGGGSGGGGS GGGGSGGGGS GGGGSGGGGS GGGGSGGGGS GGGGSGGGGS GGGGSGGGGS  60
GGGGSGGGGS GGGGSGGGGS                                              80

SEQ ID NO: 1204         moltype = AA  length = 85
FEATURE                 Location/Qualifiers
REGION                  1..85
                        note = Synthetic polymer.
source                  1..85
                        mol_type = protein
                        organism = synthetic construct
SEQUENCE: 1204
GGGGSGGGGS GGGGSGGGGS GGGGSGGGGS GGGGSGGGGS GGGGSGGGGS GGGGSGGGGS  60
```

```
GGGGSGGGGS GGGGSGGGGS GGGGS                                       85

SEQ ID NO: 1205        moltype = AA  length = 90
FEATURE                Location/Qualifiers
REGION                 1..90
                       note = Synthetic polymer.
source                 1..90
                       mol_type = protein
                       organism = synthetic construct
SEQUENCE: 1205
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS                                   90

SEQ ID NO: 1206        moltype = AA  length = 95
FEATURE                Location/Qualifiers
REGION                 1..95
                       note = Synthetic polymer.
source                 1..95
                       mol_type = protein
                       organism = synthetic construct
SEQUENCE: 1206
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGS                             95

SEQ ID NO: 1207        moltype = AA  length = 100
FEATURE                Location/Qualifiers
REGION                 1..100
                       note = Synthetic polymer.
source                 1..100
                       mol_type = protein
                       organism = synthetic construct
SEQUENCE: 1207
GGGGSGGGGS GGGGSGGGGS GGGGSGGGGS GGGGSGGGGS GGGGSGGGGS GGGGSGGGGS  60
GGGGSGGGGS GGGGSGGGGS GGGGSGGGGS GGGGSGGGGS                        100

SEQ ID NO: 1208        moltype = AA  length = 5
FEATURE                Location/Qualifiers
REGION                 1..5
                       note = Synthetic polymer.
source                 1..5
                       mol_type = protein
                       organism = synthetic construct
SEQUENCE: 1208
GGGSE                                                              5

SEQ ID NO: 1209        moltype = AA  length = 5
FEATURE                Location/Qualifiers
REGION                 1..5
                       note = Synthetic polymer.
source                 1..5
                       mol_type = protein
                       organism = synthetic construct
SEQUENCE: 1209
GSESG                                                              5

SEQ ID NO: 1210        moltype = AA  length = 5
FEATURE                Location/Qualifiers
REGION                 1..5
                       note = Synthetic polymer.
source                 1..5
                       mol_type = protein
                       organism = synthetic construct
SEQUENCE: 1210
GSEGS                                                              5

SEQ ID NO: 1211        moltype = AA  length = 35
FEATURE                Location/Qualifiers
REGION                 1..35
                       note = Synthetic polymer.
source                 1..35
                       mol_type = protein
                       organism = synthetic construct
SEQUENCE: 1211
GEGGSGEGSS GEGSSSEGGG SEGGGSEGGG SEGGS                             35

SEQ ID NO: 1212        moltype = AA  length = 4
FEATURE                Location/Qualifiers
REGION                 1..4
                       note = Synthetic polymer.
```

```
source                  1..4
                        mol_type = protein
                        organism = synthetic construct
SEQUENCE: 1212
CPPC                                                                4

SEQ ID NO: 1213         moltype = AA  length = 6
FEATURE                 Location/Qualifiers
REGION                  1..6
                        note = Synthetic polymer.
source                  1..6
                        mol_type = protein
                        organism = synthetic construct
SEQUENCE: 1213
HHHHHH                                                              6

SEQ ID NO: 1214         moltype = AA  length = 10
FEATURE                 Location/Qualifiers
REGION                  1..10
                        note = Synthetic polymer.
source                  1..10
                        mol_type = protein
                        organism = synthetic construct
SEQUENCE: 1214
YPYDVPDYGS                                                          10

SEQ ID NO: 1215         moltype = AA  length = 19
FEATURE                 Location/Qualifiers
REGION                  1..19
                        note = Synthetic polymer.
source                  1..19
                        mol_type = protein
                        organism = synthetic construct
SEQUENCE: 1215
AAAYPYDVPD YGSHHHHHH                                                19

SEQ ID NO: 1216         moltype = AA  length = 131
FEATURE                 Location/Qualifiers
REGION                  1..131
                        note = Synthetic polymer.
source                  1..131
                        mol_type = protein
                        organism = synthetic construct
SEQUENCE: 1216
QVQLQESGGG LVQAGGSLRL SCAVSGFTFD NYAIGWFRQA PGKEREGVSS ISRSDGSTYY  60
ADSVRGRFTI SSDNAKNTVY LQMNSLKPED TAVYYCAAET SADSGEFRFG WVLKPSLYDY  120
WGQGTQVTVS S                                                        131

SEQ ID NO: 1217         moltype = AA  length = 120
FEATURE                 Location/Qualifiers
REGION                  1..120
                        note = Synthetic polymer.
source                  1..120
                        mol_type = protein
                        organism = synthetic construct
SEQUENCE: 1217
QVQLQESGGG LVQPGGSLRL SCAASGSIFS INVMGWYRQT PGKERELVAK ITNFGITSYA  60
DSAQGRFTIS RGNAKNTVYL QMNSLKPEDT AVYYCNLDTT GWGPPPYQYW GQGTQVTVSS  120

SEQ ID NO: 1218         moltype = AA  length = 121
FEATURE                 Location/Qualifiers
REGION                  1..121
                        note = Synthetic polymer
source                  1..121
                        mol_type = protein
                        organism = synthetic construct
SEQUENCE: 1218
QVQLQESGGG LVQAGDSLRL TCTASGRTFS NYGIGWFRQA PGKEREFVAG INWSGESADY  60
ADSVKGRFTI SRDNAKNTVY LQMNSLKPED TAVYYCAAGE SGVWVGGLDY WXQGTQVTVS  120
S                                                                   121

SEQ ID NO: 1219         moltype = AA  length = 128
FEATURE                 Location/Qualifiers
REGION                  1..128
                        note = Synthetic polymer
source                  1..128
                        mol_type = protein
                        organism = synthetic construct
SEQUENCE: 1219
```

-continued

```
QVQLQESGGG LVQAGGSLRL SCAASGRTFS SYVMGWFRQA PGKEREFVAQ ISWSAGSIYY  60
ADSVKGRFTI SNDNAKRTVY LQMNSLKPED TAVYYCAERG YAYCSDDGCQ RTQDYDYWGQ  120
GTQVTVSS                                                           128

SEQ ID NO: 1220        moltype = AA  length = 133
FEATURE                Location/Qualifiers
REGION                 1..133
                       note = Synthetic polymer
source                 1..133
                       mol_type = protein
                       organism = synthetic construct
SEQUENCE: 1220
QVQLQESGGG LVQAGGSLRL SCAASGFSSD DYTIGWFRQA PGKEREGISC FSSSDGSTGF  60
ADSVKGRFTI SSDNATNTVY LEMNSLKPED TAVYYCAADF NVWSPPICGS RWYGPPPGGM  120
EYWGKGTQVT VSS                                                     133

SEQ ID NO: 1221        moltype = AA  length = 11
FEATURE                Location/Qualifiers
REGION                 1..11
                       note = Synthetic polymer
source                 1..11
                       mol_type = protein
                       organism = synthetic construct
SEQUENCE: 1221
SSISRSDGST Y                                                       11
```